(12) United States Patent
Sakaguchi et al.

(10) Patent No.: US 11,203,763 B2
(45) Date of Patent: Dec. 21, 2021

(54) MICROBIAL OIL CONTAINING FATTY ACIDS OBTAINED FROM STRAMENOPILE AND METHOD OF PRODUCING THE SAME

(71) Applicants: KYUSHU UNIVERSITY, NAT'L UNIVERSITY CORPORATION, Fukuoka (JP); UNIVERSITY OF MIYAZAKI, Miyazaki (JP); KONAN GAKUEN, Kobe (JP); NIPPON SUISAN KAISHA, LTD., Tokyo (JP)

(72) Inventors: Keishi Sakaguchi, Fukuoka (JP); Rie Hamaguchi, Fukuoka (JP); Takanori Matsuda, Fukuoka (JP); Makoto Ito, Fukuoka (JP); Naoki Nagano, Miyazaki (JP); Masahiro Hayashi, Miyazaki (JP); Yuji Okita, Tokyo (JP); Shinichi Sugimoto, Tokyo (JP); Daisuke Honda, Kobe (JP)

(73) Assignee: KYUSHU UNIVERSITY, NATIONAL UNIVERSITY CORPORATION, Fukuoka (JP)

(*) Notice: Subject to any disclaimer, the term of this patent is extended or adjusted under 35 U.S.C. 154(b) by 442 days.

(21) Appl. No.: 16/208,047

(22) Filed: Dec. 3, 2018

(65) Prior Publication Data
US 2019/0119689 A1  Apr. 25, 2019

Related U.S. Application Data

(62) Division of application No. 14/711,075, filed on May 13, 2015, now abandoned, which is a division of application No. 13/877,225, filed as application No. PCT/JP2011/072650 on Sep. 30, 2011, now Pat. No. 9,062,315.

(30) Foreign Application Priority Data

Oct. 1, 2010 (JP) ................ 2010-224225
Aug. 18, 2011 (JP) ................ 2011-179194

(51) Int. Cl.
| | | |
|---|---|---|
| *C12N 15/79* | (2006.01) | |
| *C12N 9/02* | (2006.01) | |
| *C12N 9/10* | (2006.01) | |
| *C12P 7/64* | (2006.01) | |
| *C12N 15/52* | (2006.01) | |
| *C12N 15/89* | (2006.01) | |
| *C12N 15/113* | (2010.01) | |

(52) U.S. Cl.
CPC .......... *C12N 15/79* (2013.01); *C12N 9/0071* (2013.01); *C12N 9/0083* (2013.01); *C12N 9/1029* (2013.01); *C12N 15/113* (2013.01); *C12N 15/52* (2013.01); *C12N 15/895* (2013.01); *C12P 7/6409* (2013.01); *C12P 7/6427* (2013.01); *C12P 7/6472* (2013.01); *C12Y 114/19001* (2013.01); *C12Y 114/19006* (2013.01); *C12Y 203/01119* (2013.01); *C12N 2310/11* (2013.01); *C12N 2310/14* (2013.01)

(58) Field of Classification Search
CPC ....................................................... C12N 15/79
See application file for complete search history.

(56) References Cited

U.S. PATENT DOCUMENTS

| | | | |
|---|---|---|---|
| 6,172,188 B1 | 1/2001 | Thastrup et al. | |
| 7,217,856 B2 | 5/2007 | Weaver et al. | |
| 7,259,006 B2 | 8/2007 | Komazawa et al. | |
| 7,556,949 B2 | 7/2009 | Yadav et al. | |
| 2002/0107362 A1 | 8/2002 | Thastrup et al. | |
| 2005/0014231 A1 | 1/2005 | Mukerji et al. | |
| 2005/0054050 A1 | 3/2005 | Thastrup et al. | |
| 2006/0275904 A1 | 12/2006 | Ono et al. | |
| 2006/0286650 A1 | 12/2006 | Ono et al. | |
| 2008/0009045 A1 | 1/2008 | Komazawa et al. | |
| 2009/0093033 A1 | 4/2009 | Luy et al. | |

(Continued)

FOREIGN PATENT DOCUMENTS

| | | |
|---|---|---|
| JP | 2005-102680 A | 4/2005 |
| JP | 2006-304685 A | 11/2006 |

(Continued)

OTHER PUBLICATIONS

Poulos, Alf, "Very Long Chain Fatty Acids in Higher Animals—A Review", Lipids, 1995, vol. 30, No. 1, pp. 1-14, cited in Specification (14 pages).

(Continued)

*Primary Examiner* — Scott Long
(74) *Attorney, Agent, or Firm* — Westerman, Hattori, Daniels & Adrian, LLP

(57) ABSTRACT

A microbial oil is obtained from Labyrinthulomycetes in which a gene for fatty acid biosynthesis has been disrupted or an expression of the gene has been inhibited to highly accumulate the fatty acid. The microbial oil typically contains: (a) 1.5% or more of arachidonic acid (AA) based on a total amount of fatty acid; (b) 0.2% or more of dihomo-γ-linolenic acid (DGLA) based on the total amount of fatty acid; (c) 0.04% or more of eicosatetraenoic acid (ETA) based on the total amount of fatty acid; (d) 3.8% or more of eicosapentaenoic acid (EPA) based on the total amount of fatty acid; (e) 13.7% or less of n-6 docosapentaenoic acid (n-6DPA) based on the total amount of fatty acid; and (f) 43.9% or less of docosahexaenoic acid (DHA) based on the total amount of fatty acid.

17 Claims, 65 Drawing Sheets

Specification includes a Sequence Listing.

(56) References Cited

U.S. PATENT DOCUMENTS

2010/0323085 A1* 12/2010 Ochiai ................ C12P 7/6427
                                                            426/607
2012/0322116 A1    12/2012 Sakaguchi et al.

FOREIGN PATENT DOCUMENTS

| JP | 2006-304686 A | 11/2006 |
| JP | 2007-143479 A | 6/2007 |
| JP | 2007-532104 A | 11/2007 |
| WO | 1997/011094 A1 | 3/1997 |
| WO | 2006/044646 A2 | 4/2006 |
| WO | 2011/037207 A1 | 3/2011 |

OTHER PUBLICATIONS

Horrocks, Lloyd A. et al., "Health Benefits of Docosahexaenoic Acid (DHA)", Pharmacological Research, 1999, vol. 40, No. 3, pp. 211-225, cited in Specification (15 pages).
Yokoyama, Rinka et al., "Taxonomic rearrangement of the genus Schizochytrium sensu lato based on morphology, chemotaxonomic characteristics, and 18S rRNA gene phylogeny (Thraustochytriaceae, Labyrmthulomycetes): emendation for Schizochytrium and erection of *Aurantiochytrium* and *Oblongichytrium* gen. nov.", Mycoscience, 2007, vol. 48, pp. 199-211, cited in Specification (13 pages).
Iwasaka, Hiroaki et al., "Modification of lipid composition by genetic engineering in oleaginous microorganisms, Labyrinthulida", Lecture Summary for the 60th Conference of The Society for Biotechnology, Japan, 2008, p. 136, cited in ISR and Specification, w/ English abstract (2 pages).
Lippmeier, J. Casey et al., "Characterization of Both Polyunsaturated Fatty Acid Biosynthetic Pathways in *Schizochytrium* sp.", Lipids, 2009, vol. 44, No. 7, pp. 621-630, cited in ISR and Specification (10 pages).
Tonon, Thierry et al., "Identification of a very long chain polyunsaturated fatty acid D4-desaturase from the microalga *Pavlova lutheri*", FEBS Letters, 2003, vol. 553, pp. 440-444, cited in Specification (5 pages).
International Search Report dated Oct. 26, 2011, issued in corresponding application No. PCT/JP2011/072650 (2 pages).
Thompson, Julie D. et al., "CLUSTAL W: improving the sensitivity of progressive multiple sequence alignment through sequence weighting, position-specific gap penalties and weight matrix choice", Nucleic Acids Research, 1994, vol. 22, No. 22, pp. 4673-4680, cited in Specification (8 pages).
Yazawa, Kazunaga, "Production of Eicosapentaenoic Acid from Marine Bacteria", Lipids, vol. 31, Supplement, 1996, pp. 197-300, cited in Specification (4 pages).
Jiang, X. et al., "Cloning and expression of two elongase genes involved in the biosynthesis of docosahexaenoic acid in *Thraustochytrium* sp. FJN-10", Wei Sheng Wu Xue Bao, 2008, vol. 48, No. 2, pp. 176-183, cited in Specification, w/ English abstract (9 pages).
Pereira, Suzette L. et al., "A novel w3-fatty acid desaturase involved in the biosynthesis of eicosapentaenoic acid", Biochem. J., 2004, vol. 378, pp. 665-671, cited in Specification (7 pages).
Prasher, Douglas C. et al., "Primary structure of the Aequorea victoria green-fluorescent protein", Gene, 1992, vol. 111, pp. 229-233, cited in Specification (5 pages).
Chalfie, Martin et al., "Green Fluorescent Protein as a Marker for Gene Expression", Science, 1994, vol. 263, pp. 802-805, cited in Specification (4 pages).
Southern, P. J. et al., "Transformation of Mammalian Cells to Antibiotic Resistance with a Bacterial Gene Under Control of the SV40 Early Region Promoter", Journal of Molecular and Applied Genetics, 1982, vol. 1, pp. 327-341, cited in Specification (15 pages).
Saitou, Naruya et al., "The Neighbor-joining Method: A New Method for Reconstructing Phylogenetic Trees", Mol. Biol. Evol., 1987, vol. 4, No. 4, pp. 406-425, cited in Specification (20 pages).
Schiestl, Rober H. et al., "High efficiency transformation of intact yeast cells using single stranded nucleic acids as a carrier", Current Genetics, 1989, vol. 16, pp. 339-346 (8 pages).
Abe, Eriko et al., "A Novel Phosphatidylcholine Which Contains Pentadecanoic Acid at sn-1 and Docosahexaenoic Acid at sn-2 in *Schizochytrium* sp. F26-b", J. Biochem, 2006, vol. 140, pp. 247-253 (7 pages).
Bio-Experiment Illustrated 2, Fundamentals of Gene Anlysis, 1995, Shujunsha, pp. 117-128, cited in Specification, w/ English translation (29 pages).
"Gene Knockout Construct Producing Method by PCR", Japan Society for Bioscience, Biotechnology, and Agrochemistry, 2003, vol. 77, No. 2, pp. 150-153, cited in Specification, w/ English translation (11 pages).
U.S. Non-Final Office Action dated Nov. 3, 2014, issued in co-pending U.S. Appl. No. 13/877,225 (14 pages).
Bio-Experiment Illustrated 2, Fundamentals of Gene Analysis, 1995, Shujunsha, pp. 63-68, cited in Specification, w/ English translation (12 pages).
Sanger, F. et al., "DNA sequencing with chain-terminating inhibitors", Proc. Natl. Acad. Sci. USA, 1977, vol. 74, No. 12, pp. 5463-5467, cited in Specification (5 pages).
Meyer, Astrid et al., "Novel fatty acid elongases and their use for the reconstitution of docosahexaenoic acid biosynthesis", Journal of Lipid Research, 2004, vol. 45, pp. 1899-1909, cited in Specification (11 pages).
Cigan, A. Mark et al., "Sequence and structural features associated with translational initiator regions in yeast—a review", Gene, 1987, vol. 59, pp. 1-18, cited in Specification (18 pages).
Romanos, Michael A. et al., "Foreign Gene Expression in Yeast: a Review", Yeast, 1992, vol. 8, pp. 423-488, cited in Specification (66 pages).
Qiu, Xiao et al., "Identification of a D4 Fatty Acid Desaturase from *Thraustochytrium* sp. Involved in the Biosynthesis of Docosahexanoic Acid by Heterologous Expression in *Saccharomyces cerevisiae* and *Brassica juncea*", Journal of Biol. Chem., 2001, vol. 276, No. 34, pp. 31561-31566, cited in Specification (6 pages).
"PCR DIG Probe Synthesis Kit", DIG Application Manual 8th, Roche Applied Science, pp. 1-6, cited in Specification (6 pages).
Kobayashi, Takumi et al., "Expression of a delta-5 desaturase gene results in the alternation of fatty acid composition of *Aurantiochytrium* sp. mh0186", Japanese Biochemical Society, 2009, 2P-200, cited in ISR, w/ English translation (3 pages).
Matsuda, Takanori et al., "Isolation of a delta-12 desaturase from Pinguiochrysis pyriformis MBIC 10872 and its expression in thraustochytrids", Japanese Biochemical Society, 2009, 2P-199, cited in ISR, w/ English translation (3 pages).
Kang, Dong Hoon et al., "Identification and Characterization of a Novel Enzyme Related to the Synthesis of PUFAs Derived from Thraustochytrium aureum ATCC 34304", Biotechnology and Bioprocess Engineering, 2010, vol. 15, pp. 261-272, cited in ISR (12 pages).
Kang, Dong-Hoon et al., "Coexpression of Elo-like Enzyme and D5, D4-Desaturases Derived from Thraustochytrium aureum ATCC 34304 and the Production of DHA and DPA in Pichia pastoris", Biotechnology and Bioprocess Engineering, 2008, vol. 13, pp. 483-490, cited in ISR (8 pages).
Lewis et al. (Marine Biotechnology . Nov. 1999, 1(6): 580-587).

* cited by examiner

[Fig.1]
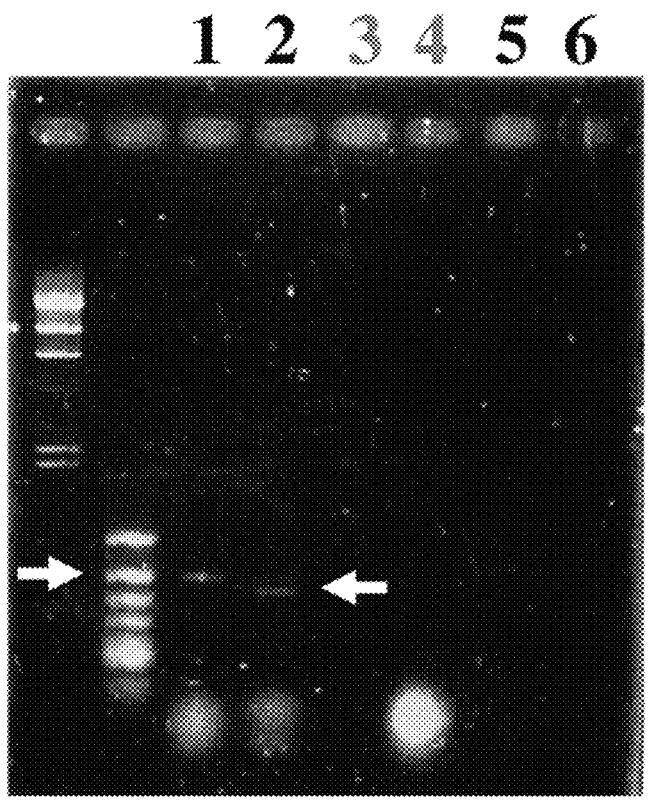
[Fig.2]
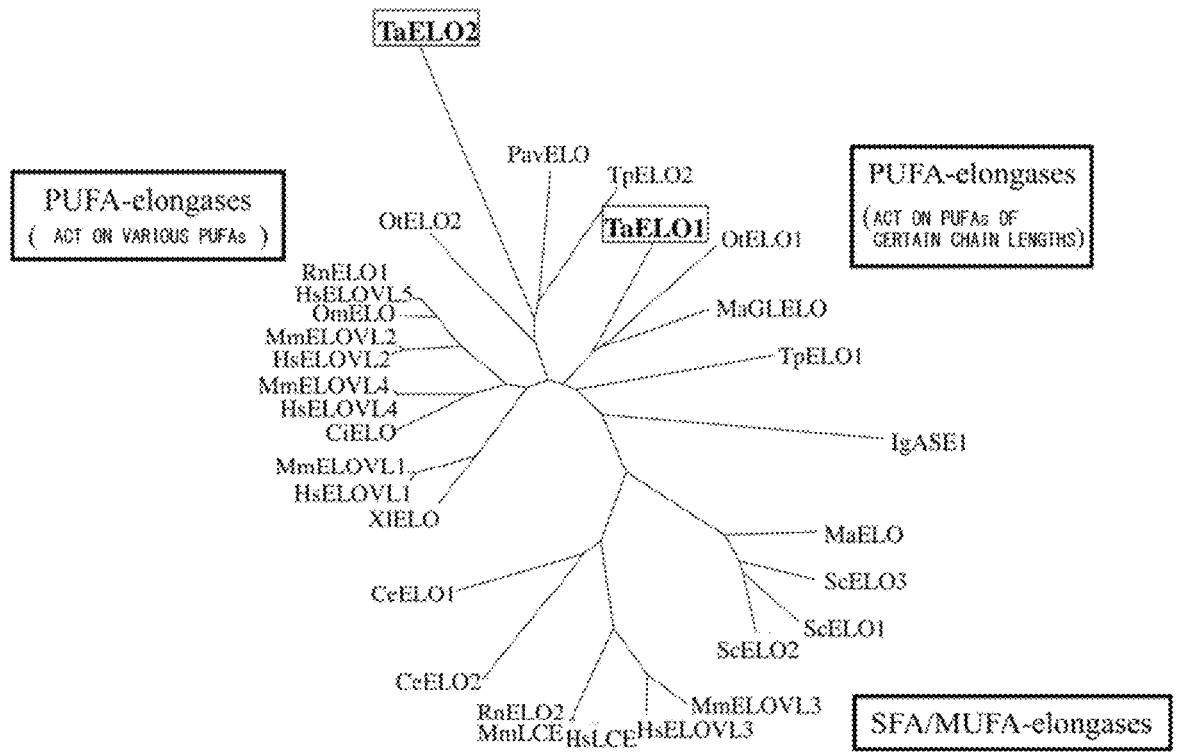

[Fig. 3]
(A)
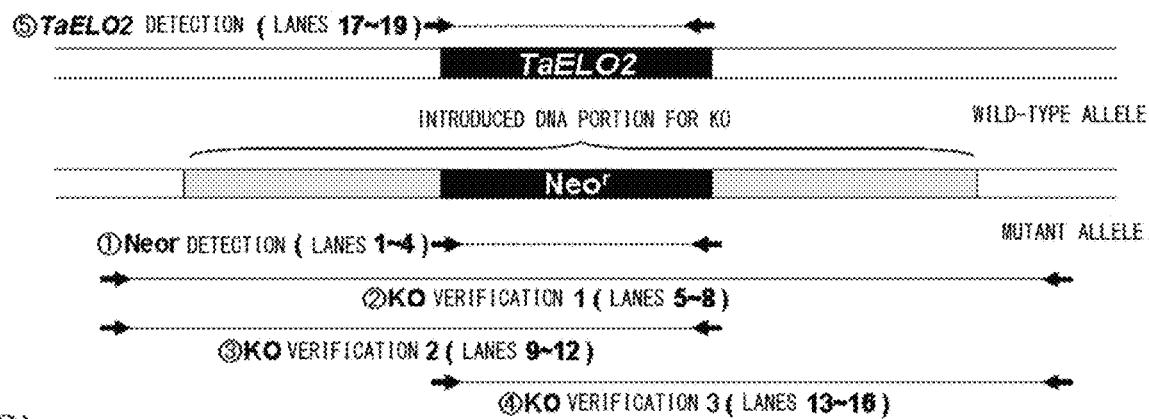
(B)
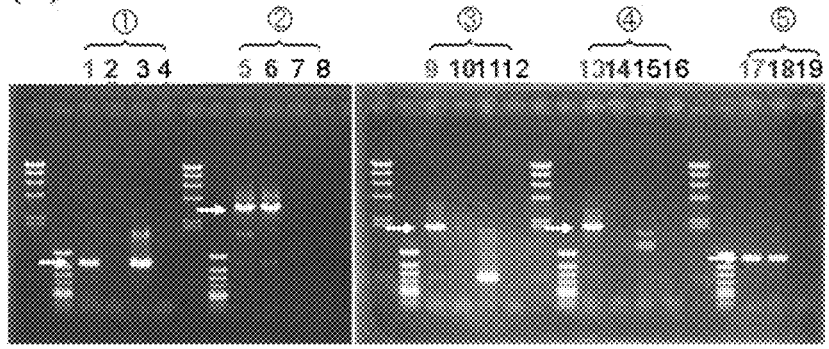
[Fig. 4]
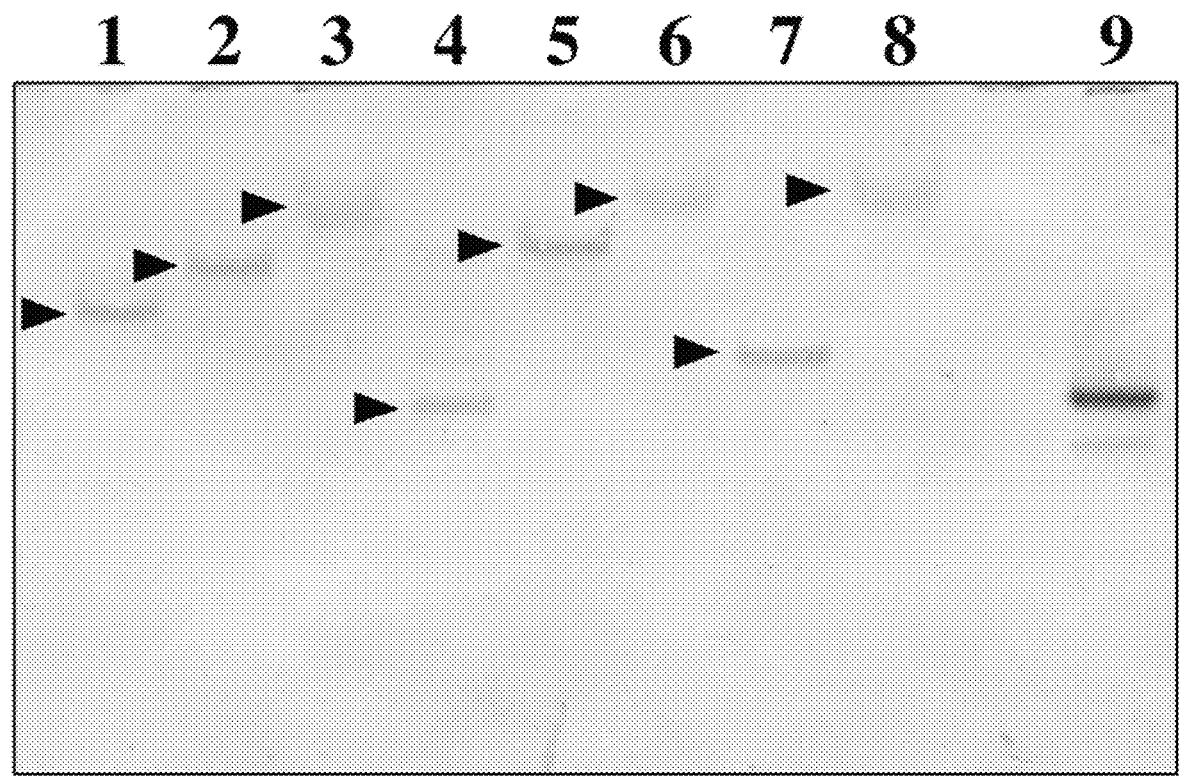

[Fig.5]
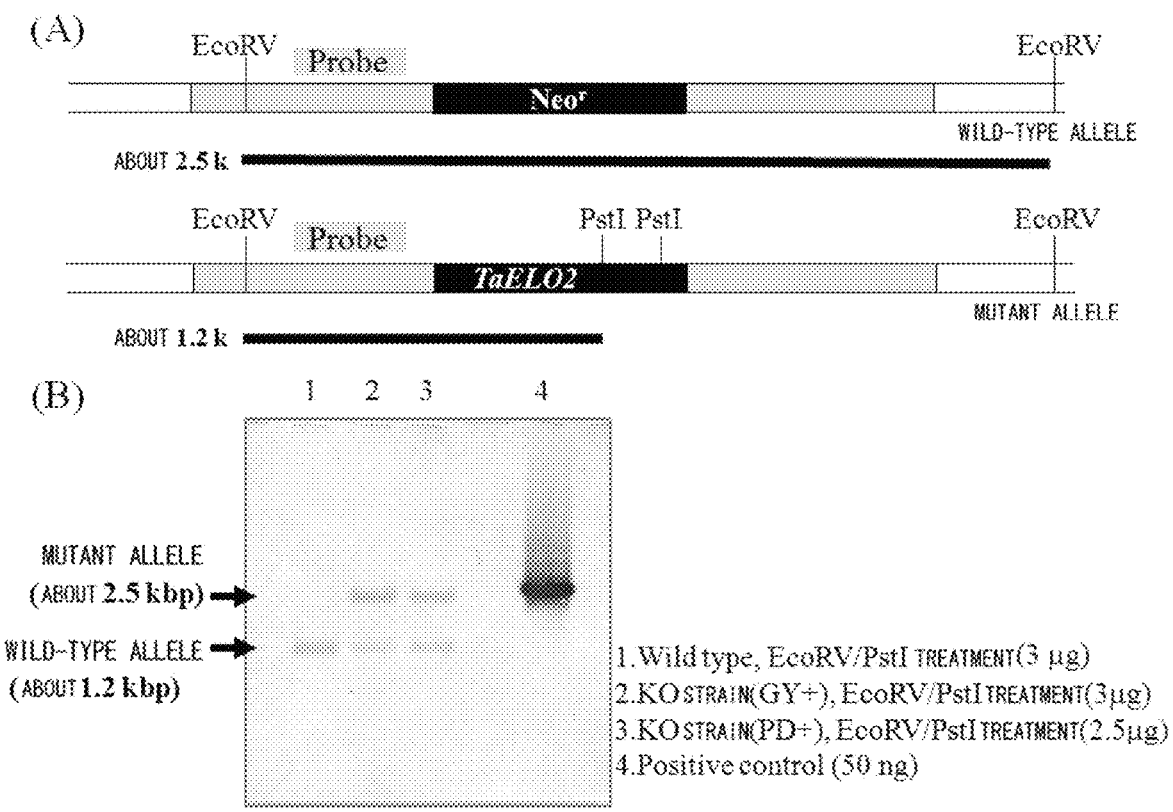

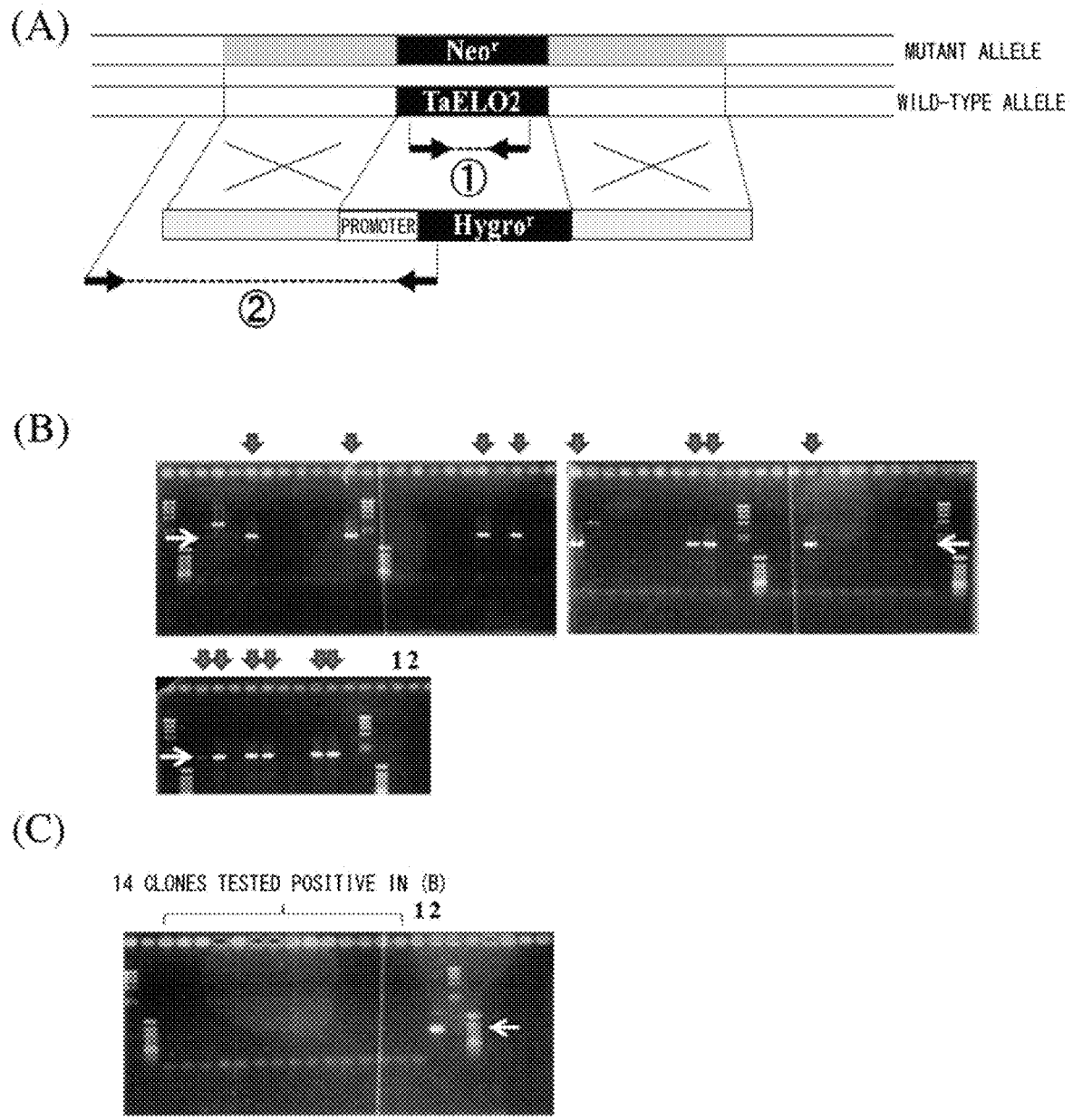

[Fig.7]
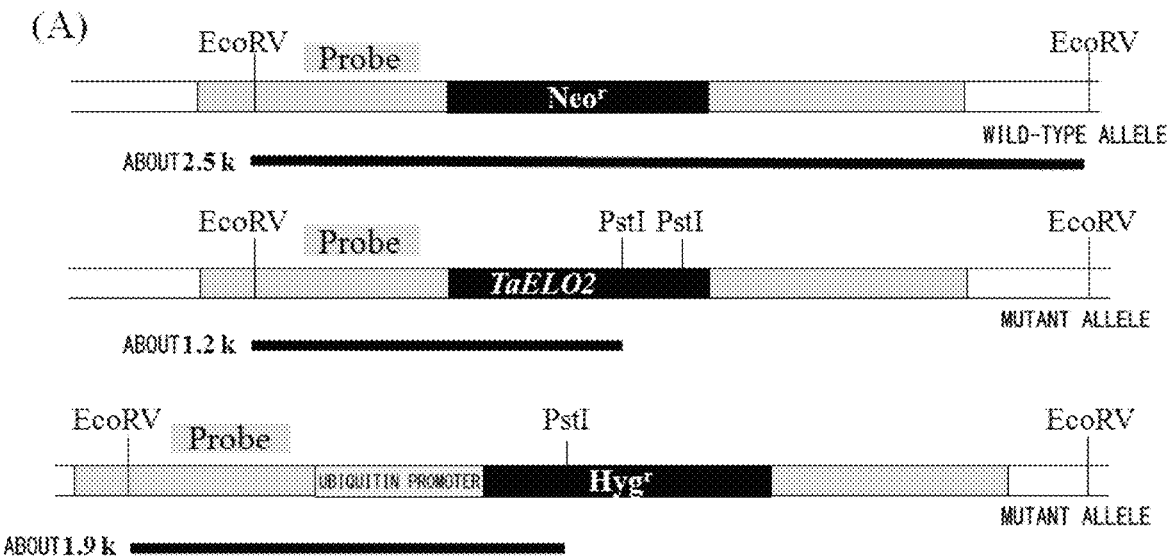
[Fig.8]
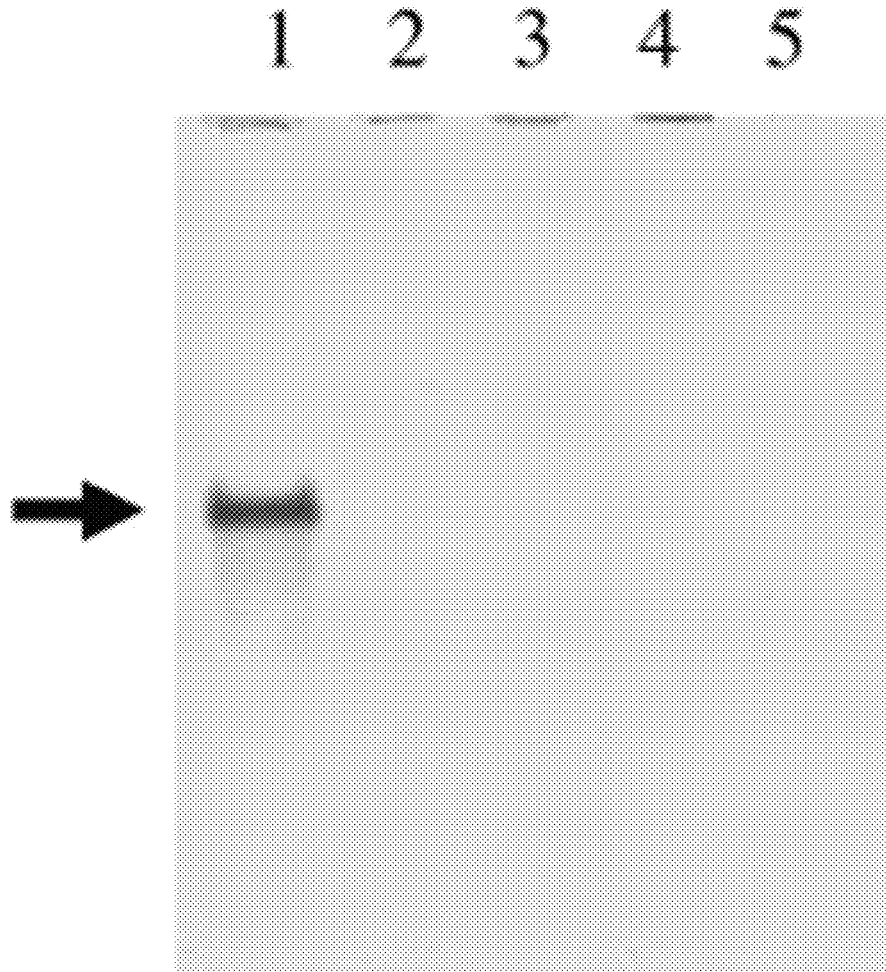

[Fig.9]
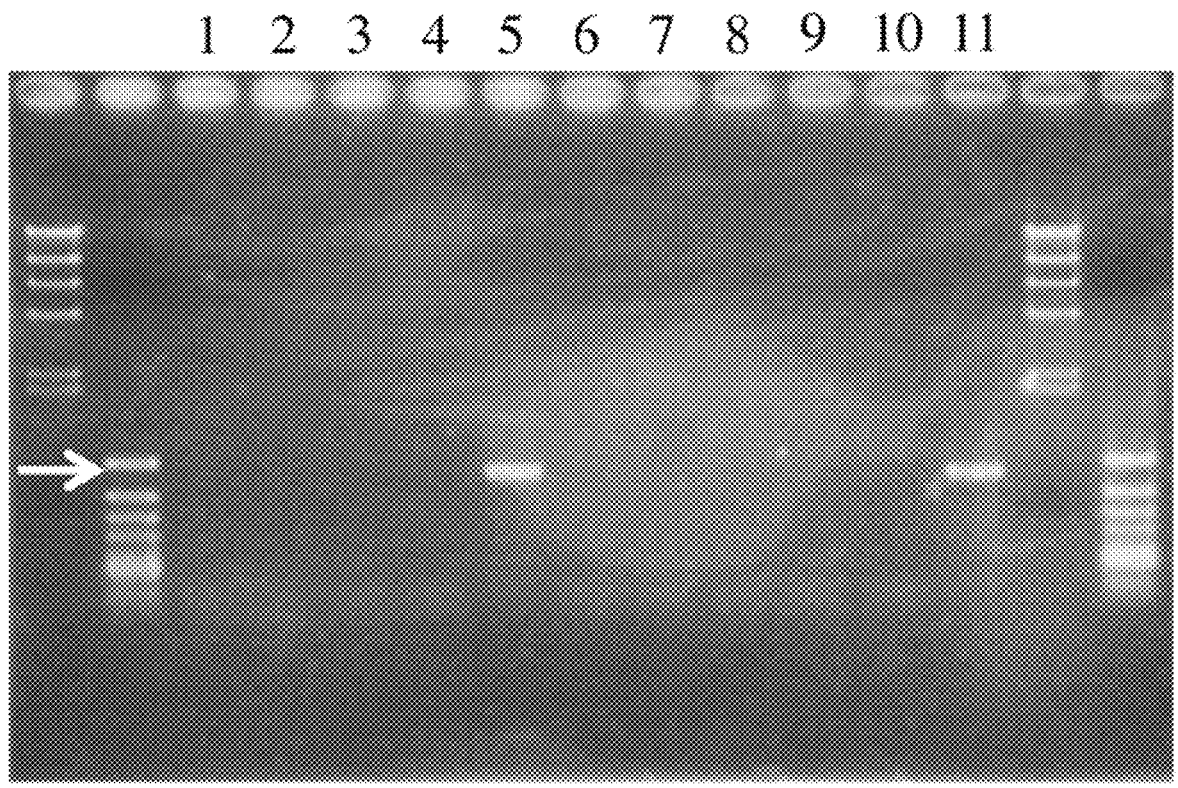
[Fig.10]
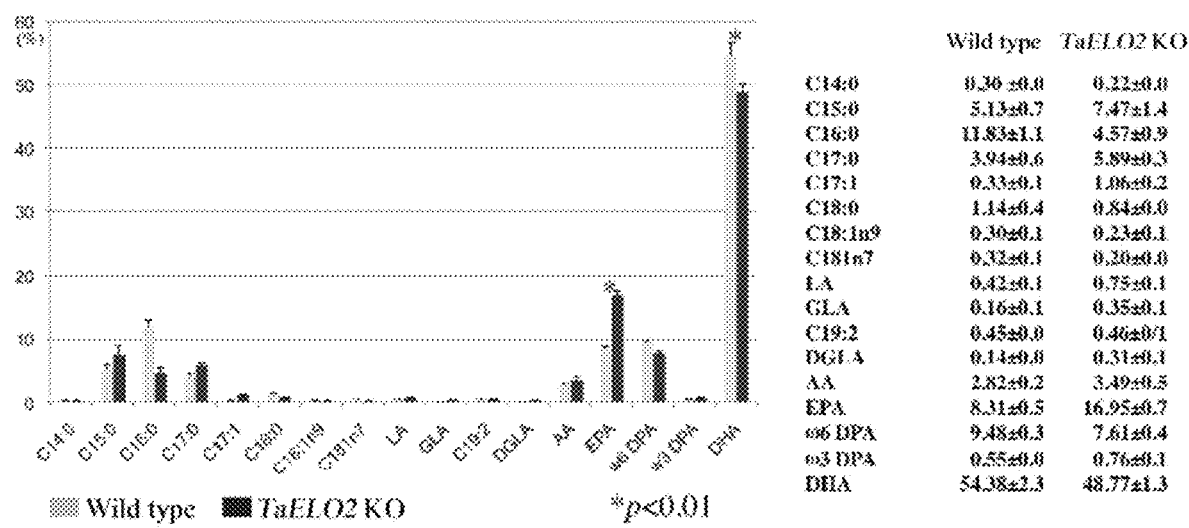

[Fig.11]
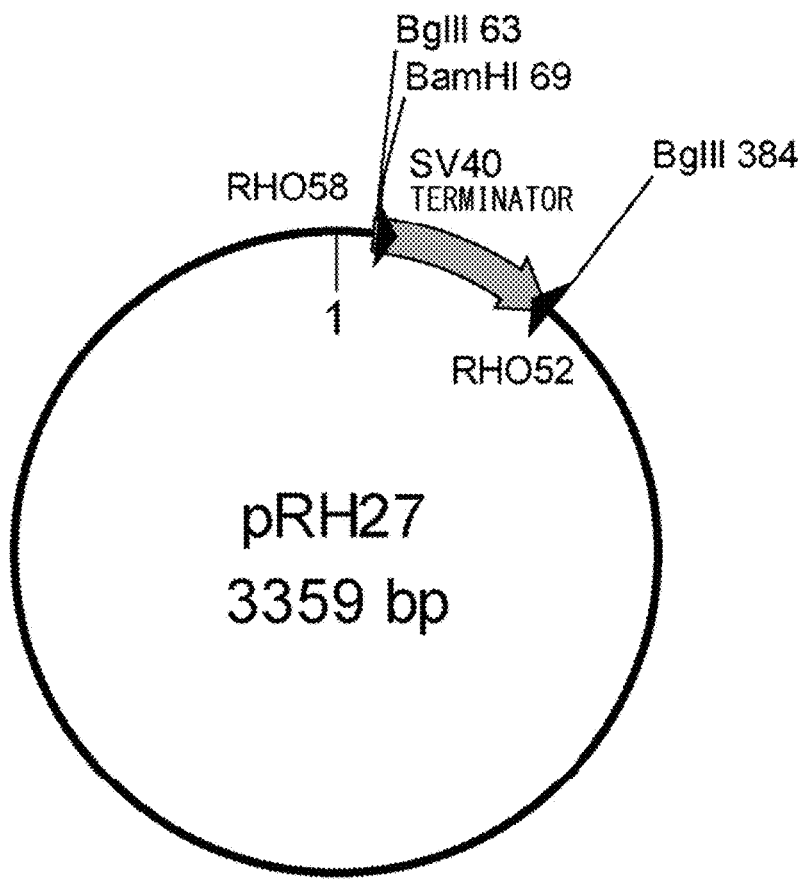
[Fig.12]
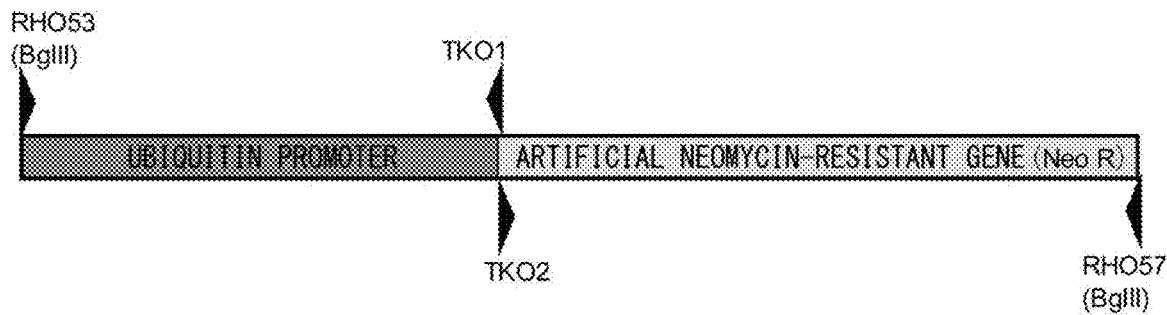

[Fig.13]
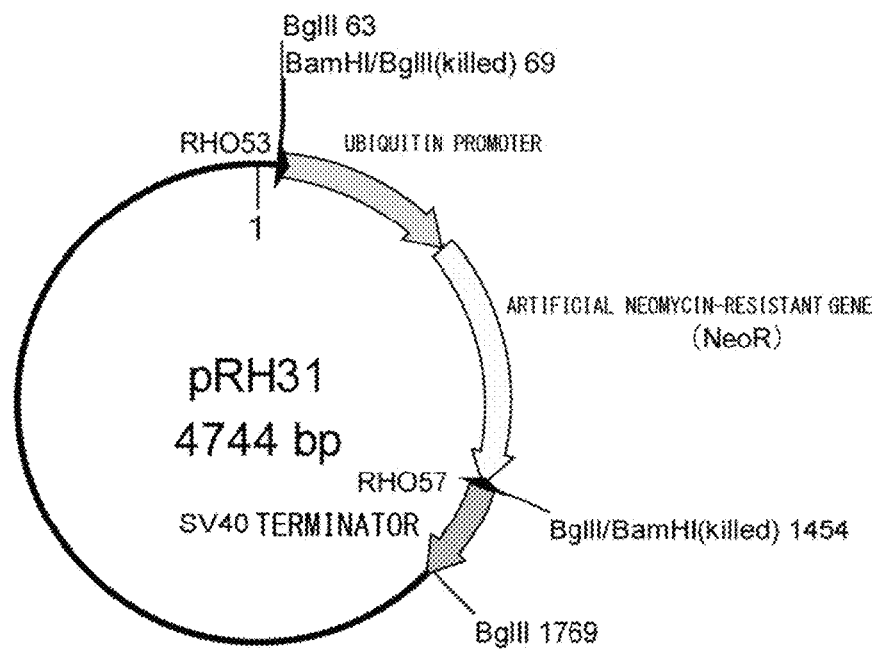
[Fig.14]
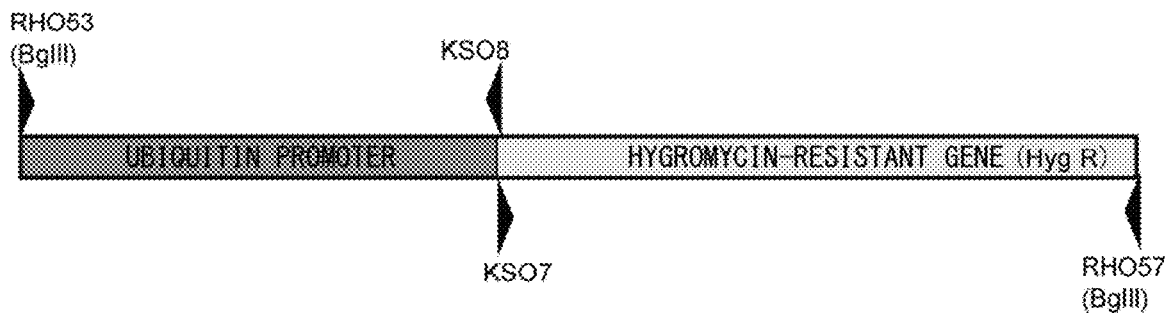

[Fig.15]
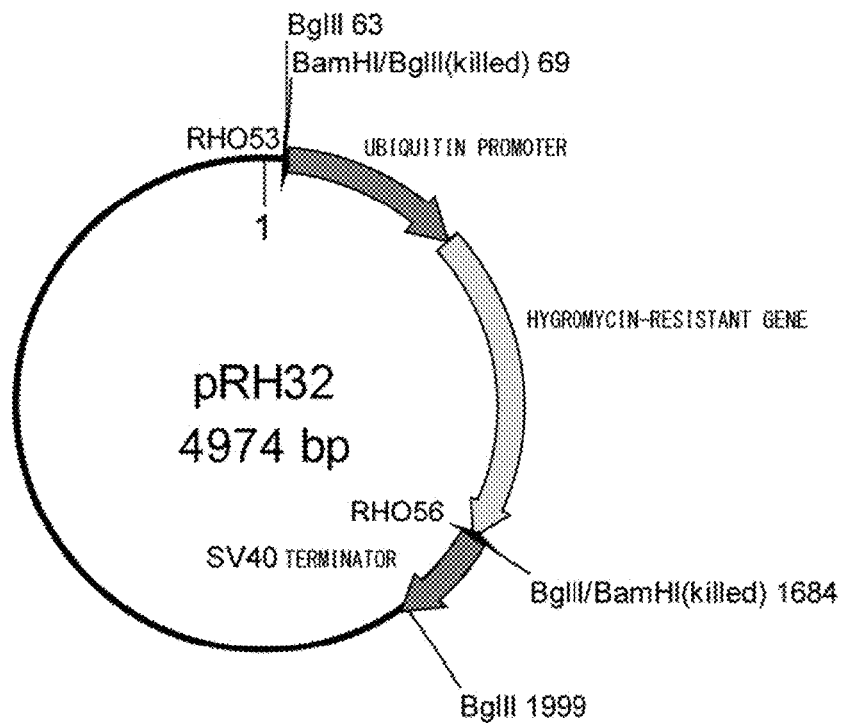
[Fig.16]
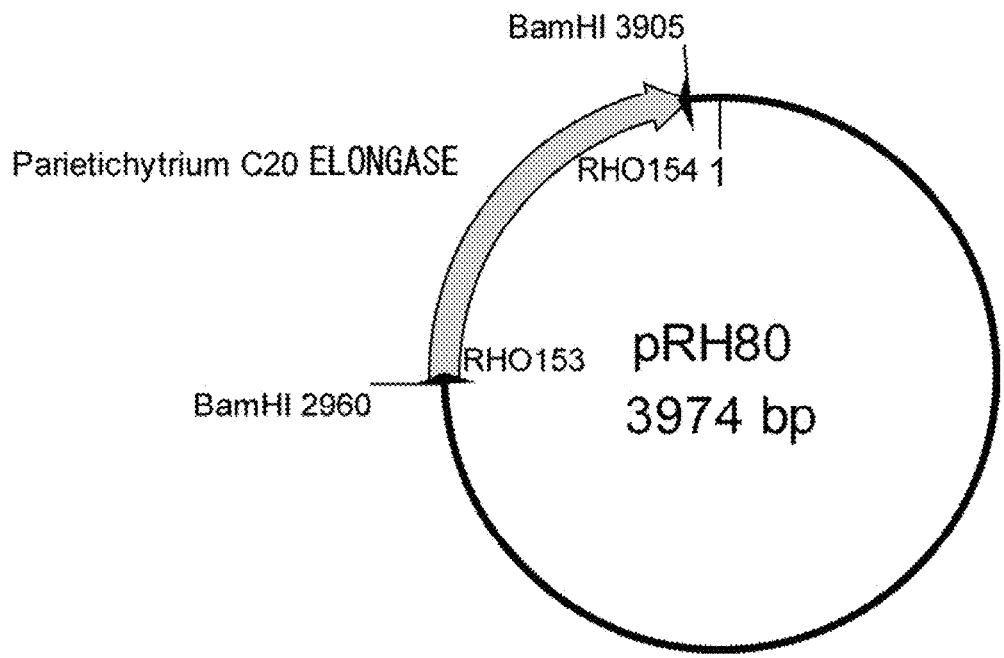

[Fig.17]
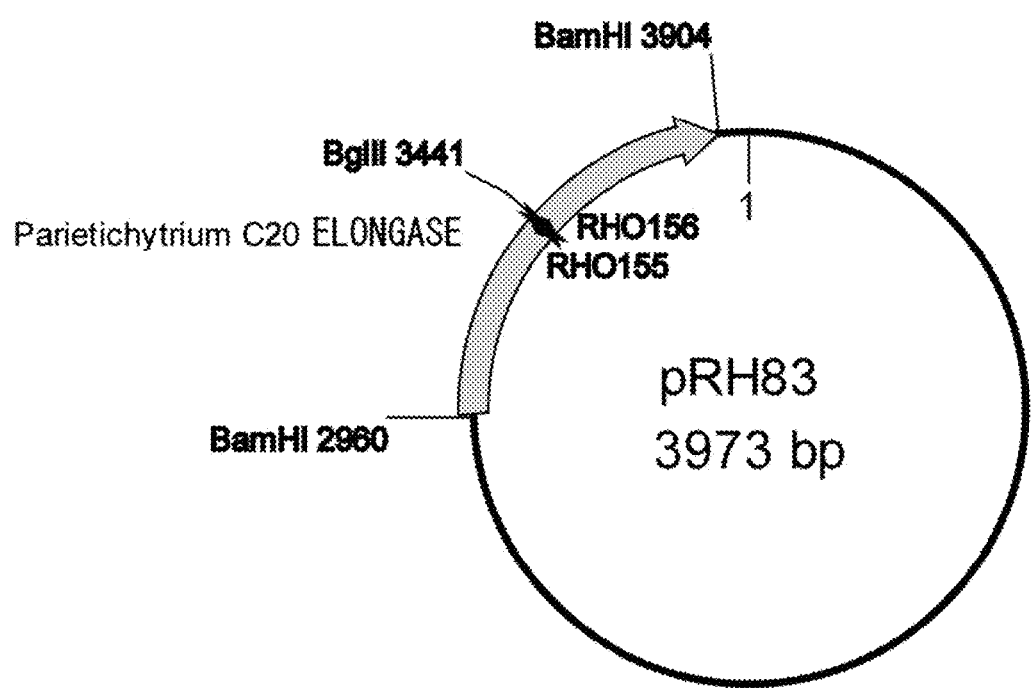

[Fig.18]
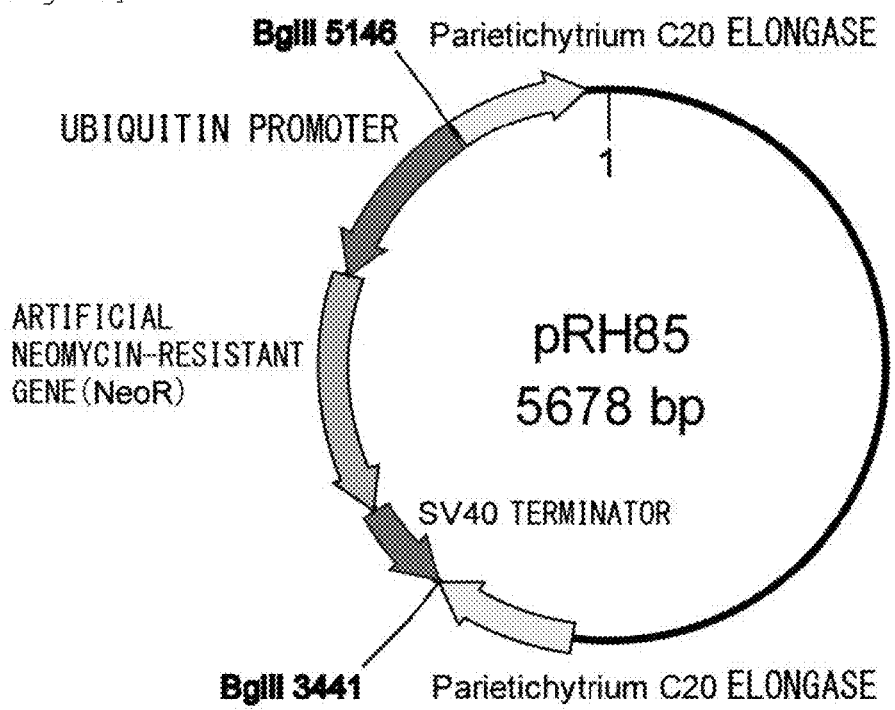
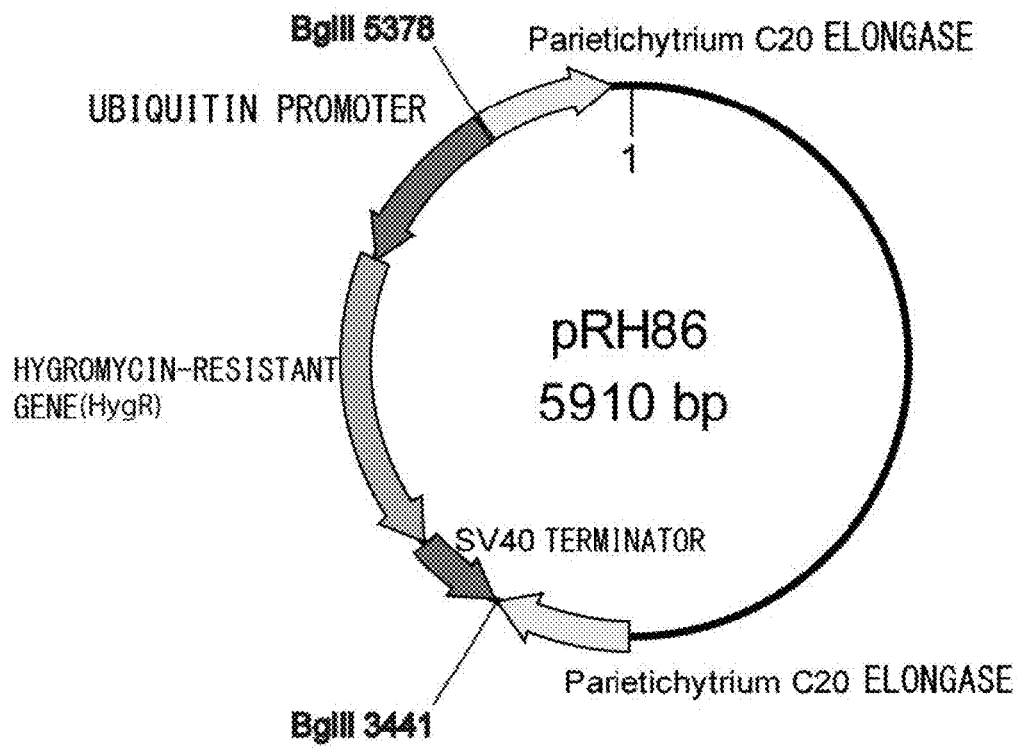

[Fig.19]
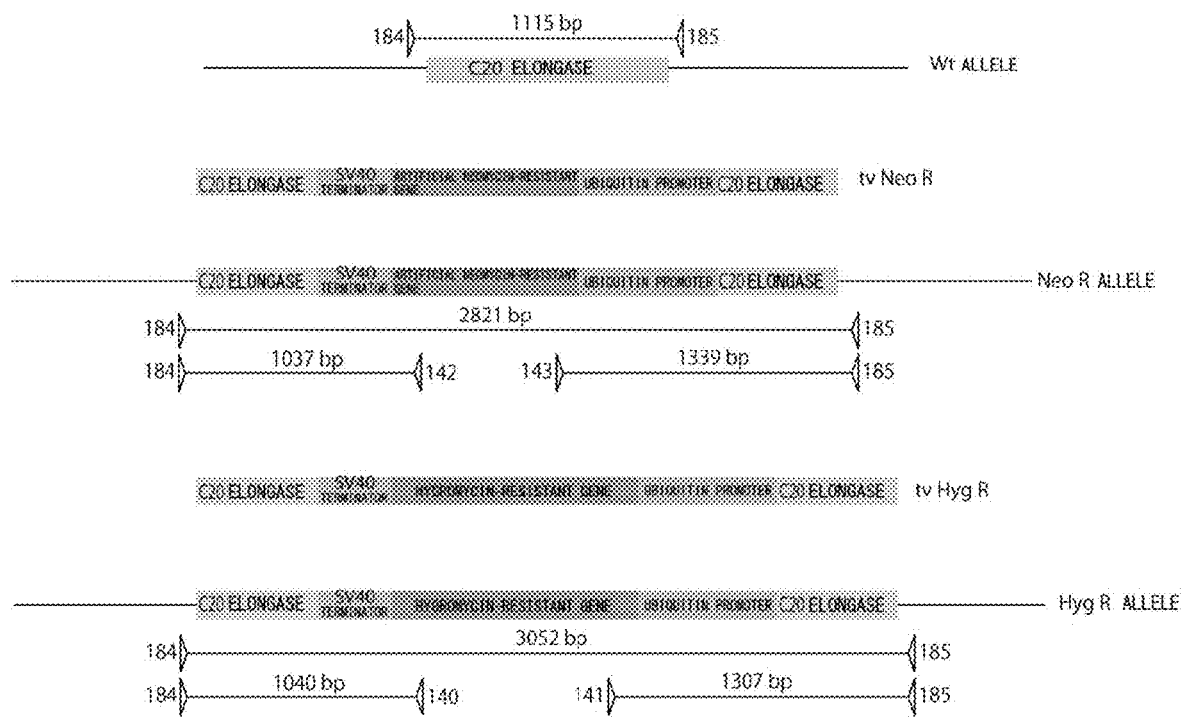
[Fig.20]
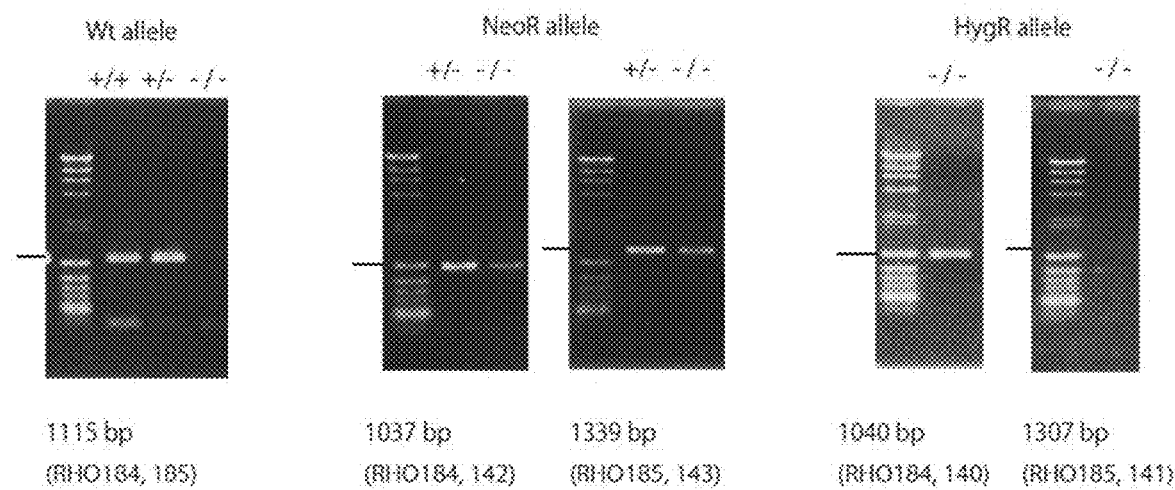

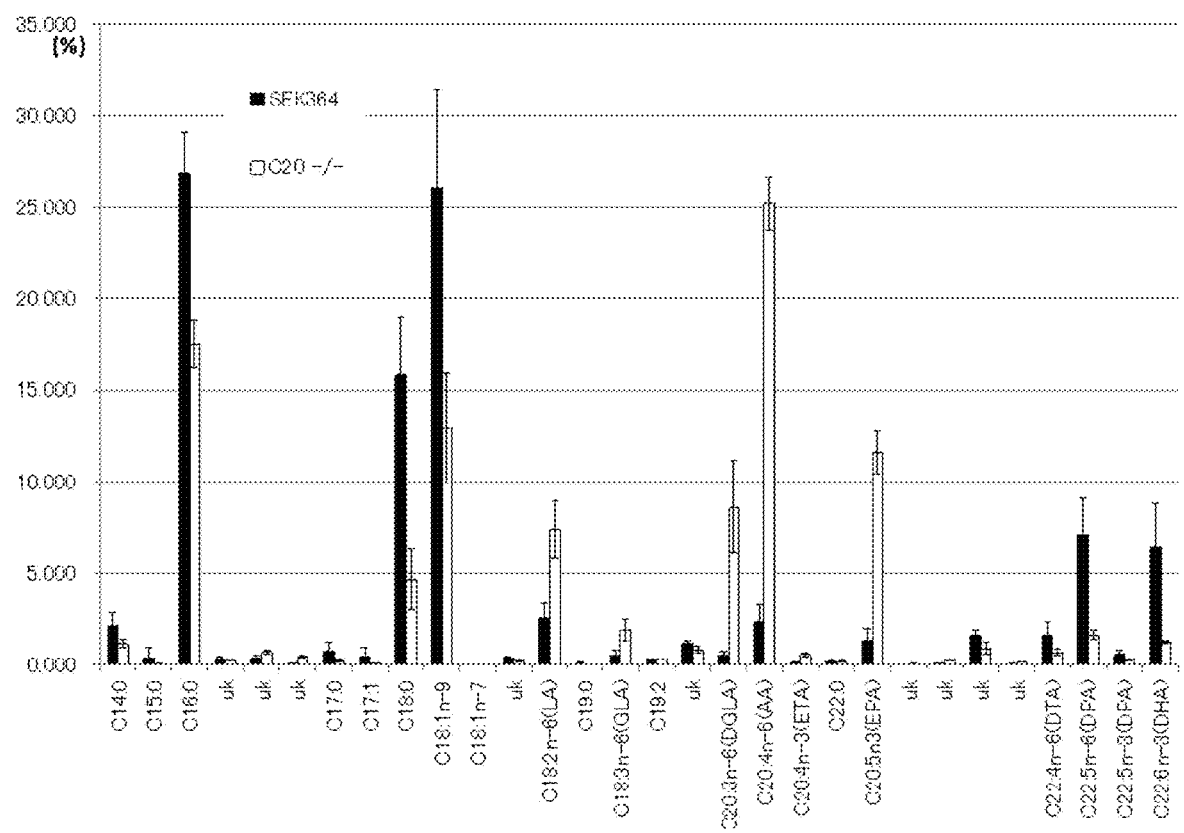
[Fig.21]

[Fig. 22]

| COMPARISON WITH WILD-TYPE STRAIN | C20 -/- | SEK364 | FA |
|---|---|---|---|
| 54.4% | 1.16 | 2.13 | C14:0 |
| 6.5% | 0.02 | 0.38 | C15:0 |
| 65.4% | 17.55 | 26.83 | C16:0 |
| 31.6% | 0.24 | 0.76 | C17:0 |
| 12.0% | 0.05 | 0.42 | C17:1 |
| 29.4% | 4.66 | 15.84 | C18:0 |
| 49.5% | 12.91 | 26.08 | C18:1n-9 |
| – | 0.00 | 0.00 | C18:1n-7 |
| 289.4% | 7.38 | 2.55 | C18:2n-6(LA) |
| 35.3% | 0.02 | 0.05 | C19:0 |
| 366.7% | 1.91 | 0.52 | C18:3n-6(GLA) |
| 99.5% | 0.31 | 0.31 | C19:2 |
| 1673.7% | 8.62 | 0.51 | C20:3n-6(DGLA) |
| 1079.4% | 25.22 | 2.34 | C20:4n-6(AA) |
| 722.8% | 0.56 | 0.08 | C20:4n-3(ETA) |
| 105.7% | 0.18 | 0.17 | C22:0 |
| 851.2% | 11.58 | 1.36 | C20:5n3(EPA) |
| 42.2% | 0.67 | 1.59 | C22:4n-6(DTA) |
| 23.1% | 1.64 | 7.07 | C22:5n-6(DPA) |
| 45.4% | 0.26 | 0.56 | C22:5n-3(DPA) |
| 20.0% | 1.28 | 6.38 | C22:6n-3(DHA) |

[Fig. 23]
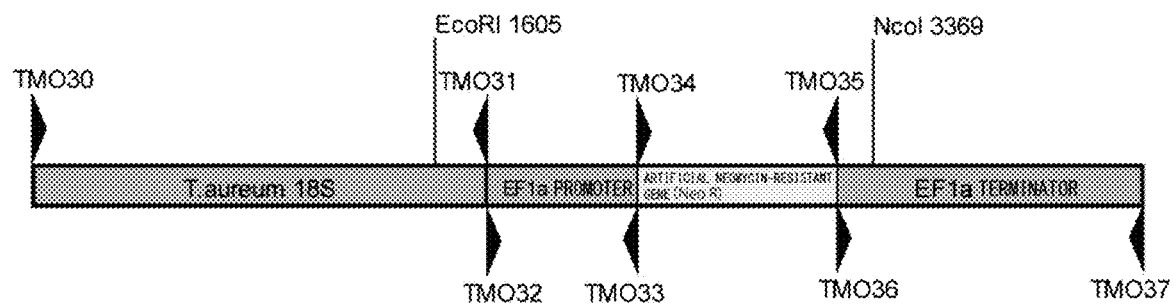
[Fig. 24]
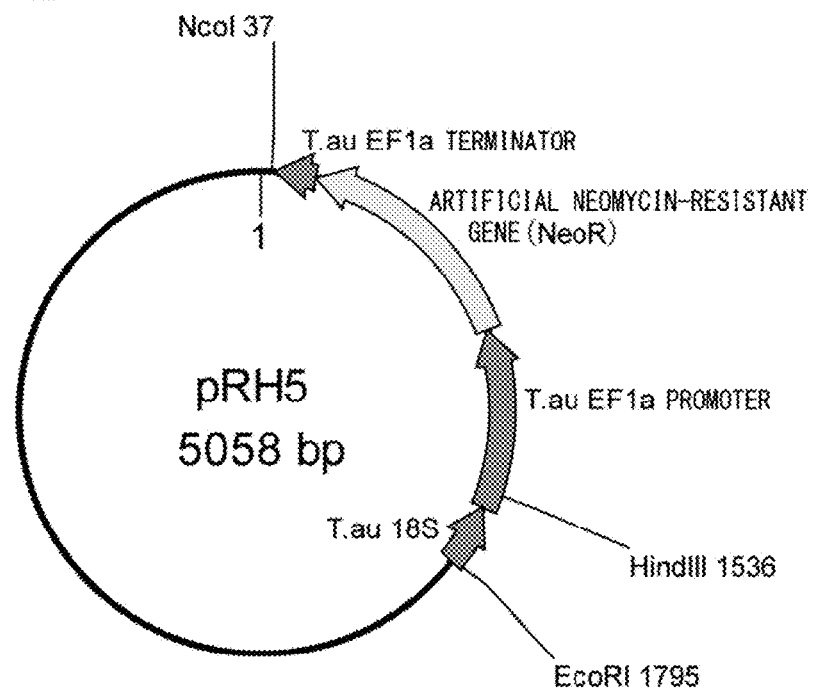

[Fig.25]
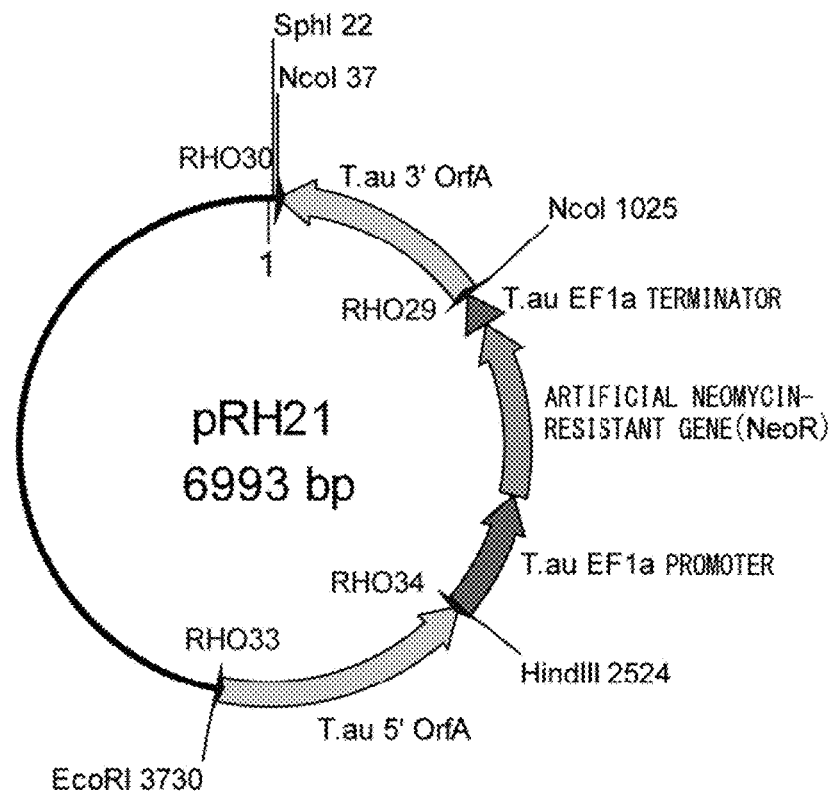
[Fig.26]
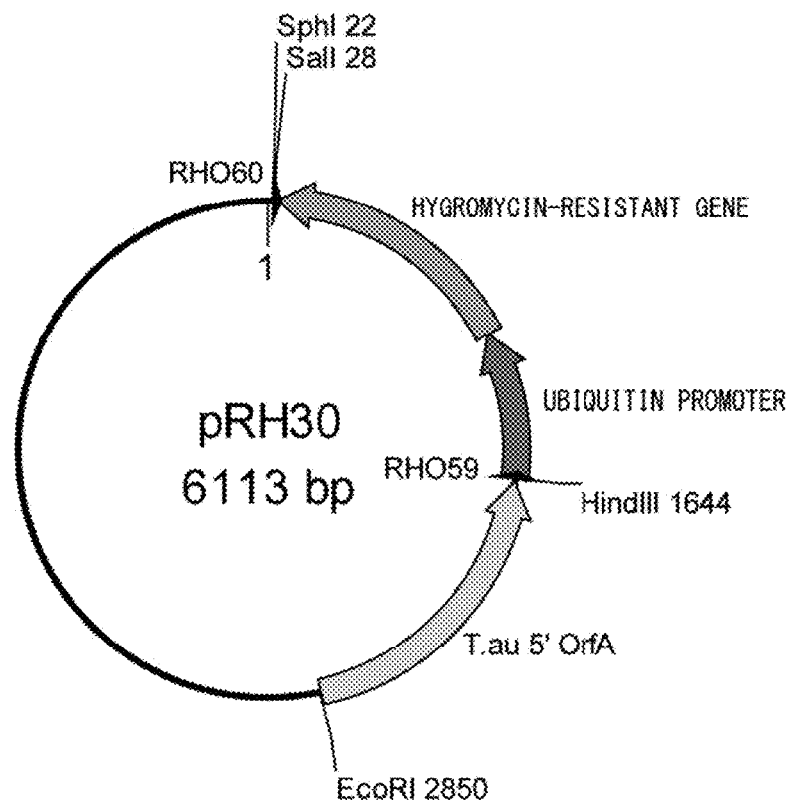

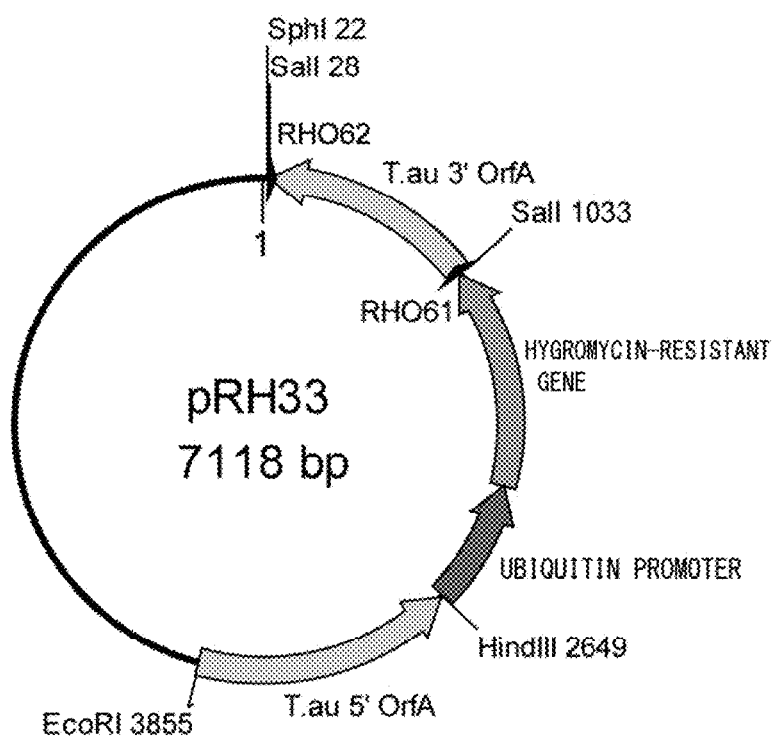
[Fig.27]

[Fig.28]
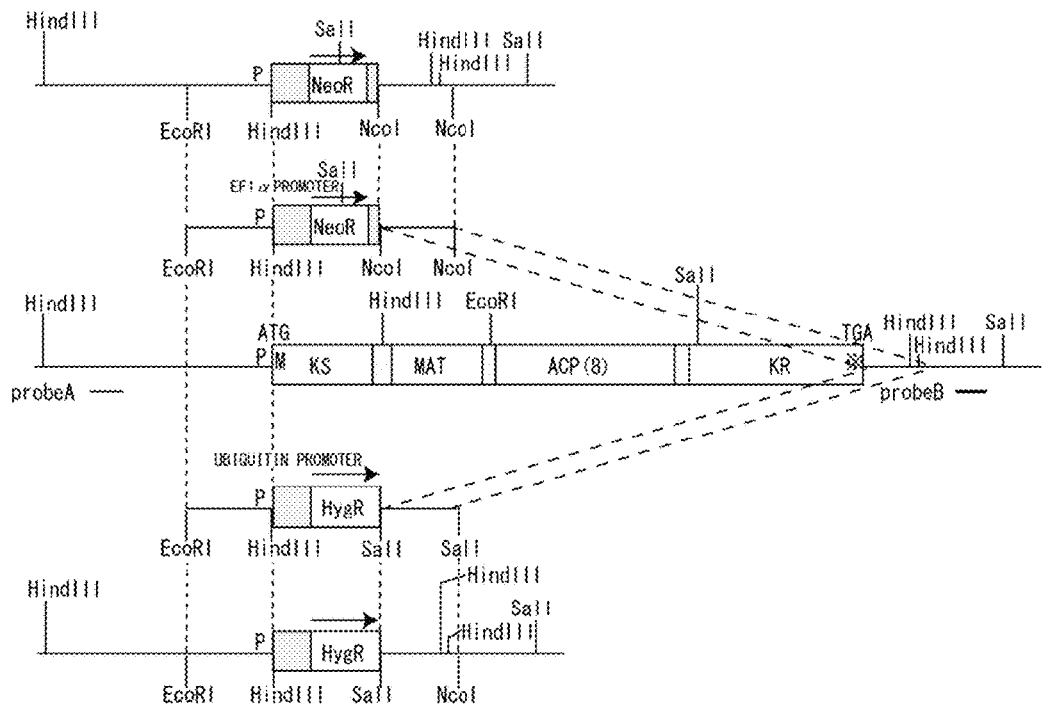
[Fig.29]
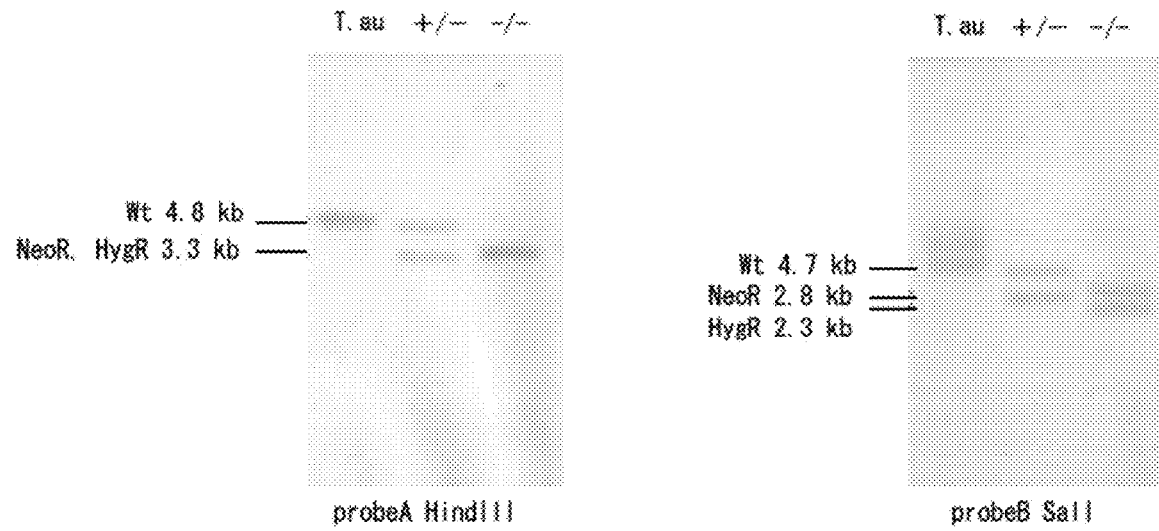

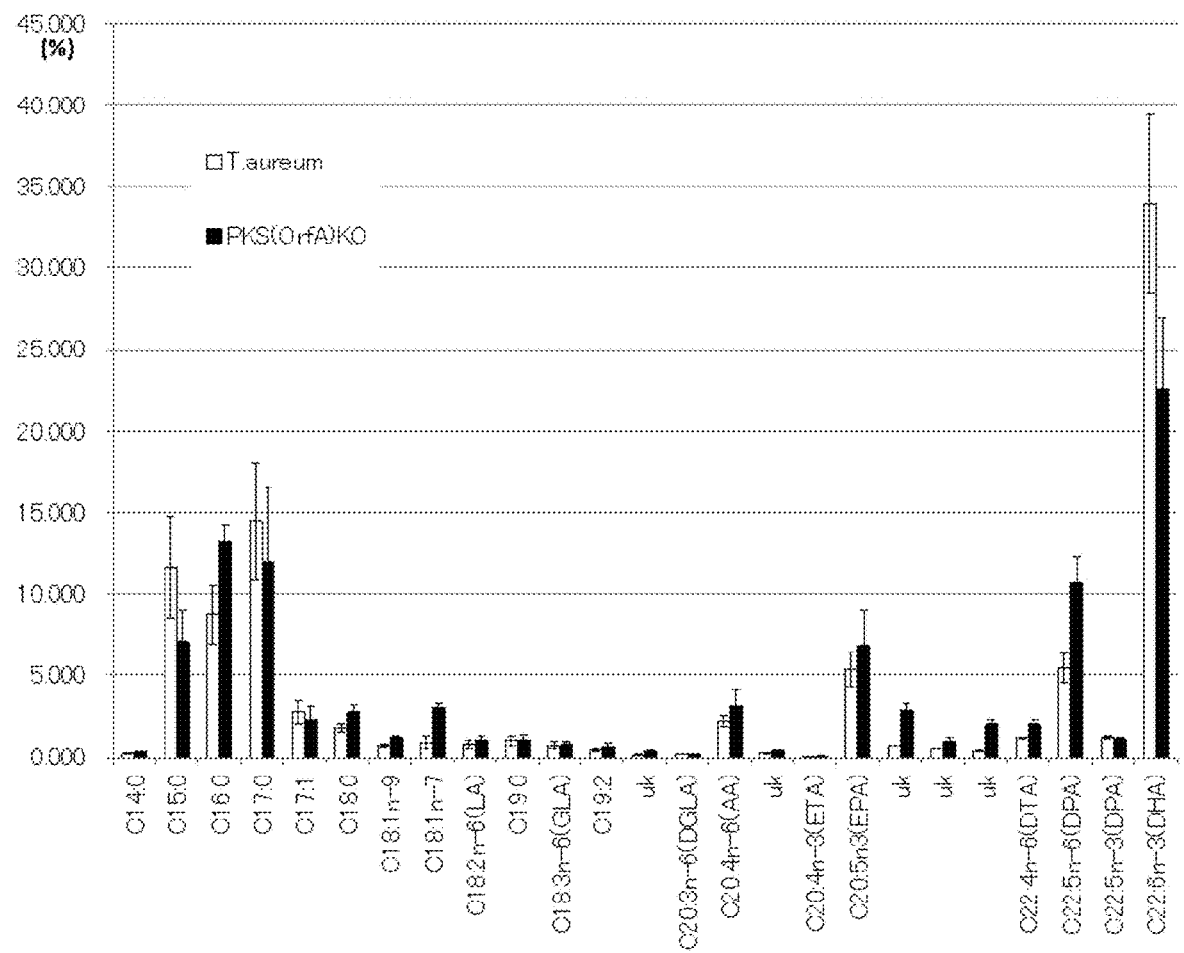
[Fig.30]

[Fig.31]

| PKS(OrfA)KO | | T.aureum | FA |
|---|---|---|---|
| 121.2% | 0.33 | 0.27 | C14:0 |
| 60.9% | 7.07 | 11.61 | C15:0 |
| 151.2% | 13.21 | 8.74 | C16:0 |
| 82.8% | 11.97 | 14.46 | C17:0 |
| 83.4% | 2.30 | 2.76 | C17:1 |
| 153.7% | 2.77 | 1.80 | C18:0 |
| 172.6% | 1.21 | 0.70 | C18:1n-9 |
| 339.0% | 3.03 | 0.89 | C18:1n-7 |
| 130.6% | 1.07 | 0.82 | C18:2n-6(LA) |
| 101.5% | 1.02 | 1.01 | C19:0 |
| 105.2% | 0.77 | 0.73 | C18:3n-6(GLA) |
| 131.6% | 0.65 | 0.49 | C19:2 |
| 125.9% | 0.23 | 0.18 | C20:3n-6(DGLA) |
| 141.2% | 3.10 | 2.19 | C20:4n-6(AA) |
| 184.6% | 0.04 | 0.02 | C20:4n-3(ETA) |
| 126.9% | 6.82 | 5.38 | C20:5n3(EPA) |
| 169.6% | 2.00 | 1.18 | C22:4n-6(DTA) |
| 196.3% | 10.66 | 5.43 | C22:5n-6(DPA) |
| 93.6% | 1.13 | 1.20 | C22:5n-3(DPA) |
| 66.5% | 22.58 | 33.97 | C22:6n-3(DHA) |

[Fig.32]
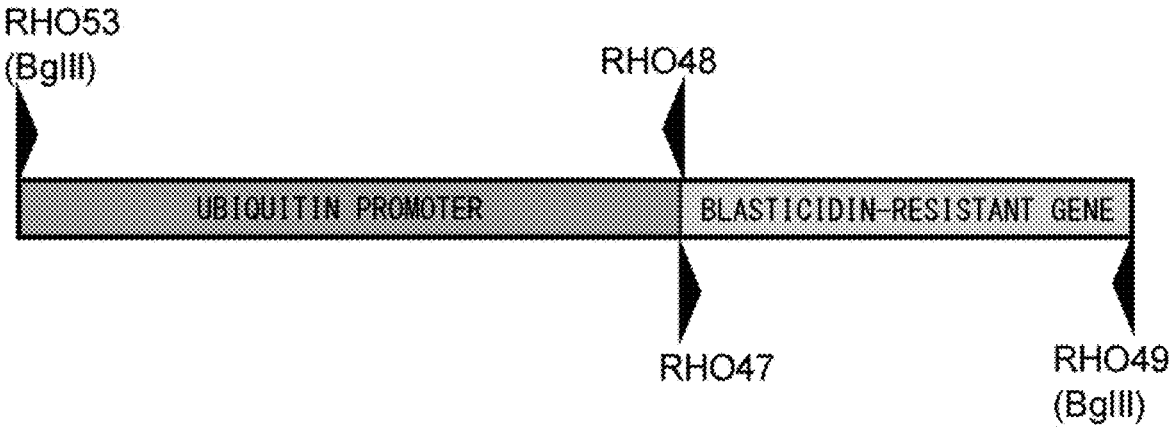
[Fig.33]
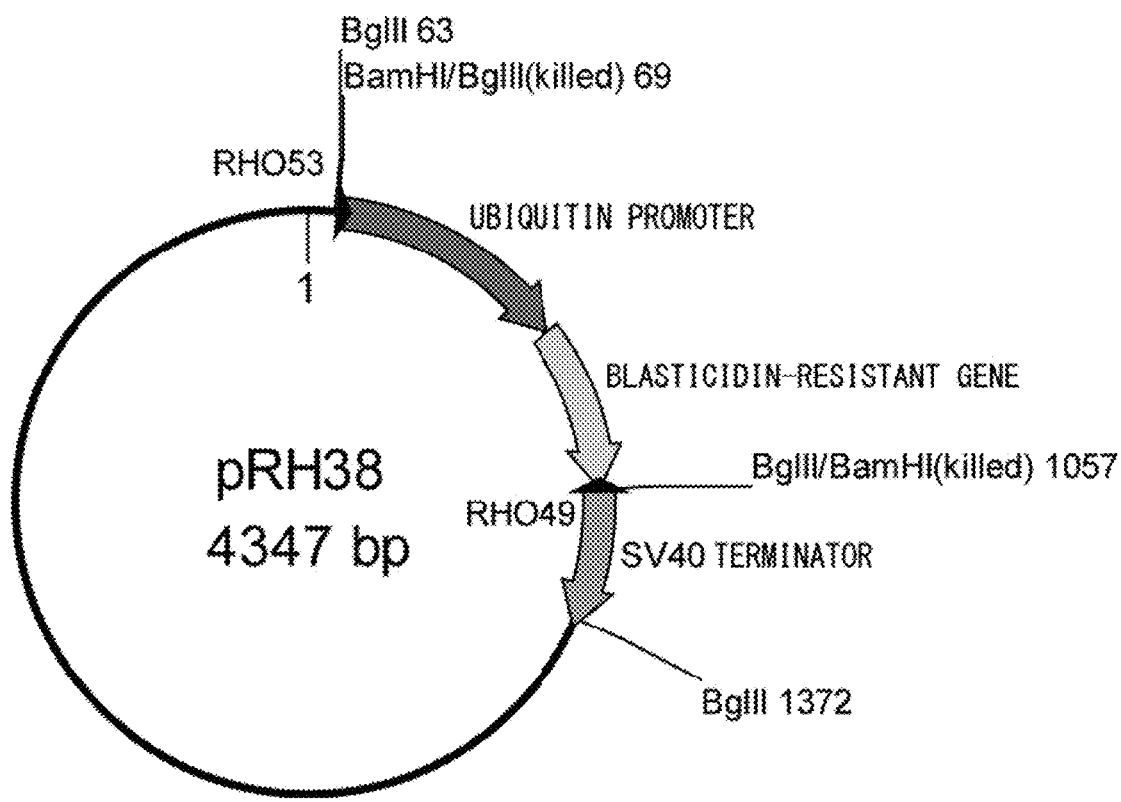

[Fig.34]
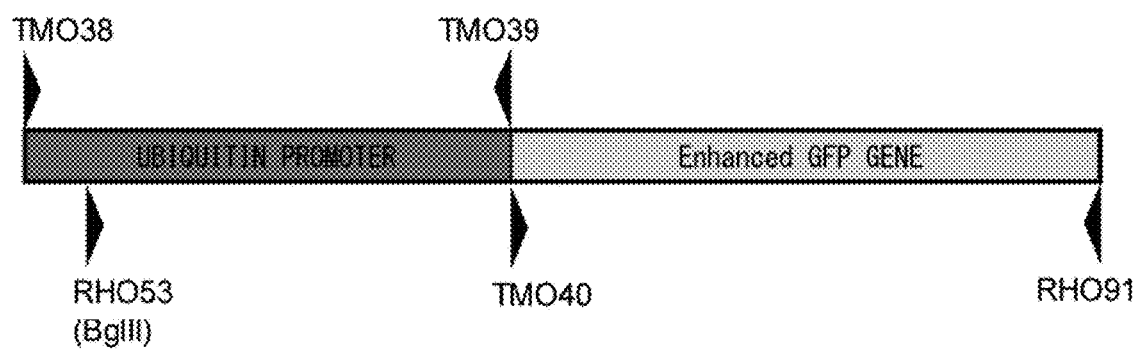
[Fig.35]
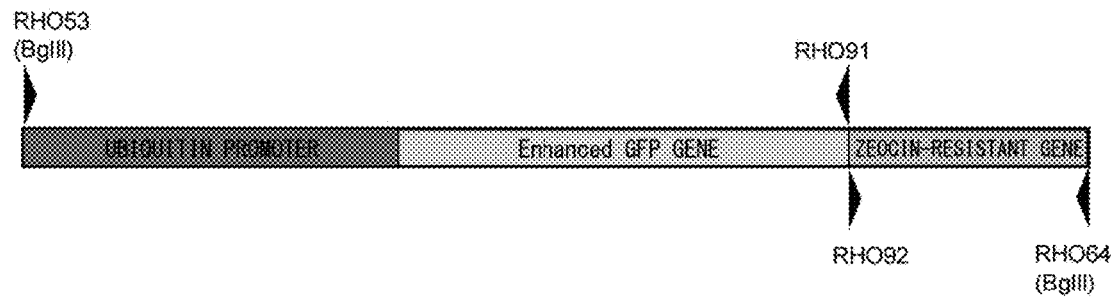

[Fig.36]
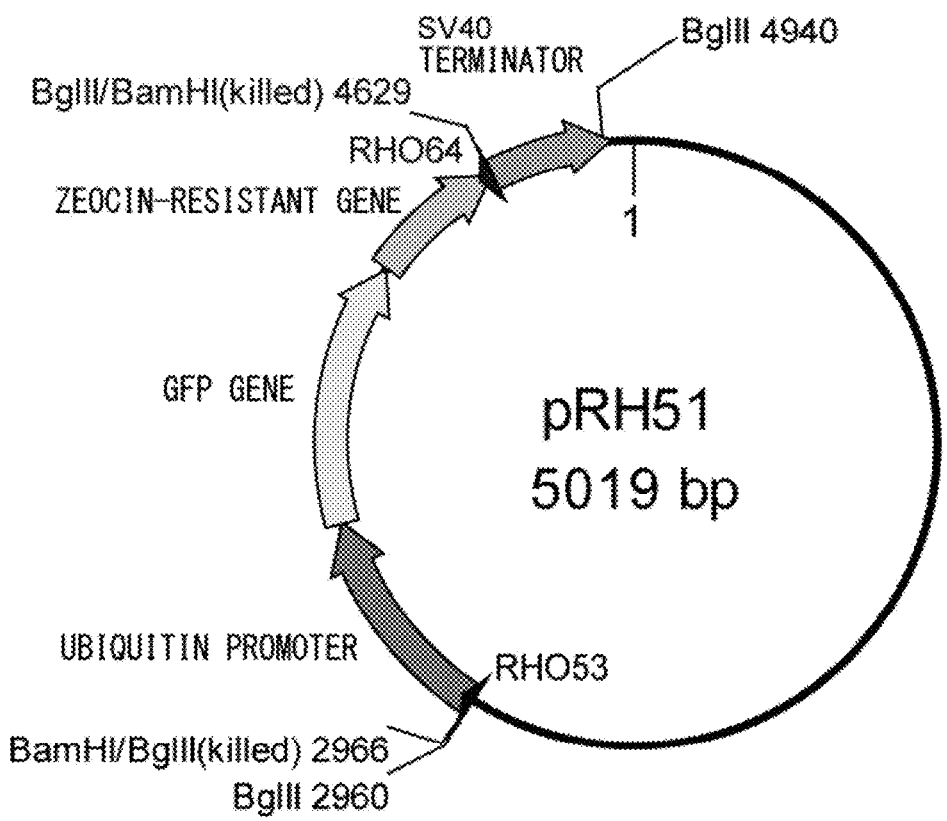
[Fig.37]
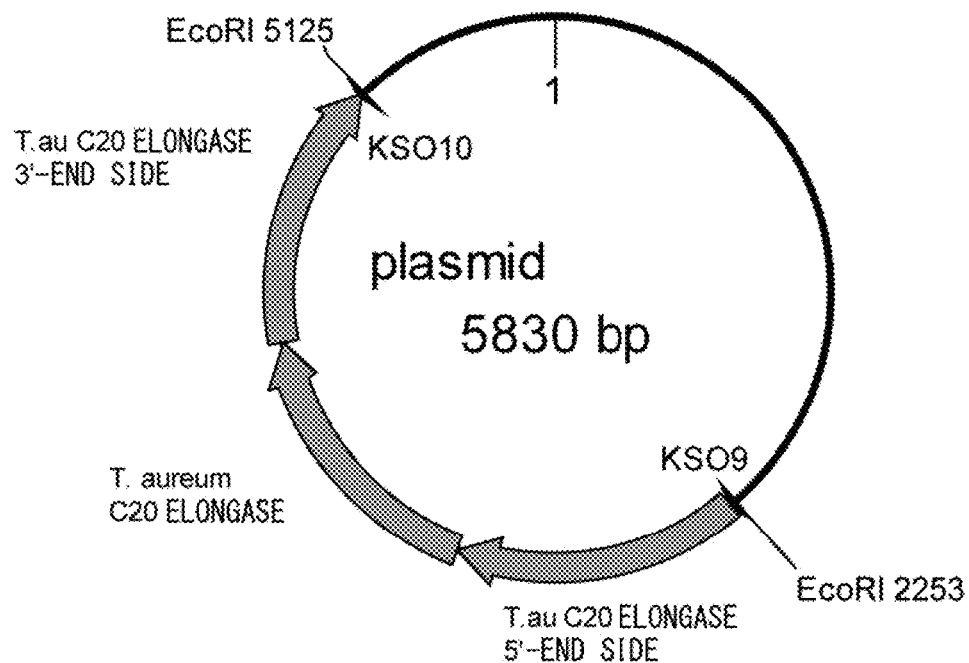

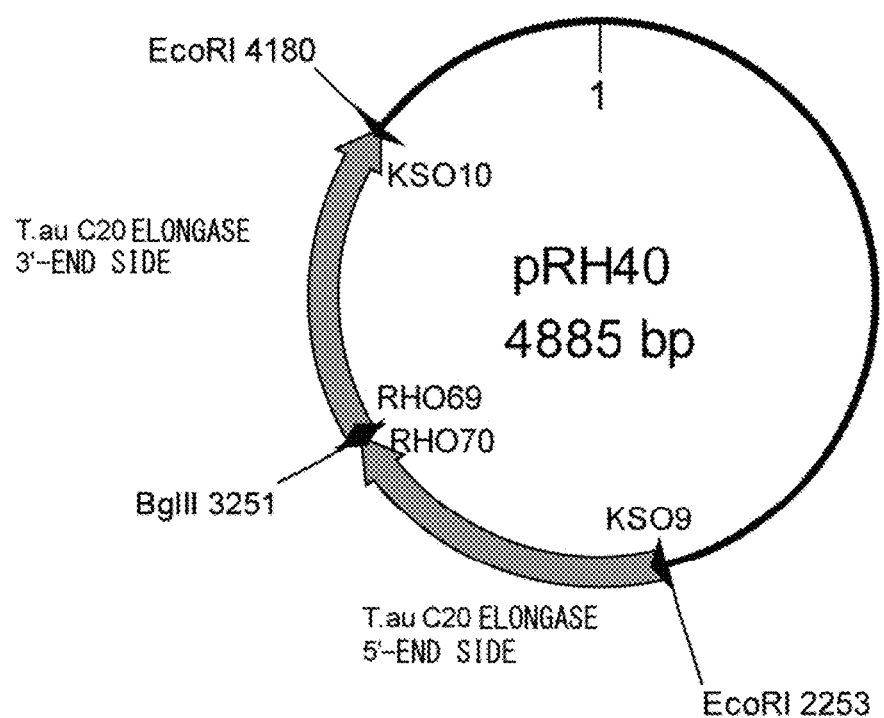
[Fig.38]

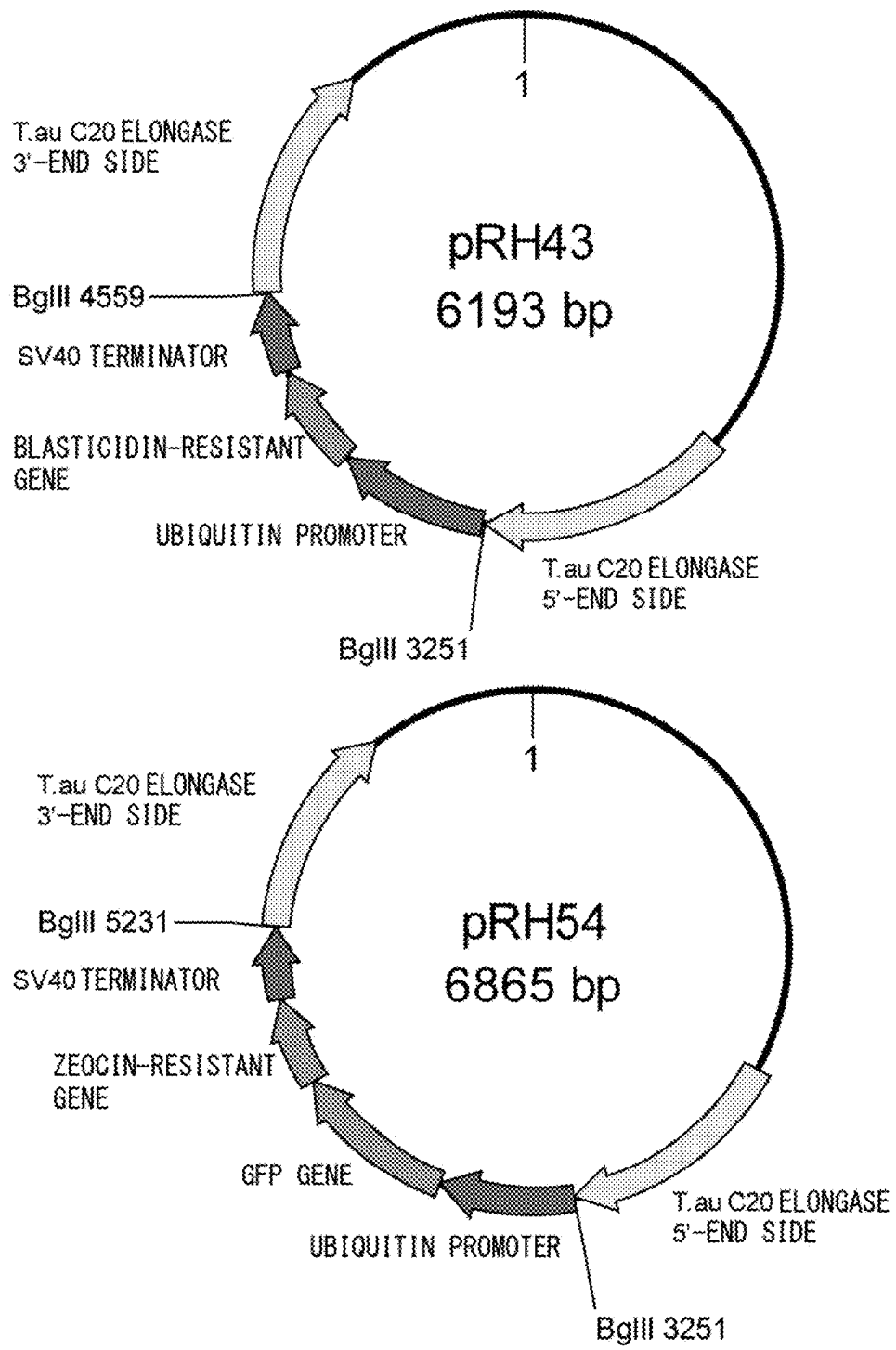
[Fig.39]

[Fig.40]
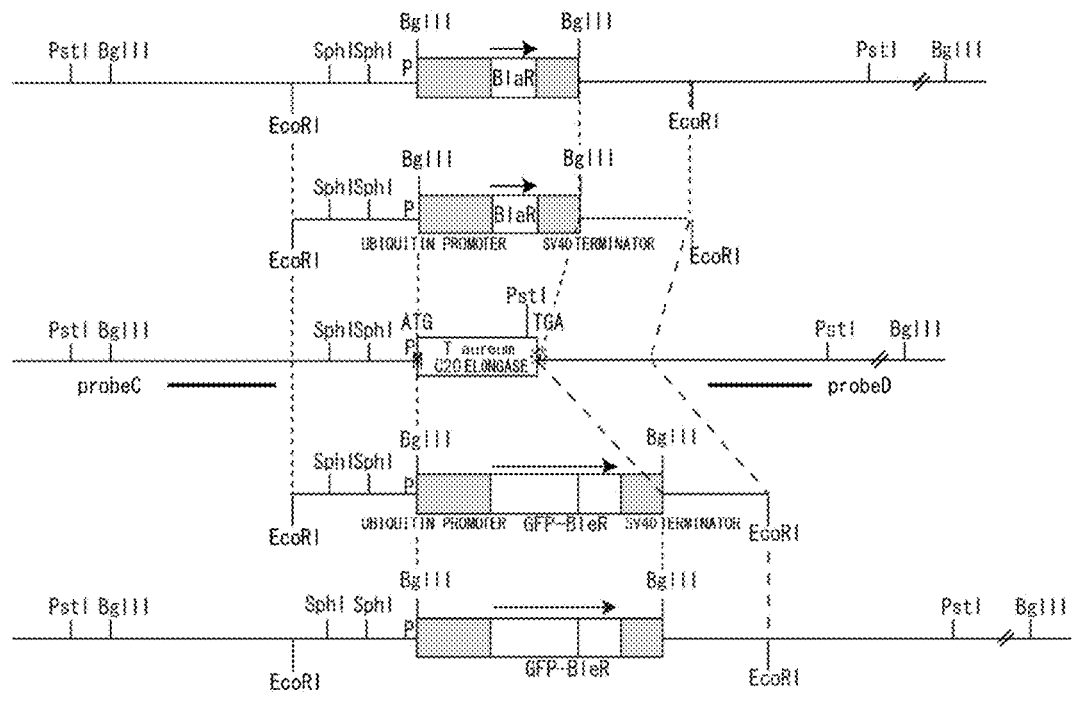
[Fig.41]
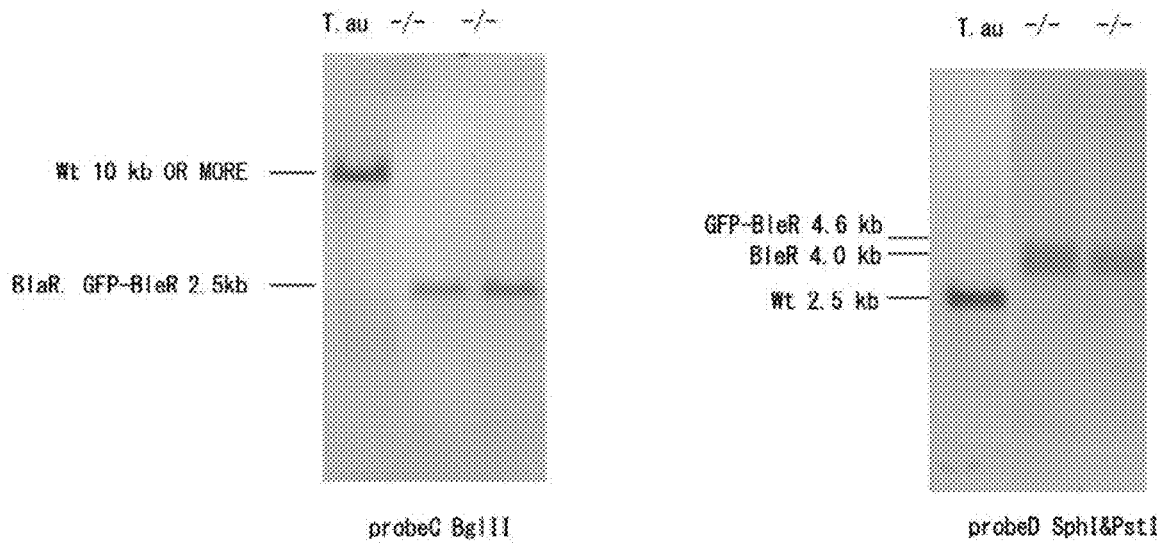

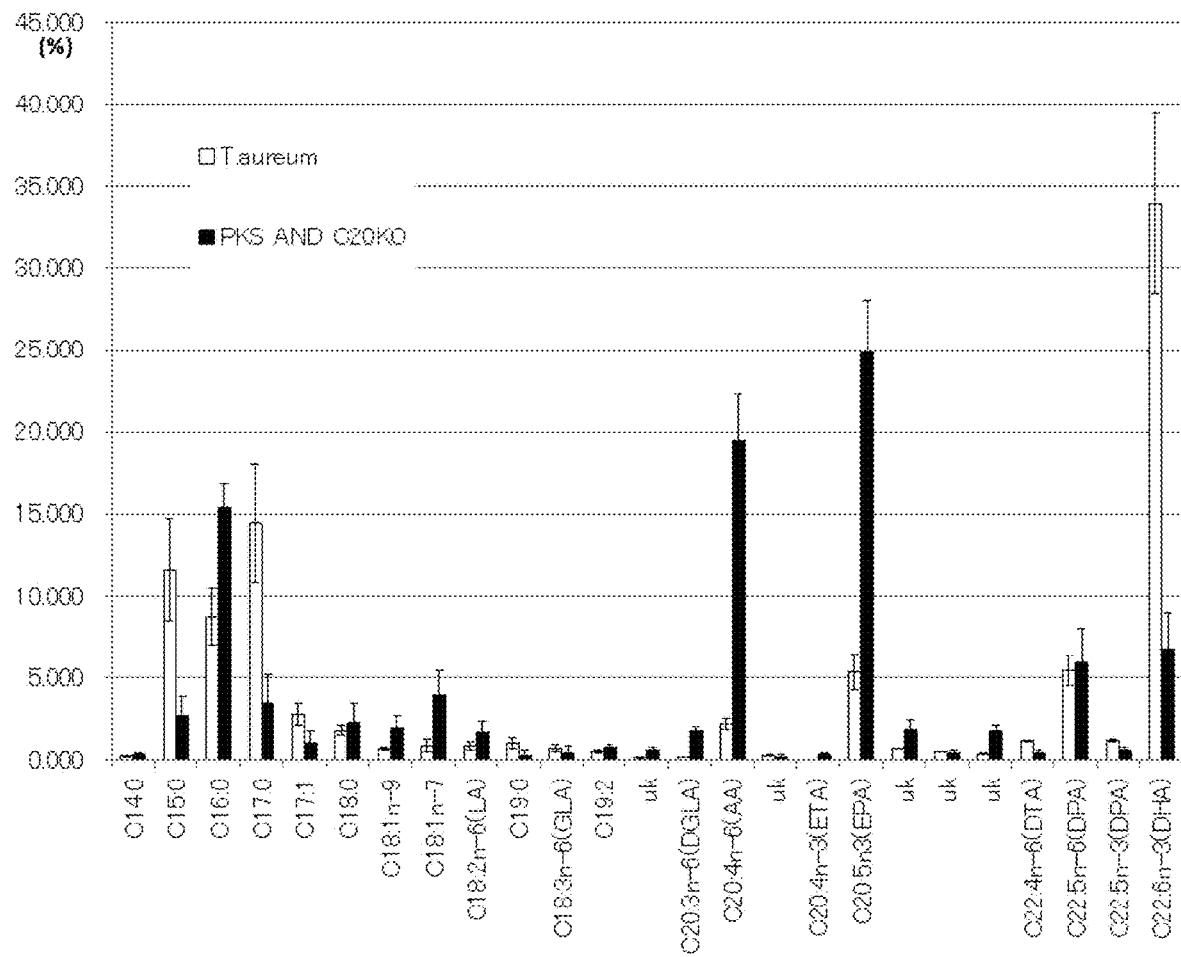
[Fig. 42]

[Fig.43]

| PKS AND C20KO | T.aureum | | FA |
|---|---|---|---|
| 113.0% | 0.31 | 0.27 | C14:0 |
| 23.3% | 2.71 | 11.61 | C15:0 |
| 176.4% | 15.41 | 8.74 | C16:0 |
| 23.8% | 3.44 | 14.46 | C17:0 |
| 37.0% | 1.02 | 2.76 | C17:1 |
| 125.2% | 2.26 | 1.80 | C18:0 |
| 279.4% | 1.96 | 0.70 | C18:1n-9 |
| 443.0% | 3.96 | 0.89 | C18:1n-7 |
| 208.2% | 1.71 | 0.82 | C18:2n-6(LA) |
| 26.0% | 0.26 | 1.01 | C19:0 |
| 60.9% | 0.45 | 0.73 | C18:3n-6(GLA) |
| 163.7% | 0.81 | 0.49 | C19:2 |
| 996.6% | 1.81 | 0.18 | C20:3n-6(DGLA) |
| 889.0% | 19.50 | 2.19 | C20:4n-6(AA) |
| 1550.6% | 0.31 | 0.02 | C20:4n-3(ETA) |
| 463.3% | 24.92 | 5.38 | C20:5n3(EPA) |
| 40.3% | 0.47 | 1.18 | C22:4n-6(DTA) |
| 108.6% | 5.90 | 5.43 | C22:5n-6(DPA) |
| 47.9% | 0.58 | 1.20 | C22:5n-3(DPA) |
| 20.0% | 6.78 | 33.97 | C22:6n-3(DHA) |

[Fig.44]
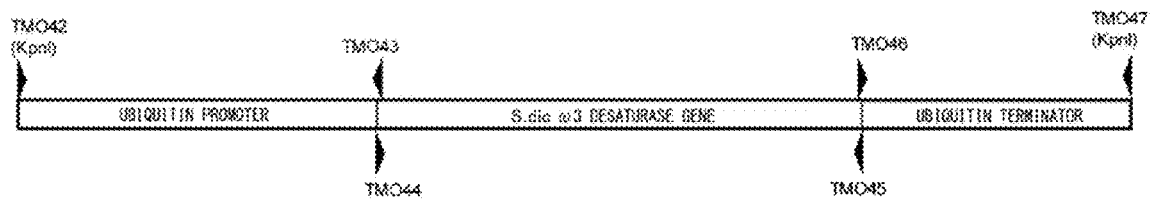
[Fig.45]
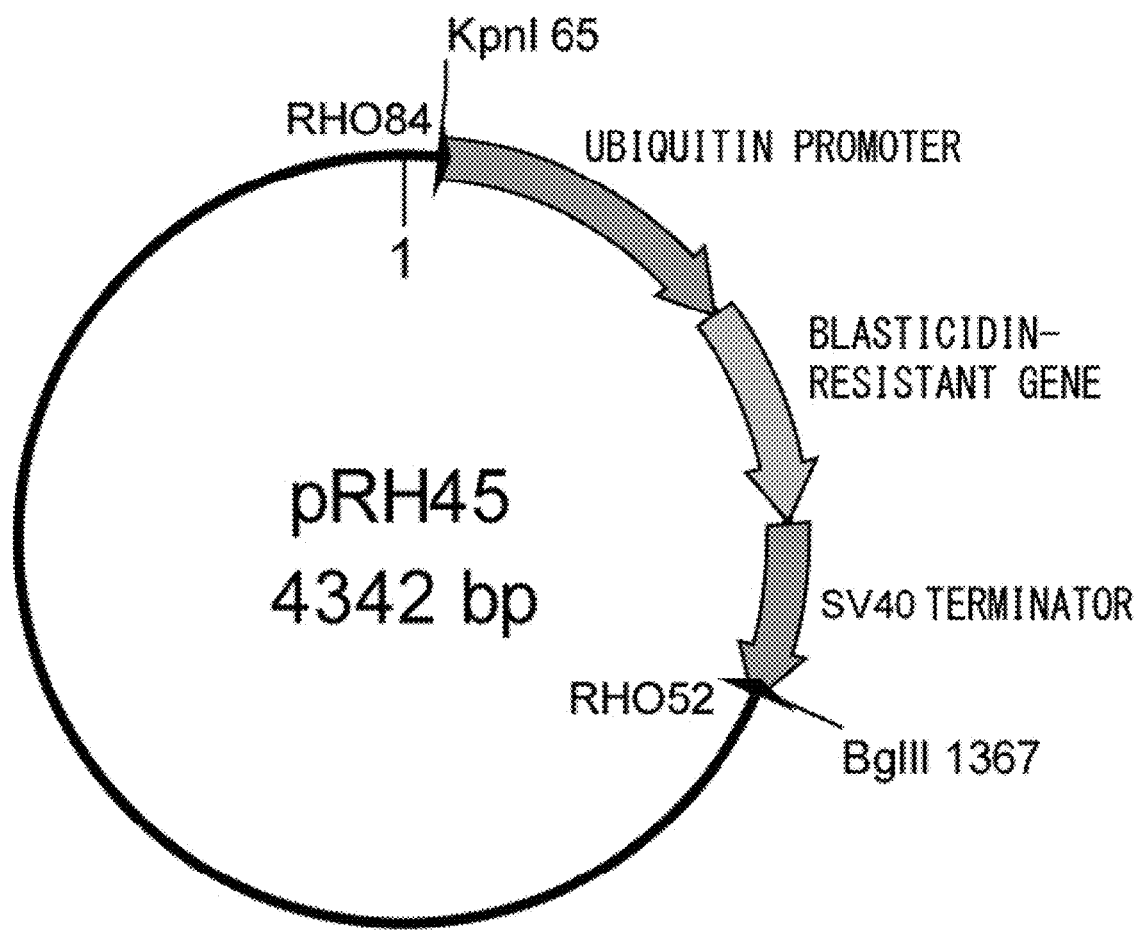

[Fig.46]
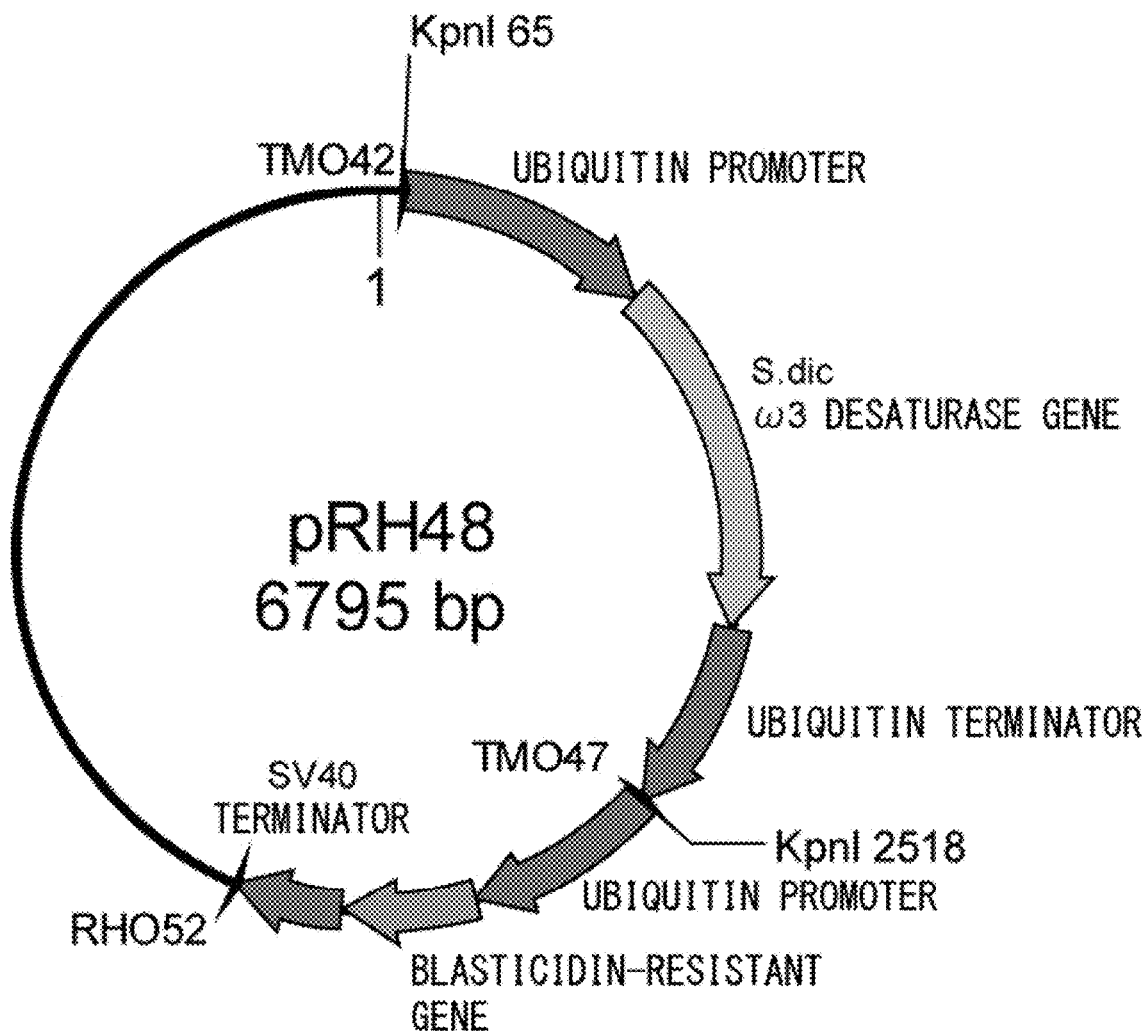
[Fig.47]
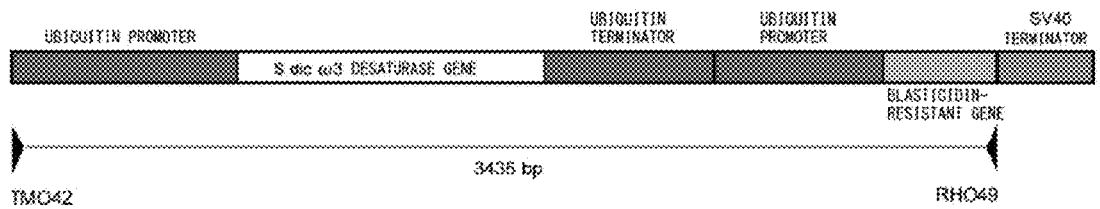

[Fig.48]
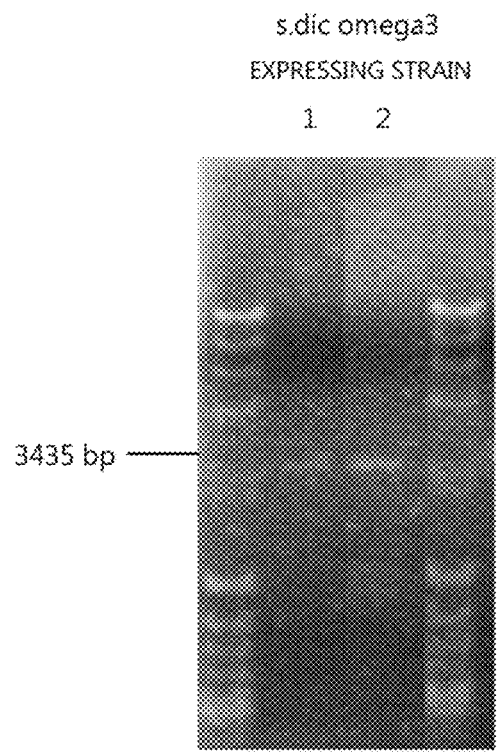
[Fig.49]
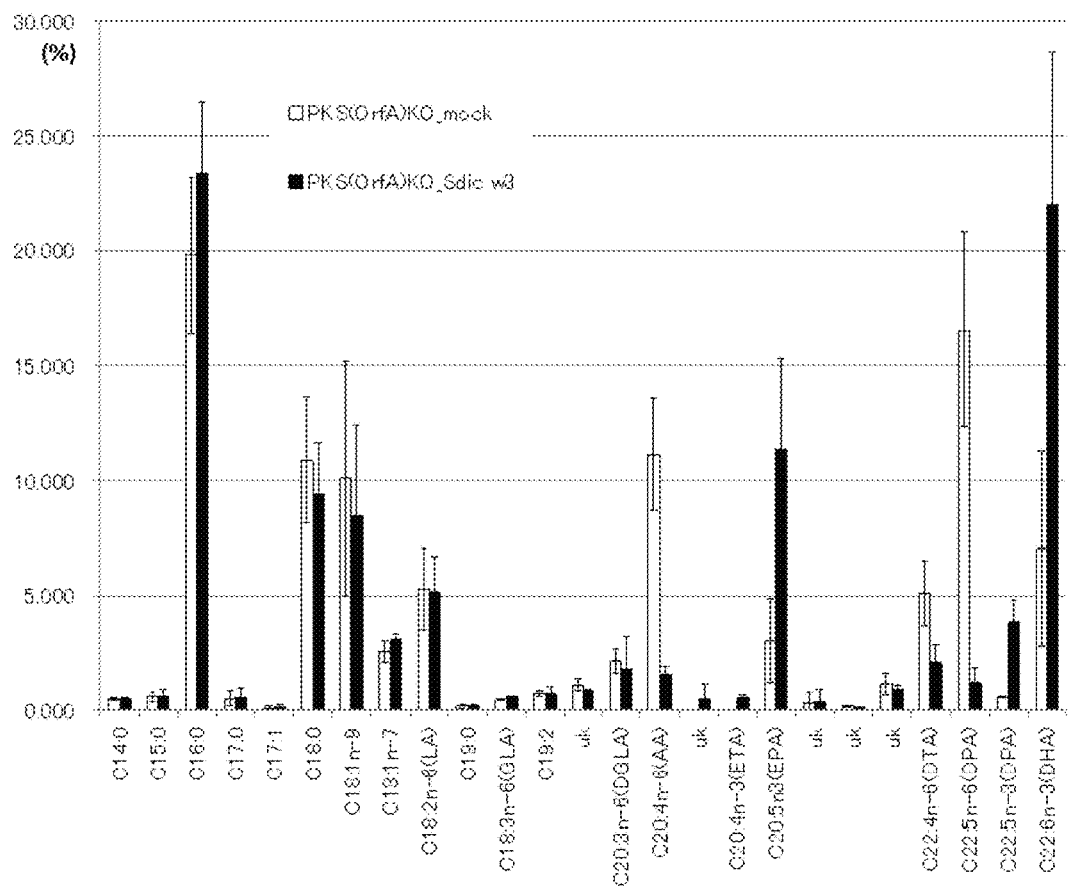

[Fig.50]

| COMPARISON WITH WILD-TYPE STRAIN | PKS(OrfA)KO Sdic w3 | PKS(OrfA)KO mock | FA |
|---|---|---|---|
| 106.1% | 0.52 | 0.49 | C14:0 |
| 105.7% | 0.63 | 0.59 | C15:0 |
| 118.1% | 23.39 | 19.81 | C16:0 |
| 109.6% | 0.56 | 0.51 | C17:0 |
| 147.4% | 0.13 | 0.09 | C17:1 |
| 86.7% | 9.43 | 10.87 | C18:0 |
| 84.2% | 8.50 | 10.09 | C18:1n-9 |
| 120.5% | 3.09 | 2.56 | C18:1n-7 |
| 98.4% | 5.18 | 5.26 | C18:2n-6(LA) |
| 94.4% | 0.17 | 0.18 | C19:0 |
| 124.3% | 0.59 | 0.47 | C18:3n-6(GLA) |
| 99.4% | 0.70 | 0.70 | C19:2 |
| 83.7% | 1.77 | 2.12 | C20:3n-6(DGLA) |
| 13.8% | 1.53 | 11.13 | C20:4n-6(AA) |
| 5398.4% | 0.54 | 0.01 | C20:4n-3(ETA) |
| 375.8% | 11.36 | 3.02 | C20:5n3(EPA) |
| 40.0% | 2.04 | 5.11 | C22:4n-6(DTA) |
| 7.0% | 1.16 | 16.55 | C22:5n-6(DPA) |
| 669.3% | 3.85 | 0.58 | C22:5n-3(DPA) |
| 314.1% | 22.04 | 7.02 | C22:6n-3(DHA) |

[Fig.51]
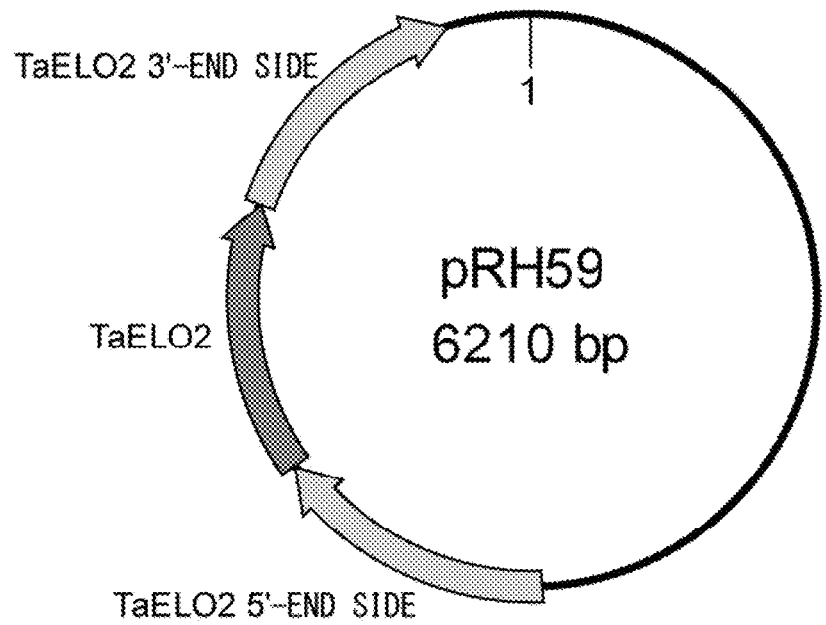
[Fig.52]
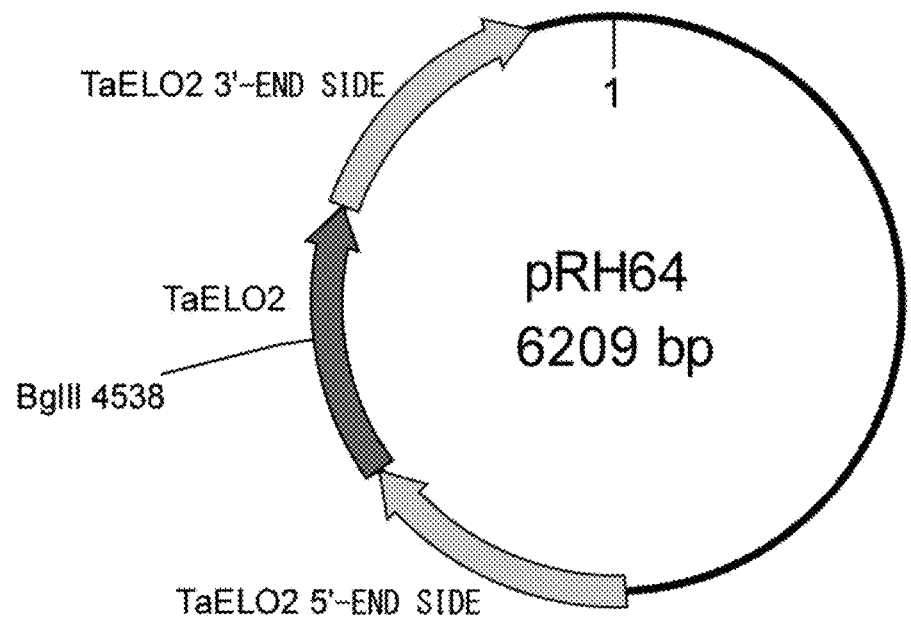

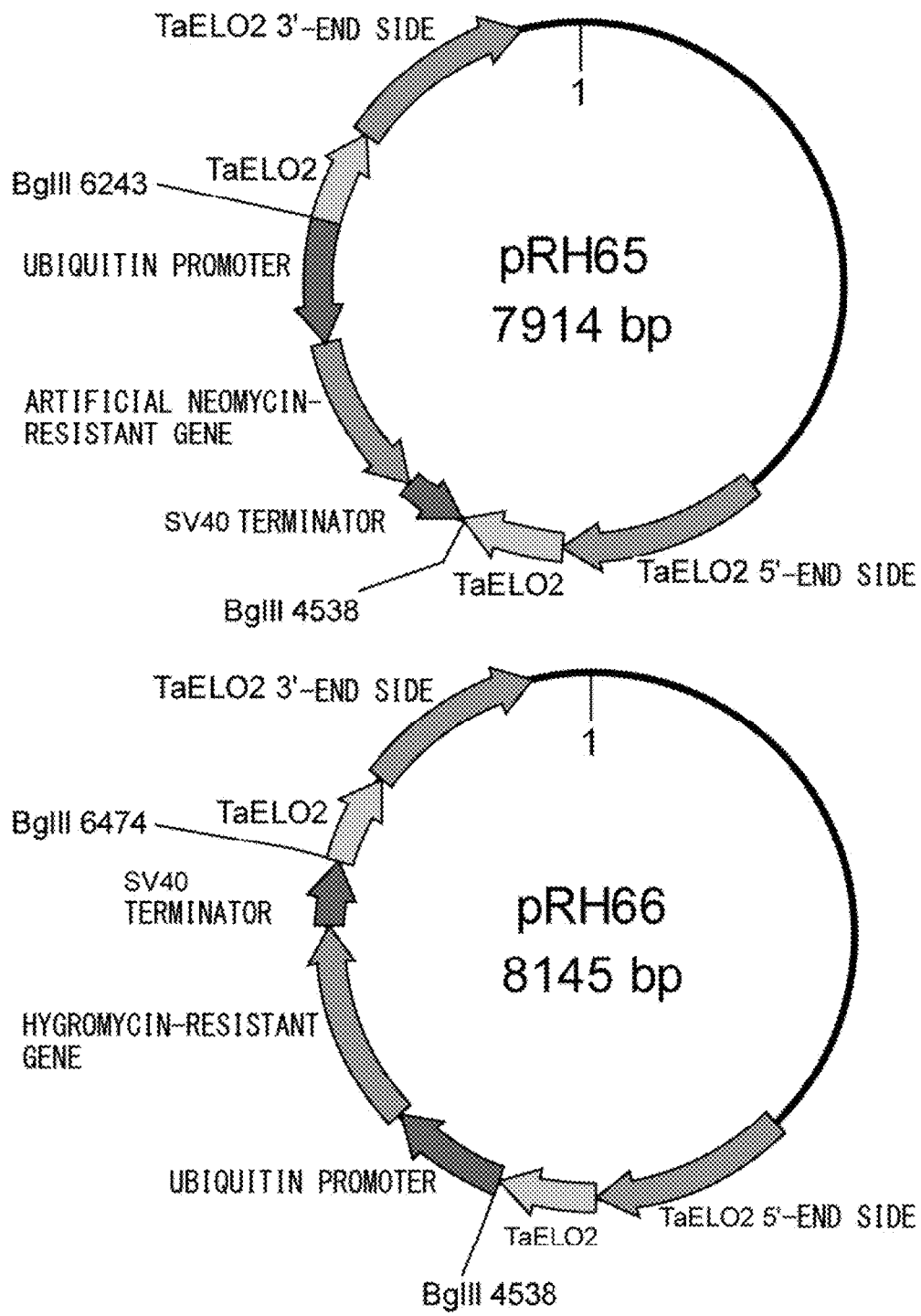
[Fig.53]

[Fig.54]
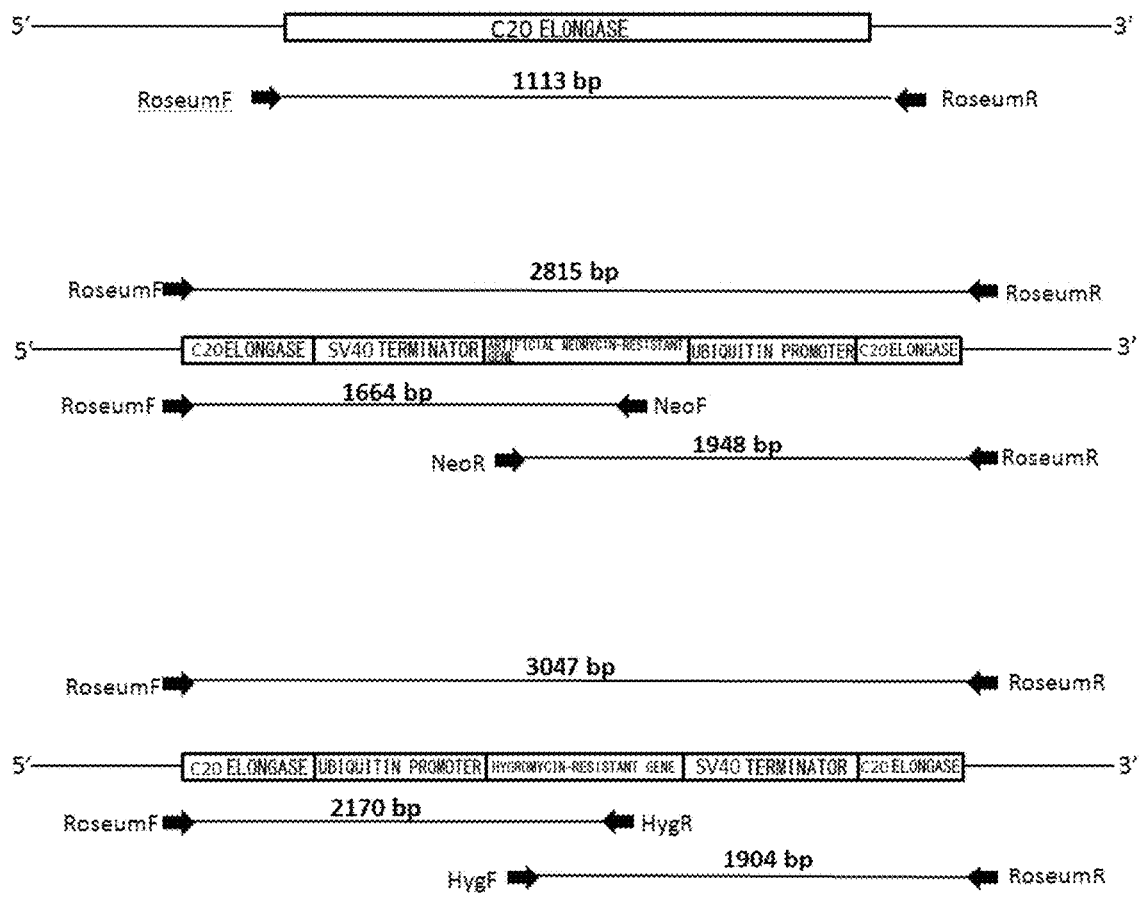
[Fig.55]
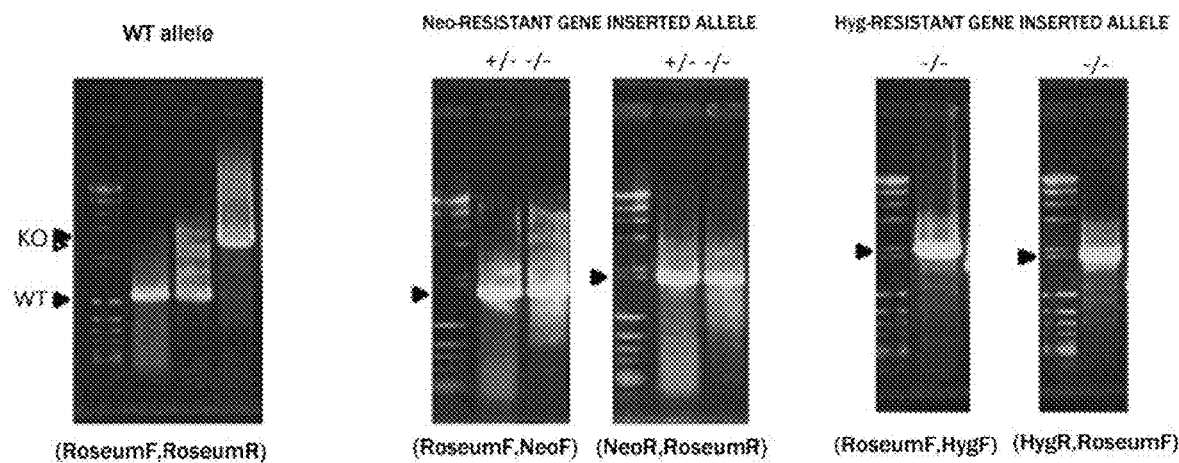

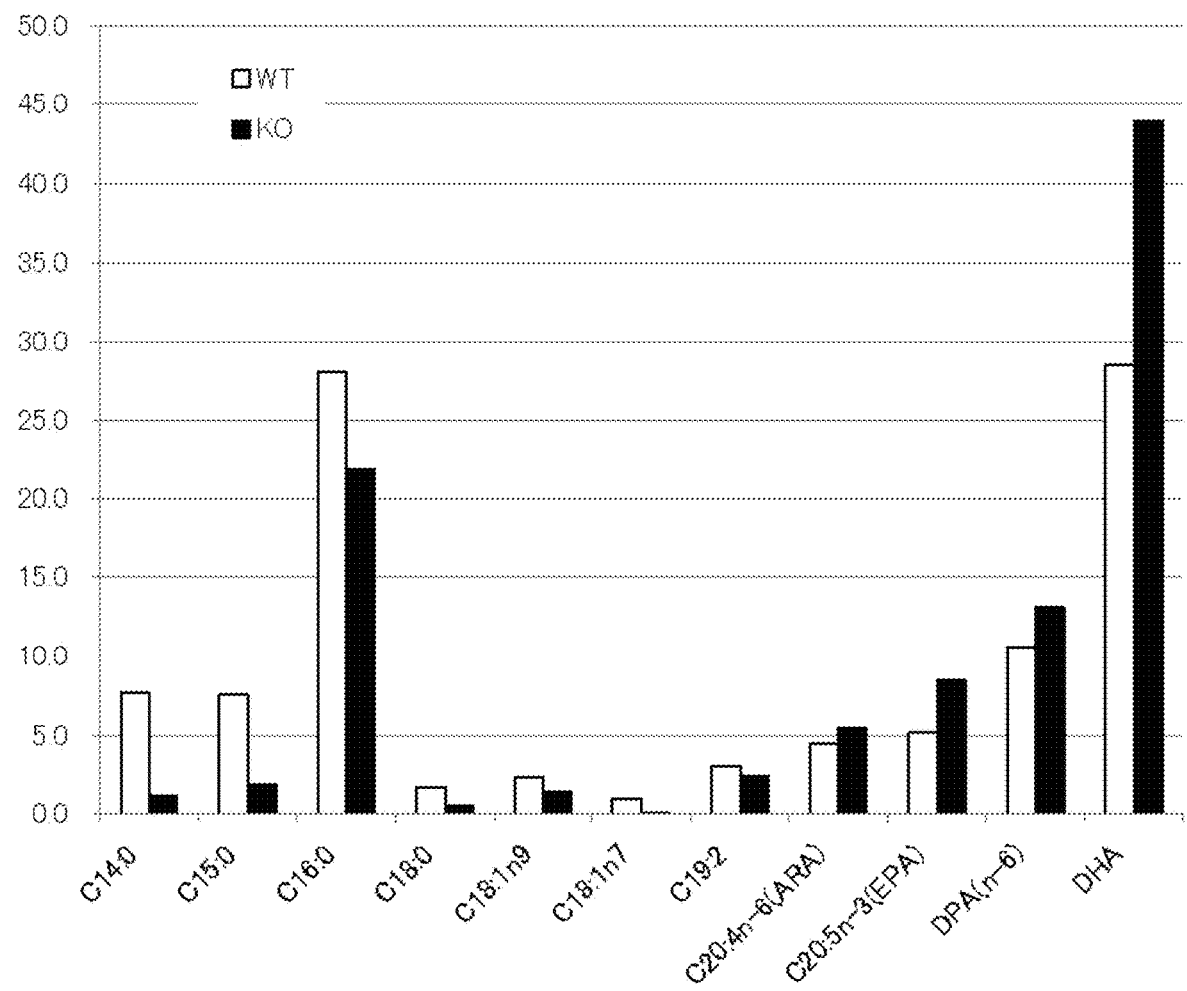

[Fig.57]

| COMPARISON WITH WILD-TYPE STRAIN | C20elo KO | T. roseum | FA |
|---|---|---|---|
| 14.5% | 1.11 | 7.65 | C14:0 |
| 23.9% | 1.81 | 7.57 | C15:0 |
| 78.2% | 21.89 | 27.99 | C16:0 |
| 28.8% | 0.48 | 1.68 | C18:0 |
| 59.9% | 1.42 | 2.37 | C18:1n9 |
| 8.4% | 0.08 | 0.99 | C18:1n7 |
| 79.9% | 2.47 | 3.09 | C19:2 |
| 121.8% | 5.50 | 4.51 | C20:4n-6(ARA) |
| 163.8% | 8.45 | 5.16 | C20:5n-3(EPA) |
| 124.8% | 13.17 | 10.55 | DPA(n-6) |
| 154.5% | 43.94 | 28.44 | DHA |
|  | 100 | 100 | total |

[Fig.58]
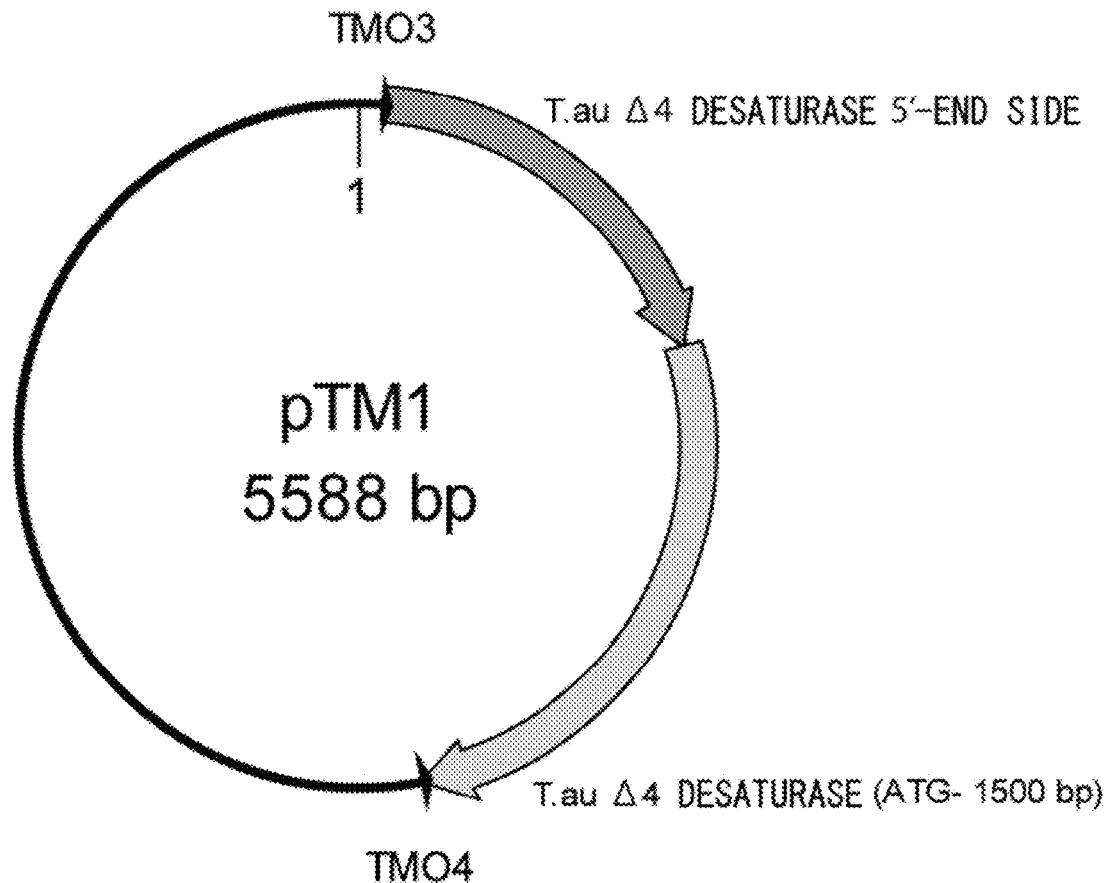
[Fig.59]
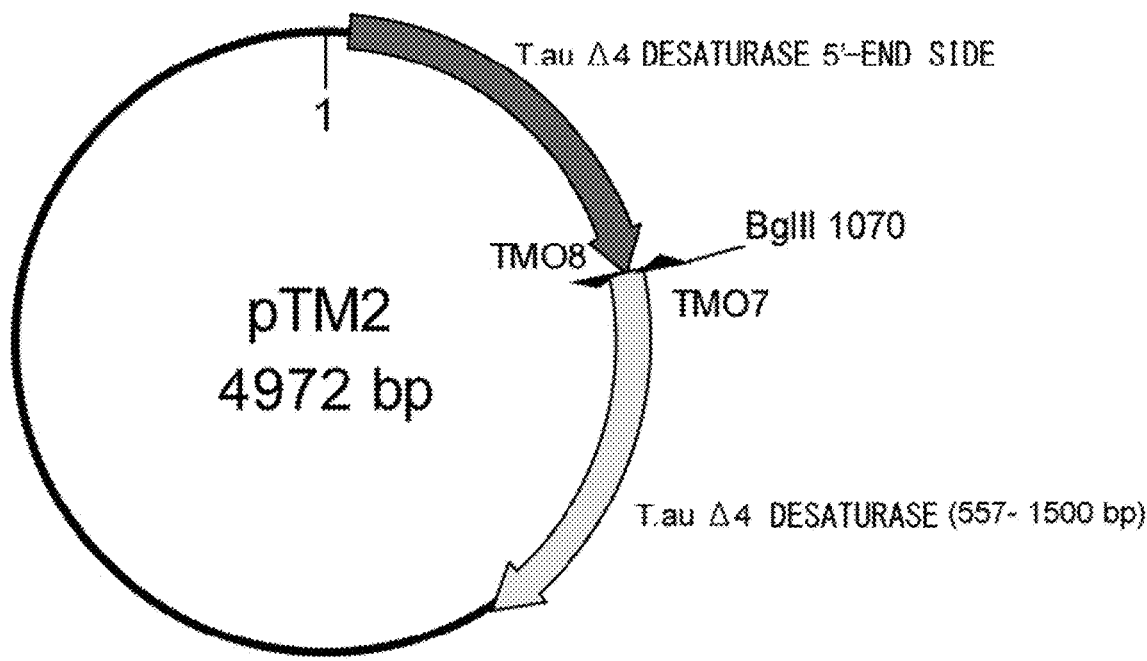

[Fig.60]
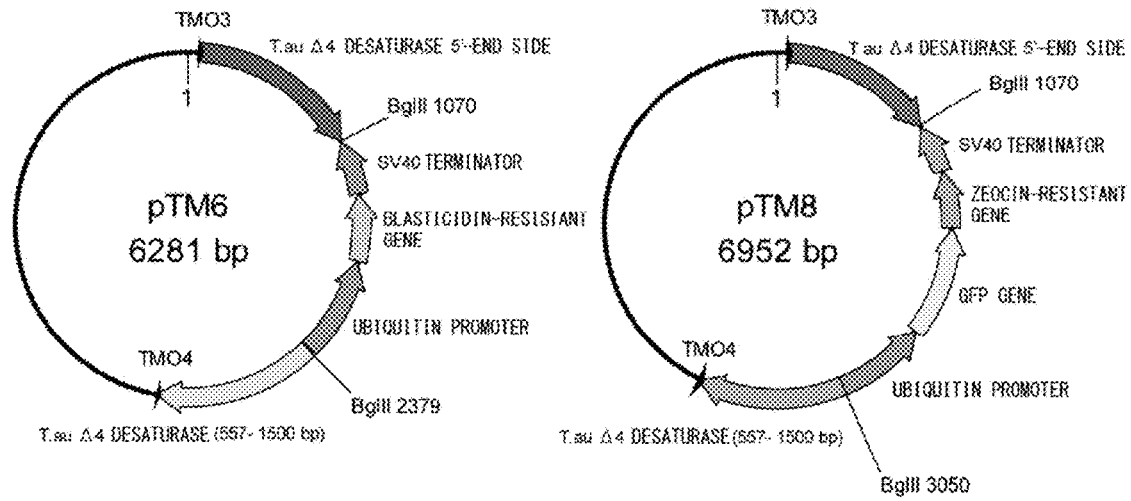
[Fig.61]
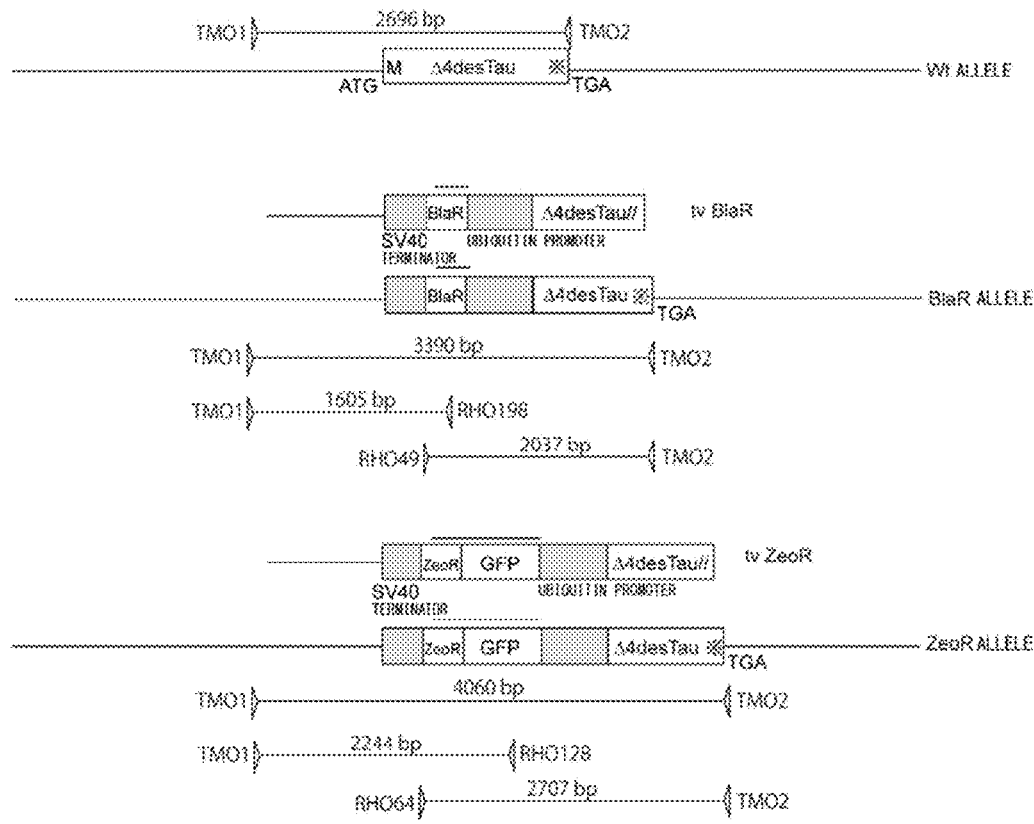

[Fig.62]
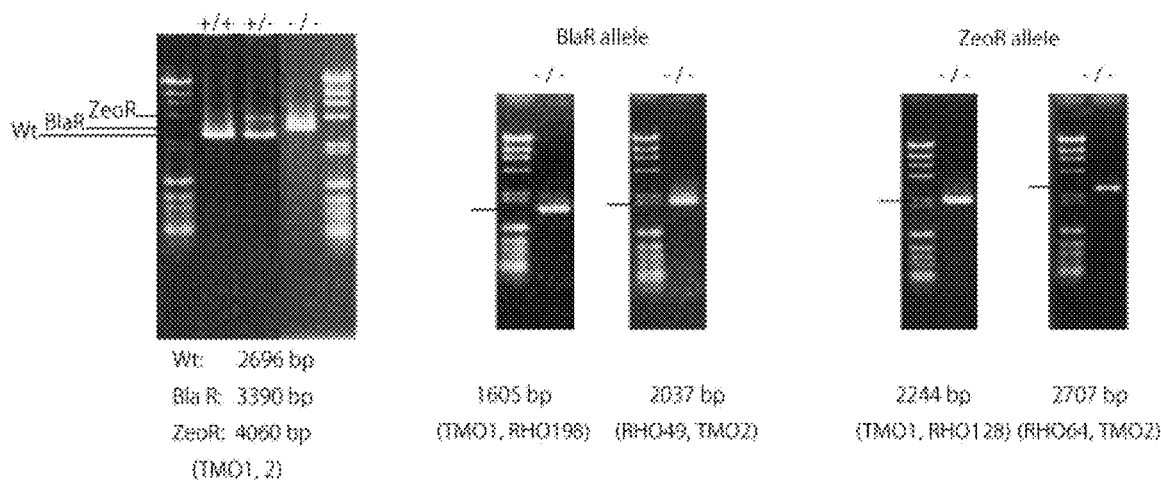
[Fig.63]
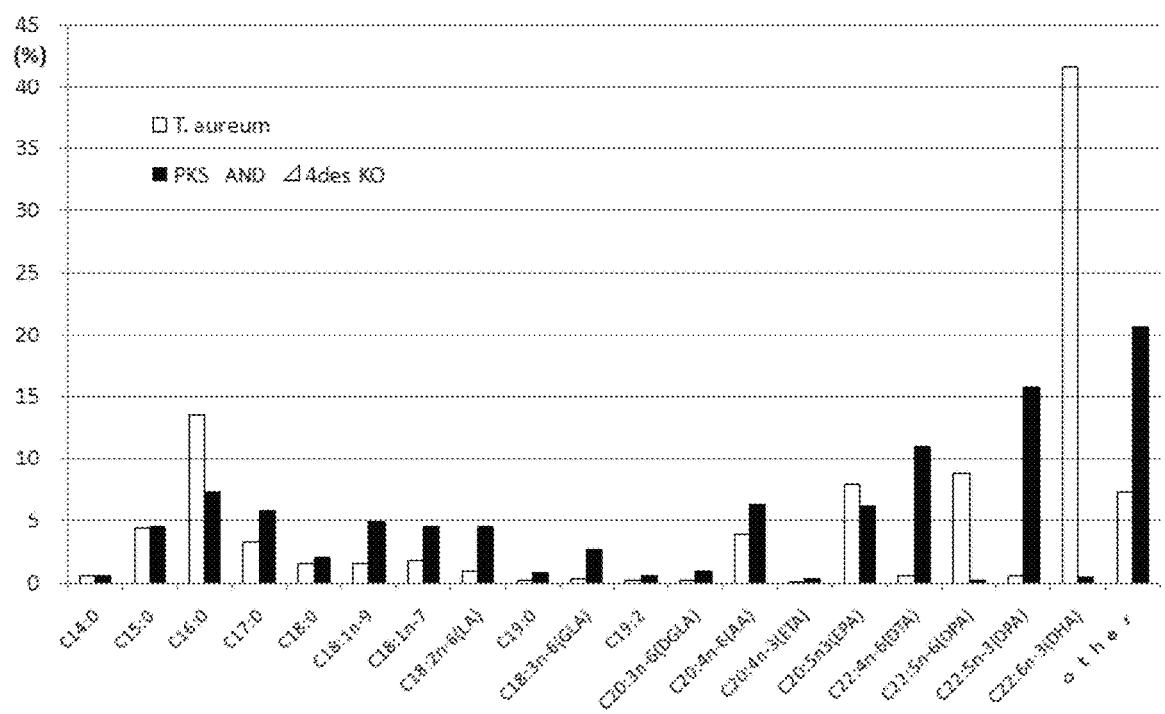

[Fig.64]

| PKS AND Δ4des KO | T.aureum | FA |
|---|---|---|
| 92.6% | 0.58 | 0.62 | C14:0 |
| 101.0% | 4.48 | 4.43 | C15:0 |
| 53.7% | 7.28 | 13.56 | C16:0 |
| 176.1% | 5.84 | 3.32 | C17:0 |
| 128.4% | 2.05 | 1.60 | C18:0 |
| 304.9% | 4.83 | 1.58 | C18:1n-9 |
| 250.1% | 4.49 | 1.80 | C18:1n-7 |
| 450.5% | 4.47 | 0.99 | C18:2n-6(LA) |
| 310.7% | 0.81 | 0.26 | C19:0 |
| 784.5% | 2.67 | 0.34 | C18:3n-6(GLA) |
| 229.0% | 0.59 | 0.26 | C19:2 |
| 353.7% | 0.90 | 0.25 | C20:3n-6(DGLA) |
| 164.2% | 6.35 | 3.87 | C20:4n-6(AA) |
| 182.8% | 0.28 | 0.15 | C20:4n-3(ETA) |
| 78.1% | 6.22 | 7.96 | C20:5n3(EPA) |
| 2008.9% | 11.01 | 0.55 | C22:4n-6(DTA) |
| 2.4% | 0.21 | 8.79 | C22:5n-6(DPA) |
| 2695.8% | 15.78 | 0.59 | C22:5n-3(DPA) |
| 1.2% | 0.51 | 41.71 | C22:6n-3(DHA) |

[Fig.65]
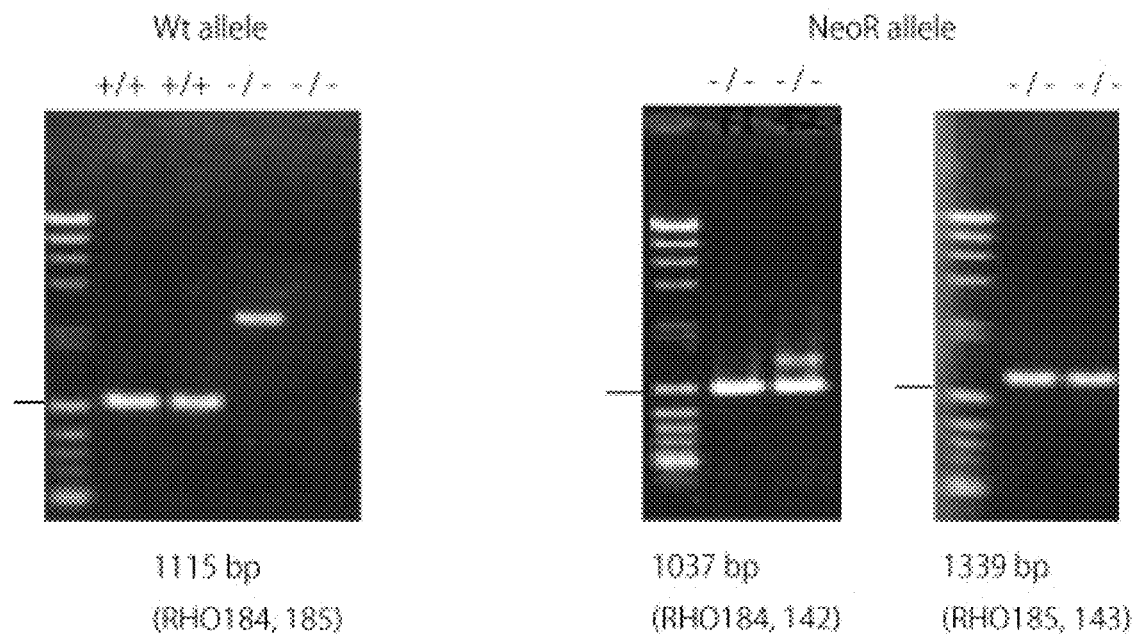
[Fig.66]
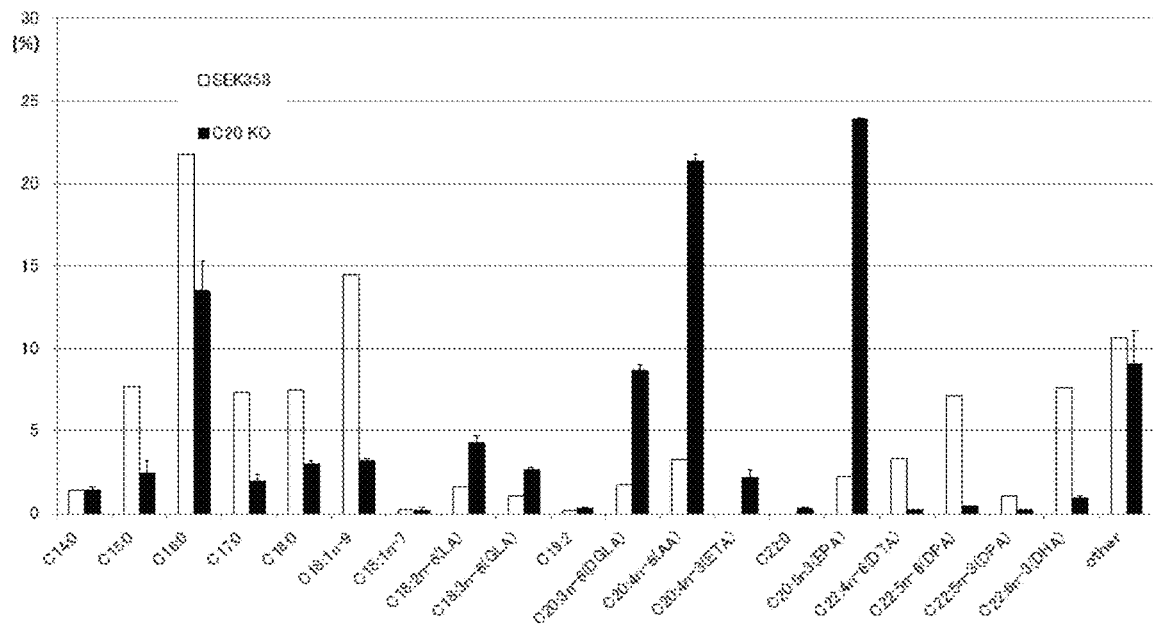

[Fig.67]

| C20 elongase KO | SEK358 | | FA |
|---|---|---|---|
| 101.0% | 1.41 | 1.40 | C14:0 |
| 32.0% | 2.44 | 7.63 | C15:0 |
| 62.1% | 13.49 | 21.73 | C16:0 |
| 26.6% | 1.96 | 7.34 | C17:0 |
| 39.6% | 2.95 | 7.46 | C18:0 |
| 22.0% | 3.19 | 14.47 | C18:1n-9 |
| 84.5% | 0.19 | 0.23 | C18:1n-7 |
| 269.4% | 4.28 | 1.59 | C18:2n-6(LA) |
| 247.0% | 2.61 | 1.06 | C18:3n-6(GLA) |
| 201.5% | 0.34 | 0.17 | C19:2 |
| 499.9% | 8.64 | 1.73 | C20:3n-6(DGLA) |
| 654.8% | 21.35 | 3.26 | C20:4n-6(AA) |
|  | 2.14 | 0.00 | C20:4n-3(ETA) |
|  | 0.30 | 0.00 | C22:0 |
| 1069.6% | 23.83 | 2.23 | C20:5n3(EPA) |
| 8.0% | 0.26 | 3.28 | C22:4n-6(DTA) |
| 6.4% | 0.46 | 7.10 | C22:5n-6(DPA) |
| 21.6% | 0.23 | 1.06 | C22:5n-3(DPA) |
| 12.3% | 0.94 | 7.61 | C22:6n-3(DHA) |

[Fig.68]
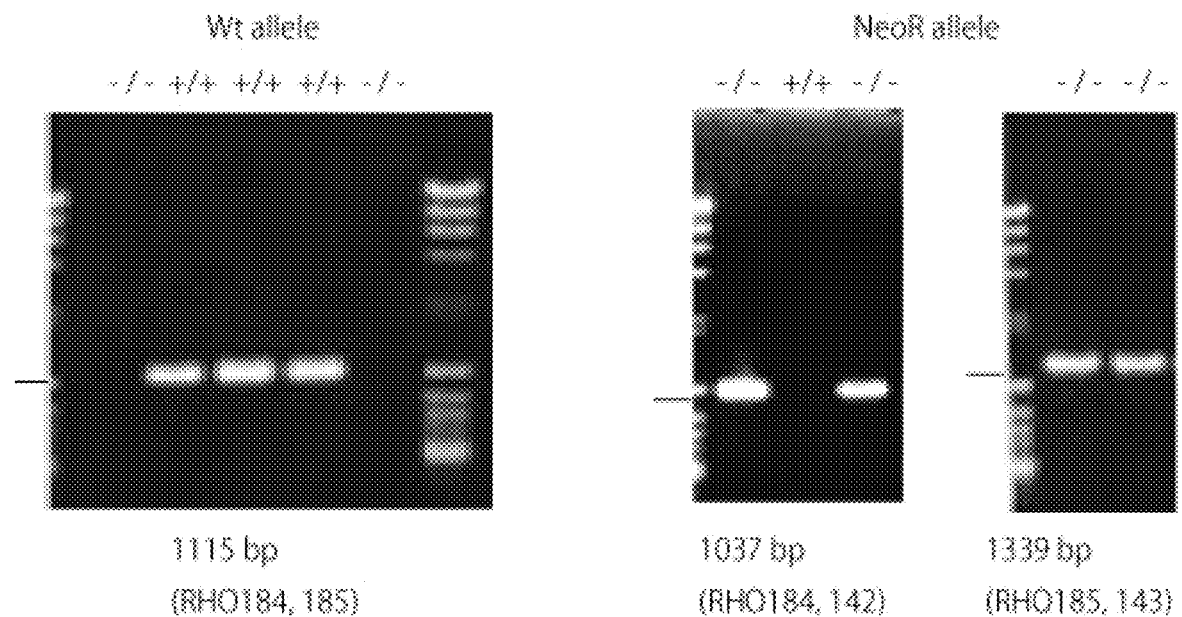
[Fig.69]
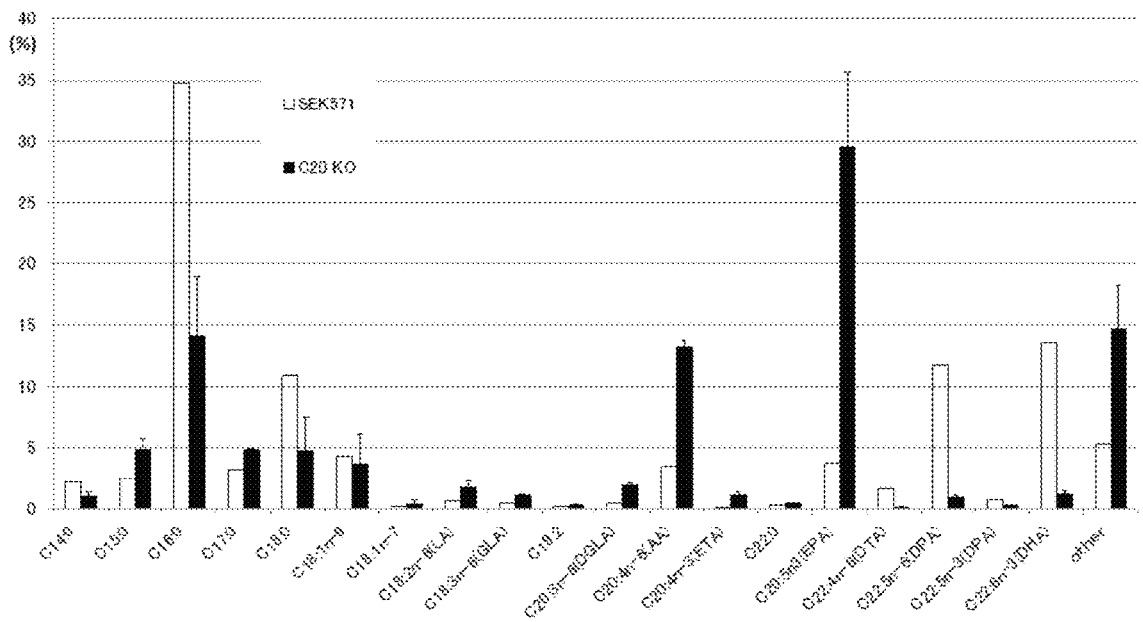

[Fig.70]

| C20 elongase KO | SEK571 | FA | |
|---|---|---|---|
| 43.8% | 0.98 | 2.23 | C14:0 |
| 197.0% | 4.86 | 2.47 | C15:0 |
| 40.6% | 14.13 | 34.78 | C16:0 |
| 152.7% | 4.80 | 3.14 | C17:0 |
| 43.4% | 4.71 | 10.86 | C18:0 |
| 85.5% | 3.66 | 4.28 | C18:1n-9 |
| 234.8% | 0.37 | 0.16 | C18:1n-7 |
| 251.6% | 1.70 | 0.67 | C18:2n-6(LA) |
| 228.6% | 1.07 | 0.47 | C18:3n-6(GLA) |
| 156.9% | 0.24 | 0.16 | C19:2 |
| 450.2% | 1.93 | 0.43 | C20:3n-6(DGLA) |
| 388.5% | 13.24 | 3.41 | C20:4n-6(AA) |
| 1048.8% | 1.14 | 0.11 | C20:4n-3(ETA) |
| 182.8% | 0.43 | 0.24 | C22:0 |
| 796.8% | 29.58 | 3.71 | C20:5n3(EPA) |
| 9.0% | 0.15 | 1.61 | C22:4n-6(DTA) |
| 8.2% | 0.96 | 11.69 | C22:5n-6(DPA) |
| 34.0% | 0.25 | 0.75 | C22:5n-3(DPA) |
| 8.6% | 1.17 | 13.62 | C22:6n-3(DHA) |

[Fig.71]

[Fig.72]
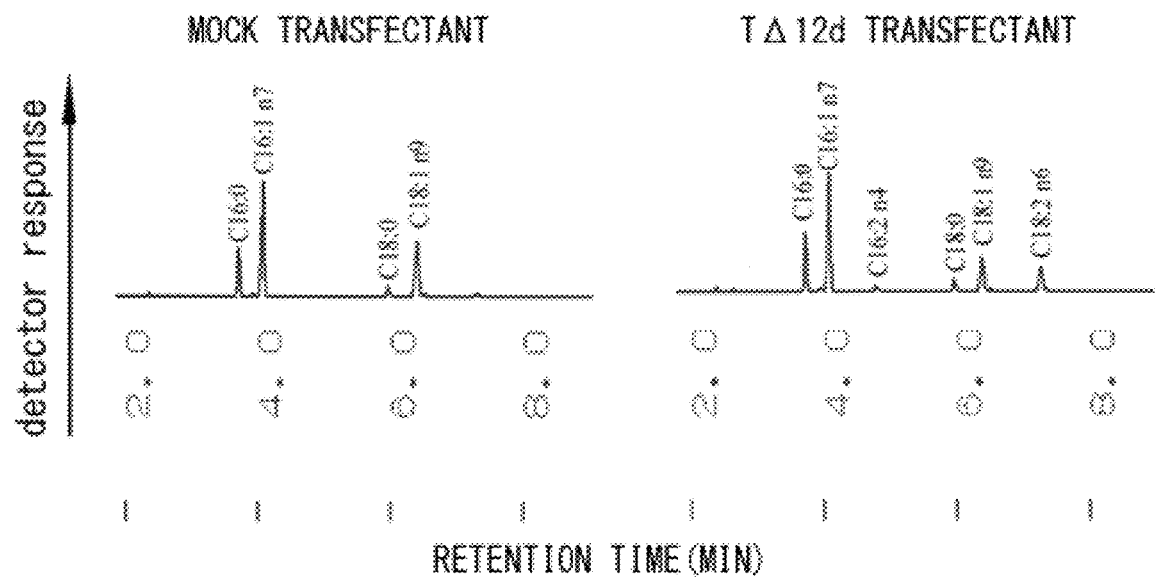
FA LEVEL (μg) DRAY CELL WEIGHT 1mg
| | mock ave. | mock std. | TΔ12d ave. | TΔ12d std. |
|---|---|---|---|---|
| C14:0 | 0.483883 | 0.118188 | 0.5181282 | 0.03081 |
| C16:0 | 7.127198 | 1.223085 | 7.451359 | 0.579578 |
| C16:1n7 | 19.16444 | 2.936704 | 17.042456 | 2.69802 |
| C18:0 | 1.910871 | 0.255276 | 1.9670849 | 0.22879 |
| C18:1n9 | 11.05722 | 0.945736 | 6.1005013 | 0.498143 |
| C18:2n6 | 0 | 0 | 3.5566365 | 0.98697 |
| Total | 40.45796 | 5.459088 | 37.350518 | 4.913859 |
n=3

[Fig.73]
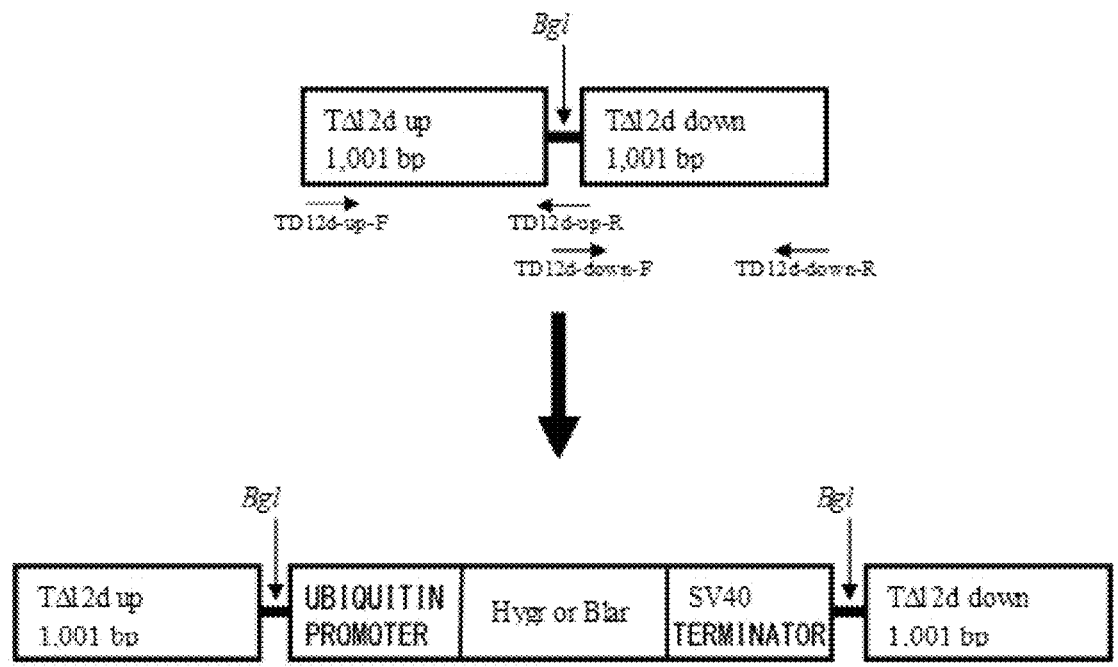
[Fig.74]
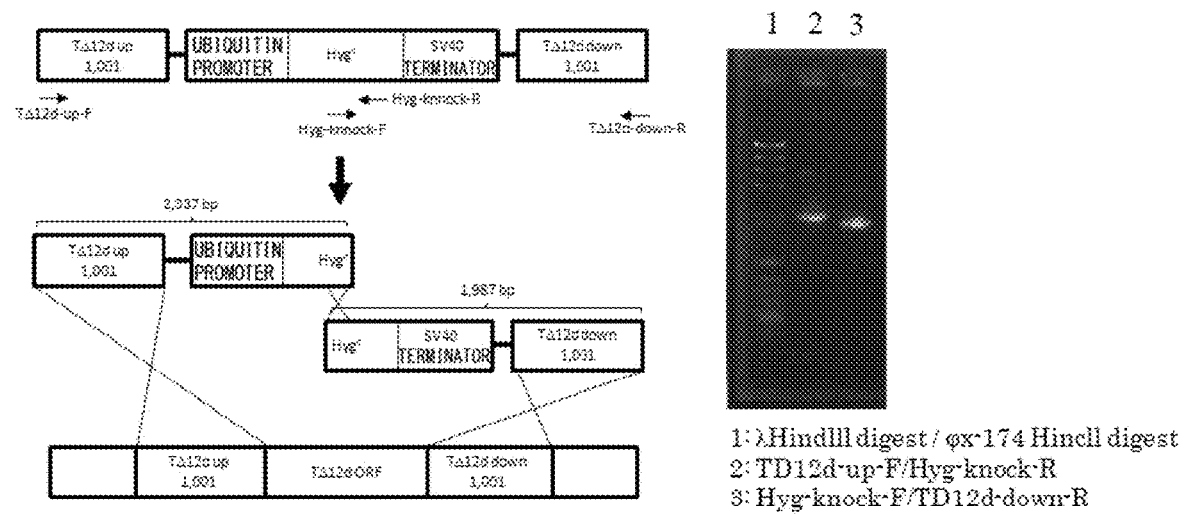

[Fig. 75]
Hygr INHERITANCE
Blar GENE
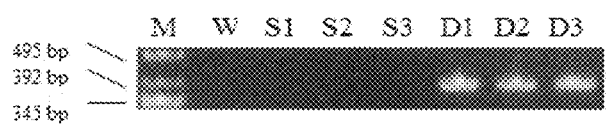
Δ12 desaturase GENE
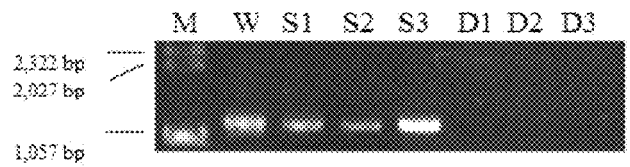
[Fig. 76]
Hygr INHERITANCE
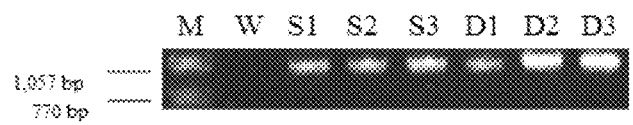
Blar GENE
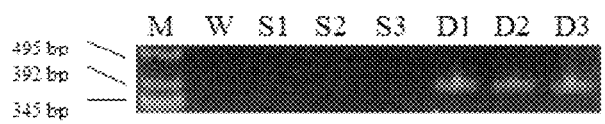
Δ12 desaturase GENE
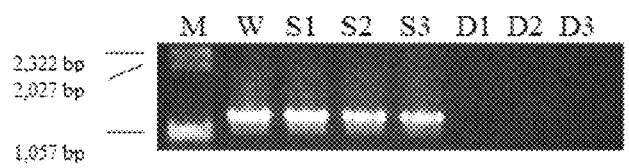

[Fig.77]
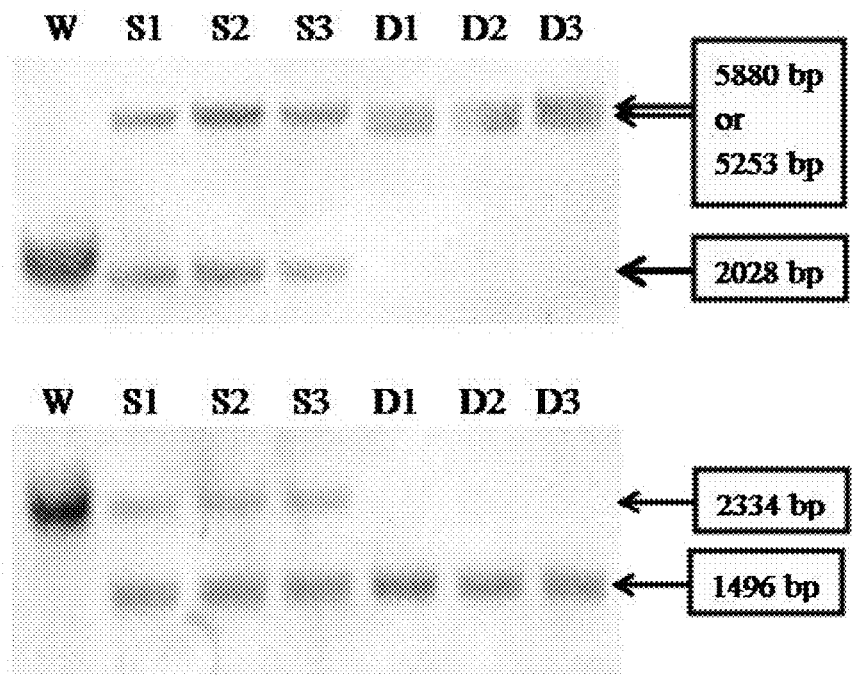

[Fig.78]
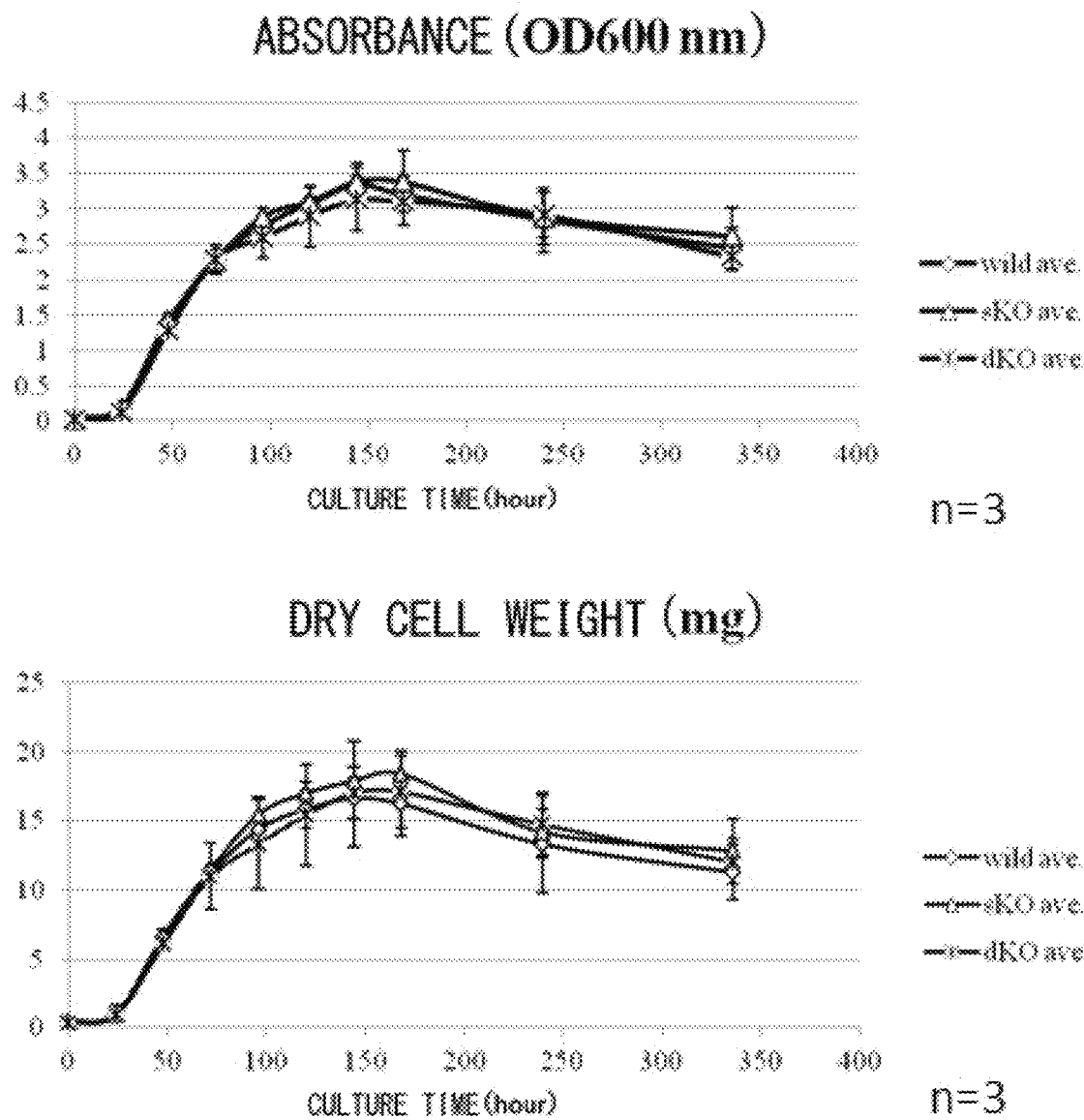

[Fig.79]
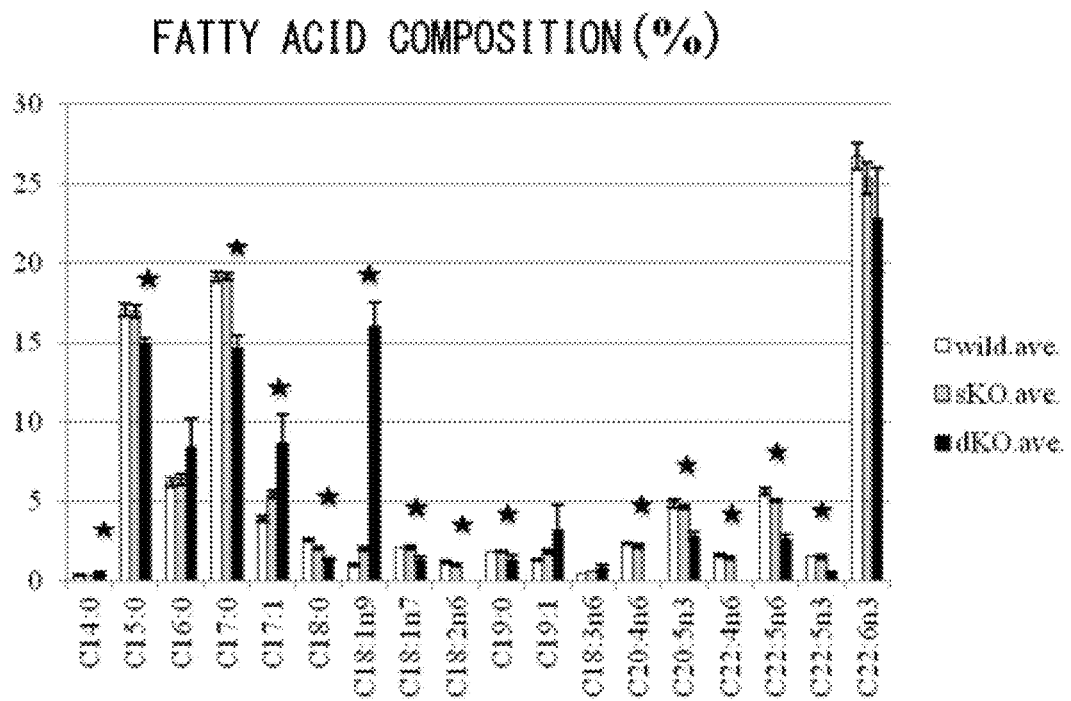
[Fig.80]
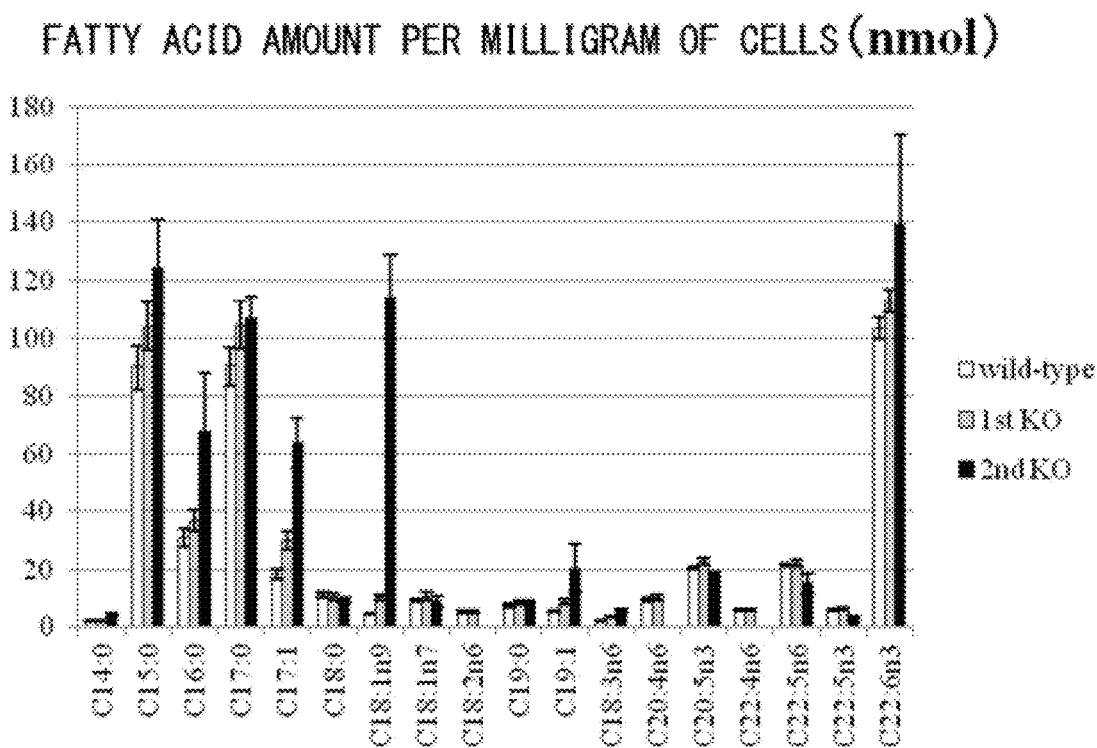

[Fig.81]
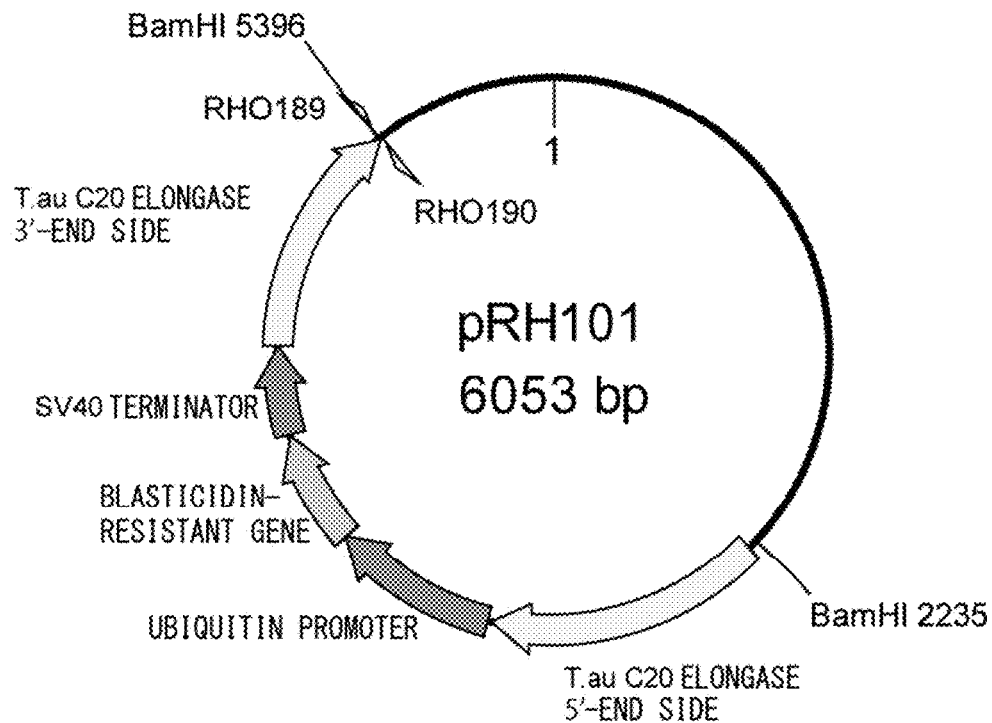
[Fig.82]
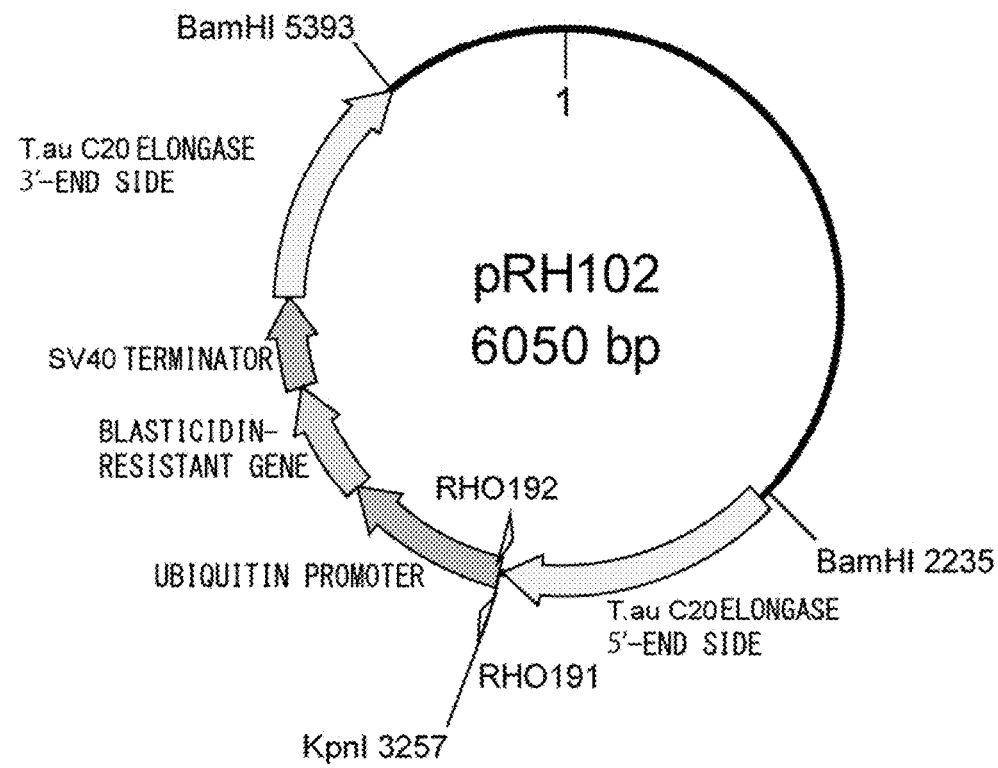

[Fig.83]
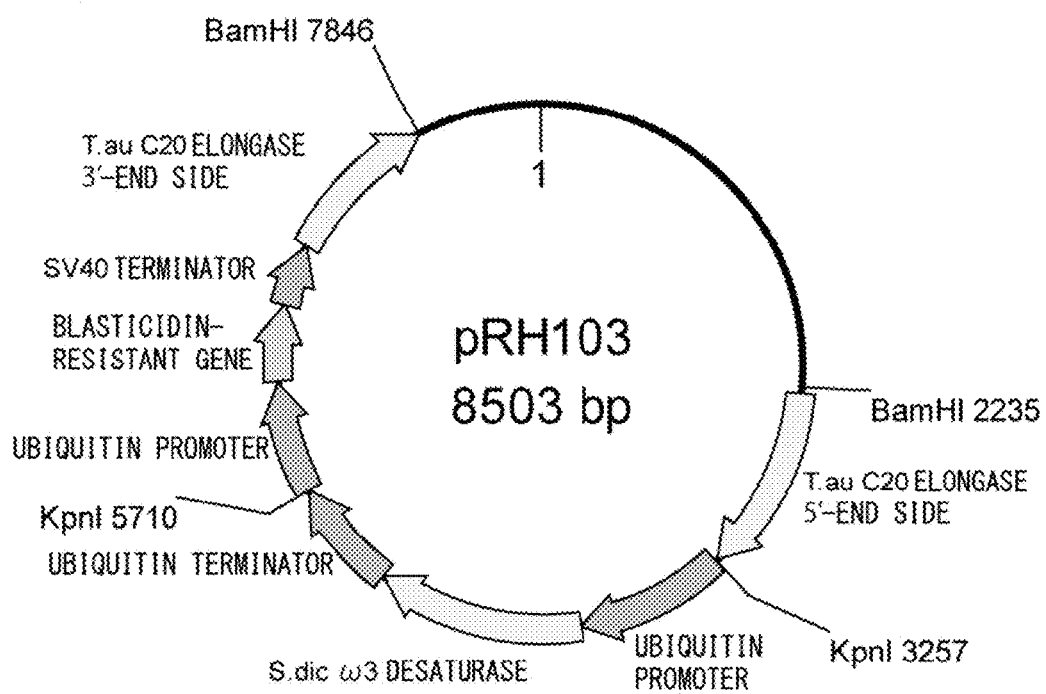
[Fig.84]
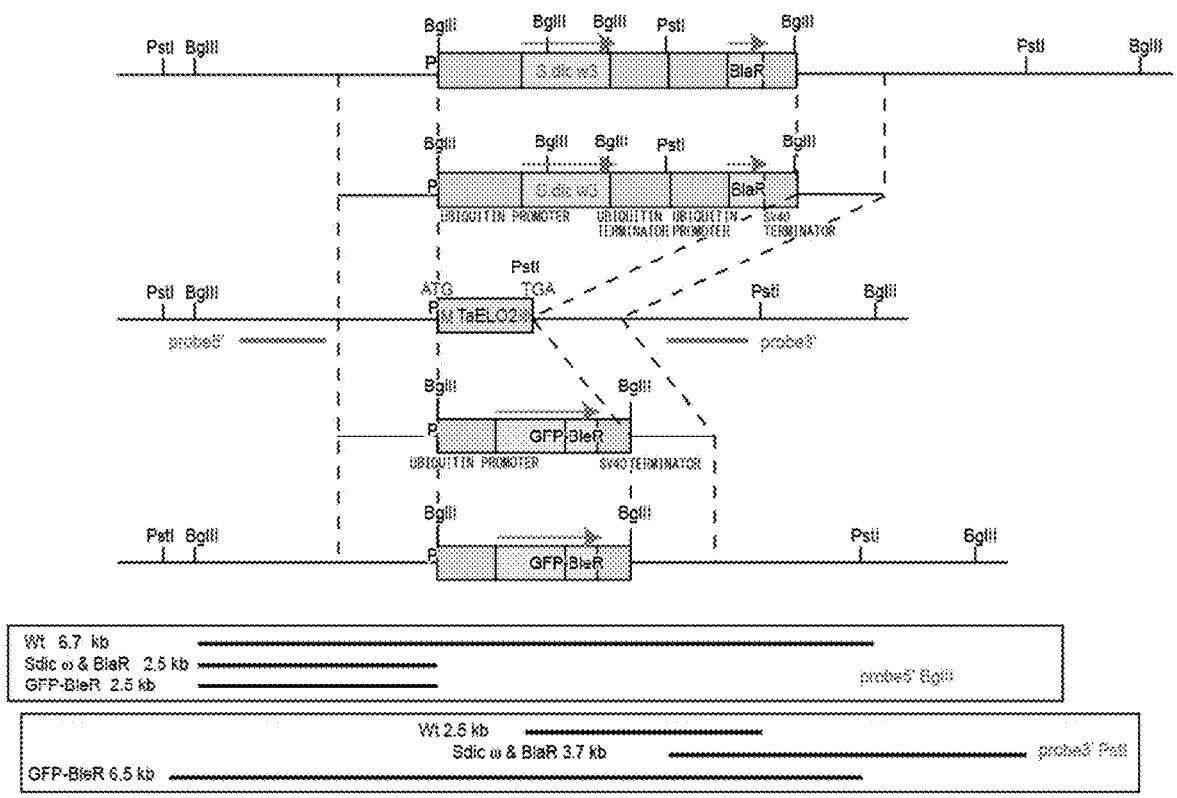

[Fig.85]
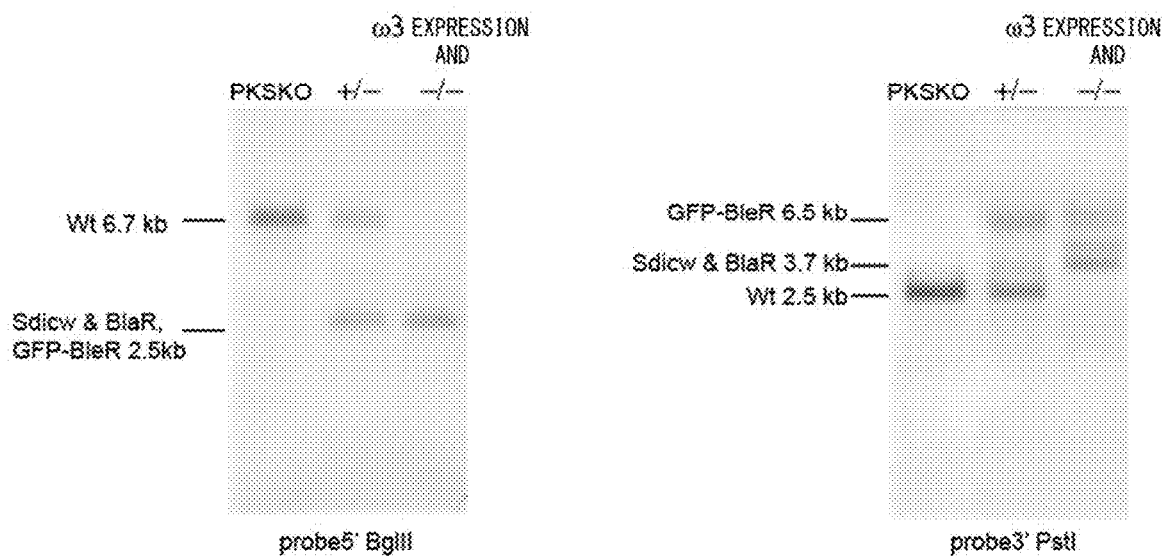
[Fig.86]
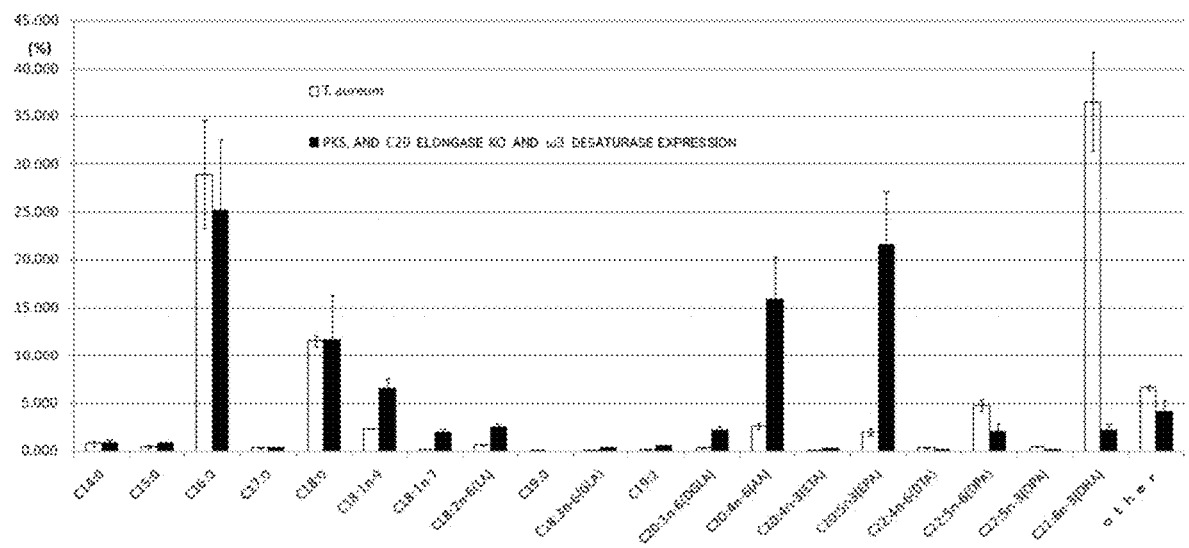

[Fig.87]

| PKS, AND C20 ELONGASE KO AND ω3 DESATURASE EXPRESSION | T.aureum | FA | |
|---|---|---|---|
| 106.7% | 0.89 | 0.83 | C14:0 |
| 162.2% | 0.84 | 0.52 | C15:0 |
| 87.1% | 25.22 | 28.96 | C16:0 |
| 86.7% | 0.36 | 0.42 | C17:0 |
| 101.1% | 11.75 | 11.62 | C18:0 |
| 281.5% | 6.55 | 2.33 | C18:1n-9 |
| 795.0% | 2.01 | 0.25 | C18:1n-7 |
| 372.7% | 2.55 | 0.69 | C18:2n-6(LA) |
| 0.0% | 0.00 | 0.06 | C19:0 |
| 333.5% | 0.37 | 0.11 | C18:3n-6(GLA) |
| 300.4% | 0.59 | 0.20 | C19:2 |
| 576.4% | 2.19 | 0.38 | C20:3n-6(DGLA) |
| 601.0% | 15.95 | 2.65 | C20:4n-6(AA) |
| 235.5% | 0.31 | 0.13 | C20:4n-3(ETA) |
| 1075.4% | 21.58 | 2.01 | C20:5n-3(EPA) |
| 60.2% | 0.22 | 0.36 | C22:4n-6(DTA) |
| 43.9% | 2.10 | 4.77 | C22:5n-6(DPA) |
| 40.4% | 0.21 | 0.52 | C22:5n-3(DPA) |
| 5.9% | 2.17 | 36.59 | C22:6n-3(DHA) |

[Fig.88]
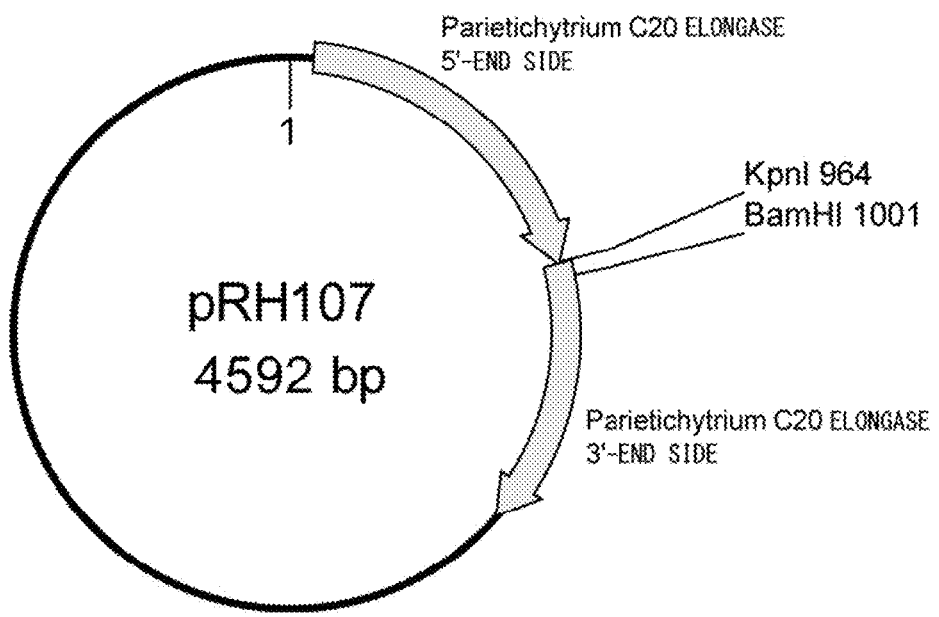
[Fig.89]
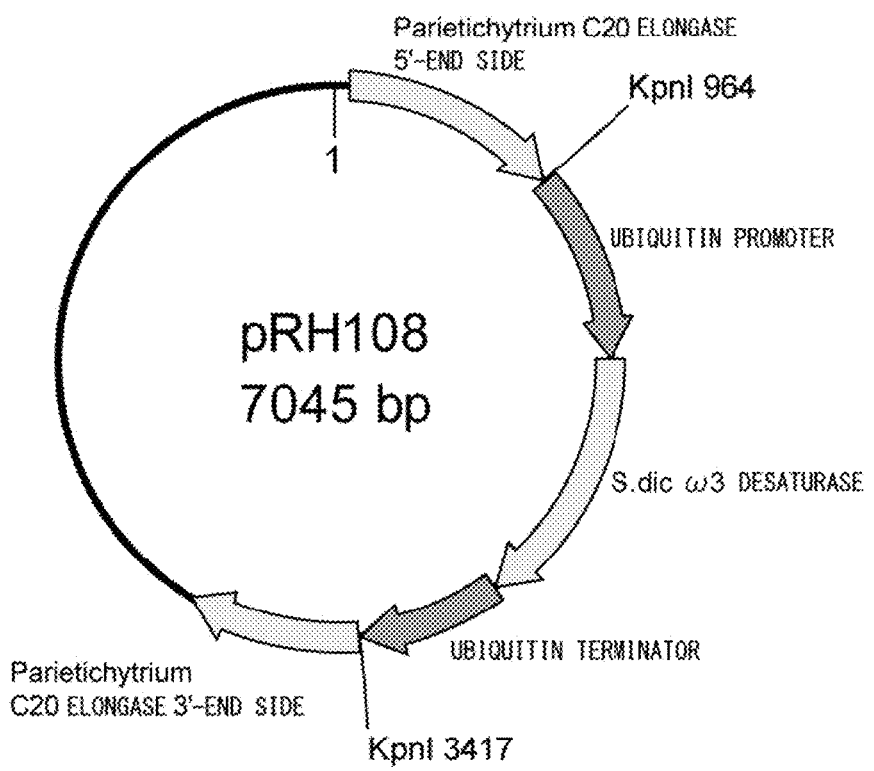

[Fig.90]
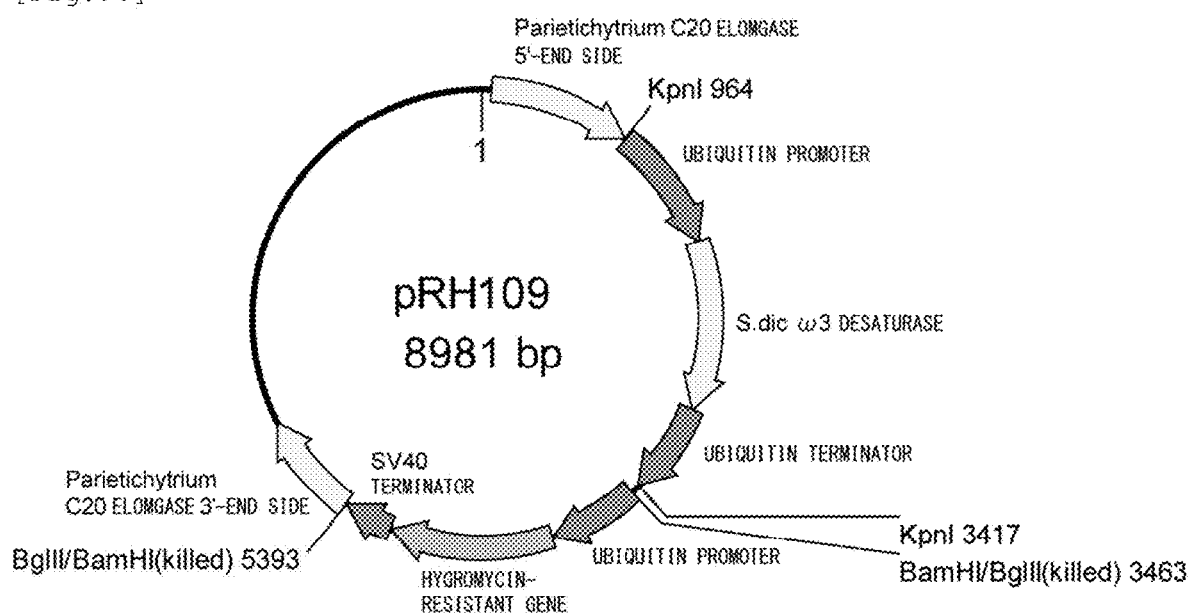
[Fig.91]
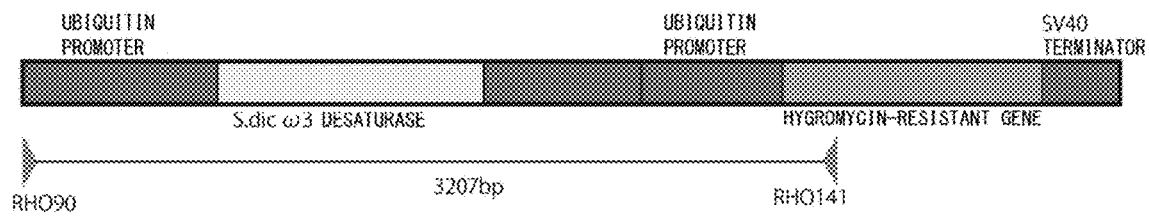

[Fig.92]
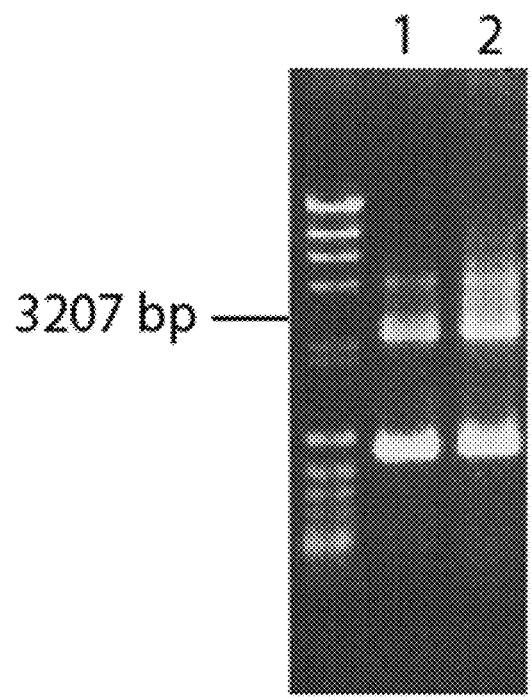

[Fig.93]
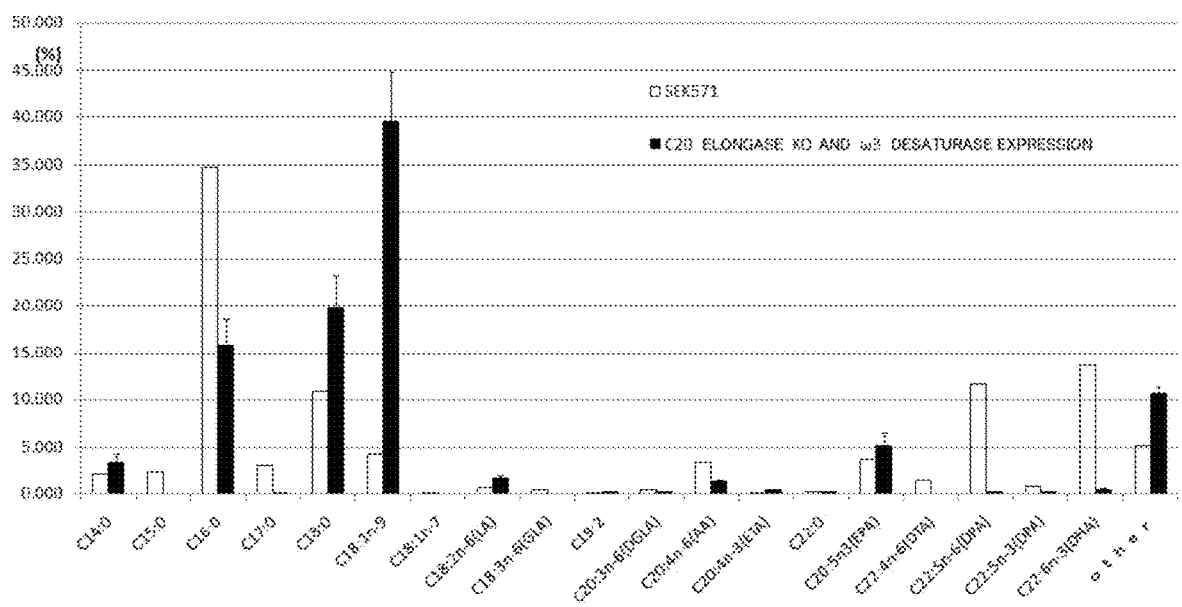

[Fig.94]

| C20 ELONGASE KO AND ω3 DESATURASE EXPRESSION | SEK571 | FA | |
|---|---|---|---|
| 154.8% | 3.45 | 2.23 | C14:0 |
| 0.0% | 0.00 | 2.47 | C15:0 |
| 45.6% | 15.86 | 34.78 | C16:0 |
| 4.7% | 0.15 | 3.14 | C17:0 |
| 182.1% | 19.77 | 10.86 | C18:0 |
| 925.2% | 39.58 | 4.28 | C18:1n-9 |
| 0.0% | 0.00 | 0.16 | C18:1n-7 |
| 265.2% | 1.79 | 0.67 | C18:2n-6(LA) |
| 0.0% | 0.00 | 0.47 | C18:3n-6(GLA) |
| 141.0% | 0.22 | 0.16 | C19:2 |
| 57.1% | 0.24 | 0.43 | C20:3n-6(DGLA) |
| 42.9% | 1.46 | 3.41 | C20:4n-6(AA) |
| 449.2% | 0.49 | 0.11 | C20:4n-3(ETA) |
| 108.3% | 0.26 | 0.24 | C22:0 |
| 139.6% | 5.18 | 3.71 | C20:5n3(EPA) |
| 0.0% | 0.00 | 1.61 | C22:4n-6(DTA) |
| 1.8% | 0.21 | 11.69 | C22:5n-6(DPA) |
| 28.5% | 0.21 | 0.75 | C22:5n-3(DPA) |
| 3.2% | 0.44 | 13.62 | C22:6n-3(DHA) |

[Fig.95]
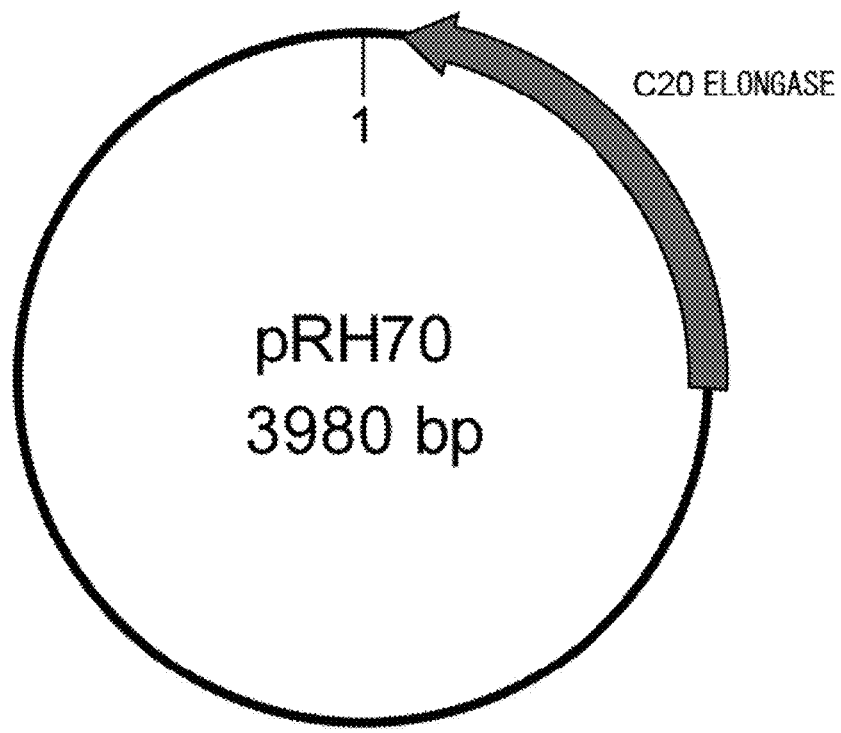
[Fig.96]
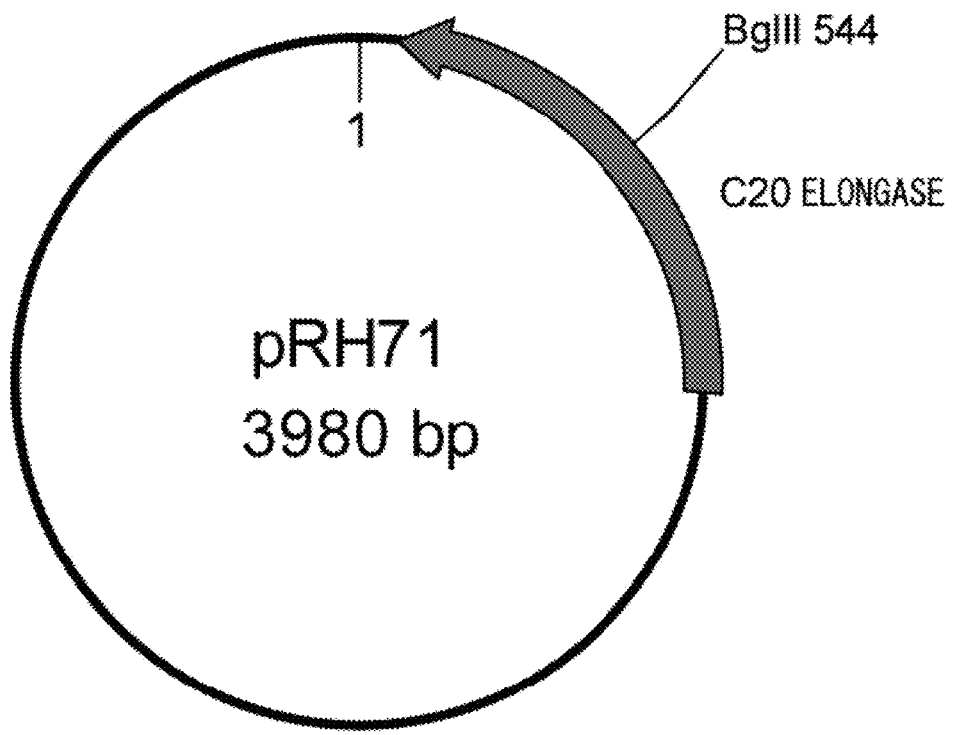

[Fig.97]
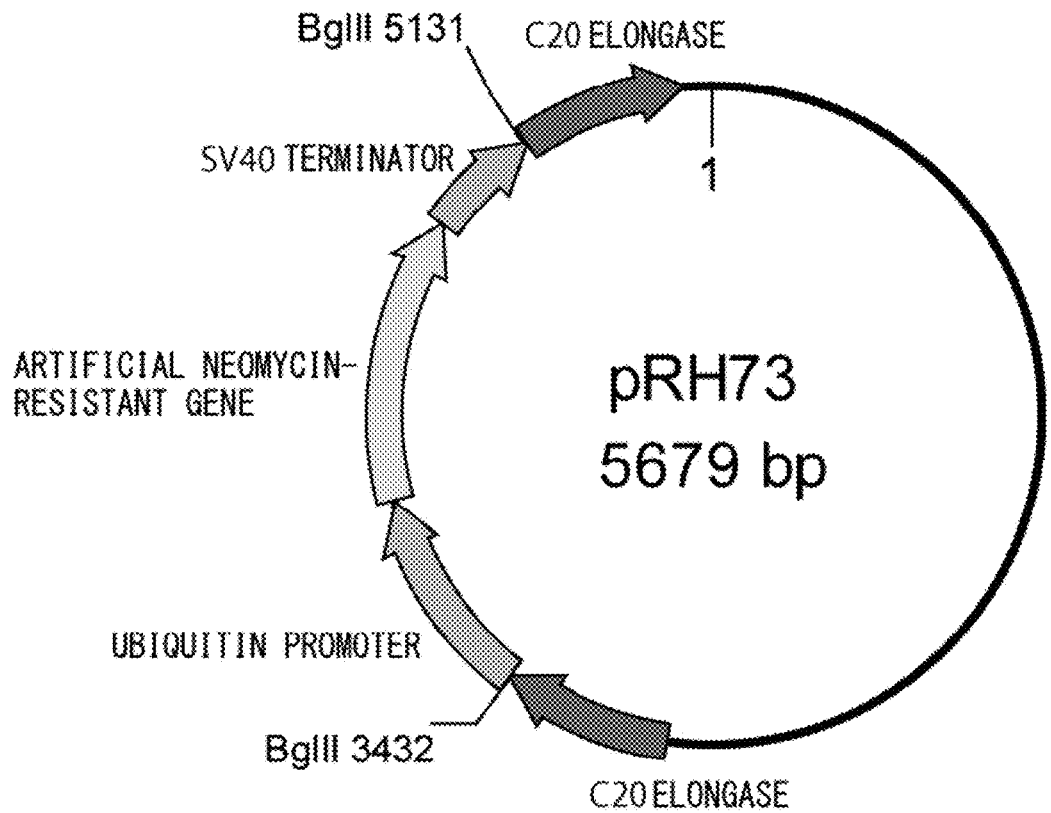
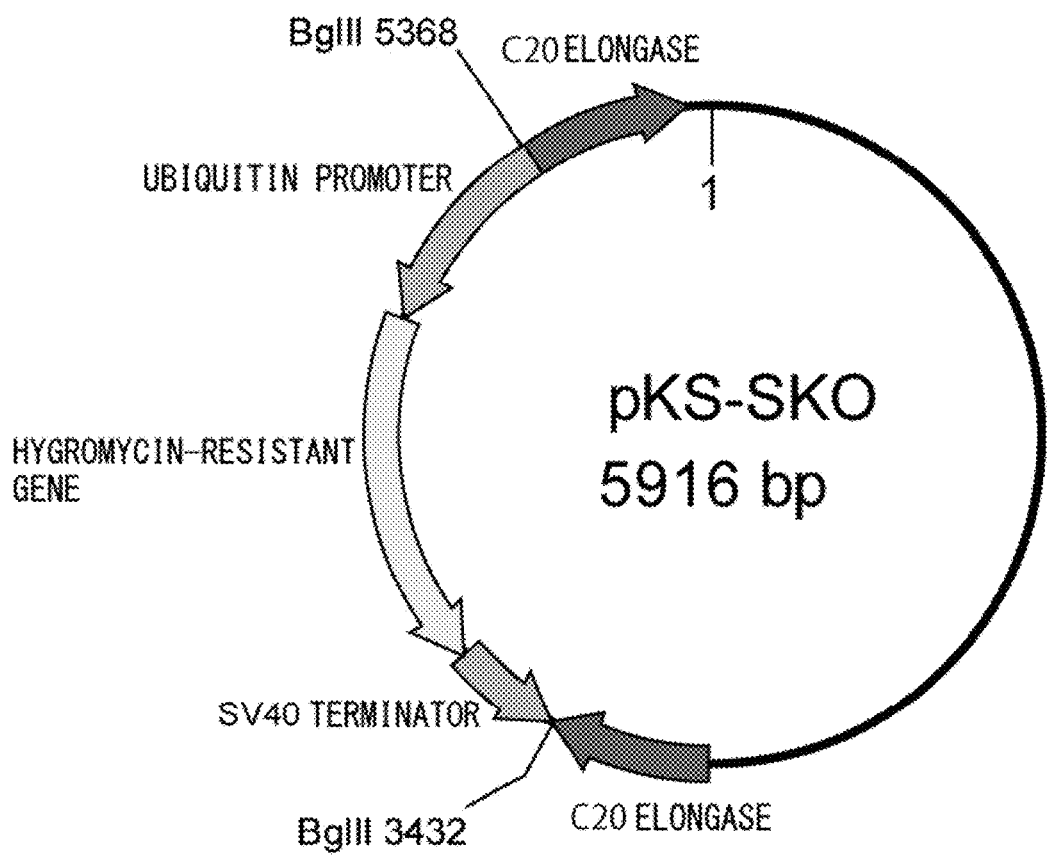

[Fig.98]
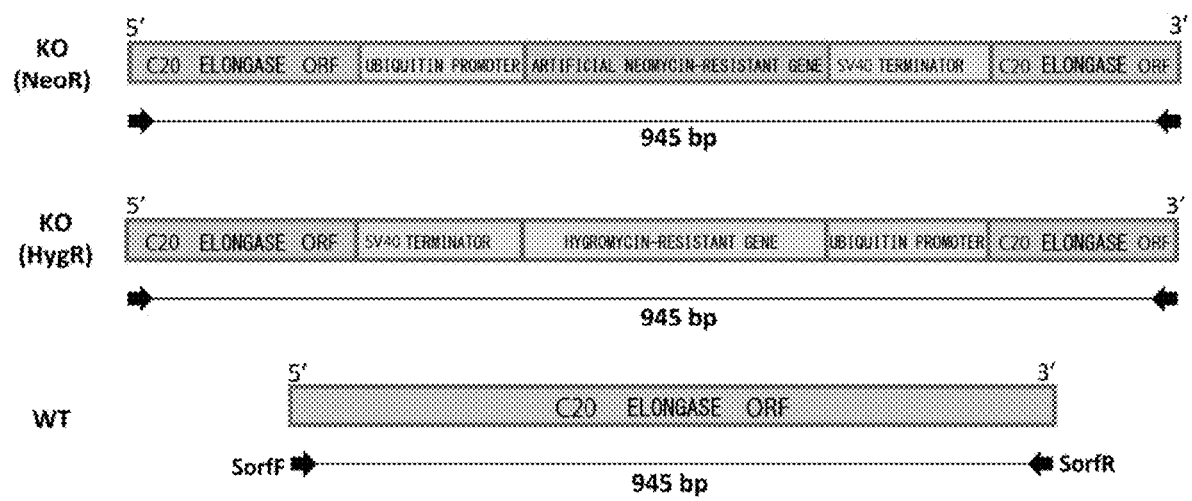
[Fig.99]
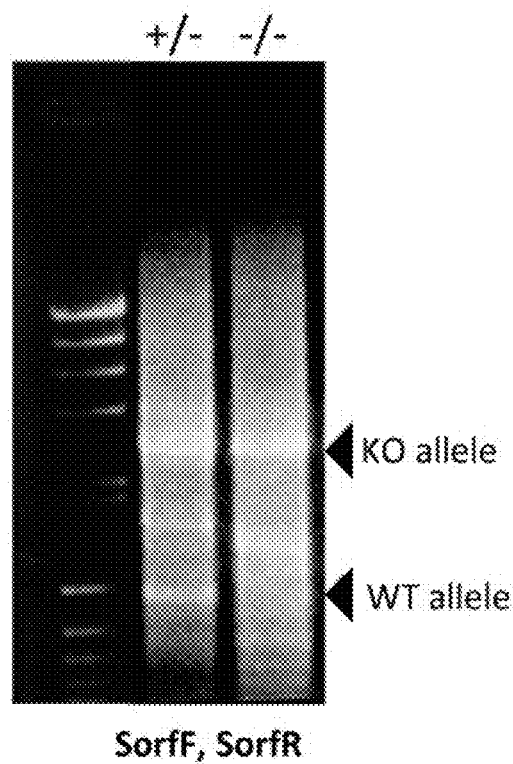

[Fig.100]
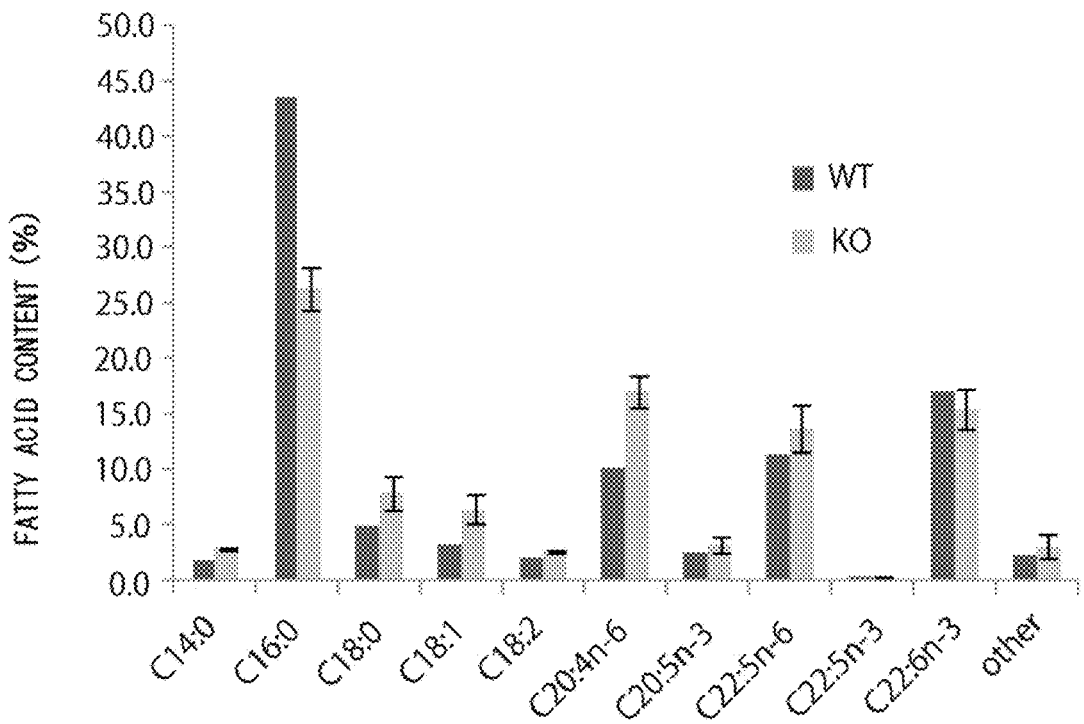
[Fig.101]
| COMPARISON WITH WILD-TYPE STRAIN | C20elo KO | S. sp TY12Ab | FA |
|---|---|---|---|
| 150.0% | 3.0±0.06 | 2.0 | C14:0 |
| 59.8% | 26.4±1.97 | 43.5 | C16:0 |
| 160.0% | 8.0±1.52 | 5.0 | C18:0 |
| 197.0% | 6.5±1.32 | 3.3 | C18:1 |
| 127.3% | 2.8±0.12 | 2.2 | C18:2 |
| 168.7% | 17.2±1.46 | 10.2 | C20:4n-6 |
| 132.0% | 3.3±0.64 | 2.5 | C20:5n-3 |
| 114.0% | 13.7±2.19 | 11.4 | C22:5n-6 |
| 66.7% | 0.4±0.10 | 0.6 | C22:5n-3 |
| 87.7% | 15.6±1.81 | 17.1 | C22:6n-3 |
| 139.1% | 3.2±1.08 | 2.3 | other |
|  | 100 | 100 | total |

SEQUENCE LISTING

```
<160> NUMBER OF SEQ ID NOS: 255

<210> SEQ ID NO 1
<211> LENGTH: 21
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 1
ttyytncayg tntaycayca y                                            21

<210> SEQ ID NO 2
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 2
gcrtgrtgrt anacrtgnar raa                                          23

<210> SEQ ID NO 3
<211> LENGTH: 190
<212> TYPE: DNA
<213> ORGANISM: Artificial
<220> FEATURE:
<223> OTHER INFORMATION: cDNA (DNA fragment contains elo1)
```

<400> SEQUENCE: 3

```
cgccaccatc tttgctatct ggtttatgat cgccaagtac gccccgggcg gcgacgcata    60
ctttagcgtc atcctgaact cgttcgtgca caccgtcatg tacgcgtact acttcttctc   120
gtcgcagggc ttcgggttcg tcaagccgat caagccgtac atcacctcgc tgcagatgac   180
gcagttcatg                                                          190
```

<210> SEQ ID NO 4
<211> LENGTH: 210
<212> TYPE: DNA
<213> ORGANISM: Artificial
<220> FEATURE:
<223> OTHER INFORMATION: cDNA (DNA fragment contains elo2)

<400> SEQUENCE: 4

```
ccgacgacca gcacaccgag tgggtctcgt gcgtgcgctt ctcgccctcg accaccaacc    60
cgctgatcgt gtcgtgcggc tgggacaagc tcgtcaaggt ctggaacctc tcgaactgca   120
agcttcgggc caacctcatc ggccacgacg gctacctcaa ctcggtcacc gtcagcccgg   180
acggctccct gtgcgcttcg ggcggcaagg                                    210
```

<210> SEQ ID NO 5
<211> LENGTH: 200
<212> TYPE: DNA
<213> ORGANISM: Artificial
<220> FEATURE:
<223> OTHER INFORMATION: cDNA (DNA fragment contains elo3)

<400> SEQUENCE: 5

```
aagctaacct gggcgtagtt tttcttgagg atcatcatga acgtgtcgct ccagtcgaga    60
aactttgtca ggaggtgcac gaacacgaaa aactcgatgt tcgagtcgcg cgacttgttg   120
aggccgaaag ggttgccgtt ggccaggtcg acctgcggcc agaggcccca caccatccag   180
ccgcacaccg cgatttggac                                               200
```

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6

```
tatgatcgcc aagtacgccc c                                              21
```

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7

```
gaactgcgtc atctgcagcg a                                              21
```

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8

```
tctcgccctc gaccaccaac                                                  20

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
cggtgaccga gttgaggtag cc                                               22

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10 caacccttc ggcctcaaca ag                                                22

<210> SEQ ID NO 11
<211> LENGTH: 26
<212> TYPE: DNA
<213> ORGANISM: Artificial
<220> FEATURE:
<223> OTHER INFORMATION: primer

<400> SEQUENCE: 11
ttcttgagga tcatcatgaa cgtgtc                                           26

<210> SEQ ID NO 12
<211> LENGTH: 1139
<212> TYPE: DNA
<213> ORGANISM: Artificial
<220> FEATURE:
<223> OTHER INFORMATION: cDNA (elo1)

<400> SEQUENCE: 12
ctaatacgac tcactatagg gcaagcagtg gtaacaacgc agagtacgcg gggacccaa        60 acgcccgacg acaaccaaga agacagccag ccgaacaatc ggacgaagat gacgagcaac      120
atgagcgcgt ggggcgtcgc cgtcgaccag acgcagcagg tcgtcgacca gatcatgggc      180
ggcgccgagc cgtacaagct gacagaaggg cgcatgacga acgtcgagac gatgctggcg      240
atcgagtgcg gctacgccgc catgctgctg ttcctgaccc cgatcatgaa gcaggccgag      300
aagcccttcg agctcaagtc cttcaagctc gcccacaacc tgttcctgtt cgtcctgtcc      360
gcctacatgt gcctcgagac cgtccgccag gcctaccttg cgggctactc ggtgttcggc      420
aacgacatgg agaagggcag cgagccgcac gcgcacggca tggcccaaat cgtgtggatc      480
ttttacgtgt ccaaggcgta cgagttcgtg gacacgctga tcatgatcct gtgcaaaaag      540
ttcaaccagg tctccgtcct gcacgtgtac caccacgcca ccatctttgc tatctggttt      600
atgatcgcca agtacgcccc gggcggcgac gcatacttta gcgtcatcct gaactcgttc      660
gtgcacaccg tcatgtacgc gtactacttc ttctcgtcgc agggcttcgg gttcgtcaag      720
ccgatcaagc cgtacatcac ctcgctgcag atgacgcagt tcatggcgat gctcgtgcag      780
tcgctgtacg actaccttta cccgtgcgac tacccgcagg ggctcgtcaa gctcctcggc      840
gtgtacatgc tcaccctgct tgcgctcttc ggcaacttt tcgtgcagag ctacctcaag      900
```

```
aagtcgaaca agcccaaggc caagtcggcc taagccgacc cgctcgccgg caaccgagca      960
gcacctaggc gcatctcggc ccggaacctt ttcgacctgc tgtggagcgc gcgacgcgtt     1020
tcgcgaccgt ccgcgcgttc ttgacactct ttgctctgtg tgtttcgcac ttgacaacct     1080
ggaacagaca catacacgat acaaatcatc agaacagaca aaaacaaccc tcaaattat     1139
```

<210> SEQ ID NO 13
<211> LENGTH: 1261
<212> TYPE: DNA
<213> ORGANISM: Artificial
<220> FEATURE:
<223> OTHER INFORMATION: cDNA (elo3)

<400> SEQUENCE: 13

```
ctaatacgac tcactatagg gcaagcagtg gtatcaacgc agagtacgcg gggaccccga       60
acgtgtttct cccaggacgt gccgctgtcg ctcgctgatc cacccgaagc gcggtcggct      120
ggcacggtcg ctcggctgga agttgagtag tttgctttct gttactgcgc tgctttgtaa      180
acgcgaccat ggcgacgcgc acctcgaaga gcgctccggc ggtttccaag tcggccaagg      240
ttgccgcgcc ggcgaagaag cggtcggtcg acaggagcga cggtttcttc cgcacgttca      300
acctgtgcgc cctgtacggg tctgccctcg cctatgcgta caagcacggc ccggtggaca      360
atgacggcca ggggctgtac tttcacaagt cgcccatgta cgcgttcgcc gtgtcggacg      420
tcatgacctt cggcgcgccg ctgatgtacg tgctcggtgt gatgctgctc agcaggtaca      480
tggcggacaa aaagcccctg actggcttca tcaagaccta catccagccc gtctacaacg      540
tggtccaaat cgcggtgtgc ggctggatgg tgtggggcct ctggccgcag gtcgacctgg      600
ccaacggcaa ccctttcggc ctcaacaagt cgcgcgactc gaacatcgag tttttcgtgt      660
tcgtgcacct cctgacaaag tttctcgact ggagcgacac gttcatgatg atcctcaaga      720
aaaactacgc ccaggttagc tttctgcagg tgttccacca cgcaacgatc ggcatggtgt      780
ggtcgttcct tcttcagcgt ggctggggct cgggcaccgc cgcgtacggt gctttcatca      840
actcggtcac gcacgtgatc atgtactcgc actactttgc cacctcgctc aacatcaaca      900
acccgttcaa gcggtacatc acgagcttcc agctcgccca gtttgcaagc tgcatcgtgc      960
atgccctact ggtgcttgcc ttcgaggagg tgtacccgct cgagtacgct tacctgcaga     1020
tcagctacca catcatcatg ctctacctgt tcggacgccg catgaactgg agccccgagt     1080
ggtgcaccgg tgagatcgac ggccttgacg ccccaagcgc ccccaccaag tccgagtaaa     1140 cctgttttccg gctggctccc gagccatgct taccatgaat gaacctgcaa acagtctgag     1200
gtccttgtgc aaaccgctca gtgggacgtc gacgaagaaa gaaacaatgt gtactcgtcc     1260
c                                                                     1261
```

<210> SEQ ID NO 14
<211> LENGTH: 275
<212> TYPE: PRT
<213> ORGANISM: T. aureum ATCC 34304
<220> FEATURE:
<221> NAME/KEY: misc_feature
<222> LOCATION: (275)..(275)
<223> OTHER INFORMATION: Xaa can be any naturally occurring amino acid

<400> SEQUENCE: 14

Met Thr Ser Asn Met Ser Ala Trp Gly Val Ala Val Asp Gln Thr Gln
1               5                   10                  15

Gln Val Val Asp Gln Ile Met Gly Gly Ala Glu Pro Tyr Lys Leu Thr
            20                  25                  30

Glu Gly Arg Met Thr Asn Val Glu Thr Met Leu Ala Ile Glu Cys Gly
         35                  40                  45

Tyr Ala Ala Met Leu Leu Phe Leu Thr Pro Ile Met Lys Gln Ala Glu
 50                  55                  60

Lys Pro Phe Glu Leu Lys Ser Phe Lys Leu Ala His Asn Leu Phe Leu
 65                  70                  75                  80

Phe Val Leu Ser Ala Tyr Met Cys Leu Glu Thr Val Arg Gln Ala Tyr
                 85                  90                  95

Leu Ala Gly Tyr Ser Val Phe Gly Asn Asp Met Glu Lys Gly Ser Glu
            100                 105                 110

Pro His Ala His Gly Met Ala Gln Ile Val Trp Ile Phe Tyr Val Ser
            115                 120                 125

Lys Ala Tyr Glu Phe Val Asp Thr Leu Ile Met Ile Leu Cys Lys Lys
        130                 135                 140

Phe Asn Gln Val Ser Val Leu His Val Tyr His Ala Thr Ile Phe
145                 150                 155                 160

Ala Ile Trp Phe Met Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
            195                 200                 205

Tyr Ile Thr Ser Leu Gln Met Thr Gln Phe Met Ala Met Leu Val Gln
            210                 215                 220

Ser Leu Tyr Asp Tyr Leu Tyr Pro Cys Asp Tyr Pro Gln Gly Leu Val
225                 230                 235                 240

Lys Leu Leu Gly Val Tyr Met Leu Thr Leu Leu Ala Leu Phe Gly Asn
                245                 250                 255

Phe Phe Val Gln Ser Tyr Leu Lys Lys Ser Asn Lys Pro Lys Ala Lys
            260                 265                 270

Ser Ala Xaa
    275

<210> SEQ ID NO 15
<211> LENGTH: 825
<212> TYPE: DNA
<213> ORGANISM: Artificial
<220> FEATURE:
<223> OTHER INFORMATION: cDNA (T. aureum ATCC 34304 elo1)

<400> SEQUENCE: 15
atgacgagca acatgagcgc gtggggcgtc gccgtcgacc agacgcagca ggtcgtcgac    60
cagatcatgg cggcgccga gccgtacaag ctgacagaag gcgcatgac gaacgtcgag     120 acgatgctgg cgatcgagtg cggctacgcc gccatgctgc tgttcctgac cccgatcatg    180
aagcaggccg agaagccctt cgagctcaag tccttcaagc tcgcccacaa cctgttcctg    240
ttcgtcctgt ccgcctacat gtgcctcgag accgtccgcc aggcctacct tgcgggctac    300
tcggtgttcg gcaacgacat ggagaagggc agcgagccgc acgcgcacgg catggcccaa    360
atcgtgtgga tcttttacgt gtccaaggcg tacgagttcg tggacacgct gatcatgatc    420
ctgtgcaaaa agttcaacca ggtctccgtc ctgcacgtgt accaccacgc caccatcttt    480
gctatctggt ttatgatcgc caagtacgcc ccgggcggcg acgcatactt tagcgtcatc    540
ctgaactcgt tcgtgcacac cgtcatgtac gcgtactact tcttctcgtc gcagggcttc    600

```
gggttcgtca agccgatcaa gccgtacatc acctcgctgc agatgacgca gttcatggcg    660
atgctcgtgc agtcgctgta cgactacctt tacccgtgcg actacccgca ggggctcgtc    720
aagctcctcg gcgtgtacat gctcaccctg cttgcgctct cggcaacttt tttcgtgcag    780
agctacctca agaagtcgaa caagcccaag gccaagtcgg cctaa                    825
```

<210> SEQ ID NO 16
<211> LENGTH: 317
<212> TYPE: PRT
<213> ORGANISM: T. aureum ATCC 34304
<220> FEATURE:
<221> NAME/KEY: misc_feature
<222> LOCATION: (317)..(317)
<223> OTHER INFORMATION: Xaa can be any naturally occurring amino acid

<400> SEQUENCE: 16

```
Met Ala Thr Arg Thr Ser Lys Ser Ala Pro Ala Val Ser Lys Ser Ala
1               5                   10                  15

Lys Val Ala Ala Pro Lys Lys Arg Ser Val Asp Arg Ser Asp Gly
            20                  25                  30

Phe Phe Arg Thr Phe Asn Leu Cys Ala Leu Tyr Gly Ser Ala Leu Ala
            35                  40                  45

Tyr Ala Tyr Lys His Gly Pro Val Asp Asn Asp Gly Gln Gly Leu Tyr
        50                  55                  60

Phe His Lys Ser Pro Met Tyr Ala Phe Ala Val Ser Asp Val Met Thr
65                  70                  75                  80

Phe Gly Ala Pro Leu Met Tyr Val Leu Gly Val Met Leu Leu Ser Arg
                85                  90                  95

Tyr Met Ala Asp Lys Lys Pro Leu Thr Gly Phe Ile Lys Thr Tyr Ile
            100                 105                 110

Gln Pro Val Tyr Asn Val Val Gln Ile Ala Val Cys Gly Trp Met Val
        115                 120                 125

Trp Gly Leu Trp Pro Gln Val Asp Leu Ala Asn Gly Asn Pro Phe Gly
130                 135                 140

Leu Asn Lys Ser Arg Asp Ser Asn Ile Glu Phe Val Phe Val His
145                 150                 155                 160

Leu Leu Thr Lys Phe Leu Asp Trp Ser Asp Thr Phe Met Met Ile Leu
                165                 170                 175

Lys Lys Asn Tyr Ala Gln Val Ser Phe Leu Gln Val Phe His His Ala
            180                 185                 190

Thr Ile Gly Met Val Trp Ser Phe Leu Leu Gln Arg Gly Trp Gly Ser
        195                 200                 205

Gly Thr Ala Ala Tyr Gly Ala Phe Ile Asn Ser Val Thr His Val Ile
    210                 215                 220

Met Tyr Ser His Tyr Phe Ala Thr Ser Leu Asn Ile Asn Asn Pro Phe
225                 230                 235                 240

Lys Arg Tyr Ile Thr Ser Phe Gln Leu Ala Gln Phe Ala Ser Cys Ile
                245                 250                 255

Val His Ala Leu Leu Val Leu Ala Phe Glu Glu Val Tyr Pro Leu Glu
            260                 265                 270

Tyr Ala Tyr Leu Gln Ile Ser Tyr His Ile Ile Met Leu Tyr Leu Phe
        275                 280                 285

Gly Arg Arg Met Asn Trp Ser Pro Glu Trp Cys Thr Gly Glu Ile Asp
    290                 295                 300

Gly Leu Asp Ala Pro Ser Ala Pro Thr Lys Ser Glu Xaa
305                 310                 315
```

<210> SEQ ID NO 17
<211> LENGTH: 951
<212> TYPE: DNA
<213> ORGANISM: Artificial
<220> FEATURE:
<223> OTHER INFORMATION: cDNA (T. aureum ATCC 34304 elo3)

<400> SEQUENCE: 17

| | | | | | | |
|---|---|---|---|---|---|---|
| atggcgacgc | gcacctcgaa | gagcgctccg | gcggtttcca | agtcggccaa | ggttgccgcg | 60 |
| ccggcgaaga | agcggtcggt | cgacaggagc | gacggtttct | tccgcacgtt | caacctgtgc | 120 |
| gccctgtacg | ggtctgccct | cgcctatgcg | tacaagcacg | gccgggtgga | caatgacggc | 180 |
| caggggctgt | actttcacaa | gtcgcccatg | tacgcgttcg | ccgtgtcgga | cgtcatgacc | 240 |
| ttcggcgcgc | cgctgatgta | cgtgctcggt | gtgatgctgc | tcagcaggta | catggcggac | 300 |
| aaaaagcccc | tgactggctt | catcaagacc | tacatccagc | ccgtctacaa | cgtggtccaa | 360 |
| atcgcggtgt | gcggctggat | ggtgtggggc | ctctggccgc | aggtcgacct | ggccaacggc | 420 |
| aaccctttcg | gcctcaacaa | gtcgcgcgac | tcgaacatcg | agttttcgt | gttcgtgcac | 480 |
| ctcctgacaa | agtttctcga | ctggagcgac | acgttcatga | tgatcctcaa | gaaaaactac | 540 |
| gcccaggtta | gctttctgca | ggtgttccac | cacgcaacga | tcggcatggt | gtggtcgttc | 600 |
| cttcttcagc | gtggctgggg | ctcgggcacc | ccgcgcgtacg | tgctttcat | caactcggtc | 660 |
| acgcacgtga | tcatgtactc | gcactacttt | gccacctcgc | tcaacatcaa | caacccgttc | 720 |
| aagcggtaca | tcacgagctt | ccagctcgcc | cagtttgcaa | gctgcatcgt | gcatgcccta | 780 |
| ctggtgcttg | ccttcgagga | ggtgtacccg | ctcgagtacg | cttacctgca | gatcagctac | 840 |
| cacatcatca | tgctctacct | gttcggacgc | cgcatgaact | ggagcccga | gtggtgcacc | 900 |
| ggtgagatcg | acggccttga | cgccccaagc | gcccccacca | agtccgagta | a | 951 |

<210> SEQ ID NO 18
<211> LENGTH: 38
<212> TYPE: DNA
<213> ORGANISM: Artificial
<220> FEATURE:
<223> OTHER INFORMATION: primer

<400> SEQUENCE: 18

| | | | |
|---|---|---|---|
| ataagcttaa | aatgtctagc | aacatgagcg | cgtggggc | 38 |

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19

| | | | |
|---|---|---|---|
| tgtctagaac | gcgcggacgg | tcgcgaaa | 28 |

<210> SEQ ID NO 20
<211> LENGTH: 40
<212> TYPE: DNA
<213> ORGANISM: Artificial
<220> FEATURE:
<223> OTHER INFORMATION: primer

<400> SEQUENCE: 20

| | | | |
|---|---|---|---|
| taaagcttaa | aatgtctacg | cgcacctcga | agagcgctcc | 40 |

<210> SEQ ID NO 21
<211> LENGTH: 31
<212> TYPE: DNA
<213> ORGANISM: Artificial
<220> FEATURE:
<223> OTHER INFORMATION: primer

<400> SEQUENCE: 21
catctagact cggacttggt gggggcgctt g                              31

<210> SEQ ID NO 22
<211> LENGTH: 949
<212> TYPE: DNA
<213> ORGANISM: Artificial
<220> FEATURE:
<223> OTHER INFORMATION: cDNA (TaELO1 coding region)

<400> SEQUENCE: 22
ataagcttaa aatgacgagc aacatgagcg cgtggggcgt cgccgtcgac cagacgcagc    60
aggtcgtcga ccagatcatg ggcggcgccg agccgtacaa gctgacagaa gggcgcatga   120
cgaacgtcga gacgatgctg gcgatcgagt gcggctacgc cgccatgctg ctgttcctga   180
ccccgatcat gaagcaggcc gagaagccct tcgagctcaa gtccttcaag ctcgcccaca   240
acctgttcct gttcgtcctg tccgcctaca tgtgcctcga ccgtccgc caggcctacc     300 ttgcgggcta ctcggtgttc ggcaacgaca tggagaaggg cagcgagccg cacgcgcacg   360
gcatggccca aatcgtgtgg atcttttacg tgtccaaggc gtacgagttc gtggacacgc   420
tgatcatgat cctgtgcaaa aagttcaacc aggtctccgt cctgcacgtg taccaccacg   480
ccaccatctt tgctatctgg tttatgatcg ccaagtacgc cccgggcggc gacgcatact   540
ttagcgtcat cctgaactcg ttcgtgcaca ccgtcatgta cgcgtactac ttcttctcgt   600
cgcagggctt cgggttcgtc aagccgatca agccgtacat cacctcgctg cagatgacgc   660
agttcatggc gatgctcgtg cagtcgctgt acgactacct ttacccgtgc gactacccgc   720
aggggctcgt caagctcctc ggcgtgtaca tgctcaccct gcttgcgctc ttcggcaact   780
ttttcgtgca gagctacctc aagaagtcga acaagcccaa ggccaagtcg gcctaagccg   840
acccgctcgc cggcaaccga gcagcaccta ggcgcatctc ggcccggaac ctttcgacc   900 tgctgtggag cgcgcgacgc gtttcgcgac cgtccgcgcg ttctagaca              949

<210> SEQ ID NO 23
<211> LENGTH: 967
<212> TYPE: DNA
<213> ORGANISM: Artificial
<220> FEATURE:
<223> OTHER INFORMATION: cDNA (TaELO2 coding region)

<400> SEQUENCE: 23
taaagcttaa aatggcgacg cgcacctcga agagcgctcc ggcggtttcc aagtcggcca    60
aggttgccgc gccggcgaag aagcggtcgg tcgacaggag cgacggtttc ttccgcacgt   120
tcaacctgtg cgccctgtac gggtctgccc tcgcctatgc gtacaagcac ggcccggtgg   180
acaatgacgg ccaggggctg tactttcaca gtcgcccat gtacgcgttc gccgtgtcgg    240
acgtcatgac cttcggcgcg ccgctgatgt acgtgctcgg tgtgatgctg ctcagcaggt   300
acatggcgga caaaaagccc ctgactggct tcatcaagac ctacatccag cccgtctaca   360
acgtggtcca aatcgcggtg tgcggctgga tggtgtgggg cctctggccg caggtcgacc   420
tggccaacgg caaccctttc ggcctcaaca gtcgcgcga ctcgaacatc gagttttcg     480

```
tgttcgtgca cctcctgaca aagtttctcg actggagcga cacgttcatg atgatcctca    540
agaaaaacta cgcccaggtt agctttctgc aggtgttcca ccacgcaacg atcggcatgg    600
tgtggtcgtt ccttcttcag cgtggctggg gctcgggcac cgccgcgtac ggtgctttca    660
tcaactcggt cacgcacgtg atcatgtact cgcactactt tgccacctcg ctcaacatca    720
acaacccgtt caagcggtac atcacgagct ccagctcgc ccagtttgca agctgcatcg    780
tgcatgccct actggtgctt gccttcgagg aggtgtaccc gctcgagtac gcttacctgc    840
agatcagcta ccacatcatc atgctctacc tgttcggacg ccgcatgaac tggagccccg    900
agtggtgcac cggtgagatc gacggccttg acgccccaag cgcccccacc aagtccgagt    960
ctagatg                                                               967
```

<210> SEQ ID NO 24
<211> LENGTH: 1122
<212> TYPE: DNA
<213> ORGANISM: Artificial
<220> FEATURE:
<223> OTHER INFORMATION: cDNA (TaELO2 ORF upstream region)

<400> SEQUENCE: 24

```
cgttagaacg cgtaatacga ctcactatag ggatatcccc cgcgaggcga tggctgctcc     60
gacgacgtgg gctggcgacg tcgctcgcaa aggcgttccg caaccgcgcg ttccgctgta    120
acgagaccgt tttccctgcg ctgctgggtg gacctagcgc gtgtgtcacc tgccggcccc    180
cgttgcgtgc aaccgaattg atcgataata gaattacata acaaacaact tgctggatga    240
gtacaagacc agcgtagtgt ggctgtggga cgttgaacgg agcgggtcct gtgacggcgc    300
agaaaggaac tccgcccgag gtgaaacccc gatgcgcagg actctgcggc cacagcccct    360
ccgccagtat tccactaaaa atccgccccc tttgacaaag atcgcaaccc cgtcccatca    420
actcctcaca ataggctttc cactggcgga aacgtcccg gcacaggagt gcctcccgcg    480
gttctgcgca tacggctgac cactacgcag cgcgatatcc tccatccgcg tatatatccg    540
taaacaacgg aacattctcc ctctcaacga ggcgtggttt tcgaagccat gcctttcttc    600
cttcctactt gccttccttc tttctttctt tcttccttc ttttgcaagc gtgcgcgaac    660
ttgaaggtac tacttacact tgacagagag agatagagac ggcaattcga ccaagtactt    720
tccacgattt tttttttttt tgttttggtc gctttcgttg gtcgtgcatg atggatggcc    780
gggattttta caattggatg cgccaggctg ccacgcatgc cgtgacgctc gctcgcggcg    840
actcatgatg cttgccagtg gcagtgcatc cagctcttcc ctctgctcgt cgtgtactca    900
ctggcgatgc tctcggcgct cgttcaaggg ccatcgatcg atcgatcgat cgatcgatcg    960
atcaatcacg tttggtggac tcggcagacc ccgaacgtgt ttctcccagg acgtgccgct   1020
gtcgctcgct gatccacccg aagcgcggtc ggctggcacg gtcgctcggc tggaagttga   1080
gtagtttgct ttctgttgct gcgctgcttt gtaaacgcga cc                      1122
```

<210> SEQ ID NO 25
<211> LENGTH: 1204
<212> TYPE: DNA
<213> ORGANISM: Artificial
<220> FEATURE:
<223> OTHER INFORMATION: cDNA (TaELO2 downstream region)

<400> SEQUENCE: 25

```
acctgtttcc ggctggctcc cgagccatgc ttaccatgaa tgaacctgca aacagtctga     60
```

```
ggtccttgtg caaaccgctc agtgggacgt cgacgaagaa agaaacaatg tgtactcgtc    120
ttgctctgct cccgcgccgt tttttatcgt tgttgagacc tctcgcgcag ttttgggaat    180
caaccaaaac aagagcccgg cgtcagcgtt tgcttcgccc tcggctgcac tcgctcggca    240
cgcaggtata actgggtgag taccaagccc cgcatttgtc tgtccgcgat ccgcgcacgc    300
tgcgggtcag gacgacatcg cgctgcacgt cacagtgggt cccttttgac gtggctgcgg    360
cgatgaggag gcttggctcg gcttcatggc aaggcaacag actcgcttcc aggacgcgca    420
cgacgagcag cgctgctttg atcgaccttg cctgcgtcac cgcctcggct gctttgatcg    480
atcgttgtca ccggccgagt gaccgcgaac gcattgcccg cacggctcgg ctcggctcgg    540
accggaccgg ctcgccttgg cggcgcggcg cgatggcgac ccagacgcga ccggagccgc    600
gcgcggagga caaggccatg ttcatcttcg ggctcgggta cgttgggagc aggctcgcca    660
accagctggc ggaacagggg tggcgcgtcg cggggtcggt gagggagctc gggcgcgagg    720
acgactttgc cgagttcgaa aagtccaagc tgagcggcaa ggtgcaggtg ttccgactcc    780
cgcttgaggg cgaggacaac acgcccgctc gcgcgcggga gatacttagc gggtaccagc    840
acctgctgtt cacggcgcca gtggaccgcg cccggaactg tgaccccttc ttgggcgacc    900
ccgttctcgg ccccgtgatc gtcgagctag cagaggaggg ccgcatcgac tgggccggct    960
atctctcaac cacttcggtc tacggcaacc acgacggcga gtgggtggac gagaccacgc    1020
cgctcatgcc cacgctcaaa cgcggcgagc agcgcgtcat ggtggagcgc gccttcctgt    1080
acgagtcggg cctccggcc catatctttc ggctgccagg aatctacggc ccagggcgcg    1140
gcccgatatc acgaattctc tccctatagt gagtcgtatt acgcgttcta acgacaatat    1200
gtac                                                                 1204

<210> SEQ ID NO 26
<211> LENGTH: 31
<212> TYPE: DNA
<213> ORGANISM: Artificial
<220> FEATURE:
<223> OTHER INFORMATION: primer

<400> SEQUENCE: 26
ctcccgggtg gacctagcgc gtgtgtcacc t                                   31

<210> SEQ ID NO 27
<211> LENGTH: 25
<212> TYPE: DNA
<213> ORGANISM: Artificial
<220> FEATURE:
<223> OTHER INFORMATION: primer

<400> SEQUENCE: 27
ggtcgcgttt acaaagcagc gcagc                                          25

<210> SEQ ID NO 28
<211> LENGTH: 52
<212> TYPE: DNA
<213> ORGANISM: Artificial
<220> FEATURE:
<223> OTHER INFORMATION: primer

<400> SEQUENCE: 28
gctgcgctgc tttgtaaacg cgaccatgat tgaacaggac ggccttcacg ct            52

<210> SEQ ID NO 29
<211> LENGTH: 52
```

<212> TYPE: DNA
<213> ORGANISM: Artificial
<220> FEATURE:
<223> OTHER INFORMATION: primer

<400> SEQUENCE: 29
tcgggagcca gccggaaaca ggttcaaaag aactcgtcca ggaggcggta ga        52

<210> SEQ ID NO 30
<211> LENGTH: 23
<212> TYPE: DNA
<213> ORGANISM: Artificial
<220> FEATURE:
<223> OTHER INFORMATION: primer

<400> SEQUENCE: 30
acctgtttcc ggctggctcc cga                                        23

<210> SEQ ID NO 31
<211> LENGTH: 27
<212> TYPE: DNA
<213> ORGANISM: Artificial
<220> FEATURE:
<223> OTHER INFORMATION: primer

<400> SEQUENCE: 31
atcccggggc cgagaacggg gtcgccc                                    27

<210> SEQ ID NO 32
<211> LENGTH: 2696
<212> TYPE: DNA
<213> ORGANISM: Artificial
<220> FEATURE:
<223> OTHER INFORMATION: cDNA (TaELO2 ORF upstream/Neor/ TaELO2 ORF
      downstream)

<400> SEQUENCE: 32
ctcccgggtg gacctagcgc gtgtgtcacc tgccggcccc cgttgcgtgc aaccgaattg       60
atcgataata gaattacata caaacaact tgctggatga gtacaagacc agcgtagtgt     120
ggctgtggga cgttgaacgg agcgggtcct gtgatgcgc agaaaggaac tccgcccgag     180
gtgaaacccc gatgcgcagg actctgcggc cacagcccct ccgccagtat tccactaaaa     240
atccgcccc tttgacaaag atcgcaaccc cgtcccatca actcctcaca ataggctttc     300
cactggcgga aacgtccccg gcacaggagt gcctcccgcg gttctgcgca tacggctgac     360
cactacgcag cgcgatatcc tccatccgcg tatatatccg taaacaacgg aacattctcc     420
ctctcaacga ggcgtggttt tcgaagccat gcctttcttc cttcctactt gccttccttc     480
tttctttctt tctttccttc ttttgcaagc gtgcgcgaac ttgaaggtac tacttacact     540
tgacagagag agatagagac ggcaattcga ccaagtactt tccacgattt tttttttttt     600
tgttttggtc gctttcgttg gtcgtgcatg atggatggcc gggatttta caattggatg     660
cgccaggctg ccacgcatgc cgtgacgctt gctcgcggcg actcatgatg cttgccagtg     720
gcagtgcatc cagctcttcc ctctgctcgt cgtgtactca ctggcgatgc tctcggcgct     780
cgttcaaggg ccatcgatcg atcgatcgat cgatcgatcg atcaatcacg tttggtggac     840
tcggcagacc ccgaacgtgt ttctcccagg acgcgccgct gtcgctcgct gatccacccg     900
aagcgcggtc ggctggcacg gtcgctcggc tggaagttga gtagtttgct ttctgttgct     960
gcgctgcttt gtaaacgcga ccatgattga acaggacggc cttcacgctg gctcgcccgc    1020
tgcttgggtg gaacggctgt tcggctacga ctgggctcag cagacgatcg gctgctcgga    1080

-continued

```
cgcggccgtg ttccgcctta gcgcgcaggg ccggccggtc ctgtttgtca agaccgacct    1140
tagcggcgcc ctcaacgagc tccaggacga agctgcccgc ctcagctggc ttgccacgac    1200
gggggttccg tgcgccgctg tgctcgacgt cgtcaccgaa gccggccgcg actggctgct    1260
cctcggggaa gtgcccggcc aggacctcct cagcagccac ctcgcgcccg ctgagaaggt    1320
gtccatcatg gccgacgcca tgcgccgcct gcacaccctc gaccccgcca cctgcccctt    1380
cgaccaccag gcgaagcaca ggatcgaacg cgcccgcacg cggatggagg ctggcctcgt    1440
cgaccaagac gacctcgacg aggagcacca gggcctcgcg ccggcggaac tgttcgccag    1500
gcttaaggct aggatgccgg acggcgagga cctcgtggtc acgcacggcg acgcctgcct    1560
ccccaacatc atggtcgaga acggccgctt ctcgggcttt atcgactgcg ggcgcctggg    1620
cgtggcggac cgctaccaag acatcgcgct cgccacgcgg gacatcgccg aggagcttgg    1680
cggcgagtgg gccgaccgct ttctcgtgct ctacggcatc gccgccccgg acagccagag    1740
gattgcgttc taccgcctcc tggacgagtt cttttgaacc tgtttccggc tggctcccga    1800
gccatgctta ccatgaatga acctgcaaac agtctgaggt ccttgtgcaa accgctcagt    1860
gggacgtcga cgaagaaaga aacaatgtgt actcgtcttg ctctgctccc gcgccgtttt    1920
ttatcgttgt tgagacctct cgcgcagttt tgggaatcaa ccaaaacaag agcccggcgt    1980
cagcgtttgc ttcgccctcg gctgcactcg ctcggcacgc aggtataact gggtgagtac    2040
caagccccgc atttgtctgt ccgcgatccg cgcacgctgc gggtcaggac gacatcgcgc    2100
tgcacgtcac agtgggtccc ttttgacgtg gctgcggcga tgaggaggct tggctcggct    2160
tcatggcaag gcaacagact cgcttccggg acgcgcacga cgagcagcgc tgctttgatc    2220
gaccttgcct gcgtcaccgc ctcggctgct tgatcgatc gttgtcaccg gccgagtgac    2280
cgcgaacgca ttgcccgcac ggctcggctc ggcccggacc ggaccggctc gccttggcgg    2340
cgcggcgcga tggcgaccca gacgcggccg gagccgcgcg cggaggacaa ggccatgttc    2400
atcttcgggc tcgggtacgt tgggagcagg ctcgccaacc agctggcgga acaggggtgg    2460
cgcgtcgcgg ggtcggtgag ggagctcggg cgcgaggacg actttgccga gttcgaaaag    2520
tccaagctga gcggcaaggt gcaggtgttc cgactcccgc ttgagggcga ggacaacacg    2580
cccgctcgcg cgcgggagat acttagcggg taccagcacc tgctgttcac ggcgccagtg    2640
gaccgcgccc ggaactgtga ccccttcttg ggcgaccccg ttctcggccc cgggat       2696
```

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
ggatatcccc cgcgaggcga tggctgctcc                                      30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
tgatatcggg ccgcgccctg ggccgtagat                                      30

<210> SEQ ID NO 35
<211> LENGTH: 25
<212> TYPE: DNA
<213> ORGANISM: Artificial
<220> FEATURE:
<223> OTHER INFORMATION: primer

<400> SEQUENCE: 35
gtacgtgctc ggtgtgatgc tgctc                                    25

<210> SEQ ID NO 36
<211> LENGTH: 24
<212> TYPE: DNA
<213> ORGANISM: Artificial
<220> FEATURE:
<223> OTHER INFORMATION: primer

<400> SEQUENCE: 36
gcggcgtccg aacaggtaga gcat                                     24

<210> SEQ ID NO 37
<211> LENGTH: 35
<212> TYPE: DNA
<213> ORGANISM: Artificial
<220> FEATURE:
<223> OTHER INFORMATION: primer

<400> SEQUENCE: 37
atccgcgtat atatccgtaa acaacggaac attct                         35

<210> SEQ ID NO 38
<211> LENGTH: 26
<212> TYPE: DNA
<213> ORGANISM: Artificial
<220> FEATURE:
<223> OTHER INFORMATION: primer

<400> SEQUENCE: 38
cttcgggtgg atcagcgagc gacagc                                   26

<210> SEQ ID NO 39
<211> LENGTH: 27
<212> TYPE: DNA
<213> ORGANISM: Artificial
<220> FEATURE:
<223> OTHER INFORMATION: primer

<400> SEQUENCE: 39
gccgcagcgc ctggtgcacc cgccggg                                  27

<210> SEQ ID NO 40
<211> LENGTH: 59
<212> TYPE: DNA
<213> ORGANISM: Artificial
<220> FEATURE:
<223> OTHER INFORMATION: primer

<400> SEQUENCE: 40
tcgcgggtga gttcaggctt tttcatgttg gctagtgttg cttaggtcgc ttgctgctg    59

<210> SEQ ID NO 41
<211> LENGTH: 57
<212> TYPE: DNA
<213> ORGANISM: Artificial
<220> FEATURE:
<223> OTHER INFORMATION: primer

<400> SEQUENCE: 41
agcgacctaa gcaacactag gccaacatga aaaagcctga actcaccgcg acgtctg    57

<210> SEQ ID NO 42
<211> LENGTH: 29
<212> TYPE: DNA
<213> ORGANISM: Artificial
<220> FEATURE:
<223> OTHER INFORMATION: primer

<400> SEQUENCE: 42 ctattcctttgccctcggacgagtgctgg    29

<210> SEQ ID NO 43
<211> LENGTH: 1636
<212> TYPE: DNA
<213> ORGANISM: Artificial
<220> FEATURE:
<223> OTHER INFORMATION: cDNA (T. aureum ATCC 34304 ubiruitin promoter/
      Hygr)

<400> SEQUENCE: 43
gctagccgca gcgcctggtg cacccgccgg gcgttggttg tgtgtgctat ttactatgcc    60
taccgagaga gagagcggag cggatgcata ggaaatcggg ccacgcggga gggccatgcg   120
ttcgccccac acgccactta taccacgccc gctctctctc cggccggcag gcagcgcata   180
actataccga cgctggcagg cttggtagca actggcaggg acaactcgcg cgcgggtccc   240
ggtcgttcga tgtgccaacc cgagagaatc cagccagcag gcggttggc  ctcatcgccc   300 acctgctatg gtgcagcgaa ccaactcccg aagcggccgg ttccgcgatt ccctcttctg   360
aattctgaat tctgaactga ttccggagga gaaccctctg gaagcgcggg ttgcctctcc   420
agttctgccg aactagacag gggagtgagc atgatgagtg accctgacgc gtgagctgag   480
ctggttgctg aatatagtc gctgaacgct gggctgtgtc acgcgtccac ttcgggcaga   540
ccccaaacga caagcagaac aagcaacacc agcagcagca agcgacctaa gcaacactag   600
ccaacatgaa aaagcctgaa ctcaccgcga cgtctgtcga aagtttctg atcgaaaagt   660 tcgacagcgt ctccgacctg atgcagctct cggagggcga agaatctcgt gctttcagct   720
tcgatgtagg agggcgtgga tatgtcctgc gggtaaatag ctgcgccgat ggtttctaca   780
aagatcgtta tgtttatcgg cactttgcat cggccgcgct cccgattccg gaagtgcttg   840
acattgggga attcagcgag agcctgacct attgcatctc ccgccgtgca cagggtgtca   900
cgttgcaaga cctgcctgaa accgaactgc ccgctgttct gcagccggtc gcggaggcca   960
tggatgcgat cgctgcggcc gatcttagcc agacgagcgg ttcggccca ttcggaccgc   1020 aaggaatcgg tcaatacact acatggcgtg atttcatatg cgcgattgct gatccccatg   1080
tgtatcactg gcaaactgtg atggacgaca ccgtcagtgc gtccgtcgcg caggctctcg   1140
atgagctgat gctttgggcc gaggactgcc ccgaagtccg gcacctcgtg cacgcggatt   1200
tcggctccaa caatgtcctg acggacaatg gccgcataac agcggtcatt gactggagcg   1260
aggcgatgtt cggggattcc caatacgagg tcgccaacat cttcttctgg aggccgtggt   1320
tggcttgtat ggagcagcag acgcgctact tcgagcggag gcatccggag cttgcaggat   1380
cgccgcggct ccgggcgtat atgctccgca ttggtcttga ccaactctat cagagcttgg   1440
ttgacggcaa tttcgatgat gcagcttggg cgcaggtcg atgcgacgca atcgtccgat   1500
ccggagccgg gactgtcggg cgtacacaaa tcgcccgcag aagcgcggcc gtctggaccg   1560

```
atggctgtgt agaagtactc gccgatagtg aaaccgacg ccccagcact cgtccgaggg    1620
caaaggaata gtctag                                                  1636
```

<210> SEQ ID NO 44
<211> LENGTH: 33
<212> TYPE: DNA
<213> ORGANISM: Artificial
<220> FEATURE:
<223> OTHER INFORMATION: primer

<400> SEQUENCE: 44

```
gtgctagccg cagcgcctgg tgcacccgcc ggg                                33
```

<210> SEQ ID NO 45
<211> LENGTH: 37
<212> TYPE: DNA
<213> ORGANISM: Artificial
<220> FEATURE:
<223> OTHER INFORMATION: primer

<400> SEQUENCE: 45

```
gttctagact attcctttgc cctcggacga gtgctgg                            37
```

<210> SEQ ID NO 46
<211> LENGTH: 37
<212> TYPE: DNA
<213> ORGANISM: Artificial
<220> FEATURE:
<223> OTHER INFORMATION: primer

<400> SEQUENCE: 46

```
gttctagacc tgtttccggc tggctcccga gccatgc                            37
```

<210> SEQ ID NO 47
<211> LENGTH: 40
<212> TYPE: DNA
<213> ORGANISM: Artificial
<220> FEATURE:
<223> OTHER INFORMATION: primer

<400> SEQUENCE: 47

```
gtgctagcgg tcgcgtttac aaagcagcgc agcaacagaa                         40
```

<210> SEQ ID NO 48
<211> LENGTH: 3537
<212> TYPE: DNA
<213> ORGANISM: Artificial
<220> FEATURE:
<223> OTHER INFORMATION: cDNA (TaELO2 ORF upstream region/T. aureum ATCC
      34304 ubiquitin promotor/ Hygr /TaELO2 ORF downstream region)

<400> SEQUENCE: 48

```
ctcccgggtg gacctagcgc gtgtgtcacc tgccggcccc cgttgcgtgc aaccgaattg    60
atcgataata gaattacata acaaacaact tgctggatga gtacaagacc agcgtagtgt   120
ggctgtggga cgttgaacgg agcgggtcct gtgacggcgc agaaaggaac tccgcccgag   180
gtgaaacccc gatgcgcagg actctgcggc cacagcccct ccgccagtat tccactaaaa   240
atccgccccc tttgacaaag atcgcaaccc cgtcccatca actcctcaca ataggctttc   300
cactggcgga acgtccccg gcacaggagt gcctccgcg gttctgcgca tacggctgac    360
cactacgcag cgcgatatcc tccatccgcg tatatatccg taaacaacgg aacattctcc   420
ctctcaacga ggcgtggttt tcgaagccat gcctttcttc cttcctactt gccttccttc   480
```

```
tttctttctt tctttctttc ttttgtaagc gtgcgcgaac ttgaaggtac tacttacact    540
tgacagagag agatagagac ggcaattcga ccaagtactt tccacgattt ttttttttt    600 tgttttggtc gctttcgttg gtcgtgcatg atggatggcc gggattttta caattggatg    660
cgccaggctg ccacgcatgc cgtgacgctc gctcgcggcg actcatggtg cttgccagtg    720
gcagtgcatc cagctcttcc ctctgctcgt cgtgtactca ctggcgatgc tctcggcgct    780
cgttcaaggg ccatcgatcg atcgatcgat cgatcgatcg atcaatcacg tttggtggac    840
tcggcagacc ccgaacgtgt ttctcccagg acgtgccgct gtcgctcgct gatccacccg    900
aagcgcggtc ggctggcacg gtcgctcggc tggaagttga gtagtttgct ttctgttgct    960
gcgctgcttt gtaaacgcga ccgctagccg cagcgcctgg tgcacccgcc gggcgttggt   1020
tgtgtgtgct atttactatg cctaccgaga gagagagcgg agcggatgca taggaaatcg   1080
ggccacgcgg gagggccatg cgttcgcccc acacgccact tataccacgc ccgctctctc   1140
tccggccggc aggcagcgca taactatacc gacgctggca ggcttggtag caactggcag   1200
ggacaactcg cgcgcgggtc ccggtcgttc gatgtgccaa cccgagagaa tccagccagc   1260
agggcggttg gcctcatcgc ccacctgcta tggtgcagcg aaccaactcc cgaagcggcc   1320
ggttccgcga ttccctcttc tgaattctga attctgaact gattccggag gagaaccctc   1380
tggaagcgcg ggttgcctct ccagttctgc cgaactagac aggggagtga gcatgatgag   1440
tgaccctgac gcgtgagctg agctggttgc tggaatatag tcgctgaacg ctgggctgtg   1500
tcacgcgtcc acttcgggca gaccccaaac gacaagcaga acaagcaaca ccagcagcag   1560
caagcgacct aagcaacact agccaacatg aaaaagcctg aactcaccgc gacgtctgtc   1620
gagaagtttc tgatcgaaaa gttcgacagc gtctccgacc tgatgcagct ctcggagggc   1680
gaagaatctc gtgctttcag cttcgatgta ggagggcgtg gatatgtcct gcgggtaaat   1740
agctgcgccg atggtttcta caaagatcgt tatgtttatc ggcactttgc atcggccgcg   1800
ctcccgattc cggaagtgct tgacattggg gaattcagcg agagcctgac ctattgcatc   1860
tcccgccgtg cacagggtgt cacgttgcaa gacctgcctg aaaccgaact gcccgctgtt   1920
ctgcagccgg tcgcggaggc catggatgcg atcgctgcgg ccgatcttag ccagacgagc   1980
gggttcggcc cattcggacc gcaaggaatc ggtcaataca ctacatggcg tgatttcata   2040
tgcgcgattg ctgatcccca tgtgtatcac tggcaaactg tgatggacga caccgtcagt   2100
gcgtccgtcg cgcaggctct cgatgagctg atgctttggg ccgaggactg ccccgaagtc   2160
cggcacctcg tgcacgcgga tttcggctcc aacaatgtcc tgacggacaa tggccgcata   2220
acagcggtca ttgactggag cgaggcgatg ttcggggatt cccaatacga ggtcgccaac   2280
atcttcttct ggaggccgtg gttggcttgt atggagcagc agacgcgcta cttcgagcgg   2340
aggcatccgg agcttgcagg atcgccgcgg ctccgggcgt atatgctccg cattggtctt   2400
gaccaactct atcagagctt ggttgacggc aatttcgatg atgcagcttg ggcgcagggt   2460
cgatgcgacg caatcgtccg atccggagcc gggactgtcg ggcgtacaca atcgcccgc    2520 agaagcgcgg ccgtctggac cgatggctgt gtagaagtac tcgccgatag tggaaaccga   2580
cgccccagca ctcgtccgag ggcaaaggaa tagtctagac ctgtttccgg ctggctcccg   2640
agccatgctt accatgaatg aacctgcaaa cagtctgagg tccttgtgca aaccgctcag   2700
tgggacgtcg acgaagaaag aaacaatgtg tactcgtctt gctctgctcc cgcgccgttt   2760
tttatcgttg ttgagacctc tcgcgcagtt ttgggaatca accaaaacaa gagcccggcg   2820
```

```
tcagcgtttg cttcgccctc ggctgcactc gctcggcacg caggtataac tgggtgagta    2880
ccaagccccg catttgtctg tccgcgatcc gcgcacgctg cgggtcagga cgacatcgcg    2940
ctgcacgtca cagtgggtcc cttttgacgt ggctgcggcg atgaggaggc ttggctcggc    3000
ttcatggcaa ggcaacagac tcgcttccgg gacgcgcacg acgagcagcg ctgctttgat    3060
cgaccttgcc tgcgtcaccg cctcggctgc tttgatcgat cgttgtcacc ggccgagtga    3120
ccgcgaacgc attgcccgca cggctcggct cggcccggac cggaccggct cgccttggcg    3180
gcgcggcgcg atggcgaccc agacgcggcc ggagccgcgc gcggaggaca aggccatgtt    3240
catcttcggg ctcgggtacg ttgggagcag gctcgccaac cagctggcgg aacagggggtg   3300 gcgcgtcgcg gggtcggtga gggagctcgg gcgcgaggac gactttgccg agttcgaaaa    3360
gtccaagctg agcggcaagg tgcaggtgtt ccgactcccg cttgagggcg aggacaacac    3420
gcccgctcgc gcgcgggaga tacttagcgg gtaccagcac ctgctgttca cggcgccagt    3480
ggaccgcgcc cggaactgtg accccttctt gggcgacccc gttctcggcc ccgggat      3537
```

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
atggcgacgc gcacctcgaa gagcgctccg                                     30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
aggatcatca tgaacgtgtc gctccagtcg                                     30

<210> SEQ ID NO 51
<211> LENGTH: 34
<212> TYPE: DNA
<213> ORGANISM: Artificial
<220> FEATURE:
<223> OTHER INFORMATION: primer

<400> SEQUENCE: 51
cagatctgga tccgcgaaat gaccgaccaa gcga                                34

<210> SEQ ID NO 52
<211> LENGTH: 24
<212> TYPE: DNA
<213> ORGANISM: Artificial
<220> FEATURE:
<223> OTHER INFORMATION: primer

<400> SEQUENCE: 52
acgcaattaa tgtgagatct agct                                           24

<210> SEQ ID NO 53
<211> LENGTH: 342
<212> TYPE: DNA
<213> ORGANISM: Artificial
<220> FEATURE:
<223> OTHER INFORMATION: SV40 terminator

<400> SEQUENCE: 53

```
cagatctgga tccgcgaaat gaccgaccaa gcgacgccca acctgccatc acgagatttc      60
gattccaccg ccgccttcta tgaaaggttg ggcttcggaa tcgttttccg ggacgccggc     120
tggatgatcc tccagcgcgg ggatctcatg ctggagttct tcgcccaccc caacttgttt    180
attgcagctt ataatggtta caaataaagc aatagcatca caaatttcac aaataaagca    240
ttttttcac tgcattctag ttgtggtttg tccaaactca tcaatgtatc ttatcatgtc     300
tgtataccgt cgacctctag ctagatctca cattaattgc gt                       342
```

<210> SEQ ID NO 54
<211> LENGTH: 619
<212> TYPE: DNA
<213> ORGANISM: Artificial
<220> FEATURE:
<223> OTHER INFORMATION: ubiquitin promoter

<400> SEQUENCE: 54

```
cccagatctg ccgcagcgcc tggtgcaccc gccgggcgtt gttggtgtgc tcttcttgcc      60
tccgagagag agagcggagc ggatgcatag gaaatcgggc cacgcgggag gccatgcgt     120
tcgccccaca cgccactttc cacgcccgct ctctctccgg ccggcaggca gcgcataact    180
ctccgacgct ggcaggctgg tagcaactgg caggacaac tcgcgcgcgg gtcccggtcg     240
ttcgatgtgc caacccgaga gaatccagcc agcagggcgg ttggcctcat cgcccacctg    300
ctatggtgca gcgaaccaac tcccgaagcg gccggttctg cgattccctc ttctgaattc    360
tgaattctga actgattccg gaggagaacc ctctggaagc gcgggttgcc tctccagttc    420
tgccgaacta gacaggggag tgagcagaga gtgaccctga cgcggagcg agctggttgc     480
tggaaaagtc gcgaacgctg ggctgtgtca cgcgtccact tcgggcagac cccaaacgac    540
aagcagaaca gcaacacca gcagcagcaa gcgacctaag caacactagc caacatgatt    600
gaacaggacg gccttcacg                                                619
```

<210> SEQ ID NO 55
<211> LENGTH: 36
<212> TYPE: DNA
<213> ORGANISM: Artificial
<220> FEATURE:
<223> OTHER INFORMATION: primer

<400> SEQUENCE: 55

```
cccagatctg ccgcagcgcc tggtgcaccc gccggg                               36
```

<210> SEQ ID NO 56
<211> LENGTH: 58
<212> TYPE: DNA
<213> ORGANISM: Artificial
<220> FEATURE:
<223> OTHER INFORMATION: primer

<400> SEQUENCE: 56

```
cgtgaaggcc gtcctgttca atcatgttgg ctagtgttgc ttaggtcgct tgctgctg       58
```

<210> SEQ ID NO 57
<211> LENGTH: 826
<212> TYPE: DNA
<213> ORGANISM: Artificial
<220> FEATURE:
<223> OTHER INFORMATION: Neomycin resistance gene (Neor)

<400> SEQUENCE: 57

```
agcgacctaa gcaacactag ccaacatgat tgaacaggac ggccttcacg ctggctcgcc    60
cgctgcttgg gtggaacggc tgttcggcta cgactgggct cagcagacga tcggctgctc   120
ggacgcggcc gtgttccgcc ttagcgcgca gggccggccg gtcctgtttg tcaagaccga   180
ccttagcggc gccctcaacg agctccagga cgaagctgcc cgcctcagct ggcttgccac   240
gacgggggtt ccgtgcgccg ctgtgctcga cgtcgtcacc gaagccggcc gcgactggct   300
gctcctcggg gaagtgcccg gccaggacct cctcagcagc acctcgcgc ccgctgagaa   360
ggtgtccatc atggccgacg ccatgcgccg cctgcacacc ctcgaccccg ccacctgccc   420
cttcgaccac caggcgaagc acaggatcga acgcgcccgc acgcggatgg aggctggcct   480
cgtcgaccaa gacgacctcg acgaggagca ccagggcctc cgcgccggcgg aactgttcgc   540
caggcttaag gctaggatgc cggacggcga ggacctcgtg gtcacgcacg cgacgcctg   600
cctccccaac atcatggtcg agaacggccg cttctcgggc tttatcgact gcgggcgcct   660
gggcgtggcg gaccgctacc aagacatcgc gctcgccacg cggacatcg ccgaggagct   720
tggcggcgag tgggccgacc gctttctcgt gctctacggc atcgccgccc cggacagcca   780
gaggattgcg ttctaccgcc tcctggacga gttcttttga gatctg                 826
```

<210> SEQ ID NO 58
<211> LENGTH: 54
<212> TYPE: DNA
<213> ORGANISM: Artificial
<220> FEATURE:
<223> OTHER INFORMATION: primer

<400> SEQUENCE: 58

```
agcgacctaa gcaacactag ccaacatgat tgaacaggac ggccttcacg ctgg          54
```

<210> SEQ ID NO 59
<211> LENGTH: 26
<212> TYPE: DNA
<213> ORGANISM: Artificial
<220> FEATURE:
<223> OTHER INFORMATION: primer

<400> SEQUENCE: 59

```
cagatctcaa aagaactcgt ccagga                                         26
```

<210> SEQ ID NO 60
<211> LENGTH: 1395
<212> TYPE: DNA
<213> ORGANISM: Artificial
<220> FEATURE:
<223> OTHER INFORMATION: fusion DNA (T. aureum ATCC 34304 ubiquitin
      promoter/Neor)

<400> SEQUENCE: 60

```
cccagatctg ccgcagcgcc tggtgcaccc gccgggcgtt gttggtgtgc tcttcttgcc    60
tccgagagag agagcggagc ggatgcatag gaaatcgggc cacgcgggag ggccatgcgt   120
tcgccccaca cgccactttc cacgcccgct ctctctccgg ccggcaggca gcgcataact   180
ctccgacgct ggcaggctgg tagcaactgg caggacaac tcgcgcgcgg gtcccggtcg   240
ttcgatgtgc caacccgaga gaatccagcc agcagggcgg ttggcctcat cgcccacctg   300
ctatggtgca gcgaaccaac tcccgaagcg gccggttctg cgattccctc ttctgaattc   360
tgaattctga actgattccg gaggagaacc ctctggaagc gcgggttgcc ctctccagttc   420
```

```
tgccgaacta gacagggag tgagcagaga gtgaccctga cgcgggagcg agctggttgc      480
tggaaaagtc gcgaacgctg gctgtgtca cgcgtccact cgggcagac cccaaacgac      540 aagcagaaca agcaacacca gcagcagcaa gcgacctaag caacactagc caacatgatt    600
gaacaggacg gccttcacgc tggctcgccc gctgcttggg tggaacggct gttcggctac    660
gactgggctc agcagacgat cggctgctcg gacgcggccg tgttccgcct tagcgcgcag    720
ggccggccgg tcctgtttgt caagaccgac cttagcggcg ccctcaacga gctccaggac    780
gaagctgccc gcctcagctg gcttgccacg acggggttc cgtgcgccgc tgtgctcgac     840
gtcgtcaccg aagccggccg cgactggctg ctcctcgggg aagtgccgg ccaggacctc     900 ctcagcagcc acctcgcgcc cgctgagaag gtgtccatca tggccgacgc catgcgccgc   960
ctgcacaccc tcgaccccgc cacctgcccc ttcgaccacc aggcgaagca caggatcgaa  1020
cgcgcccgca cgcggatgga ggctggcctc gtcgaccaag acgacctcga cgaggagcac  1080
cagggcctcg cgccggcgga actgttcgcc aggcttaagg ctaggatgcc ggacggcgag  1140
gacctcgtgg tcacgcacgg cgacgcctgc ctccccaaca tcatggtcga aacggccgc   1200 ttctcgggct ttatcgactg cgggcgcctg ggcgtggcgg accgctacca agacatcgcg  1260
ctcgccacgc gggacatcgc cgaggagctt ggcggcgagt gggccgaccg ctttctcgtg  1320
ctctacggca tcgccgcccc ggacagccag aggattgcgt tctaccgcct cctggacgag  1380
ttcttttgag atctg                                                    1395
```

<210> SEQ ID NO 61
<211> LENGTH: 617
<212> TYPE: DNA
<213> ORGANISM: Artificial
<220> FEATURE:
<223> OTHER INFORMATION: ubiquitin promoter

<400> SEQUENCE: 61

```
cccagatctg ccgcagcgcc tggtgcaccc gccgggcgtt gttgtgtgct cttcttgcct    60
ccgagagaga gagcggagcg gatgcatagg aaatcgggcc acgcgggagg gccatgcgtt   120
cgccccacac gccactttcc acgcccgctc tctctccggc cggcaggcag cgcataactc   180
tccgacgctg gcaggctggt agcaactggc agggacaact cgcgcgcggg tcccggtcgt   240
tcgatgtgcc aacccgagag aatccagcca gcagggcggt tggcctcatc gcccacctgc   300
tatggtgcag cgaaccaact cccgaagcgg ccggttctgc gattccctct tctgaattct   360
gaattctgaa ctgattccgg aggagaaccc tctggaagcg cgggttgcct ctccagttct   420
gccgaactag acaggggagt gagcagagag tgaccctgac gcggagcgag ctggttgctg   480
gaaaagtcgc gaacgctggg ctgtgtcacg cgtccacttc gggcagaccc caaacgacaa   540
gcagaacaag caacaccagc agcagcaagc gacctaagca acactagcca acatgaaaaa   600
gcctgaactc accgcga                                                   617
```

<210> SEQ ID NO 62
<211> LENGTH: 58
<212> TYPE: DNA
<213> ORGANISM: Artificial
<220> FEATURE:
<223> OTHER INFORMATION: primer

<400> SEQUENCE: 62

```
tcgcggtgag ttcaggcttt ttcatgttgg ctagtgttgc ttaggtcgct tgctgctg      58
```

<210> SEQ ID NO 63
<211> LENGTH: 1058
<212> TYPE: DNA
<213> ORGANISM: Artificial
<220> FEATURE:
<223> OTHER INFORMATION: Hygromycin resistance gene (Hygr)

<400> SEQUENCE: 63

```
agcgacctaa gcaacactag ccaacatgaa aaagcctgaa ctcaccgcga cgtctgtcga      60
gaagtttctg atcgaaaagt tcgacagcgt ctccgacctg atgcagctct cggagggcga     120
agaatctcgt gctttcagct tcgatgtagg agggcgtgga tatgtcctgc gggtaaatag     180
ctgcgccgat ggtttctaca agatcgtta tgtttatcgg cactttgcat cggccgcgct     240
cccgattccg gaagtgcttg acattgggga attcagcgag agcctgacct attgcatctc     300
cgccgtgca cagggtgtca cgttgcaaga cctgcctgaa accgaactgc ccgctgttct     360
gcagccggtc gcggaggcca tggatgcgat cgctgcggcc gatcttagcc agacgagcgg     420
gttcggccca ttcggaccgc aaggaatcgg tcaatacact acatggcgtg atttcatatg     480
cgcgattgct gatccccatg tgtatcactg gcaaactgtg atggacgaca ccgtcagtgc     540
gtccgtcgcg caggctctcg atgagctgat gctttgggcc gaggactgcc ccgaagtccg     600
gcacctcgtg cacgcggatt tcggctccaa caatgtcctg acggacaatg gccgcataac     660
agcggtcatt gactggagcg aggcgatgtt cggggattcc caatacgagg tcgccaacat     720
cttcttctgg aggccgtggt tggcttgtat ggagcagcag acgcgctact cgagcggag     780
gcatccggag cttgcaggat cgccgcggct ccgggcgtat atgctccgca ttggtcttga     840
ccaactctat cagagcttgg ttgacggcaa tttcgatgat gcagcttggg cgcagggtcg     900
atgcgacgca atcgtccgat ccggagccgg gactgtcggg cgtacacaaa tcgcccgcag     960
aagcgcggcc gtctggaccg atggctgtgt agaagtactc gccgatagtg gaaaccgacg    1020
ccccagcact cgtccgaggg caaaggaata gagatctg                             1058
```

<210> SEQ ID NO 64
<211> LENGTH: 56
<212> TYPE: DNA
<213> ORGANISM: Artificial
<220> FEATURE:
<223> OTHER INFORMATION: primer

<400> SEQUENCE: 64

```
agcgacctaa gcaacactag ccaacatgaa aaagcctgaa ctcaccgcga cgtctg         56
```

<210> SEQ ID NO 65
<211> LENGTH: 36
<212> TYPE: DNA
<213> ORGANISM: Artificial
<220> FEATURE:
<223> OTHER INFORMATION: primer

<400> SEQUENCE: 65

```
cagatctcta ttcctttgcc ctcggacgag tgctgg                               36
```

<210> SEQ ID NO 66
<211> LENGTH: 1625
<212> TYPE: DNA
<213> ORGANISM: Artificial
<220> FEATURE:
<223> OTHER INFORMATION: fusion DNA (Thraustochytrium aureum ATCC 34304
       ubiquitin promoter-pcDNA 3.1/ Hygr)

<400> SEQUENCE: 66

-continued

| | |
|---|---|
| cccagatctg ccgcagcgcc tggtgcaccc gccgggcgtt gttgtgtgct cttcttgcct | 60 |
| ccgagagaga gagcggagcg gatgcatagg aaatcgggcc acgcgggagg gccatgcgtt | 120 |
| cgccccacac gccactttcc acgcccgctc tctctccggc cggcaggcag cgcataactc | 180 |
| tccgacgctg gcaggctggt agcaactggc agggacaact cgcgcgcggg tcccggtcgt | 240 |
| tcgatgtgcc aacccgagag aatccagcca gcagggcggt tggcctcatc gcccacctgc | 300 |
| tatggtgcag cgaaccaact cccgaagcgg ccggttctgc gattccctct tctgaattct | 360 |
| gaattctgaa ctgattccgg aggagaaccc tctggaagcg cgggttgcct ctccagttct | 420 |
| gccgaactag acaggggagt gagcagagag tgaccctgac gcggagcgag ctggttgctg | 480 |
| gaaaagtcgc gaacgctggg ctgtgtcacg cgtccacttc gggcagaccc caaacgacaa | 540 |
| gcagaacaag caacaccagc agcagcaagc gacctaagca acactagcca acatgaaaaa | 600 |
| gcctgaactc accgcgacgt ctgtcgagaa gtttctgatc gaaaagttcg acagcgtctc | 660 |
| cgacctgatg cagctctcgg agggcgaaga atctcgtgct ttcagcttcg atgtaggagg | 720 |
| gcgtggatat gtcctgcggg taaatagctg cgccgatggt ttctacaaag atcgttatgt | 780 |
| ttatcggcac tttgcatcgg ccgcgctccc gattccggaa gtgcttgaca ttggggaatt | 840 |
| cagcgagagc ctgacctatt gcatctcccg ccgtgcacag ggtgtcacgt tgcaagacct | 900 |
| gcctgaaacc gaactgcccg ctgttctgca gccggtcgcg gaggcatgg atgcgatcgc | 960 |
| tgcggccgat cttagccaga cgagcgggtt cggcccattc ggaccgcaag gaatcggtca | 1020 |
| atacactaca tggcgtgatt tcatatgcgc gattgctgat ccccatgtgt atcactggca | 1080 |
| aactgtgatg gacgacaccg tcagtgcgtc cgtcgcgcag gctctcgatg agctgatgct | 1140 |
| ttgggccgag gactgccccg aagtccggca cctcgtgcac gcggatttcg gctccaacaa | 1200 |
| tgtcctgacg gacaatggcc gcataacagc ggtcattgac tggagcgagg cgatgttcgg | 1260 |
| ggattcccaa tacgaggtcg ccaacatctt cttctggagg ccgtggttgg cttgtatgga | 1320 |
| gcagcagacg cgctacttcg agcggaggca tccggagctt gcaggatcgc cgcggctccg | 1380 |
| ggcgtatatg ctccgcattg gtcttgacca actctatcag agcttggttg acggcaattt | 1440 |
| cgatgatgca gcttgggcgc agggtcgatg cgacgcaatc gtccgatccg gagccgggac | 1500 |
| tgtcgggcgt acacaaatcg cccgcagaag cgcggccgtc tggaccgatg gctgtgtaga | 1560 |
| agtactcgcc gatagtggaa accgacgccc cagcactcgt ccgagggcaa aggaatagag | 1620 |
| atctg | 1625 |

<210> SEQ ID NO 67
<211> LENGTH: 25
<212> TYPE: DNA
<213> ORGANISM: Artificial
<220> FEATURE:
<223> OTHER INFORMATION: primer

<400> SEQUENCE: 67

| | |
|---|---|
| ccttcggcgc tcctcttatg tatgt | 25 |

<210> SEQ ID NO 68
<211> LENGTH: 25
<212> TYPE: DNA
<213> ORGANISM: Artificial
<220> FEATURE:
<223> OTHER INFORMATION: primer

<400> SEQUENCE: 68
caatgcaaga ggcgaactgg gagag          25

<210> SEQ ID NO 69
<211> LENGTH: 25
<212> TYPE: DNA
<213> ORGANISM: Artificial
<220> FEATURE:
<223> OTHER INFORMATION: primer

<400> SEQUENCE: 69
tggggctctg gaaccgctgc ttacg          25

<210> SEQ ID NO 70
<211> LENGTH: 25
<212> TYPE: DNA
<213> ORGANISM: Artificial
<220> FEATURE:
<223> OTHER INFORMATION: primer

<400> SEQUENCE: 70
cttccagctc tcccagttcg cctct          25

<210> SEQ ID NO 71
<211> LENGTH: 25
<212> TYPE: DNA
<213> ORGANISM: Artificial
<220> FEATURE:
<223> OTHER INFORMATION: primer

<400> SEQUENCE: 71
cgggttgttg atgttgagcg aggtg          25

<210> SEQ ID NO 72
<211> LENGTH: 25
<212> TYPE: DNA
<213> ORGANISM: Artificial
<220> FEATURE:
<223> OTHER INFORMATION: primer

<400> SEQUENCE: 72
cccacgccat ccacgagcac accac          25

<210> SEQ ID NO 73
<211> LENGTH: 957
<212> TYPE: DNA
<213> ORGANISM: Artificial
<220> FEATURE:
<223> OTHER INFORMATION: cDNA (Parietichytrium genomic DNA contains C20
     elongase coding region)

<400> SEQUENCE: 73
cccggatcca tggcagctcg cgtggagaaa cagcaggcac ctgcgaaggc cgccaagaag      60
gtggggtcgc gtgtggaccg cagtgatggg ttctttcgca ctttcaacct ctgtgcgctg     120
tacggaagcg cgttcgcgta cgcttacaac aatgggccag tggacaacga cggcaagggc     180
ttgtactttt caaagtctcc attctacgca ttcctcgtct cggacgccat gaccttcggc     240
gctcctctta tgtatgtaat tgctgtcatg gcactcagcc gatacatggc agacaagcag     300
cccctcactg gcttcattaa aagctacatt cagccagttt acaacattgt gcaaatcgtg     360
gtgtgctcgt ggatggcgtg gggccttttg ccacaggtgg acatcttcaa cctcaaccca     420
ttcggtctca acaagcagcg tgatgccaac atcgagttct tgtcatggt ccacctcctg      480 acaaagttcc tcgactggac cgacaccttc atcatgattt tcaagaagaa ctatgcacag     540

```
gtctcttttc tccaggtgtt ccaccatgcc accatcggaa tggtgtggtc cttcctcctc    600
cagcgcggct ggggctctgg aaccgctgct tacggagcgt tcatcaactc ggtcacccat    660
gtcatcatgt acactcatta ctttgtcacc tcgctcaaca tcaacaaccc gttcaagagg    720
tacatcaccg gcttccagct ctcccagttc gcctcttgca ttgtacatgc tctcctcgtc    780
cttgccttcg aggaggtgta ccccctcgag tacgcttacc ttcagatcag ctaccacatc    840
atcatgctct acctcttcgg caggagaatg aactggagcc ctctctggtg cactggcgag    900
gtcgacgggc ttgacgtcaa cgtcgagacc tccaagaagg ctcagtaagg atccggg      957
```

<210> SEQ ID NO 74
<211> LENGTH: 32
<212> TYPE: DNA
<213> ORGANISM: Artificial
<220> FEATURE:
<223> OTHER INFORMATION: primer

<400> SEQUENCE: 74

```
cccggatcca tggcagctcg cgtggagaaa ca                                   32
```

<210> SEQ ID NO 75
<211> LENGTH: 33
<212> TYPE: DNA
<213> ORGANISM: Artificial
<220> FEATURE:
<223> OTHER INFORMATION: primer

<400> SEQUENCE: 75

```
cccggatcct tactgagcct tcttggaggt ctc                                  33
```

<210> SEQ ID NO 76
<211> LENGTH: 936
<212> TYPE: DNA
<213> ORGANISM: Artificial
<220> FEATURE:
<223> OTHER INFORMATION: genomic DNA (Parietichytrium C20 elongase gene)

<400> SEQUENCE: 76

```
atggcagctc gcgtggagaa acagcaggca cctgcgaagg ccgccaagaa ggtggggtcg    60
cgtgtggacc gcagtgatgg gttctttcgc actttcaacc tctgtgcgct gtacggaagc   120
gcgttcgcgt acgcttacaa caatgggcca gtggacaacg acggcaaggg cttgtacttt   180
tcaaagtctc cattctacgc attcctcgtc tcggacgcca tgaccttcgg cgctcctctt   240
atgtatgtaa ttgctgtcat ggcactcagc cgatacatgg cagacaagca gcccctcact   300
ggcttcatta aaagctacat tcagccagtt tacaacattg tgcaaatcgt ggtgtgctcg   360
tggatggcgt ggggcctttt gccacaggtg gacatcttca acctcaaccc attcggtctc   420
aacaagcagc gtgatgccaa catcgagttc tttgtcatgg tccacctcct gacaaagttc   480
ctcgactgga ccgacacctt catcatgatt ttcaagaaga actatgcaca ggtctctttt   540
ctccaggtgt tccaccatgc caccatcgga atggtgtggt ccttcctcct ccagcgcggc   600
tggggctctg gaaccgctgc ttacggagcg ttcatcaact cggtcaccca tgtcatcatg   660
tacactcatt actttgtcac ctcgctcaac atcaacaacc cgttcaagag gtacatcacc   720
ggcttccagc tctcccagtt cgcctcttgc attgtacatg ctctcctcgt ccttgccttc   780
gaggaggtgt accccctcga gtacgcttac cttcagatca gctaccacat catcatgctc   840
tacctcttcg gcaggagaat gaactggagc cctctctggt gcactggcga ggtcgacggg   900
cttgacgtca acgtcgagac ctccaagaag gctcag                             936
```

<210> SEQ ID NO 77
<211> LENGTH: 312
<212> TYPE: PRT
<213> ORGANISM: Parietichytrium

<400> SEQUENCE: 77

Met Ala Ala Arg Val Glu Lys Gln Gln Ala Pro Ala Lys Ala Lys
1               5                   10                  15

Lys Val Gly Ser Arg Val Asp Arg Ser Asp Gly Phe Phe Arg Thr Phe
            20                  25                  30

Asn Leu Cys Ala Leu Tyr Gly Ser Ala Phe Ala Tyr Ala Tyr Asn Asn
            35                  40                  45

Gly Pro Val Asp Asn Asp Gly Lys Gly Leu Tyr Phe Ser Lys Ser Pro
50                  55                  60

Phe Tyr Ala Phe Leu Val Ser Asp Ala Met Thr Phe Gly Ala Pro Leu
65                  70                  75                  80

Met Tyr Val Ile Ala Val Met Ala Leu Ser Arg Tyr Met Ala Asp Lys
                85                  90                  95

Gln Pro Leu Thr Gly Phe Ile Lys Ser Tyr Ile Gln Pro Val Tyr Asn
            100                 105                 110

Ile Val Gln Ile Val Val Cys Ser Trp Met Ala Trp Gly Leu Leu Pro
            115                 120                 125

Gln Val Asp Ile Phe Asn Leu Asn Pro Phe Gly Leu Asn Lys Gln Arg
130                 135                 140

Asp Ala Asn Ile Glu Phe Phe Val Met Val His Leu Leu Thr Lys Phe
145                 150                 155                 160

Leu Asp Trp Thr Asp Thr Phe Ile Met Ile Phe Lys Lys Asn Tyr Ala
                165                 170                 175

Gln Val Ser Phe Leu Gln Val Phe His His Ala Thr Ile Gly Met Val
            180                 185                 190

Trp Ser Phe Leu Leu Gln Arg Gly Trp Gly Ser Gly Thr Ala Ala Tyr
            195                 200                 205

Gly Ala Phe Ile Asn Ser Val Thr His Val Ile Met Tyr Thr His Tyr
210                 215                 220

Phe Val Thr Ser Leu Asn Ile Asn Asn Pro Phe Lys Arg Tyr Ile Thr
225                 230                 235                 240

Gly Phe Gln Leu Ser Gln Phe Ala Ser Cys Ile Val His Ala Leu Leu
                245                 250                 255

Val Leu Ala Phe Glu Glu Val Tyr Pro Leu Gly Tyr Ala Tyr Leu Gln
            260                 265                 270

Ile Ser Tyr His Ile Ile Met Leu Tyr Leu Phe Gly Arg Arg Met Asn
            275                 280                 285

Trp Ser Pro Leu Trp Cys Thr Gly Glu Val Asp Gly Leu Asp Val Asn
290                 295                 300

Val Glu Thr Ser Lys Lys Ala Gln
305                 310

<210> SEQ ID NO 78
<211> LENGTH: 26
<212> TYPE: DNA
<213> ORGANISM: Artificial
<220> FEATURE:
<223> OTHER INFORMATION: primer

<400> SEQUENCE: 78
acaaagatct cgactggacc gacacc                                          26

<210> SEQ ID NO 79
<211> LENGTH: 27
<212> TYPE: DNA
<213> ORGANISM: Artificial
<220> FEATURE:
<223> OTHER INFORMATION: primer

<400> SEQUENCE: 79
agtcgagatc tttgtcagga ggtggac                                         27

<210> SEQ ID NO 80
<211> LENGTH: 935
<212> TYPE: DNA
<213> ORGANISM: Artificial
<220> FEATURE:
<223> OTHER INFORMATION: BglII inserted C20 elongase

<400> SEQUENCE: 80
atggcagctc gcgtggagaa acagcaggca cctgcgaagg ccgccaagaa ggtggggtcg     60
cgtgtggacc gcagtgatgg gttctttcgc actttcaacc tctgtgcgct gtacggaagc    120
gcgttcgcgt acgcttacaa caatgggcca gtggacaacg acggcaaggg cttgtacttt    180
tcaaagtctc cattctacgc attcctcgtc tcggacgcca tgaccttcgg cgctcctctt    240
atgtatgtaa ttgctgtcat ggcactcagc cgatacatgg cagacaagca gcccctcact    300
ggcttcatta aaagctacat tcagccagtt tacaacattg tgcaaatcgt ggtgtgctcg    360
tggatggcgt ggggcctttt gccacaggtg gacatcttca acctcaaccc attcggtctc    420
aacaagcagc gtgatgccaa catcgagttc tttgtcatgg tccacctcct gacaaagatc    480
tcgactggac cgacaccttc atcatgattt caagaagaa ctatgcacag gtctcttttc    540
tccaggtgtt ccaccatgcc accatcggaa tggtgtggtc cttcctcctc agcgcggct    600 gggggctctgg aaccgctgct tacgagcgt tcatcaactc ggtcacccat gtcatcatgt    660
acactcatta ctttgtcacc tcgctcaaca tcaacaaccc gttcaagagg tacatcaccg    720
gcttccagct ctcccagttc gcctcttgca ttgtacatgc tctcctcgtc cttgccttcg    780
aggaggtgta ccccctcgag tacgcttacc ttcagatcag ctaccacatc atcatgctct    840
acctcttcgg caggagaatg aactggagcc ctctctggtg cactggcgag gtcgacgggc    900
ttgacgtcaa cgtcgagacc tccaagaagg ctcag                               935

<210> SEQ ID NO 81
<211> LENGTH: 2661
<212> TYPE: DNA
<213> ORGANISM: Artificial
<220> FEATURE:
<223> OTHER INFORMATION: fusion DNA (Parietichytrium C20 elongase 5'
      region/SV40 terminator/Neor/ubiquitin promoter/Parietichytrium C20
      elongase 3' region)

<400> SEQUENCE: 81
cccggatcca tggcagctcg cgtggagaaa cagcaggcac ctgcgaaggc cgccaagaag     60
gtggggtcgc gtgtggaccg cagtgatggg ttctttcgca ctttcaacct ctgtgcgctg    120
tacggaagcg cgttcgcgta cgcttacaac aatgggccag tggacaacga cggcaagggc    180
ttgtactttt caaagtctcc attctacgca ttcctcgtct cggacgccat gaccttcggc    240
gctcctctta tgtatgtaat tgctgtcatg gcactcagcc gatacatggc agacaagcag    300
cccctcactg gcttcattaa aagctacatt cagccagttt acaacattgt gcaaatcgtg    360

-continued

```
gtgtgctcgt ggatggcgtg gggccttttg ccacaggtgg acatcttcaa cctcaaccca      420
ttcggtctca acaagcagcg tgatgccaac atcgagttct tgtcatggt ccacctcctg       480 acaaagatct agctagaggt cgacggtata cagacatgat aagatacatt gatgagtttg      540
gacaaaccac aactagaatg cagtgaaaaa aatgctttat ttgtgaaatt tgtgatgcta      600
ttgctttatt tgtaaccatt ataagctgca ataaacaagt tggggtgggc aagaactcc       660 agcatgagat ccccgcgctg gaggatcatc cagccggcgt cccggaaaac gattccgaag      720
cccaaccttt catagaaggc ggcggtggaa tcgaaatctc gtgatggcag gttgggcgtc      780
gcttggtcgg tcatttcgcg gatctcaaaa gaactcgtcc aggaggcggt agaacgcaat      840
cctctggctg tccggggcgg cgatgccgta gagcacgaga aagcggtcgg cccactcgcc      900
gccaagctcc tcggcgatgt cccgcgtggc gagcgcgatg tcttggtagc ggtccgccac      960
gcccaggcgc ccgcagtcga taaagcccga gaagcggccg ttctcgacca tgatgttggg     1020
gaggcaggcg tcgccgtgcg tgaccacgag gtcctcgccg tccggcatcc tagccttaag     1080
cctggcgaac agttccgccg gcgcgaggcc ctggtgctcc tcgtcgaggt cgtcttggtc     1140
gacgaggcca gcctccatcc gcgtgcgggc gcgttcgatc ctgtgcttcg cctggtggtc     1200
gaaggggcag gtggcggggt cgagggtgtg caggcggcgc atggcgtcgg ccatgatgga     1260
caccttctca gcgggcgcga ggtggctgct gaggaggtcc tggccgggca cttccccgag     1320
gagcagccag tcgcggccgg cttcggtgac gacgtcgagc acagcggcgc acggaacccc     1380
cgtcgtggca agccagctga ggcgggcagc ttcgtcctgg agctcgttga gggcgccgct     1440
aaggtcggtc ttgacaaaca ggaccggccg gccctgcgcg ctaaggcgga cacggccgc      1500 gtccgagcag ccgatcgtct gctgagccca gtcgtagccg aacagccgtt ccacccaagc     1560
agcgggcgag ccagcgtgaa ggccgtcctg ttcaatcatg ttggctagtg ttgcttaggt     1620
cgcttgctgc tgctggtgtt gcttgttctg cttgtcgttt ggggtctgcc cgaagtggac     1680
gcgtgacaca gcccagcgtt cgcgacttt ccagcaacca gctcgctccg cgtcagggtc      1740
actctctgct cactcccctg tctagttcgg cagaactgga gaggcaaccc gcgcttccag     1800
agggttctcc tccggaatca gttcagaatt cagaattcag aagagggaat cgcagaaccg     1860
gccgcttcgg gagttggttc gctgcaccat agcaggtggg cgatgaggcc aaccgccctg     1920
ctggctggat tctctcgggt tggcacatcg aacgaccggg accgcgcgc gagttgtccc      1980 tgccagttgc taccagcctg ccagcgtcgg agagttatgc gctgcctgcc ggccggagag     2040
agagcgggcg tggaaagtgg cgtgtggggc gaacgcatgg ccctcccgcg tggcccgatt     2100
tcctatgcat ccgctccgct ctctctctcg gaggcaagaa gagcacacca acaacgcccg     2160
gcgggtgcac caggcgctgc ggcagatcca gatctcgact ggaccgacac cttcatcatg     2220
attttcaaga agaactatgc acaggtctct tttctccagg tgttccacca tgccaccatc     2280
ggaatggtgt ggtccttcct cctccagcgc ggctgggct ctggaaccgc tgcttacgga      2340
gcgttcatca actcggtcac ccatgtcatc atgtacactc attactttgt cacctcgctc     2400
aacatcaaca acccgttcaa gaggtacatc accggcttcc agctctccca gttcgcctct     2460
tgcattgtac atgctctcct cgtccttgcc ttcgaggagt gtaccccct cgagtacgct      2520 taccttcaga tcagctacca catcatcatg ctctacctct tcggcaggag aatgaactgg     2580
agccctctct ggtgcactgg cgaggtcgac gggcttgacg tcaacgtcga gacctccaag     2640
aaggctcagt aaggatccgg g                                                2661
```

<210> SEQ ID NO 82
<211> LENGTH: 2892
<212> TYPE: DNA
<213> ORGANISM: Artificial
<220> FEATURE:
<223> OTHER INFORMATION: fusion DNA (Parietichytrium C20 elongase 5'
      region/SV40 terminator/Hygr/ubiquitin promoter/Parietichytrium C20
      elongase 3' region)

<400> SEQUENCE: 82

| | | | | | |
|---|---|---|---|---|---|
| cccggatcca | tggcagctcg | cgtggagaaa | cagcaggcac | ctgcgaaggc | cgccaagaag | 60 |
| gtggggtcgc | gtgtggaccg | cagtgatggg | ttctttcgca | cttcaacct | ctgtgcgctg | 120 |
| tacggaagcg | cgttcgcgta | cgcttacaac | aatgggccag | tggacaacga | cggcaagggc | 180 |
| ttgtactttt | caaagtctcc | attctacgca | ttcctcgtct | cggacgccat | gaccttcggc | 240 |
| gctcctctta | tgtatgtaat | tgctgtcatg | gcactcagcc | gatacatggc | agacaagcag | 300 |
| cccctcactg | gcttcattaa | aagctacatt | cagccagttt | acaacattgt | gcaaatcgtg | 360 |
| gtgtgctcgt | ggatggcgtg | gggccttttg | ccacaggtgg | acatcttcaa | cctcaaccca | 420 |
| ttcggtctca | acaagcagcg | tgatgccaac | atcgagttct | tgtcatggt | ccacctcctg | 480 |
| acaaagatct | agctagaggt | cgacggtata | cagacatgat | aagatacatt | gatgagtttg | 540 |
| gacaaaccac | aactagaatg | cagtgaaaaa | aatgctttat | ttgtgaaatt | tgtgatgcta | 600 |
| ttgctttatt | tgtaaccatt | ataagctgca | ataaacaagt | tggggtgggc | gaagaactcc | 660 |
| agcatgagat | ccccgcgctg | gaggatcatc | cagccggcgt | cccggaaaac | gattccgaag | 720 |
| cccaaccttt | catagaaggc | ggcggtggaa | tcgaaatctc | gtgatggcag | gttgggcgtc | 780 |
| gcttggtcgg | tcatttcgcg | gatctctatt | cctttgccct | cggacgagtg | ctggggcgtc | 840 |
| ggtttccact | atcggcgagt | acttctacac | agccatcggt | ccagacgcc | gcgcttctgc | 900 |
| gggcgatttg | tgtacgcccg | acagtcccgg | ctccggatcg | acgattgcg | tcgcatcgac | 960 |
| cctgcgccca | agctgcatca | tcgaaattgc | cgtcaaccaa | gctctgatag | agttggtcaa | 1020 |
| gaccaatgcg | gagcatatac | gcccggagcc | gcggcgatcc | tgcaagctcc | ggatgcctcc | 1080 |
| gctcgaagta | gcgcgtctgc | tgctccatac | aagccaacca | cggcctccag | aagaagatgt | 1140 |
| tggcgacctc | gtattgggaa | tccccgaaca | tcgcctcgct | ccagtcaatg | accgctgtta | 1200 |
| tgcggccatt | gtccgtcagg | acattgttgg | agccgaaatc | cgcgtgcacg | aggtgccgga | 1260 |
| cttcggggca | gtcctcggcc | caaagcatca | gctcatcgag | agcctgcgcg | acggacgcac | 1320 |
| tgacggtgtc | gtccatcaca | gtttgccagt | gatacacatg | gggatcagca | atcgcgcata | 1380 |
| tgaaatcacg | ccatgtagtg | tattgaccga | ttccttgcgg | tccgaatggg | ccgaacccgc | 1440 |
| tcgtctggct | aagatcggcc | gcagcgatcg | catccatggc | ctccgcgacc | ggctgcagaa | 1500 |
| cagcgggcag | ttcggtttca | ggcaggtctt | gcaacgtgac | accctgtgca | cggcgggaga | 1560 |
| tgcaataggt | caggctctcg | ctgaattccc | caatgtcaag | cacttccgga | atcgggagcg | 1620 |
| cggccgatgc | aaagtgccga | taaacataac | gatctttgta | gaaaccatcg | gcgcagctat | 1680 |
| ttacccgcag | gacatatcca | cgccctccta | catcgaagct | gaaagcacga | gattcttcgc | 1740 |
| cctccgagag | ctgcatcagg | tcggagacgc | tgtcgaactt | ttcgatcaga | aacttctcga | 1800 |
| cagacgtcgc | ggtgagttca | ggcttttca | tgttggctag | tgttgcttag | gtcgcttgct | 1860 |
| gctgctggtg | ttgcttgttc | tgcttgtcgt | ttggggtctg | cccgaagtgg | acgcgtgaca | 1920 |
| cagcccagct | ttcgcgactt | ttccagcaac | cagctcgctc | cgcgtcaggg | tcactctctg | 1980 |
| ctcactcccc | tgtctagttc | ggcagaactg | gagaggcaac | ccgcgcttcc | agagggttct | 2040 |

-continued

```
cctccggaat cagttcagaa ttcagaattc agaagaggga atcgcagaac cggccgcttc    2100
gggagttggt tcgctgcacc atagcaggtg ggcgatgagg ccaaccgccc tgctggctgg    2160
attctctcgg gttggcacat cgaacgaccg gacccgcgc gcgagttgtc cctgccagtt     2220
gctaccagcc tgccagcgtc ggagagttat gcgctgcctg ccggccggag agagagcggg    2280
cgtggaaagt ggcgtgtggg gcgaacgcat ggccctcccg cgtggcccga tttcctatgc    2340
atccgctccg ctctctctct cggaggcaag aagagcacac aacaacgccc ggcgggtgca    2400
ccaggcgctg cggcagatcc agatctcgac tggaccgaca ccttcatcat gattttcaag    2460
aagaactatg cacaggtctc ttttctccag gtgttccacc atgccaccat cggaatggtg    2520
tggtccttcc tcctccagcg cggctgggc tctggaaccg ctgcttacgg agcgttcatc      2580
aactcggtca cccatgtcat catgtacact cattactttg tcacctcgct caacatcaac    2640
aacccgttca agaggtacat caccggcttc cagctctccc agttcgcctc ttgcattgta    2700
catgctctcc tcgtccttgc cttcgaggag gtgtaccccc tcgagtacgc ttaccttcag    2760
atcagctacc acatcatcat gctctacctc ttcggcagga gaatgaactg gagccctctc    2820
tggtgcactg gcgaggtcga cgggcttgac gtcaacgtcg agacctccaa gaaggctcag    2880
taaggatccg gg                                                        2892
```

<210> SEQ ID NO 83
<211> LENGTH: 20
<212> TYPE: DNA
<213> ORGANISM: Artificial
<220> FEATURE:
<223> OTHER INFORMATION: primer

<400> SEQUENCE: 83
ggttgacggc aatttcgatg                                                  20

<210> SEQ ID NO 84
<211> LENGTH: 22
<212> TYPE: DNA
<213> ORGANISM: Artificial
<220> FEATURE:
<223> OTHER INFORMATION: primer

<400> SEQUENCE: 84
cctcctacat cgaagctgaa ag                                               22

<210> SEQ ID NO 85
<211> LENGTH: 21
<212> TYPE: DNA
<213> ORGANISM: Artificial
<220> FEATURE:
<223> OTHER INFORMATION: primer

<400> SEQUENCE: 85
cttctcgggc tttatcgact g                                                21

<210> SEQ ID NO 86
<211> LENGTH: 22
<212> TYPE: DNA
<213> ORGANISM: Artificial
<220> FEATURE:
<223> OTHER INFORMATION: primer

<400> SEQUENCE: 86
taaggtcggt cttgacaaac ag                                               22

<210> SEQ ID NO 87
<211> LENGTH: 24
<212> TYPE: DNA
<213> ORGANISM: Artificial
<220> FEATURE:
<223> OTHER INFORMATION: primer

<400> SEQUENCE: 87
agtagtcccc gatttggtag ttga                                          24

<210> SEQ ID NO 88
<211> LENGTH: 22
<212> TYPE: DNA
<213> ORGANISM: Artificial
<220> FEATURE:
<223> OTHER INFORMATION: primer

<400> SEQUENCE: 88
ggcagagagc aaaaacacga gc                                            22

<210> SEQ ID NO 89
<211> LENGTH: 23
<212> TYPE: DNA
<213> ORGANISM: Artificial
<220> FEATURE:
<223> OTHER INFORMATION: primer

<400> SEQUENCE: 89
cgatgaaagg tcacagaaga gtc                                           23

<210> SEQ ID NO 90
<211> LENGTH: 3181
<212> TYPE: DNA
<213> ORGANISM: Artificial
<220> FEATURE:
<223> OTHER INFORMATION: genomic DNA (T. aureum ATCC 34304 OrfA
      upstream)

<400> SEQUENCE: 90
aagcttttgc tctgcggctc tgcttgttcg aagccaacgc gcctcgcgaa gtatctgcaa    60
tctgcactcc tccggagagt aagtacgtaa gtacgtgcgt ggtgcgcgcg gattgcggtg   120
acgaaagaga gggttgggtt ggagatgctg cggcatgccg ggcgactcga gcagcatgtc   180
gccgcgagag gacctggaaa gctttcggtt tggtccgctg ccgaggcgag gctggcagag   240
tactgcgggc ggagctctcg agggaatatg ctcctcaaag acggcgtgcg cgtttgtgcc   300
cccgaatccg aatgcggaga gtcctgcgcg tttcggcccg ccgcgcgtat ccggccacgg   360
gagcgccgct gtgacgacga ggggatcaat ctgggtgcca gagtcaacgc ccagggtcgg   420
ggggatcacg ccgcgctcca ttgcaaggag aaccttgcac attcccgcaa agccggccgc   480
gacgagggtg tgtccgaagt tgcctttcgt ggacccgatc cgggggcttg cgccctcaaa   540
gcaggctttg acggcttgga gctcgacggt gtcgccctgc ggcgtgccgg tggcgtggca   600
ctcgacgtac tggacgtctc ggggcggcac gccgacgagc tcgtaggtgg cttcaagca    660 ggcctcctcg cttggctggt gcggcttgag aggaagcccg cagcctgcgt tgctcaagct   720
ggccccaaga agcgtcccgt agatgtggtc tccgtcgcgc tcggcgtccg cgaggcgctt   780
gagcaccatc accgagccgc cctcgccggg cgtcagccct tgcgtgtccc gatgaaacgg   840
catcgagaca ccgttctcac cgactggcat cgcgtggaac gtgctaaacc cagtcaggat   900
gaagaagggc tctgggaagc acgtcgctcc gcacagcatc aagtcagcct cgcccgagag   960

```
gaggtggtcc tgagcgagtc gcagaacgta aagggccgag gcgcaggcgg cgtcgagcga   1020
gtagtgcagc gggccgaggc cgagctgtcc ggcgacgaag gaggctgggt cgcggtgggt   1080
cctcgggtcc ccgggcagcg ggtgaagcgc tctggttcgc gtcgaccagg gcgtttggtc   1140
cgcgaagcaa tgcttgccaa tccgcctctc agcatgggct tggtaaaggt tgagcagctc   1200
gccttgcagg ttgtccatcg ggaaggacag gcagccgctg acaatgccgc agcgcttgag   1260
ctgcgctggg tcgaacttgc cgccgtcgct gcgcctgtcc tgcgcgtctt gaagcgcagc   1320
cgcggcgagg ccgaggagca ggtcgtgctc gttgtcgact ttgggatcga tgcatccgta   1380
cctctcgttg cagaacgtat cggcgtactt tgacctctcg ggcgcatagt gctcttctcg   1440
tcgtgctgac ccgaggcgat cgtctgagat acaggcagag ttgattttgc cgttcatgag   1500
cgtgtcccag aacgcttcct tgccgcggca ccctgcatac tcgaccgcca tgcccacgac   1560
agcgatccgc gtgtcagggc atgggtccgc gcgcgccacc gagacgccct cgtcatttct   1620
cccgccctgg ttcatctctt tctgagcctt gtggcctctt gctttcgatt tcgatcggca   1680
gctccaacgc gcagctcgat ggccgattgc ttgctaaggc ggcgtgcaga caaccgctgc   1740
tcgaggttct gggcaagccg aggttcgccg cagggttcgt ggaggcactg ggatgttgtt   1800
ttgcggcagc tgcagcgctt gcggagcgag cggcgcagga cgacgttttc cgcgttcgcg   1860
cgaagctgcc tctcggctat tgtgacccgc cgccgacgct ggcagagacg tcgccgtcgg   1920
ccaccgcacc tcgagatcaa ttcgcagagg ctggcagagc cggtagcatt gcggcgtggc   1980
attgcgtgtg ccatgtgcat gtgtggcaaa caaatccagc caacctccga gtcgggcaga   2040
ccgaccgtgt gagttctcgc tgttgactga tctcttgatt gagcccaata atgatcacgg   2100
cctgagatcc ttcgcgctga gagatgcatg cgggcgctcg ttcctgggtt ggcgacccaa   2160
cggcgagtca cgtcgcccac tccgccacgc cccacacatg gccgccgatc cctcccgcca   2220
cacgaacggc gggccaagat cgcacgcctc cgtcggacga tgactgactg actgattggc   2280
tgacgacggc cgccctcgtg cgcggcgtcg ggcgtcgtcg caaaccaggc aggcaggcag   2340
gaaggaagga aggaagggcc aggccctggt gcgaaacgct ggcctgctcc gctgcaagcc   2400
aagccgcgct cgcaggtgta cttccgagtc ctcgcgatga ttaggcaagc ctgagcgagc   2460
acgtaagctg cactgcggct gttcaaccag agagagagtt ggctctcttg cgtcaaggcg   2520
gcgcgcagcc cacttgcgtc gcggctgagg gcccctggag gggaggaagg aggccggcga   2580
gcggcgagtg gcggcccctca ctggcaccag gtcgcaggag gccaggcagc ccgccacgga   2640
caggaatcct cagggcgcag cagcgcacta cgtagtgcag agacgcagag cgggccggat   2700
ccgcagtgcg gtcgcgccac cccgccgcgc agctcgctcg cggacggggt ccgtggccgc   2760
gcgaaaacgg acacggtgtg ggagcggaca tgggatcgag aacgccgttc gccctgctcg   2820
cgctgccagc agcaggagcc gtccgaagga cgagcggccg gccgcctgtc ccccctccgc   2880
gcactcgaag cgcgcccggc agcgccccat tgcgtgcgcg gatggcgtct tggctggtcc   2940
ctctcgaggc gcttgctcgt gctcgccacg ccttgtccgc ctcctcgctg agcaagcgat   3000
gagctgagca cggaccgcct gcaagtgcaa gtgttcttgt gctgcagggc gccgaagaat   3060
tggattctgg cccatgatca gtttgattgg gccgagggag ggaggaggc tgggcgagtg   3120 ggcgacacca gcaagccgga ctgcgagagg ggcggggcag gatgtgagcg caggaaagtg   3180
a                                                                   3181

<210> SEQ ID NO 91
<211> LENGTH: 3377
```

```
<212> TYPE: DNA
<213> ORGANISM: Artificial
<220> FEATURE:
<223> OTHER INFORMATION: genomic DNA (T. aureum  ATCC 34304 OrfA
      upstream genomic DNA fragment)

<400> SEQUENCE: 91
```

| | | | | | |
|---|---|---|---|---|---|
| gaattcgatt | aatacgactc | actataggga | gaagcttttg | ctctgcggct | ctgcttgttc | 60 |
| gaagccaacg | cgcctcgcga | agtatctgca | atctgcactc | ctccggagag | taagtacgta | 120 |
| agtacgtgcg | tggtgcgcgc | ggattgcggt | gacgaaagag | agggttgggt | tggagatgct | 180 |
| gcggcatgcc | gggcgactcg | agcagcatgt | cgccgcgaga | ggacctggaa | agctttcggt | 240 |
| ttggtccgct | gccgaggcga | ggctggcaga | gtactgcggg | cggagctctc | gagggaatat | 300 |
| gctcctcaaa | gacggcgtgc | gcgtttgtgc | ccccgaatcc | gaatgcggag | agtcctgcgc | 360 |
| gtttcggccc | gccgcgcgta | tccggccacg | ggagcgccgc | tgtgacgacg | aggggatcaa | 420 |
| tctgggtgcc | agagtcaacg | cccagggtcg | ggggatcac | gccgcgctcc | attgcaagga | 480 |
| gaaccttgca | cattcccgca | aagccggccg | cgacgagggt | gtgtccgaag | ttgcctttcg | 540 |
| tggacccgat | ccgggggctt | gcgccctcaa | agcaggcttt | gacggcttgg | agctcgacgg | 600 |
| tgtcgccctg | cggcgtgccg | gtggcgtggc | actcgacgta | ctggacgtct | cggggcggca | 660 |
| cgccgacgag | ctcgtaggtg | gctttcaagc | aggcctcctc | gcttggctgg | tgcggcttga | 720 |
| gaggaagccc | gcagcctgcg | ttgctcaagc | tggcccaag | aagcgtcccg | tagatgtggt | 780 |
| ctccgtcgcg | ctcggcgtcc | gcgaggcgct | tgagcaccat | caccgagccg | ccctcgccgg | 840 |
| gcgtcagccc | ttgcgtgtcc | cgatgaaacg | gcatcgagac | accgttctca | ccgactggca | 900 |
| tcgcgtggaa | cgtgctaaac | ccagtcagga | tgaagaaggg | ctctgggaag | cacgtcgctc | 960 |
| cgcacagcat | caagtcagcc | tcgcccgaga | ggaggtggtc | ctgagcgagt | cgcagaacgt | 1020 |
| aaagggccga | ggcgcaggcg | gcgtcgagcg | agtagtgcag | cgggccgagg | ccgagctgtc | 1080 |
| cggcgacgaa | ggaggctggg | tcgcggtggg | tcctcgggtc | cccgggcagc | gggtgaagcg | 1140 |
| ctctggttcg | cgtcgaccag | ggcgtttggt | ccgcgaagca | atgcttgcca | atccgcctct | 1200 |
| cagcatgggc | ttggtaaagg | ttgagcagct | cgccttgcag | gttgtccatc | gggaaggaca | 1260 |
| ggcagccgct | gacaatgccg | cagcgcttga | gctgcgctgg | gtcgaacttg | ccgccgtcgc | 1320 |
| tgcgcctgtc | ctgcgcgtct | tgaagcgcag | ccgcggcgag | gccgaggagc | aggtcgtgct | 1380 |
| cgttgtcgac | tttgggatcg | atgcatccgt | acctctcgtt | gcagaacgta | tcggcgtact | 1440 |
| ttgacctctc | gggcgcatag | tgctcttctc | gtcgtgctga | cccgaggcga | tcgtctgaga | 1500 |
| tacaggcaga | gttgattttg | ccgttcatga | gcgtgtccca | gaacgcttcc | ttgccgcggc | 1560 |
| accctgcata | ctcgaccgcc | atgcccacga | cagcgatccg | cgtgtcaggg | catgggtccg | 1620 |
| cgcgcgccac | cgagacgccc | tcgtcatttc | tcccgccctg | gttcatctct | ttctgagcct | 1680 |
| tgtggcctct | tgctttcgat | ttcgatcggc | agctccaacg | cgcagctcga | tggccgattg | 1740 |
| cttgctaagg | cggcgtgcag | acaaccgctg | ctcgaggttc | tgggcaagcc | gaggttcgcc | 1800 |
| gcagggttcg | tggaggcact | gggatgttgt | tttgcggcag | ctgcagcgct | tgcggagcga | 1860 |
| gcggcgcagg | acgacgtttt | ccgcgttcgc | gcgaagctgc | ctctcggcta | ttgtgacccg | 1920 |
| ccgccgacgc | tggcagagac | gtcgccgtcg | gccaccgcac | ctcgagatca | attcgcagag | 1980 |
| gctggcagag | ccggtagcat | tgcggcgtgg | cattgcgtgt | gccatgtgca | tgtgtggcaa | 2040 |
| acaaatccag | ccaacctccg | agtcgggcag | accgaccgtg | tgagttctcg | ctgttgactg | 2100 |
| atctcttgat | tgagcccaat | aatgatcacg | gcctgagatc | cttcgcgctg | agagatgcat | 2160 |

```
gcgggcgctc gttcctgggt tggcgaccca acggcgagtc acgtcgccca ctccgccacg    2220
ccccacacat ggccgccgat ccctcccgcc acacgaacgg cgggccaaga tcgcacgcct    2280
ccgtcggacg atgactgact gactgattgg ctgacgacgg ccgccctcgt gcgcggcgtc    2340
gggcgtcgtc gcaaaccagg caggcaggca ggaaggaagg aaggaagggc caggccctgg    2400
tgcgaaacgc tggcctgctc cgctgcaagc caagccgcgc tcgcaggtgt acttccgagt    2460
cctcgcgatg attaggcaag cctgagcgag cacgtaagct gcactgcggc tgttcaacca    2520
gagagagagt tggctctctt gcgtcaaggc ggcgcgcagc ccacttgcgt cgcggctgag    2580
ggcccctgga ggggaggaag gaggccggcg agcggcgagt ggcggccctc actggcacca    2640
ggtcgcagga ggccaggcag cccgccacgg acaggaatcc tcagggcgca gcagcgcact    2700
acgtagtgca gagacgcaga gcgggccgga tccgcagtgc ggtcgcgcca ccccgccgcg    2760
cagctcgctc gcggacgggg tccgtggccg cgcgaaaacg gacacggtgt gggagcggac    2820
atgggatcga gaacgccgtt cgccctgctc gcgctgccag cagcaggagc cgtccgaagg    2880
acgagcggcc ggccgcctgt cccccctccg cgcactcgaa gcgcgccgg cagcgcccca    2940 ttgcgtgcgc ggatggcgtc ttggctggtc cctctcgagg cgcttgctcg tgctcgccac    3000
gccttgtccg cctcctcgct gagcaagcga tgagctgagc acggaccgcc tgcaagtgca    3060
agtgttcttg tgctgcaggg cgccgaagaa ttggattctg gcccatgatc agtttgattg    3120
ggccgaggga gggagggagg ctgggcgagt gggcgacacc agcaagccgg actgcgagag    3180
gggcggggca ggatgtgagc gcaggaaagt gacgcaagtg catccggcca tcattgggcc    3240
atcattgggc catcattggt gttttgggcc gcgctttgcg gatcgtccgg ccgatcaggt    3300
acgaggccac gaacctacgt cgtttgccgc gctcaggctg gttggttgca cttggactct    3360
tctgtgacct ttcatcg                                                    3377

<210> SEQ ID NO 92
<211> LENGTH: 21
<212> TYPE: DNA
<213> ORGANISM: Artificial
<220> FEATURE:
<223> OTHER INFORMATION: primer

<400> SEQUENCE: 92
cagggcgagc gagtgtggtt c                                                21

<210> SEQ ID NO 93
<211> LENGTH: 1160
<212> TYPE: DNA
<213> ORGANISM: Artificial
<220> FEATURE:
<223> OTHER INFORMATION: genomic DNA (T. aureum  ATCC 34304 OrfA
      downstream)

<400> SEQUENCE: 93
tggctctcga ccaaagccga gtagagtact ctactcagta ctcttttcac ataccggcag      60
gcagtgttgc tgtgggattg gtccgggggc tcttctgcac gcggcctccg tcgcgcgcag     120
aaatgccccg tcactggctg cccaggaggc agccgaatcc ctctagctag ctagctaggc     180
tagagcgtct tttccgtagt ttttcacaaa gccagtatca catggataac gaacgaaggt     240
ttcgggctcg cgctcgcagg cgttaggacg aagttgatcg ccccacgtca cttcaaacga     300
gtgaaccaag atcacgttgc atctgctcgc aagatcttct tcttccacgc cgcatcgatg     360
cgatggattt caaactcttt tcagggcttt taggtgagta tggcagcgct gtttgcgtgg     420
```

-continued

| | |
|---|---|
| cagcgctgtt tgcgtggttg tactctctaa aggtgcttcc acgcatgcgc gcacaaaggg | 480 |
| gcatggcatg gttggcggcg cactctggcc ctcatttgaa gcagactatc gaagggtcca | 540 |
| gttggtactg cggcaggtcc ggcgagagca agcgcggcgg tcgctcccac tcgtccctgc | 600 |
| acagttgctg gactggcgac ggctggcgca cctgactacg agaagactcg agacgcacag | 660 |
| aggtagtcag ggacgaccga ccgcaaagca caaccgctc caaaacggcc gcaccaggca | 720 |
| gggcagtaaa ctaaaaacga atgtacctcc atcgcgcgta tctgccgagc ctcctcccac | 780 |
| gcttcggctg ggcttgattc accagtgtcc gcaagctgaa ccgaccgtct tcgatgtcat | 840 |
| gaagcttggc gcggcattag tcagacgacg cggcacgcca ggattctgtc ggtttctggg | 900 |
| aaatgggcat ctatatagct gattccctct gtcatgaggc ggccttgttc tggccctggg | 960 |
| ccgccgttcg gatgatctat gatgtcgttg tacgcataaa gcttgtcgaa acgtcggcc | 1020 |
| atgtcttcct cagagatgta accgagcggc gcgtcgtggc gattgatgcc gatgctacaa | 1080 |
| aagccgccga gttagctcga atgtcagatg cattgcgggc tggcccgcat ggcgcgggcg | 1140 |
| cagcagcgag aggttctaga | 1160 |

<210> SEQ ID NO 94
<211> LENGTH: 1204
<212> TYPE: DNA
<213> ORGANISM: Artificial
<220> FEATURE:
<223> OTHER INFORMATION: genomic DNA (T. aureum ATCC 34304 OrfA
      downstream genomic DNA fragment)

<400> SEQUENCE: 94

| | |
|---|---|
| cagggcgagc gagtgtggtt ctgaacaagg ctctttcgtt ttgatggctc tcgaccaaag | 60 |
| ccgagtagag tactctactc agtactcttt tcacataccg gcaggcagtg ttgctgtggg | 120 |
| attggtccgg gggctcttct gcacgcggcc tccgtcgcgc gcagaaatgc cccgtcactg | 180 |
| gctgcccagg aggcagccga atccctctag ctagctagct aggctagagc gtcttttccg | 240 |
| tagttttca caaagccagt atcacatgga taacgaacga aggtttcggg ctcgcgctcg | 300 |
| caggcgttag gacgaagttg atcgccccac gtcacttcaa acgagtgaac caagatcacg | 360 |
| ttgcatctgc tcgcaagatc ttcttcttcc acgccgcatc gatgcgatgg atttcaaact | 420 |
| cttttcaggg cttttaggtg agtatggcag cgctgtttgc gtggcagcgc tgtttgcgtg | 480 |
| gttgtactct ctaaaggtgc ttccacgcat gcgcgcacaa aggggcatgg catggttggc | 540 |
| ggcgcactct ggccctcatt tgaagcagac tatcgaaggg tccagttggt actgcggcag | 600 |
| gtccggcgag agcaagcgcg gcggtcgctc ccactcgtcc ctgcacagtt gctggactgg | 660 |
| cgacggctgg cgcacctgac tacgagaaga ctcgagacgc acagaggtag tcagggacga | 720 |
| ccgaccgcaa agcacaaacc gctccaaaac ggccgcacca ggcagggcag taaactaaaa | 780 |
| acgaatgtac ctccatcgcg cgtatctgcc gagcctcctc ccacgcttcg gctgggcttg | 840 |
| attcaccagt gtccgcaagc tgaaccgacc gtcttcgatg tcatgaagct ggcgcggca | 900 |
| ttagtcagac gacgcggcac gccaggattc tgtcggtttc tgggaaatgg gcatctatat | 960 |
| agctgattcc ctctgtcatg aggcggcctt gttctggccc tgggccgccg ttcggatgat | 1020 |
| ctatgatgtc gttgtacgca taaagcttgt cgaaaacgtc ggccatgtct tcctcagaga | 1080 |
| tgtaaccgag cggcgcgtcg tggcgattga tgccgatgct acaaaagccg ccgagttagc | 1140 |
| tcgaatgtca gatgcattgc gggctggccc gcatggcgcg ggcgcagcag cgagaggttc | 1200 |
| taga | 1204 |

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95
tgatgccgat gctacaaaag                                                20

<210> SEQ ID NO 96
<211> LENGTH: 1488
<212> TYPE: DNA
<213> ORGANISM: Artificial
<220> FEATURE:
<223> OTHER INFORMATION: genomic DNA (T. aureum ATCC 34304 OrfA
      downstream genomic DNA fragment)

<400> SEQUENCE: 96
aagcttgtac ggtgaaaagc cctttggcgc agcccgaaac aagtcttgct tctcctgccc      60
cgtcaaactc gcaaactctg cagcaactc ccgcacgctc tgtaccacgg cgaacccaag     120
ggcaggcacg cggtgaaacg acttgcatgc ttgcacaaca accccttgc cgacgtcgac     180 gcggtcgcct tcggagagcc caaacacagc gaacgccgga tccgcctgcg cctctgcatg     240
cgcctctgca tgcgcctcga catgcgcctc ggcctccgtg cctgcttgcc gggccggcgg     300
ggcagcagga agtgcgtggc cgaggtccat cgcatcaaag gctcgcttcg cggcgtgaaa     360
ggcctcgagc gcctccgccg gcaagtacac cttggtcttg cacttgagca tgctcctgat     420
ccgcgcgtag aggaagacgg ccgcgcagtg gtccaggtgc ccgtgcgaca agaacacgtg     480
ctccgccctc gccgcggcct tgtccggctc gtccccgagc gacccgcagt cgaactgcaa     540
gcagacccgc gagcccaggt ccacttgcag cgccgtgccg cagccggccc tcgactgccc     600
cgtcacgcgc acgtgcgagg ccatctcccg ccgcgagcct ggagcgccag agcctcctgc     660
tgctgccgtg ccgcctcggg gggcgcgagg agggtctcgc ctgatgcagc gcgcggggcc     720
gacgcagcag cgcgggtgga ggaagactgc gctgtgggcg gcggccctcg ggctgctgct     780
cttgtggctc ctgtccgtgc gctcgttcgt gcacggcgtg gcggacaggg aggcggacgc     840
cgtcgccccg cgcgagggcc ccagggcgcc ggcgccaaag aggactggcg ggaggaatga     900
tatgcccgct gagcctgccg ctggtaggcc cgcgcacagc tcgcctcgag ggacgcccga     960
cggcaacgcg gtcgagtgct ccacgaccaa gggcccgttc cgcgtggtcc tcacgcctag    1020
cctagcgccg aacgggacca agttttttcat cgggctggtg gaagcaggct atttcgacca    1080
aggcatcgcc ttctttcgcg tcaacaaggc catcacgcag ttcgggatca ccaagcgaag    1140
gccacgcgat gaggatccgt tcgtgcagtt cagaggcggg gccagcgcg acgagaaccc    1200 tttcggtggc gtggaggatg acgaggagag tgtccatcgc aggcacatgc acccgtggcg    1260
gcgcggcacg attgcctcga taggcggctt ccactttgtt gtcacgatcc gcgggacaa     1320 aaagtaagtt cttgaatgtt gtgaagtgcg ccaactcgcg ttcggagcgg acctggaccg    1380
atattcagca atctagaacc tctcgctgct gcgcccgcgc catgcgggcc agcccgcaat    1440
gcatctgaca ttcgagctaa ctcggcggct tttgtagcat cggcatca              1488

<210> SEQ ID NO 97
<211> LENGTH: 2551
<212> TYPE: DNA
<213> ORGANISM: Artificial
<220> FEATURE:
<223> OTHER INFORMATION: genomic DNA (T. aureum ATCC 34304 OrfA downstream genomic DNA fragment)

<400> SEQUENCE: 97

```
tggctctcga ccaaagccga gtagagtact ctactcagta ctcttttcac ataccggcag      60
gcagtgttgc tgtgggattg gtccgggggc tcttctgcac gcggcctccg tcgcgcgcag     120
aaatgccccg tcactggctg cccaggaggc agccgaatcc ctctagctag ctagctaggc     180
tagagcgtct tttccgtagt ttttcacaaa gccagtatca catggataac gaacgaaggt     240
ttcgggctcg cgctcgcagg cgttaggacg aagttgatcg ccccacgtca cttcaaacga     300
gtgaaccaag atcacgttgc atctgctcgc aagatcttct tcttccacgc cgcatcgatg     360
cgatggattt caaactcttt tcagggcttt taggtgagta tggcagcgct gtttgcgtgg     420
cagcgctgtt tgcgtggttg tactctctaa aggtgcttcc acgcatgcgc gcacaaaggg     480
gcatggcatg gttggcggcg cactctggcc ctcatttgaa gcagactatc gaagggtcca     540
gttggtactg cggcaggtcc ggcgagagca agcgcggcgg tcgctcccac tcgtccctgc     600
acagttgctg gactggcgac ggctggcgca cctgactacg agaagactcg agacgcacag     660
aggtagtcag ggacgaccga ccgcaaagca caaaccgctc caaaacggcc gcaccaggca     720
gggcagtaaa ctaaaaacga atgtacctcc atcgcgcgta tctgccgagc ctcctcccac     780
gcttcggctg gcttgattc accagtgtcc gcaagctgaa ccgaccgtct tcgatgtcat     840
gaagcttggc gcggcattag tcagacgacg cggcacgcca ggattctgtc ggtttctggg     900
aaatgggcat ctatatagct gattccctct gtcatgaggc ggccttgttc tggccctggg     960
ccgccgttcg gatgatctat gatgtcgttg tacgcataaa gcttgtcgaa acgtcggcc    1020
atgtcttcct cagagatgta accgagcggc gcgtcgtggc gattgatgcc gatgctacaa    1080
aagccgccga gttagctcga atgtcagatg cattgcgggc tggcccgcat ggcgcgggcg    1140
cagcagcgag aggttctaga ttgctgaata tcggtccagg tccgctccga acgcgagttg    1200
gcgcacttca caacattcaa gaacttactt tttgtccccg cggatcgtga caacaaagtg    1260
gaagccgcct atcgaggcaa tcgtgccgcg ccgccacggg tgcatgtgcc tgcgatggac    1320
actctcctcg tcatcctcca cgccaccgaa agggttctcg tcgcgctggg ccccgcctct    1380
gaactgcacg aacggatcct catcgcgtgg ccttcgcttg gtgatcccga actgcgtgat    1440
ggccttgttg acgcgaaaga aggcgatgcc ttggtcgaaa tagcctgctt ccaccagccc    1500
gatgaaaaac ttggtcccgt tcggcgctag gctaggcgtg aggaccacgc ggaacgggcc    1560
cttggtcgtg gagcactcga ccgcgttgcc gtcgggcgtc cctcgaggcg agctgtgcgc    1620
gggcctacca gcggcaggct cagcgggcat atcattcctc ccgccagtcc tctttggcgc    1680
cggcgccctg gggccctcgc gcggggcgac ggcgtccgcc tccctgtccg ccacgccgtg    1740
cacgaacgag cgcacggaca ggagccacaa gagcagcagc ccgagggccg ccgcccacag    1800
cgcagtcttc ctccacccgc gctgctgcgt cggccccgcg cgctgcatca ggcgagaccc    1860
tcctcgcgcc ccccgaggcg gcacggcagc agcaggaggc tctggcgctc caggctcgcg    1920
gcgggagatg gcctcgcacg tccgcgtgac ggggcagtcg agggccggct gcggcacggc    1980
gctgcaagtg gacctgggct cgcgggtctg cttgcagttc gactgcgggt cgctcgggga    2040
cgagccggac aaggccgcgg cgagggcgga gcacgtgttc ttgtcgcacg gcacctgga    2100
ccactgcgcg gccgtcttcc tctacgcgcg gatcaggagc atgctcaagt gcaagaccaa    2160
ggtgtacttg ccggcggagg cgctcgaggc cttcacgcc gcgaagcgag cctttgatgc    2220
```

```
gatggacctc ggccacgcac ttcctgctgc cccgccggcc cggcaagcag gcacggaggc    2280
cgaggcgcat gtcgaggcgc atgcagaggc gcatgcagag gcgcaggcgg atccggcgtt    2340
cgctgtgttt gggctctccg aaggcgaccg cgtcgacgtc ggcaaggggg ttgttgtgca    2400
agcatgcaag tcgtttcacc gcgtgcctgc ccttgggttc gccgtggtac agagcgtgcg    2460
ggagttgctg ccagagtttg cgagtttgac ggggcaggag aagcaagact tgtttcgggc    2520
tgcgccaaag ggcttttcac cgtacaagct t                                    2551
```

<210> SEQ ID NO 98
<211> LENGTH: 1835
<212> TYPE: DNA
<213> ORGANISM: Artificial
<220> FEATURE:
<223> OTHER INFORMATION: 18S rDNA (T. aureum ATCC 34304)

<400> SEQUENCE: 98

```
cgaatattcc tggttgatcc tgccagtagt catacgctta tctcaaagat taagccatgc      60
atgtctaagt ataaaggctt atactctgaa actgcgaacg gctcattata tcagttatag     120
tttctttgat agtgtttttt ctacatggat acttgtggca aatctagaaa caatacatgc     180
gtacaggcct gactttgggg gagggctgca tttatttgac ttaagccaat acccctcggg     240
gttgttttgg tgattcagaa taactgagcg aatcgcatag ctttcgggcg gcgatgaatc     300
atttcaagtt tctgccccat cagctgtcga tggtagggta taggcctacc atggctgtca     360
cgggtgacgg agaattaggg ttcgattccg gagagggagc ctgagagacg gctaccacat     420
ccaaggaagg cagcaggcgc gtaaattact caatgttgac tcgacgaagt agtgacgaga     480
attaacaatg cggagcgctc agcgttttgc aattggaatg agagcaatgt aaaagcctca     540
tcgaggatcc attggagggc aagtctggtg ccagcagccg cggtaattcc agctccaata     600
gcgtatacta aagttgttgc agttaaaaag ctcgtagttg aacctctggt agggccgacc     660
ttggcgcgcg gtgaatgccg cgtcgtttag aagcgtcgtg cccggccatc ctcccccggt     720
cttttgggct gggggtcgtt tactgtaaaa aaaatagagt gttccaagca ggggtaata      780 tcccggtata tagtagtatg gaataatgag ataggacttt ggtactattt tgttggtttg     840
catgccaagg taatgattaa gagggacagt tgggggtatt cgtatttaga tgtcagaggt     900
gaaattcttg gattttcgaa agacgaacta ctgcgaaagc atttaccaag gatgttttca     960
ttaatcaaga acgaaagtta ggggatcgaa gatgattaga taccatcgta gtcttaaccg    1020
taaactatgc cgacttgcga ttgtccggcg tcgcttttag atgacctggg cagcagcaca    1080
tgagaaatca agtctttggg ttccggggg gagtatggtc gcaaggctga aacttaaagg     1140
aattgacgga agggcaccac caggagtgga gcctgcggct taatttgact caacacggga    1200
aaacttacca ggtccggaca taggaaggat tgacagattg agagctcttt cttgattcta    1260
tgggtggtgt gcatggccg ttcttagttg gtggagtgat ttgtctggtt aattccgtta    1320
acgaacgaga ccacagccta ctaaatagtg gccgttatgg cgacatagcg gtgaacttct    1380
tagagggaca tttcgggtat accggaagga agtttgtggc aataacaggt ctgtgatgcc    1440
cttagatgtt ctgggccgca cgcgcgctac actgatcggt caacgagta tttgtttttt    1500 tctcattttg ggaggggggca gagtccttgg ccggaaggtc tgggtaatct tttgaatgcc    1560
gatcgtgatg gggctagatt tttgcaatta ttaatctcca acgaggaatt cctagtagac    1620
gcaagtcatc agcttgcatc gattacgtcc ctgccctttg tacacaccgc ccgtcgcacc    1680
```

```
taccgattga acgatccggt gagaccttgg gattctgttg tggctgattc attttggctg    1740
cgatgggaga acttgagcaa accttatcgt ttagaggaag gtgaagtcgt aacaaggttt    1800
ccgtagtgaa cctgcaattc aaaaaaagcc gttac                               1835
```

<210> SEQ ID NO 99
<211> LENGTH: 30
<212> TYPE: DNA
<213> ORGANISM: Artificial
<220> FEATURE:
<223> OTHER INFORMATION: primer

<400> SEQUENCE: 99

```
cgaatattcc tggttgatcc tgccagtagt                                       30
```

<210> SEQ ID NO 100
<211> LENGTH: 46
<212> TYPE: DNA
<213> ORGANISM: Artificial
<220> FEATURE:
<223> OTHER INFORMATION: primer

<400> SEQUENCE: 100

```
gtaacggctt tttttgaatt gcaggttcac tacgcttgtt agaaac                     46
```

<210> SEQ ID NO 101
<211> LENGTH: 661
<212> TYPE: DNA
<213> ORGANISM: Artificial
<220> FEATURE:
<223> OTHER INFORMATION: EF1 alpha promoter (T. aureum ATCC 34304)

<400> SEQUENCE: 101

```
ggtttccgta gtgaacctgc aattcaaaaa aagccgttac tcacatcagg ccgccactca      60
tccgggcgaa agcttcgcgc attcgtcctc gtcacctcgg gtccctgtg tcgtgacgga      120 aagcgcgacg agacgcggcc gcagcagaga gccccggggg cccgcgtcac ggggggcctg    180
gcggcggtcc tccttaagcc aaaccgaggg ttagggctcc aggctgttcg gcggggtcgc    240
gggcgcggtg gacgcgcggg gccgcctagc acctcctagc gcgcgactac caggatagcc    300
cccgcgagtg cgcagggcgg tccgcggggc ggagggcggc ccagcagcgc ggcgcggcgg    360
gcgggtgcgg ctgcgtaagg tggcggcggg cgcgggcggt tagtgttggt gttaggtcgc    420
ggcggggctg tgttccgggc atccgcctta cggcggtgca tactggttgg ctgggaggcg    480
gtttgcgggg ttagataggc ggccaaggtg agctgcgttg gcggataaa tccgtggagg      540 cgctcgttga cggcgcggca gagacggaac gcggagcagc acggagtagc aagcaggagt    600
agcaggagta gcaagcagcg gcaaaggaag gctagatgat tgaacaggac ggccttcacg    660
c                                                                     661
```

<210> SEQ ID NO 102
<211> LENGTH: 46
<212> TYPE: DNA
<213> ORGANISM: Artificial
<220> FEATURE:
<223> OTHER INFORMATION: primer

<400> SEQUENCE: 102

```
ggtttccgta gtgaacctgc aattcaaaaa aagccgttac tcacat                    46
```

<210> SEQ ID NO 103
<211> LENGTH: 46

```
<212> TYPE: DNA
<213> ORGANISM: Artificial
<220> FEATURE:
<223> OTHER INFORMATION: primer

<400> SEQUENCE: 103
gcgtgaaggc cgtcctgttc aatcatctag ccttcctttg ccgctg            46

<210> SEQ ID NO 104
<211> LENGTH: 835
<212> TYPE: DNA
<213> ORGANISM: Artificial
<220> FEATURE:
<223> OTHER INFORMATION: Neomycin resistance gene (Neor)

<400> SEQUENCE: 104
catcggcaaa ggaaggctag atgattgaac aggacggcct tcacgctggc tcgcccgctg    60
cttgggtgga acggctgttc ggctacgact gggctcagca cgcgatcggc tgctcggacg   120
cggccgtgtt ccgccttagc gcgcagggcc ggcggtcct gtttgtcaag accgacctta    180
gcggcgccct caacgagctc caggacgaag ctgcccgcct cagctggctt gccacgacgg   240
gggttccgtg cgccgctgtg ctcgacgtcg tcaccgaagc cggccgcgac tggctgctcc   300
tcggggaagt gcccggccag gacctcctca gcagccacct cgcgcccgct gagaaggtgt   360
ccatcatggc cgacgccatg cgccgcctgc acacctcga ccccgccacc tgccccttcg    420
accaccaggc gaagcacagg atcgaacgcg cccgcacgcg gatggaggct ggcctcgtcg   480
accaagacga cctcgacgag gagcaccagg gcctcgcgcc ggcggaactg ttcgccaggc   540
ttaaggctag gatgccggac ggcgaggacc tcgtggtcac gcacggcgac gcctgcctcc   600
ccaacatcat ggtcgagaac ggccgcttct cgggctttat cgactgcggg cgcctgggcg   660
tggcggaccg ctaccaagac atcgcgctcg ccacgcggga catcgccgag gagcttggcg   720
gcgagtgggc cgaccgcttt ctcgtgctct acggcatcgc cgccccggac agccagagga   780
ttgcgttcta ccgcctcctg gacgagttct tttgagatcc gcgccggcta tgcgc        835

<210> SEQ ID NO 105
<211> LENGTH: 45
<212> TYPE: DNA
<213> ORGANISM: Artificial
<220> FEATURE:
<223> OTHER INFORMATION: primer

<400> SEQUENCE: 105
catcggcaaa ggaaggctag atgattgaac aggacggcct tcacg             45

<210> SEQ ID NO 106
<211> LENGTH: 46
<212> TYPE: DNA
<213> ORGANISM: Artificial
<220> FEATURE:
<223> OTHER INFORMATION: primer

<400> SEQUENCE: 106
gcgcatagcc ggcgcggatc tcaaaagaac tcgtccagga ggcggt            46

<210> SEQ ID NO 107
<211> LENGTH: 1249
<212> TYPE: DNA
<213> ORGANISM: Artificial
<220> FEATURE:
<223> OTHER INFORMATION: EF1 alpha terminator (T. aureum ATCC 34304)
```

-continued

```
<400> SEQUENCE: 107
tcctggacga gttcttttga gatccgcgcc ggctatgcgc ccgtgctcga ctgccacact      60
gcccacattg cctgcaagtt cgctgagctc cagaacaaga tggaccgccg ctcgggcaag     120
attctcgagg agaccccgaa gttcatcaag tcgggtggac tctgccatgg tcaagatgta    180 tccctccaa gcgcatgtgc gtcgagtcct tcaccgagta cccgccgctc ggccgctttg     240
ccgtgcgcga catgcgcgtc accgtcgctg tcggcgtcat caagtccgtc accaagggcg    300
acaaataaat tctacgaaag attttttttcc tcaagaagcg ccctaaagtt gaccctagc     360 agcgacgact gtgtgtgccg ttgtgagtcg agttgcgatg tcgtgcagcg cccgtcgcgt    420
cccatgctcg cgcgcgactc cgtctctgct tttcatctca agtcaagagt gggaagttcc    480
cttgctttat ctcactattt agaggtcgct cacggctgct ggttcctcgt cgcatgtagc    540
acagcctcgt ccaatcgcag cctgcaccac cccgctcgcc tgggaaaatg cgctcagcgg    600
attcgcactg gcactcctct cctcggacag gtgcgatgtg gaagcggtca catcctcggc    660
gccctcggcc acgccagcat ctgcgcaatc gctctcctcg ttctcagccg caaccgcagg    720
caggccgacg tcgtttacct cggaatccac cgagcatttc gagcccatcg cgctggcgtc    780
cacctcgatc ataccttctc catcgccgtc cgctgcggct tccgattctt ctgctgccgc    840
aaccgcgacg tcggcccccg tctcctccgt tctttccgat gccggcgcag tggccgcgcc    900
ctctgctcga accggctcgt gttcagcgtc agggcctgcg cttgagctcg gcggctctt    960 ccgagtgatc cggccccgcg aggcaaggaa tcggcggctc tggagtgtcg gggcagccgc   1020
tctcactgcc ggtctttggc tggctgcctg tcctgcctcg cgttggcctt tgcttttgcc   1080
taggctttcg ccttggtgac ggcgtttgcc tgctgcggcg acttggcgcg ccgcggaat    1140 agcgcctcaa agtcctgctc gaggcgcccc agctctgact tgatttgcga ggtcccggtg   1200
gcatgagctc cgctgccctc gtccttacgg cccgtctttc gctgcagtg               1249

<210> SEQ ID NO 108
<211> LENGTH: 46
<212> TYPE: DNA
<213> ORGANISM: Artificial
<220> FEATURE:
<223> OTHER INFORMATION: primer

<400> SEQUENCE: 108
tcctggacga gttcttttga gatccgcgcc ggctatgcgc ccgtgc                    46

<210> SEQ ID NO 109
<211> LENGTH: 30
<212> TYPE: DNA
<213> ORGANISM: Artificial
<220> FEATURE:
<223> OTHER INFORMATION: primer

<400> SEQUENCE: 109
cactgcagcg aaagacgggc cgtaaggacg                                      30

<210> SEQ ID NO 110
<211> LENGTH: 4453
<212> TYPE: DNA
<213> ORGANISM: Artificial
<220> FEATURE:
<223> OTHER INFORMATION: fusion DNA (T. aureum ATCC 34304 18S rDNA/T.
      aureum ATCC 34304 EF1 alpha promoter/Neor/T. aureum ATCC 34304 EF1
      alpha terminator)

<400> SEQUENCE: 110
```

```
cgaatattcc tggttgatcc tgccagtagt catacgctta tctcaaagat taagccatgc      60
atgtctaagt ataaaggctt atactctgaa actgcgaacg gctcattata tcagttatag     120
tttctttgat agtgtttttt ctacatggat acttgtggca aatctagaaa caatacatgc     180
gtacaggcct gactttgggg gagggctgca tttatttgac ttaagccaat acccctcggg     240
gttgttttgg tgattcagaa taactgagcg aatcgcatag ctttcgggcg gcgatgaatc     300
atttcaagtt tctgccccat cagctgtcga tggtagggta taggcctacc atggctgtca     360
cgggtgacgg agaattaggg ttcgattccg agagggagc ctgagagacg gctaccacat      420
ccaaggaagg cagcaggcgc gtaaattact caatgttgac tcgacgaagt agtgacgaga     480
attaacaatg cggagcgctc agcgttttgc aattggaatg agagcaatgt aaaagcctca     540
tcgaggatcc attggagggc aagtctggtg ccagcagccg cggtaattcc agctccaata     600
gcgtatacta aagttgttgc agttaaaaag ctcgtagttg aacctctggt agggccgacc     660
ttggcgcgcg gtgaatgccg cgtcgtttag aagcgtcgtg cccggccatc ctcccccggt     720
cttttgggct gggggtcgtt tactgtaaaa aaaatagagt gttccaagca gggggtaata     780
tcccggtata tagtagtatg gaataatgag ataggacttt ggtactattt tgttggtttg     840
catgccaagg taatgattaa gagggacagt tgggggtatt cgtatttaga tgtcagaggt     900
gaaattcttg gattttcgaa agacgaacta ctgcgaaagc atttaccaag gatgttttca     960
ttaatcaaga acgaaagtta ggggatcgaa gatgattaga taccatcgta gtcttaaccg    1020
taaactatgc cgacttgcga ttgtccggcg tcgcttttag atgacctggg cagcagcaca    1080
tgagaaatca aagtctttgg gttccggggg gagtatggtc gcaaggctga aacttaaagg    1140
aattgacgga agggcaccac caggagtgga gcctgcggct taatttgact caacacggga    1200
aaacttacca ggtccggaca taggaaggat tgacagattg agagctcttt cttgattcta    1260
tgggtggtgg tgcatggccg ttcttagttg gtggagtgat ttgtctggtt aattccgtta    1320
acgaacgaga ccacagccta ctaaatagtg gccgttatgg cgacatagcg gtgaacttct    1380
tagagggaca tttcgggtat accggaagga agtttgtggc aataacaggt ctgtgatgcc    1440
cttagatgtt ctgggccgca cgcgcgctac actgatcggt tcaacgagta tttgtttttt    1500
tctcattttg gagggggca gagtccttgg ccggaaggtc tgggtaatct tttgaatgcc     1560
gatcgtgatg gggctagatt tttgcaatta ttaatctcca acgaggaatt cctagtagac    1620
gcaagtcatc agcttgcatc gattacgtcc ctgccctttg tacacaccgc ccgtcgcacc    1680
taccgattga acgatccggt gagaccttgg gattctgttg tggctgattc attttggctg    1740
cgatgggaga acttgagcaa accttatcgt ttagaggaag gtgaagtcgt aacaaggttt    1800
ccgtagtgaa cctgcaattc aaaaaaagcc gttactcaca tcaggccgcc actcatccgg    1860
gcgaaagctt cgcgcattcg tcctcgtcac ctcgggtccc ctgtgtcgtg acggaaagcg    1920
cgacgagacg cggccgcagc agagagcccc ggggccccgc gtcacggggg gcctggcggc    1980
ggtcctcctt aagccaaacc gagggttagg gctccaggct gttcggcggg gtcgcgggcg    2040
cggtggacgc gcggggccgc ctagcacctc ctagcgcgcg actaccagga tagccccgc     2100 gagtgcgcag ggcggtccgc ggggcggagg gcggcccagc agcgcggcgc ggcgggcggg    2160
tgcggctgcg taaggtggcg gcgggcgcgg gcggttagtg ttggtgttag gtcgcgcgg     2220 ggctgtgttc cgggcatccg ccttacgcg gtgcatactg gttggctggg aggcggtttg     2280
cggggttaga taggcggcca aggtgagctg cgttgggcgg ataaatccgt ggaggcgctc    2340
```

-continued

```
gttgacggcg cggcagagac ggaacgcgga gcagcacgga gtagcaagca ggagtagcag      2400
gagtagcaag catggcaaag gaaggctaga tgattgaaca ggacggcctt cacgctggct      2460
cgcccgctgc ttgggtggaa cggctgttcg gctacgactg ggctcagcag acgatcggct      2520
gctcggacgc ggccgtgttc cgccttagcg cgcaggcccg gccggtcctg tttgtcaaga      2580
ccgaccttag cggcgccctc aacgagctcc aggacgaagc tgcccgcctc agctggcttg      2640
ccacgacggg ggttccgtgc gccgctgtgc tcgacgtcgt caccgaagcc ggccgcgact      2700
ggctgctcct cggggaagtg cccggccagg acctcctcag cagccacctc gcgcccgctg      2760
agaaggtgtc catcatggcc gacgccatgc gccgcctgca cccctcgac cccgccacct       2820 gccccttcga ccaccaggcg aagcacagga tcgaacgcgc ccgcacgcgg atggaggctg      2880
gcctcgtcga ccaagacgac ctcgacgagg agcaccaggg cctcgcgccg gcggaactgt      2940
tcgccaggct taaggctagg atgccggacg gcgaggacct cgtggtcacg cacggcgacg      3000
cctgcctccc caacatcatg gtcgagaacg gccgcttctc gggctttatc gactgcgggc      3060
gcctgggcgt ggcggaccgc taccaagaca tcgcgctcgc cacgcgggac atcgccgagg      3120
agcttggcgg cgagtgggcc gaccgctttc tcgtgctcta cggcatcgcc gccccggaca      3180
gccagaggat tgcgttctac cgcctcctgg acgagttctt tgagatccg cgccggctat       3240 gcgcccgtgc tcgactgcca cactgcccac attgcctgca gttcgctga gctccagaac       3300 aagatggacc gccgctcggg caagattctc gaggagaccc ccaagttcat caagtcgggt     3360
ggactctgcc atggtcaaga tgtatcccct ccaagcgcat gtgcgtcgag tccttcaccg      3420
agtacccgcc gctcggccgc tttgccgtgc gcgacatgcg cgtcaccgtc gctgtcggcg      3480
tcatcaagtc cgtcaccaag ggcgacaaat aaattctacg aaagattttt ttcctcaaga     3540
agcgccctaa agttgacccc tagcagcgac gactgtgtgt gccgttgtga gtcgagttgc      3600
gatgtcgtgc agcgcccgtc gcgtcccatg ctcgcgcgcg actccgtctc tgcttttcat     3660
ctcaagtcaa gagtgggaag ttcccttgct ttatctcact attagaggt cgctcacggc       3720 tgctggttcc tcgtcgcatg tagcacagcc tcgtccaatc gcagcctgca ccaccccgct     3780
cgcctgggaa aatgcgctca gcggattcgc actggcactc ctctcctcgg acaggtcgca    3840
tgtggaagcg gtcacatcct cggcgccctc ggccacgcca gcatctgcgc aatcgctctc    3900
ctcgttctca gccgcaaccg caggcaggcc gacgtcgttt acctcggaat ccaccgagca    3960
tttcgagccc atcgcgctgg cgtccacctc gatcatacct tctccatcgc cgtccgctgc    4020
ggcttccgat tcttctgctg ccgcaaccgc gacgtcggcc ccgtctcct ccgttctttc      4080 cgatgccggc gcagtggccg cgccctctgc tcgaaccggc tcgtgttcag cgtcagggcc    4140
tgcgcttgag ctcgggcggc tcttccgagt gatccggccc cgcgaggcaa ggaatcggcg     4200
gctctggagt gtcggggcag ccgctctcac tgccggtctt tggctggctg cctgtcctgc    4260
ctcgcgttgg cctttgcttt tgcctaggct ttcgccttgg tgacggcgtt tgcctgctgc    4320
ggcgacttgg cgcggccgcg gaatagcgcc tcaaagtcct gctcgaggcg ccccagctct    4380
gacttgattt gcgaggtccc ggtggcatga gctccgctgc cctcgtcctt acggcccgtc    4440
tttcgctgca gtg                                                        4453
```

<210> SEQ ID NO 111
<211> LENGTH: 1218
<212> TYPE: DNA
<213> ORGANISM: Artificial
<220> FEATURE:
<223> OTHER INFORMATION: genomic DNA (T. aureum ATCC 34304 OrfA upstream genomic DNA fragment)

<400> SEQUENCE: 111

```
cccgaattcg dacgatgact gactgactga ttggctgacg acggccgccc tcgtgcgcgg      60
cgtcgggcgt cgtcgcaaac caggcaggca ggcaggaagg aaggaaggaa gggccaggcc     120
ctggtgcgaa acgctggcct gctccgctgc aagccaagcc gcgctcgcag gtgtacttcc     180
gagtcctcgc gatgattagg caagcctgag cgagcacgta agctgactg cggctgttca      240
accagagaga gagttggctc tcttgcgtca aggcggcgcg cagcccactt gcgtcgcggc     300
tgagggcccc tggaggggag gaaggaggcc ggcgagcggc gagtggcggc cctcactggc     360
accaggtcgc aggaggccag gcagcccgcc acggacagga atcctcaggg cgcagcagcg     420
cactacgtag tgcagagacg cagagcgggc cggatccgca gtgcggtcgc gccaccccgc     480
cgcgcagctc gctcgcggac ggggtccgtg gccgcgcgaa aacggacacg gtgtgggagc     540
ggacatggga tcgagaacgc cgttcgccct gctcgcgctg ccagcagcag gagccgtccg     600
aaggacgagc ggccggccgc ctgtcccccc tccgcgcact cgaagcgcgc ccggcagcgc     660
cccattgcgt gcgcggatgg cgtcttggct ggtccctctc gaggcgcttg ctcgtgctcg     720
ccacgccttg tccgcctcct cgctgagcaa gcgatgagct gagcacggac cgcctgcaag     780
tgcaagtgtt cttgtgctgc agggcgccga agaattggat tctggcccat gatcagtttg     840
attgggccga gggagggagg gaggctgggc gagtgggcga caccagcaag ccggactgcg     900
agaggggcgg ggcaggatgt gagcgcagga aagtgacgca agtgcatccg gccatcattg     960
ggccatcatt gggccatcat tggtgttttg ggccgcgctt tgcggatcgt ccggccgatc    1020
aggtacgagg ccacgaacct acgtcgtttg ccgcgctcag gctggttggt tgcacttgga    1080
ctcttctgtg acctttcatc gtgtgcaggc aaactcgatt tgcagacccg agacacggcg    1140
aaggatccgt gctgcaaacg caagtggagt gcgtcgagag caccgccgag accaagagcc    1200
gaggcagaca agcttggg                                                  1218
```

<210> SEQ ID NO 112
<211> LENGTH: 32
<212> TYPE: DNA
<213> ORGANISM: Artificial
<220> FEATURE:
<223> OTHER INFORMATION: primer

<400> SEQUENCE: 112

```
cccgaattcg gacgatgact gactgactga tt                                    32
```

<210> SEQ ID NO 113
<211> LENGTH: 28
<212> TYPE: DNA
<213> ORGANISM: Artificial
<220> FEATURE:
<223> OTHER INFORMATION: primer

<400> SEQUENCE: 113

```
cccaagcttg tctgcctcgg ctcttggt                                         28
```

<210> SEQ ID NO 114
<211> LENGTH: 1000
<212> TYPE: DNA
<213> ORGANISM: Artificial
<220> FEATURE:
<223> OTHER INFORMATION: genomic DNA (T. aureum ATCC 34304 OrfA
      downstream genomic DNA fragment)

<400> SEQUENCE: 114

```
cccccatggt gttgctgtgg gattggtccg ggggctcttc tgcacgcggc ctccgtcgcg      60
cgcagaaatg ccccgtcact ggctgcccag gaggcagccg aatccctcta gctagctagc     120
taggctagag cgtctttttcc gtagtttttc acaaagccag tatcacatgg ataacgaacg    180
aaggtttcgg gctcgcgctc gcaggcgtta ggacgaagtt gatcgcccca cgtcacttca    240
aacgagtgaa ccaagatcac gttgcatctg ctcgcaagat cttcttcttc cacgccgcat    300
cgatgcgatg gatttcaaac tcttttcagg gcttttaggt gagtatggca gcgctgtttg    360
cgtggcagcg ctgtttgcgt ggttgtactc tctaaaggtg cttccacgca tgcgcgcaca    420
aaggggcatg gcatggttgg cggcgcactc tggccctcat ttgaagcaga ctatcgaagg    480
gtccagttgg tactgcggca ggtccggcga gagcaagcgc ggcggtcgct cccactcgtc    540
cctgcacagt tgctggactg gcgacggctg gcgcacctga ctacgagaag actcgagacg    600
cacagaggta gtcagggacg accgaccgca aagcacaaac cgctccaaaa cggccgcacc    660
aggcagggca gtaaactaaa aacgaatgta cctccatcgc gcgtatctgc cgagcctcct    720
cccacgcttc ggctgggctt gattcaccag tgtccgcaag ctgaaccgac cgtcttcgat    780
gtcatgaagc ttggcgcggc attagtcaga cgacgcggca cgccaggatt ctgtcggttt    840
ctggaaaatg ggcatctata tagctgattc cctctgtcat gaggcggcct tgttctggcc    900
ctgggccgcc gttcggatga tctatgatgt cgttgtacgc ataaagcttg tcgaaaacgt    960
cggccatgtc ttcctcagag atgtaaccga gccatggggg              1000
```

<210> SEQ ID NO 115
<211> LENGTH: 28
<212> TYPE: DNA
<213> ORGANISM: Artificial
<220> FEATURE:
<223> OTHER INFORMATION: primer

<400> SEQUENCE: 115

```
cccccatggt gttgctgtgg gattggtc                                          28
```

<210> SEQ ID NO 116
<211> LENGTH: 30
<212> TYPE: DNA
<213> ORGANISM: Artificial
<220> FEATURE:
<223> OTHER INFORMATION: primer

<400> SEQUENCE: 116

```
cccccatggc tcggttacat ctctgaggaa                                        30
```

<210> SEQ ID NO 117
<211> LENGTH: 1632
<212> TYPE: DNA
<213> ORGANISM: Artificial
<220> FEATURE:
<223> OTHER INFORMATION: fusion DNA (T. aureum ATCC 34304 ubiqitin
      promoter/Hygr)

<400> SEQUENCE: 117

```
cccaagcttg ccgcagcgcc tggtgcaccc gccgggcgtt gttgtgtgct cttcttgcct      60
ccgagagaga gagcggagcg gatgcatagg aaatcgggcc acgcgggagg gccatgcgtt    120
cgccccacac gccactttcc acgcccgctc tctctccggc cggcaggcag cgcataactc    180
tccgacgctg gcaggctggt agcaactggc agggacaact cgcgcgcggg tcccggtcgt    240
```

```
tcgatgtgcc aacccgagag aatccagcca gcagggcggt tggcctcatc gcccacctgc      300
tatggtgcag cgaaccaact cccgaagcgg ccggttctgc gattccctct tctgaattct      360
gaattctgaa ctgattccgg aggagaaccc tctggaagcg cgggttgcct ctccagttct      420
gccgaactag acaggggagt gagcagagag tgaccctgac gcggagcgag ctggttgctg      480
gaaaagtcgc gaacgctggg ctgtgtcacg cgtccacttc gggcagaccc caaacgacaa      540
gcagaacaag caacaccagc agcagcaagc gacctaagca acactagcca acatgaaaaa      600
gcctgaactc accgcgacgt ctgtcgagaa gtttctgatc gaaaagttcg acagcgtctc      660
cgacctgatg cagctctcgg agggcgaaga atctcgtgct ttcagcttcg atgtaggagg      720
gcgtggatat gtcctgcggg taaatagctg cgccgatggt ttctacaaag atcgttatgt      780
ttatcggcac tttgcatcgg ccgcgctccc gattccggaa gtgcttgaca ttggggaatt      840
cagcgagagc ctgacctatt gcatctcccg ccgtgcacag ggtgtcacgt tgcaagacct      900
gcctgaaacc gaactgcccg ctgttctgca gccggtcgcg gaggccatgg atgcgatcgc      960
tgcggccgat cttagccaga cgagcgggtt cggcccattc ggaccgcaag gaatcggtca     1020
atacactaca tggcgtgatt tcatatgcgc gattgctgat ccccatgtgt atcactggca     1080
aactgtgatg gacgacaccg tcagtgcgtc cgtcgcgcag gctctcgatg agctgatgct     1140
ttgggccgag gactgccccg aagtccggca cctcgtgcac gcggatttcg gctccaacaa     1200
tgtcctgacg gacaatggcc gcataacagc ggtcattgac tggagcgagg cgatgttcgg     1260
ggattcccaa tacgaggtcg ccaacatctt cttctggagg ccgtggttgg cttgtatgga     1320
gcagcagacg cgctacttcg agcggaggca tccggagctt gcaggatcgc cgcggctccg     1380
ggcgtatatg ctccgcattg gtcttgacca actctatcag agcttggttg acggcaattt     1440
cgatgatgca gcttgggcgc agggtcgatg cgacgcaatc gtccgatccg gagccgggac     1500
tgtcgggcgt acacaaatcg cccgcagaag cgcggccgtc tggaccgatg gctgtgtaga     1560
agtactcgcc gatagtggaa accgacgccc cagcactcgt ccgagggcaa aggaatagtc     1620
gacgcatgcg gg                                                         1632

<210> SEQ ID NO 118
<211> LENGTH: 36
<212> TYPE: DNA
<213> ORGANISM: Artificial
<220> FEATURE:
<223> OTHER INFORMATION: primer

<400> SEQUENCE: 118
cccaagcttg ccgcagcgcc tggtgcaccc gccggg                                36

<210> SEQ ID NO 119
<211> LENGTH: 43
<212> TYPE: DNA
<213> ORGANISM: Artificial
<220> FEATURE:
<223> OTHER INFORMATION: primer

<400> SEQUENCE: 119
cccgcatgcg tcgactattc ctttgccctc ggacgagtgc tgg                        43

<210> SEQ ID NO 120
<211> LENGTH: 1000
<212> TYPE: DNA
<213> ORGANISM: Artificial
<220> FEATURE:
<223> OTHER INFORMATION: genomic DNA (T. aureum ATCC 34304 OrfA
``` downstream genomic DNA fragment)

<400> SEQUENCE: 120

```
cccgtcgacg tgttgctgtg ggattggtcc gggggctctt ctgcacgcgg cctccgtcgc      60
gcgcagaaat gccccgtcac tggctgccca ggaggcagcc gaatccctct agctagctag     120
ctaggctaga gcgtcttttc cgtagttttt cacaaagcca gtatcacatg gataacgaac     180
gaaggtttcg ggctcgcgct cgcaggcgtt aggacgaagt tgatcgcccc acgtcacttc     240
aaacgagtga accaagatca cgttgcatct gctcgcaaga tcttcttctt ccacgccgca     300
tcgatgcgat ggatttcaaa ctcttttcag ggcttttagg tgagtatggc agcgctgttt     360
gcgtggcagc gctgtttgcg tggttgtact ctctaaaggt gcttccacgc atgcgcgcac     420
aaagggcat ggcatggttg gcggcgcact ctggccctca tttgaagcag actatcgaag     480
ggtccagttg gtactgcggc aggtccggcg agagcaagcg cggcggtcgc tcccactcgt     540
ccctgcacag ttgctggact ggcgacggct ggcgcacctg actacgagaa gactcgagac     600
gcacagaggt agtcagggac gaccgaccgc aaagcacaaa ccgctccaaa acggccgcac     660
caggcagggc agtaaactaa aaacgaatgt acctccatcg cgcgtatctg ccgagcctcc     720
tcccacgctt cggctgggct tgattcacca gtgtccgcaa gctgaaccga ccgtcttcga     780
tgtcatgaag cttggcgcgg cattagtcag acgacgcggc acgccaggat tctgtcggtt     840
tctgggaaat gggcatctat atagctgatt ccctctgtca tgaggcggcc ttgttctggc     900
cctgggccgc cgttcggatg atctatgatg tcgttgtacg cataaagctt gtcgaaaacg     960
tcggccatgt cttcctcaga gatgtaaccg agtcgacggg                          1000
```

<210> SEQ ID NO 121
<211> LENGTH: 29
<212> TYPE: DNA
<213> ORGANISM: Artificial
<220> FEATURE:
<223> OTHER INFORMATION: primer

<400> SEQUENCE: 121

```
cccgtcgacg tgttgctgtg ggattggtc                                        29
```

<210> SEQ ID NO 122
<211> LENGTH: 29
<212> TYPE: DNA
<213> ORGANISM: Artificial
<220> FEATURE:
<223> OTHER INFORMATION: primer

<400> SEQUENCE: 122

```
cccgtcgact cggttacatc tctgaggaa                                        29
```

<210> SEQ ID NO 123
<211> LENGTH: 3705
<212> TYPE: DNA
<213> ORGANISM: Artificial
<220> FEATURE:
<223> OTHER INFORMATION: fusion DNA (T. aureum OrfA upstream/EF1 alpha
      promoter/Neor/T. aureum OrfA downstream)

<400> SEQUENCE: 123

```
cccccatggc tcggttacat ctctgaggaa gacatggccg acgttttcga caagctttat      60
gcgtacaacg acatcataga tcatccgaac ggcggcccag ggccagaaca aggccgcctc     120
atgacagagg gaatcagcta tatagatgcc catttcccag aaaccgacag aatcctggcg     180
```

-continued

```
tgccgcgtcg tctgactaat gccgcgccaa gcttcatgac atcgaagacg gtcggttcag      240
cttgcggaca ctggtgaatc aagcccagcc gaagcgtggg aggaggctcg gcagatacgc      300
gcgatggagg tacattcgtt tttagtttac tgccctgcct ggtgcggccg ttttggagcg      360
gtttgtgctt tgcggtcggt cgtccctgac tacctctgtg cgtctcgagt cttctcgtag      420
tcaggtgcgc cagccgtcgc cagtccagca actgtgcagg gacgagtggg agcgaccgcc      480
gcgcttgctc tcgccggacc tgccgcagta ccaactggac ccttcgatag tctgcttcaa      540
atgagggcca gagtgcgccg ccaaccatgc catgcccctt tgtgcgcgca tgcgtggaag      600
cacctttaga gagtacaacc acgcaaacag cgctgccacg caaacagcgc tgccatactc      660
acctaaaagc cctgaaaaga gtttgaaatc catcgcatcg atgcggcgtg aagaagaag      720 atcttgcgag cagatgcaac gtgatcttgg ttcactcgtt tgaagtgacg tggggcgatc      780
aacttcgtcc taacgcctgc gagcgcgagc ccgaaacctt cgttcgttat ccatgtgata      840
ctggctttgt gaaaaactac ggaaaagacg ctctagccta gctagctagc tagagggatt      900
cggctgcctc ctgggcagcc agtgacgggg catttctgcg cgcgacggag gccgcgtgca      960
gaagagcccc cggaccaatc ccacagcaac accatggcag agtcgcccga cttgatgaac     1020
ttgggggtct cctcgagaat cttgcccgag cggcggtcca tcttgttctg gagctcagcg     1080
aacttgcagg caatgtgggc agtgtggcgg tcgagcacgg gcgcatagcc ggcgcggatc     1140
tcaaaagaac tcgtccagga ggcggtagaa cgcaatcctc tggctgtccg gggcggcgat     1200
gccgtagagc acgagaaagc ggtcggccca ctcgccgcca agctcctcgg cgatgtcccg     1260
cgtggcgagc gcgatgtctt ggtagcggtc cgccacgccc aggcgcccgc agtcgataaa     1320
gcccgagaag cggccgttct cgaccatgat gttggggagg caggcgtcgc cgtgcgtgac     1380
cacgaggtcc tcgccgtccg gcatcctagc cttaagcctg gcgaacagtt ccgccggcgc     1440
gaggccctgg tgctcctcgt cgaggtcgtc ttggtcgacg aggccagcct ccatccgcgt     1500
gcgggcgcgt tcgatcctgt gcttcgcctg gtggtcgaag gggcaggtgg cggggtcgag     1560
ggtgtgcagg cggcgcatgg cgtcggccat gatggacacc ttctcagcgg gcgcgaggtg     1620
gctgctgagg aggtcctggc cgggcacttc cccgaggagc agccagtcgc ggccggcttc     1680
ggtgacgacg tcgagcacag cggcgcacgg aacccccgtc gtggcaagcc agctgaggcg     1740
ggcagcttcg tcctggagct cgttgagggc gccgctaagg tcggtcttga caaacaggac     1800
cggccggccc tgcgcgctaa ggcggaacac ggccgcgtcc gagcagccga tcgtctgctg     1860
agcccagtcg tagccgaaca gccgttccac ccaagcagcg ggcgagccag cgtgaaggcc     1920
gtcctgttca atcatctagc cttcctttgc cgctgcttgc tactcctgct actcctgctt     1980
gttacttcgt gttgctccgc gttccgtctc tgccgcgccg tccacgagcg cctcacgga      2040 tttatccgcc caacgcggct caccttggcc gcctatctaa ccccgcaaac cgcctcccag     2100
ccaaccattg cgccgccgta aggcggattc ccagaacaca gccccgccgc gacctaaccc     2160
aacctaaccg cccgcgcccg ccgccacctt acgcagccgc accgcccgc cgcgccgcgc      2220 tgctgggccg ccctcgcccc gcagaccgcc ctgcgcgctc gcggggggcta tcctggtagt    2280 cgcgcgctag gaggtgctag gcggcccgt gcttccacct cgcccgcgac ccgccgaac       2340 agcctggagc cctaaccctc ggtttggctt aaggaggact gccgccaggc ccccgtgac      2400 gcgggccccc ggggctctct gctgcggccg cgtctcgtcg cactttccgt cccgacacag     2460
gggacccgag gtgacgagga cgaatgcgcg aagcttgtct gcctcggctc ttggtctcgg     2520
cggtgctctc gacgcactcc acttgcgttt gcagcacgga tccttcgccg tgtctcgggt     2580
```

```
ctgcaaatcg agtttgcctg cacacgatga aggtcacag aagagtccaa gtgcaaccaa      2640
ccagcctgag cgcggcaaac gacgtaggtt cgtggcctcg tacctgatcg gccggacgat     2700
ccgcaaagcg cggcccaaaa caccaatgat ggcccaatga tggcccaatg atggccggat     2760
gcacttgcgt cactttcctg cgctcacatc ctgccccgcc cctctcgcag tccggcttgc     2820
tggtgtcgcc cactcgccca gcctccctcc ctccctcggc ccaatcaaac tgatcatggg     2880
ccagaatcca attcttcggc gccctgcagc acaagaacac ttgcacttgc aggcggtccg     2940
tgctcagctc atcgcttgct cagcgaggag gcggacaagg cgtggcgagc acgagcaagc     3000
gcctcgagag ggaccagcca agacgccatc cgcgcacgca atggggcgct gccgggcgcg     3060
cttcgagtgc gcggaggggg gacaggcggc cggccgctcg tccttcggac ggctcctgct     3120
gctggcagcg cgagcagggc gaacggcgtt ctcgatccca tgtccgctcc cacaccgtgt     3180
ccgttttcgc gcggccacgg accccgtccg cgagcgagct gcgcggcggg gtggcgcgac     3240
cgcactgcgg atccggcccg ctctgcgtct ctgcactacg tagtgcgctg ctgcgccctg     3300
aggattcctg tccgtggcgg gctgcctggc ctcctgcgac ctggtgccag tgagggccgc     3360
cactcgccgc tcgccggcct ccttcctccc ctccagggc cctcagccgc gacgcaagtg      3420
ggctgcgcgc cgccttgacg caagagagcc aactctctct ctggttgaac agccgcagtg    3480
cagcttacgt gctcgctcag gcttgcctaa tcatcgcgag gactcggaag tacacctgcg    3540
agcgcggctt ggcttgcagc ggagcaggcc agcgtttcgc caagggcct ggcccttcct     3600 tccttccttc ctgcctgcct gcctggtttg cgacgacgcc cgacgccgcg cacgagggcg    3660
gccgtcgtca gccaatcagt cagtcagtca tcgtccgaat tcggg                    3705
```

<210> SEQ ID NO 124
<211> LENGTH: 3826
<212> TYPE: DNA
<213> ORGANISM: Artificial
<220> FEATURE:
<223> OTHER INFORMATION: fusion DNA (T. aureum OrfA upstream/ubiquitin
      promoter/Hygr/T. aureum OrfA downstream)

<400> SEQUENCE: 124

```
cccccatggc tcggttacat ctctgaggaa gacatggccg acgttttcga caagctttat      60
gcgtacaacg acatcataga tcatccgaac ggcggcccag ggccagaaca aggccgcctc     120
atgacagagg gaatcagcta tatagatgcc catttcccag aaaccgacag aatcctggcg     180
tgccgcgtcg tctgactaat gccgcgccaa gcttcatgac atcgaagacg gtcggttcag     240
cttgcggaca ctggtgaatc aagcccagcc gaagcgtggg aggaggctcg gcagatacgc     300
gcgatggagg tacattcgtt tttagtttac tgccctgcct ggtgcggccg ttttggagtg     360
gtttgtgctt tgcggtcggt cgtccctgac tacctctgtg cgtctcgagt cttctcgtag     420 tcaggtcgc cagccgtcgc cagtccagca actgtgcagg gacgagtggg agcgaccgcc      480
gcgcttgctc tcgccggacc tgccgcagta ccaactggac ccttcgatag tctgcttcaa     540
atgagggcca gagtgcgccg ccaaccatgc catgcccctt tgtgcgcgca tgcgtggaag    600 caccctttaga gagtacaacc acgcaaacag cgctgccacg caaacagcgc tgccacgcaa    660
acagcgctgc catactcacc taaaagccct gaaaagagtt tgaaatccat cgcgtcgatg     720
cggcgtggaa gaagaagatc ttgcgagcag acgcaacgtg atcttggttc actcgtttga    780
agtgacgcgg gacgatcaac ttcgtcctaa cgcctgcgag cgcgagcccg aaaccttcgt    840
tcgttatcca tgtgatactg gctttgtgaa aaactacgga aaagacgcta gctagaggga     900
```

```
ttcggctgcc tccttgggca gccagtgacg gggcatttct gcgcgcgacg gaggccgcgt    960
gcaaaagagc ccccggacca atcccacagc aacacgtcga ctattcctttt gccctcggac   1020
gagtgctggg gcgtcggttt ccactatcgg cgagtacttc tacacagcca tcggtccaga   1080
cggccgcgct tctgcgggcg atttgtgtac gcccgacagt cccggctccg gatcggacga   1140
ttgcgtcgca tcgaccctgc gcccaagctg catcatcgaa attgccgtca accaagctct   1200
gatagagttg gtcaagacca atgcggagca tatacgcccg gagccgcggc gatcctgcaa   1260
gctccggatg cctccgctcg aagtagcgcg tctgctgctc catacaagcc aaccacggcc   1320
tccagaagaa gatgttggcg acctcgtatt gggaatcccc gaacatcgcc tcgctccagt   1380
caatgaccgc tgttatgcgg ccattgtccg tcaggacatt gttggagccg aaatccgcgt   1440
gcacgaggtg ccggacttcg gggcagtcct cggcccaaag catcagctca tcgagagcct   1500
gcgcgacgga cgcactgacg gtgtcgtcca tcacagtttg ccagtgatac acatggggat   1560
cagcaatcgc gcatatgaaa tcacgccatg tagtgtattg accgattcct tgcggtccga   1620
atgggccgaa cccgctcgtc tggctaagat cggccgcagc gatcgcatcc atggcctccg   1680
cgaccggctg cagaacagcg ggcagttcgg tttcaggcag gtcttgcaac gtgacaccct   1740
gtgcacggcg ggagatgcaa taggtcaggc tctcgctgaa ttccccaatg tcaagcactt   1800
ccggaatcgg gagcgcggcc gatgcaaagt gccgataaac ataacgatct ttgtagaaac   1860
catcggcgca gctatttacc cgcaggacat atccacgccc tcctacatcg aagctgaaag   1920
cacgagattc ttcgccctcc gagagctgca tcaggtcgga gacgctgtcg aactttttcga  1980
tcagaaactt ctcgacagac gtcgcggtga gttcaggctt tttcatgttg gctagtgttg   2040
cttaggtcgc ttgctgctgc tggtgttgct tgttctgctt gtcgtttggg gtctgcccga   2100
agtggacgcg tgacacagcc cagcgttcgc gacttttcca gcaaccagct cgctcccgcg   2160
tcagggtcac tctctgctca ctcccctgtc tagttcggca gaactggaga ggcaacccgc   2220
gcttccagag ggttctcctc cggaatcagt tcagaattca gaattcagaa gagggaatcg   2280
cagaaccggc cgcttcggga gttggttcgc tgcaccatag caggtgggcg atgaggccaa   2340
ccgccctgct ggctggattc tctcggggttg gcacatcgaa cgaccgggac ccgcgcgcga   2400
gttgtccctg ccagttgcta ccagcctgcc agcgtcggag agttatgcgc tgcctgccgg   2460
ccggagagag agcgggcgtg gaaagtggcg tgtggggcga acgcatggcc ctcccgcgtg   2520
gcccgatttc ctatgcatcc gctccgctct ctctctcgga ggcaagaaga gcacaccaac   2580
aacgcccggc gggtgcacca ggcgctgcgg caagcttgtc tgcctcggct cttggtctcg   2640
gcggtgctct cgacgcactc cacttgcgtt tgcagcacgg atccttcgcc gtgtctcggg   2700
tctgcaaatc gagtttgcct gcacacgatg aaaggtcaca gaagagtcca agtgcaacca   2760
accagcctga gcgcggcaaa cgacgtaggt tcgtggcctc gtacctgatc ggccggacga   2820
tccgcaaagc gcgccccaaa acaccaatga tgcccaatg atggcccaat gatgccggaa   2880
tgcacttgcg tcactttcct gcgctcacat cctgccccgc ccctctcgca gtccggcttg   2940
ctggtgtcgc ccactcgccc agcctccctc cctccctcgg cccaatcaaa ctgatcatgg   3000
gccagaatcc aattcttcgg cgccctgcag cacaagaaca cttgcacttg caggcggtcc   3060
gtgctcagct catcgcttgc tcagcgagga ggcggacaag gcgtggcgag cacgagcaag   3120
cgcctcgaga gggaccagcc aagacgccat ccgcgcacgc aatggggcgc tgccgggcgc   3180
gcttcgagtg cgcggagggg ggacaggcgg ccggccgctc gtccttcgga cggctcctgc   3240
```

| | |
|---|---|
| tgctggcagc gcgagcaggg cgaacggcgt tctcgatccc atgtccgctc ccacaccgtg | 3300 |
| tccgttttcg cgcggccacg gaccccgtcc gcgagcgagc tgcgcggcgg ggtggcgcga | 3360 |
| ccgcactgcg gatccggccc gctctgcgtc tctgcactac gtagtgcgct gctgcgccct | 3420 |
| gaggattcct gtccgtggcg ggctgcctgg cctcctgcga cctggtgcca gtgagggccg | 3480 |
| ccactcgccg ctcgccggcc tccttcctcc cctccagggg ccctcagccg cgacgcaagt | 3540 |
| gggctgcgcg ccgccttgac gcaagagagc caactctctc tctggttgaa cagccgcagt | 3600 |
| gcagcttacg tgctcgctca ggcttgccta atcatcgcga ggactcggaa gtacacctgc | 3660 |
| gagcgcggct tggcttgcag cggagcaggc cagcgtttcg caccagggcc tggcccttcc | 3720 |
| ttccttcctt cctgcctgcc tgcctggttt gcgacgacgc ccgacgccgc gcacgagggc | 3780 |
| ggccgtcgtc agccaatcag tcagtcagtc atcgtccgaa ttcggg | 3826 |

```
<210> SEQ ID NO 125
<211> LENGTH: 22
<212> TYPE: DNA
<213> ORGANISM: Artificial
<220> FEATURE:
<223> OTHER INFORMATION: primer

<400> SEQUENCE: 125
gaagcgtccc gtagatgtgg tc                                              22

<210> SEQ ID NO 126
<211> LENGTH: 21
<212> TYPE: DNA
<213> ORGANISM: Artificial
<220> FEATURE:
<223> OTHER INFORMATION: primer

<400> SEQUENCE: 126
gcccgagagg tcaaagtacg c                                               21

<210> SEQ ID NO 127
<211> LENGTH: 20
<212> TYPE: DNA
<213> ORGANISM: Artificial
<220> FEATURE:
<223> OTHER INFORMATION: primer

<400> SEQUENCE: 127
gcgagcccag gtccacttgc                                                 20

<210> SEQ ID NO 128
<211> LENGTH: 22
<212> TYPE: DNA
<213> ORGANISM: Artificial
<220> FEATURE:
<223> OTHER INFORMATION: primer

<400> SEQUENCE: 128
cagcccgatg aaaaacttgg tc                                              22

<210> SEQ ID NO 129
<211> LENGTH: 22
<212> TYPE: DNA
<213> ORGANISM: Artificial
<220> FEATURE:
<223> OTHER INFORMATION: primer

<400> SEQUENCE: 129
gggagcgcag ggaaaacggt ct                                              22
```

```
<210> SEQ ID NO 130
<211> LENGTH: 20
<212> TYPE: DNA
<213> ORGANISM: Artificial
<220> FEATURE:
<223> OTHER INFORMATION: primer

<400> SEQUENCE: 130
ccagcccacg tcgtcggagc                                                   20

<210> SEQ ID NO 131
<211> LENGTH: 2297
<212> TYPE: DNA
<213> ORGANISM: Artificial
<220> FEATURE:
<223> OTHER INFORMATION: genomic DNA (T. aureum  ATCC 34304 C20 elongase
      upstream genomic DNA fragment)

<400> SEQUENCE: 131
ggccggggca gcccgcccag cacgccgctg cgctgctttc ggtcatgcga acctggctcc       60
ccacagcaat gctgcgcggt cgctgcgcct cttgaggctc ggcgacgttg gcccggtttg      120
gggcaccctg acgttgcacg aacgtccgct gcatctcagg cgcactcgga tcgacaactg      180
tgcaaccggt cagcctttcg cggcagattg ggcacttgcc gcgctcgcgt atccgcgtgg      240
cgcattcttc gcacacgcag gcgtgccggc agggaagcag gagggtgttt atcgtggcgt      300
ccatgtagac cttgcacagc gcgggctcac tttccctcgg cgcagtcccg tgcccaacgt      360
cggggccggg cgccggcgcc ggcgagggcg tcggttctgg gatgggatca ggatccgccg      420
aggctgcaga ttgctgtgcg ggggtgccgg ggcgcggccc attagcaccg tcctgcggaa      480
tatccaggag ggtgctcatc acggaagcca tgtccgggcg ctggctgccg tcttcgtgcg      540
tgcaacgatc caccaggtca aggagcaccc gagccacgtt ttggcgggtg cgaaaagcgg      600
cttggtcaac gcagcgctcc gggtcgaagc cgttgtcgcg catccagtac ggaagcaggt      660
cgaggccgcg gcggcaggga agcaaggcg gcttgccgga cacaagctcg ccgagcacga      720
cgccaaaggc gtaaacgtcc acggggcgat tgtactcgac atgggtggcg ccctccaggt      780
cggagatctc gggcgccatg tagccaagcg tgcccacttg tgtcatcgtt tgcatggtgt      840
ggagcgtggt actggcggcc accttggaca cgccaaagtc cgtccagcac agccttaggc      900
ccgcgccctt gttcaggttg accagagcgt tgtcgctctt ggatgtctct gtgcagcacg      960
ccagcagcgt gcagcgccct gaggccgtgc gccgcctggt atgccagcgc ctcgcgagcg     1020
ctgccgtcca aaagcggcgc gctccccgaa tcatcgcgga gctggatggc cttcttgagc     1080
gacatttcca tgcggggcat gatgatcgca aacctgccgc cgctctgtgg ctcgagcgcg     1140
gtcgccagga ccgtgagcac gttctcgtgc gttgcgctcg ccatccgcga ggcctcagcg     1200
cgaaagtcat cgaggacgcc gagcgtctgc ccgggccgcg gtaccttgac agcgcagcgc     1260
ccgaacggcg ccacgtccgc ttcaaacacc tcgccaaagg cgccttgtcc gagcagctcg     1320
ccccagccgc agccgcgacc actcgatctc gggcacgcgt gccatcgacc cttgcagcgt     1380
ggccttgcca agtcacagtc cagcgcgcag ttcagtgtct gccgcgccag gtccaccacg     1440
atcaattcat ccgagtcggc tgcgaactgg acaagtgcca tttgggtgcg ggcaacgcgc     1500
aagatcaccc agcactggca tgaagaccat gaatgaatga atgaccgtgc gcgagtgacc     1560
gaccaacacg agtccagccg actccttctt cttctccttc ttcttcttct tcttcttctc     1620
gtagcgggcg tcaacagcat caatcaggca tggcggcatt cactctgcgc gatggatggc     1680
```

```
acgagcgctg gaggtgatga acgcactgcc cggattggct ctcggtcact gtcagcacat    1740
gatgcctgtg cttgcgcgga gcgcgctatg tctcgttctg tgtcaagaca caggcgcaac    1800
tcttgatgga ttcttgaagc gcatgtaact gaagtctgac agactcggaa gtccattgtg    1860
aacaatgttg ttccacaatt gctccaattg ttccgattat tccacaattg ttgttccaat    1920
tgttccaatt gttccgatta ttccgattat tccactttag ttgttccagt tgttccgatt    1980
gttccacaat tgttgttccg attattccag ttgttccagt tgttccaatt attccaattg    2040
ttccagttcc ttactcttga catcggggga ataacgggtg tgtatttagg ggttcggcga    2100
aagcagaatg gccgaacgta acagcggaga ggaacctctt tagcggggtt tgcgtatcgg    2160
ggaaaccagg tgttgtgctg gcgaggagga tcccccgcga ggcgatggct gctccgacga    2220
cgtgggctgg cgacgtcgct cgcaaaggcg ttccgcaacc gcgcgttccg ctgtaacgag    2280
accgttttcc ctgcgct                                                   2297
```

```
<210> SEQ ID NO 132
<211> LENGTH: 23
<212> TYPE: DNA
<213> ORGANISM: Artificial
<220> FEATURE:
<223> OTHER INFORMATION: primer

<400> SEQUENCE: 132
gccgctcatg cccacgctca aac                                              23

<210> SEQ ID NO 133
<211> LENGTH: 23
<212> TYPE: DNA
<213> ORGANISM: Artificial
<220> FEATURE:
<223> OTHER INFORMATION: primer

<400> SEQUENCE: 133
ctttcggctg ccaggaatct acg                                              23

<210> SEQ ID NO 134
<211> LENGTH: 2189
<212> TYPE: DNA
<213> ORGANISM: Artificial
<220> FEATURE:
<223> OTHER INFORMATION: genomic DNA (T. aureum  ATCC 34304 OrfA
      downstream genomic DNA fragment)

<400> SEQUENCE: 134
ctttcggctg ccaggaatct acggcccagg gcgcggcccg atctcacgaa ttcgcaaggg     60
ccaggcccgc agtatcgtca aggagggcca ggtcttctcg cgggcgcacg tcgacgatat    120
caccggtgcg atccgcgctt cgctggccaa cccaaacccg ggccgcgcct acaacgtttg    180
cgacgacgag cctgcaatga accatgtcgt gacagagttt gcctgcgaac tcatggacgt    240
cccgcccccg aagcgcgaag actttgacaa ggtgcgcgag accatgtcaa gcatgtcgct    300
ctccttcttc tcagagagca agcgggtctt caacaagcgg ctcaaggaag agctgcggta    360
cgcgctattg tacccgacct accgcgaagg gatcaaagcc caactggagg aggagcttgc    420
caacggctgg acgctcatcg acgcctcggg tgcttctgct ggaaccgact ccctgcctc    480 gcccaaagcg cccgcccca tcgccgcctc aagtgacgag tcgagcgggc agagcgcgac    540
agcggccgag ccggtgcgcc ggcgcaggcg ccccgagcgc aaggcgctcc cgcctgctgg    600
gccgagtggg ccgtcggtct tgcagagggt ttctcgggca atttatgggc cgttcagttg    660
```

```
gctcctcggt cgcctgtttg ggccactttc gagccgcgct gtcggcttgt ttcgcggctg      720
ggcgcactgg ctgttgcgtc tcgtggggct gcgcgcatcc gcgccgggcg gcggccgtac      780
aacctgcctc cttgttgaca acggctcgct caaaccagag cctttcgcc  agctgcgcgt      840 gcacgcggcg aacctcgaag agtctcttag gagcgacgcg cgtgcccac  atcccgtgca      900 ggtggtggcc gtcagcgcga ggtacagcga ccgcatcgac gcctcccttc tggacggcaa      960
gcccggcgtc gccctcgccg ggttcctgag ttccttcaag gccgacgccg agtcgcagcc     1020
agcaaccagc gaggttggcc gcatcatcgc gctccctac  tttctgggcc caagcaagac     1080
ggccacgtcg tatgttgctt cccagctcgc agagcacttt ccaggagccg agcgcaccat     1140
tgccgctccg ctcgtgtcgc gggacggcgc cattgcgcag ctcctcgctg acatggtcca     1200
tgacgtcgct cgggcgcgcg cgctgcaggc cccgtacgcg gtagttctcg tcgaccacgg     1260
gtccccgagc cgagcggtca accgcgttcg gcgggccatc gctgcgcgga tgcgccgccg     1320
ccttggcccg aacgcgcgct gcgttgtcga ctgctccatg gagcgccgcg agggcgacgc     1380
tttcgccttc aacgagcctc tgctagagtc ggttttcacc aagggtggtc tcgactctgg     1440
cgacgtcatt ctcgcgatgg cattttttggc gcctggtcgc cacgctggcg agggcggcga     1500
tatcgcggag atccttgacg aggctatcgc aaagtcggct ggcaagctgc gcgttcacca     1560
aacgcggttg attggtgacg tggacaggaa cggtacgcag atttgcgccc tcctcaagaa     1620
caggccgctt gccgcgctgt aacggcaaga gcatccacaa ttcctgacct gagcaaacca     1680
gcccacgcga gagaccgaac acgtcaagcc gatgaggcgc agaaaacaaa gaaaaaaagc     1740
aaaaagaaca aaaacccaag gcaaaatgat ggcaattttc ttggtatgga aagccgatga     1800
tcgccgagtg tcgctggcta tttgctctgg tggggcatcg agctcgatga ccgaaatcca     1860
ccaattatct gcgtgtcaat catttggagc ataagacccg ggaaggcctt gagcaagcga     1920
agaaaccggc gcgtgttcac acgatagtac gagacgtcgc tctctgcgcg gatctcaatc     1980
tgagcctcct tgtctccgcg gatgaaagtg ttcatgtccc cgacaagggc gccgcgccca     2040 accctcgtt tgggctgcgc cgcgctactg gaaatggtga ttccgcgaaa cgtgcccgat     2100
tcgccttcct caacagggct caccgtgaca gaaccctcag cgacaagaac gatgccgtca     2160
atcttttcgc cgggcgaggc tttctgcag                                      2189
```

<210> SEQ ID NO 135
<211> LENGTH: 618
<212> TYPE: DNA
<213> ORGANISM: Artificial
<220> FEATURE:
<223> OTHER INFORMATION: genomic DNA (T. aureum ATCC 34304 ubiquitin promoter)

<400> SEQUENCE: 135

```
cccagatctg ccgcagcgcc tggtgcaccc gccgggcgtt gttggtgtgc tcttcttgcc       60
tccgagagag agagcggagc ggatgcatag gaaatcgggc cacgcgggag ggccatgcgt      120
tcgccccaca cgccactttc cacgcccgct ctctctccgg ccggcaggca gcgcataact      180
ctccgacgct ggcaggctgg tagcaactgg caggacaac  tcgcgcgcgg gtcccggtcg      240
ttcgatgtgc caacccgaga gaatccagcc agcagggcgg ttggcctcat cgcccacctg      300
ctatggtgca gcgaaccaac tcccgaagcg gccggttctg cgattccctc ttctgaattc      360
tgaattctga actgattccg gaggagaacc ctctggaagc gcgggttgcc tctccagttc      420
tgccgaacta gacaggggag tgagcagaga gtgaccctga cgcggagcga gctggttgct      480
```

```
ggaaaagtcg cgaacgctgg gctgtgtcac gcgtccactt cgggcagtcc ccaaacgaca       540
agcagaacaa gcaacaccag cagcagcaag cgacctaagc aacactagcc aacatggcca       600
agcctttgtc tcaagaag                                                    618
```

<210> SEQ ID NO 136
<211> LENGTH: 58
<212> TYPE: DNA
<213> ORGANISM: Artificial
<220> FEATURE:
<223> OTHER INFORMATION: primer

<400> SEQUENCE: 136

```
cttcttgaga caaaggcttg gccatgttgg ctagtgttgc ttaggtcgct tgctgctg         58
```

<210> SEQ ID NO 137
<211> LENGTH: 432
<212> TYPE: DNA
<213> ORGANISM: Artificial
<220> FEATURE:
<223> OTHER INFORMATION: Blasticidin resistance gene (Blar)

<400> SEQUENCE: 137

```
agcgacctaa gcaacactag ccaacatggc caagcctttg tctcaagaag aatccaccct       60
cattgaaaga gcaacggcta caatcaacag catccccatc tctgaagact acagcgtcgc      120
cagcgcagct ctctctagcg acggccgcat cttcactggt gtcaatgtat atcattttac      180
tgggggacct tgtgcagaac tcgtggtgct gggcactgct gctgctgcgg cagctggcaa      240
cctgacttgt atcgtcgcga tcggaaatga gaacagggggc atcttgagcc cctgcggacg      300
gtgccgacag gtgcttctcg atctgcatcc tgggatcaaa gccatagtga aggacagtga      360
tggacagccg acggcagttg ggattcgtga attgctgccc tctggttatg tgtgggaggg      420
ctaagatctg gg                                                         432
```

<210> SEQ ID NO 138
<211> LENGTH: 54
<212> TYPE: DNA
<213> ORGANISM: Artificial
<220> FEATURE:
<223> OTHER INFORMATION: primer

<400> SEQUENCE: 138

```
agcgacctaa gcaacactag ccaacatggc caagcctttg tctcaagaag aatc             54
```

<210> SEQ ID NO 139
<211> LENGTH: 38
<212> TYPE: DNA
<213> ORGANISM: Artificial
<220> FEATURE:
<223> OTHER INFORMATION: primer

<400> SEQUENCE: 139

```
cccagatctt agccctccca cacataacca gagggcag                               38
```

<210> SEQ ID NO 140
<211> LENGTH: 1000
<212> TYPE: DNA
<213> ORGANISM: Artificial
<220> FEATURE:
<223> OTHER INFORMATION: fusion DNA (T. aureum ATCC 34304 ubiquitin
      promoter/pTracer-CMV/Bsd/lacZ Blar)

<400> SEQUENCE: 140

```
cccagatctg ccgcagcgcc tggtgcaccc gccgggcgtt gttggtgtgc tcttcttgcc      60
tccgagagag agagcggagc ggatgcatag gaaatcgggc cacgcgggag ggccatgcgt     120
tcgccccaca cgccactttc cacgcccgct ctctctccgg ccggcaggca gcgcataact     180
ctccgacgct ggcaggctgg tagcaactgg cagggacaac tcgcgcgcgg gtcccggtcg     240
ttcgatgtgc caacccgaga gaatccagcc agcagggcgg ttggcctcat cgcccacctg     300
ctatggtgca gcgaaccaac tcccgaagcg gccggttctg cgattccctc ttctgaattc     360
tgaattctga actgattccg gaggagaacc ctctggaagc gcgggttgcc tctccagttc     420
tgccgaacta gacaggggag tgagcagaga gtgaccctga cgcggagcga gctggttgct     480
ggaaaagtcg cgaacgctgg gctgtgtcac gcgtccactt cgggcagtcc caaacgaca     540 agcagaacaa gcaacaccag cagcagcaag cgacctaagc aacactagcc aacatggcca     600
agcctttgtc tcaagaagaa tccaccctca ttgaaagagc aacggctaca atcaacagca     660
tccccatctc tgaagactac agcgtcgcca gcgcagctct ctctagcgac ggccgcatct     720
tcactggtgt caatgtatat cattttactg ggggaccttg tgcagaactc gtggtgctgg     780
gcactgctgc tgctgcggca gctggcaacc tgacttgtat cgtcgcgatc ggaaatgaga     840 acagggcat cttgagcccc tgcggacggt gccgacaggt gcttctcgat ctgcatcctg      900
ggatcaaagc catagtgaag gacagtgatg gacagccgac ggcagttggg attcgtgaat     960
tgctgccctc tggttatgtg tgggagggct aagatctggg                         1000

<210> SEQ ID NO 141
<211> LENGTH: 812
<212> TYPE: DNA
<213> ORGANISM: Artificial
<220> FEATURE:
<223> OTHER INFORMATION: cDNA (T.aureum ATCC 34304 ubiquitin promoter)

<400> SEQUENCE: 141
tcggtacccg ttagaacgcg taatacgact cactataggg agagtcgact gagcacaact      60
ctgctgcgag cgggcctcga gagcgtttgc ttcgagccgc ggagcaaggg ggatggatcg     120
ctcatgcggt cgtgcggccc tcggtcaccc ggtgggtcct gcactgacgc atctgttctg     180
atcagacaca cgaacgaaca aaccgaggag ccgcagcgcc tggtgcaccc gccgggcgtt     240
gttgtgtgct cttcttgcct ccgagagaga gagcggagcg gatgcatagg aaatcgggcc     300
acgcgggagg gccatgcgtt tgccccacac gccactttcc acgcccgctc tctctccggc     360
cggcaggcag cgcataactc tccgacgctg gcaggctggt agcaactggc agggacaact     420
cgcgcgcggg tcccggtcgt tcgatgtgcc aacccgagag aatccagcca gcagggcggt     480
tggcctcatc gcccacctgc tatggtgcag cgaaccaact cccgaagctg ccggttctgc     540
gattccctct tctgaattct gaattctgaa ctgattccgg aggagaaccc tctggaagcg     600
cgggttgcct ctccagttct gccgaactag acagggagt gagcagagag tgaccctgac     660
gcggagcgag ctggttgctg gaaaagtcgc gaacgctggg ctgtgtcacg cgtccacttc     720
gggcagaccc caaacgacaa gcagaacaag caacaccagc agcagcaagc gatctaagca     780
acactagcca acatggtgag caagggcgag ga                                  812

<210> SEQ ID NO 142
<211> LENGTH: 29
<212> TYPE: DNA
<213> ORGANISM: Artificial
<220> FEATURE:
```

<223> OTHER INFORMATION: primer

<400> SEQUENCE: 142
tcggtacccg ttagaacgcg taatacgac                                         29

<210> SEQ ID NO 143
<211> LENGTH: 41
<212> TYPE: DNA
<213> ORGANISM: Artificial
<220> FEATURE:
<223> OTHER INFORMATION: primer

<400> SEQUENCE: 143
tcctcgccct tgctcaccat gttggctagt gttgcttagg t                           41

<210> SEQ ID NO 144
<211> LENGTH: 748
<212> TYPE: DNA
<213> ORGANISM: Artificial
<220> FEATURE:
<223> OTHER INFORMATION: Enhanced GFP gene (Enhanced GFP DNA fragment)

<400> SEQUENCE: 144
acctaagcaa cactagccaa catggtgagc aagggcgagg agctgttcac cggggtggtg       60
cccatcctgg tcgagctgga cggcgacgta aacggccaca gttcagcgt gtccggcgag      120 ggcgagggcg atgccaccta cggcaagctg accctgaagt tcatctgcac caccggcaag     180
ctgcccgtgc cctggcccac cctcgtgacc accctgacct acggcgtgca gtgcttcagc     240
cgctaccccg accacatgaa gcagcacgac ttcttcaagt ccgccatgcc cgaaggctac     300
gtccaggagc gcaccatctt cttcaaggac gacggcaact acaagacccg cgccgaggtg     360
aagttcgagg gcgacaccct ggtgaaccgc atcgagctga agggcatcga cttcaaggag     420
gacggcaaca tcctggggca caagctggag tacaactaca acagccacaa cgtctatatc     480
atggccgaca gcagaagaa cggcatcaag gtgaacttca gatccgcca caacatcgag      540 gacggcagcg tgcagctcgc cgaccactac cagcagaaca cccccatcgg cgacggcccc     600
gtgctgctgc ccgacaacca ctacctgagc acccagtccg ccctgagcaa agaccccaac     660
gagaagcgcg atcacatggt cctgctggag ttcgtgaccg ccgccgggat cactctcggc     720
atggacgcca agttgaccag tgccgttc                                        748

<210> SEQ ID NO 145
<211> LENGTH: 41
<212> TYPE: DNA
<213> ORGANISM: Artificial
<220> FEATURE:
<223> OTHER INFORMATION: primer

<400> SEQUENCE: 145
acctaagcaa cactagccaa catggtgagc aagggcgagg a                           41

<210> SEQ ID NO 146
<211> LENGTH: 58
<212> TYPE: DNA
<213> ORGANISM: Artificial
<220> FEATURE:
<223> OTHER INFORMATION: primer

<400> SEQUENCE: 146
gaacggcact ggtcaacttg gcgtccatgc cgagagtgat cccggcggcg gtcacgaa        58

<210> SEQ ID NO 147
<211> LENGTH: 1519
<212> TYPE: DNA
<213> ORGANISM: Artificial
<220> FEATURE:
<223> OTHER INFORMATION: fusion DNA (T. aureum ATCC 34304 ubiquitin promoter/ Enhanced GFP)

<400> SEQUENCE: 147

```
tcggtacccg ttagaacgcg taatacgact cactataggg agagtcgact gagcacaact    60
ctgctgcgag cgggcctcga gagcgtttgc ttcgagccgc ggagcaaggg ggatggatcg   120
ctcatgcggt cgtgcggccc tcggtcaccc ggtgggtcct gcactgacgc atctgttctg   180
atcagacaca cgaacgaaca aaccgaggag ccgcagcgcc tggtgcaccc gccgggcgtt   240
gttgtgtgct cttcttgcct ccgagagaga gagcggagcg gatgcatagg aaatcgggcc   300
acgcgggagg gccatgcgtt tgccccacac gccactttcc acgcccgctc tctctccggc   360
cggcaggcag cgcataactc tccgacgctg gcaggctggt agcaactggc agggacaact   420
cgcgcgcggg tcccggtcgt tcgatgtgcc aacccgagag aatccagcca gcagggcggt   480
tggcctcatc gcccacctgc tatggtgcag cgaaccaact cccgaagctg ccggttctgc   540
gattccctct tctgaattct gaattctgaa ctgattccgg aggagaaccc tctggaagcg   600
cgggttgcct ctccagttct gccgaactag acaggggagt gagcagagag tgaccctgac   660
gcggagcgag ctggttgctg gaaaagtcgc gaacgctggg ctgtgtcacg cgtccacttc   720
gggcagaccc caaacgacaa gcagaacaag caacaccagc agcagcaagc gacctaagca   780
acactagcca acatggtgag caagggcgag gagctgttca ccggggtggt gcccatcctg   840
gtcgagctgg acggcgacgt aaacggccac aagttcagcg tgtccggcga gggcgagggc   900
gatgccacct acggcaagct gaccctgaag ttcatctgca ccaccggcaa gctgcccgtg   960
ccctggccca ccctcgtgac caccctgacc tacggcgtgc agtgcttcag ccgctacccc  1020
gaccacatga gcagcacga cttcttcaag tccgccatgc ccgaaggcta cgtccaggag  1080
cgcaccatct tcttcaagga cgacggcaac tacaagaccc gcgccgaggt gaagttcgag  1140
ggcgacaccc tggtgaaccg catcgagctg aagggcatcg acttcaagga ggacggcaac  1200
atcctggggc acaagctgga gtacaactac aacagccaca acgtctatat catggccgac  1260
aagcagaaga acggcatcaa ggtgaacttc aagatccgcc acaacatcga ggacggcagc  1320
gtgcagctcg ccgaccacta ccagcagaac ccccatcg gcgacggccc cgtgctgctg  1380
cccgacaacc actacctgag cacccagtcc gccctgagca agacccccaa cgagaagcgc  1440
gatcacatgg tcctgctgga gttcgtgacc gccgccggga tcactctcgg catggacgcc  1500
aagttgacca gtgccgttc                                              1519
```

<210> SEQ ID NO 148
<211> LENGTH: 1319
<212> TYPE: DNA
<213> ORGANISM: Artificial
<220> FEATURE:
<223> OTHER INFORMATION: fusion DNA (T. aureum ATCC 34304 ubiquitin promoter/ Enhanced GFP)

<400> SEQUENCE: 148

```
cccagatctg ccgcagcgcc tggtgcaccc gccgggcgtt gttgtgtgct cttcttgcct    60
ccgagagaga gagcggagcg gatgcatagg aaatcgggcc acgcgggagg gccatgcgtt   120
tgccccacac gccactttcc acgcccgctc tctctccggc cggcaggcag cgcataactc   180
```

| | |
|---|---|
| tccgacgctg gcaggctggt agcaactggc agggacaact cgcgcgcggg tcccggtcgt | 240 |
| tcgatgtgcc aacccgagag aatccagcca gcagggcgt tggcctcatc gcccacctgc | 300 |
| tatggtgcag cgaaccaact cccgaagctg ccggttctgc gattccctct tctgaattct | 360 |
| gaattctgaa ctgattccgg aggagaaccc tctggaagcg cggggttgcct ctccagttct | 420 |
| gccgaactag acaggggagt gagcagagag tgaccctgac gcggagcgag ctggttgctg | 480 |
| gaaaagtcgc gaacgctggg ctgtgtcacg cgtccacttc gggcagaccc caaacgacaa | 540 |
| gcagaacaag caacaccagc agcagcaagc gacctaagca acactagcca acatggtgag | 600 |
| caagggcgag gagctgttca ccggggtggt gcccatcctg gtcgagctgg acggcgacgt | 660 |
| aaacggccac aagttcagcg tgtccggcga gggcgagggc gatgccacct acggcaagct | 720 |
| gaccctgaag ttcatctgca ccaccggcaa gctgcccgtg ccctggccca ccctcgtgac | 780 |
| caccctgacc tacggcgtgc agtgcttcag ccgctacccc gaccacatga gcagcacga | 840 |
| cttcttcaag tccgccatgc ccgaaggcta cgtccaggag cgcaccatct tcttcaagga | 900 |
| cgacggcaac tacaagaccc gcgccgaggt gaagttcgag ggcgacaccc tggtgaaccg | 960 |
| catcgagctg aagggcatcg acttcaagga ggacggcaac atcctggggc acaagctgga | 1020 |
| gtacaactac aacagccaca acgtctatat catggccgac aagcagaaga acggcatcaa | 1080 |
| ggtgaacttc aagatccgcc acaacatcga ggacggcagc gtgcagctcg ccgaccacta | 1140 |
| ccagcagaac accccatcg cgacggccc cgtgctgctg cccgacaacc actacctgag | 1200 |
| cacccagtcc gccctgagca agaccccaa cgagaagcgc gatcacatgg tcctgctgga | 1260 |
| gttcgtgacc gccgccggga tcactctcgg catggacgcc aagttgacca gtgccgttc | 1319 |

<210> SEQ ID NO 149
<211> LENGTH: 408
<212> TYPE: DNA
<213> ORGANISM: Artificial
<220> FEATURE:
<223> OTHER INFORMATION: cDNA (Zeor)

<400> SEQUENCE: 149

| | |
|---|---|
| cgccgccggg atcactctcg gcatggacgc caagttgacc agtgccgttc cggtgctcac | 60 |
| cgcgcgcgac gtcgccggag cggtcgagtt ctggaccgac cggctcgggt tctcccggga | 120 |
| cttcgtggag gacgacttcg ccggtgtggt ccgggacgac gtgaccctgt tcatcagcgc | 180 |
| ggtccaggac caggtggtgc cggacaacac cctggcctgg gtgtgggtgc gcggcctgga | 240 |
| cgagctgtac gccgagtggt cggaggtcgt gtccacgaac ttccgggacg cctccgggcc | 300 |
| ggccatgacc gagatcggcg agcagccgtg ggggcgggag ttcgccctgc gcgacccggc | 360 |
| cggcaactgc gtgcacttcg tggccgagga gcaggactga gatctggg | 408 |

<210> SEQ ID NO 150
<211> LENGTH: 54
<212> TYPE: DNA
<213> ORGANISM: Artificial
<220> FEATURE:
<223> OTHER INFORMATION: primer

<400> SEQUENCE: 150

| | |
|---|---|
| cgccgccggg atcactctcg gcatggacgc caagttgacc agtgccgttc cggt | 54 |

<210> SEQ ID NO 151
<211> LENGTH: 38
<212> TYPE: DNA
<213> ORGANISM: Artificial

<220> FEATURE:
<223> OTHER INFORMATION: primer

<400> SEQUENCE: 151
cccagatctc agtcctgctc ctcggccacg aagtgcac          38

<210> SEQ ID NO 152
<211> LENGTH: 1677
<212> TYPE: DNA
<213> ORGANISM: Artificial
<220> FEATURE:
<223> OTHER INFORMATION: fusion DNA (T. aureum ATCC 34304 ubiquitin
      promoter/Enhanced GFP/pcDNA3.1 Zeo(+) Zeor)

<400> SEQUENCE: 152

```
cccagatctg ccgcagcgcc tggtgcaccc gccgggcgtt gttgtgtgct cttcttgcct    60
ccgagagaga gagcggagcg gatgcatagg aaatcgggcc acgcgggagg gccatgcgtt   120
tgccccacac gccactttcc acgcccgctc tctctccggc cggcaggcag cgcataactc   180
tccgacgctg gcaggctggt agcaactggc agggacaact cgcgcgcggg tcccggtcgt   240
tcgatgtgcc aacccgagag aatccagcca gcagggcggt tggcctcatc gcccacctgc   300
tatggtgcag cgaaccaact cccgaagctg ccggttctgc gattccctct ctgaattct    360
gaattctgaa ctgattccgg aggagaaccc tctggaagcg cgggttgcct ctccagttct   420
gccgaactag acaggggagt gagcagagag tgacccctgac gcggagcgag ctggttgctg   480
gaaaagtcgc gaacgctggg ctgtgtcacg cgtccacttc gggcagaccc caaacgacaa   540
gcagaacaag caacaccagc agcagcaagc gacctaagca acactagcca acatggtgag   600
caagggcgag gagctgttca ccggggtggt gcccatcctg gtcgagctgg acggcgacgt   660
aaacggccac aagttcagcg tgtccggcga gggcgagggc gatgccacct acggcaagct   720
gaccctgaag ttcatctgca ccaccggcaa gctgcccgtg ccctggccca cctcgtgac    780
cacccctgacc tacggcgtgc agtgcttcag ccgctacccc gaccacatga gcagcacga   840
cttcttcaag tccgccatgc ccgaaggcta cgtccaggag cgcaccatct tcttcaagga   900
cgacggcaac tacaagaccc gcgccgaggt gaagttcgag ggcgacaccc tggtgaaccg   960
catcgagctg aagggcatcg acttcaagga ggacggcaac atcctggggc acaagctgga  1020
gtacaactac aacagccaca acgtctatat catggccgac aagcagaaga acggcatcaa  1080
ggtgaacttc aagatccgcc acaacatcga ggacggcagc gtgcagctcg ccgaccacta  1140
ccagcagaac ccccccatcg gcgacggccc cgtgctgctg cccgacaacc actacctgag  1200
cacccagtcc gccctgagca agaccccaa cgagaagcgc gatcacatgg tcctgctgga  1260
gttcgtgacc gccgccggga tcactctcgg catggacgcc aagttgacca gtgccgttcc  1320
ggtgctcacc gcgcgcgacg tcgccggagc ggtcgagttc tggaccgacc ggctcgggtt  1380
ctcccgggac ttcgtggagg acgacttcgc cggtgtggtc cggacgacg tgaccctgtt  1440
catcagcgcg gtccaggacc aggtggtgcc ggacaacacc ctggcctggg tgtgggtgcg  1500
cggcctggac gagctgtacg ccgagtggtc ggaggtcgtg tccacgaact ccgggacgc   1560
ctccggggccg gccatgaccg agatcggcga gcagccgtgg gggcgggagt cgccctgcg   1620
cgacccggcc ggcaactgcg tgcacttcgt ggccgaggag caggactgag atctggg      1677
```

<210> SEQ ID NO 153
<211> LENGTH: 2884
<212> TYPE: DNA
<213> ORGANISM: Artificial
<220> FEATURE:
<223> OTHER INFORMATION: genomic DNA (T. aureum ATCC 34304 C20 elongase
      upstream/C20 elongase/C20 elongase downstream)

<400> SEQUENCE: 153

```
cccgaattca ctagtgattc tcccgggtgg acctagcgcg tgtgtcacct gccggccccc      60
gttgcgtgca accgaattga tcgataatag aattacataa caaacaactt gctggatgag     120
tacaagacca gcgtagtgtg gctgtgggac gttgaacgga gcgggtcctg tgatggcgca     180
gaaaggaact ccgcccgagg tgaaacccccg atgcgcagga ctctgcggcc acagcccctc    240
cgccagtatt ccactaaaaa tccgcccccct ttgacaaaga tcgcaacccc gtcccatcaa    300
ctcctcacaa taggctttcc actggcggaa acgtccccgg cacaggagtg cctcccgcgg    360
ttctgcgcat acggctgacc actacgcagc gcgatatcct ccatccgcgt atatatccgt    420
aaacaacgga acattctccc tctcaacgag gcgtggtttt cgaagtcatg cctttcttcc    480
ttcctacttt ccttccttct ttctttcttt ctttccttct tttgcaagcg tgcgcgaact    540
tgaaggtact acttacactt gacagagaga gatagagacg gcaattcgac caagtacttt    600
ccacgatttt tttttttttt gttttggtcg ctttcgttgg tcgtgcatga tggatggccg    660
ggattttac aattggatgc gccaggctgc cacgcatgcc gtgacgcttg ctcgcggcga     720
ctcatgatgc ttgccagtgg cagtgcatcc agctcttccc tctgctcgtc gtgtactcac    780
tggcgatgct ctcggcgctc gttcaagggc catcgatcga tcgatcgatc gatcgatcga    840
tcaatcacgt ttggtggact cggcagaccc cgaacgtgtt ctcccagga cgcgccgctg     900
tcgctcgcta atccacccga agcgcggtcg gctggcacgg tcgctcggct ggaagttgag    960
tagtttgctt tctgttgctg cgctgctttg taaacgcgac catggcgacg cgcacctcga   1020
agagcgctcc ggcggtttcc aagtcggcca aggttgccgc gccggcgaag aagcggtcgg   1080
tcgacaggag cgacggtttc ttccgcacgt tcaacctgtg cgccctgtac gggtctgccc   1140
tcgcctatgc gtacaagcac ggcccggtgg acaatgacgg ccaggggctg tactttcaca   1200
agtcgcccat gtacgcgttc gccgtgtcgg acgtcatgac cttcggcgcg ccgctgatgt   1260
acgtgctcgg tgtgatgctg ctcagcaggt acatggcgga caaaaagccc ctgactggct   1320
tcatcaagac ctacatccag cccgtctaca acgtggtcca aatcgcggtg tgcggctgga   1380
tggtgtgggg cctctggccg caggtcgacc tggccaacgg caaccctttc ggcctcaaca   1440
agtcgcgcga ctcgaacatc gagttttttcg tgttcgtgca cctcctgaca aagtttctcg   1500
actggagcga cacgttcatg atgatcctca agaaaaacta cgcccaggtt agctttctgc   1560
aggtgttcca ccacgcaacg atcggcatgg tgtggtcgtt ccttcttcag cgtggctggg   1620
gctcgggcac cgccgcgtac ggtgctttca tcaactcggt cacgcacgtg atcatgtact   1680
cgcactactt tgccacctcg ctcaacatca acaacccgtt caagcggtac atcacgagct   1740
tccagctcgc ccagtttgca agctgcatcg tgcatgccct actggtgctt gccttcgagg   1800
aggtgtaccc gctcgagtac gcttacctgc agatcagcta ccacatcatc atgctctacc   1860
tgttcggacg ccgcatgaac tggagccccg agtggtgcac cggtgagatc gacggccttg   1920
acgcccccaag cgcccccacc aagtccgagt aaacctgttt ccggctggct cccgagccat   1980
gcttaccatg aatgaacctg caaacagtct gaggtccttg tgcaaaccgc tcagtgggac   2040
gtcgacgaag aaagaaacaa tgtgtactcg tcttgctctg ctcccgcgcc gttttttatc   2100
gttgttgaga cctctcgcgc agttttggga atcaaccaaa acaagagccc ggcgtcagcg   2160
tttgcttcgc cctcggctgc actcgctcgg cacgcaggta taactgggtg agtaccaagc   2220
```

```
cccgcatttg tctgtccgcg atccgcgcac gctgcgggtc aggacgacat cgcgctgcac    2280
gtcacagtgg gtccctttg acgtggctgc ggcgatgagg aggcttggct cggcttcatg     2340
gcaaggcaac agactcgctt ccgggacgcg cacgacgagc agcgctgctt tgatcgacct    2400
tgcctgcgtc accgcctcgg ctgctttgat cgatcgttgt caccggccga gtgaccgcga    2460
acgcattgcc cgcacggctc ggctcggccc ggaccggacc ggctcgcctt ggcggcgcgg    2520
cgcgatggcg acccagacgc ggccggagcc gcgcgcggag gacaaggcca tgttcatctt    2580
cgggctcggg tacgttggga gcaggctcgc caaccagctg gcggaacagg ggtggcgcgt    2640
cgcggggtcg gtgagggagc tcgggcgcga ggacgacttt gccgagttcg aaaagtccaa    2700
gctgagcggc aaggtgcagg tgttccgact cccgcttgag ggcgaggaca acacgcccgc    2760
tcgcgcgcgg gagatactta gcgggtacca gcacctgctg ttcacggcgc cagtggaccg    2820
cgcccggaac tgtgacccct tcttgggcga cccgttctc ggccccggga taatcgaatt    2880
cggg                                                                 2884
```

<210> SEQ ID NO 154
<211> LENGTH: 50
<212> TYPE: DNA
<213> ORGANISM: Artificial
<220> FEATURE:
<223> OTHER INFORMATION: primer

<400> SEQUENCE: 154

```
cccgaattca ctagtgattc tcccgggtgg acctagcgcg tgtgtcacct                50
```

<210> SEQ ID NO 155
<211> LENGTH: 40
<212> TYPE: DNA
<213> ORGANISM: Artificial
<220> FEATURE:
<223> OTHER INFORMATION: primer

<400> SEQUENCE: 155

```
cccgaattcg attatcccgg ggccgagaac ggggtcgccc                           40
```

<210> SEQ ID NO 156
<211> LENGTH: 1939
<212> TYPE: DNA
<213> ORGANISM: Artificial
<220> FEATURE:
<223> OTHER INFORMATION: fusion DNA (T. aureum ATCC 34304 C20 elongase
      upstream/C20 elongase downstream)

<400> SEQUENCE: 156

```
cccgaattca ctagtgattc tcccgggtgg acctagcgcg tgtgtcacct gccggccccc     60
gttgcgtgca accgaattga tcgataatag aattacataa caaacaactt gctggatgag    120
tacaagacca gcgtagtgtg gctgtgggac gttgaacgga gcgggtcctg tgatggcgca    180
gaaaggaact ccgcccgagg tgaaacccg atgcgcagga ctctgcggcc acagcccctc     240
cgccagtatt ccactaaaaa tccgcccct ttgacaaaga tcgcaacccc gtcccatcaa     300
ctcctcacaa taggctttcc actggcgaa acgtccccgg cacaggagtg cctcccgcgg    360
ttctgcgcat acggctgacc actacgcagc gcgatatcct ccatccgcgt atatatccgt    420
aaacaacgga acattctccc tctcaacgag gcgtggtttt cgaagtcatg cctttcttcc    480
ttcctacttt ccttccttct ttctttcttt ctttccttct tttgcaagcg tgcgcgaact    540
tgaaggtact acttacactt gacagagaga gatagagacg gcaattcgac caagtacttt    600
```

```
ccacgatttt ttttttttt gttttggtcg ctttcgttgg tcgtgcatga tggatggccg    660
ggatttttac aattggatgc gccaggctgc cacgcatgcc gtgacgcttg ctcgcggcga    720
ctcatgatgc ttgccagtgg cagtgcatcc agctcttccc tctgctcgtc gtgtactcac    780
tggcgatgct ctcggcgctc gttcaagggc catcgatcga tcgatcgatc gatcgatcga    840
tcaatcacgt ttggtggact cggcagaccc cgaacgtgtt tctcccagga cgcgccgctg    900
tcgctcgcta atccacccga agcgcggtcg gctggcacgg tcgctcggct ggaagttgag    960
tagtttgctt tctgttgctg cgctgctttg taaacgcgac cagatctacc tgtttccggc   1020
tggctcccga gccatgctta ccatgaatga acctgcaaac agtctgaggt ccttgtgcaa   1080
accgctcagt gggacgtcga cgaagaaaga acaatgtgt actcgtcttg ctctgctccc   1140
gcgccgtttt ttatcgttgt tgagacctct cgcgcagttt tgggaatcaa ccaaaacaag   1200
agcccggcgt cagcgtttgc ttcgccctcg gctgcactcg ctcggcacgc aggtataact   1260
gggtgagtac caagccccgc atttgtctgt ccgcgatccg cgcacgctgc gggtcaggac   1320
gacatcgcgc tgcacgtcac agtgggtccc ttttgacgtg gctgcggcga tgaggaggct   1380
tggctcggct tcatggcaag gcaacagact cgcttccggg acgcgcacga cgagcagcgc   1440
tgctttgatc gaccttgcct gcgtcaccgc ctcggctgct ttgatcgatc gttgtcaccg   1500
gccgagtgac cgcgaacgca ttgcccgcac ggctcggctc ggcccggacc ggaccggctc   1560
gccttggcgg cgcggcgcga tggcgaccca gacgcggccg gagccgcgcg cggaggacaa   1620
ggccatgttc atcttcgggc tcgggtacgt tgggagcagg ctcgccaacc agctggcgga   1680
acaggggtgg cgcgtcgcgg ggtcggtgag ggagctcggg cgcgaggacg actttgccga   1740
gttcgaaaag tccaagctga gcggcaaggt gcaggtgttc cgactcccgc ttgagggcga   1800
ggacaacacg cccgctcgcg cgcgggagat acttagcggg taccagcacc tgctgttcac   1860
ggcgccagtg gaccgcgccc ggaactgtga cccccttcttg ggcgaccccg ttctcggccc   1920
cgggataatc gaattcggg                                                 1939

<210> SEQ ID NO 157
<211> LENGTH: 38
<212> TYPE: DNA
<213> ORGANISM: Artificial
<220> FEATURE:
<223> OTHER INFORMATION: primer

<400> SEQUENCE: 157
cccagatcta cctgtttccg gctggctccc gagccatg                             38

<210> SEQ ID NO 158
<211> LENGTH: 38
<212> TYPE: DNA
<213> ORGANISM: Artificial
<220> FEATURE:
<223> OTHER INFORMATION: primer

<400> SEQUENCE: 158
cccagatctg gtcgcgttta caaagcagcg cagcaaca                             38

<210> SEQ ID NO 159
<211> LENGTH: 31
<212> TYPE: DNA
<213> ORGANISM: Artificial
<220> FEATURE:
<223> OTHER INFORMATION: primer
```

```
<400> SEQUENCE: 159
ctcccgggtg gacctagcgc gtgtgtcacc t                                31

<210> SEQ ID NO 160
<211> LENGTH: 27
<212> TYPE: DNA
<213> ORGANISM: Artificial
<220> FEATURE:
<223> OTHER INFORMATION: primer

<400> SEQUENCE: 160
atcccggggc cgagaacgcc ctcgccc                                     27

<210> SEQ ID NO 161
<211> LENGTH: 3215
<212> TYPE: DNA
<213> ORGANISM: Artificial
<220> FEATURE:
<223> OTHER INFORMATION: fusion DNA (T. aureum C20 elongase
      upstream/ubiquitin promoter/Blar/SV40 terminator/T. aureum C20
      elongase downstream)

<400> SEQUENCE: 161
ctcccgggtg gacctagcgc gtgtgtcacc tgccggcccc cgttgcgtgc aaccgaattg    60
atcgataata gaattacata acaaacaact tgctggatga gtacaagacc agcgtagtgt   120
ggctgtggga cgttgaacgg agcgggtcct gtgatgcgc agaaaggaac tccgcccgag    180
gtgaaacccc gatgcgcagg actctgcggc cacagcccct ccgccagtat tccactaaaa   240
atccgccccc tttgacaaag atcgcaaccc cgtcccatca actcctcaca ataggctttc   300
cactggcgga aacgtccccg gcacaggagt gcctcccgcg gttctgcgca tgcggctgac   360
cactacgcag cgcgatatcc tccatccgcg tatatatccg taaacaacgg aacattctcc   420
ctctcaacga ggcgtggttt tcgaagtcat gcctttcttc cttcctactt tccttccttc   480
tttctttctt tctttccttc ttttgcaagc gtgcgcgaac ttgaaggtac tacttacact   540
tgacagagag agatagagac ggcaattcga ccaagtactt tccacgattt ttttttttt    600 tgttttggtc gctttcgttg gtcgtgcatg atggatggcc gggatttta caattggatg    660 cgccaggctg ccacgcatgc cgtgacgctt gctcgcggcg actcatgatg cttgccagtg   720
gcagtgcatc cagctcttcc ctctgctcgt cgtgtactca ctggcgatgc tctcggcgct   780
cgttcaaggg ccatcgatcg atcgatcgat cgatcgatcg atcaatcacg tttggtggac   840
tcggcagacc ccgaacgtgt ttctcccagg acgcgccgct gtcgctcgct aatccacccg   900
aagcgcggtc ggctggcacg gtcgctcggc tggaagttga gtagtttgct ttctgttgct   960
gcgctgcttt gtaaacgcga ccagatctgg atctgccgca gcgcctggtg cacccgccgg  1020
gcgttgttgt gtgctcttct tgcctccgag agagagagcg gagcggatgc ataggaaatc  1080
gggccacgcg ggagggccat gcgttcgccc cacacgccac tttccacgcc cgctctctct  1140
ccggccggca ggcagcgcat aactctccga cgctggcagg ctggtagcaa ctggcaggga  1200
caactcgcgc gcgggtcccg gtcgttcgat gtgccaaccc gagagaatcc agccagcagg  1260
gcggttggcc tcatcgccca cctgctatgg tgcagcgaac caactcccga agcggccggt  1320
tctgcgattc cctcttctga attctgaatt ctgaactgat tccggaggag aaccctctgg  1380
aagcgcgggt tgcctctcca gttctgccga actagacagg ggagtgagca gagagtgacc  1440
ctgacgcgga gcgagctggt tgctggaaaa gtcgcgaacg ctgggctgtg tcacgcgtcc  1500
acttcgggca gtccccaaac gacaagcaga acaagcaaca ccagcagcag caagcgacct  1560
```

```
aagcaacact agccaacatg gccaagcctt tgtctcaaga agaatccacc ctcattgaaa    1620
gagcaacggc tacaatcaac agcatcccca tctctgaaga ctacagcgtc gccagcgcag    1680
ctctctctag cgacggccgc atcttcactg gtgtcaatgt atatcatttt actggggac    1740 cttgtgcaga actcgtggtg ctgggcactg ctgctgctgc ggcagctggc aacctgactt    1800
gtatcgtcgc gatcggaaat gagaacaggg gcatcttgag ccctgcgga cggtgccgac     1860 aggtgcttct cgatctgcat cctgggatca aagccatagt gaaggacagt gatgacagc     1920 cgacggcagt tgggattcgt gaattgctgc cctctggtta tgtgtgggag gctaagatc     1980 cgcgaaatga ccgaccaagc gacgcccaac ctgccatcac gagatttcga ttccaccgcc    2040
gccttctatg aaaggttggg cttcggaatc gttttccggg acgccggctg gatgatcctc    2100
cagcgcgggg atctcatgct ggagttcttc gcccacccca acttgtttat tgcagcttat    2160
aatggttaca aataaagcaa tagcatcaca aatttcacaa ataaagcatt ttttcactg     2220 cattctagtt gtggtttgtc caaactcatc aatgtatctt atcatgtctg tataccgtcg    2280
acctctagct agatctacct gtttccggct ggctcccgag ccatgcttac catgaatgaa    2340
cctgcaaaca gtctgaggtc cttgtgcaaa ccgctcagtg gacgtcgac gaagaaagaa     2400 acaatgtgta ctcgtcttgc tctgctcccg cgccgttttt tatcgttgtt gagacctctc    2460
gcgcagtttt gggaatcaac caaaacaaga gcccggcgtc agcgtttgct tcgccctcgg    2520
ctgcactcgc tcggcacgca ggtataactg ggtgagtacc aagccccgca tttgtctgtc    2580
cgcgatccgc gcacgctgcg ggtcaggacg acatcgcgct gcacgtcaca gtgggtccct    2640
tttgacgtgg ctgcggcgat gaggaggctt ggctcggctt catggcaagg caacagactc    2700
gcttccggga cgcgcacgac gagcagcgct gctttgatcg accttgcctg cgtcaccgcc    2760
tcggctgctt tgatcgatcg ttgtcaccgg ccgagtgacc gcgaacgcat tgcccgcacg    2820
gctcggctcg gcccggaccg gaccggctcg ccttggcggc gcggcgcgat ggcgacccag    2880
acgcggccgg agccgcgcgc ggaggacaag gccatgttca tcttcgggct cgggtacgtt    2940
gggagcaggc tcgccaacca gctggcggaa caggggtggc gcgtcgcggg gtcggtgagg    3000
gagctcgggc gcgaggacga ctttgccgag ttcgaaaagt ccaagctgag cggcaaggtg    3060
caggtgttcc aactcccgct tgagggcgag acaacacgc ccgctcgcgc gcgggagata     3120
cttagcgggt accagcacct gctgttcacg gcgccagtgg accgcgcccg gaactgtgac    3180
cccttcttgg gcgaccccgt tctcggcccc gggat                               3215
```

<210> SEQ ID NO 162
<211> LENGTH: 3887
<212> TYPE: DNA
<213> ORGANISM: Artificial
<220> FEATURE:
<223> OTHER INFORMATION: fusion DNA (T. aureum C20 elongase upstream/ubiquitin promoter/Enhanced GFP/Zeor/SV40 terminator/T. aureum C20 elogase downstream)

<400> SEQUENCE: 162

```
ctcccgggtg gacctagcgc gtgtgtcacc tgccggcccc cgttgcgtgc aaccgaattg     60
atcgataata gaattacata acaaacaact tgctggatga gtacaagacc agcgtagtgt    120
ggctgtggga cgttgaacgg agcgggtcct gtgatggcgc agaaaggaac tccgcccgag    180
gtgaaacccc gatgcgcagg actctgcggc cacagcccct ccgccagtat tccactaaaa    240
atccgccccc tttgacaaag atcgcaaccc cgtcccatca actcctcaca ataggctttc    300
```

```
cactggcgga aacgtccccg gcacaggagt gcctcccgcg gttctgcgca tacggctgac    360
cactacgcag cgcgatatcc tccatccgcg tatatatccg taaacaacgg aacattctcc    420
ctctcaacga ggcgtggttt tcgaagtcat gcctttcttc cttcctactt tccttccttc    480
tttctttctt tctttccttc ttttgcaagc gtgcgcgaac ttgaaggtac tacttacact    540
tgacagagag agatagagac ggcaattcga ccaagtactt tccacgattt ttttttttt     600 tgttttggtc gctttcgttg gtcgtgcatg atggatggcc gggattttta caattggatg    660
cgccaggctg ccacgcatgc cgtgacgctt gctcgcggcg actcatgatg cttgccagtg    720
gcagtgcatc cagctcttcc ctctgctcgt cgtgtactca ctggcgatgc tctcggcgct    780
cgttcaaggg ccatcgatcg atcgatcgat cgatcgatcg atcaatcacg tttggtggac    840
tcggcagacc ccgaacgtgt ttctcccagg acgcgccgct gtcgctcgct aatccacccg    900
aagcgcggtc ggctggcacg gtcgctcggc tggaagttga gtagtttgct ttctgttgct    960
gcgctgcttt gtaaacgcga ccagatctgc cgcagcgcct ggtgcacccg ccgggcgttg   1020
ttgtgtgctc ttcttgcctc cgagagagag agcggagcgg atgcatagga aatcgggcca   1080
cgcgggaggg ccatgcgttt gccccacacg ccactttcca cgcccgctct ctctccggcc   1140
ggcaggcagc gcataactct ccgacgctgg caggctggta gcaactggca gggacaactc   1200
gcgcgcgggt cccggtcgtt cgatgtgcca acccgagaga atccagccag cagggcggtt   1260
ggcctcatcg cccacctgct atggtgcagc gaaccaactc ccgaagctgc cggttctgcg   1320
attccctctt ctgaattctg aattctgaac tgattccgga ggagaaccct ctggaagcgc   1380
gggttgcctc tccagttctg ccgaactaga caggggagtg agcagagagt gaccctgacg   1440
cggagcgagc tggttgctgg aaaagtcgcg aacgctgggc tgtgtcacgc gtccacttcg   1500
ggcagacccc aaacgacaag cagaacaagc aacaccagca gcagcaagcg atctaagcaa   1560
cactagccaa catggtgagc aagggcgagg agctgttcac cggggtggtg cccatcctgg   1620
tcgagctgga cggcgacgta aacggccaca agttcagcgt gtccggcgag ggcgagggcg   1680
atgccaccta cggcaagctg accctgaagt tcatctgcac caccggcaag ctgcccgtgc   1740
cctggcccac cctcgtgacc accctgacct acggcgtgca gtgcttcagc cgctaccccg   1800
accacatgaa gcagcacgac ttcttcaagt ccgccatgcc cgaaggctac gtccaggagc   1860
gcaccatctt cttcaaggac gacggcaact acaagacccg cgccgaggtg aagttcgagg   1920
gcgacaccct ggtgaaccgc atcgagctga agggcatcga cttcaaggag gacggcaaca   1980
tcctggggca caagctggag tacaactaca acagccacaa cgtctatatc atggccgaca   2040
agcagaagaa cggcatcaag gtgaacttca agatccgcca caacatcgag gacggcagcg   2100
tgcagctcgc cgaccactac cagcagaaca cccccatcgg cgacggcccc gtgctgctgc   2160
ccgacaacca ctacctgagc acccagtccg ccctgagcaa agaccccaac gagaagcgcg   2220
atcacatggt cctgctggag ttcgtgaccg ccgcgggat cactctcggc atggacgcca   2280
agttgaccag tgccgttccg gtgctcaccg cgcgcgacgt cgccggagcg gtcgagttct   2340
ggaccgaccg gctcgggttc tcccgggact tcgtggagga cgacttcgcc ggtgtggtcc   2400
gggacgacgt gaccctgttc atcagcgcgg tccaggacca ggtggtgccg gacaacaccc   2460
tggcctgggt gtgggtgcgc ggcctggacg agctgtacgc cgagtggtcg gaggtcgtgt   2520
ccacgaactt ccgggacgcc tccgggccgg ccatgaccga gatcggcgag cagccgtggg   2580
ggcgggagtt cgccctgcgc gacccggccg gcaactgcgt gcacttcgtg gccgaggagc   2640
aggactgaga tccgcgaaat gaccgaccaa gcgacgccca acctgccatc acgagatttc   2700
```

-continued

```
gattccaccg ccgccttcta tgaaaggttg ggcttcggaa tcgttttccg ggacgccggc    2760
tggatgatcc tccagcgcgg ggatctcatg ctggagttct tcgcccaccc caacttgttt    2820
attgcagctt ataatggtta caaataaagc aatagcatca caaatttcac aaataaagca    2880 ttttttcac tgcattctag ttgtggtttg tccaaactca tcaatgtatc ttatcatgtc    2940
tgtataccgt cgacctctag ctagatctac ctgtttccgg ctggctcccg agccatgctt    3000
accatgaatg aacctgcaaa cagtctgagg tccttgtgca aaccgctcag tgggacgtcg    3060
acgaagaaag aaacaatgtg tactcgtctt gctctgctcc cgcgccgttt tttatcgttg    3120
ttgagacctc tcgcgcagtt ttgggaatca accaaaacaa gagcccggcg tcagcgtttg    3180
cttcgccctc ggctgcactc gctcggcacg caggtataac tgggtgagta ccaagccccg    3240
catttgtctg tccgcgatcc gcgcacgctg cgggtcagga cgacatcgcg ctgcacgtca    3300
cagtgggtcc cttttgacgt ggctgcggcg atgaggaggc ttggctcggc ttcatggcaa    3360
ggcaacagac tcgcttccgg gacgcgcacg acgagcagcg ctgctttgat cgaccttgcc    3420
tgcgtcaccg cctcggctgc tttgatcgat cgttgtcacc ggccgagtga ccgcgaacgc    3480
attgcccgca cggctcggct cggcccggac cggaccggct cgccttggcg gcgcggcgcg    3540
atggcgaccc agacgcggcc ggagccgcgc gcggaggaca aggccatgtt catcttcggg    3600
ctcgggtacg ttgggagcag gctcgccaac cagctggcgg aacaggggtg gcgcgtcgcg    3660
gggtcggtga gggagctcgg gcgcgaggac gactttgccg agttcgaaaa gtccaagctg    3720
agcggcaagg tgcaggtgtt ccgactcccg cttgagggcg aggacaacac gcccgctcgc    3780
gcgcgggaga tacttagcgg gtaccagcac ctgctgttca cggcgccagt ggaccgcgcc    3840
cggaactgtg accccttctt gggcgacccc gttctcggcc ccgggat              3887
```

<210> SEQ ID NO 163
<211> LENGTH: 21
<212> TYPE: DNA
<213> ORGANISM: Artificial
<220> FEATURE:
<223> OTHER INFORMATION: primer

<400> SEQUENCE: 163
acgtccgctt caaacacctc g                                              21

<210> SEQ ID NO 164
<211> LENGTH: 24
<212> TYPE: DNA
<213> ORGANISM: Artificial
<220> FEATURE:
<223> OTHER INFORMATION: primer

<400> SEQUENCE: 164
tcggaacaac tggaacaact aaag                                           24

<210> SEQ ID NO 165
<211> LENGTH: 22
<212> TYPE: DNA
<213> ORGANISM: Artificial
<220> FEATURE:
<223> OTHER INFORMATION: primer

<400> SEQUENCE: 165
atgtcgctct ccttcttctc ag                                             22

<210> SEQ ID NO 166

<211> LENGTH: 21
<212> TYPE: DNA
<213> ORGANISM: Artificial
<220> FEATURE:
<223> OTHER INFORMATION: primer

<400> SEQUENCE: 166
tcggctcctg gaaagtgctc t                                              21

<210> SEQ ID NO 167
<211> LENGTH: 812
<212> TYPE: DNA
<213> ORGANISM: Artificial
<220> FEATURE:
<223> OTHER INFORMATION: ubiquitin promoter

<400> SEQUENCE: 167
tcggtacccg ttagaacgcg taatacgact cactataggg agagtcgact gagcacaact      60
ctgctgcgag cgggcctcga gagcgtttgc ttcgagccgc ggagcaaggg ggatggatcg     120
ctcatgcggt cgtgcggccc tcggtcaccc ggtgggtcct gcactgacgc atctgttctg     180
atcagacaca cgaacgaaca aaccgaggag ccgcagcgcc tggtgcaccc gccgggcgtt     240
gttgtgtgct cttcttgcct ccgagagaga gagcggagcg gatgcatagg aaatcgggcc     300
acgcgggagg gccatgcgtt cgccccacac gccactttcc acgcccgctc tctctccggc     360
cggcaggcag cgcataactc tccgacgctg gcaggctggt agcaactggc agggacaact     420
cgcgcgcggg tcccggtcgt tcgatgtgcc aacccgagag aatccagcca gcagggcggt     480
tggcctcatc gcccacctgc tatggtgcag cgaaccaact cccgaagcgg ccggttctgc     540
gattccctct tctgaattct gaattctgaa ctgattccgg aggagaaccc tctggaagcg     600
cgggttgcct ctccagttct gccgaactag acagggagt gagcagagag tgaccctgac      660
gcggagcgag ctggttgctg gaaaagtcgc gaacgctggg ctgtgtcacg cgtccacttc     720
gggcagaccc caaacgacaa gcagaacaag caacaccagc agcagcaagc gacctaagca     780
acactagcca acatgactga ggataagacg aa                                   812

<210> SEQ ID NO 168
<211> LENGTH: 29
<212> TYPE: DNA
<213> ORGANISM: Artificial
<220> FEATURE:
<223> OTHER INFORMATION: primer

<400> SEQUENCE: 168
tcggtacccg ttagaacgcg taatacgac                                      29

<210> SEQ ID NO 169
<211> LENGTH: 45
<212> TYPE: DNA
<213> ORGANISM: Artificial
<220> FEATURE:
<223> OTHER INFORMATION: primer

<400> SEQUENCE: 169
ttcgtcttat cctcagtcat gttggctagt gttgcttagg tcgct                    45

<210> SEQ ID NO 170
<211> LENGTH: 1116
<212> TYPE: DNA
<213> ORGANISM: Artificial
<220> FEATURE:
<223> OTHER INFORMATION: cDNA (Saprolegnia diclina omega3 desaturase)

<400> SEQUENCE: 170

```
cctaagcaac actagccaac atgactgagg ataagacgaa ggtcgagttc ccgacgctca    60
cggagctcaa gcactcgatc ccgaacgcgt gctttgagtc gaacctcggc ctctcgctct   120
actacacggc ccgcgcgatc ttcaacgcgt cggcctcggc ggcgctgctc tacgcggcgc   180
gctcgacgcc gttcattgcc gataacgttc tgctccacgc gctcgtttgc gccacctaca   240
tctacgtgca gggcgtcatc ttctggggct tcttcacggt cggccacgac tgcggccact   300
cggccttctc gcgctaccac agcgtcaact ttatcatcgg ctgcatcatg cactctgcga   360
ttttgacgcc gttcgagagc tggcgcgtga cgcaccgcca ccaccacaag aacacgggca   420
acattgataa ggacgagatc ttttacccgc accggtcggt caaggacctc caggacgtgc   480
gccaatgggt ctacacgctc ggcggtgcgt ggtttgtcta cttgaaggtc gggtatgccc   540
cgcgcacgat gagccacttt gacccgtggg acccgctcct ccttcgccgc cgtcggccg    600
tcatcgtgtc gctcggcgtc tgggccgcct tcttcgccgc gtacgcgtac ctcacatact   660
cgctcggctt tgccgtcatg ggcctctact actatgcgcc gctctttgtc tttgcttcgt   720
tcctcgtcat tacgaccttc ttgcaccaca cgacgaagc gacgccgtgg tacggcgact   780
cggagtggac gtacgtcaag ggcaacctct cgagcgtcga ccgctcgtac ggcgcgttcg   840
tggacaacct gagccaccac attggcacgc accaggtcca ccacttgttc ccgatcattc   900
cgcactacaa gctcaacgaa gccaccaagc actttgcggc gcgtacccg cacctcgtgc    960
gcaagaacga cgagcccatc atctcggcct tcttcaagac cgcgcacctc tttgtcaact  1020
acggcgctgt gcccgagacg cgcagatct tcacgctcaa agagtcggcc gcggccgcca  1080
aggccaagtc ggactaaact aagctatctg tagtat                           1116
```

<210> SEQ ID NO 171
<211> LENGTH: 43
<212> TYPE: DNA
<213> ORGANISM: Artificial
<220> FEATURE:
<223> OTHER INFORMATION: primer

<400> SEQUENCE: 171

```
cctaagcaac actagccaac atgactgagg ataagacgaa ggt                     43
```

<210> SEQ ID NO 172
<211> LENGTH: 40
<212> TYPE: DNA
<213> ORGANISM: Artificial
<220> FEATURE:
<223> OTHER INFORMATION: primer

<400> SEQUENCE: 172

```
atactacaga tagcttagtt ttagtccgac ttggccttgg                         40
```

<210> SEQ ID NO 173
<211> LENGTH: 614
<212> TYPE: DNA
<213> ORGANISM: Artificial
<220> FEATURE:
<223> OTHER INFORMATION: ubiquitin terminator

<400> SEQUENCE: 173

```
ccaaggccaa gtcggactaa actaagctat ctgtagtatg tgctatactc gaatcatgct    60
gccctgtacg tacctaccta tatctgattg agcgtgctgc gtcgaccata gacgcgggaa   120
```

| | |
|---|---|
| cgcgggccag cctaccacgt tgccgccgcc ggtatccacg ggcacgccaa agcattggtc | 180 |
| gataacgctc tgcccagggc ttcctggcga ggacccgagg ccaacatgca tgcatgtgct | 240 |
| atcagcggtc atcatcgccc tcatcagcgc gcatcggcga gctcgcgcac gaacggcaag | 300 |
| cgcccaactc aactcactta ctcacactat ggtcttgccg ttggcggttg cttagctaat | 360 |
| gcgtgacgtc actctgcctc caacatcgcg aggcagagtc gcgagcagtg cagaggccac | 420 |
| ggcggacgcc aacaaagcgc caaccagcgc aacgcaccag cgggtctgtg ggcgtagctc | 480 |
| gagcgggcgt cttcaagagc cgccgtggag ccgacgcccc tgcgaagggc tcgagtgcaa | 540 |
| gcggggccgt tgagccgcgt ggtaggaaca actgcagtct ccctatagtg agtcgtatta | 600 |
| cgcggtggta ccga | 614 |

<210> SEQ ID NO 174
<211> LENGTH: 44
<212> TYPE: DNA
<213> ORGANISM: Artificial
<220> FEATURE:
<223> OTHER INFORMATION: primer

<400> SEQUENCE: 174

| | |
|---|---|
| ccaaggccaa gtcggactaa aactaagcta tctgtagtat gtgc | 44 |

<210> SEQ ID NO 175
<211> LENGTH: 45
<212> TYPE: DNA
<213> ORGANISM: Artificial
<220> FEATURE:
<223> OTHER INFORMATION: primer

<400> SEQUENCE: 175

| | |
|---|---|
| tcggtaccac cgcgtaatac gactcactat agggagactg cagtt | 45 |

<210> SEQ ID NO 176
<211> LENGTH: 2463
<212> TYPE: DNA
<213> ORGANISM: Artificial
<220> FEATURE:
<223> OTHER INFORMATION: fusion DNA (T. aureum ATCC 34304 ubiquitin
      promoter/Saprolegnia diclina omega3 desaturase/T. aureum
      ATCC 34304 ubiquitin terminator)

<400> SEQUENCE: 176

| | |
|---|---|
| tcggtacccg ttagaacgcg taatacgact cactataggg agagtcgact gagcacaact | 60 |
| ctgctgcgag cgggcctcga gagcgtttgc ttcgagccgc ggagcaaggg ggatggatcg | 120 |
| ctcatgcggt cgtgcggccc tcggtcaccc ggtgggtcct gcactgacgc atctgttctg | 180 |
| atcagacaca cgaacgaaca aaccgaggag ccgcagcgcc tggtgcaccc gccgggcgtt | 240 |
| gttgtgtgct cttcttgcct ccgagagaga gagcggagcg gatgcatagg aaatcgggcc | 300 |
| acgcgggagg gccatgcgtt cgccccacac gccactttcc acgcccgctc tctctccggc | 360 |
| cggcaggcag cgcataactc tccgacgctg gcaggctggt agcaactggc agggacaact | 420 |
| cgcgcgcggg tcccggtcgt tcgatgtgcc aacccgagag aatccagcca gcagggcggt | 480 |
| tggcctcatc gcccacctgc tatggtgcag cgaaccaact cccgaagcgg ccggttctgc | 540 |
| gattccctct tctgaattct gaattctgaa ctgattccgg aggagaaccc tctggaagcg | 600 |
| cgggttgcct ctccagttct gccgaactag acaggggagt gagcagagag tgaccctgac | 660 |
| gcggagcgag ctggttgctg gaaaagtcgc gaacgctggg ctgtgtcacg cgtccacttc | 720 |
| gggcagaccc caaacgacaa gcagaacaag caacaccagc agcagcaagc gacctaagca | 780 |

| | |
|---|---|
| acactagcca acatgactga ggataagacg aaggtcgagt tcccgacgct cacggagctc | 840 |
| aagcactcga tcccgaacgc gtgctttgag tcgaacctcg gcctctcgct ctactacacg | 900 |
| gcccgcgcga tcttcaacgc gtcggcctcg gcggcgctgc tctacgcggc gcgctcgacg | 960 |
| ccgttcattg ccgataacgt tctgctccac gcgctcgttt gcgccaccta catctacgtg | 1020 |
| cagggcgtca tcttctgggg cttcttcacg gtcggccacg actgcggcca ctcggccttc | 1080 |
| tcgcgctacc acagcgtcaa ctttatcatc ggctgcatca tgcactctgc gattttgacg | 1140 |
| ccgttcgaga gctggcgcgt gacgcaccgc caccaccaca agaacacggg caacattgat | 1200 |
| aaggacgaga tcttttaccc gcaccggtcg gtcaaggacc tccaggacgt gcgccaatgg | 1260 |
| gtctacacgc tcggcggtgc gtggtttgtc tacttgaagg tcgggtatgc cccgcgcacg | 1320 |
| atgagccact ttgacccgtg ggacccgctc ctccttcgcc gcgcgtcggc cgtcatcgtg | 1380 |
| tcgctcggcg tctgggccgc cttcttcgcc gcgtacgcgt acctcacata ctcgctcggc | 1440 |
| tttgccgtca tgggcctcta ctactatgcg ccgctctttg tctttgcttc gttcctcgtc | 1500 |
| attacgacct tcttgcacca caacgacgaa gcgacgccgt ggtacggcga ctcggagtgg | 1560 |
| acgtacgtca agggcaacct ctcgagcgtc gaccgctcgt acggcgcgtt cgtggacaac | 1620 |
| ctgagccacc acattggcac gcaccaggtc caccacttgt tcccgatcat tccgcactac | 1680 |
| aagctcaacg aagccaccaa gcactttgcg gccgcgtacc cgcacctcgt gcgcaagaac | 1740 |
| gacgagccca tcatctcggc cttcttcaag accgcgcacc tctttgtcaa ctacggcgct | 1800 |
| gtgcccgaga cggcgcagat cttcacgctc aaagagtcgg ccgcggccgc caaggccaag | 1860 |
| tcggactaaa ctaagctatc tgtagtatgt gctatactcg aatcatgctg ccctgtacgt | 1920 |
| acctacctat atctgattga gcgtgctgcg tcgaccatag acgcgggaac gcgggccagc | 1980 |
| ctaccacgtt gccgccgccg gtatccacgg gcacgccaaa gcattggtcg ataacgctct | 2040 |
| gcccagggct tcctggcgag gacccgaggc caacatgcat gcatgtgcta tcagcggtca | 2100 |
| tcatcgccct catcagcgcg catcggcgag ctcgcgcacg aacggcaagc gcccaactca | 2160 |
| actcacttac tcacactatg gtcttgccgt tggcggttgc ttagctaatg cgtgacgtca | 2220 |
| ctctgcctcc aacatcgcga ggcagagtcg cgagcagtgc agaggccacg gcggacgcca | 2280 |
| acaaagcgcc aaccagcgca acgcaccagc gggtctgtgg gcgtagctcg agcgggcgtc | 2340 |
| ttcaagagcc gccgtggagc cgacgcccct gcgaagggct cgagtgcaag cggggccgtt | 2400 |
| gagccgcgtg gtaggaacaa ctgcagtctc cctatagtga gtcgtattac gcggtggtac | 2460 |
| cga | 2463 |

<210> SEQ ID NO 177
<211> LENGTH: 36
<212> TYPE: DNA
<213> ORGANISM: Artificial
<220> FEATURE:
<223> OTHER INFORMATION: primer

<400> SEQUENCE: 177

| | |
|---|---|
| cccggtaccg ccgcagcgcc tggtgcaccc gccggg | 36 |

<210> SEQ ID NO 178
<211> LENGTH: 3777
<212> TYPE: DNA
<213> ORGANISM: Artificial
<220> FEATURE:
<223> OTHER INFORMATION: fusion DNA (ubiquitin promoter/omega 3
desaturase/ubiquitin terminator/ubiquitin promoter/Blar/SV40 terminator)

<400> SEQUENCE: 178

| | | | | | |
|---|---|---|---|---|---|
| tcggtacccg | ttagaacgcg | taatacgact | cactataggg | agagtcgact | gagcacaact | 60 |
| ctgctgcgag | cgggcctcga | gagcgtttgc | ttcgagccgc | ggagcaaggg | ggatggatcg | 120 |
| ctcatgcggt | cgtgcggccc | tcggtcaccc | ggtgggtcct | gcactgacgc | atctgttctg | 180 |
| atcagacaca | cgaacgaaca | aaccgaggag | ccgcagcgcc | tggtgcaccc | gccgggcgtt | 240 |
| gttgtgtgct | cttcttgcct | ccgagagaga | gagcggagcg | gatgcatagg | aaatcgggcc | 300 |
| acgcgggagg | gccatgcgtt | cgccccacac | gccactttcc | acgcccgctc | tctctccggc | 360 |
| cggcaggcag | cgcataactc | tccgacgctg | gcaggctggt | agcaactggc | agggacaact | 420 |
| cgcgcgcggg | tcccggtcgt | tcgatgtgcc | aacccgagag | aatccagcca | gcagggcggt | 480 |
| tggcctcatc | gcccacctgc | tatggtgcag | cgaaccaact | cccgaagcgg | ccggttctgc | 540 |
| gattccctct | tctgaattct | gaattctgaa | ctgattccgg | aggagaaccc | tctggaagcg | 600 |
| cgggttgcct | ctccagttct | gccgaactag | acagggagt | gagcagagag | tgaccctgac | 660 |
| gcggagcgag | ctggttgctg | gaaaagtcgc | gaacgctggg | ctgtgtcacg | cgtccacttc | 720 |
| gggcagaccc | caaacgacaa | gcagaacaag | caacaccagc | agcagcaagc | gacctaagca | 780 |
| acactagcca | acatgactga | ggataagacg | aaggtcgagt | tcccgacgct | cacggagctc | 840 |
| aagcactcga | tcccgaacgc | gtgctttgag | tcgaacctcg | gcctctcgct | ctactacacg | 900 |
| gcccgcgcga | tcttcaacgc | gtcggcctcg | gcggcgctgc | tctacgcggc | gcgctcgacg | 960 |
| ccgttcattg | ccgataacgt | tctgctccac | gcgctcgttt | gcgccaccta | catctacgtg | 1020 |
| cagggcgtca | tcttctgggg | cttcttcacg | gtcgccacg | actgcggcca | ctcggccttc | 1080 |
| tcgcgctacc | acagcgtcaa | ctttatcatc | ggctgcatca | tgcactctgc | gattttgacg | 1140 |
| ccgttcgaga | gctggcgcgt | gacgcaccgc | caccaccaca | agaacacggg | caacattgat | 1200 |
| aaggacgaga | tcttttaccc | gcaccggtcg | gtcaaggacc | tccaggacgt | gcgccaatgg | 1260 |
| gtctacacgc | tcggcggtgc | gtggtttgtc | tacttgaagg | tcgggtatgc | cccgcgcacg | 1320 |
| atgagccact | tgacccgtg | ggacccgctc | ctccttcgcc | gcgcgtcggc | cgtcatcgtg | 1380 |
| tcgctcggcg | tctgggccgc | cttcttcgcc | gcgtacgcgt | acctcacata | tcgctcggc | 1440 |
| tttgccgtca | tgggcctcta | ctactatgcg | ccgctctttg | tctttgcttc | gttcctcgtc | 1500 |
| attacgacct | tcttgcacca | caacgacgaa | gcgacgccgt | ggtacggcga | tcggagtgg | 1560 |
| acgtacgtca | agggcaacct | ctcgagcgtc | gaccgctcgt | acggcgcgtt | cgtggacaac | 1620 |
| ctgagccacc | acattggcac | gcaccaggtc | caccacttgt | tcccgatcat | tccgcactac | 1680 |
| aagctcaacg | aagccaccaa | gcactttgcg | gccgcgtacc | cgcacctcgt | gcgcaagaac | 1740 |
| gacgagccca | tcatctcggc | cttcttcaag | accgcgcacc | tctttgtcaa | ctacggcgct | 1800 |
| gtgcccgaga | cggcgcagat | cttcacgctc | aaagagtcgg | ccgcggccgc | caaggccaag | 1860 |
| tcggactaaa | ctaagctatc | tgtagtatgt | gctatactcg | aatcatgctg | ccctgtacgt | 1920 |
| acctacctat | atctgattga | gcgtgctgcg | tcgaccatag | acgcgggaac | gcgggccagc | 1980 |
| ctaccacgtt | gccgccgccg | gtatccacgg | gcacgccaaa | gcattggtcg | ataacgctct | 2040 |
| gcccagggct | tcctggcgag | gacccgaggc | caacatgcat | gcatgtgcta | tcagcggtca | 2100 |
| tcatcgccct | catcagcgcg | catcggcgag | tcgcgcacg | aacggcaagc | gcccaactca | 2160 |
| actcacttac | tcacactatg | gtcttgccgt | tggcggttgc | ttagctaatg | cgtgacgtca | 2220 |
| ctctgcctcc | aacatcgcga | ggcagagtcg | cgagcagtgc | agaggccacg | gcggacgcca | 2280 |

-continued

```
acaaagcgcc aaccagcgca acgcaccagc gggtctgtgg gcgtagctcg agcgggcgtc    2340
ttcaagagcc gccgtggagc cgacgccct  gcgaagggct cgagtgcaag cggggccgtt    2400
gagccgcgtg gtaggaacaa ctgcagtctc cctatagtga gtcgtattac gcggtggtac    2460
cgccgcagcg cctggtgcac ccgccgggcg ttgttgtgtg ctcttcttgc ctccgagaga    2520
gagagcggag cggatgcata ggaaatcggg ccacgcggga gggccatgcg ttcgcccac    2580 acgccacttt ccacgcccgc tctctctccg gccggcaggc agcgcataac tctccgacgc    2640
tggcaggctg gtagcaactg cagggacaa  ctcgcgcgcg ggtcccggtc gttcgatgtg    2700
ccaacccgag agaatccagc cagcagggcg gttggcctca tcgcccacct gctatggtgc    2760
agcgaaccaa ctcccgaagc ggccggttct gcgattccct cttctgaatt ctgaattctg    2820
aactgattcc ggaggagaac cctctggaag cgcgggttgc ctctccagtt ctgccgaact    2880
agacagggga gtgagcagag agtgaccctg acgcggagcg agctggttgc tggaaaagtc    2940
gcgaacgctg ggctgtgtca cgcgtccact tcgggcagtc cccaaacgac aagcagaaca    3000
agcaacacca gcagcagcaa gcgacctaag caacactagc caacatggcc aagcctttgt    3060
ctcaagaaga atccaccctc attgaaagag caacggctac aatcaacagc atccccatct    3120
ctgaagacta cagcgtcgcc agcgcagctc tctctagcga cggccgcatc ttcactggtg    3180
tcaatgtata tcattttact gggggacctt gtgcagaact cgtggtgctg ggcactgctg    3240
ctgctgcggc agctggcaac ctgacttgta tcgtcgcgat cggaaatgag aacagggca     3300 tcttgagccc ctgcggacgg tgccgacagg tgcttctcga tctgcatcct gggatcaaag    3360
ccatagtgaa ggacagtgat ggacagccga cggcagttgg gattcgtgaa ttgctgccct    3420
ctggttatgt gtgggagggc taagatccgc gaaatgaccg accaagcgac gcccaacctg    3480
ccatcacgag atttcgattc caccgccgcc ttctatgaaa ggttgggctt cggaatcgtt    3540
ttccgggacg ccggctggat gatcctccag cgcggggatc tcatgctgga gttcttcgcc    3600 cacccccaact tgtttattgc agcttataat ggttacaaat aaagcaatag catcacaaat    3660
ttcacaaata aagcattttt ttcactgcat tctagttgtg gtttgtccaa actcatcaat    3720
gtatcttatc atgtctgtat accgtcgacc tctagctaga tctcacatta attgcgt      3777
```

<210> SEQ ID NO 179
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (15)..(15)
<223> OTHER INFORMATION: n is inosine.
<220> FEATURE:
<221> NAME/KEY: misc_feature
<222> LOCATION: (21)..(21)
<223> OTHER INFORMATION: n is inosine.

<400> SEQUENCE: 179
athgartwyt kbrtnttygt nca          23

<210> SEQ ID NO 180
<211> LENGTH: 23
<212> TYPE: DNA
<213> ORGANISM: Artificial
<220> FEATURE:
<223> OTHER INFORMATION: primer
<220> FEATURE:

```
<221> NAME/KEY: misc_feature
<222> LOCATION: (6)..(6)
<223> OTHER INFORMATION: n is inosine.
<220> FEATURE:
<221> NAME/KEY: misc_feature
<222> LOCATION: (15)..(15)
<223> OTHER INFORMATION: n is inosine.
<220> FEATURE:
<221> NAME/KEY: misc_feature
<222> LOCATION: (18)..(18)
<223> OTHER INFORMATION: n is inosine.

<400> SEQUENCE: 180
tartrnswrt acatnadnam rtg                                          23

<210> SEQ ID NO 181
<211> LENGTH: 28
<212> TYPE: DNA
<213> ORGANISM: Artificial
<220> FEATURE:
<223> OTHER INFORMATION: primer

<400> SEQUENCE: 181
ctgacaaagt ttctcgactg gagcgaca                                     28

<210> SEQ ID NO 182
<211> LENGTH: 24
<212> TYPE: DNA
<213> ORGANISM: Artificial
<220> FEATURE:
<223> OTHER INFORMATION: primer

<400> SEQUENCE: 182
tacgcggcgg tgcccgagcc ccag                                         24

<210> SEQ ID NO 183
<211> LENGTH: 28
<212> TYPE: DNA
<213> ORGANISM: Artificial
<220> FEATURE:
<223> OTHER INFORMATION: primer

<400> SEQUENCE: 183
tgccgatcgt tgcgtggtgg aacacctg                                     28

<210> SEQ ID NO 184
<211> LENGTH: 20
<212> TYPE: DNA
<213> ORGANISM: Artificial
<220> FEATURE:
<223> OTHER INFORMATION: primer

<400> SEQUENCE: 184
atggcgacgc gcacctcgaa                                              20

<210> SEQ ID NO 185
<211> LENGTH: 22
<212> TYPE: DNA
<213> ORGANISM: Artificial
<220> FEATURE:
<223> OTHER INFORMATION: primer

<400> SEQUENCE: 185
ttactcggac ttggtggggg cg                                           22

<210> SEQ ID NO 186
<211> LENGTH: 951
```

```
<212> TYPE: DNA
<213> ORGANISM: Thraustochytrium aureum
<220> FEATURE:
<223> OTHER INFORMATION: genomic C20 elongase

<400> SEQUENCE: 186
atggcgacgc gcacctcgaa gagcgctccg gcggtttcca agtcggccaa ggttgccgcg      60
ccggcgaaga gcggtcggt cgacaggagc gacggtttct tccgcacgtt caacctgtgc     120
gccctgtacg ggtctgccct cgcctatgcg tacaagcacg gcccggtgga caatgacggc     180
caggggctgt actttcacaa gtcgcccatg tacgcgttcg ccgtgtcgga cgtcatgacc     240
ttcggcgcgc cgctgatgta cgtgctcggt gtgatgctgc tcagcaggta catggcggac     300
aaaaagcccc tgactggctt catcaagacc tacatccagc ccgtctacaa cgtggtccaa     360
atcgcggtgt gcggctggat ggtgtggggc ctctggccgc aggtcgacct ggccaacggc     420 aacccttcg gcctcaacaa gtcgcgcgac tcgaacatcg agttttcgt gttcgtgcac     480 ctcctgacaa agtttctcga ctggagcgac acgttcatga tgatcctcaa gaaaaactac     540
gcccaggtta gctttctgca ggtgttccac cacgcaacga tcggcatggt gtggtcgttc     600
cttcttcagc gtggctgggg ctcgggcacc gccgcgtacg tgctttttcat caactcggtc     660 acgcacgtga tcatgtactc gcactacttt gccacctcgc tcaacatcaa caaccccgttc     720 aagcggtaca tcacgagctt ccagctcgcc cagtttgcaa gctgcatcgt gcatgcccta     780
ctggtgcttg ccttcgagga ggtgtacccg ctcgagtacg cttacctgca gatcagctac     840
cacatcatca tgctctacct gttcggacgc cgcatgaact ggagccccga gtggtgcacc     900
ggtgagatcg acggccttga cgccccaagc gcccccacca agtccgagta a             951

<210> SEQ ID NO 187
<211> LENGTH: 317
<212> TYPE: PRT
<213> ORGANISM: Thraustochytrium aureum
<220> FEATURE:
<221> NAME/KEY: misc_feature
<222> LOCATION: (317)..(317)
<223> OTHER INFORMATION: Xaa can be any naturally occurring amino acid
<220> FEATURE:
<223> OTHER INFORMATION: C20 elongase

<400> SEQUENCE: 187

Met Ala Thr Arg Thr Ser Lys Ser Ala Pro Ala Val Ser Lys Ser Ala
1               5                   10                  15

Lys Val Ala Ala Pro Ala Lys Lys Arg Ser Val Asp Arg Ser Asp Gly
            20                  25                  30

Phe Phe Arg Thr Phe Asn Leu Cys Ala Leu Tyr Gly Ser Ala Leu Ala
        35                  40                  45

Tyr Ala Tyr Lys His Gly Pro Val Asp Asn Asp Gly Gln Gly Leu Tyr
    50                  55                  60

Phe His Lys Ser Pro Met Tyr Ala Phe Ala Val Ser Asp Val Met Thr
65                  70                  75                  80

Phe Gly Ala Pro Leu Met Tyr Val Leu Gly Val Met Leu Leu Ser Arg
                85                  90                  95

Tyr Met Ala Asp Lys Lys Pro Leu Thr Gly Phe Ile Lys Thr Tyr Ile
            100                 105                 110

Gln Pro Val Tyr Asn Val Val Gln Ile Ala Val Cys Gly Trp Met Val
        115                 120                 125

Trp Gly Leu Trp Pro Gln Val Asp Leu Ala Asn Gly Asn Pro Phe Gly
    130                 135                 140
```

```
Leu Asn Lys Ser Arg Asp Ser Asn Ile Glu Phe Phe Val Phe Val His
145                 150                 155                 160

Leu Leu Thr Lys Phe Leu Asp Trp Ser Asp Thr Phe Met Met Ile Leu
            165                 170                 175

Lys Lys Asn Tyr Ala Gln Val Ser Phe Leu Gln Val Phe His His Ala
        180                 185                 190

Thr Ile Gly Met Val Trp Ser Phe Leu Leu Gln Arg Gly Trp Gly Ser
    195                 200                 205

Gly Thr Ala Ala Tyr Gly Ala Phe Ile Asn Ser Val Thr His Val Ile
    210                 215                 220

Met Tyr Ser His Tyr Phe Ala Thr Ser Leu Asn Ile Asn Asn Pro Phe
225                 230                 235                 240

Lys Arg Tyr Ile Thr Ser Phe Gln Leu Ala Gln Phe Ala Ser Cys Ile
            245                 250                 255

Val His Ala Leu Leu Val Leu Ala Phe Glu Glu Val Tyr Pro Leu Glu
            260                 265                 270

Tyr Ala Tyr Leu Gln Ile Ser Tyr His Ile Ile Met Leu Tyr Leu Phe
        275                 280                 285

Gly Arg Arg Met Asn Trp Ser Pro Glu Trp Cys Thr Gly Glu Ile Asp
    290                 295                 300

Gly Leu Asp Ala Pro Ser Ala Pro Thr Lys Ser Glu Xaa
305                 310                 315

<210> SEQ ID NO 188
<211> LENGTH: 3193
<212> TYPE: DNA
<213> ORGANISM: Artificial
<220> FEATURE:
<223> OTHER INFORMATION: genomic DNA (Thraustochytrium aureum genomic
      DNA contains C20 elongase coding region)

<400> SEQUENCE: 188
ggatatcccc cgcgaggcga tggctgctcc gacgacgtgg gctggcgacg tcgctcgcaa      60
aggcgttccg caaccgcgcg ttccgctgta acgagaccgt tttccctgcg ctgctgggtg     120
gacctagcgc gtgtgtcacc tgccggcccc cgttgcgtgc aaccgaattg atcgataata     180
gaattacata acaaacaact tgctggatga gtacaagacc agcgtagtgt ggctgtggga     240
cgttgaacgg agcgggtcct gtgacggcgc agaaaggaac tccgcccgag gtgaaacccc     300
gatgcgcagg actctgcggc acagccccct ccgccagtat ccactaaaaa atccgccccc     360
tttgacaaag atcgcaaccc cgtcccatca actcctcaca ataggctttc cactggcgga     420
aacgtccccg gcacaggagt gcctcccgcg gttctgcgca tacggctgac cactacgcag     480
cgcgatatcc tccatccgcg tatatatccg taaacaacgg aacattctcc ctctcaacga     540
ggcgtggttt tcgaagccat gcctttcttc cttcctactt gccttccttc tttctttctt     600
tctttctttc ttttgcaagc gtgcgcgaac ttgaaggtac tacttacact tgacagagag     660
agatagagac ggcaattcga ccaagtactt tccacgattt ttttttttt gttttggtcg     720 ctttcgttgg tcgtgcatga tggatggccg ggattttac aattggatgc gccaggctgc     780
cacgcatgcc gtgacgctcg ctcgcggcga ctcatgatgc ttgccagtgg cagtgcatcc     840
agctcttccc tctgctcgtc gtgtactcac tggcgatgct ctcggcgctc gttcaggggc     900
catcgaccga tcgatcgatc gatcgatcga tcaatcacgt tcggtggact cggcagaccc     960
cgaacgtgtt tctcccagga cgtgccgctg tcgctcgctg atccacccga agcgcggtcg    1020
```

```
gctggcacgg tcgctcggct ggaagttgag tagtttgctt tctgttgctg cgctgctttg    1080
taaacgcgac catggcgacg cgcacctcga agagcgctcc ggcggtttcc aagtcggcca    1140
aggttgccgc gccggcgaag aagcggtcgg tcgacaggag cgacggtttc ttccgcacgt    1200
tcaacctgtg cgccctgtac gggtctgccc tcgcctatgc gtacaagcac ggcccggtgg    1260
acaatgacgg ccaggggctg tactttcaca agtcgcccat gtacgcgttc gccgtgtcgg    1320
acgtcatgac cttcggcgcg ccgctgatgt acgtgctcgg tgtgatgctg ctcagcaggt    1380
acatggcgga caaaaagccc ctgactggct tcatcaagac ctacatccag cccgtctaca    1440
acgtggtcca aatcgcggtg tgcggctgga tggtgtgggg cctctggccg caggtcgacc    1500
tggccaacgg caacccttc ggcctcaaca agtcgcgcga ctcgaacatc gagtttttcg    1560
tgttcgtgca cctcctgaca aagtttctcg actggagcga cacgttcatg atgatcctca    1620
agaaaaacta cgcccaggtt agcttctgc aggtgttcca ccacgcaacg atcggcatgg    1680
tgtggtcgtt ccttcttcag cgtggctggg gctcgggcac cgccgcgtac ggtgctttca    1740
tcaactcggt cacgcacgtg atcatgtact cgcactactt tgccacctcg ctcaacatca    1800
acaacccgtt caagcggtac atcacgagct tccagctcgc ccagtttgca agctgcatcg    1860
tgcatgccct actggtgctt gccttcgagg aggtgtaccc gctcgagtac gcttacctgc    1920
agatcagcta ccacatcatc atgctctacc tgttcggacg ccgcatgaac tggagccccg    1980
agtggtgcac cggtgagatc gacggccttg acgcccaag cgcccccacc aagtccgagt    2040
aaacctgttt ccggctggct cccgagccat gcttaccatg aatgaacctg caaacagtct    2100
gaggtccttg tgcaaaccgc tcagtgggac gtcgacgaag aaagaaacaa tgtgtactcg    2160
tcttgctctg ctcccgcgcc gttttttatc gttgttgaga cctctcgcgc agttttggga    2220
atcaaccaaa acaagagccc ggcgtcagcg tttgcttcgc cctcggctgc actcgctcgg    2280
cacgcaggta taactgggtg agtaccaagc cccgcatttg tctgtccgcg atccgcgcac    2340
gctgcgggtc aggacgacat cgcgctgcac gtcacagtgg gtccctttg acgtggctgc    2400 ggcgatgagg aggcttggct cggcttcatg gcaaggcaac agactcgctt ccaggacgcg    2460
cacgacgagc agcgctgctt tgatcgacct tgcctgcgtc accgcctcgg ctgctttgat    2520
cgatcgttgt caccggccga gtgaccgcga acgcattgcc cgcacggctc ggctcggctc    2580
ggaccggacc ggctcgcctt ggcggcgcgg cgcgatggcg acccagacgc gaccggagcc    2640
gcgcgcggag gacaaggcca tgtacatctt cgggctcggg tacgttggga gcaggctcgc    2700
caaccagctg gcggaacagg ggtggcgcgt cgcggggtcg gtgagggagc tcggcgcga    2760 ggacgacttt gccgagttcg aaaagtccaa gctgagcggc aaggtgcagg tgttccaact    2820
cccgcttgag ggcgaggaca acacgcccgc tcgcgcgcgg gagatactta gcgggtacca    2880
gcgcctgctg ttcacggcgc cagtggaccg cgcccggaac tgtgaccct tcttgggcga    2940 ccccgttctc ggccccgtga tcgtcgagct agcagaggag ggccgcatcg actgggccgg    3000
ctatctctca accacttcgg tctacggcaa ccacgacggc gagtgggtgg acgagaccac    3060
gccgctcatg cccacgctca acgcggcga gcagcgcgtc atggtggagc gcgccttcct    3120
gtacgagtcg ggcctcccgg cccatatctt tcggctgcca ggaatctacg gcccagggcg    3180
cggcccgata tca                                                      3193
```

<210> SEQ ID NO 189
<211> LENGTH: 27
<212> TYPE: DNA
<213> ORGANISM: Artificial

```
<220> FEATURE:
<223> OTHER INFORMATION: primer

<400> SEQUENCE: 189
gacaaagatc tcgactggag cgaccac                                               27

<210> SEQ ID NO 190
<211> LENGTH: 27
<212> TYPE: DNA
<213> ORGANISM: Artificial
<220> FEATURE:
<223> OTHER INFORMATION: primer

<400> SEQUENCE: 190
gtcgagatct tttgtcagga ggtgcac                                               27

<210> SEQ ID NO 191
<211> LENGTH: 951
<212> TYPE: DNA
<213> ORGANISM: Artificial
<220> FEATURE:
<223> OTHER INFORMATION: BglII inserted C20 elongase

<400> SEQUENCE: 191
atggcgacgc gcacctcgaa gagcgctccg gcggtttcca agtcggccaa ggttgccgcg          60
ccggcgaaga gcggtcggt cgacaggagc gacggttttct tccgcacgtt caacctgtgc        120
gccctgtacg ggtctgccct cgcctatgcg tacaagcacg gcccggtgga caatgacggc        180
caggggctgt actttcacaa gtcgcccatg tacgcgttcg ccgtgtcgga cgtcatgacc        240
ttcggcgcgc cgctgatgta cgtgctcggt gtgatgctgc tcagcaggta catggcggac        300
aaaaagcccc tgactggctt catcaagacc tacatccagc ccgtctacaa cgtggtccaa        360
atcgcggtgt gcggctggat ggtgtggggc ctctggccgc aggtcgacct ggccaacggc        420 aacccctttcg gcctcaacaa gtcgcgcgac tcgaacatcg agttttttcgt gttcgtgcac        480 ctcctgacaa agatctcgac tggagcgaca cgttcatgat gatcctcaag aaaaactacg        540
cccaggttag cttttctgcag gtgttccacc acgcaacgat cggcatggtg tggtcgttcc        600
ttcttcagcg tggctggggc tcgggcaccg ccgcgtacgg tgctttcatc aactcggtca        660
cgcacgtgat catgtactcg cactactttg ccacctcgct caacatcaac aacccgttca        720
agcggtacat cacgagcttc cagctcgccc agtttgcaag ctgcatcgtg catgccctac        780
tggtgcttgc cttcgaggag gtgtacccgc tcgagtacgc ttacctgcag atcagctacc        840
acatcatcat gctctacctg ttcggacgcc gcatgaactg gagccccgag tggtgcaccg        900
gtgagatcga cggccttgac gccccaagcg cccccaccaa gtccgagtaa a                 951

<210> SEQ ID NO 192
<211> LENGTH: 23
<212> TYPE: DNA
<213> ORGANISM: Artificial
<220> FEATURE:
<223> OTHER INFORMATION: primer

<400> SEQUENCE: 192
atggcgacgc gcacctcgaa gag                                                  23

<210> SEQ ID NO 193
<211> LENGTH: 23
<212> TYPE: DNA
<213> ORGANISM: Artificial
<220> FEATURE:
```

<223> OTHER INFORMATION: primer

<400> SEQUENCE: 193
ttactcggac ttgctggggg cgc                                                    23

<210> SEQ ID NO 194
<211> LENGTH: 2655
<212> TYPE: DNA
<213> ORGANISM: Artificial
<220> FEATURE:
<223> OTHER INFORMATION: fusion DNA(Thraustochytrium aureum C20 elongase
    5' region/SV40 terminator/Neor/ubiquitin promoter/
    Thraustochytrium aureum C20 elongase 3' region)

<400> SEQUENCE: 194

| | |
|---|---|
| atggcgacgc gcacctcgaa gagcgctccg gcggtttcca agtcggccaa ggttgccgcg | 60 |
| ccggcgaaga agcggtcggt cgacaggagc gacggtttct tccgcacgtt caacctgtgc | 120 |
| gccctgtacg ggtctgccct cgcctatgcg tacaagcacg gcccggtgga caatgacggc | 180 |
| caggggctgt actttcacaa gtcgcccatg tacgcgttcg ccgtgtcgga cgtcatgacc | 240 |
| ttcggcgcgc cgctgatgta cgtgctcggt gtgatgctgc tcagcaggta catggcggac | 300 |
| aaaaagcccc tgactggctt catcaagacc tacatccagc ccgtctacaa cgtggtccaa | 360 |
| atcgcggtgt gcggctggat ggtgtggggc ctctggccgc aggtcgacct ggccaacggc | 420 |
| aaccctttcg gcctcaacaa gtcgcgcgac tcgaacatcg agttttttcgt gttcgtgcac | 480 |
| ctcctgacaa agatctagct agaggtcgac ggtatacaga catgataaga tacattgatg | 540 |
| agtttggaca aaccacaact agaatgcagt gaaaaaaatg ctttatttgt gaaatttgtg | 600 |
| atgctattgc tttatttgta accattataa gctgcaataa acaagttggg gtgggcgaag | 660 |
| aactccagca tgagatcccc gcgctggagg atcatccagc cggcgtcccg gaaaacgatt | 720 |
| ccgaagccca acctttcata gaaggcggcg gtggaatcga atctcgtga tggcaggttg | 780 |
| ggcgtcgctt ggtcggtcat ttcgcggatc tcaaaagaac tcgtccagga ggcggtagaa | 840 |
| cgcaatcctc tggctgtccg gggcggcgat gccgtagagc acgagaaagc ggtcggccca | 900 |
| ctcgccgcca agctcctcgg cgatgtcccg cgtggcgagc gcgatgtctt ggtagcggtc | 960 |
| cgccacgccc aggcgcccgc agtcgataaa gcccgagaag cggccgttct cgaccatgat | 1020 |
| gttggggagg caggcgtcgc cgtgcgtgac cacgaggtcc tcgccgtccg gcatcctagc | 1080 |
| cttaagcctg gcgaacagtt ccgccggcgc gaggccctgg tgctcctcgt cgaggtcgtc | 1140 |
| ttggtcgacg aggccagcct ccatccgcgt cggggcgcgt cgatcctgt gcttcgcctg | 1200 |
| gtggtcgaag gggcaggtgg cggggtcgag ggtgtgcagg cggcgcatgg cgtcggccat | 1260 |
| gatggacacc ttctcagcgg gcgcgaggtg gctgctgagg aggtcctggc cgggcacttc | 1320 |
| cccgaggagc agccagtcgc ggccggcttc ggtgacgacg tcgagcacag cggcgcacgg | 1380 |
| aaccccgtc gtggcaagcc agctgaggcg ggcagcttcg tcctggagct cgttgagggc | 1440 |
| gccgctaagg tcggtcttga caaacaggac cggccggccc tgcgcgctaa ggcggaacac | 1500 |
| ggccgcgtcc gagcagccga tcgtctgctg agcccagtcg tagccgaaca gccgttccac | 1560 |
| ccaagcagcg ggcgagccag cgtgaaggcc gtcctgttca atcatgttgg ctagtgttgc | 1620 |
| ttaggtcgct tgctgctgct ggtgttgctt gttctgcttg tcgtttgggg tctgcccgaa | 1680 |
| gtggacgcgt gacacagccc agcgttcgcg actttttccag caaccagctc gctccgcgtc | 1740 |
| agggtcactc tctgctcact cccctgtcta gttcggcaga actggagagg caacccgcgc | 1800 |
| ttccagaggg ttctcctccg gaatcagttc agaattcaga attcagaaga gggaatcgca | 1860 |

-continued

```
gaaccggccg cttcgggagt tggttcgctg caccatagca ggtgggcgat gaggccaacc    1920
gccctgctgg ctggattctc tcgggttggc acatcgaacg accggaccc gcgcgcgagt    1980 tgtccctgcc agttgctacc agcctgccag cgtcggagag ttatgcgctg cctgccggcc    2040
ggagagagag cgggcgtgga aagtggcgtg tggggcgaac gcatgccct ccgcgtggc     2100 ccgatttcct atgcatccgc tccgctctct ctctcggagg caagaagagc acaccaacaa    2160
cgcccggcgg gtgcaccagg cgctgcggca gatccagatc tcgactggag cgacacgttc    2220
atgatgatcc tcaagaaaaa ctacgcccag gttagctttc tgcaggtgtt ccaccacgca    2280
acgatcggca tggtgtggtc gttccttctt cagcgtggct ggggctcggg caccgccgcg    2340
tacggtgctt tcatcaactc ggtcacgcac gtgatcatgt actcgcacta ctttgccacc    2400
tcgctcaaca tcaacaaccc gttcaagtgg tacatcacga gcttccagct cgcccagttt    2460
gcaagctgca tcgtgcatgc cctactggtg cttgccttcg aggaggtgta cccgctcgag    2520
tacgcttacc tgcagatcag ctaccacatc atcatgctct acctgttcgg acgccgcatg    2580
aactggagcc ccgagtggtg caccggtgag atcgacggcc ttgacgcccc aagcgccccc    2640
accaagtccg agtaa                                                    2655
```

<210> SEQ ID NO 195
<211> LENGTH: 2886
<212> TYPE: DNA
<213> ORGANISM: Artificial
<220> FEATURE:
<223> OTHER INFORMATION: fusion DNA(Thraustochytrium aureum C20 elongase
    5' region/ubiquitin promoter/Hygr/SV40
    terminator/Thraustochytrium aureum C20 elongase 3' region)

<400> SEQUENCE: 195

```
atggcgacgc gcacctcgaa gagcgctccg gcggttttcca agtcggccaa ggttgccgcg    60
ccggcgaaga agcggtcggt cgacaggagc gacggtttct tccgcacgtt caacctgtgc    120
gccctgtacg ggtctgccct cgcctatgcg tacaagcacg gccggtgga caatgacggc    180 caggggctgt actttcacaa gtcgcccatg tacgcgttcg ccgtgtcgga cgtcatgacc    240
ttcggcgcgc cgctgatgta cgtgctcggt gtgatgctgc tcagcaggta catggcggac    300
aaaaagcccc tgactggctt catcaagacc tacatccagc ccgtctacaa cgtggtccaa    360
atcgcggtgt gcggctggat ggtgtggggc ctctggccgc aggtcgacct ggccaacggc    420 aacccttcg gcctcaacaa gtcgcgcgac tcgaacatcg agttttttcgt gttcgtgcac    480 ctcctgacaa agatctggat ctgccgcagc gcctggtgca cccgccgggc gttgttgtgt    540
gctcttcttg cctccgagag agagagcgga gcggatgcat aggaaatcgg gccacgcggg    600
agggccatgc gttcgcccca cacgccactt tccacgcccg ctctctctcc ggccggcagg    660
cagcgcataa ctctccgacg ctggcaggct ggtagcaact ggcagggaca actcgcgcgc    720
gggtcccggt cgttcgatgt gccaacccga gagaatccag ccagcagggc ggttggcctc    780
atcgcccacc tgctatggtg cagcgaacca actcccgaag cggccggttc tgcgattccc    840
tcttctgaat tctgaattct gaactgattc cggaggagaa ccctctggaa gcgcgggttg    900
cctctccagt tctgccgaac tagacagggg agtgagcaga gagtgaccct gacgcggagc    960
gagctggttg ctggaaaagt cgcgaacgct gggctgtgtc acgcgtccac ttcgggcaga    1020
ccccaaacga caagcagaac aagcaacacc agcagcagca agcgacctaa gcaacactag    1080
ccaacatgaa aaagcctgaa ctcaccgcga cgtctgtcga gaagtttctg atcgaaaagt    1140
```

| | |
|---|---|
| tcgacagcgt ctccgacctg atgcagctct cggagggcga agaatctcgt gctttcagct | 1200 |
| tcgatgtagg agggcgtgga tatgtcctgc gggtaaatag ctgcgccgat ggtttctaca | 1260 |
| aagatcgtta tgtttatcgg cactttgcat cggccgcgct cccgattccg gaagtgcttg | 1320 |
| acattgggga attcagcgag agcctgacct attgcatctc ccgccgtgca cagggtgtca | 1380 |
| cgttgcaaga cctgcctgaa accgaactgc ccgctgttct gcagccggtc gcggaggcca | 1440 |
| tggatgcgat cgctgcggcc gatcttagcc agacgagcgg gttcggccca ttcggaccgc | 1500 |
| aaggaatcgg tcaatacact acatggcgtg atttcatatg cgcgattgct gatccccatg | 1560 |
| tgtatcactg gcaaactgtg atggacgaca ccgtcagtgc gtccgtcgcg caggctctcg | 1620 |
| atgagctgat gctttgggcc gaggactgcc ccgaagtccg gcacctcgtg cacgcggatt | 1680 |
| tcggctccaa caatgtcctg acggacaatg gccgcataac agcggtcatt gactggagcg | 1740 |
| aggcgatgtt cggggattcc caatacgagg tcgccaacat cttcttctgg aggccgtggt | 1800 |
| tggcttgtat ggagcagcag acgcgctact cgagcggag gcatccggag cttgcaggat | 1860 |
| cgccgcggct ccgggcgtat atgctccgca ttggtcttga ccaactctat cagagcttgg | 1920 |
| ttgacggcaa tttcgatgat gcagcttggg cgcagggtcg atgcgacgca atcgtccgat | 1980 |
| ccggagccgg gactgtcggg cgtacacaaa tcgcccgcag aagcgcggcc gtctggaccg | 2040 |
| atggctgtgt agaagtactc gccgatagtg gaaaccgacg ccccagcact cgtccgaggg | 2100 |
| caaaggaata gagatccgcg aaatgaccga ccaagcgacg cccaacctgc catcacgaga | 2160 |
| tttcgattcc accgccgcct tctatgaaag gttgggcttc ggaatcgttt tccgggacgc | 2220 |
| cggctggatg atcctccagc gcggggatct catgctggag ttcttcgccc accccaactt | 2280 |
| gtttattgca gcttataatg gttacaaata aagcaatagc atcacaaatt tcacaaataa | 2340 |
| agcattttt tcactgcatt ctagttgtgg tttgtccaaa ctcatcaatg tatcttatca | 2400 |
| tgtctgtata ccgtcgacct cyagctagat ctcgactgga gcgacacgtt catgatgatc | 2460 |
| ctcaagaaaa actacgccca ggttagcttt ctgcaggtgt tccaccacgc aacgatcggc | 2520 |
| atggtgtggt cgttccttct tcagcgtggc tggggctcgg gcaccgccgc gtacggtgct | 2580 |
| ttcatcaact cggtcacgca cgtgatcatg tactcgcact actttgccac ctcgctcaac | 2640 |
| atcaacaacc cgttcaagtg gtacatcacg agcttccagc tcgcccagtt tgcaagctgc | 2700 |
| atcgtgcatg ccctactggt gcttgccttc gaggaggtgt acccgctcga gtacgcttac | 2760 |
| ctgcagatca gctaccacat catcatgctc tacctgttcg gacgccgcat gaactggagc | 2820 |
| cccgagtggt gcaccggtga gatcgacggc cttgacgccc aagcgcccc caccaagtcc | 2880 |
| gagtaa | 2886 |

<210> SEQ ID NO 196
<211> LENGTH: 26
<212> TYPE: DNA
<213> ORGANISM: Artificial
<220> FEATURE:
<223> OTHER INFORMATION: primer

<400> SEQUENCE: 196
gctcggctgg aagttgagta gtttgc                                          26

<210> SEQ ID NO 197
<211> LENGTH: 24
<212> TYPE: DNA
<213> ORGANISM: Artificial
<220> FEATURE:
<223> OTHER INFORMATION: primer

```
<400> SEQUENCE: 197
tctttcttcg tcgacgtccc actg                                              24

<210> SEQ ID NO 198
<211> LENGTH: 24
<212> TYPE: DNA
<213> ORGANISM: Artificial
<220> FEATURE:
<223> OTHER INFORMATION: primer

<400> SEQUENCE: 198
atgattgaac aggacggcct tcac                                              24

<210> SEQ ID NO 199
<211> LENGTH: 24
<212> TYPE: DNA
<213> ORGANISM: Artificial
<220> FEATURE:
<223> OTHER INFORMATION: primer

<400> SEQUENCE: 199
tcaaaagaac tcgtccagga ggcg                                              24

<210> SEQ ID NO 200
<211> LENGTH: 24
<212> TYPE: DNA
<213> ORGANISM: Artificial
<220> FEATURE:
<223> OTHER INFORMATION: primer

<400> SEQUENCE: 200
atgaaaaagc ctgaactcac cgcg                                              24

<210> SEQ ID NO 201
<211> LENGTH: 25
<212> TYPE: DNA
<213> ORGANISM: Artificial
<220> FEATURE:
<223> OTHER INFORMATION: primer

<400> SEQUENCE: 201 ctattcctttt gccctcggac gagtg                                            25

<210> SEQ ID NO 202
<211> LENGTH: 23
<212> TYPE: DNA
<213> ORGANISM: Artificial
<220> FEATURE:
<223> OTHER INFORMATION: primer

<400> SEQUENCE: 202
ggcggagcga agtgtgaaag tta                                               23

<210> SEQ ID NO 203
<211> LENGTH: 24
<212> TYPE: DNA
<213> ORGANISM: Artificial
<220> FEATURE:
<223> OTHER INFORMATION: primer

<400> SEQUENCE: 203
gcgacagcat cttgaaatag gcag                                              24

<210> SEQ ID NO 204
```

<211> LENGTH: 2571
<212> TYPE: DNA
<213> ORGANISM: Thraustochytrium aureum
<220> FEATURE:
<223> OTHER INFORMATION: Genomic delta 4 desaturase upstream/T. aureum delta 4 desaturase

<400> SEQUENCE: 204

```
ggcggagcga agtgtgaaag ttacaaccca gttactgccc attcccggga aaagttgcgc      60
agctcacgcg gttcgctttt ctggtggcct ggcgacgttc gccgcttgcc ggatactccc     120
tcgtgccccc gcgccaggtt tgcccgctgt cgctcgagga gtggactcgc gagtcgcgac     180
agcagcagca ccaaggggga tggatcctcg ttgacagcac caagatgctc tctgcctttc     240
aggtgaaatc gatcgatcaa ttgatcaatc aagatcattg gaagcaaatg ggaagcaaat     300
gcgaagggggg aagaccctcg gtctctgctc gggaacccga cacgaggctg agggcgcgct     360
tctacaggtt gtgcagcggc cgcactgcga gcttgcgccg ggccaaggcg ctcgccagaa     420
ttgctgcgtc tgccgcctcg ggatcagcca ctcggttttt cgtcatcagg gtccaccttc     480
aacctggaag tggactcggc aagtcggcag atccactccg gaattccaag atccccggtc     540
gatcggtgct ggtgcgaatt aggatggacc caggctatgt gagagtcgga gggtggcggt     600
tgtctccacc gtgacagcgc gcgtgtggtg agtaacgcga agcgcgtggt ggagaaatgg     660
ggggagattc gtaggacgcg atgcgctcgt cactgagggt gcgccggtga cgaagcttcg     720
gacccagatt ccgtcggtat ggctcgtgtt cgcacaccct caggaacccg catgacgaga     780
ccactggagt tttcaacgtc acgaagccgc tctgtgtgac gagaattggc ttgcgagtga     840
cgtgaggcgc cgagcatgtc gttggtttgc ctcttcacaa cagaatcaga cgactgggag     900
gctgcacgag gctaaggcca agggcactca ctgactcgga cgtgaagcag aagcagaagc     960
agagcgctcg acggcacgtg gcggcagacc ggcttcggga cgggcaggag acgcaaggcg    1020
cgcaacacta gggggctgga cgtgaccac tggctaagga gcgctggaaa gatgacggtc    1080
gggtttgacg aaacggtgac tatggacacg gtccgcaacc acaacatgcc ggacgacgcc    1140
tggtgcgcga tccacggcac cgtgtacgac atcaccaagt tcagcaaggt gcaccccggc    1200
ggggacatca tcatgctggc cgctggcaag gaggccacca tcctgttcga gacctaccac    1260
atcaagggcg tcccggacgc ggtgctgcgc aagtacaagg tcggcaagct cccccagggc    1320
aagaagggcg aaacgagcca cgtgcccacc gggctcgact cggcctccta ctactcgtgg    1380
gacagcgagt tttacagggt gctccgcgag cgcgtcgcca agaagctggc cgagcccggc    1440
ctcatgcagc gcgcgcgcat ggagctctgg gccaaggcga tcttcctcct ggcaggtttc    1500
tggggctccc tttacgccat gtgcgtgcta gacccgcacg cggtgccat ggtagccgcc    1560
gttacgctcg gcgtgttcgc tgcctttgtc ggaacttgca tccagcacga cggcagccac    1620
ggcgccttct ccaagtcgcg attcatgaac aaggcggcgg gctggaccct cgacatgatc    1680
ggcgcgagcg cgatgacctg ggagatgcag cacgttcttg ccaccacccc gtacaccaac    1740
ctcatcgaga tggagaacgg tttggccaag gtcaagggcg ccgacgtcga cccgaagaag    1800
gtcgaccagg agagcgaccc ggacgtcttc agtacgtacc cgatgcttcg cctgcacccg    1860
tggcaccgcc agcggtttta ccacaagttc cagcacctgt acgccccgtt tatctttggg    1920
tttatgacga ttaacaaggt gatttcccag gatgtcgggg ttgtgctgcg caagcgcctg    1980
ttccagatcg acgccaactg ccggtatggc agccctggt acgtgcccg cttctggatc    2040
atgaagctcc tcaccacgct ctacatggtg gcgcttccca tgtacatgca ggggcctgct    2100
```

| | |
|---|---|
| cagggcttga agcttttctt catggcccac ttcacctgcg agagggtcct cgccaccatg | 2160 |
| tttattgtca accacatcat cgagggcgtc agctacgctt ccaaggacgc ggtcaagggc | 2220 |
| gtcatggctc cgccgcgcac tgtgcacggt gtcaccccga tgcaggtgac gcaaaaggcg | 2280 |
| ctcagtgcgg ccgagtcgac caagtcggac gccgacaaga cgaccatgat cccccctcaac | 2340 |
| gactgggccg ctgtgcagtg ccagacctct gtgaactggg ctgtcgggtc gtggttttgg | 2400 |
| aaccactttt cgggcggcct caaccaccag attgagcacc actgcttccc caaaaccccc | 2460 |
| acacggtcaa cgtctacatc tcgggcatcg tcaaggagac ctgcgaagaa tacggcgtgc | 2520 |
| cgtaccaggc tgagatcagc ctcttctctg cctatttcaa gatgctgtcg c | 2571 |

<210> SEQ ID NO 205
<211> LENGTH: 616
<212> TYPE: DNA
<213> ORGANISM: Thraustochytrium aureum
<220> FEATURE:
<223> OTHER INFORMATION: genomic delta 4 desaturase upstream/T. aureum
     delta 4 desaturase

<400> SEQUENCE: 205

| | |
|---|---|
| cgcaaggcgc gcaacactag ggggctggac gtggaccact ggctaaggag cgctggaaag | 60 |
| atgacggtcg ggtttgacga acggtgact atggacacgg tccgcaacca caacatgccg | 120 |
| gacgacgcct ggtgcgcgat ccacggcacc gtgtacgaca tcaccaagtt cagcaaggtg | 180 |
| caccccggcg gggacatcat catgctggcc gctggcaagg aggccaccat cctgttcgag | 240 |
| acctaccaca tcaagggcgt cccggacgcg gtgctgcgca agtacaaggt cggcaagctc | 300 |
| ccccagggca agaagggcga aacgagccac gtgcccaccg ggctcgactc ggcctcctac | 360 |
| tactcgtggg acagcgagtt ttacaggggtg ctccgcgagc gcgtcgccaa gaagctggcc | 420 |
| gagcccggcc tcatgcagcg cgcgcgcatg gagctctggg ccaaggcgat cttcctcctg | 480 |
| gcaggtttct ggggctccct ttacgccatg tgcgtgctag acccgcacgg cggtgccatg | 540 |
| gtagccgccg ttacgctcgg cgtgttcgct gcctttgtcg aacttgcat ccagcacgac | 600 |
| ggcagccacg gcgcct | 616 |

<210> SEQ ID NO 206
<211> LENGTH: 25
<212> TYPE: DNA
<213> ORGANISM: Artificial
<220> FEATURE:
<223> OTHER INFORMATION: primer

<400> SEQUENCE: 206

| | |
|---|---|
| caggagatct ccaagtcgcg attca | 25 |

<210> SEQ ID NO 207
<211> LENGTH: 26
<212> TYPE: DNA
<213> ORGANISM: Artificial
<220> FEATURE:
<223> OTHER INFORMATION: primer

<400> SEQUENCE: 207

| | |
|---|---|
| cttggagatc tcctgcccgt cccgaa | 26 |

<210> SEQ ID NO 208
<211> LENGTH: 3264
<212> TYPE: DNA
<213> ORGANISM: Artificial
<220> FEATURE:

<223> OTHER INFORMATION: fusion DNA (T. aureum delta 4 desaturase upstream/SV40 terminator /BlaR/ubiquitin promoter/T. aureum delta 4 desaturase)

<400> SEQUENCE: 208

| | | | | |
|---|---|---|---|---|
| ggcggagcga | agtgtgaaag | ttacaaccca | gttactgccc | attcccggga | aaagttgcgc | 60 |
| agctcacgcg | gttcgctttt | ctggtggcct | ggcgacgttc | gccgcttgcc | ggatactccc | 120 |
| tcgtgccccc | gcgccaggtt | tgcccgctgt | cgctcgagga | gtggactcgc | gagtcgcgac | 180 |
| agcagcagca | ccaaggggga | tggatcctcg | ttgacagcac | caagatgctc | tctgcctttc | 240 |
| aggtgaaatc | gatcgatcaa | ttgatcaatc | aagatcattg | gaagcaaatg | ggaagcaaat | 300 |
| gcgaaggggg | aagaccctcg | gtctctgctc | gggaacccga | cacgaggctg | agggcgcgct | 360 |
| tctacaggtt | gtgcagcggc | cgcactgcga | gcttgcgccg | ggccaaggcg | ctcgccagaa | 420 |
| ttgctgcgtc | tgccgcctcg | ggatcagcca | ctcggttttt | cgtcatcagg | gtccaccttc | 480 |
| aacctggaag | tggactcggc | aagtcggcag | atccactccg | gaattccaag | atccccggtc | 540 |
| gatcggtgct | ggtgcgaatt | aggatggacc | caggctatgt | gagagtcgga | gggtggcggt | 600 |
| tgtctccacc | gtgacagcgc | gcgtgtggtg | agtaacgcga | agcgcgtggt | ggagaaatgg | 660 |
| ggggagattc | gtaggacgcg | atgcgctcgt | cactgagggt | gcgccggtga | cgaagcttcg | 720 |
| gacccagatt | ccgtcggtat | ggctcgtgtt | cgcacacctt | caggaacccg | catgacgaga | 780 |
| ccactggagt | tttcaacgtc | acgaagccgc | tctgtgtgac | gagaattggc | ttgcgagtga | 840 |
| cgtgaggcgc | cgagcatgtc | gttggtttgc | ctcttcacaa | cagaatcaga | cgactgggag | 900 |
| gctgcacgag | gctaaggcca | agggcactca | ctgactcgga | cgtgaagcag | aagcagaagc | 960 |
| agagcgctcg | acggcacgtg | gcggcagacc | ggcttcggga | cgggcaggag | atctagctag | 1020 |
| aggtcgacgg | tatacagaca | tgataagata | cattgatgag | tttggacaaa | ccacaactag | 1080 |
| aatgcagtga | aaaaaatgct | ttatttgtga | aatttgtgat | gctattgctt | tatttgtaac | 1140 |
| cattataagc | tgcaataaac | aagttggggt | gggcgaagaa | ctccagcatg | agatccccgc | 1200 |
| gctggaggat | catccagccg | gcgtcccgga | aaacgattcc | gaagcccaac | ctttcataga | 1260 |
| aggcggcggt | ggaatcgaaa | tctcgtgatg | gcaggttggg | cgtcgcttgg | tcggtcattt | 1320 |
| cgcggatctt | agccctccca | cataaacca | gagggcagca | attcacgaat | cccaactgcc | 1380 |
| gtcggctgtc | catcactgtc | cttcactatg | gctttgatcc | caggatgcag | atcgagaagc | 1440 |
| acctgtcggc | accgtccgca | ggggctcaag | atgcccctgt | tctcatttcc | gatcgcgacg | 1500 |
| atacaagtca | ggttgccagc | tgccgcagca | gcagcagtgc | ccagcaccac | gagttctgca | 1560 |
| caaggtcccc | cagtaaaatg | atatacattg | acaccagtga | agatgcggcc | gtcgctagag | 1620 |
| agagctgcgc | tggcgacgct | gtagtcttca | gagatgggga | tgctgttgat | tgtagccgtt | 1680 |
| gctctttcaa | tgagggtgga | ttcttcttga | gacaaaggct | tggccatgtt | ggctagtgtt | 1740 |
| gcttaggtcg | cttgctgctg | ctggtgttgc | ttgttctgct | tgtcgtttgg | ggactgcccg | 1800 |
| aagtggacgc | gtgacacagc | ccagcgttcg | cgacttttcc | agcaaccagc | tcgctccgcg | 1860 |
| tcagggtcac | tctctgctca | ctccctgtc | tagttcggca | gaactggaga | ggcaacccgc | 1920 |
| gcttccagag | ggttctcctc | cggaatcagt | tcagaattca | gaattcagaa | gagggaatcg | 1980 |
| cagaaccggc | cgcttcggga | gttggttcgc | tgcaccatag | caggtgggcg | atgaggccaa | 2040 |
| ccgccctgct | ggctggattc | tctcgggttg | gcacatcgaa | cgaccggac | ccgcgcgcga | 2100 |
| gttgtccctg | ccagttgcta | ccagcctgcc | agcgtcggga | agttatgcgc | tgcctgccgg | 2160 |
| ccggagagag | agcgggcgtg | gaaagtggcg | tgtggggcga | acgcatggcc | ctcccgcgtg | 2220 |

```
gcccgatttc ctatgcatcc gctccgctct ctctctcgga ggcaagaaga gcacaccaac    2280
aacgcccggc gggtgcacca ggcgctgcgg cagatccaga tctccaagtc gcgattcatg    2340
aacaaggcgg cgggctggac cctcgacatg atcggcgcga gcgcgatgac ctgggagatg    2400
cagcacgttc ttggccacca cccgtacacc aacctcatcg agatggagaa cggtttggcc    2460
aaggtcaagg gcgccgacgt cgacccgaag aaggtcgacc aggagagcga cccggacgtc    2520
ttcagtacgt acccgatgct cgcctgcac ccgtggcacc gccagcggtt ttaccacaag    2580
ttccagcacc tgtacgcccc gtttatcttt gggtttatga cgattaacaa ggtgatttcc    2640
caggatgtcg gggttgtgct cgcaagcgc ctgttccaga tcgacgccaa ctgccggtat    2700
ggcagcccct ggtacgtggc ccgcttctgg atcatgaagc cctcaccac gctctacatg    2760 gtggcgcttc ccatgtacat gcaggggcct gctcagggct tgaagctttt cttcatggcc    2820
cacttcacct gcggagaggt cctcgccacc atgtttattg tcaaccacat catcgagggc    2880
gtcagctacg cttccaagga cgcggtcaag ggcgtcatgg ctccgccgcg cactgtgcac    2940
ggtgtcaccc cgatgcaggt gacgcaaaag gcgctcagtg cggccgagtc gaccaagtcg    3000
gacgccgaca agacgaccat gatcccctc aacgactggg ccgctgtgca gtgccagacc    3060
tctgtgaact gggctgtcgg gtcgtggttt tggaaccact tttcgggcgg cctcaaccac    3120
cagattgagc accactgctt ccccaaaacc cccacacggt caacgtctac atctcgggca    3180
tcgtcaagga gacctgcgaa gaatacggcg tgccgtacca ggctgagatc agcctcttct    3240
ctgcctattt caagatgctg tcgc                                          3264

<210> SEQ ID NO 209
<211> LENGTH: 3935
<212> TYPE: DNA
<213> ORGANISM: Artificial
<220> FEATURE:
<223> OTHER INFORMATION: fusion DNA (T. aureum delta 4 desaturase
      upstream/SV40 terminator/ZeoR/Enhanced GFP/ubiquitin promoter/T.
      aureum delta 4 desaturase)

<400> SEQUENCE: 209
ggcggagcga agtgtgaaag ttacaaccca gttactgccc attcccggga aaagttgcgc      60
agctcacgcg gttcgctttt ctggtggcct ggcgacgttc gccgcttgcc ggatactccc     120
tcgtgccccc gcgccaggtt tgcccgctgt cgctcgagga gtggactcgc gagtcgcgac     180
agcagcagca ccaaggggga tggatcctcg ttgacagcac caagatgctc tctgcctttc     240
aggtgaaatc gatcgatcaa ttgatcaatc aagatcattg gaagcaaatg ggaagcaaat     300
gcgaaggggg aagaccctcg gtctctgctc gggaacccga cacgaggctg agggcgcgct     360
tctacaggtt gtgcagcggc cgcactgcga gcttgcgccg ggcaaggcg ctcgccagaa     420 ttgctgcgtc tgccgcctcg ggatcagcca ctcgtttttt cgtcatcagg gtccaccttc     480
aacctggaag tggactcggc aagtcggcag atccactccg gaattccaag atccccggtc     540
gatcggtgct ggtgcgaatt aggatggacc caggctatgt gagagtcgga gggtggcggt     600
tgtctccacc gtgacagcgc gcgtgtggtg agtaacgcga agcgcgtggt ggagaaatgg     660
ggggagattc gtaggacgcg atgcgctcgt cactgagggt gcgccggtga cgaagcttcg     720
gacccagatt ccgtcggtat ggctcgtgtt cgcacacctt caggaacccg catgacgaga     780
ccactggagt tttcaacgtc acgaagccgc tctgtgtgac gagaattggc ttgcgagtga     840
cgtgaggcgc cgagcatgtc gttggtttgc ctcttcacaa cagaatcaga cgactgggag     900
```

```
gctgcacgag gctaaggcca agggcactca ctgactcgga cgtgaagcag aagcagaagc    960
agagcgctcg acggcacgtg gcggcagacc ggcttcggga cgggcaggag atctagctag   1020
aggtcgacgg tatacagaca tgataagata cattgatgag tttggacaaa ccacaactag   1080
aatgcagtga aaaaaatgct ttatttgtga aatttgtgat gctattgctt tatttgtaac   1140
cattataagc tgcaataaac aagttggggt gggcgaagaa ctccagcatg atccccgc     1200
gctggaggat catccagccg gcgtcccgga aaacgattcc gaagcccaac ctttcataga   1260
aggcggcggt ggaatcgaaa tctcgtgatg gcaggttggg cgtcgcttgg tcggtcattt   1320
cgcggatctc agtcctgctc ctcggccacg aagtgcacgc agttgccggc cgggtcgcgc   1380
agggcgaact cccgccccca cggctgctcg ccgatctcgg tcatggccgg cccggaggcg   1440
tcccggaagt tcgtggacac gacctccgac cactcggcgt acagctcgtc caggccgcgc   1500
acccacaccc aggccagggt gttgtccggc accacctggt cctggaccgc gctgatgaac   1560
agggtcacgt cgtcccggac cacaccggcg aagtcgtcct ccacgaagtc ccgggagaac   1620
ccgagccggt cggtccagaa ctcgaccgct ccggcgacgt cgcgcgcggt gagcaccgga   1680
acggcactgg tcaacttggc gtccatgccg agagtgatcc cggcggcggt cacgaactcc   1740
agcaggacca tgtgatcgcg cttctcgttg gggtctttgc tcagggcgga ctgggtgctc   1800
aggtagtggt tgtcgggcag cagcacgggg ccgtcgccga tgggggtgtt ctgctggtag   1860
tggtcggcga gctgcacgct gccgtcctcg atgttgtggc ggatcttgaa gttcaccttg   1920
atgccgttct tctgcttgtc ggccatgata tagacgttgt ggctgttgta gttgtactcc   1980
agcttgtgcc ccaggatgtt gccgtcctcc ttgaagtcga tgcccttcag ctcgatgcgg   2040
ttcaccaggg tgtcgccctc gaacttcacc tcggcgcggg tcttgtagtt gccgtcgtcc   2100
ttgaagaaga tggtgcgctc ctggacgtag ccttcgggca tggcggactt gaagaagtcg   2160
tgctgcttca tgtggtcggg gtagcggctg aagcactgca cgccgtaggt cagggtggtc   2220
acgagggtgg gccagggcac gggcagcttg ccggtggtgc agatgaactt cagggtcagc   2280
ttgccgtagg tggcatcgcc ctcgccctcg ccggacacgc tgaacttgtg ccgtttacg    2340
tcgccgtcca gctcgaccag gatgggcacc accccggtga acagctcctc gcccttgctc   2400
accatgttgg ctagtgttgc ttagatcgct tgctgctgct ggtgttgctt gttctgcttg   2460
tcgtttgggg tctgccccgaa gtggacgcgt gacacagccc agcgtcgcg acttttccag    2520
caaccagctc gctccgcgtc agggtcactc tctgctcact cccctgtcta gttcggcaga   2580
actggagagg caacccgcgc ttccagaggg ttctcctccg gaatcagttc agaattcaga   2640
attcagaaga gggaatcgca gaaccggcag cttcgggagt tggttcgctg caccatagca   2700
ggtgggcgat gaggccaacc gccctgctgg ctggattctc tcgggttggc acatcgaacg   2760
accgggaccc gcgcgcgagt tgtccctgcc agttgctacc agcctgccag cgtcggagag   2820
ttatgcgctg cctgccggcc ggagagagag cgggcgtgga aagtggcgtg tggggcaaac   2880
gcatggccct cccgcgtggc ccgatttcct atgcatccgc tccgctctct ctctcggagg   2940
caagaagagc acacaacaac gcccggcggg tgcaccaggc gctgcggcag atctccaagt   3000
cgcgattcat gaacaaggcg gcgggctgga ccctcgacat gatcggcgcg agcgcgatga   3060
cctgggagat gcagcacgtt cttggccacc acccgtacac caacctcatc gagatggaga   3120
acggtttggc caaggtcaag ggcgccgacg tcgacccgaa gaaggtcgac caggagagcg   3180
accccggacgt cttcagtacg taccccgatgc ttcgcctgca cccgtggcac cgccagcggt   3240
tttaccacaa gttccagcac ctgtacgccc cgtttatctt tgggtttatg acgattaaca   3300
```

| | |
|---|---|
| aggtgatttc ccaggatgtc ggggttgtgc tgcgcaagcg cctgttccag atcgacgcca | 3360 |
| actgccggta tggcagcccc tggtacgtgg cccgcttctg gatcatgaag ctcctcacca | 3420 |
| cgctctacat ggtggcgctt cccatgtaca tgcaggggcc tgctcagggc ttgaagcttt | 3480 |
| tcttcatggc ccacttcacc tgcggagagg tcctcgccac catgtttatt gtcaaccaca | 3540 |
| tcatcgaggg cgtcagctac gcttccaagg acgcggtcaa gggcgtcatg gctccgccgc | 3600 |
| gcactgtgca cggtgtcacc ccgatgcagg tgacgcaaaa ggcgctcagt gcggccgagt | 3660 |
| cgaccaagtc ggacgccgac aagacgacca tgatccccct caacgactgg gccgctgtgc | 3720 |
| agtgccagac ctctgtgaac tgggctgtcg ggtcgtggtt ttggaaccac ttttcgggcg | 3780 |
| gcctcaacca ccagattgag caccactgct tccccaaaac ccccacacgg tcaacgtcta | 3840 |
| catctcgggc atcgtcaagg agacctgcga agaatacggc gtgccgtacc aggctgagat | 3900 |
| cagcctcttc tctgcctatt tcaagatgct gtcgc | 3935 |

<210> SEQ ID NO 210
<211> LENGTH: 23
<212> TYPE: DNA
<213> ORGANISM: Artificial
<220> FEATURE:
<223> OTHER INFORMATION: primer

<400> SEQUENCE: 210
aaaagaacaa gccctctcct gga                                              23

<210> SEQ ID NO 211
<211> LENGTH: 23
<212> TYPE: DNA
<213> ORGANISM: Artificial
<220> FEATURE:
<223> OTHER INFORMATION: primer

<400> SEQUENCE: 211
gaggtttgta tgttcggcgg ttt                                              23

<210> SEQ ID NO 212
<211> LENGTH: 26
<212> TYPE: DNA
<213> ORGANISM: Artificial
<220> FEATURE:
<223> OTHER INFORMATION: primer

<400> SEQUENCE: 212
tgggggacct tgtgcagaac tcgtgg                                           26

<210> SEQ ID NO 213
<211> LENGTH: 22
<212> TYPE: DNA
<213> ORGANISM: Artificial
<220> FEATURE:
<223> OTHER INFORMATION: primer

<400> SEQUENCE: 213
gacctacggc gtgcagtgct tc                                               22

<210> SEQ ID NO 214
<211> LENGTH: 22
<212> TYPE: DNA
<213> ORGANISM: Artificial
<220> FEATURE:
<223> OTHER INFORMATION: primer

<400> SEQUENCE: 214
atgtgcaagg tcgatgggac aa                                    22

<210> SEQ ID NO 215
<211> LENGTH: 22
<212> TYPE: DNA
<213> ORGANISM: Artificial
<220> FEATURE:
<223> OTHER INFORMATION: primer

<400> SEQUENCE: 215
tcacaaacat cgcagccttc gg                                    22

<210> SEQ ID NO 216
<211> LENGTH: 395
<212> TYPE: PRT
<213> ORGANISM: Thraustochytrium aureum ATCC 34304
<220> FEATURE:
<221> NAME/KEY: misc_feature
<222> LOCATION: (395)..(395)
<223> OTHER INFORMATION: Xaa can be any naturally occurring amino acid

<400> SEQUENCE: 216

Met Cys Lys Val Asp Gly Thr Asn Arg Ala Ser Ser Ala Gln Ala Gln
1               5                   10                  15

Ala Glu Gln Glu Lys Leu Pro Thr Ile Gly Glu Leu Arg Lys Ala Val
            20                  25                  30

Pro Ala His Cys Phe Glu Lys Ser Thr Leu Lys Ser Leu Phe Phe Val
        35                  40                  45

Ala Arg Asp Leu Ala Phe Cys Ser Ala Ile Gly Tyr Ala Ala Trp Glu
    50                  55                  60

Tyr Ile Pro Val Glu Trp Ser Ile Lys Ala Ile Ala Leu Trp Thr Leu
65                  70                  75                  80

Tyr Ala Ile Val Gln Gly Thr Val Ala Thr Gly Val Trp Val Leu Gly
                85                  90                  95

His Glu Gly Gly His Gly Ile Ser Ser Tyr Ser Ile Val Asn Asp
            100                 105                 110

Thr Val Gly Tyr Val Leu His Ser Ile Leu Leu Val Pro Tyr Phe Ser
        115                 120                 125

Trp Gln Asp Ser His Arg Arg His Ala Arg Cys Asn His Leu Leu
    130                 135                 140

Asp Gly Glu Ser His Asn Pro Asp Leu Lys Arg Lys Val Tyr Lys Met
145                 150                 155                 160

Tyr Glu Lys Ile Leu Asp Thr Val Gly Glu Asp Ala Phe Val Ile Met
                165                 170                 175

Gln Ile Val Leu His Leu Val Leu Gly Trp Pro Met Tyr Leu Leu Met
            180                 185                 190

His Ala Thr Gly Ser Arg Arg Ser Pro Val Thr Gly Gln Lys Tyr Thr
        195                 200                 205

Lys Lys Pro Asn His Phe Asn Trp Gly Ala Ser Asn Glu Gln Tyr Pro
    210                 215                 220

Ala Lys Leu Arg Phe Lys Ile Phe Leu Ser Ser Leu Gly Val Ile Ala
225                 230                 235                 240

Thr Leu Ala Gly Ile Ala Val Leu Ala Asn Lys Leu Gly Ala Ala Lys
                245                 250                 255

Val Ser Leu Met Tyr Phe Gly Pro Tyr Leu Val Val Asn Ala Trp Leu
            260                 265                 270

```
Val Gly Tyr Thr Trp Leu Gln His Thr Asp Gln Asp Ala Pro His Tyr
            275                 280                 285

Gly Glu Asp Glu Trp Thr Trp Ile Lys Gly Ala Met Thr Thr Ile Asp
        290                 295                 300

Arg Pro Tyr Pro Trp Ile Val Asp Glu Leu His His Ile Gly Thr
305                 310                 315                 320

Thr His Val Cys His His Leu Phe Ser Asp Met Pro His Tyr Lys Ala
                325                 330                 335

Gln Glu Ala Thr Glu Ala Leu Lys Pro Val Leu Gly Lys His Tyr Arg
            340                 345                 350

Phe Asp Pro Thr Pro Leu Ala Gln Ala Met Trp Asn Thr Ala Arg Asp
            355                 360                 365

Cys His Tyr Val Glu Gly Leu Asp Gly Val Gln Tyr Pro Gln Ser Ile
        370                 375                 380

Ile Ala Glu Lys Arg Ala Ala Lys Lys Leu Xaa
385                 390                 395
```

<210> SEQ ID NO 217
<211> LENGTH: 1185
<212> TYPE: DNA
<213> ORGANISM: Artificial
<220> FEATURE:
<223> OTHER INFORMATION: genomic DNA (T. aureum ATCC34304 delta 4 desaturase DNA)

<400> SEQUENCE: 217

```
atgtgcaagg tcgatgggac aaaccgggcg agctcggctc aagcccaggc agagcaggaa     60
aagctgccca ccatcggcga gctgcgcaag gctgtgcccg cgcactgttt cgaaaagtcg    120
acgttgaaga gcctgttctt cgtggctcgt gacctggcgt tttgcagcgc catcgggtac    180
gcggcctggg agtacatccc cgtcgagtgg tcaatcaagg ccatcgccct gtggaccctg    240
tacgccatag tgcagggcac cgtggcgacc ggggtctggg ttctgggcca cgaaggcgga    300
cacggaggga tctcgagcta ctctattgtc aacgatactg tcgggtacgt gctgcactcg    360
atcctgctcg tgccgtactt ttcctggcag gacagccaca ggcgccacca cgcgcggtgc    420
aaccacctcc tggacgggga gtcgcacaac ccggacctca agcgcaaggt ttacaagatg    480
tacgaaaaga tcctcgacac ggtgggcgag gacgcctttg tgatcatgca gatcgtcctt    540
caccttgtct tagggtggcc catgtacctg ctgatgcacg cgaccgggtc tcgccgcagc    600
cccgtgactg ggcaaaagta caccaaaaag cccaatcact tcaactgggg tgcgagcaac    660
gagcagtacc cggccaagtt gcgcttcaag atttttctgt cctcgcttgg cgtgatcgcg    720
acgctcgcag ggatcgccgt gctggccaac aagctcggcg ccgccaaggt ctcgctcatg    780
tactttggcc cctacctcgt ggtgaatgcc tggctcgtgg atacacctg gctccagcac     840
accgaccagg acgccccgca ctatggcgag gacgagtgga cctggatcaa gggcgccatg    900
acgacgatcg accgccccta ccctggatt gtggacgagc tccaccacca tcggcacg       960
acgcacgttt gccaccacct gttttccgac atgccgcact acaaggccca ggaagccacc    1020
gaggcgctca gccggtgct cggcaagcac taccgcttcg acccgacccc gctggcgcag    1080
gccatgtgga acaccgctcg cgactgccac tacgtcgagg gcctcgacgg agtgcagtac    1140
ccgcagtcaa tcatcgccga gaagcgtgcg gccaaaaagc tctag                    1185
```

<210> SEQ ID NO 218
<211> LENGTH: 30
<212> TYPE: DNA

<213> ORGANISM: Artificial
<220> FEATURE:
<223> OTHER INFORMATION: primer

<400> SEQUENCE: 218
ggaagcttat gtgcaaggtc gatgggacaa    30

<210> SEQ ID NO 219
<211> LENGTH: 29
<212> TYPE: DNA
<213> ORGANISM: Artificial
<220> FEATURE:
<223> OTHER INFORMATION: primer

<400> SEQUENCE: 219
ttctagacta gagcttttg gccgcacgc    29

<210> SEQ ID NO 220
<211> LENGTH: 23
<212> TYPE: DNA
<213> ORGANISM: Artificial
<220> FEATURE:
<223> OTHER INFORMATION: primer

<400> SEQUENCE: 220
agtcagccca ggcaccgatg acg    23

<210> SEQ ID NO 221
<211> LENGTH: 39
<212> TYPE: DNA
<213> ORGANISM: Artificial
<220> FEATURE:
<223> OTHER INFORMATION: primer

<400> SEQUENCE: 221
agccagagct agatctcttg tgctcctttt caatccttt    39

<210> SEQ ID NO 222
<211> LENGTH: 39
<212> TYPE: DNA
<213> ORGANISM: Artificial
<220> FEATURE:
<223> OTHER INFORMATION: primer

<400> SEQUENCE: 222
ggagcacaag agatctagct ctggctcaag ggacaccgt    39

<210> SEQ ID NO 223
<211> LENGTH: 24
<212> TYPE: DNA
<213> ORGANISM: Artificial
<220> FEATURE:
<223> OTHER INFORMATION: primer

<400> SEQUENCE: 223
cacagaaact gccttcacgg gtct    24

<210> SEQ ID NO 224
<211> LENGTH: 24
<212> TYPE: DNA
<213> ORGANISM: Artificial
<220> FEATURE:
<223> OTHER INFORMATION: primer

<400> SEQUENCE: 224
tgttatgcgg ccattgtccg tcag    24

<210> SEQ ID NO 225
<211> LENGTH: 24
<212> TYPE: DNA
<213> ORGANISM: Artificial
<220> FEATURE:
<223> OTHER INFORMATION: primer

<400> SEQUENCE: 225
tgcgatcgct gcggccgatc ttag					24

<210> SEQ ID NO 226
<211> LENGTH: 26
<212> TYPE: DNA
<213> ORGANISM: Artificial
<220> FEATURE:
<223> OTHER INFORMATION: primer

<400> SEQUENCE: 226 atgaaaagc ctgaactcac cgcgac					26

<210> SEQ ID NO 227
<211> LENGTH: 25
<212> TYPE: DNA
<213> ORGANISM: Artificial
<220> FEATURE:
<223> OTHER INFORMATION: primer

<400> SEQUENCE: 227 ctattcctttt gccctcggac gagtg					25

<210> SEQ ID NO 228
<211> LENGTH: 27
<212> TYPE: DNA
<213> ORGANISM: Artificial
<220> FEATURE:
<223> OTHER INFORMATION: primer

<400> SEQUENCE: 228
atggccaagc ctttgtctca agaagaa					27

<210> SEQ ID NO 229
<211> LENGTH: 30
<212> TYPE: DNA
<213> ORGANISM: Artificial
<220> FEATURE:
<223> OTHER INFORMATION: primer

<400> SEQUENCE: 229
ttagccctcc cacacataac cagagggcag					30

<210> SEQ ID NO 230
<211> LENGTH: 23
<212> TYPE: DNA
<213> ORGANISM: Artificial
<220> FEATURE:
<223> OTHER INFORMATION: primer

<400> SEQUENCE: 230
ggggtcggcc ggtgcagcct tag					23

<210> SEQ ID NO 231
<211> LENGTH: 24
<212> TYPE: DNA
<213> ORGANISM: Artificial
<220> FEATURE:

<223> OTHER INFORMATION: primer

<400> SEQUENCE: 231
ggcggtcagc gatcggtcgg actc                                      24

<210> SEQ ID NO 232
<211> LENGTH: 23
<212> TYPE: DNA
<213> ORGANISM: Artificial
<220> FEATURE:
<223> OTHER INFORMATION: primer

<400> SEQUENCE: 232
gcttgcggct cctgttgggt gac                                       23

<210> SEQ ID NO 233
<211> LENGTH: 23
<212> TYPE: DNA
<213> ORGANISM: Artificial
<220> FEATURE:
<223> OTHER INFORMATION: primer

<400> SEQUENCE: 233
acgcctggct gcccaccata aac                                       23

<210> SEQ ID NO 234
<211> LENGTH: 28
<212> TYPE: DNA
<213> ORGANISM: Artificial
<220> FEATURE:
<223> OTHER INFORMATION: primer

<400> SEQUENCE: 234
ttagcgggat cccaattcgc cctatagt                                  28

<210> SEQ ID NO 235
<211> LENGTH: 27
<212> TYPE: DNA
<213> ORGANISM: Artificial
<220> FEATURE:
<223> OTHER INFORMATION: primer

<400> SEQUENCE: 235
aattgggatc ccgctaagta tctcccg                                   27

<210> SEQ ID NO 236
<211> LENGTH: 28
<212> TYPE: DNA
<213> ORGANISM: Artificial
<220> FEATURE:
<223> OTHER INFORMATION: primer

<400> SEQUENCE: 236
agatctggta ccgcagcgcc tggtgcac                                  28

<210> SEQ ID NO 237
<211> LENGTH: 27
<212> TYPE: DNA
<213> ORGANISM: Artificial
<220> FEATURE:
<223> OTHER INFORMATION: primer

<400> SEQUENCE: 237
gctgcggtac cagatctggt cgcgttt                                   27

<210> SEQ ID NO 238
<211> LENGTH: 5611
<212> TYPE: DNA
<213> ORGANISM: Artificial
<220> FEATURE:
<223> OTHER INFORMATION: fusion DNA (Thraustochytrium aureum C20
      elongase upstream/ubiquitin promoter/ 3 desaturase/ubiquitin
      terminator/ubiquitin promoter/BlaR/SV40
      terminator/T.aureum C20 elongase downstream)

<400> SEQUENCE: 238

```
tccccggggc tgcaggaatt cactagtgat tctcccgggt ggacctagcg cgtgtgtcac     60
ctgccggccc ccgttgcgtg caaccgaatt gatcgataat agaattacat aacaaacaac    120
ttgctggatg agtacaagac cagcgtagtg tggctgtggg acgttaacg gagcgggtcc    180
tgtgatggcg cagaaaggaa ctccgcccga ggtgaaaccc cgatgcgcag gactctgcgg    240
ccacagcccc tccgccagta ttccactaaa aatccgcccc ctttgacaaa gatcgcaacc    300
ccgtcccatc aactcctcac aataggcttt ccactggcgg aaacgtcccc ggcacaggag    360
tgcctcccgc ggttctgcgc atgcggctga ccactacgca gcgcgatatc ctccatccgc    420
gtatatatcc gtaaacaacg gaacattctc cctctcaacg aggcgtggtt ttcgaagtca    480
tgcctttctt ccttcctact ttccttcctt cttttctttct ttctttcctt cttttgcaag    540
cgtgcgcgaa cttgaaggta ctacttacac ttgacagaga gagatagaga cggcaattcg    600
accaagtact ttccacgatt ttttttttttt ttgttttggt cgctttcgtt ggtcgtgcat    660
gatggatggc cgggattttt acaattggat gcgccaggct gccacgcatg ccgtgacgct    720
tgctcgcggc gactcatgat gcttgccagt ggcagtgcat ccagctcttc cctctgctcg    780
tcgtgtactc actggcgatg ctctcggcgc tcgttcaagg gccatcgatc gatcgatcga    840
tcgatcgatc gatcaatcac gtttggtgga ctcggcagac cccgaacgtg tttctcccag    900
gacgcgccgc tgtcgctcgc taatccaccc gaagcgcggt cggctggcac ggtcgctcgg    960
ctggaagttg agtagtttgc tttctgttgc tgcgctgctt tgtaaacgcg accagatctg   1020
gtaccgtta gaacgcgtaa tacgactcac tatagggaga gtcgactgag cacaactctg   1080
ctgcgagcgg gcctcgagag cgtttgcttc gagccgcgga gcaaggggga tggatcgctc   1140
atgcggtcgt gcggccctcg gtcacccggt gggtcctgca ctgacgcatc tgttctgatc   1200
agacacacga acgaacaaac cgaggagccg cagcgcctgg tgcacccgcc gggcgttgtt   1260
gtgtgctctt cttgcctccg agagagagag cggagcggat gcataggaaa tcgggccacg   1320
cgggagggcc atgcgttcgc cccacacgcc actttccacg cccgctctct ctccggccgg   1380
caggcagcgc ataactctcc gacgctggca ggctggtagc aactggcagg gacaactcgc   1440
gcgcgggtcc cggtcgttcg atgtgccaac ccgagagaat ccagccagca gggcggttgg   1500
cctcatcgcc cacctgctat ggtgcagcga accaactccc gaagcggccg ttctgcgat    1560
tccctcttct gaattctgaa ttctgaactg attccggagg agaaccctct ggaagcgcgg   1620
gttgcctctc cagttctgcc gaactagaca ggggagtgag cagagagtga ccctgacgcg   1680
gagcgagctg gttgctggaa aagtcgcgaa cgctgggctg tgtcacgcgt ccacttcggg   1740
cagaccccaa acgacaagca gaacaagcaa caccagcagc agcaagcgac ctaagcaaca   1800
ctagccaaca tgactgagga taagacgaag gtcgagttcc cgacgctcac ggagctcaag   1860
cactcgatcc cgaacgcgtg ctttgagtcg aacctcggcc tctcgctcta ctacacggcc   1920
cgcgcgatct tcaacgcgtc ggcctcggcg gcgctgctct acgcggcgcg ctcgacgccg   1980
ttcattgccg ataacgttct gctccacgcg ctcgtttgcg ccacctacat ctacgtgcag   2040
```

-continued

```
ggcgtcatct tctggggctt cttcacggtc ggccacgact gcggccactc ggccttctcg    2100
cgctaccaca gcgtcaactt tatcatcggc tgcatcatgc actctgcgat tttgacgccg    2160
ttcgagagct ggcgcgtgac gcaccgccac caccaagaa acacgggcaa cattgataag    2220
gacgagatct tttacccgca ccggtcggtc aaggacctcc aggacgtgcg ccaatgggtc    2280
tacacgctcg gcggtgcgtg gtttgtctac ttgaaggtcg ggtatgcccc gcgcacgatg    2340
agccactttg acccgtggga cccgctcctc cttcgccgcg cgtcggccgt catcgtgtcg    2400
ctcggcgtct gggccgcctt cttcgccgcg tacgcgtacc tcacatactc gctcggcttt    2460
gccgtcatgg gcctctacta ctatgcgccg ctctttgtct ttgcttcgtt cctcgtcatt    2520
acgaccttct tgcaccacaa cgacgaagcg acgccgtggt acggcgactc ggagtggacg    2580
tacgtcaagg gcaacctctc gagcgtcgac cgctcgtacg gcgcgttcgt ggacaacctg    2640
agccaccaca ttggcacgca ccaggtccac cacttgttcc cgatcattcc gcactacaag    2700
ctcaacgaag ccaccaagca ctttgcggcc gcgtacccgc acctcgtgcg caagaacgac    2760
gagcccatca tctcggcctt cttcaagacc gcgcacctct tgtcaacta cggcgctgtg    2820 cccgagacgg cgcagatctt cacgctcaaa gagtcggccg cggccgccaa ggccaagtcg    2880
gactaaacta agctatctgt agtatgtgct atactcgaat catgctgccc tgtacgtacc    2940
tacctatatc tgattgagcg tgctgcgtcg accatagacg cgggaacgcg ggccagccta    3000
ccacgttgcc gccgccggta tccacgggca cgccaaagca ttggtcgata acgctctgcc    3060
cagggcttcc tggcgaggac ccgaggccaa catgcatgca tgtgctatca gcggtcatca    3120
tcgccctcat cagcgcgcat cggcgagctc gcgcacgaac ggcaagcgcc caactcaact    3180
cacttactca cactatggtc ttgccgttgg cggttgctta gctaatgcgt gacgtcactc    3240
tgcctccaac atcgcgaggc agagtcgcga gcagtgcaga ggccacggcg gacgccaaca    3300
aagcgccaac cagcgcaacg caccagcggg tctgtgggcg tagctcgagc gggcgtcttc    3360
aagagccgcc gtggagccga cgcccctgcg aagggctcga gtgcaagcgg ggccgttgag    3420
ccgcgtggta ggaacaactg cagtctccct atagtgagtc gtattacgcg gtggtaccgc    3480
agcgcctggt gcaccgccg ggcgttgttg tgtgctcttc ttgcctccga gagagagagc    3540
ggagcggatg cataggaaat cgggccacgc gggagggcca tgcgttcgcc ccacacgcca    3600 cttttccacgc ccgctctctc tccggccggc aggcagcgca taactctccg acgctggcag    3660
gctggtagca actggcaggg acaactcgcg cgcgggtccc ggtcgttcga tgtgccaacc    3720
cgagagaatc cagccagcag gcggttggc ctcatcgccc acctgctatg gtgcagcgaa    3780
ccaactcccg aagcggccgg ttctgcgatt ccctcttctg aattctgaat tctgaactga    3840
ttccggagga gaaccctctg gaagcgcggg ttgcctctcc agttctgccg aactagacag    3900
gggagtgagc agagagtgac cctgacgcgg agcgagctgg ttgctggaaa agtcgcgaac    3960
gctgggctgt gtcacgcgtc cacttcgggc agtccccaaa cgacaagcag aacaagcaac    4020
accagcagca gcaagcgacc taagcaacac tagccaacat ggccaagcct tgtctcaag    4080 aagaatccac cctcattgaa agagcaacgg ctacaatcaa cagcatcccc atctctgaag    4140
actacagcgt cgccagcgca gctctctcta gcgacggccg catcttcact ggtgtcaatg    4200
tatatcattt tactggggga ccttgtgcag aactcgtggt gctgggcact gctgctgctg    4260
cggcagctgg caacctgact tgtatcgtcg cgatcggaaa tgagaacagg ggcatcttga    4320
gcccctgcgg acggtgccga caggtgcttc tcgatctgca tcctgggatc aaagccatag    4380
```

-continued

```
tgaaggacag tgatggacag ccgacggcag ttgggattcg tgaattgctg ccctctggtt      4440
atgtgtggga gggctaagat ccgcgaaatg accgaccaag cgacgcccaa cctgccatca      4500
cgagatttcg attccaccgc cgccttctat gaaaggttgg gcttcggaat cgttttccgg      4560
gacgccggct ggatgatcct ccagcgcggg gatctcatgc tggagttctt cgcccacccc      4620
aacttgttta ttgcagctta taatggttac aaataaagca atagcatcac aaatttcaca      4680
aataaagcat ttttttcact gcattctagt tgtggtttgt ccaaactcat caatgtatct      4740
tatcatgtct gtataccgtc gacctctagc tagatctacc tgtttccggc tggctcccga      4800
gccatgctta ccatgaatgg acctgcaaac agtctgaggt ccttgtgcaa accgctcagt      4860
gggacgtcga cgaagaaaga aacaatgtgt actcgtcttg ctctgctccc gcgccgtttt      4920
ttatcgttgt tgagacctct cgcgcagttt gggaatcaa ccaaaacaag agcccggcgt       4980
cagcgtttgc ttcgccctcg gctgcactcg ctcggcacgc aggtataact gggtgagtac      5040
caagccccgc atttgtctgt ccgcgatccg cgcacgctgc gggtcaggac gacatcgcgc      5100
tgcacgtcac agtgggtccc ttttgacgtg gctgcggcga tgaggaggct tggctcggct      5160
tcatggcaag gcaacagact cgcttccggg acgcgcacga cgagcagcgc tgctttgatc      5220
gaccttgcct gcgtcaccgc ctcggctgct ttgatcgatc gttgtcaccg gccgagtgac      5280
cgcgaacgca ttcccgcac ggctcggctc ggcccggacc ggaccggctc gccttggcgg       5340
cgcggcgcga tggcgaccca gacgcggccg gagccgcgcg cggaggacaa ggccatgttc      5400
atcttcgggc tcgggtacgt tgggagcagg ctcgccaacc agctggcgga acagggtgg      5460 cgcgtcgcgg ggtcggtgag ggagctcggg cgcgaggacg actttgccga gttcgaaaag      5520
tccaagctga gcggcaaggt gcaggtgttc caactcccgc ttgagggcga ggacaacacg      5580
cccgctcgcg cgcgggagat acttagcggg a                                    5611
```

<210> SEQ ID NO 239
<211> LENGTH: 904
<212> TYPE: DNA
<213> ORGANISM: Artificial
<220> FEATURE:
<223> OTHER INFORMATION: Genomic DNA (Parietichytrium C20 elongase upstream)

<400> SEQUENCE: 239

```
gacgtcgatt cccggaagag agaggacttg taaggaactt ttgtgtaaaa agatgtaaaa       60
agatggaaag tattcaacgc gttggcgtga cgcctcactc acggttgcac gggcagagtc      120
aggcgtggtg agtggtgact ccaaaagaaa gaaagaaaga aggagggctt tcgtttcttg      180
cttgagatca agattgaaag ttttctgaa ttttgaattc ttttttttg gcggtctgac        240 tcgtgtgttt gtgccaagtt cgaaaagcat tgcagtcttg ccacgtgaac acgagaacca     300
gcattctttg atttctttgg actggaaaag acgagactca tgcgctaaag gagagaagct     360
gtctcggggg gtccaatcat gtggaaatgt gtgagtgtgt aattggcggt tccatgcctc     420
gcctagagag tcgggtagac ggctttgcca gtctgcagcg gagtcatcgg accacgtatc     480
cggaaactcg tgtgtctccg atgtctcagc ctctctctct cgacaacttt gtttctaata     540
ttttctaatt gtcgtgatcg tcgtgacagg tgagcatagg tgagcccgca tcatcatcga     600
tcggtgggtg tctctgacgg gggttgggac tccgatgaac tttgaaaaga gacgtggtag     660
tacaagtatg taataaacac cggtacatat catgaaggtt acgcttgcta ggctactgga     720
agaggaaagt ggagcttaga ctttacgaga tgaagggtgt agcgccttga gtgtggcgct     780
```

```
gacgggtctg caaatcctga aacgccggat tggttgcgtg gtcgagctga aaacgacaga    840
acggtggtcc agtgcagtag tccccgattt ggtagttgac caaaagttga gagaaacgga    900
gagg                                                                 904
```

<210> SEQ ID NO 240
<211> LENGTH: 721
<212> TYPE: DNA
<213> ORGANISM: Artificial
<220> FEATURE:
<223> OTHER INFORMATION: Genomic DNA (Parietichytrium C20 elongase
      downstream)

<400> SEQUENCE: 240

```
taccgacctt gtactcgagg agttgttgtg cgcgcggatc cgagcgcaaa agtggacgtc     60
ggtgagagac aggacaatgt ttggtagcag agcagcagtt cgcgctttgc aaagcagcgg    120
cttgcgactt gggagcacag cgcggagggc ctctcaccat gggctgtttt cgctggaagg    180
cacggcgccc agagtgcacc cggaggcgtg gattgcgcat aacgcagttg tcgtgggcga    240
tgtagaaatc ggggccaggt cgagcgtgtg gtttgggggcc tgcattcgcg gtgaccgcga    300
cttgatatcg atcggggaag agacaaacat tcaggacggg agtgtgctgc acacggatgc    360
aggcgtccct atgaagatac atgatcgcgt caccatcgga cacatggtca tgctgcacgg    420
ctgcacggtg cattctgggt ctctgatcgg cattggggcg acaatactaa acaagtaggt    480
ttctatgaag tgaggaaggg ggaaggaatt cggttgtgtg tttcctgact gtgcaccgct    540
tctctgcagg gccgtcatcg ggaagaattg cctgattggt gcgaacgctc taatcacgga    600
agggaaagtc atcccggacg gaagtctagt gatgggccgc aaccaggtgg ttcgacagct    660
caccgagaag gagatcgagg gaattcagcg cactgcggct ggctatgtgc agaaccaagg    720
g                                                                    721
```

<210> SEQ ID NO 241
<211> LENGTH: 4592
<212> TYPE: DNA
<213> ORGANISM: Artificial
<220> FEATURE:
<223> OTHER INFORMATION: fusion DNA (pGEM-T easy vector/ Parietichytrium
      C20 elongase upstream / Parietichytrium C20 elongase
      downstream / pGEM-T easy vector)

<400> SEQUENCE: 241

```
gggcgaattg ggcccgacgt cgcatgctcc cggccgccat ggcggccgcg ggaattcgat     60
tgacgtcgat tcccggaaga gagaggactt gtaaggaact tttgtgtaaa agatgtaaa    120 aagatggaaa gtattcaacg cgttggcgtg acgcctcact cacggttgca cgggcagagt    180
caggcgtggt gagtggtgac tccaaaagaa agaaagaaag aaggagggct ttcgtttctt    240
gcttgagatc aagattgaaa gttttttctga attttgaatt cttttttttt ggcggtctga    300
ctcgtgtgtt tgtgccaagt tcgaaaagca ttgcagtctt gccacgtgaa cacgagaacc    360
agcattcttt gatttctttg gactggaaaa gacgagactc atgcgctaaa ggagagaagc    420
tgtctcgggg ggtccaatca tgtggaaatg tgtgagtgtg taattggcgg ttccatgcct    480
cgcctagaga gtcgggtaga cggctttgcc agtctgcagc ggagtcatcg gaccacgtat    540
ccggaaactc gtgtgtctcc gatgtctcag cctctctctc tcgacaactt gtttctaat    600 atttttctaat tgtcgtgatc gtcgtgacag gtgagcatag gtgagcccgc atcatcatcg    660
atcggtgggt gtctctgacg ggggttggga ctccgatgaa ctttgaaaag agacgtggta    720
```

```
gtacaagtat gtaataaaca ccggtacata tcatgaaggt tacgcttgct aggctactgg    780
aagaggaaag tggagcttag actttacgag atgaagggtg tagcgccttg agtgtggcgc    840
tgacgggtct gcaaatcctg aaacgccgga ttggttgcgt ggtcgagctg aaaacgacag    900
aacggtggtc cagtgcagta gtccccgatt tggtagttga ccaaaagttg agagaaacgg    960
agaggtaccg accttgtact cgaggagttg ttgtgcgcgc ggatccgagc gcaaaagtgg   1020
acgtcggtga gagacaggac aatgtttggt agcagagcag cagttcgcgc tttgcaaagc   1080
agcggcttgc gacttgggag cacagcgcgg agggcctctc accatgggct gttttcgctg   1140
gaaggcacgg cgcccagagt gcacccggag gcgtggattg cgcataacgc agttgtcgtg   1200
ggcgatgtag aaatcggggc caggtcgagc gtgtggtttg gggcctgcat tcgcggtgac   1260
cgcgacttga tatcgatcgg ggaagagaca aacattcagg acgggagtgt gctgcacacg   1320
gatgcaggcg tccctatgaa gatacatgat cgcgtcacca tcggacacat ggtcatgctg   1380
cacggctgca cggtgcattc tgggtctctg atcggcattg gggcgacaat actaaacaag   1440
taggtttcta tgaagtgagg aagggggaag gaattcggtt gtgtgtttcc tgactgtgca   1500
ccgcttctct gcagggccgt catcgggaag aattgcctga ttggtgcgaa cgctctaatc   1560
acggaaggga aagtcatccc ggacggaagt ctagtgatgg gccgcaacca ggtggttcga   1620
cagctcaccg agaaggagat cgagggaatt cagcgcactg cggctggcta tgtgcagaac   1680
caagggccca acgcgttgga tgcatagctt gagtattcta tagtgtcacc taaatagctt   1740
ggcgtaatca tggtcatagc tgtttcctgt gtgaaattgt tatccgctca caattccaca   1800
caacatacga gccggaagca taagtgtaa agcctgggt gcctaatgag tgagctaact   1860
cacattaatt gcgttgcgct cactgcccgc tttccagtcg ggaaacctgt cgtgccagct   1920
gcattaatga atcggccaac gcgcggggag aggcggtttg cgtattgggc gctcttccgc   1980
ttcctcgctc actgactcgc tgcgctcggt cgttcggctg cggcgagcgg tatcagctca   2040
ctcaaaggcg gtaatacggt tatccacaga atcaggggat aacgcaggaa agaacatgtg   2100
agcaaaaggc cagcaaaagg ccaggaaccg taaaaaggcc gcgttgctgg cgttttttcca   2160 taggctccgc ccccctgacg agcatcacaa aaatcgacgc tcaagtcaga ggtggcgaaa   2220
cccgacagga ctataaagat accaggcgtt tcccctgga agctccctcg tgcgctctcc   2280
tgttccgacc ctgccgctta ccggatacct gtccgccttt ctcccttcgg gaagcgtggc   2340
gctttctcat agctcacgct gtaggtatct cagttcggtg taggtcgttc gctccaagct   2400
gggctgtgtg cacgaacccc ccgttcagcc cgaccgctgc gccttatccg gtaactatcg   2460
tcttgagtcc aacccggtaa gacacgactt atcgccactg gcagcagcca ctggtaacag   2520
gattagcaga gcgaggtatg taggcggtgc tacagagttc ttgaagtggt ggcctaacta   2580
cggctacact agaagaacag tatttggtat ctgcgctctg ctgaagccag ttaccttcgg   2640
aaaaagagtt ggtagctctt gatccggcaa acaaaccacc gctggtagcg gtggtttttt   2700
tgtttgcaag cagcagatta cgcgcagaaa aaaaggatct caagaagatc ctttgatctt   2760
ttctacgggg tctgacgctc agtggaacga aaactcacgt taagggattt tggtcatgag   2820
attatcaaaa aggatcttca cctagatcct tttaaattaa aaatgaagtt ttaaatcaat   2880
ctaaagtata tatgagtaaa cttggtctga cagttaccaa tgcttaatca gtgaggcacc   2940
tatctcagcg atctgtctat ttcgttcatc catagttgcc tgactccccg tcgtgtagat   3000
aactacgata cgggagggct taccatctgg ccccagtgct gcaatgatac cgcgagaccc   3060
acgctcaccg gctccagatt tatcagcaat aaaccagcca gccggaaggg ccgagcgcag   3120
```

```
aagtggtcct gcaactttat ccgcctccat ccagtctatt aattgttgcc gggaagctag    3180
agtaagtagt tcgccagtta atagtttgcg caacgttgtt gccattgcta caggcatcgt    3240
ggtgtcacgc tcgtcgtttg gtatggcttc attcagctcc ggttcccaac gatcaaggcg    3300
agttacatga tcccccatgt tgtgcaaaaa agcggttagc tccttcggtc ctccgatcgt    3360
tgtcagaagt aagttggccg cagtgttatc actcatggtt atggcagcac tgcataattc    3420
tcttactgtc atgccatccg taagatgctt ttctgtgact ggtgagtact caaccaagtc    3480
attctgagaa tagtgtatgc ggcgaccgag ttgctcttgc ccggcgtcaa tacgggataa    3540
taccgcgcca catagcagaa ctttaaaagt gctcatcatt ggaaaacgtt cttcggggcg    3600
aaaactctca aggatcttac cgctgttgag atccagttcg atgtaaccca ctcgtgcacc    3660
caactgatct tcagcatctt ttactttcac cagcgtttct gggtgagcaa aacaggaag     3720 gcaaaatgcc gcaaaaaagg gaataagggc gacacggaaa tgttgaatac tcatactctt    3780 ccttttcaa tattattgaa gcatttatca gggttattgt ctcatgagcg gatacatatt     3840
tgaatgtatt tagaaaaata aacaaatagg ggttccgcgc acatttcccc gaaaagtgcc    3900
acctgatgcg gtgtgaaata ccgcacagat gcgtaaggag aaaataccgc atcaggaaat    3960
tgtaagcgtt aatattttgt taaaattcgc gttaaatttt tgttaaatca gctcattttt    4020
taaccaatag gccgaaatcg gcaaaatccc ttataaatca aaagaataga ccgagatagg    4080
gttgagtgtt gttccagttt ggaacaagag tccactatta agaacgtgg actccaacgt     4140 caaagggcga aaaccgtct atcagggcga tggcccacta cgtgaaccat caccctaatc     4200
aagttttttg gggtcgaggt gccgtaaagc actaaatcgg aaccctaaag ggagccccg     4260 atttagagct tgacggggaa agccggcgaa cgtggcgaga aaggaaggga agaaagcgaa    4320
aggagcgggc gctagggcgc tggcaagtgt agcggtcacg ctgcgcgtaa ccaccacacc    4380
cgccgcgctt aatgcgccgc tacagggcgc gtccattcgc cattcaggct gcgcaactgt    4440
tgggaagggc gatcggtgcg ggcctcttcg ctattacgcc agctggcgaa aggggggatgt   4500 gctgcaaggc gattaagttg ggtaacgcca gggttttccc agtcacgacg ttgtaaaacg    4560
acggccagtg aattgtaata cgactcacta ta                                  4592
```

<210> SEQ ID NO 242
<211> LENGTH: 37
<212> TYPE: DNA
<213> ORGANISM: Artificial
<220> FEATURE:
<223> OTHER INFORMATION: Genomic DNA (Parietichytrium C20 elongase downstream)

<400> SEQUENCE: 242

```
accgaccttg tactcgagga gttgttgtgc gcgcgga                              37
```

<210> SEQ ID NO 243
<211> LENGTH: 4448
<212> TYPE: DNA
<213> ORGANISM: Artificial
<220> FEATURE:
<223> OTHER INFORMATION: fusion DNA fusion DNA (ubiquitin promoter/omega 3 desaturase/ubiquitin terminator/ubiquitin promoter/HygR/SV40 terminator)

<400> SEQUENCE: 243

```
tcggtacccg ttagaacgcg taatacgact cactataggg agagtcgact gagcacaact    60
ctgctgcgag cgggcctcga gagcgtttgc ttcgagccgc ggagcaaggg ggatggatcg    120
```

```
ctcatgcggt cgtgcggccc tcggtcaccc ggtgggtcct gcactgacgc atctgttctg    180
atcagacaca cgaacgaaca aaccgaggag ccgcagcgcc tggtgcaccc gccgggcgtt    240
gttgtgtgct cttcttgcct ccgagagaga gagcggagcg gatgcatagg aaatcgggcc    300
acgcgggagg gccatgcgtt cgccccacac gccactttcc acgcccgctc tctctccggc    360
cggcaggcag cgcataactc tccgacgctg gcaggctggt agcaactggc agggacaact    420
cgcgcgcggg tcccggtcgt tcgatgtgcc aacccgagag aatccagcca gcagggcggt    480
tggcctcatc gcccacctgc tatggtgcag cgaaccaact cccgaagcgg ccggttctgc    540
gattccctct tctgaattct gaattctgaa ctgattccgg aggagaaccc tctggaagcg    600
cgggttgcct ctccagttct gccgaactag acagggagt gagcagagag tgaccctgac    660
gcggagcgag ctggttgctg aaaagtcgc gaacgctggg ctgtgtcacg cgtccacttc    720
gggcagaccc caaacgacaa gcagaacaag caacaccagc agcagcaagc gacctaagca    780
acactagcca acatgactga ggataagacg aaggtcgagt tcccgacgct cacgagctc    840 aagcactcga tcccgaacgc gtgctttgag tcgaacctcg gcctctcgct ctactacacg    900
gcccgcgcga tcttcaacgc gtcggcctcg cgggcgctgc tctacgcggc gcgctcgacg    960
ccgttcattg ccgataacgt tctgctccac gcgctcgttt gcgccaccta catctacgtg   1020
cagggcgtca tcttctgggg cttcttcacg gtcggccacg actgcggcca ctcggccttc   1080
tcgcgctacc acagcgtcaa ctttatcatc ggctgcatca tgcactctgc gattttgacg   1140
ccgttcgaga gctggcgcgt gacgcaccgc caccaccaca agaacacggg caacattgat   1200
aaggacgaga tcttttaccc gcaccggtcg gtcaaggacc tccaggacgt gcgccaatgg   1260
gtctacacgc tcggcggtgc gtggtttgtc tacttgaagg tcgggtatgc cccgcgcacg   1320
atgagccact ttgacccgtg ggacccgctc ctccttcgcc gcgcgtcggc cgtcatcgtg   1380
tcgctcggcg tctgggccgc cttcttcgcc gcgtacgcgt acctcacata tcgctcggc   1440 tttgccgtca tgggcctcta ctactatgcg ccgctctttg tctttgcttc gttcctcgtc   1500
attacgacct tcttgcacca caacgacgaa gcgacgccgt ggtacggcga ctcggagtgg   1560
acgtacgtca agggcaacct ctcgagcgtc gaccgctcgt acggcgcgtt cgtggacaac   1620
ctgagccacc acattggcac gcaccaggtc caccacttgt tcccgatcat tccgcactac   1680
aagctcaacg aagccaccaa gcactttgcg gccgcgtacc cgcacctcgt gcgcaagaac   1740
gacgagccca tcatctcggc cttcttcaag accgcgcacc tctttgtcaa ctacggcgct   1800
gtgcccgaga cggcgcagat cttcacgctc aaagagtcgg ccgcggccgc caaggccaag   1860
tcggactaaa ctaagctatc tgtagtatgt gctatactcg aatcatgctg ccctgtacgt   1920
acctacctat atctgattga gcgtgctgcg tcgaccatag acgcgggaac gcgggccagc   1980
ctaccacgtt gccgccgccg gtatccacgg gcacgccaaa gcattggtcg ataacgctct   2040
gcccagggct tcctggcgag gacccgaggc caacatgcat gcatgtgcta tcagcggtca   2100
tcatcgccct catcagcgcg catcggcgag ctcgcgcacg aacggcaagc gcccaactca   2160
actcacttac tcacactatg gtcttgccgt tggcggttgc ttagctaatg cgtgacgtca   2220
ctctgcctcc aacatcgcga ggcagagtcg cgagcagtgc agaggccacg gcggacgcca   2280
acaaagcgcc aaccagcgca acgcaccagc gggtctgtgg gcgtagctcg agcgggcgtc   2340
ttcaagagcc gccgtggagc cgacgcccct gcgaagggct cgagtgcaag cggggccgtt   2400
gagccgcgtg gtaggaacaa ctgcagtctc cctatagtga gtcgtattac gcggtggtac   2460
```

-continued

```
cgaccttgta ctcgaggagt tgttgtgcgc gcggatctgg atctgccgca gcgcctggtg    2520
cacccgccgg gcgttgttgt gtgctcttct tgcctccgag agagagagcg gagcggatgc    2580
ataggaaatc gggccacgcg ggagggccat gcgttcgccc cacacgccac tttccacgcc    2640
cgctctctct ccggccggca ggcagcgcat aactctccga cgctggcagg ctggtagcaa    2700
ctggcaggga caactcgcgc gcgggtcccg gtcgttcgat gtgccaaccc gagagaatcc    2760
agccagcagg gcggttggcc tcatcgccca cctgctatgg tgcagcgaac caactcccga    2820
agcggccggt tctgcgattc cctcttctga attctgaatt ctgaactgat tccggaggag    2880
aaccctctgg aagcgcgggt tgcctctcca gttctgccga actagacagg ggagtgagca    2940
gagagtgacc ctgacgcgga gcgagctggt tgctggaaaa gtcgcgaacg ctgggctgtg    3000
tcacgcgtcc acttcgggca gaccccaaac gacaagcaga acaagcaaca ccagcagcag    3060
caagcgacct aagcaacact agccaacatg aaaaagcctg aactcaccgc gacgtctgtc    3120
gagaagtttc tgatcgaaaa gttcgacagc gtctccgacc tgatgcagct ctcggagggc    3180
gaagaatctc gtgctttcag cttcgatgta ggagggcgtg gatatgtcct gcgggtaaat    3240
agctgcgccg atggtttcta caaagatcgt tatgtttatc ggcactttgc atcggccgcg    3300
ctcccgattc cggaagtgct tgacattggg gaattcagcg agagcctgac ctattgcatc    3360
tcccgccgtg cacagggtgt cacgttgcaa gacctgcctg aaaccgaact gcccgctgtt    3420
ctgcagccgt cgcggaggc catggatgcg atcgctgcgg ccgatcttag ccagacgagc    3480
gggttcggcc cattcggacc gcaaggaatc ggtcaataca ctacatggcg tgatttcata    3540
tgcgcgattg ctgatcccca tgtgtatcac tggcaaactg tgatggacga ccgcgtcagt    3600
gcgtccgtcg cgcaggctct cgatgagctg atgctttggg ccgaggactg ccccgaagtc    3660
cggcacctcg tgcacgcgga tttcggctcc aacaatgtcc tgacggacaa tggccgcata    3720
acagcggtca ttgactggag cgaggcgatg ttcggggatt cccaatacga ggtcgccaac    3780
atcttcttct ggaggccgtg gttggcttgt atggagcagc agacgcgcta cttcgagcgg    3840
aggcatccgg agcttgcagg atcgccgcgg ctccgggcgt atatgctccg cattggtctt    3900
gaccaactct atcagagctt ggttgacggc aatttcgatg atgcagcttg gcgcagggt    3960 cgatgcgacg caatcgtccg atccggagcc gggactgtcg ggcgtacaca aatcgcccgc    4020
agaagcgcgg ccgtctggac cgatggctgt gtagaagtac tcgccgatag tggaaaccga    4080
cgccccagca ctcgtccgag ggcaaaggaa tagagatccg cgaaatgacc gaccaagcga    4140
cgcccaacct gccatcacga gatttcgatt ccaccgccgc cttctatgaa aggttgggct    4200
tcggaatcgt tttccgggac gccggctgga tgatcctcca gcgcggggat ctcatgctgg    4260
agttcttcgc ccaccccaac ttgtttattg cagcttataa tggttacaaa taaagcaata    4320
gcatcacaaa tttcacaaat aaagcatttt tttcactgca ttctagttgt ggtttgtcca    4380
aactcatcaa tgtatcttat catgtctgta taccgtcgac ctctagctag atctgagatt    4440
aattgcgt                                                             4448
```

<210> SEQ ID NO 244
<211> LENGTH: 27
<212> TYPE: DNA
<213> ORGANISM: Artificial
<220> FEATURE:
<223> OTHER INFORMATION: primer

<400> SEQUENCE: 244
cgttagaacg cgtaatacga ctcacta                                          27

<210> SEQ ID NO 245
<211> LENGTH: 32
<212> TYPE: DNA
<213> ORGANISM: Artificial
<220> FEATURE:
<223> OTHER INFORMATION: primer

<400> SEQUENCE: 245
cccggatcca tggtggccag cgaggtgctc ag                              32

<210> SEQ ID NO 246
<211> LENGTH: 34
<212> TYPE: DNA
<213> ORGANISM: Artificial
<220> FEATURE:
<223> OTHER INFORMATION: primer

<400> SEQUENCE: 246
cccggatcct tagtcgcgct tgagctcagc atcc                            34

<210> SEQ ID NO 247
<211> LENGTH: 314
<212> TYPE: PRT
<213> ORGANISM: Schizochytrium

<400> SEQUENCE: 247

Met Val Ala Ser Glu Val Leu Ser Ala Pro Lys Ala Ala Asp Ala
1               5                   10                  15

Ala Ala Lys Pro Lys Gln Ala Arg Arg Pro Val Lys Val Asp Arg Asp
            20                  25                  30

Asp Ala Phe Phe Arg Thr Phe Asn Leu Gly Ala Leu Tyr Cys Ser Ala
        35                  40                  45

Leu Tyr Tyr Ala Ile Gln Val Gly Pro Val Asp Asn Asp Gly Lys Gly
    50                  55                  60

Leu Tyr Phe Ala Lys Asn Lys Phe Tyr Gln Ile Met Leu Ser Asp Ala
65                  70                  75                  80

Val Val Phe Gly Ala Pro Val Leu Tyr Val Leu Ala Val Met Gly Leu
                85                  90                  95

Ser Arg Phe Met Val Asn Lys Lys Pro Leu Thr Ala Phe Leu Arg Ala
            100                 105                 110

Tyr Val Gln Pro Leu Tyr Asn Val Gln Ile Val Val Cys Ala Trp
        115                 120                 125

Met Val Tyr Gly Ile Met Pro Gln Val Asp Ile Leu Asn Gly Asn Pro
    130                 135                 140

Phe Gly Leu Asn Thr Lys Arg Asp Ala Arg Ile Glu Phe Val Phe
145                 150                 155                 160

Val His Tyr Leu Thr Lys Phe Leu Asp Trp Thr Asp Thr Phe Ile Met
                165                 170                 175

Ile Leu Ser Lys Ser Tyr His Gln Val Ser Phe Leu Gln Val Phe His
            180                 185                 190

His Ala Thr Ile Gly Met Val Trp Gly Phe Leu Leu Gln Arg Gly Trp
        195                 200                 205

Gly Ser Gly Thr Cys Ala Tyr Gly Ala Phe Ile Asn Ser Val Thr His
    210                 215                 220

Val Leu Met Tyr Ser His Tyr Leu Trp Thr Ser Phe Gly Phe Lys Asn
225                 230                 235                 240

Pro Leu Lys Lys Trp Leu Thr Lys Phe Gln Leu Ala Gln Phe Ala Ser

```
                  245                 250                 255
Cys Ile Val His Ala Leu Leu Val Leu Ala Phe Glu Glu Ala Tyr Pro
            260                 265                 270
Leu Glu Phe Ala Phe Met Gln Ile Ser Tyr His Ile Ile Met Leu Tyr
        275                 280                 285
Leu Phe Gly Lys Arg Met Ser Trp Ala Pro Leu Trp Cys Thr Gly Met
    290                 295                 300
Thr Asp Met Asp Ala Glu Leu Lys Arg Asp
305                 310

<210> SEQ ID NO 248
<211> LENGTH: 945
<212> TYPE: DNA
<213> ORGANISM: Schizochytrium
<220> FEATURE:
<223> OTHER INFORMATION: cDNA (genomic DNA contains C20 elongase coding
      region)

<400> SEQUENCE: 248
atggtggcca gcgaggtgct cagcgccccc aaggccgcgg ccgacgccgc ggccaagccc     60
aagcaggcgc gtcgcccggt caaggtggac cgcgacgatg cattcttccg caccttaac    120 ctgggggcac tctactgcag cgcactctac tacgccatcc aggttggccc cgtcgacaat    180
gacggcaagg gcctctactt tgccaagaac aagttctacc agatcatgct ctccgacgcg    240
gtcgtctttg gcgcccccgt cctctacgtc ctcgccgtca tgggtctctc ccgcttcatg    300
gtcaacaaga agcccctcac cgccttcctc cgcgcctacg tgcagccgct ctacaacgtc    360
gtgcagatcg tcgtgtgcgc ctggatggtc tacggcatca tgccccaggt cgatatcctc    420
aacgggaacc ccttcggcct caacaccaag cgggacgccc gcatcgagtt cttcgtgttt    480
gtccactacc tcaccaagtt tcttgactgg accgacacct tcatcatgat cctctccaag    540
agctaccacc aggtctccct cctgcaggtc ttccaccacg ccaccatcgg catggtctgg    600
ggctttcttc tgcagcgcgg ctggggatcg ggcacctgtg cttacggcgc cttcatcaac    660
tcggtcaccc acgtcctcat gtactcgcac tacctctgga cctcctttgg cttcaagaac    720
ccgctcaaga agtggctcac caagttccag ctcgcgcagt ttgcctcgtg cattgtccac    780
gccctcctgg tccttgcctt cgaggaggcc tacccgctcg agtttgcttt catgcagatc    840
agctaccaca ttatcatgct ctacctttt ggcaagcgca tgagctgggc cccgctttgg    900
tgcacgggga tgactgatat ggatgctgag ctcaagcgcg actaa                    945

<210> SEQ ID NO 249
<211> LENGTH: 24
<212> TYPE: DNA
<213> ORGANISM: Artificial
<220> FEATURE:
<223> OTHER INFORMATION: primer

<400> SEQUENCE: 249
catcgagatc ttcgtgtttg tcca                                           24

<210> SEQ ID NO 250
<211> LENGTH: 25
<212> TYPE: DNA
<213> ORGANISM: Artificial
<220> FEATURE:
<223> OTHER INFORMATION: primer

<400> SEQUENCE: 250
```
acgaagatct cgatgcgggc gtccc                                           25

<210> SEQ ID NO 251
<211> LENGTH: 945
<212> TYPE: DNA
<213> ORGANISM: Artificial
<220> FEATURE:
<223> OTHER INFORMATION: Schizochytrium derived BglII inserted C20
      elongase

<400> SEQUENCE: 251
atggtggccg cgagggtgct cagcgccccc aaggccgcgg ccgacgccgc ggccaagccc      60
aagcaggcgc gccgcccggt caaggtggac cgtgacgatg cattcttccg cacctttaac     120
ctgggggcac tctactgcag cgcactctac tacgccatcc aggttggtcc cgtcgacaat     180
gacggcaagg gcctctactt tgccaagaac aagttctacc agatcatgct ctccgacgcg     240
gtcgtctttg gcgcccccgt cctctacgtc ctcgccgtca tgggcctctc ccgcttcatg     300
gtcaacaaga agcccctcac cgccttcctc cgcgcctacg tgcagccgct ctacaacgtc     360
gtgcagatcg tcgtgtgcgc ctggatggtc tacggcatca tgccccaggt cgatatcctc     420
aacgggaacc ccttcggcct caacaccaag cgggacgccc gcatcgagat cttcgtgttt     480
gtccactacc tcaccaagtt tcttgactgg accgacacct tcatcatgat cctctccaag     540
agctaccacc aggtctcctt cctgcaggtc ttccaccacg ccaccatcgg catggtctgg     600
ggctttcttc tgcagcgcgg ctggggatcg ggcacctgtg cttacggcgc cttcatcaac     660
tcggtcaccc acgtcctcat gtactcgcac tacctctgga cctcctttgg cttcaagaac     720
ccgctcaaga agtggctcac caagttccag ctcgcgcagt ttgcctcgtg cattgtccac     780
gccctcctgg tccttgcctt cgaggaggcc tacccgctcg agtttgcttt catgcagatc     840
agctaccaca ttatcatgct ctaccttttt ggcaagcgca tgagctgggc cccgctttgg     900
tgcacgggga tgactgatat ggatgctgag ctcaagcgcg actaa                      945

<210> SEQ ID NO 252
<211> LENGTH: 20
<212> TYPE: DNA
<213> ORGANISM: Artificial
<220> FEATURE:
<223> OTHER INFORMATION: primer

<400> SEQUENCE: 252
agatggtggc cagcgaggtg                                                  20

<210> SEQ ID NO 253
<211> LENGTH: 25
<212> TYPE: DNA
<213> ORGANISM: Artificial
<220> FEATURE:
<223> OTHER INFORMATION: primer

<400> SEQUENCE: 253
ttagtcgcgc ttgagctcag catcc                                            25

<210> SEQ ID NO 254
<211> LENGTH: 2644
<212> TYPE: DNA
<213> ORGANISM: Artificial
<220> FEATURE:
<223> OTHER INFORMATION: fusion DNA (Schizochytrium C20 elongase 5'
      region/SV40 terminator/Neor/ubiquitin promoter/Schizochytrium C20
      elongase 3' region)

```
<400> SEQUENCE: 254
atggtggccg gcgaggtgct cagcgccccc aaggccgcgg ccgacgccgc ggccaagccc      60
aagcaggcgc gccgcccggt caaggtggac cgtgacgatg cattcttccg cacctttaac     120
ctggggcac tctactgcag cgcactctac tacgccatcc aggttggtcc cgtcgacaat     180
gacggcaagg gcctctactt tgccaagaac aagttctacc agatcatgct ctccgacgcg     240
gtcgtctttg gcgccccgt cctctacgtc ctcgccgtca tgggcctctc ccgcttcatg     300
gtcaacaaga agcccctcac cgccttcctc cgcgcctacg tgcagccgct ctacaacgtc     360
gtgcagatcg tcgtgtgcgc ctggatggtc tacggcatca tgccccaggt cgatatcctc     420
aacgggaacc ccttcggcct caacaccaag cgggacgccc gcatcgagat ctgccgcagc     480
gcctggtgca cccgccgggc gttgttggtg tgctcttctt gcctccgaga gagagagcgg     540
agcggatgca taggaaatcg ggccacgcgg gagggccatg cgttcgcccc acacgccact     600
ttccacgccc gctctctctc cggccggcag gcagcgcata actctccgac gctggcaggc     660
tggtagcaac tggcagggac aactcgcgcg cgggtcccgg tcgttcgatg tgccaacccg     720
agagaatcca gccagcaggg cggttggcct catcgcccac ctgctatggt gcagcgaacc     780
aactcccgaa gcggccggtt ctgcgattcc ctcttctgaa ttctgaattc tgaactgatt     840
ccggaggaga accctctgga agcgcgggtt gcctctccag ttctgccgaa ctagacaggg     900
gagtgagcag agagtgaccc tgacgcggag cgagctggtt gctggaaaag tcgcgaacgc     960
tgggctgtgt cacgcgtcca cttcgggcag accccaaacg acaagcagaa caagcaacac    1020
cagcagcagc aagcgaccta agcaacacta gccaacatga ttgaacagga cggccttcac    1080
gctggctcgc ccgctgcttg ggtggaacgg ctgttcggct acgactgggc tcagcagacg    1140
atcggctgct cggacgcggc cgtgttccgc cttagcgcgc agggccggcc ggtcctgttt    1200
gtcaagaccg accttagcgg cgccctcaac gagctccagg acgaagctgc ccgcctcagc    1260
tggcttgcca cgacggggt tccgtgcgcc gctgtgctcg acgtcgtcac cgaagccggc    1320
cgcgactggc tgctcctcgg ggaagtgccc ggccaggacc tcctcagcag ccacctcgcg    1380
cccgctgaga aggtgtccat catggccgac gccatgcgcc gctgcacac cctcgacccc    1440
gccacctgcc ccttcgacca ccaggcgaag cacaggatcg aacgcgcccg cacgcggatg    1500
gaggctggcc tcgtcgacca agacgacctc gacgaggagc accagggcct cgcgccggcg    1560
gaactgttcg ccaggcttaa ggctaggatg ccggacggcg aggacctcgt ggtcacgcac    1620
ggcgacgcct gcctccccaa catcatggtc gagaacggcc gcttctcggg ctttatcgac    1680
tgcgggcgcc tgggcgtggc ggaccgctac caagacatcg cgctcgccac gcgggacatc    1740
gccgaggagc ttggcggcga gtgggccgac cgctttctcg tgctctacgg catcgccgcc    1800
ccggacagcc agaggattgc gttctaccgc ctcctggacg agttcttttg agatccgcga    1860
aatgaccgac caagcgacgc ccaacctgcc atcacgagat ttcgattcca ccgccgcctt    1920
ctatgaaagg ttgggcttcg gaatcgtttt ccgggacgcc ggctggatga tcctccagcg    1980
cggggatctc atgctggagt tcttcgccca ccccaacttg tttattgcag cttataatgg    2040
ttacaaataa agcaatagca tcacaaattt cacaaataaa gcattttttt cactgcattc    2100
tagttgtggt ttgtccaaac tcatcaatgt atcttatcat gtctgtatac cgtcgacctc    2160
tagctagatc ttcgtgtttg tccactacct caccaagttt cttgactgga ccgacacctt    2220
catcatgatc ctctccaaga gctaccacca ggtctccttc ctgcaggtct tccaccacgc    2280
caccatcggc atggtctggg gctttcttct gcagcgcggc tggggatcgg gcacctgtgc    2340
```

```
ttacggcgcc ttcatcaact cggtcaccca cgtcctcatg tactcgcact acctctggac    2400
ctcctttggc ttcaagaacc cgctcaagaa gtggctcacc aagttccagc tcgcgcagtt    2460
tgcctcgtgc attgtccacg ccctcctggt ccttgccttc gaggaggcct acccgctcga    2520
gtttgctttc atgcagatca gctaccacat tatcatgctc tacttttttg gcaagcgcat    2580
gagctgggcc ccgctttggt gcacggggat gactgatatg gatgctgagc tcaagcgcga    2640
ctaa                                                                 2644

<210> SEQ ID NO 255
<211> LENGTH: 2881
<212> TYPE: DNA
<213> ORGANISM: Artificial
<220> FEATURE:
<223> OTHER INFORMATION: fusion DNA (Schizochytrium C20 elongase 5'
      region/ ubiquitin promoter/Hygr/SV40 terminator/Schizochytrium C20
      elongase 3' region)

<400> SEQUENCE: 255
atggtggccg gcgaggtgct cagcgccccc aaggccgcgg ccgacgccgc ggccaagccc      60
aagcaggcgc gccgcccggt caaggtggac cgtgacgatg cattcttccg cacctttaac     120
ctgggggcac tctactgcag cgcactctac tacgccatcc aggttggtcc cgtcgacaat     180
gacggcaagg gcctctactt tgccaagaac aagttctacc agatcatgct ctccgacgcg     240
gtcgtctttg gcgcccccgt cctctacgtc ctcgccgtca tgggcctctc ccgcttcatg     300
gtcaacaaga agcccctcac cgccttcctc cgcgcctacg tgcagccgct ctacaacgtc     360
gtgcagatcg tcgtgtgcgc ctggatggtc tacggcatca tgccccaggt cgatatcctc     420
aacgggaacc ccttcggcct caacaccaag cgggacgccc gcatcgagat ctagctrgag     480
gtcgacggta tacagacatg ataagataca ttgatgagtt tggacaaacc acaactagaa     540
tgcagtgaaa aaaatgcttt atttgtgaaa tttgtgatgc tattgcttta tttgtaacca     600
ttataagctg caataaacaa gttggggtgg gcgaagaact ccagcatgag atccccgcgc     660
tggaggatca tccagccggc gtcccggaaa acgattccga agcccaacct tcatagaag      720 gcggcggtgg aatcgaaatc tcgtgatggc aggttgggcg tcgcttggtc ggtcatttcg     780
cggatctcta ttccttttgc ctcggacgag tgctggggcg tcggtttcca ctatcggcga     840
gtacttctac acagccatcg gtccagacgg ccgcgcttct gcgggcgatt tgtgtacgcc     900
cgacagtccc ggctccggat cggacgattg cgtcgcatcg accctgcgcc caagctgcat     960
catcgaaatt gccgtcaacc aagctctgat agagttggtc aagaccaatg cggagcatat    1020
acgcccggag ccgcggcgat cctgcaagct ccggatgcct ccgctcgaag tagcgcgtct    1080
gctgctccat acaagccaac cacggcctcc agaagaagat gttggcgacc tcgtattggg    1140
aatccccgaa catcgcctcg ctccagtcaa tgaccgctgt tatgcggcca ttgtccgtca    1200
ggacattgtt ggagccgaaa tccgcgtgca cgaggtgccg gacttcgggg cagtcctcgg    1260
cccaaagcat cagctcatcg agagcctgcg cgacggacgc actgacggtg tcgtccatca    1320
cagtttgcca gtgatacaca tggggatcag caatcgcgca tatgaaatca cgccatgtag    1380
tgtattgacc gattccttgc ggtccgaatg ggccgaaccc gctcgtctgg ctaagatcgg    1440
ccgcagcgat cgcatccatg gcctccgcga ccggctgcag aacagcgggc agttcggttt    1500
caggcaggtc ttgcaacgtg acaccctgtg cacggcggga gatgcaatag gtcaggctct    1560
cgctgaattc cccaatgtca agcacttccg gaatcgggag cgcggccgat gcaaagtgcc    1620
```

-continued

```
gataaacata acgatctttg tagaaaccat cggcgcagct atttaccegc aggacatatc    1680 cacgccctcc tacatcgaag ctgaaagcac gagattcttc gccctccgag agctgcatca    1740
ggtcggagac gctgtcgaac ttttcgatca gaaacttctc gacagacgtc gcggtgagtt    1800
caggcttttt catgttggct agtgttgctt aggtcgcttg ctgctgctgg tgttgcttgt    1860
tctgcttgtc gtttggggtc tgcccgaagt ggacgcgtga cacagcccag cgttcgcgac    1920
ttttccagca accagctcgc tccgcgtcag ggtcactctc tgctcactcc cctgtctagt    1980
tcggcagaac tggagaggca acccgcgctt ccagagggtt ctcctccgga atcagttcag    2040
aattcagaat tcagaagagg gaatcgcaga accggccgct tcgggagttg gttcgctgca    2100
ccatagcagg tgggcgatga ggccaaccgc cctgctggct ggattctctc gggttggcac    2160
atcgaacgac cgggacccgc gcgcgagttg tccctgccag ttgctaccag cctgccagcg    2220
tcggagagtt atgcgctgcc tgccggccgg agagagagcg ggcgtggaaa gtggcgtgtg    2280
gggcgaacgc atgccctcc cgcgtggccc gatttcctat gcatccgctc cgctctctct     2340
ctcggaggca agaagagcac acaacaacgc ccggcgggtg caccaggcgc tgcggcagat    2400
ccagatcttc gtgtttgtcc actacctcac caagtttctt gactggaccg acaccttcat    2460
catgatcctc tccaagagct accaccaggt ctccttcctg caggtcttcc accacgccac    2520
catcggcatg gtctggggct ttcttctgca gcgcggctgg ggatcgggca cctgtgctta    2580
cggcgccttc atcaactcgg tcacccacgt cctcatgtac tcgcactacc tctggacctc    2640
ctttggcttc aagaacccgc tcaagaagtg gctcaccaag ttccagctcg cgcagtttgc    2700
ctcgtgcatt gtccacgccc tcctggtcct tgccttcgag gaggcctacc cgctcgagtt    2760
tgctttcatg cagatcagct accacattat catgctctac cttttttggca agcgcatgag   2820 ctgggccccg ctttggtgca cggggatgac tgatatggat gctgagctca agcgcgacta    2880
a                                                                    2881
```

MICROBIAL OIL CONTAINING FATTY ACIDS OBTAINED FROM STRAMENOPILE AND METHOD OF PRODUCING THE SAME

CROSS-REFERENCE TO RELATED APPLICATIONS

This application is a Divisional of copending application Ser. No. 14/711,075, filed on May 13, 2015, which is a Divisional of application Ser. No. 13/877,225, filed on Aug. 1, 2013, and currently issued under U.S. Pat. No. 9,062,315, which is a 371 of PCT International Application No. PCT/JP2011/072650 filed on Sep. 30, 2011, which is based upon and claims the benefit of priority of the prior Japanese Patent Application No. 2011-179194, filed on Aug. 18, 2011, and Japanese Patent Application No. 2010-224225,filed on Oct. 1, 2010. The entire contents of each of the above documents are hereby incorporated by reference into the present application.

The sequence listing submitted was submitted in copending application Ser. No. 14/711,075 in a computer readable form under the name of "130412-revised_sequence_listing.txt" is hereby incorporated by reference into the present application. The electronic copy of the sequence listing in the computer readable form, the file size of which is 242 K bytes, was created on Jan. 29, 2016.

TECHNICAL FIELD

The present invention relates to a method for transforming stramenopile whereby genes of stramenopile are disrupted and/or expression thereof is inhibited by genetic engineering. Particularly, the invention relates to a transformation method for disrupting genes associated with fatty acid biosynthesis and/or inhibiting expression thereof, a method for modifying the fatty acid composition of a stramenopile, a method for highly accumulating fatty acids in a stramenopile, a stramenopile having an enhanced unsaturated fatty acid content, a method for producing unsaturated fatty acid from the unsaturated fatty acid content-enhanced stramenopile, a microbial oil comprising the fatty acid obtained from microorganisms belonging to stramenopile, especially from the class Labyrinthulomycetes, and a method of producing the microbial oil from the microorganisms, among others.

BACKGROUND ART

Polyunsaturated fatty acids (PUFA) represent an important component of animal and human nutrition. ω3 polyunsaturated fatty acids (also called n-3 polyunsaturated fatty acids) such as eicosapentaenoic acid (EPA) and docosahexaenoic acid (DHA) have a wide range of roles in many aspects of health, including brain development in children, eye functions, syntheses of hormones and other signaling substances, and prevention of cardiovascular disease, cancer, and diabetes mellitus (Non-Patent Documents 1 and 2). These fatty acids therefore represent an important component of human nutrition. Accordingly, there is a need for polyunsaturated fatty acid production.

Meanwhile, microorganisms of the class Labyrinthulomycetes are known to produce polyunsaturated fatty acids. Concerning microorganisms of the family *Thraustochytrium*, there are reports of, for example, a polyunsaturated fatty acid-containing phospholipid producing method using *Schizochytrium* microorganisms (Patent Document 1), and *Thraustochytrium* microorganisms having a docosahexaenoic acid producing ability (Patent Document 2). For enhancement of food and/or feed by the unsaturated fatty acids, there is a strong demand for a simple economical process for producing these unsaturated fatty acids, particularly in the eukaryotic system.

With regard to the class Labyrinthulomycetes, there have been reported foreign gene introducing methods for specific strains of the genus *Schizochytrium* (the genus *Auranthiochytrium* (Non-Patent Document 4) in the current classification scheme (Non-Patent Document 3)) (Patent Documents 3 and 4). Further, a method that causes a change in fatty acid composition by means of transformation is known in which a polyketide synthase (PKS) gene is destroyed to change the resulting fatty acid composition (Non-Patent Document 5). However, there is no report directed to changing a fatty acid composition by manipulating the enzymes of the elongase/desaturase pathway. Under these circumstances, the present inventors found ways to change fatty acid compositions through introduction of elongase/desaturase genes into various species of Labyrinthulomycetes, and have filed a patent application therefor (Patent Document 5).

CITATION LIST

Patent Documents
Patent Document 1: JP-A-2007-143479
Patent Document 2: JP-A-2005-102680
Patent Document 3: JP-A-2006-304685
Patent Document 4: JP-A-2006-304686
Patent Document 5: WO2011/037207
Patent Document 6: WO1997/011094
Patent Document 7: US Patent Application US2005/0014231
Patent Document 8: JP-T-2007-532104 (the term "JP-T" as used herein means a published Japanese translation of a PCT patent application)

Non-Patent Documents

Non-Patent Document 1: Poulos A., Lipids, 30, 1-14 (1995)
Non-Patent Document 2: Horrocks L. A. and Yeo Y. K., Pharmacol Res., 40, 211-225 (1999)
Non-Patent Document 3: Yokoyama R., Honda D., Mycoscience, 48, 199-211 (2007)
Non-Patent Document 4: Lecture Summary for the 60th Conference of The Society for Biotechnology, Japan, p 136 (2008)
Non-Patent Document 5: Lippmeier J. C. et al., Lipids, 44(7), 621-630 (2009)
Non-Patent Document 6: Tonon T. et al., FEBS Lett., 553, 440-444 (2003).
Non-Patent Document 7: Thompson J. D. et al., Nucleic Acids Res., 22, 4673-4680 (1994)
Non-Patent Document 8: Yazawa K., Lipids, 31, Supple. 297-300 (1996)
Non-Patent Document 9: Jiang X. et al., Wei Sheng Wu Xue Bao., 48(2), 176-183 (2008)
Non-Patent Document 10: PEREIRA S. L. et al., Biochem. J., 378, 665-671 (2004)
Non-Patent Document 11: Prasher D. C. et al., Gene, 111(2), 229-233 (1992)
Non-Patent Document 12: Chalfie M. et al., Science, 263, 802-805 (1994)
Non-Patent Document 13: Southern P. J., and Berg, P., J. Molec. Appl. Gen., 1, 327-339 (1982)
Non-Patent Document 14: Saitou N. et al., Mol. Biol. Evol., 4, 406-425 (1987)

Non-Patent Document 15: Ausubel F. M. et al., Current Protocols in Molecular Biology, Unit 13 (1994)

Non-Patent Document 16: Guthrie C., Fink G. et al., Methods in Enzymology: Guide to Yeast Genetics and Molecular Biology, Volume 194 (1991)

Non-Patent Document 17: Abe E., et al., J. Biochem, 142, 31561-31566 (2006)

Non-Patent Document 18: Bio-Experiment Illustrated 2, Fundamentals of Gene Analysis, p 117-128, Shujunsha, 1995

Non-Patent Document 19: Japan Society for Bioscience, Biotechnology, and Agrochemistry, 77, 2, 150-153 (2003)

Non-Patent Document 20: Bio-Experiment Illustrated 2, Fundamentals of Gene Analysis, p 63-68, Shujunsha, 1995

Non-Patent Document 21: Sanger, F. et al., Proc. Natl. Acad. Sci, 74, 5463 (1977)

Non-Patent Document 22: Meyer, A., et al. J. Lipid Res., 45, 1899-1909 (2004)

Non-Patent Document 23: Cigan and Donahue, 1987; Romanos et al., 1992

Non-Patent Document 24: Qiu, X., et al. J. Biol. Chem., 276, 31561-6 (2001)

Non-Patent Document 25: DIG Application Manual [Japanese version] 8th, Roche Applied Science

SUMMARY OF THE INVENTION

Problems that the Invention is to Solve

The present invention is directed to improving the ability of a stramenopile to produce useful substances by way of transformation through disruption of stramenopile genes and/or inhibition of expression thereof by genetic engineering. By modifying the ability to produce useful substances through disruption of stramenopile genes associated with production of useful substances and/or inhibition of expression thereof by genetic engineering, the invention provides a modification method of a fatty acid composition produced by a stramenopile, a method for highly accumulating fatty acids in a stramenopile, an unsaturated fatty acid producing method, a stramenopile having an enhanced unsaturated fatty acid content, and production of unsaturated fatty acid from the unsaturated fatty acid content-enhanced stramenopile. With the modification of a fatty acid composition produced by a stramenopile, and the method for highly accumulating fatty acids in a stramenopile, the present invention enables more efficient production of polyunsaturated fatty acids.

Means for Solving the Problems

The present inventors conducted intensive studies under the foregoing circumstances of the conventional techniques, and succeeded in transforming a stramenopile by way of disrupting stramenopile genes and/or inhibiting expression thereof by genetic engineering to greatly improve the ability of the stramenopile to produce an unsaturated fatty acid. The present inventors also found a method for modifying the fatty acid composition produced by a stramenopile through disruption of stramenopile genes or inhibition of expression thereof by genetic engineering, and a method for highly accumulating unsaturated fatty acids in the transformed stramenopile. The present invention was completed after further studies and development for practical applications.

The gist of the present invention includes the following stramenopile transformation methods (1) to (12).

(1) A method for transforming stramenopile, the method including disrupting a stramenopile gene and/or inhibiting expression thereof by genetic engineering.

(2) The method according to (1), wherein the stramenopile belongs to the class Labyrinthulomycetes.

(3) The method according to (2), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium*, or *Sicyoidochytrium*.

(4) The method according to (3), wherein the microorganisms are *Thraustochytrium aureum, Parietichytrium sarkarianum, Thraustochytrium roseum, Parietichytrium* sp., or *Schizochytrium* sp.

(5) The method according to (4), wherein the microorganisms are *Thraustochytrium aureum* ATCC 34304, *Parietichytrium sarkarianum.* SEK 364 (FERM BP-11298), *Thraustochytrium roseum* ATCC 28210, *Parietichytrium* sp. SEK358 (FERM BP-11405), *Parietichytrium* sp. SEK571 (FERM BP-11406), or *Schizochytrium* sp. TY12Ab (FERM BP-11421).

(6) The method according to any one of (1) to (5), wherein the stramenopile gene is a gene associated with fatty acid biosynthesis.

(7) The method according to (6), wherein the gene associated with fatty acid biosynthesis is a gene associated with polyketide synthase, fatty acid chain elongase, and/or fatty acid desaturase.

(8) The method according to (7), wherein the fatty acid chain elongase is a C20 elongase.

(9) The method according to (7), wherein the fatty acid desaturase is a Δ12 desaturase.

(10) The method according to any one of (1) to (9), wherein the method used to disrupt the stramenopile gene by genetic engineering is electroporation or a gene-gun technique introducing a loss-of-function gene or a DNA fragment from which a coding region of the gene is deleted.

(11) The method according to any one of (1) to (10), wherein the method used to inhibit expression of the stramenopile gene by genetic engineering is an antisense technique or RNA interference.

(12) The method according to any one of (1) to (11), further including introducing a gene associated with fatty acid desaturase.

(13) The method according to (12), wherein the gene associated with fatty acid desaturase is an ω3 desaturase.

Further, the gist of the present invention includes the following methods (14) to (26) for modifying the fatty acid composition of a stramenopile.

(14) A method for modifying the fatty acid composition of a stramenopile, the method including disrupting a stramenopile gene and/or inhibiting expression thereof by genetic engineering.

(15) The method according to (14), wherein the stramenopile belongs to the class Labyrinthulomycetes.

(16) The method according to (15), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium*, or Sicyoidochytrium.

(17) The method according to (16), wherein the microorganisms are *Thraustochytrium aureum, Parietichytrium sarkarianum, Thraustochytrium roseum, Parietichytrium* sp., or *Schizochytrium* sp.

(18) The method according to (17), wherein the microorganisms are *Thraustochytrium aureum* ATCC 34304, *Parietichytrium sarkarianum* SEK 364 (FERM BP-11298), *Thraustochytrium roseum* ATCC 28210, *Parietichytrium* sp. SEK358 (FERM BP-11405), *Parietichytrium* sp. SEK571 (FERM BP-11406), or *Schizochytrium* sp. TY12Ab (FERM BP-11421).

(19) The method according to any one of (14) to (18), wherein the stramenopile gene is a gene associated with fatty acid biosynthesis.

(20) The method according to (19), wherein the gene associated with fatty acid biosynthesis is a gene associated with polyketide synthase, fatty acid chain elongase, and/or fatty acid desaturase.

(21) The method according to (20), wherein the fatty acid chain elongase is a C20 elongase.

(22) The method according to (21), wherein the fatty acid desaturase is a Δ12 desaturase.

(23) The method according to any one of (14) to (22), wherein the method used to disrupt the stramenopile gene by genetic engineering is electroporation or a gene-gun technique introducing a loss-of-function gene or a DNA fragment from which a coding region of the gene is deleted.

(24) The method according to any one of (14) to (23), wherein the method used to inhibit expression of the stramenopile gene by genetic engineering is an antisense technique or RNA interference.

(25) The method according to any one of (14) to (24), further including introducing a gene associated with fatty acid desaturase.

(26) The method according to (25), wherein the gene associated with fatty acid desaturase is an ω3 desaturase.

Further, the gist of the present invention includes the following methods (27) to (29) for highly accumulating fatty acids in a stramenopile.

(27) A method for highly accumulating a fatty acid in a stramenopile, wherein the method uses the method of any one of (14) to (26).

(28) The method according to (27), wherein the fatty acid is an unsaturated fatty acid.

(29) The method according to (28), wherein the unsaturated fatty acid is an unsaturated fatty acid of 18 to 22 carbon atoms.

Further, the gist of the present invention includes the following fatty acid (30).

(30) A fatty acid obtained from the stramenopile in which the fatty acid is highly accumulated by using the method of any one of (27) to (29).

Further, the gist of the present invention includes the following transformed stramenopiles (31) to (43).

(31) A stramenopile transformed for the modification of the fatty acid composition through disruption of its gene and/or inhibition of expression thereof by genetic engineering.

(32) The stramenopile according to (31), wherein the stramenopile belongs to the class Labyrinthulomycetes.

(33) The stramenopile according to (32), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium*, or *Sicyoidochytrium*.

(34) The stramenopile according to (33), wherein the microorganisms are *Thraustochytrium aureum, Parietichytrium sarkarianum, Thraustochytrium roseum, Parietichytrium* sp., or *Schizochytrium* sp.

(35) The stramenopile according to (34), wherein the microorganisms are *Thraustochytrium aureum* ATCC 34304, *Parietichytrium sarkarianum* SEK 364 (FERM BP-11298), *Thraustochytrium roseum* ATCC 28210, *Parietichytrium* sp. SEK358 (FERM BP-11405), *Parietichytrium* sp. SEK571 (FERM BP-11406), or *Schizochytrium* sp. TY12Ab (FERM BP-11421).

(36) The stramenopile according to any one of (31) to (35), wherein the stramenopile gene is a gene associated with fatty acid biosynthesis.

(37) The stramenopile according to (36), wherein the gene associated with fatty acid biosynthesis is a gene associated with polyketide synthase, fatty acid chain elongase, and/or fatty acid desaturase.

(38) The stramenopile according to (36), wherein the fatty acid chain elongase is a C20 elongase.

(39) The stramenopile according to (37), wherein the fatty acid desaturase is a Δ12 desaturase.

(40) The stramenopile according to any one of (31) to (39), wherein the method used to disrupt the stramenopile gene by genetic engineering is electroporation or a gene-gun technique introducing a loss-of-function gene or a DNA fragment from which a coding region of the gene is deleted.

(41) The stramenopile according to any one of (31) to (40), wherein the method used to inhibit expression of the stramenopile gene by genetic engineering is an antisense technique or RNA interference.

(42) The stramenopile according to any one of (31) to (41), further comprising introducing a gene associated with fatty acid desaturase is introduced.

(43) The stramenopile according to (42), wherein the gene associated with fatty acid desaturase is an ω3 desaturase.

Advantage of the Invention

The present invention improves the ability of a stramenopile to produce useful substances by way of transformation through disruption of stramenopile genes and/or inhibition of expression thereof by genetic engineering. By modifying the stramenopiles' ability to produce useful substances through disruption of stramenopile genes associated with production of useful substances and/or inhibition of expression thereof by genetic engineering, the invention provides a modification method of a fatty acid composition produced by a stramenopile, a method for highly accumulating fatty acids in a stramenopile, an unsaturated fatty acid producing method, a stramenopile having an enhanced unsaturated fatty acid content, and production of unsaturated fatty acid from the unsaturated fatty acid content-enhanced stramenopile. With the modification of the fatty acid composition produced by a stramenopile, and the method for highly accumulating fatty acids in a stramenopile, the present invention enables more efficient production of polyunsaturated fatty acids.

BRIEF DESCRIPTION OF THE DRAWINGS

FIG. 1 represents the result of RACE performed to amplify a *T. aureum* ATCC 34304-derived elongase gene in Example 2-2. [Brief Description of Reference Numerals] 1: 5'-RACE using a synthetic adapter-specific oligonucleotide and a denatured oligonucleotide elo-R; 2: 3'-RACE using a synthetic adapter-specific oligonucleotide and a denatured oligonucleotide elo-F; 3: 5'-RACE using only elo-R (negative control); 4: 3'-RACE using only elo-F (negative control); 5: 5'-RACE using only a synthetic adapter-specific oligonucleotide (negative control); 6: 3'-RACE using only a synthetic adapter-specific oligonucleotide (negative control).

FIG. 2 represents a molecular phylogenetic tree of *T. aureum* ATCC 34304-derived Δ6/Δ9 elongase and Δ5/Δ6 elongase (TaELO1 and TaELO2) of Example 2-3.

FIG. 3 represents the evaluation of transfectants with the introduced KONeor in Example 2-8. (A), an oligonucleotide primer set used for the evaluation of the transfectants by a PCR performed with template genomic DNA. [Brief Description of Reference Numerals] (1) Neor detection primers (SNeoF and SNeoR), (2) KO verification 1 (KO Pro F SmaI and KO Term R SmaI), (3) KO verification 2 (E2 KO ProF EcoRV and SNeoR), (4) KO verification 3 (SNeoF and E2 KO Term R EcoRV), (5) TaELO2 detection (E2 HindIII and E2 XbaI); (B), the result of agarose electrophoresis in the evaluation of the transfectants by a PCR performed with template genomic DNA. [Brief Description of Reference Numerals] 1, 5, 9, 13, 17: transfectants; 2, 6, 10, 14, 18: wild-type strains; 3, 7, 11, 15, 19: samples using KONeor as a template; 4, 8, 12, 16: no template. The numbers (1) to (5) above the lane numbers represent the oligonucleotide primer sets used.

FIG. 4 represents the result of confirming the copy numbers of TaELO2 by southern blotting in Example 2-9. [Brief Description of Reference Numerals] 1: genomic DNA (2.5 μg), BamHI treatment; 2: BglII treatment; 3: EcoRI treatment; 4: EcoRV treatment; 5: HindIII treatment; 6: KpnI treatment; 7: SmaI treatment; 8: XbaI treatment; 9: positive control (a PCR product amplified with 1-ng E2 KO ProF EcoRV and E2 KO Term R EcoRV, containing TaELO2).

FIG. 5 represents the evaluation of TKONeor-introduced transfectants by southern blotting in Example 2-10. (A), a schematic view representing the southern blotting performed for the detection of a wild-type allele or a TKONeor-introduced mutant allele; (B), the result of southern blotting. [Brief Description of Reference Numerals] 1: *T. aureum* wild-type strain (2.5-μg genomic DNA); 2, 3: TKONeor-introduced transfectants (2.5-μg genomic DNA); 4: positive control (a PCR product amplified with 50-ng E2 KO ProF EcoRV and E2 KO Term R EcoRV, containing TaELO2).

FIG. 6 represents the PCR evaluation performed in Example 2-12 by using as a template the genomic DNA of the transfectant obtained by KOub600Hygr reintroduction. (A), the oligonucleotide primer set used. [Brief Description of Reference Numerals] (1) TaELO2 ORF detection (SNeoF and SNeoR), (2) KO verification (E2 KO Pro F EcoRV and ubi-hygro R); (B), the result of agarose electrophoresis in a PCR using the oligonucleotide primer set (1) for KO verification (arrows indicate transfectants for which amplification of a specific product was confirmed, and that were assumed to be TaELO2-deficient homozygotes); (C) the result of agarose electrophoresis in a PCR performed for the transfectants identified as TaELO2-deficient homozygotes using the oligonucleotide primer set (2) for TaELO2 ORF detection. [Brief Description of Reference Numerals] 1: sample using KOub600Hygr as a template; 2: wild-type strain.

FIG. 7 represents the southern blotting evaluation of the transfectants obtained by KOub600Hygr reintroduction in Example 2-12. (A), a schematic view representing the southern blotting performed for the detection of a wild-type allele, a KONeor-introduced mutant allele, and a KOub600Hygr-introduced mutant allele; (B), the result of southern blotting. [Brief Description of Reference Numerals] 1, 9: wild-type strains; 2-8 and 10-16: TaELO2-deficient homozygotes.

FIG. 8 represents the result of the southern blotting performed for the detection of TaELO2 in Example 2-12. [Brief Description of Reference Numerals] 1: wild-type strain; 2-5: T TaELO2-deficient homozygotes.

FIG. 9 represents the result of the RT-PCR agarose gel electrophoresis performed for the detection of TaELO2 mRNA in Example 2-12. [Brief Description of Reference Numerals] 1-4: TaELO2-deficient homozygotes; 5: wild-type strain; 6-9: TaELO2-deficient homozygotes, using total RNA as a template (negative control); 10: wild-type strain, using total RNA as a template (negative control); 11: sample using wild-type strain genomic DNA as a template (positive control).

FIG. 10 represents the result of the comparison of the fatty acid compositions of the wild-type strain and a TaELO2-deficient homozygote in Example 2-13.

FIG. 11 represents a plasmid containing the SV40 terminator sequence derived from a subcloned pcDNA 3.1 Myc-His vector.

FIG. 12 is a schematic view showing the primers used for fusion PCR, and the product. The end product is the fused sequence of a *Thraustochytrium aureum* ATCC 34304-derived ubiquitin promoter and an artificial neomycin-resistant gene.

FIG. 13 represents a BglII cassette of the produced artificial neomycin-resistant gene.

FIG. 14 is a schematic view showing the primers used for fusion PCR, and the product. The end product is the fused sequence of a *Thraustochytrium aureum* ATCC 34304-derived ubiquitin promoter and a pcDNA 3.1/Hygro-derived hygromycin-resistant gene.

FIG. 15 represents a BglII cassette of the produced pcDNA 3.1/Hygro-derived hygromycin-resistant gene.

FIG. 16 represents a plasmid containing a cloned *Parietichytrium* C20 elongase sequence.

FIG. 17 represents a plasmid with a BglII site inserted into the *Parietichytrium* C20 elongase sequence of the plasmid of FIG. 16.

FIG. 18 represents produced *Parietichytrium* C20 elongase gene targeting vectors (two vectors). The vectors have a neomycin-resistant gene (pRH85) or a hygromycin-resistant gene (pRH86) as a drug-resistance marker.

FIG. 19 is a schematic view representing the positions of the PCR primers used for the identification of the C20 elongase gene disrupted strain of *Parietichytrium sarkarianum* SEK364, and the expected products.

FIG. 20 represents the C20 elongase gene disruption evaluation performed by a PCR using the *Parietichytrium sarkarianum* SEK364 genomic DNA as a template. [Description of Reference Numerals] +/+: *Parietichytrium sarkarianum* SEK364 wild-type strain; +/−: *Parietichytrium sarkarianum* SEK364-derived C20 elongase gene first allele homologous recombinant; −/−: *Parietichytrium sarkarianum* SEK364-derived C20 elongase gene disrupted strain.

FIG. 21 represents the result of the comparison of the fatty acid compositions of the *Parietichytrium sarkarianum* SEK364 wild-type strain and the C20 elongase gene disrupted strain. Blank bar and solid bar indicate the fatty acid compositions of the wild-type strain and the gene disrupted strain, respectively. All values are given as mean value±standard deviation.

FIG. 22 represents the proportions of the fatty acids of the C20 elongase gene disrupted strain relative to the *Parietichytrium sarkarianum* SEK364 wild-type strain taken as 100%.

FIG. 23 is a schematic view of the primers used for fusion PCR, and the product. The end product is the fused sequence of *Thraustochytrium aureum* ATCC 34304-derived 18S rDNA, *Thraustochytrium aureum* ATCC 34304-derived EF1α promoter, artificial neomycin-resistant gene, and *Thraustochytrium aureum* ATCC 34304-derived EF1α terminator.

FIG. 24 represents a plasmid obtained by partial cloning of the DNA fragment joined in FIG. 23. The plasmid contains a partial sequence on the 3'-end side of the EcoRI site of the *Thraustochytrium aureum* ATCC 34304-derived 18S rDNA, the *Thraustochytrium aureum*ATCC 34304-derived EF1α promoter, the artificial neomycin-resistant gene, and a partial sequence on the 5'-end side of the NcoI site of the *Thraustochytrium aureum* ATCC 34304-derived EF1α terminator.

FIG. 25 represents a produced *Thraustochytrium aureum* ATCC 34304 PKS pathway-associated gene orfA targeting vector. The vector has a neomycin-resistant gene as a drug-resistance marker.

FIG. 26 represents a plasmid containing the upstream sequence of *Thraustochytrium aureum*ATCC 34304 PKS pathway-associated gene orfA, a *Thraustochytrium aureum* ATCC 34304-derived ubiquitin promoter, and a hygromycin-resistant gene.

FIG. 27 represents a produced *Thraustochytrium aureum* ATCC 34304 PKS pathway-associated gene orfA targeting vector. The vector has a hygromycin-resistant gene as a drug-resistance marker.

FIG. 28 is a schematic view representing the positions of the southern hybridization analysis probes used for the identification of the PKS pathway-associated gene orfA disrupted strain of *Thraustochytrium aureum* ATCC 34304, and the expected gene fragment sizes.

FIG. 29 represents the evaluation of PKS pathway-associated gene orfA disruption performed by southern hybridization using the *Thraustochytrium aureum* ATCC 34304 genomic DNA. [Description of Reference Numerals] *T. au*: *Thraustochytrium aureum* ATCC 34304 wild-type strain; +/−: *Thraustochytrium aureum* ATCC 34304-derived PKS pathway-associated gene orfA first allele homologous recombinant; −/−: *Thraustochytrium aureum* ATCC 34304-derived PKS pathway-associated gene orfA disrupted strain.

FIG. 30 represents the result of the comparison of the fatty acid compositions of the *Thraustochytrium aureum* ATCC 34304 wild-type strain and the PKS pathway-associated gene orfA disrupted strain. Blank bar and solid bar indicate the fatty acid compositions of the wild-type strain and the gene disrupted strain, respectively. All values are given as mean value±standard deviation.

FIG. 31 represents the proportions of the fatty acids of the PKS pathway-associated gene orfA disrupted strain relative to the *Thraustochytrium aureum* ATCC 34304 wild-type strain taken as 100%.

FIG. 32 is a schematic view representing the primers used for fusion PCR, and the product. The end product is the fused sequence of *Thraustochytrium aureum* ATCC 34304-derived ubiquitin promoter and pTracer-CMV/Bsd/lacZ-derived blasticidin-resistant gene.

FIG. 33 represents a pTracer-CMV/Bsd/lacZ-derived blasticidin-resistant gene BglII cassette.

FIG. 34 is a schematic view representing the primers used for fusion PCR, and the product. The end product is the fused sequence of *Thraustochytrium aureum* ATCC 34304-derived ubiquitin promoter and enhanced GFP gene (clontech).

FIG. 35 is a schematic view representing the primers used for fusion PCR, and the product. The end product is the fused sequence of *Thraustochytrium aureum* ATCC 34304-derived ubiquitin promoter, enhanced GFP gene (clontech), and pcDNA3.1 Zeo(+)-derived zeocin-resistant gene.

FIG. 36 represents a produced enhanced GFP-zeocin-resistant fused gene BglII cassette.

FIG. 37 represents a plasmid containing a cloned *Thraustochytrium aureum* ATCC 34304 C20 elongase sequence and nearby sequences.

FIG. 38 represents a plasmid with the inserted BglII site after the complete deletion of the *Thraustochytrium aureum* ATCC 34304 C20 elongase sequence from the plasmid of FIG. 37.

FIG. 39 represents produced *Thraustochytrium aureum* ATCC 34304 C20 elongase gene targeting vectors (two vectors). The vectors have a blasticidin-resistant gene (pRH43) or an enhanced GFP-zeocin-resistant fused gene (pRH54) as a drug-resistance marker.

FIG. 40 is a schematic view representing the positions of the southern hybridization analysis probes used for the identification of the C20 elongase gene disrupted strain of the *Thraustochytrium aureum* ATCC 34304 PKS pathway (orfA gene) disrupted strain, and the expected gene fragment sizes.

FIG. 41 represents the evaluation of C20 elongase gene disruption performed by southern hybridization using the *Thraustochytrium aureum* ATCC 34304 genomic DNA. [Description of Reference Numerals] *T. au*: *Thraustochytrium aureum* ATCC 34304 wild-type strain; −/−: *Thraustochytrium aureum* ATCC 34304-derived PKS pathway (orfA gene) and C20 elongase gene double disrupted strain.

FIG. 42 represents the result of the comparison of the fatty acid compositions of the *Thraustochytrium aureum* ATCC 34304 wild-type strain and the PKS pathway (orfA gene) and C20 elongase gene double disrupted strain. Blank bar and solid bar indicate the fatty acid compositions of the wild-type strain and the gene disrupted strain, respectively. All values are given as mean value±standard deviation.

FIG. 43 represents the proportions of the fatty acids of the PKS pathway (orfA gene) and C20 elongase gene double disrupted strain relative to the *Thraustochytrium aureum* ATCC 34304 wild-type strain taken as 100%.

FIG. 44 is a schematic view representing the primers used for fusion PCR, and the product. The end product is the fused sequence of *Thraustochytrium aureum* ATCC 34304-derived ubiquitin promoter, *Saprolegnia diclina*-derived? ω3 desaturase gene sequence, and *Thraustochytrium aureum* ATCC 34304-derived ubiquitin terminator.

FIG. 45 represents the plasmid containing a KpnI site replacing one of the BglII sites in the blasticidin-resistant gene BglII cassette of FIG. 33.

FIG. 46 represents a produced *Saprolegnia diclina*-derived ω3 desaturase gene expression plasmid. The plasmid has a blasticidin-resistant gene as a drug-resistance marker.

FIG. 47 is a schematic view representing the positions of the PCR primers used for the confirmation of the genome insertion of the *Saprolegnia diclina*-derived ω3 desaturase gene.

FIG. 48 represents the evaluation of the transfectant strain derived from the *Thraustochytrium aureum* ATCC 34304 PKS pathway (orfA gene) disrupted strain. [Description of Reference Numerals] lanes 1 to 2: transfectants.

FIG. 49 represents the results of the comparison of the fatty acid compositions of the control *Thraustochytrium aureum* ATCC 34304 PKS pathway (orfA gene) disrupted strain and the ω3 desaturase gene introduced strain. Blank bar and solid bar indicate the fatty acid compositions of the control strain and the ω3 desaturase gene introduced strain, respectively. All values are given as mean value±standard deviation.

FIG. 50 represents the proportions of the fatty acids of the ω3 desaturase gene introduced strain relative to the *Thraustochytrium aureum* ATCC 34304 PKS pathway (orfA gene) disrupted strain taken as 100%.

FIG. 51 is a diagram representing a pRH59 cloning the sequence containing the *Thraustochytrium aureum* ATCC 34304-derived C20 elongase.

FIG. 52 is a diagram representing a pRH64 cloning the sequence containing a BglII site in the *Thraustochytrium aureum* ATCC 34304-derived C20 elongase.

FIG. 53 is a diagram representing a pRH65 containing aubiquitin promoter-, neomycin-resistant gene-, and SV40 terminator-containing sequence cloned into the *Thraustochytrium aureum* ATCC 34304-derived C20 elongase, and a pRH66 containing a ubiquitin promoter-, hygromycin-resistant gene-, and SV 40 terminator-containing sequence cloned into the *Thraustochytrium aureum* ATCC 34304-derived C20 elongase.

FIG. 54 represents the expected fragment sizes of the wild-type strain allele and knockout strains in a PCR.

FIG. 55 represents the detection results for the wild-type strain allele and knockout strains in a PCR.

FIG. 56 represents the fatty acid compositions of the wild-type strain and the C20 elongase knockout strain. Blank bar and solid bar indicate the fatty acid compositions of the wild-type strain and the strain, respectively.

FIG. 57 represents the result of the comparison of the fatty acid compositions of the wild-type strain and the knockout strain.

FIG. 58 represents a plasmid containing a sequence from 1,071 bp upstream of the Δ4 desaturase gene to 1,500 bp within the Δ4 desaturase gene of the cloned *Thraustochytrium aureum* ATCC 34304 strain.

FIG. 59 represents a plasmid containing a BglII site inserted into the deleted portion of the plasmid of FIG. 58 containing the 60 bp upstream of the Δ4 desaturase gene and the 556-bp sequence containing the start codon within the Δ4 desaturase gene (616 bp, SEQ ID NO: 205).

FIG. 60 represents produced *Thraustochytrium aureum* ATCC 34304 strain 44 desaturase gene targeting vectors (two vectors). The vectors have a blasticidin resistant gene (pTM6) or an enhanced GFP-zeocin-resistant fused gene (pTM8) as a drug-resistance marker.

FIG. 61 is a schematic view representing the positions of the PCR primers used for the identification of the 44 desaturase gene disrupted strain of the *Thraustochytrium aureum* ATCC 34304 PKS pathway (orfA gene) disrupted strain, and the expected product.

FIG. 62 represents the evaluation of Δ4 desaturase gene disruption performed by a PCR using the genomic DNA of the *Thraustochytrium aureum* ATCC 34304 strain as a template. [Description of Reference Numerals] +/+: *Thraustochytrium aureum* ATCC 34304-derived PKS pathway (orfA gene) disrupted strain; +/−: Δ4 desaturase gene first allele homologous recombinant derived from *Thraustochytrium aureum* ATCC 34304-derived PKS pathway (orfA gene) disrupted strain; −/−: *Thraustochytrium aureum* ATCC 34304-derived PKS pathway (orfA gene) and Δ4 desaturase gene double disrupted strain.

FIG. 63 represents the result of the comparison of the fatty acid compositions of the *Thraustochytrium aureum* ATCC 34304 wild-type strain, and the PKS pathway (orfA gene) and Δ4 desaturase gene double disrupted strain. Blank bar and solid bar indicate the fatty acid compositions of the wild-type strain and the gene disrupted strain, respectively.

FIG. 64 represents the proportions of the fatty acids of the PKS pathway (orfA gene) and Δ4 desaturase gene double disrupted strain relative to the *Thraustochytrium aureum* ATCC 34304 wild-type strain taken as 100%.

FIG. 65 represents the evaluation of C20 elongase gene disruption performed by a PCR using the genomic DNA of the *Parietichytrium* sp. SEK358 strain as a template. [Description of Reference Numerals] +/+: *Parietichytrium* sp. SEK358 wild-type strain; −/−: *Parietichytrium* sp. SEK358 strain-derived C20 elongase gene disrupted strain.

FIG. 66 represents the result of the comparison of the fatty acid compositions of the *Parietichytrium* sp. SEK358 wild-type strain, and the *Parietichytrium* sp. SEK358 strain-derived C20 elongase gene disrupted strain. Blank bar and solid bar indicate the fatty acid compositions of the wild-type strain and the gene disrupted strain, respectively.

FIG. 67 represents the proportions of the fatty acid compositions of the *Parietichytrium* sp. SEK358 strain-derived C20 elongase gene disrupted strain relative to the *Parietichytrium* sp. SEK358 wild-type strain taken as 100%. The diagonal line indicates that the fatty acid produced by the *Parietichytrium* sp. SEK358 wild-type strain is below the detection limit.

FIG. 68 represents the evaluation of C20 elongase gene disruption performed by a PCR using the genomic DNA of the *Parietichytrium* sp. SEK571 strain as a template. [Description of Reference Numerals] +/+: *Parietichytrium* sp. SEK571 wild-type strain; −/−: *Parietichytrium* sp. SEK571 strain-derived C20 elongase gene disrupted strain.

FIG. 69 represents the result of the comparison of the fatty acid compositions of the *Parietichytrium* sp. SEK571wild-type strain, and the *Parietichytrium* sp. SEK571 strain-derived C20 elongase gene disrupted strain. Blank bar and solid bar indicate the fatty acid compositions of the wild-type strain and the gene disrupted strain, respectively.

FIG. 70 represents the proportions of the fatty acids of the *Parietichytrium* sp. SEK571 strain-derived C20 elongase gene disrupted strain relative to the *Parietichytrium* sp. SEK571 wild-type strain taken as 100%.

FIG. 71 represents the multiple alignment of T12d with the putative amino acid sequences of the Δ12 desaturase genes derived from *Thalassiosira pseudonana, Micromonas* sp, and *Phaeodactylum tricornutum*. [Description of Reference Numerals] Underlined portion: histidine box.

FIG. 72 represents a GC analysis chart for the TΔ12d overexpressing strain of the budding yeast Sacchromyces cerevisiae, and the proportions of fatty acid compositions.

FIG. 73 is a diagram representing a TΔ12d KO targeting vector construction scheme.

FIG. 74 represents a scheme for the preparation of a homologous recombination fragment for efficiently obtaining a homologous recombinant by a split marker method.

FIG. 75 represents the result of the amplification of the hygromycin-resistant gene, blasticidin-resistant gene, and TΔ12d gene by a PCR performed by using the genomic DNAs of the wild-type strain, the TΔ12d first allele disrupted strain, and the TΔ12d disrupted strain (two alleles are disrupted). [Description of Reference Numerals] M: λHindIII digest/(φX174 HincII digest; W: wild-type; S1 to S3: 1st allele knock-out strain; D1 to D3: 2nd allele knock-out strain.

FIG. 76 represents the result of the mRNA detection of the hygromycin-resistant gene, blasticidin-resistant gene, and TΔ12d gene by a RT-PCR for the wild-type strain, the TΔ12d first allele disrupted strain, and the TΔ12d disrupted strain. [Description of Reference Numerals] M: λHindIII digest/(φX174 HincII digest; W: wild-type; S1 to S3: 1st allele knock-out strain; D1 to D3: 2nd allele knock-out strain.

FIG. 77 represents the result of the southern blotting performed for the wild-type strain, the TΔ12d first allele disrupted strain, and the TΔ12d disrupted strain.

FIG. 78 represents the result of the growth rate comparison by the measurements of OD600 and dry cell weight for the wild-type strain, the TΔ12d first allele disrupted strain, and the TΔ12d disrupted strain.

FIG. 79 represents the proportions of the fatty acid compositions of the wild-type strain, the TΔ12d first allele disrupted strain, and the TΔ12d disrupted strain. [Description of Reference Numerals] Asterisk: significant difference at p<0.01 (n=3).

FIG. 80 represents the fatty acid level per dry cell in the wild-type strain, the TΔ12d first allele disrupted strain, and the TΔ12d disrupted strain. [Description of Reference Numerals] Asterisk: significant difference at p<0.01 (n=3).

FIG. 81 represents a plasmid containing a BamHI site inserted through modification of the *Thraustochytrium aureum* C20 elongase gene targeting vector (pRH43) of FIG. 39 with a blasticidin-resistant gene.

FIG. 82 represents a plasmid containing a KpnI site inserted through modification of the plasmid of FIG. 81.

FIG. 83 represents a produced *Thraustochytrium aureum* C20 elongase gene targeting and *Saprolegnia diclina*-derived ω3 desaturase expression vector. The vector has a blasticidin-resistant gene as a drug-resistance marker.

FIG. 84 is a schematic view representing the positions of the southern hybridization analysis probes used for the identification of the C20 elongase gene disrupted and *Saprolegnia diclina*-derived ω3 desaturase expressing strain of the *Thraustochytrium aureum* PKS pathway (orfA gene) disrupted strain, and the expected gene fragment sizes.

FIG. 85 represents the evaluation of the C20 elongase gene disrupted and *Saprolegnia diclina*-derived ω3 desaturase expressing strain by southern hybridization using the *Thraustochytrium aureum* ATCC 34304 genomic DNA. [Description of Reference Numerals] PKSKO: *Thraustochytrium aureum* ATCC 34304-derived PKS pathway (orfA gene) disrupted strain; +/−: C20 elongase gene first allele homologous recombinant of the *Thraustochytrium aureum* ATCC 34304-derived PKS pathway (orfA gene) disrupted strain; −/−: *Thraustochytrium aureum*-derived PKS pathway (orfA gene) and C20 elongase gene double disrupted and *Saprolegnia diclina*-derived ω3 desaturase expressing strain.

FIG. 86 represents the result of the comparison of the fatty acid compositions of the *Thraustochytrium aureum* ATCC 34304 wild-type strain, and the PKS pathway (orfA gene) and C20 elongase gene double disrupted and *Saprolegnia diclina*-derived ω3 desaturase expressing strain. Blank bar and solid bar indicate the fatty acid compositions of the wild-type strain and the gene disrupted strain, respectively.

FIG. 87 represents the proportions of the fatty acids of the PKS pathway (orfA gene) and C20 elongase gene double disrupted and *Saprolegnia diclina*-derived ω3 desaturase expressing strain relative to the *Thraustochytrium aureum* ATCC 34304 wild-type strain taken as 100%.

FIG. 88 represents a base plasmid used for *Saprolegnia diclina*-derived ω3 desaturase expression vector production.

FIG. 89 represents a plasmid containing a *Saprolegnia diclina*-derived ω3 desaturase expression KpnI cassette inserted into the plasmid of FIG. 88.

FIG. 90 represents a *Saprolegnia diclina*-derived ω3 desaturase expression vector produced by inserting a hygromycin-resistant gene as a drug-resistance marker into the plasmid of FIG. 89.

FIG. 91 is a schematic view representing the positions of the PCR primers used for the confirmation of the genome insertion of the *Saprolegnia diclina*-derived ω3 desaturase gene.

FIG. 92 represents the evaluation of the *Parietichytrium* sp. SEK571 C20 elongase gene disrupted strain-derived transfectant strain. [Description of Reference Numerals] Lanes 1 to 2: transfectants FIG. 93 represents the result of the comparison of the fatty acid compositions of the *Parietichytrium* sp. SEK571 wild-type strain, and the C20 elongase gene disrupted and *Saprolegnia diclina*-derived ω3 desaturase expressing strain. Blank bar and solid bar indicate the fatty acid compositions of the wild-type strain and the transfectant strain, respectively.

FIG. 94 represents the proportions of the fatty acids of the C20 elongase gene disrupted and *Saprolegnia diclina*-derived ω3 desaturase expressing strain relative to the *Parietichytrium* sp. SEK571wild-type strain taken as 100%.

FIG. 95 is a diagram representing a pRH70 cloning a sequence containing a *Schizochytrium*-derived C20 elongase gene.

FIG. 96 is a diagram representing a pRH71 cloning a sequence containing a BglII site within the *Schizochytrium*-derived C20 elongase.

FIG. 97 is a diagram representing a pRH73 cloning a sequence containing a ubiquitin promoter, a neomycin-resistant gene, and an SV40 terminator within the *Schizochytrium*-derived C20 elongase, and a pKS-SKO cloning a sequence containing a ubiquitin promoter, a hygromycin-resistant gene, and an SV40 terminator within the *Schizochytrium*-derived C20 elongase.

FIG. 98 represents the expected fragment sizes of the wild-type strain allele and the knockout strains in a PCR.

FIG. 99 represents the PCR detection result for the wild-type strain allele and the knockout strain.

FIG. 100 represents the fatty acid compositions of the wild-type strain and the C20 elongase knockout strain. Blank bar and solid bar indicate the fatty acid compositions of the wild-type strain and the strain, respectively.

FIG. 101 represents the result of the comparison of the fatty acid compositions of the wild-type strain and the knockout strain.

MODE FOR CARRYING OUT THE INVENTION

The recent studies of the physiological activity and the pharmacological effects of lipids have elucidated the conversion of unsaturated fatty acids into various chemical substances, and the roles of unsaturated fatty acids in the unsaturated fatty acid metabolism. Particularly considered important in relation to disease is the nutritionally preferred proportions of saturated fatty acids, monounsaturated fatty acids, and unsaturated fatty acids, and the proportions of fish oil-derived ω3 series (also known as the n-3 series) fatty acids such as eicosapentaenoic acid and docosahexaenoic acid, and plant-derived ω6 series (also known as the n-6 series) fatty acids as represented by linoleic acid. Because animals are deficient in fatty acid desaturases (desaturases) or have low levels of fatty acid desaturases, some unsaturated fatty acids need to be ingested with food. Such fatty acids are called essential fatty acids (or vitamin F), which include linoleic acid (LA), γ-linolenic acid (GLA), and arachidonic acid (AA or ARA).

Unsaturated fatty acid production involves enzymes called fatty acid desaturases (desaturases). The fatty acid desaturases (desaturases) are classified into two types: (1) those creating a double bond (also called an unsaturated bond) at a fixed position from the carbonyl group of a fatty acid (for example, 49 desaturase creates a double bond at the 9th position as counted from the carbonyl side), and (2) those creating a double bond at a specific position from the methyl end of a fatty acid (for example, ω3 desaturase creates a double bond at the 3rd position as counted from the methyl end). It is known that the biosynthesis of unsaturated fatty acid involves the creation of a double bond by the desaturase (unsaturation), and the repeated elongation of the chain length by several different elongases. For example, 49 desaturase synthesizes oleic acid (OA) by unsaturating the stearic acid either synthesized in the body from palmitic acid or ingested directly from the outside of the body. Δ6, Δ5, and Δ4 desaturases are fatty acid desaturases (desaturases) essential for the syntheses of polyunsaturated fatty acids such as arachidonic acid (AA), eicosapentaenoic acid (EPA), and docosahexaenoic acid (DHA).

The Labyrinthulomycetes, a member of stramenopile, has two families: *Thraustochytrium* (Thraustochytriaceae) and Labyrinthulaceae. These microorganisms are known to accumulate polyunsaturated fatty acids such as arachidonic acid, EPA, DTA, DPA, and DHA.

The present invention is concerned with a stramenopile transformation method whereby stramenopile genes are disrupted and/or expression thereof is inhibited by genetic engineering. Specifically, the present invention developed and provides a transformation method for disrupting genes associated with fatty acid biosynthesis and/or inhibiting expression thereof, a method for modifying the fatty acid composition of a stramenopile with the use of the transformation method, a method for highly accumulating fatty acids in a stramenopile, a stramenopile having an enhanced unsaturated fatty acid content, and a method for producing unsaturated fatty acid from the unsaturated fatty acid content-enhanced stramenopile.

The present invention includes manipulating the enzymes of the stramenopile elongase/desaturase pathway to change the fatty acid composition produced by a stramenopile. Specifically, the present invention enables modification of the fatty acid composition produced by stramenopile through (1) disruption of a fatty acid chain elongase gene and/or inhibition of expression thereof, (2) disruption of a polyketide synthase gene and/or inhibition of expression thereof, (3) disruption of a fatty acid desaturase and/or inhibition of expression thereof, (3) disruption of two of or all of a polyketide synthase gene, a fatty acid chain elongase gene, and a fatty acid desaturase and/or inhibition of expression thereof, (4) disruption of a fatty acid chain elongase gene and/or inhibition of expression thereof, and introduction of a fatty acid desaturase gene, (5) disruption of a polyketide synthase gene and/or inhibition of expression thereof, and introduction of a fatty acid desaturase gene, (6) disruption of a fatty acid desaturase gene and/or inhibition of expression thereof, and introduction of a fatty acid desaturase gene, (6) disruption of two of or all of a polyketide synthase gene, a fatty acid chain elongase gene, and a fatty acid desaturase and/or inhibition of expression thereof, and introduction of a fatty acid desaturase gene.

The present invention is described below in more detail.

[Microorganism]

The microorganisms used in the fatty acid modification method of the present invention are not particularly limited, as long as the microorganisms are stramenopiles considered to undergo modification of the fatty acid composition through disruption of genes associated with fatty acid biosynthesis and/or inhibition of expression thereof. Particularly preferred microorganisms are those belonging to the class Labyrinthulomycetes. Examples of the Labyrinthulomycetes include those of the genus *Labyrinthula, Althornia, Aplanochytrium, Japonochytrium, Labyrinthuloides, Schizochytrium, Thraustochytrium, Ulkenia, Aurantiochytrium, Oblongichytrium, Botryochytrium, Parietichytrium,* and *Sicyoidochytrium.*

Of note, *Labyrinthuloides* and *Aplanochytrium* are regarded as being synonymous among some scholars (Leander, Celeste A. & David Porter, Mycotaxon, vol. 76, 439-444 (2000)).

The Labyrinthulomycetes used in the present invention are preferably microorganisms belonging to the genus *Thraustochytrium* and the genus *Parietichytrium,* particularly preferably *Thraustochytrium aureum, Parietichytrium sarkarianum,* and *Thraustochytrium roseum.* Specific examples include strains of *Thraustochytrium aureum* ATCC 34304, *Parietichytrium sarkarianum* SEK 364 (FERM BP-11298), *Thraustochytrium roseum* ATCC 28210, *Parietichytrium* sp. SEK358 (FERM BP-11405), and *Parietichytrium* sp. SEK571 (FERM BP-11406). *Thraustochytrium aureum* ATCC 34304 and *Thraustochytrium roseum* ATCC 28210 are deposited at the ATCC, and are commonly available. The *Parietichytrium sarkarianum* SEK364 strain was obtained from the surface water collected at the mouth of fukidougawa on Ishigakijima. The water (10 ml) was placed in a test tube, and left unattended at room temperature after adding pine pollens. After 7 days, the pine pollens were applied to a sterile agar medium (2 g glucose, 1 g peptone, 0.5 g yeast extract, 0.2 g chloramphenicol, 15 g agar, distilled water 100 mL, sea water 900 mL). Colonies appearing after 5 days were isolated and cultured. This was repeated several times to isolate the cells. This strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM BP-11298; Sep. 24, 2010). The *Parietichytrium* sp. SEK358 strain was isolated from the cells cultured as above from the sea water sample collected at the mouth of Miyaragawa on Ishigakijima. This strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM BP-11405; Aug. 11, 2011). The *Parietichytrium* sp. SEK571 strain was isolated from the cells cultured as above from the sea water sample collected at the mouth of Shiiragawa on Iriomotejima. This strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM BP-11406; Aug. 11, 2011). The *Schizochytrium* sp. TY12Ab strain was isolated from the cells cultured as above from the dead leaves collected on the coast of Tanegashima. This strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM ABP-11421; Sep. 29, 2011). Then, the RECEIPT IN THE CASE OF AN ORIGINAL DEPOSIT (FERM BP-11421) was issued by International Patent Organism Depositary on Nov. 30, 2011

[Genes Associated with Fatty Acid Biosynthesis]

In the present invention, the genes associated with fatty acid biosynthesis are not particularly limited, as long as the genes are genes of enzymes associated with the fatty acid biosynthesis in stramenopile, particularly the Labyrinthulomycetes. Examples of such genes include polyketide synthase gene, fatty acid chain elongase gene, and fatty acid desaturase gene. In the present invention, one of or both of these genes are subject to the disruption or inhibition of expression by genetic engineering. Here, the target of the gene disruption and/or inhibition of expression is, for example, the open reading frame, when, for example, the fatty acid produced by the polyketide synthase in a stramenopile is not the desired fatty acid. In the case of the fatty acid chain elongase, the target is the gene associated with an enzyme that converts the desired fatty acid into an other fatty acid. For example, when eicosapentaenoic acid (EPA) is the desired product, the gene of the fatty acid chain elongase associated with the conversion of eicosapentaenoic acid into docosapentaenoic acid (DPA), specifically C20 elongase gene may be disrupted and/or expression thereof may be inhibited. In the case of the fatty acid desaturase, the target is the gene associated with the enzyme that converts the desired fatty acid into an other fatty acid. For example, when oleic acid is the desired product, the gene of the fatty acid desaturase associated with the conversion of oleic acid into linoleic acid, specifically $\Delta 12$ desaturase gene may be disrupted and/or expression thereof may be inhibited. Further, two of or all of the polyketide synthase gene, the fatty acid chain elongase gene, and the fatty acid desaturase may be disrupted and/or expression thereof may be inhibited according to the desired fatty acid.

Further, a gene associated with fatty acid biosynthesis may be introduced into a transfectant strain produced by disrupting a gene and/or inhibiting expression thereof by genetic engineering as above. Here, the introduced gene is a gene associated with the enzyme that performs biosynthesis of the desired fatty acid. For example, when eicosapentaenoic acid is the desired product, a gene of the fatty acid desaturase that converts arachidonic acid (AA) into eicosapentaenoic acid, specifically $\omega 3$ desaturase gene may be introduced.

[Polyketide Synthase and Fatty Acid Chain Elongase]

Polyketide synthase (PKS) is an enzyme that catalyzes the multiple condensation reactions of a starter substrate (acetyl-CoA, fatty acid CoA ester, benzoyl CoA, coumaroyl CoA) with an extender substrate (such as malonyl CoA), and the enzyme is generally known to be involved in the biosyntheses of secondary metabolites in organisms such as plants and fungi. Involvement in the biosynthesis of polyunsaturated fatty acid is also reported in some species of organisms. For example, the marine bacteria *Shewanella* produce eicosapentaenoic acid (EPA) with this enzyme (Non-Patent Document 8). In some species of stramenopile, the polyketide synthase is known to be involved in the biosynthesis of polyunsaturated fatty acid, and the gene sequence has been elucidated in the Labyrinthulomycetes. For example, as described in Patent Document 7, the polyketide synthase gene of the genus *Schizochytrium* of *Labyrinthula* has three open reading frames, OrfA, OrfB, and OrfC. Further, as described in Patent Document 8, the polyketide synthase gene of the genus *Ulkenia* of *Labyrinthula* is considered to have three open reading frames.

The fatty acid chain elongase of the present invention is not particularly limited, as long as it extends the chain length of a fatty acid. Preferred examples include C18 elongase gene, and C20 elongase gene. The C18 elongase gene and the C20 elongase gene extend fatty acids of 18 and 20 carbon atoms, respectively, in two-carbon units to produce fatty acids of 20 and 22 carbon atoms. These fatty acid chain elongases are found in a wide range of organisms, including stramenopiles, and in, for example, the genus *Thraustochytrium* of Labyrinthulomycetes, as reported in Non-Patent Document 9. The C18 elongase catalyzes the conversion of γ-linolenic acid (GLA) to dihomo-γ-linolenic acid (DGLA), and the conversion of stearidonic acid (STA) into eicosatetraenoic acid (ETA). The C20 elongase catalyzes the conversion of arachidonic acid (AA) into docosatetraenoic acid (DTA), and the conversion of eicosapentaenoic acid (EPA) into n-3 docosapentaenoic acid (DPA, 22: 5n-3).

It follows from this that when the desired product is, for example, stearidonic acid (STA), a gene of the fatty acid chain elongase associated with the conversion of stearidonic acid into eicosatetraenoic acid (ETA), specifically C18 elongase gene may be disrupted and/or expression thereof may be inhibited. When the desired product is, for example, eicosapentaenoic acid (EPA), a gene of the fatty acid chain elongase associated with the conversion of the eicosapentaenoic acid into docosapentaenoic acid (DPA), specifically C20 elongase gene may be disrupted and/or expression thereof may be inhibited. Further, when the fatty acid biosynthesized with the polyketide synthase in a stramenopile is not the desired fatty acid, the polyketide synthase gene may be disrupted and/or expression thereof may be inhibited. As reported in Non-Patent Document 5, a strain of the genus *Schizochytrium* of *Labyrinthula* loses the ability to biosynthesize docosahexaenoic acid after the disruption of the polyketide synthase gene, and cannot grow in media unless supplemented with polyunsaturated fatty acid. In the present invention, however, some species of *Labyrinthula*, even with the disrupted polyketide synthase gene, are able to grow in media without adding polyunsaturated fatty acid, and the desired polyunsaturated fatty acid can thus be obtained by disrupting the gene or inhibiting gene expression in the manner described above.

[Fatty Acid Desaturase]

The fatty acid desaturase (desaturase) of the present invention is not particularly limited, as long as it functions as a fatty acid desaturase. The origin of the fatty acid desaturase gene is not particularly limited, and may be, for example, animals and plants. Examples of the preferred fatty acid desaturase genes include $\Delta 4$ desaturase gene $\Delta 5$ desaturase gene, $\Delta 6$ desaturase gene, $\Delta 12$ desaturase gene, and $\omega 3$ desaturase gene, and these may be used either alone or in combination. The $\Delta 4$ desaturase gene, $\Delta 5$ desaturase gene, $\Delta 6$ desaturase gene, and $\Delta 12$ desaturase gene form an unsaturated bond at carbon 4, 5, 6, and 12, respectively, as counted from the carbon atom of the terminal carboxyl group (delta end) of the fatty acid. A specific example of these fatty acid desaturase genes is the microalgae-derived $\Delta 4$ desaturase gene (Non-Patent Document 6). Specific examples of $\Delta 5$ desaturase include *T. aureum*-derived $\Delta 5$ desaturase, and $\Delta 5$ desaturases derived from *Thraustochytrium* sp. ATCC 26185, *Dictyostelium discoideum*, *Rattus norvegicus*, *Mus musculus*, *Homo sapiens*, *Caenorhabditis elegans*, and *Leishmania major*. Examples of $\Delta 12$ desaturase include *Pinguiochrysis pyriformis*-derived $\Delta 12$ desaturase, and fungus- and protozoa-derived $\Delta 12$ desaturases. The ω3 desaturase forms a double bond at the third position as counted from the methyl terminal of the fatty acid carbon chain. Examples include *Saprolegnia*-derived ω3 desaturase (Non-Patent Document 10). The Δ5 desaturase catalyzes, for example, the conversion of dihomo-γ-linolenic acid (DGLA) to arachidonic acid (AA), and the conversion of eicosatetraenoic acid (ETA) to eicosapentaenoic acid (EPA). Δ6 desaturase catalyzes, for example, the conversion of linoleic acid (LA) to γ-linolenic acid (GLA), and the conversion of α-linolenic acid (ALA) to stearidonic acid (STA). The ω3 desaturase catalyzes the conversion of arachidonic acid to eicosapentaenoic acid. Linoleic acid (LA) is produced from oleic acid (OA) by the action of Δ12 desaturase.

[Product Unsaturated Fatty Acid]

The unsaturated fatty acid produced by the fatty acid desaturase expressed in a stramenopile is, for example, an unsaturated fatty acid of 18 to 22 carbon atoms. Preferred examples include docosahexaenoic acid (DHA) and eicosapentaenoic acid (EPA), though the preferred unsaturated fatty acids vary depending on the types of the fatty acid desaturase and the fatty acid substrate used. Other examples include α-linolenic acid (ALA), octadecatetraenoic acid (OTA, 18:4n-3), eicosatetraenoic acid (ETA, 20:4n-3), n-3 docosapentaenoic acid (DPA, 22:5n-3), tetracosapentaenoic acid (TPA, 24:5n-3), tetracosahexaenoic acid (THA, 24:6n-3), linoleic acid (LA), γ-linolenic acid (GLA), eicosatrienoic acid (20:3n-6), arachidonic acid (AA), and n-6 docosapentaenoic acid (DPA, 22:5n-6).

[Gene Source of Enzyme Associated with Fatty Acid Biosynthesis]

The organisms that can be used as the gene sources of the polyketide synthase, fatty acid chain elongase, and/or fatty acid desaturase in the present invention are not limited to particular genuses, species, or strains, and may be any organisms having an ability to produce polyunsaturated fatty acids. For example, in the case of microorganisms, such organisms are readily available from microorganism depositary authorities. Examples of such microorganisms include the bacteria *Moritella marina* MP-1 strain (ATCC15381) of the genus *Moritella*. The following describes a method using this strain as an example of desaturase and elongase gene sources. The method, however, is also applicable to the isolation of the constituent desaturase and elongase genes from all biological species having the desaturase/elongase pathway.

Isolation of the desaturase and/or elongase gene from the MP-1 strain requires estimation of a conserved region in the amino acid sequence of the target enzyme gene. For example, in desaturase, it is known that a single cytochrome b5 domain and three histidine boxes are conserved across biological species, and that elongase has two conserved histidine boxes across biological species. More specifically, the conserved region of the target enzyme can be estimated by the multiple alignment comparison of the known amino acid sequences of the desaturase or elongase genes derived from various biological species using the clustal w program (Non-Patent Document 7). It is also possible to estimate conserved regions specific to desaturase and/or elongase having the same substrate specificity by the multiple alignment comparison of the amino acid sequences of desaturase or elongase genes having the same substrate specificity in the desaturase and/or elongase derived from known other organisms. Various degenerate oligonucleotide primers are then produced based on the estimated conserved regions, and the partial sequence of the target gene derived from the MP-1 strain is amplified using an MP-1 strain-derived cDNA library as a template, by using methods such as PCR and RACE. The resulting amplification product is cloned into a plasmid vector, and the base sequence is determined using an ordinary method. The sequence is then compared with a known enzyme gene to confirm isolation of a part of the target enzyme gene from the MP-1 strain. The full-length target enzyme gene can be obtained by hybridization screening using the obtained partial sequence as a probe, or by the RACE technique using the oligonucleotide primers produced from the partial sequence of the target gene.

The polyketide synthase can be cloned by using an ordinary method, using the PUFA PKS sequence of Patent Document 7 as a reference.

[Other Gene Sources]

Reference should be made to Non-Patent Document 11 or 12 for GFP (Green Fluorescent Protein), Patent Document 6 for EGFP (enhanced GFP), and Non-Patent Document 13 for neomycin-resistant gene.

[Disruption of Gene Associated with Fatty Acid Biosynthesis in Stramenopile]

The stramenopile gene associated with fatty acid biosynthesis may be disrupted by using conventional gene disruption methods used for microorganisms. An example of such a method is the transformation introducing a recombinant expression vector into a cell.

For example, for the disruption of a *Thraustochytrium aureum* gene, genomic DNA is extracted from a *Thraustochytrium aureum* by using an ordinary method, and a genome library is created. Then, genome walking primers are set using the DNA sequence of the target gene to be disrupted, and a PCR is run using the produced genome library as a template to obtain the upstream and downstream sequences of the target gene of *Thraustochytrium aureum*. These sequences are flanked on both sides to provide homologous recombination regions for gene disruption, and a drug marker gene is inserted therebetween for selection. The DNA is then linearized, and introduced into a *Thraustochytrium aureum* using a gene-gun technique, and the cells are cultured for about 1 week on a drug-containing plate. By using an ordinary method, genomic DNA is extracted from cells that have acquired drug resistance, and strains that underwent homologous recombination are identified by PCR or southern hybridization. Because the *Thraustochytrium aureum* is a diploid, the procedures from the introduction of the linearized DNA into the cells using a gene-gun technique to the identification of homologous recombinant strains are repeated twice. In this way, a *Thraustochytrium aureum* with the disrupted target gene can be obtained. When two or more target genes are present, a strain with the disrupted multiple target genes can be obtained by repeating the foregoing procedures. Here, because the *Thraustochytrium aureum* is a diploid, two selection markers need to be prepared for each gene.

For the disruption of, for example, the C20 elongase of *Parietichytrium sarkarianum*, genomic DNA is extracted from a *Parietichytrium* species by using an ordinary method, and the genome is decoded. Then, a search is made for a gene sequence highly homologous to a known C20 elongase gene, and the gene sequence is amplified by PCR from the start codon to the stop codon. This is followed by insertion of a restriction enzyme site at substantially the center of the gene sequence by using a mutagenesis method, and insertion of a drug marker gene cassette to the restriction enzyme site for selection. The DNA is linearized, and introduced into a *Parietichytrium sarkarianum* SEK364 using a gene-gun technique. The cells are then cultured for about 1 week on a drug-containing plate. By using an ordinary method, genomic DNA is extracted from cells that have acquired drug resistance, and strains that underwent homologous recombination are identified by PCR. Because the *Parietichytrium sarkarianum* SEK364 is a diploid, the procedures from the introduction of the linearized DNA into the cells using a gene-gun technique to the identification of the homologous recombinant strains are repeated twice. In this way, a *Parietichytrium sarkarianum* SEK364 with the disrupted C20 elongase gene can be obtained. Here, because the *Parietichytrium sarkarianum* SEK364 is a diploid, two selection markers need to be prepared. For the disruption of, for example, the Δ4 desaturase of a *Thraustochytrium aureum* ATCC 34304-derived OrfA disrupted strain, genomic DNA is extracted from a *Thraustochytrium aureum* ATCC 34304 by using an ordinary method, and the genome is decoded. Then, a search is made for a gene sequence highly homologous to a known 44 desaturase, and the gene sequence is amplified by PCR from the upstream region to a region in the vicinity of the stop codon. By using a mutagenesis method, a restriction enzyme site is inserted at the same time as deleting a part of the ORF containing the start codon, and a drug marker gene cassette is inserted to the restriction enzyme site for selection. The DNA is linearized, and introduced into a *Thraustochytrium aureum* ATCC 34304-derived OrfA disrupted strain by using a gene-gun technique. The cells are then cultured for about 1 week on a drug-containing plate. By using an ordinary method, genomic DNA is extracted from cells that have acquired drug resistance, and strains that underwent homologous recombination are identified by PCR. Because the *Thraustochytrium aureum* ATCC 34304 is a diploid, the procedures from the introduction of the linearized DNA using a gene-gun technique to the identification of homologous recombinant strains are repeated twice. In this way, a *Thraustochytrium aureum* ATCC 34304-derived OrfA disrupted strain with the disrupted Δ4 desaturase gene can be obtained. Here, because the *Thraustochytrium aureum* ATCC 34304 is a diploid, two selection markers need to be prepared.

The C20 elongase gene sequence of *Thraustochytrium aureum* was used for disrupting the C20 elongase of *Thraustochytrium roseum*. Genomic DNA is extracted from a *Thraustochytrium aureum* by using an ordinary method, and the C20 elongase gene is amplified from the start codon to the stop codon by PCR. A restriction enzyme site is inserted to substantially the center of the gene sequence by using a mutagenesis method, and a drug marker gene cassette is inserted to the restriction enzyme site for selection. The DNA is linearized, and introduced into a *Thraustochytrium roseum* by using a gene-gun technique. The cells are then cultured for about 1 week on a drug-containing plate. By using an ordinary method, genomic DNA is extracted from cells that have acquired drug resistance, and strains that underwent homologous recombination are identified by PCR. Because the *Thraustochytrium roseum* is a diploid, the procedures from the introduction of the linearized DNA using a gene-gun technique to the identification of the homologous recombinant strain are repeated twice. In this way, a *Thraustochytrium roseum* with the disrupted C20 elongase gene can be obtained. Here, because the *Thraustochytrium roseum* is a diploid, two selection markers need to be prepared.

Details of the disruption of stramenopile genes associated with fatty acid biosynthesis according to the present invention will be specifically described later in Examples. The stramenopile subject to transformation is not particularly limited, and those belonging to the class Labyrinthulomycetes can preferably be used, as described above.

For example, for the disruption of the C20 elongase of the *Parietichytrium* sp. SEK358 strain, the *Parietichytrium* C20 elongase gene targeting vector produced in Example 3-6 was used. The DNA is linearized, and introduced into a *Parietichytrium* sp. SEK358 strain by using a gene-gun technique. The cells are then cultured for about 1 week on a drug-containing plate. By using an ordinary method, genomic DNA is extracted from cells that have acquired drug resistance, and strains that underwent homologous recombination were identified by PCR (see Example 9). For the disruption of, for example, the C20 elongase of the *Parietichytrium* sp. SEK571 strain, the *Parietichytrium* C20 elongase gene targeting vector produced in Example 3-6 was used. The DNA is linearized, and introduced into a *Parietichytrium* sp. SEK571 strain by using a gene-gun technique. The cells are then cultured for about 1 week on a drug-containing plate. By using an ordinary method, genomic DNA was extracted from cells that had acquired drug resistance, and the homologous recombinant strain was identified by PCR (see Example 10).

The expression vector is not particularly limited, and a recombinant expression vector with an inserted gene may be used. The vehicle used to produce the recombinant expression vector is not particularly limited, and, for example, a plasmid, a phage, and a cosmid may be used. A known method may be used for the production of the recombinant expression vector. The vector is not limited to specific types, and may be appropriately selected from vectors expressible in a host cell. Specifically, the expression vector may be one that is produced by incorporating the gene of the present invention into a plasmid or other vehicles with a promoter sequence appropriately selected according to the type of the host cell for reliable expression of the gene. The vector may be a cyclic or a linear vector. The expression vector preferably includes at least one selection marker. Examples of such selection markers include auxotrophic markers, drug-resistance markers, fluorescent protein markers, and fused markers of these. Examples of the auxotrophic markers include dihydrofolate reductase genes. Examples of the drug-resistance markers include neomycin-resistant genes, hygromycin-resistant genes, blasticidin-resistant genes, and zeocin-resistant genes. Examples of the fluorescent protein markers include GFPs, and enhanced GFPs (EGFPs). Examples of the fused markers include fused markers of fluorescent protein markers and drug-resistance markers, specifically, for example, GFP-fused zeocin-resistant genes. These selection markers allow for confirmation of whether the polynucleotide according to the present invention has been introduced into a host cell, or whether the polynucleotide is reliably expressed in the host cell. Alternatively, the fatty acid desaturase according to the present invention may be expressed as a fused polypeptide. For example, the fatty acid desaturase according to the present invention may be expressed as a GFP-fused polypeptide, using GFP as a marker.

Preferably, electroporation or a gene gun is used as the method of gene introduction for the gene disruption. In the present invention, the disruption of the gene associated with fatty acid biosynthesis changes the fatty acid composition of the cell from that before the gene disruption. Specifically, the fatty acid composition is modified by the disruption of the gene associated with fatty acid biosynthesis. A stramenopile with the disrupted fatty acid biosynthesis-related enzyme gene can produce the desired fatty acid in greater amounts when further introduced with a fatty acid desaturase gene. Preferably, an ω3 desaturase gene is introduced as the fatty acid desaturase gene.

The stramenopile transformation produces a stramenopile (microorganism) in which the composition of the fatty acid it produces is modified. The stramenopile with the disrupted gene associated with fatty acid biosynthesis can be used for, for example, the production of unsaturated fatty acids. Unsaturated fatty acid production is possible with the stramenopile that has been modified to change its produced fatty acid composition as above, and other conditions, including steps, equipment, and instruments are not particularly limited. The unsaturated fatty acid production includes the step of culturing a microorganism that has been modified to change its produced fatty acid composition by the foregoing modification method, and the microorganism is used with its medium to produce unsaturated fatty acids.

The cell culture conditions (including medium, culture temperature, and aeration conditions) may be appropriately set according to such factors as the type of the cell, and the type and amount of the unsaturated fatty acid to be produced. As used herein, the term "unsaturated fatty acids" encompasses substances containing unsaturated fatty acids, and attributes such as the content, purity, shape, and composition are not particularly limited. Specifically, in the present invention, the cell or its medium itself having a modified fatty acid composition may be regarded as unsaturated fatty acids. Further, a step of purifying the unsaturated fatty acids from such cells or media also may be included. A known method of purifying unsaturated fatty acids and other lipids (including conjugate lipids) may be used for the purification of the unsaturated fatty acids.

[Method of Highly Accumulating Unsaturated Fatty Acid in Stramenopile]

Accumulation of unsaturated fatty acids in stramenopile is realized by culturing the transformed stramenopile of the present invention. For example, the culture is performed using a common solid or liquid medium. The type of medium used is not particularly limited, as long as it is one commonly used for culturing Labyrinthulomycetes, and that contains, for example, a carbon source (such as glucose, fructose, saccharose, starch, and glycerine), a nitrogen source (such as a yeast extract, a corn steep liquor, polypeptone, sodium glutamate, urea, ammonium acetate, ammonium sulfate, ammonium nitrate, ammonium chloride, and sodium nitrate), and an inorganic salt (such as potassium phosphate) appropriately combined with other necessary components. Particularly preferably, a yeast extract/glucose medium (GY medium) is used. The prepared medium is adjusted to a pH of 3.0 to 8.0, and used after being sterilized with an autoclave or the like. The culture may be performed by aerated stirred culture, shake culture, or static culture at 10 to 40° C., preferably 15 to 35° C., for 1 to 14 days.

For the collection of the produced unsaturated fatty acids, the stramenopile is grown in a medium, and the intracellular lipids (oil and fat contents with the polyunsaturated fatty acids, or the polyunsaturated fatty acids) are released by processing the microorganism cells obtained from the medium. The lipids are then collected from the medium containing the released intracellular lipids. Specifically, the cultured stramenopile is collected by using a method such as centrifugation. The cells are then disrupted, and the intracellular fatty acids are extracted using a suitable organic solvent according to an ordinary method. Oil and fat with the enhanced polyunsaturated fatty acid content can be obtained in this manner.

In the present invention, the composition of the fatty acids produced by a stramenopile is modified by culturing a stramenopile transformed through disruption of genes associated with fatty acid biosynthesis, and/or inhibition of expression thereof, specifically disruption of the polyketide synthase, the fatty acid chain elongase, and/or the fatty acid desaturase gene, and/or inhibition of expression of these genes. Because the genes associated with fatty acid biosynthesis are disrupted and/or expression thereof is inhibited, the desired fatty acid can be accumulated in the stramenopile without being converted into other fatty acids. Further, by introducing the gene associated with fatty acid desaturase into a stramenopile transformed through gene disruption and/or inhibition of gene expression, the ability to convert the precursor fatty acid of the desired fatty acid into the desired fatty acid can be enhanced, and the desired fatty acid is accumulated.

The unsaturated fatty acids of the present invention encompass various drugs, foods, and industrial products, and the applicable areas of the unsaturated fatty acids are not particularly limited. Examples of the food containing oil and fat that contain the unsaturated fatty acids of the present invention include foods with health claims such as supplements, and food additives. Examples of the industrial products include feeds for non-human organisms, films, biodegradable plastics, functional fibers, lubricants, and detergents.

The present invention is described below in more detail based on examples. Note, however, that the present invention is in no way limited by the following examples.

EXAMPLE 1

[Labyrinthulomycetes, Culture Method, and Preservation Method]

(1) Strains Used in the Present Invention

*Thraustochytrium aureum* ATCC 34304 and *Thraustochytrium roseum* ATCC 28210 were obtained from ATCC. *Parietichytrium sarkarianum* SEK364 (FERM BP-11298), *Parietichytrium* sp. SEK358 (FERM BP-11405), and *Parietichytrium* sp. SEK571 (FERM BP-11406) were obtained from Konan University, Faculty of Science and Engineering. *Schizochytrium* sp. TY12Ab (FERM BP-11421) was obtained from University of Miyazaki, Faculty of Agriculture.

(2) Medium Composition i. Agar Plate Medium Composition

PDA Agar Plate Medium

A 0.78% (w/v) potato dextrose agar medium (Nissui Pharmaceutical Co., Ltd.), 1.75% (w/v) Sea Life (Marine Tech), and 1.21% (w/v) agar powder (nacalai tesque) were mixed, and sterilized with an autoclave at 121° C. for 20 min. After sufficient cooling, ampicillin sodium (nacalai tesque) was added in a final concentration of 100 µg/ml to prevent bacterial contamination. The medium was dispensed onto a petri dish, and allowed to stand on a flat surface to solidify.

ii. Liquid Medium Composition

GY Liquid Medium 3.18% (w/v) glucose (nacalai tesque), 1.06% (w/v) dry yeast extract (nacalai tesque), and 1.75% (w/v) Sea Life (Marine Tech) were mixed, and sterilized with an autoclave at 121° C. for 20 min. Then, 100 µg/ml ampicillin sodium (nacalai tesque) was added.

PD Liquid Medium 0.48% (w/v) potato dextrose (Difco), and 1.75% (w/v) Sea Life (Marine Tech) were mixed, and sterilized with an autoclave at 121° C. for 20 min. Then, 100 µg/ml ampicillin sodium (nacalai tesque) was added.

(3) Culture Method i. Agar Plate Culture

*Labyrinthula* cells were inoculated using a platinum loop or a spreader, and static culture was performed at 25° C. to produce colonies. Subcultures were produced by collecting the colonies with a platinum loop, suspending the collected colonies in a sterilized physiological saline, and applying the suspension using a platinum loop or a spreader. As required, the cells on the plate were inoculated in a liquid medium for conversion into a liquid culture.

ii. Liquid Culture

*Labyrinthula* cells were inoculated, and suspension culture was performed by stirring at 25° C., 150 rpm in an Erlenmeyer flask or in a test tube. Subcultures were produced by adding a culture fluid to a new GY or PD liquid medium in a ½00 to ⅒ volume after confirming proliferation from the logarithmic growth phase to the stationary phase. As required, the cell culture fluid was applied onto a PDA agar plate medium for conversion into an agar plate culture.

(4) Maintenance and Preservation Method of Labyrinthulomycetes

In addition to the subculture, cryopreservation was performed by producing a glycerol stock. Specifically, glycerol (nacalai tesque) was added in a final concentration of 15% (v/v) to the logarithmic growth phase to stationary phase of a cell suspension in a GY liquid medium, and the cells were conserved in a −80° C. deep freezer.

EXAMPLE 2

[Disruption of *Thraustochytrium aureum* C20 Elongase Gene]

Example 2-1

Extraction of *T. aureum* ATCC 34304-Derived Total RNA, and mRNA Purification

A *T. aureum*. ATCC 34304 culture fluid grown for 3 days using a GY liquid medium was centrifuged at 3,500×g for 15 min, and the cells were collected. After being suspended in sterilized physiological saline, the cells were washed by being recentrifuged. The cells were then rapidly frozen with liquid nitrogen, and ground into a powdery form with a mortar. Total RNA was extracted from the resulting cell disruption liquid, using Sepasol-RNA I Super (nacalai tesque). This was followed by purification of mRNA from the total RNA using the Oligotex™-dT30<Super>mRNA Purification Kit (Takara Bio) according to the manufacturer's protocol. The resulting total RNA and the mRNA were dissolved in a suitable amount of TE, and electrophoresed with a formalin-denatured gel (1% agarose/MOPS buffer). The result confirmed successful extraction of the total RNA, and purification of mRNA from the total RNA. It was also confirmed that the RNA was not degraded by the RNase. In order to minimize RNA degradation, all experimental procedures were performed with sanitary equipment such as rubber gloves and a mask. All instruments were RNase free, or were used after a diethylpyrocarbonate (nacalai tesque) treatment to deactivate the RNase. The solution used to dissolve the RNA was prepared by adding the recombinant RNase inhibitor RNaseOUT™ (invitrogen) to sterilized Milli Q water treated with diethylpyrocarbonate.

Example 2-2

Isolation of *T. aureum* ATCC 34304-Derived Elongase Gene by RACE

Forward (elo-F;5'-TTY YTN CAY GTN TAY CAY CAY-3') (SEQ ID NO: 1), and reverse (elo-R;5'-GCR TGR TGR TAN ACR TGN ARR AA-3') (SEQ ID NO: 2) denatured oligonucleotides were synthesized, targeting the histidine box (His box) highly conserved in elongase genes. The oligonucleotides were synthesized with a DNA synthesizer (Applied Biosystems). Then, by addition of synthetic adapters to the 3'- and 5'-ends, 3'- and 5'-RACE cDNA libraries were produced by using the SMART™ RACE cDNA Amplification Kit (clontech) according to the manufacturer's protocol, respectively. By using these as templates, 3'- and 5'-RACE were performed using the synthetic adapter-specific oligonucleotides, and the denatured oligonucleotides elo-F and elo-R [PCR cycles: 94° C. 1 min/94° C. 30 sec, 60° C. 30 sec, 72° C. 3 min, 30 cycles/72° C. 10 min/4° C. 00]. The result confirmed bands for the specifically amplified 3'- and 5'-RACE products (FIG. 1). The total RACE product amounts were subjected to electrophoresis with 1% agarose gel, and the isolated DNA fragments were cut out with a clean cutter or the like and extracted from the agarose gel according to the method described in Non-Patent Document 20. The DNA fragments were then TA cloned with a pGEM-T easy Vector (Promega), and the base sequences were determined by the method of Sanger et al. (Non-Patent Document 21). Specifically, the base sequences were determined by using a dye terminator method, using a BigDyeR Terminator v3.1 Cyele Sequencing Kit and a 3130 genetic analyzer (Applied Biosystems) according to the manufacturers' protocols.

As a result, two sequences, 190 bp and 210 bp, named elo1 (SEQ ID NO: 3) and elo2 (SEQ ID NO: 4) were successfully identified for the 3'-RACE product, and one sequence, 200 bp, named elo3 (SEQ ID NO: 5) was successfully identified for the 5'-RACE product. Because the elo1, elo2, and elo3 sequences had significant homology to the sequences of various elongase genes, the results suggested that these sequences were partial sequences of the *T. aureum* ATCC 34304-derived elongase gene. In an attempt to obtain cDNA sequences by RACE, oligonucleotide primers were redesigned for the elo1, elo2, and elo3. The oligonucleotide primers produced are as follows.

```
elo1 forward oligonucleotide primer
                                   (SEQ ID NO: 6)
(elo1-F1; 5'-TAT GAT CGC CAA GTA CGC CCC-3')
and reverse oligonucleotide primer
                                   (SEQ ID NO: 7)
(elo1-R1; 5'-GAA CTG CGT CAT CTG CAG CGA-3')

elo2 forward oligonucleotide primer
                                   (SEQ ID NO: 8)
(elo2-F1; 5'-TCT CGC CCT CGA CCA CCA AC-3')
and reverse oligonucleotide primer
                                   (SEQ ID NO: 9)
(elo2-R1; 5'-CGG TGA CCG AGT TGA GGT AGC C-3')

elo3 forward oligonucleotide primer
                                  (SEQ ID NO: 10)
(elo3-F1; 5'-CAA CCC TTT CGG CCT CAA CAA G-3')
and reverse oligonucleotide primer
                                  (SEQ ID NO: 11)
(elo3-R1; 5'-TTC TTG AGG ATC ATC ATG AAC GTG
TC-3')
```

By using these forward and reverse oligonucleotide primers, RACE and base sequence analysis of the amplification products were performed as above. As a result, specifically amplified 3'- and 5'-RACE products were obtained for elo1, and there was a complete match in the overlapping portion, identifying the sequence as a 1,139-bp elo1 cDNA sequence (SEQ ID NO: 12). Similarly, specifically amplified 3'- and 5'-RACE products were obtained for elo3, and there was a complete match in the overlapping portion, identifying the sequence as a 1,261-bp elo3 cDNA sequence (SEQ ID NO: 13).

It was found from the sequence analysis result that elo1 consisted of an 825-bp translated region (SEQ ID NO: 15) coding for 275 amino acid residues (SEQ ID NO: 14). It was also found from the result of a BLAST search that the sequence had significant homology to various elongase genes, and completely coincided with the sequence of a known *T. aureum*-derived putative 45 elongase gene (NCBI accession No. C5486301). On the other hand, it was assumed that the elo3 consisted of a 951-bp translated region (SEQ ID NO: 17) coding for 317 amino acid residues (SEQ ID NO: 16). It was also found from the result of a BLAST search that the sequence had significant homology to various elongase genes, and thus represented a *T. aureum* ATCC 34304-derived putative elongase gene. Note that the putative amino acid sequences of these genes contained His boxes highly conserved in elongase genes. From these results, elo1 and elo3 genes were identified as *T. aureum* ATCC 34304-derived putative elongase genes, and were named TaELO1 and TaELO2, respectively, Example 2-3

TaELO1 and TaELO2 Phylogenetic Analysis

Elongases are broadly classified into three groups on the basis of substrate specificity.
1. SFA/MUFA elongases (act on saturated fatty acids or monovalent unsaturated fatty acids)
2. PUFA-elongases (single-step) (act on polyvalent unsaturated fatty acids of certain chain lengths)
3. PUFA elongases (multi-step) (act on polyvalent unsaturated fatty acids of various chain lengths)

According to the elongase phylogenetic analysis conducted by Meyer et al. (Non-Patent Document 22), there is a good correlation between the substrate specificity and the phylogenetic relationships.

Accordingly, a phylogenetic analysis was performed for TaELO1, TaELO2, and various other elongase genes derived from other organisms, using the method of Meyer et al. Specifically, a molecular phylogenetic tree was created according to the neighbor-joining method (Non-Patent Document 14), using the CLUSTAL W program (Non-Patent Document 7). It was found as a result that the TaELO1 and TaELO2 were classified into the PUFA-elongases (single-step) group, suggesting that these elongases act on polyvalent unsaturated fatty acids of certain chain lengths (FIG. 2).

Example 2-4

TaELO1 and TaELO2 Expression in Budding Yeast *Saccharomyces cerevisiae* Host, and Fatty Acid Composition Analysis of Gene Introduced Strain Expression vectors were constructed for TaELO1 and TaELO2 for their expression in budding yeast *S. cerevisiae* used as a host, as briefly described below. A set of oligonucleotide primer (E1 HindIII; 5'-ATA AGC TTA AAA TGT CTA GCA ACA TGA GCG CGT GGG GC-3') (SEQ ID NO: 18) and E1 XbaI; 5'-TGT CTA GAA CGC GCG GAC GGT CGC GAA A-3') (SEQ ID NO: 19) was produced using the sequence of the TaELO1 translated region. The E1 HindIII is a forward oligonucleotide primer, and has a restriction enzyme HindIII site (AAGCTT) at the 5'-end. The sequence in the vicinity of the TaELO1 start codon is modified by referring to a yeast consensus sequence ((A/Y) A (A/U) AAUGUCU; the start codon is underlined) (Non-Patent Document 23). The E1 XbaI is a reverse oligonucleotide primer, and has an XbaI site (TCTAGA) at the 5'-end.

In the same manner, a set of oligonucleotide primer (E2 HindIII; 5'-TAA AGC TTA AAA TGT CTA CGC GCA CCT CGA AGA GCG CTC C-3') (SEQ ID NO: 20) and E2 XbaI; 5'-CAT CTA GAC TCG GAC TTG GTG GGG GCG CTT G-3') (SEQ ID NO: 21) was produced using the sequence of the TaELO2 translated region. The E2 HindIII is a forward oligonucleotide primer, and has a restriction enzyme HindIII site at the 5'-end. The sequence in the vicinity of the TaELO2 start codon is modified by referring to a yeast consensus sequence. The E2 XbaI is a reverse oligonucleotide primer, and has an XbaI site at the 5'-end.

By using the two oligonucleotide primer sets, a PCR was performed using the 5'-RACE cDNA library of Example 2-2 as a template. The PCR amplified a 949-bp TaELO1 translated region (SEQ ID NO: 22) and a 967-bp TaELO2 translated region (SEQ ID NO: 23) having the restriction enzyme HindII and the restriction enzyme XbaI site at the 5'-end and the 3'-end, and modified to the yeast consensus sequence in the vicinity of the start codon. Note that a PrimeSTARR DNA polymerase (Takara Bio) of high proofreading activity was used as the PCR enzyme to avoid extension errors [PCR cycles: 98° C. 2 min/98° C. 5 sec, 60° C. 5 sec, 72° C. 1.5 min, 30 cycles/72° C. 7 min/4° C. ∞].

After isolating the amplified PCR products with a 1% agarose gel, the DNA fragments were cut and extracted from the agarose gel. After treatment with restriction enzymes HindIII and XbaI, the product was purified again with an agarose gel. To construct a cyclic vector, the product was joined to a budding yeast expression vector pYES2/CT (invitrogen) with a DNA Ligation Kit <Mighty Mix>(Takara Bio) after linearizing the pYES2/CT vector with restriction enzymes HindIII and XbaI. This was followed by a base sequence analysis, which confirmed that no PCR extension error occurred and no mutation was introduced to the TaELO1 and TaELO2 translated region sequences introduced into the pYES2/CT. In this manner, a TaELO1 expression vector pYEELO1, and a TaELO2 expression vector pYEELO2 were successfully constructed.

The two expression vectors constructed above, and the pYES2/CT were introduced into the budding yeast *S. cerevisiae* by using the lithium acetate technique according to the methods described in Non-Patent Documents 15 and 16, and the transfectants were screened for. The resulting transfectants (pYEELO1 introduced strain, pYEELO2 introduced strain, and mock introduced strain) were cultured according to the method of Qiu et al. (Non-Patent Document 24), and the cell-derived fatty acids were extracted and methylesterificated. Note that each culture was performed in a medium supplemented with α-linolenic acid (ALA, C18:3Δ9, 12, 15) and linoleic acid (LA, C18:2Δ9, 12) added as 49 elongase substrates, stearidonic acid (STA, C18:4Δ6, 9, 12, 15) and γ-linolenic acid (GLA, C18:3Δ6, 9, 12) added as Δ6 elongase substrates, and eicosapentaenoic acid (EPA, C20:5Δ5, 8, 11, 14, 17) and arachidonic acid (AA, C20:4Δ5, 8, 11, 14) added as Δ5 elongase substrates. Here, each supplement was added in a final concentration of 0.2 mM. This was followed by the gas chromatography (GC) analysis of the methylesterificated fatty acids according to the method of Abe et al. (Non-Patent Document 17). The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C. →(5° C./min)→220° C. (10 min)

Carrier gas: He (1.3 mL/min).

It was found as a result that, the pYEELO1 introduced strain had the Δ6 elongase activity not found in the host (mock introduced strain), converting the stearidonic acid (STA) into eicosatetraenoic acid (ETA, C20:4Δ8, 11, 14, 17), and the γ-linolenic acid (GLA) into dihomo-γ-linolenic acid (DGLA, C20:3Δ8, 11, 14). The pYEELO1 introduced strain also had the Δ9 elongase activity of converting the α-linolenic acid (ALA) into eicosatrienoic acid (ETrA, C20:3Δ11, 14, 17), and the linoleic acid (LA) into eicosadienoic acid (EDA, C20:3Δ11, 14), and the 45 elongase activity of converting the eicosapentaenoic acid (EPA) into ω3 docosapentaenoic acid (ω3 DPA, C22:5Δ7, 10, 13, 16, 19), and the arachidonic acid (AA) into docosatetraenoic acid (DTA, C22:4Δ7, 10, 13, 16) (Table 1).

As for the pYEELO2 introduced strain, it was found that this strain had the 45 elongase activity not found in the host, converting EPA to ω3 DPA (C22:5Δ7, 10, 13, 16, 19), and AA to DTA. The pYEELO2 introduced strain also had a weak Δ6 elongase activity, converting STA to ETA, and GLA to DGLA (Table 1). These results confirmed that the TaELO1 was a Δ6/Δ9/Δ5 elongase, and the TaELO2 was a Δ5/Δ6elongase, contrary to the results expected from the TaELO1 and TaELO2 substrate specificity in the phylogenetic analysis described in Example 2-3 and FIG. 2.

TABLE 1

|  | mock | TaELO1 | TaELO2 |
|---|---|---|---|
| LA addition (0.2 mM) | | | |
| LA | 30.5 | 23.5 | 36.3 |
| EDA | 0.2 | 8.9 | 0.2 |
| Conversion efficiency (%) |  | 27.4 |  |
| GLA addition (0.2 mM) | | | |
| GLA | 44.0 | 7.6 | 43.6 |
| DGLA | 0.2 | 29.0 | 0.8 |
| Conversion efficiency (%) |  | 79.3 | 1.9 |
| ARA addition (0.2 mM) | | | |
| ARA | 30.9 | 23.2 | 8.9 |
| ADA | — | 5.8 | 13.6 |
| Conversion efficiency (%) |  | 20.1 | 60.3 |
| ALA addition (0.2 mM) | | | |
| ALA | 49.1 | 25.8 | 47.1 |
| ETrA | 0.2 | 17.9 | 0.3 |
| Conversion efficiency (%) |  | 41 |  |
| STA addition (0.2 mM) | | | |
| STA | 46.2 | 8.3 | 40.5 |
| ETA | 0.3 | 28.1 | 1.7 |
| Conversion efficiency (%) |  | 77.2 | 4.0 |

TABLE 1-continued

|  | mock | TaELO1 | TaELO2 |
|---|---|---|---|
| EPA addition (0.2 mM) | | | |
| EPA | 42.0 | 31.2 | 13.1 |
| DPA | 0.1 | 19.6 | 24.5 |
| Conversion efficiency (%) |  | 25.3 | 65.1 |

Conversion efficiency (%) = 100 × product (area)/substrate (area) + product (area) (n = 1)

Example 2-5

Obtaining TaELO2 ORF Upstream and Downstream Regions by PCR Genome Walking

The TaELO2 ORF upstream and downstream regions as the homologous recombination sites in a targeting vector for disrupting TaELO2 were obtained by using the PCR genome walking technique, as briefly described below.

*T. aureum*. ATCC 34304 cell grown for 3 days using a GY liquid medium was rapidly frozen with liquid nitrogen, and ground into a powdery form with a mortar. Then, genomic DNA was extracted according to the method described in Non-Patent Document 18, and dissolved in a suitable amount of TE. Genomic DNA levels and purity were assayed by O.D. 260 and O.D. 280 measurements. This was followed by construction of a genomic DNA library by adding a cassette sequence with restriction enzyme sites to the genomic DNA cut with various restriction enzymes, using a TaKaRa LA PCRTM in vitro Cloning Kit (Takara Bio) according to the manufacturer's protocol. Then, by using the genomic DNA library as a template, a nested PCR was performed according to the manufacturer's protocol, using the forward oligonucleotide primers E2 XbaI (Example 2-4; SEQ ID NO: 21) and elo3-F1 (Example 2-2; SEQ ID NO: 10) or the reverse oligonucleotide primers E2 HindIII (Example 2-4; SEQ ID NO: 20) and elo3-R1 (Example 2-2; SEQ ID NO: 11) produced from the TaELO2 sequence, and the oligonucleotide primers complementary to the cassette sequence (attached to the kit). As a result, a 1,122-bp TaELO2 ORF upstream sequence (SEQ ID NO: 24), and a 1,204-bp TaELO2 ORF downstream sequence (SEQ ID NO: 25) were successfully obtained.

Example 2-6

Construction of TaELO2 Targeting Vector Using Selection Marker Neor

A DNA fragment joining TaELO2 ORF upstream sequence/artificial Neor/TaELO2 ORF downstream sequence was produced by fusion PCR. The following oligonucleotide primers were used.

```
KO Pro F SmaI
                                        (SEQ ID NO: 26)
(31 mer:
5'- CTC CCG GGT GGA CCT AGC GCG TGT GTC ACC T-3')

Pro R
                                        (SEQ ID NO: 27)
(25 mer:
5'-GGT CGC GTT TAC AAA GCA GCG CAG C-3')
```

-continued

SNeo F (SEQ ID NO: 28)
(52 mer;
5'-GCT GCG CTG CTT TGT AAA CGC GAC CAT GAT TGA ACA GGA CGG CCT TCA CGC T-3')

SNeoR (SEQ ID NO: 29)
(52 mer;
5'-TCG GGA GCC AGC CGG AAA CAG GTT CAA AAG AAC TCG TCC AGG AGG CGG TAG A-3')

Term F (SEQ ID NO: 30)
(23 mer:
5'-ACC TGT TTC CGG CTG GCT CCC GA-3')

KO Term R SmaI (SEQ ID NO: 31)
(27 mer:
5'-ATC CCG GGG CCG AGA ACG GGG TCG CCC-3')

The oligonucleotide primers KO Pro F SmaI/Pro R were used for the amplification of the TaELO2 ORF upstream sequence using the *T. aureum* ATCC 34304 genomic DNA of Example 2-5 as a template. The oligonucleotide primers SNeo F/SNeo R were used for the amplification of the artificial Neor using artificial Neor as a template. The oligonucleotide primers Term F/KO Term R SmaI were used for the amplification of the TaELO2 ORF downstream sequence using the *T. aureum* ATCC 34304 genomic DNA of Example 2-5 as a template. The PCR reaction was performed at a denature temperature of 98° C. for 10 seconds, and the annealing and the extension reaction were performed while appropriately adjusted according to the primer Tm and the amplification product length.

As a result, a 2, 696-bp sequence (SEQ ID NO: 32) joining TaELO2 ORF upstream sequence/artificial Neor/TaELO2 ORF downstream sequence was successfully obtained, and the sequence after TA cloning with a pGEM-T easy Vector (Promega) was used as a knockout vector, named pTKO-Neor.

Example 2-7

Introduction of TKONeor into *T. aureum* ATCC 34304

The TaELO2 targeting vector pTKONeor using artificial Neor as a selection marker (Example 2-6) was used as a template, and the TaELO2 ORF upstream sequence/artificial Neor/TaELO2 ORF downstream sequence was amplified using a set of oligonucleotide primers KO Pro F SmaI (Example 2-6, SEQ ID NO: 26)/K0 Term R SmaI (Example 2-6, SEQ ID NO: 31), and PrimeSTAR HS DNA polymerase (Takara Bio) [PCR cycles: 98° C. 2 min/98° C. 10 sec, 68° C. 3 min, 30 cycles/68° C. 10 min/4° C. $\infty$]. The DNA fragments were extracted after electrophoresis using a 1% agarose gel, and dissolved in a suitable amount of TE after ethanol precipitation. The DNA fragment levels and the purity were assayed by O.D.260 and O.D.280 measurements. In the following, the DNA fragment will be referred to as TKONeor.

This was followed by DNA penetration using the gene-gun technique. Specifically, *T. aureum* ATCC 34304 was cultured in a GY liquid medium from the middle to late stage of the logarithmic growth phase at 25° C., 150 rpm, and the supernatant was removed by centrifugation at 3,500×g, 4° C. for 10 min. The resulting cells were resuspended in a GY liquid medium in 100 times the concentration of the original culture fluid, and a 20-µl portion of the cell suspension was evenly applied as a thin layer of about a 3-cm diameter on a 5-cm diameter PDA agar plate medium containing 1 mg/ml G418 (nacalai tesque). After drying, penetration was performed using a PDS-1000/He system (BioRad) under the following conditions.

Target distance: 6 cm
Vacuum: 26 inches Hg
Micro carrier size: 0.6 µm
Rupture disk (penetration pressure): 1,100 psi Thereafter, a PD liquid medium (100 µl) was dropped onto the PDA agar plate medium, and the cells were spread and statically cultured. As a result, transfectants with the conferred G418 resistance were obtained at the efficiency of $4.7 \times 10^1$ cfu/µg DNA.

Example 2-8

PCR Using TKONeor-Introduced Transfectant Genomic DNA as a Template

Seven colonies of transfectants were collected with a toothpick, and inoculated in a GY liquid medium containing 0.5 mg/ml G418 (nacalai tesque). After multiple subculturing, genomic DNA was extracted from the cells using the method of Example 2-5, and dissolved in a suitable amount of TE after ethanol precipitation. The levels of extracted genomic DNA and the purity were assayed by O.D.260 and O.D.280 measurements. By using the genomic DNAs of the transfectants and the wild-type strain as templates, a PCR was performed with various oligonucleotide primer sets. The following oligonucleotide primer sets were used.

(1) Neor detection: SNeoF (Example 2-6; SEQ ID NO: 28) and SNeoR (Example 2-6; SEQ ID NO: 29)
(2) KO verification 1: KO Pro F SmaI (Example 2-6; SEQ ID NO: 26) and KO Term R SmaI (Example 2-6; SEQ ID NO: 31)
(3) KO verification 2: E2 KO ProF EcoRV (30 mer: 5'-GGA TAT CCC CCG CGA GGC GAT GGC TGC TCC-3') (SEQ ID NO: 33) and SNeoR (4) KO verification 3: SNeoF and E2 KO Term R EcoRV (30 mer: 5'-TGA TAT CGG GCC GCG CCC TGG GCC GTA GAT-3') (SEQ ID NO: 34) (5) TaELO2 amplification: E2 HindIII (Example 2-4; SEQ ID NO: 20) and E2 XbaI (Example 2-4; SEQ ID NO:21) (FIG. 3A)

Six out of the seven clones analyzed were transfectants by random integration, and the homologous recombination replacement of TaELO2 ORF with Neor was confirmed in the remaining clone (FIG. 3B, lanes 9 and 13). It was also found that this was accompanied by the simultaneous TaELO2 ORF amplification (FIG. 3B, lane 17). These results suggested the possibility that the *T. aureum* ATCC 34304 was a diploid or higher ploidy, or the TaELO2 was a multicopy gene.

Example 2-9

Confirmation of TaELO2 Copy Number by Southern Blotting

The following experiments were conducted according to the methods described in DIG Application Manual [Japanese version] 8th, Roche Applied Science (Non-Patent Document 25). Specifically, the genomic DNA of the wild-type strain was cut with various restriction enzymes, and electrophoresed in 2.5 µg per lane using a 0.7% SeaKemR GTGR agarose (Takara Bio). This was transferred to a nylon membrane (Hybond™-N+, GE Healthcare), and hybridized at 48° C. for 16 hours with DIG-labeled probes produced by using a PCR DIG Probe Synthesis Kit (Roche Applied Science). The following oligonucleotide primer set was used for the production of the DIG-labeled probes.

```
TaELO2 det F
                                 (SEQ ID NO: 35)
(25 mer:
5'-GTA CGT GCT CGG TGT GAT GCT GCT C-3')

TaELO2 det R
                                 (SEQ ID NO: 36)
(24 mer:
5'-GCG GCG TCC GAA CAG GTA GAG CAT-3')
```

[PCR cycles: 98° C. 2 min/98° C. 30 sec, 65° C. 30 sec, 72° C. 1 min, 30 cycles/72° C. 7 min/4° C. ∞]

Detection of the hybridized probes was made by using a chromogenic method (NBT/BCIP solution).

As a result, a single band was detected in all lanes treated with the various restriction enzymes (FIG. 4), suggesting that the TaELO2 was a single copy gene. The result thus suggested that the *T. aureum* ATCC 34304 was a diploid or higher ploidy.

Example 2-10

Evaluation of TKONeor-Introduced Transfectants by

Southern Blotting

Southern blotting was performed by using the method of Example 2-9. Specifically, the genomic DNAs of the wild-type strain and the transfectants digested with EcoRV and PstI were subjected to southern blotting using a chromogenic method (NBT/BCIP solution), using DIG-labeled probes PCR amplified with a set of oligonucleotide primers uprobe F (35 mer: 5'-ATC CGC GTA TAT ATC CGT AAA CAA CGG AAC ATT CT-3') (SEQ ID NO: 37) and uprobe R (26 mer: 5'-CTT CGG GTG GAT CAG CGA GCG ACA GC-3') (SEQ ID NO: 38) [PCR cycles: 98° C. 2 min/98° C. 30 sec, 65° C. 30 sec, 72° C. 1 min, 30 cycles/72° C. 7 min/4° C. Do]. Here, in contrast to about a 1.2-kbp DNA fragment detected for the wild-type allele, about a 2.5-kbp DNA fragment was detected for the mutant allele that underwent the homologous recombination replacement of TaELO2 ORF with Neor (FIG. 5A).

Because the wild-type allele band was simultaneously detected with the mutant allele band in the transfectants (FIG. 5B), the analysis result suggested that the *T. aureum* ATCC 34304 was a diploid or higher ploidy.

Example 2-11

Construction of TaELO2 Targeting Vector Using Selection Marker Hygr

A TaELO2 targeting vector was constructed with a selection marker Hygr to disrupt the remaining wild-type allele.

First, a fusion PCR was performed to join Hygr to a *T. aureum* ATCC 34304-derived ubiquitin promoter sequence. The following oligonucleotide primers were used.

```
ubi-600p F
                                 (SEQ ID NO: 39)
(27 mer:
5'-GCC GCA GCG CCT GGT GCA CCC GCC GGG-3')

ubi-hygro R
                                 (SEQ ID NO: 40)
(59 mer:
5'-TCG CGGG TGA GTT CAG GCT TTT TCA TGT TGG CTA GTG
TTG CTT AGG TCG CTT GCT GCT G-3')

ubi-hygro F
                                 (SEQ ID NO: 41)
(57 mer;
5'-AGC GAC CTA AGC AAC ACT AGGC CAA CAT GAA AAA GCC
TGA ACT CAC CGC GAC GTC TG-3')

hygro R
                                 (SEQ ID NO: 42)
(29 mer;
5'-CTA TTC CTT TGC CCT CGG ACG AGT GCT GG-3')
```

The oligonucleotide primers ubi-600p F/ubi-hygro R were used for the amplification of the *T. aureum* ATCC 34304-derived ubiquitin promoter sequence using the *T. aureum* ATCC 34304 genomic DNA of Example 2-5 as a template. The oligonucleotide primers ubi-hygro F/hygro R were used for the amplification of the artificial Hygr using pcDNA 3.1 Zeo (Invitogen) as a template. The PCR reaction was performed at a denature temperature of 98° C. for 10 seconds, and the annealing and the extension reaction were appropriately adjusted according to the primer Tm and the amplification product length.

As a result, a 1,636-bp (SEQ ID NO: 43) joining T. aureum ATCC 34304-derived ubiquitin promoter sequence/Hygr was successfully obtained, and the sequence after TA cloning with a pGEM-T easy Vector (Promega) was named pTub600Hygr.

By using the pTub600Hygr as a template, a PCR was performed with PrimeSTAR HS DNA polymerase (Takara Bio) to prepare a *T. aureum* ATCC 34304-derived ubiquitin promoter sequence/Hygr DNA fragment containing NheI and XbaI sites added to the 5' end and the 3' end, respectively. The PCR was run under the following conditions using a set of oligonucleotide primers ubi-600p F NheI (33 mer: 5'-GTG CTA GCC GCA GCG CCT GGT GCA CCC GCC GGG-3') (SEQ ID NO: 44) and hygro R XbaI (37 mer: 5'-GTT CTA GAC TAT TCC TTT GCC CTC GGA CGA GTG CTG G-3') (SEQ ID NO: 45) [PCR cycles: 98° C. 2 min/98° C. 10 sec, 68° C. 3 min, 30 cycles/68° C. 10 min/4° C. 00]. Separately, by using the pTKONeor of Example 2-6 as a template, a PCR was performed with PrimeSTAR HS DNA polymerase (Takara Bio) to prepare a linear vector that did not contain the Neor of the pTKONeor of Experiment Example 2-6 and to which NheI and XbaI sites were added to the 3' end and the 5' end, respectively. The PCR was run under the following conditions using a set of oligonucleotide primers KO vec F XbaI (37 mer: 5'-GTT CTA GAC CTG TTT CCG GCT GGC TCC CGA GCC ATG C-3') (SEQ ID NO: 46) and KO vec R NheI (40 mer: 5'-GTG CTA GCG GTC GCG TTT ACA AAG CAG CGC AGC AAC AGA A-3') (SEQ ID NO: 47) [PCR cycles: 98° C. 2 min/98° C. 10 sec, 68° C. 3 min, 30 cycles/68° C. 10 min/4° C. ∞]. The both DNA fragments were digested with restriction enzymes NheI and XbaI, and purified with an agarose gel to construct a cyclic vector using a Ligation Convinience Kit (Nippon Gene).

The TaELO2 targeting vector using Hygr as a selection marker thus constructed used the pGEM-T easy Vector (Promega) as the platform, and contained a 3,537-bp insert sequence (SEQ ID NO: 48) of TaELO2 ORF upstream sequence/*T. aureum* ATCC 34304-derived ubiquitin promoter sequence/Hygr/TaELO2 ORF downstream sequence. This was named pTKOub600Hygr.

Example 2-12

Reintroduction of KOub600Hygr, and Evaluation of Transfectants by PCR Using Genomic DNA as Template, and by Southern Blotting and RT-PCR The constructed TaELO2 targeting vector pTKOub600Hygr (Example 2-11) using Hygr as a selection marker was used as a template, and the TaELO2 ORF upstream sequence/*T. aureum* ATCC 34304-derived ubiquitin promoter sequence/Hygr/TaELO2 ORF downstream sequence was amplified with a PrimeSTAR HS DNA polymerase (TakaraBio), using a set of oligonucleotide primers KO Pro F SmaI (Example 2-6, SEQ ID NO: 26)/KO Term R SmaI (Example 2-8, SEQ ID NO: 31) [PCR cycles: 98° C. 2 min/98° C. 10 sec, 68° C. 3.5 min, 30 cycles/68° C. 10 min/4° C. ∞]. The resulting DNA fragment was named KOub600Hygr. This was introduced to the transfectants obtained in Example 2-6 by using the technique described therein, and statically cultured on a 1 mg/ml G418 (nacalai tesque)-containing PDA agar plate medium for 24 hours. The cells were collected, and statically cultured on a PDA agar plate medium supplemented with 1 mg/ml G418 (nacalai tesque) and 2 mg/ml hygromycin B (Wako Pure Chemical Industries, Ltd.). As a result, large numbers of transfectants were obtained (introduction efficiency: $1.02 \times 10^3$ cfu/µg DNA).

Fifty clones were collected, and subcultured multiple times in a GY liquid medium supplemented with 1 mg/ml G418 (nacalai tesque) and 2 mg/ml hygromycin B (Wako Pure Chemical Industries, Ltd.). Then, genomic DNA was extracted by using the same technique used in Example 2-5, and dissolved in a suitable amount of TE after ethanol precipitation. The levels of extracted genomic DNA and the purity were assayed by O.D.260 and O.D.280 measurements. By using the genomic DNAs of the resulting transfectants and the wild-type strain as templates, a PCR was performed with various oligonucleotide primer sets [PCR cycles: 98° C. 2 min/98° C. 10 sec, 68° C. 1 min, 30 cycles/68° C. 10 min/4° C. ∞]. The following oligonucleotide primer sets were used.

(1) TaELO2 ORF detection: SNeoF (Example 2-6; SEQ ID NO: 28) and SNeoR (Example 2-6; SEQ ID NO: 29)

(2) KO verification: E2 KO Pro F EcoRV (Example 2-8; SEQ ID NO: 33) and ubi-hygro R (Example 2-11; SEQ ID NO: 40) (FIG. 6A).

It was suggested that 14 out of the 50 clones analyzed were transfectants that underwent homologous recombination through TaELO2 ORF replacement (FIG. 6B, arrow). It was also confirmed that the TaELO2 ORF was not amplified in these clones (FIG. 6C).

This was followed by southern blotting using the same technique used in Example 2-10. Specifically, the genomic DNAs of the wild-type strain and the transfectants digested with EcoRV and PstI were subjected to southern blotting using a chromogenic method (NBT/BCIP solution), using DIG-labeled probes prepared with a set of oligonucleotide primers uprobe F (SEQ ID NO: 37) and uprobe R (SEQ ID NO: 38). Here, about a 1.2-kbp DNA fragment was detected for the wild-type allele. In contrast, about a 2.5-kbp DNA fragment was detected for the mutant allele that underwent the homologous recombination replacement of TaELO2 ORF with Neor, and about a 1.9-kbp DNA fragment was detected for the mutant allele that underwent the homologous recombination replacement of TaELO2 ORF with Hygr (FIG. 7A).

The analysis revealed that the wild-type allele band of about a 2.5 kbp was absent in the resulting transfectants, and a new band, about 1.9 kbp, was detected for the mutant allele in which the TaELO2 ORF was replaced with Hygr (FIG. 7B).

Southern blotting using a chromogenic method (NBT/BCIP solution) was also performed for the genomic DNAs of the wild-type strain and the transfectants (clones 1, 8, 9, and 10) digested with EcoRV, using TaELO2-detecting DIG-labeled probes prepared by PCR using a set of oligonucleotide primers TaELO2 probe F (30 mer: 5'-ATG GCG ACG CGC ACC TCG AAG AGC GCT CCG-3') (SEQ ID NO: 49) and TaELO2 probe R (30 mer: 5'-AGG ATC ATC ATG AAC GTG TCG CTC CAG TCG-3') (SEQ ID NO: 50) [PCR cycles: 98° C. 2 min/98° C. 30 sec, 65° C. 30 sec, 72° C. 1 min, 30 cycles/72° C. 7 min/4° C. ∞]. Here, TaELO2 was detected as about a 2.5-kbp DNA fragment (FIG. 7A).

The analysis revealed that in contrast to the wild-type strain in which the TaELO2 was detected (FIG. 8, lane 1), TaELO2 was not detected in any of the transfectants (FIG. 8, lanes 2 to 5).

To examine the TaELO2 disruption at the mRNA level, TaELO2 mRNA detection was performed by RT-PCR. Total RNA was extracted from the cells of the wild-type strain and the transfectants (clones 1, 8, 9, and 10) cultured for 3 days in GY liquid media, using Sepasol-RNA I Super (nacalai tesque) as in Example 2-1. The total RNA (50 µg) was cleaned up using an RNeasyMini Kit (QIAGEN) according to the manufacturer's protocol, and treated at 37° C. for 1 hour using 50 U Recombinant DNase I (Takara Bio) to degrade and remove the contaminated genomic DNA. By using the resulting total RNA as a template, a single-stranded cDNA library was created using oligo (dT) primer (Novagen) and PrimeScript Reverse Transcriptase (Takara Bio) according to the manufacturers' protocols. By using the resulting single-stranded cDNA library as a template, the TaELO2 ORF was amplified with a set of oligonucleotide primers E2 HindIII (Example 2-4; SEQ ID NO: 20) and E2 XbaI (Example 2-4; SEQ ID NO:21), and LA taq Hot Start Version (Takara Bio) [PCR cycles: 98° C. 2 min/98° C. 10 sec, 68° C. 1 min, 30 cycles/68° C. 10 min/4° C. ∞].

It was found as a result that the TaELO2 mRNA detected in the wild-type strain (FIG. 9, lane 5) was not detected in any of the transfectants (clones 1, 8, 9, and 10) (FIG. 9, lanes 1 to 4).

As demonstrated above, TaELO2-deficient homozygotes with the complete disruption of TaELO2 were successfully obtained. It was also found that the *T. aureum* ATCC 34304 was a diploid.

Example 2-13

Comparison of Fatty Acid Compositions of Wild-Type Strain and TaELO2-Deficient Homozygote The fatty acid compositions of the TaELO2-deficient homozygote and the wild-type strain of Example 2-12 were compared by the GC analysis of methylesterificated fatty acids. Specifically, the cells of the TaELO2-deficient homozygotes and the wild-type strain cultured for 5 days in GY liquid media were collected, and the fatty acids from these cells were extracted and methylesterificated by using the methods described in Example 2-4, and subjected to GC analysis. The GC analysis was performed with a gas chromatograph GC-2014 (Shimadzu Corporation) under the following conditions:

Column: HR-SS-10 (30 m×0.25 mm; Shinwa Chemical Industries Ltd.

Column temperature: 150° C.→(5° C./min)→220° C. (10 min)

Carrier gas: He (1.3 mL/min).

As a result, the level of the EPA as a TaELO2 substrate showed about a two-fold increase in the TaELO2-deficient homozygote compared to the wild-type strain, whereas the level of the downstream metabolite DHA was lower than in the wild-type strain (FIG. 10).

The present invention is the first example of the modification of fatty acid compositions through disruption of genes that form the desaturase/elongase pathways in *Labyrinthula*. Specifically, the present invention has elucidated the involvement of the desaturase/elongase pathways in the PUFA biosynthesis in the *Labyrinthula T. aureum*, and shows that modification of fatty acid composition is possible by knocking out the constitutive genes. In the future, it would be possible to perform molecular breeding of Labyrinthulomycetes that selectively produce industrially useful PUFAs in large quantities in a PUFA biosynthetic pathway artificially created from combinations of genetic modifications such as overexpression of foreign desaturase/elongase genes, and PUFA-PKS gene knockouts.

EXAMPLE 3

[Disruption of *Parietichytrium sarkarianum* C20 Elongase Gene]

Example 3-1

Subcloning of SV40 Terminator Sequence

An SV40 terminator sequence was amplified with PrimeSTAR HS DNA polymerase (Takara Bio), using a pcDNA 3.1 Myc-His vector as a template. The PCR primers used are as follows. RHO58 was set on the SV40 terminator sequence, and contains BglII and BamHI linker sequences. RHO52 was set on the SV40 terminator sequence, and contains a BglII sequence [RHO58: 34 mer: 5'-CAG ATC TGG ATC CGC GAA ATG ACC GAC CAA GCG A-3' (SEQ ID NO: 51), RHO52: 24 mer: 5'-ACG CAA TTA ATG TGA GAT CTA GCT-3' (SEQ ID NO: 52)]. The sequence was cloned into a pGEM-T easy vector (Promega) after being amplified under the following conditions [PCR cycles: 98° C. 2 min/98° C. 30 sec, 60° C. 30 sec, 72° C. 1 min, 30 cycles/72° C. 1 min]. The sequence was confirmed with a Dye Terminator Cycle Sequencing Kit (BECKMAN COULTER) after being amplified with *Escherichia coli*, and was named pRH27.

A plasmid (pRH27) containing the subcloned SV40 terminator sequence (342 bp, SEQ ID NO: 53) is shown in FIG. 11.

Example 3-2

Production of Artificial Neomycin-Resistant Gene Cassette

The *Thraustochytrium aureum* ATCC 34304 strain was cultured in GY medium, and cells at the late stage of the logarithmic growth phase were centrifuged at 4° C., 3,500×g for 5 min to obtain a pellet. The pellet was then disrupted after being frozen with liquid nitrogen. The cell disruption liquid was extracted with phenol, and precipitated with ethanol. The precipitate was then dissolved in a TE solution. The nucleic acids dissolved in the TE solution were treated with RNase at 37° C. for 30 min to degrade the RNA, and extracted again with phenol. After ethanol precipitation, the precipitate was dissolved in a TE solution. The DNA concentration was calculated by measuring A260/280.

By using this as a template, a ubiquitin promoter sequence (619 bp, SEQ ID NO: 54) was amplified using a PrimeSTAR HS DNA polymerase with GC Buffer (Takara Bio). The PCR primers used are as follows. RHO53 was set on the ubiquitin promoter sequence, and contains a BglII linker sequence. The TKO1 contains the ubiquitin promoter sequence and an artificial neomycin-resistant gene sequence [RHO53: 36 mer: 5'-CCC AGA TCT GCC GCA GCG CCT GGT GCA CCC GCC GGG-3' (SEQ ID NO: 55), TKO1: 58 mer: 5'-CGT GAA GGC CGT CCT GTT CAA TCA TGT TGG CTA GTG TTG CTT AGG TCG CTT GCT GCT G-3' (SEQ ID NO: 56)] [PCR cycles: 98° C. 2 min/98° C. 10 sec, 68° C. 1 min, 30 cycles/68° C. 1 min].

An artificial neomycin-resistant gene sequence (826 bp, SEQ ID NO: 57) was amplified with a PrimeSTAR HS DNA polymerase with GC Buffer (TakaraBio), using the artificial neomycin-resistant gene sequence as a template. The PCR primers used are as follows. TKO2 contains the ubiquitin promoter sequence and the artificial neomycin-resistant gene sequence. RHO57 contains the artificial neomycin-resistant gene sequence, and has a BglII linker sequence [TK02: 54 mer: 5'-AGC GAC CTA AGC AAC ACT AGC CAA CAT GAT TGA ACA GGA CGG CCT TCA CGC TGG-3' (SEQ ID NO: 58), RHO57: 26 mer: 5'-CAG ATC TCA AAA GAA CTC GTC CAG GA-3' (SEQ ID NO: 59)] [PCR cycles: 98° C. 2 min/98° C. 10 sec, 68° C. 1 min, 30 cycles/68° C. 1 min].

By using SEQ ID NOS: 54 and 57 as templates, a fusion PCR was performed with RHO53 (SEQ ID NO: 55) and RHO57 (SEQ ID NO: 59) according to the method described in Non-Patent Document 19. The product was amplified under the following conditions by using an LA taq Hot start version (Takara Bio) as an enzyme, and digested with BglII [PCR cycles: 94° C. 2 min/94° C. 20 sec, 55° C. 30 sec, 68° C. 1 min, 30 cycles/68° C. 1 min (1° C./10 sec from 55° C. to 68° C.) (FIG. 12).

The fused product *Thraustochytrium aureum* ATCC 34304-derived ubiquitin promoter-artificial neomycin-resistant gene sequence (1,395 bp, SEQ ID NO: 60) was digested with BglII, and ligated to the BamHI site of the pRH27 of Example 3-1. The resulting plasmid was amplified with *Escherichia coli*, and the sequence was confirmed by using a Dye Terminator Cycle Sequencing Kit (BECKMAN COULTER) and named pRH31.

The product artificial neomycin-resistant gene cassette (pRH31) is shown in FIG. 13.

Example 3-3

Production of Hygromycin-Resistant Gene Cassette

By using the genomic DNA of the *Thraustochytrium aureum* ATCC 34304 as a template, a ubiquitin promoter sequence (617 bp, SEQ ID NO: 61) was amplified with a PrimeSTAR HS DNA polymerase with GC Buffer (Takara Bio). The PCR primers used are as follows. RHO53 was set on the ubiquitin promoter sequence, and contains a BglII linker sequence. K508 contains the ubiquitin promoter sequence and a hygromycin-resistant gene sequence [RHO53: 36 mer: 5'-CCC AGA TCT GCC GCA GCG CCT GGT GCA CCC GCC GGG-3' (Example 3-2; SEQ ID NO: 55), KSO8: 58 mer: 5'-TCG CGG TGA GTT CAG GCT TTT TCA TGT TGG CTA GTG TTG CTT AGG TCG CTT GCT GCT G-3' (SEQ ID NO: 62)] [PCR cycles: 98° C. 2 min/98° C. 30 sec, 68° C. 2 min, 30 cycles/68° C. 2 min].

By using a pcDNA 3.1/Hygro (invitrogen) as a template, a hygromycin-resistant gene (1,058 bp, SEQ ID NO: 63) was amplified with a PrimeSTAR HS DNA polymerase with GC Buffer (Takara Bio). The PCR primers used are as follows. KSO7 contains the ubiquitin promoter sequence and the hygromycin-resistant gene sequence. RHO56 contains the hygromycin-resistant gene, and has a BglII linker sequence [KSO7: 56 mer: 5'-AGC GAC CTA AGC AAC ACT AGC CAA CAT GAA AAA GCC TGA ACT CAC CGC GAC GTC TG-3' (SEQ ID NO: 64), RHO56: 36 mer: 5'-CAG ATC TCT ATT CCT TTG CCC TCG GAC GAG TGC TGG-3' (SEQ ID NO: 65)] [PCR cycles: 98° C. 2 min/98° C. 30 sec, 68° C. 2 min, 30 cycles/68° C. 2 min].

By using SEQ ID NOS: 61 and 63 as templates, a fusion PCR was performed with RHO53 (Example 3-2; SEQ ID NO: 55) and RHO56 (SEQ ID NO: 65) according to the method described in Non-Patent Document 19. The product was amplified under the following conditions using an LA taq Hot start version (Takara Bio) as an enzyme, and digested with BglII [PCR cycles: 94° C. 2 min/94° C. 20 sec, 55° C. 30 sec, 68° C. 1 min, 30 cycles/68° C. 1 min (1° C./10 sec from 55° C. to 68° C.)] (FIG. 14).

The fused product Thraustochytrium aureum ATCC 34304-derived ubiquitin promoter-pcDNA 3.1/Hygro (invitrogen)-derived hygromycin-resistant gene (1,625 bp, SEQ ID NO: 66) was digested with BglII, and ligated to the BamHI site of the pRH27 of Example 3-1 (FIG. 11). The resulting plasmid was amplified with Escherichia coli, and the sequence was confirmed by using a Dye Terminator Cycle Sequencing Kit (BECKMAN COULTER). This was named pRH32.

The product artificial neomycin-resistant gene cassette (pRH32) is shown in FIG. 15.

Example 3-4

Cloning of Parietichytrium C20 Elongase Gene

The Parietichytrium sarkarianum SEK364 genomic DNA extracted by using the method of Example 3-2 was extracted, and the genome was decoded.

A forward oligonucleotide (PsTaELO2 F1; 5'-CCT TCG GCG CTC CTC TTA TGT ATG-3') (SEQ ID NO: 67) and a reverse oligonucleotide (PsTaELO2 R2;5'-CAA TGC AAG AGG CGA ACT GGG AGA G-3') (SEQ ID NO: 68) were synthesized by targeting a conserved region in the C20 elongase gene. The oligonucleotides PsTaELO2 F1 and PsTaELO2 R2 were then used for a PCR performed with an LA taq Hot start version (TaKaRa) using the Parietichytrium sarkarianum SEK364 genomic DNA prepared by using the method of Example 3-2 as a template [PCR cycles: 98° C. 1 min/98° C. 10 sec, 60° C. 30 sec, 72° C. 1 min, 30 cycles/72° C. 7 min/4° C. 00]. The resulting specific amplification product was gel purified, and the base sequence was analyzed by direct sequencing. The sequence showed significant homology with the sequence of a known C20 elongase gene, suggesting that the sequence was a partial sequence of the Parietichytrium sarkarianum SEK364-derived C20 elongase gene.

This was followed by cloning of the Parietichytrium sarkarianum SEK364-derived C20 elongase gene by 3'- and 5'-RACE, as in Example 2-2. First, forward oligonucleotide primers (PsRACE F1; 5'-TGG GGC TCT GGA ACC GCT GCT TAC G-3') (SEQ ID NO: 69) and (PsRACE F2; 5'-CTT CCA GCT CTC CCA GTT CGC CTC T-3') (SEQ ID NO: 70), and reverse oligonucleotide primers (PsRACE R1; 5'-CGG GTT GTT GAT GTT GAG CGA GGT G-3') (SEQ ID NO: 71) and (PsRACE R2; 5'-CCC ACG CCA TCC ACG AGC ACA CCA C-3') (SEQ ID NO: 72) were designed. This was followed by 3'- and 5'-RACE using a synthetic adapter-specific oligonucleotide and the oligonucleotide PsRACE F1 or PsRACE R1, using the cDNA library created with the SMART™ RACE cDNA Amplification Kit (Clontech) as a template [PCR cycles: 94° C. 30 sec 5 cycles/94° C. 30 sec, 70° C. 30 sec, 72° C. 3 min, 5 cycles/94° C. 30 sec, 68° C. 30 sec, 72° C. 3 min, 25 cycles/4° C. Do]. By using the resulting both RACE products as templates, a nested PCR was performed using a synthetic adapter-specific oligonucleotide, and the oligonucleotide PsRACE F2 or PsRACE R2 [PCR cycles: 94° C. 1 min/94° C. 30 sec, 68° C. 30 sec, 72° C. 3 min, 25 cycles/72° C. 10 min/4° C. ∞]. The resulting specific product was gel purified, and the base sequence was analyzed after being TA cloned with a pGEM-T easy Vector (Promega). The result confirmed that the product was a Parietichytrium sarkarianum SEK364-derived C20 elongase gene.

A sequence (957 bp, SEQ ID NO: 73) containing the C20 elongase gene sequence was amplified with an LA taq Hot start version (Takara Bio), using the Parietichytrium genomic DNA extracted by using the method of Example 3-2 as a template. The PCR primers used are as follows. RHO153 contains a start codon, and has a BamHI site as a linker sequence. RHO154 contains a stop codon, and has a BamHI site as a linker sequence [RHO153: 32 mer: 5'-CCC GGA TCC ATG GCA GCT CGC GTG GAG AAA CA-3' (SEQ ID NO: 74), RHO154: 33 mer: 5'-CCC GGA TCC TTA CTG AGC CTT CTT GGA GGT CTC-3' (SEQ ID NO: 75)] [PCR cycles: 98° C. 2 min/98° C. 10 sec, 68° C. 1 min, 30 cycles/68° C. 2 min].

The resulting DNA fragment was cloned into a pGEM-T easy vector, and amplified with Escherichia coli. Then, the sequence was confirmed with a Dye Terminator Cycle Sequencing Kit (BECKMAN COULTER).

The 936-bp Parietichytrium C20 elongase gene (SEQ ID NO: 76) was cloned, and named pRH80 (FIG. 16). The amino acid sequence is represented by SEQ ID NO: 77.

Example 3-5

Production of Base Plasmid for Parietichytrium C20 Elongase Gene Targeting Vector Production By using the pRH80 produced in Example 3-4 (FIG. 16) as a template, amplification was performed with a Prime-STAR Max DNA Polymerase (Takara Bio), using a primer set of the reverse orientation prepared for the insertion of the BglII site in a portion halfway along the C20 elongase gene sequence. The PCR primers used were as follows, and the both primers have BglII linker sequences [RHO155: 26 mer: 5'-ACA AAG ATC TCG ACT GGA CCG ACA CC-3' (SEQ ID NO: 78), RHO156: 27 mer: 5'-AGT CGA GAT CTT TGT CAG GAG GTG GAC-3' (SEQ ID NO: 79)] [PCR cycles: 98° C. 2 min/98° C. 10 sec, 56° C. 15 sec, 72° C. 1 min, 30 cycles/72° C. 1 min]. After the amplification under these conditions, the product was digested with BglII, and allowed to self-ligate. The ligated sample was amplified with *Escherichia coli*, and the sequence was confirmed by using a Dye Terminator Cycle Sequencing Kit (BECKMAN COULTER). This was named pRH83. The 935-bp C20 elongase gene sequence with the inserted BglII site is represented by SEQ ID NO: 80.

The produced base plasmid (pRH83) for *Parietichytrium* C20 elongase gene targeting vector production is shown in FIG. 17.

Example 3-6

Production of Targeting Vectors (Artificial Neomycin-Resistant Gene and Hygromycin-Resistant Gene)

The pRH31 (FIG. 13) of Example 3-2 was digested with BglII, and a DNA fragment containing an artificial neomycin-resistant gene cassette was ligated to the BglII site of the pRH83 (FIG. 17) of Example 3-5. This was named pRH85.

The pRH32 (FIG. 15) of Example 3-3 was digested with BglII, and a DNA fragment containing a hygromycin-resistant gene cassette was ligated to the BglII site of the pRH83 (FIG. 17) of Example 3-5. This was named pRH86.

The two targeting vectors (pRH85 and 86) produced are shown in FIG. 18.

Example 3-7

Introduction of C20 Elongase Gene Targeting Vector

By using the two targeting vectors produced in Example 3-6 as templates, the gene was amplified with a PrimeSTAR Max DNA polymerase (Takara Bio), using the RHO153 (Example 3-4; SEQ ID NO: 74) and RHO154 (Example 3-4; SEQ ID NO: 75) as primers [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was then calculated by measuring A260/280. The introduced fragment obtained from using the pRH85 (FIG. 18) of Example 3-6 as a template was 2,661 bp, and had the following sequence order: First half of *Parietichytrium* C20 elongase gene-SV40 terminator sequence-artificial neomycin-resistant gene sequence-ubiquitin promoter sequence-second half of *Parietichytrium* C20 elongase gene (SEQ ID NO: 81). The introduced fragment obtained from using the pRH86 (FIG. 18) of Example 3-6 as a template was 2,892 bp, and had the following sequence order: First half of *Parietichytrium* C20 elongase gene-SV40 terminator sequence-hygromycin-resistant gene sequence-ubiquitin promoter sequence-second half of *Parietichytrium* C20 elongase gene (SEQ ID NO: 82).

The *Parietichytrium sarkarianum* SEK364 strain was cultured in a GY medium for 4 days, and cells in the logarithmic growth phase were used for gene introduction. The DNA fragment (0.625 μg) was then introduced into cells corresponding to OD600=1 to 1.5 using the gene-gun technique (microcarrier: 0.6-micron gold particles, target distance: 6 cm, chamber vacuum: 26 mmHg, rupture disk: 1,550 PSI). After a 24-hour recovery time, the cells with the introduced gene were applied onto a PDA agar plate medium (containing 2 mg/ml G418 or 2 mg/ml hygromycin). As a result, 10 to 20 drug resistant strains were obtained per penetration.

Example 3-8

Identification of C20 Elongase Gene Gene Targeting Homologous Recombinant

Genomic DNA was extracted from the *Parietichytrium sarkarianum* SEK364 strain, the C20 elongase gene hetero homologous recombinant, and the C20 elongase gene homo homologous recombinant (gene disrupted strain) by using the method described in Example 3-2, and the DNA concentration was calculated by measuring A260/280. By using this as a template, a PCR was performed with an LA taq Hot start version (Takara Bio) to confirm the genome structure. The positions of the primers, combinations used for the amplification, and the expected sizes of the amplification products are shown in FIG. 19. RHO184 and RHO185 were set on the upstream and downstream sides, respectively, of the C20 elongase. RHO142 and RHO143 were set on the artificial neomycin-resistant gene. RHO140 and RHO141 were set on the hygromycin-resistant gene [RHO140: 20 mer: 5'-GGT TGA CGG CAA TTT CGA TG-3' (SEQ ID NO: 83), RHO141: 22 mer: 5'-CCT CCT ACA TCG AAG CTG AAA G-3' (SEQ ID NO: 84), RHO142: 21 mer: 5'-CTT CTC GGG CTT TAT CGA CTG-3' (SEQ ID NO: 85), RHO143: 22 mer: 5'-TAA GGT CGG TCT TGA CAA ACA G-3' (SEQ ID NO: 86), RHO184: 24 mer: 5'-AGT AGT CCC CGA TTT GGT AGT TGA-3' (SEQ ID NO: 87), RHO185: 22 mer: 5'-GGC AGA GAG CAA AAA CAC GAG C-3' (SEQ ID NO: 88)] [PCR cycles: 98° C. 2 min/98° C. 10 sec, 68° C. 4 min, 30 cycles/68° C. 7 min].

C20 elongase knockout strains were obtained that showed no amplification of the wild-type allele (Wt allele) and the artificial neomycin-resistant gene allele (NeoR allele) and the hygromycin-resistant gene allele (HygR allele) (FIG. 20).

Example 3-9

Changes in Fatty Acid Composition by C20 Elongase Disruption

*Parietichytrium sarkarianum* SEK364, and the gene disrupted strains were cultured in GY media. Cells from the late stage of the logarithmic growth phase were centrifuged at 4° C., 3,000 rpm for 10 min to form a pellet, suspended in 0.9% NaCl, and washed. The cells were further centrifuged at 4° C., 3,000 rpm for 10 min, and the pellet was suspended in sterile water, and washed. After further centrifugation at 3,000 rpm for 10 min, the cells were freeze dried after removing the supernatant.

Then, 2 ml of methanolic KOH (7.5% KOH in 95% methanol) was added to the freeze dried cells, and, after being vortexed, the cells were ultrasonically disrupted (80° C., 30 min). The cells were vortexed after adding sterile water (500 μl), and vortexed again after adding n-hexane (2 ml). This was followed by centrifugation at 3,000 rpm for 10 min, and the upper layer was discarded. The cells were vortexed again after adding n-hexane (2 ml), and centrifuged at 3,000 rpm for 10 min. After discarding the upper layer, 6 N HCl (1 ml) was added to the remaining lower layer, and the mixture was vortexed. The mixture was vortexed again after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. The collected upper layer was then concentrated and dried with nitrogen gas. The concentrated dry sample was incubated overnight at 80° C. after adding 3 N methanolic HCl (2 ml).

The sample was allowed to cool to room temperature, and 0.9% NaCl (1 ml) was added. The mixture was vortexed after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. After adding a small amount of anhydrous sodium sulfate to the collected upper layer, the mixture was vortexed, and centrifuged at 3,000 rpm for 10 min. After collecting the upper layer, the upper layer was concentrated and dried with nitrogen gas. The concentrated dry sample was dissolved in n-hexane (0.5 ml), and 1 µl of the sample was GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

As a result, knocking out the C20 elongase in the *Parietichytrium sarkarianum* SEK364 caused reduction of fatty acids of 22 or greater carbon chain length, and increased fatty acids of 20 carbon chain length (FIG. 21). FIG. 22 represents the proportions relative to the wild-type strain taken as 100%. FIG. 22 represents the proportion of each component based on the total amount of the fatty acids, which includes AA: about 25.2%, DGLA: about 8.6%, ETA: about 0.6%, EPA: about 11.6%, n-6DPA: about 1.6%, and DHA: about 1.3%, which can also be described as the values of GC area such as n-6DPA/DTAL: 2.4, DHA/n-3DPA: 4.9, C20PUFA/C22PUFA: 11.9, and n-6PUFA/n-3PUFA 2.6. As can be seen from these results, the arachidonic acid increased about ten-fold, and the EPA showed about an eight-fold increase. The DPA and DHA reduced to about ¼ and about ⅕, respectively.

EXAMPLE 4

[Disruption of *Thraustochytrium aureum* PUFA PKS Pathway-Associated Gene OrfA]

Example 4-1

Cloning of PUFA PKS Pathway-Associated Gene OrfA Upstream Sequence

Genomic DNA was extracted from the *Thraustochytrium aureum* ATCC 34304 by using the method described in Example 3-2, and the DNA concentration was calculated by measuring A260/280. By using this, a genome cassette library was produced with an LA PCRTM in vitro Cloning Kit (Takara Bio). A PCR lower primer [RHO20: 23 mer: 5'-CGA TGA AAG GTC ACA GAA GAG TC-3' (SEQ ID NO: 89)] was set on the PUFA PKS pathway-associated gene OrfA described in Patent Document 7, and the DNA was amplified by using this primer in combination with the cassette primer attached to the kit [1st PCR cycles: 98° C. 2 min/98° C. 30 sec, 56° C. 30 sec, 72° C. 4 min, 30 cycles/72° C. 5 min]. The 1st PCR amplification product was diluted 100 times, and amplified with the PCR lower primer [RHO20] and the nested primer attached to the kit [2nd PCR cycles: 98° C. 2 min/98° C. 30 sec, 56° C. 30 sec, 72° C. 4 min, 30 cycles/72° C. 5 min]. The resulting DNA fragment was cloned into a pGEM-T easy vector, amplified with *Escherichia coli*, and the sequence was confirmed by using a Dye Terminator Cycle Sequencing Kit (BECKMAN COULTER).

The 3,377-bp (SEQ ID NO: 91) DNA fragment containing the upstream 3,181 bp (SEQ ID NO: 90) of OrfA was cloned. The OrfA upstream DNA sequence was found to be 3,181 bp.

Example 4-2

Cloning of PUFA PKS Pathway-Associated Gene OrfA Downstream Sequence

The genome cassette library produced in Example 4-1 was used as a template. The DNA was amplified by using the method described in Example 4-1, using a PCR upper primer [RHO21: 21 mer: 5'-CAG GGC GAG CGA GTG TGG TTC-3' (SEQ ID NO: 92)] set on the PUFA PKS pathway-associated gene OrfA described in Patent Document 7. The resulting DNA fragment was cloned into a pGEM-T easy vector, amplified with *Escherichia coli*, and the sequence was confirmed by using a Dye Terminator Cycle Sequencing Kit (BECKMAN COULTER). The 1,204-bp DNA fragment (SEQ ID NO: 94) containing the downstream 1,160 bp (SEQ ID NO: 93) of OrfA was cloned.

The DNA was amplified by using the method described in Example 4-1 using the PCR upper primer [RHO28: 20 mer: 5'-TGA TGC CGA TGC TAC AAA AG-3' (SEQ ID NO: 95] produced on SEQ ID NO: 94. The resulting DNA fragment was cloned into a pGEM-T easy vector, amplified with *Escherichia coli*, and the sequence was confirmed by using a Dye Terminator Cycle Sequencing Kit (BECKMAN COULTER).

The 1,488-bp DNA fragment (SEQ ID NO: 96) containing the downstream sequence was cloned. The downstream DNA sequence of OrfA was found to be 2,551 bp in total (SEQ ID NO: 97).

Example 4-3

Production of PUFA PKS Pathway-Associated Gene OrfA Targeting Vector

By using the genomic DNA of *Thraustochytrium aureum* ATCC 34304 as a template, an 18S rDNA sequence (1,835 bp, SEQ ID NO: 98) was amplified with a PrimeSTAR HS DNA polymerase (Takara Bio). The PCR primers used are as follows. TMO30 was set on the 18S rDNA sequence. TMO31 contains the 18S rDNA sequence and an EF1α promoter sequence [TMO30: 30 mer: 5'-CGA ATA TTC CTG GTT GAT CCT GCC AGT AGT-3' (SEQ ID NO: 99), TMO31: 46 mer: 5'-GTA ACG GCT TTT TTT GAA TTG CAG GTT CAC TAC GCT TGT TAG AAA C-3' (SEQ ID NO: 100)] [PCR cycles: 98° C. 10 sec/98° C. 10 sec, 58° C. 30 sec, 72° C. 2 min, 30 cycles/72° C. 2 min]. Separately, by using the *Thraustochytrium aureum* ATCC 34304 genomic DNA as a template, the EF1α promoter sequence (661 bp, SEQ ID NO: 101) was amplified with a PrimeSTAR HS DNA polymerase (Takara Bio). The PCR primers used are as follows. TMO32 contains the 18S rDNA sequence and the EF1α promoter sequence. TMO33 contains the EF1α promoter sequence and an artificial neomycin-resistant gene sequence [TMO32: 46 mer: 5'-GGT TTC CGT AGT GAA CCT GCA ATT CAA AAA AAG CCG TTA CTC ACA T-3' (SEQ ID NO: 102), TMO33: 46 mer: 5'-GCG TGA AGG CCG TCC TGT TCA ATC ATC TAG CCT TCC TTT GCC GCT G-3' (SEQ ID NO: 103)] [PCR cycles: 98° C. 10 sec/98° C. 10 sec, 58° C. 30 sec, 72° C. 1 min, 30 cycles/72° C. 1 min].

By using the artificial neomycin-resistant gene as a template, the artificial neomycin-resistant gene sequence (835 bp, SEQ ID NO: 104) was amplified with a PrimeSTAR HS DNA polymerase (TakaraBio). The PCR primers used are as follows. TMO34 contains the EF1α promoter sequence and the artificial neomycin-resistant gene sequence. TMO35 contains the artificial neomycin-resistant gene sequence and the EF1α terminator sequence [TMO34: 45 mer: 5'-CAT CGG CAA AGG AAG GCT AGA TGA TTG AAC AGG ACG GCC TTC ACG-3' (SEQ ID NO: 105), TMO 35: 46 mer: 5'-GCG CAT AGC CGG CGC GGA TCT CAA AAG AAC TCG TCC AGG AGG CGG T-3' (SEQ ID NO: 106)] [PCR cycles: 98° C. 10 sec/98° C. 10 sec, 58° C. 30 sec, 72° C. 1 min, 30 cycles/72° C. 1 min].

Further, by using the *Thraustochytrium aureum* ATCC 34304 genomic DNA as a template, the EF1α terminator sequence (1249 bp, SEQ ID NO: 107) was amplified with a PrimeSTAR HS DNA polymerase (Takara Bio). The PCR primers used are as follows. TMO36 contains the artificial neomycin-resistant gene sequence and the EF1α terminator sequence. TMO37 was set within the EF1α terminator [TMO36: 46 mer: 5'-TCC TGG ACG AGT TCT TTT GAG ATC CGC GCC GGC TAT GCG CCC GTG C-3' (SEQ ID NO: 108), TMO37: 30 mer: 5'-CAC TGC AGC GAA AGA CGG GCC GTA AGG ACG-3' (SEQ ID NO: 109)] [PCR cycles: 98° C. 10 sec/98° C. 10 sec, 58° C. 30 sec, 72° C. 2 min, 30 cycles/72° C. 2 min].

By using SEQ ID NOS: 98, 101, 104, and 107 as templates, a fusion PCR was performed according to the method described in Non-Patent Document 19. An LA taq Hot start version (Takara Bio) was used as the enzyme. The TMO30 (SEQ ID NO: 99) and TMO33 (SEQ ID NO: 103) set, and the TMO34 (SEQ ID NO: 105) and TMO37 (SEQ ID NO: 109) set were used for the first amplification. The TMO30 (SEQ ID NO: 99) and TMO37 (SEQ ID NO: 109) set was used for the second amplification. The PCR reaction was performed at a denature temperature of 98° C. for 10 seconds, and the annealing and the extension reaction were appropriately adjusted according to the primer Tm value and the amplification fragment length (FIG. 23).

The DNA fragment (FIG. 23, SEQ ID NO: 110, 4,453 bp) joined as above was cut at the EcoRI site of the *T. aureum* 18S rDNA, and the NcoI site of the *T. aureum* EF1α terminator, and ligated to a pGEM-T easy vector-derived vector. This was named pRH5 (FIG. 24).

By using the *Thraustochytrium aureum* ATCC 34304 genomic DNA as a template, the DNA was amplified with a PrimeSTAR HS DNA polymerase with GC Buffer (Takara Bio), using PCR primers set in the upstream sequence found in Example 4-1 (SEQ ID NO: 90, and PUFA PKS pathway-associated gene OrfA described in Patent Document 7). The amplification yielded a 1,218-bp DNA fragment (SEQ ID NO: 111). This was used as the 5' homologous region of the targeting vector. The PCR primers used are as follows. An EcoRI site or a HindIII site was added as a linker sequence [RHO33: 32 mer: 5'-CCC GAA TTC GGA CGA TGA CTG ACT GAC TGA TT-3' (SEQ ID NO: 112), RHO34: 28 mer: 5'-CCC AAG CTT GTC TGC CTC GGC TCT TGG T-3' (SEQ ID NO: 113)] [PCR cycles: 98° C. 2 min/98° C. 30 sec, 57° C. 30 sec, 72° C. 1 min, 30 cycles/72° C. 3 min].

By using the *Thraustochytrium aureum* ATCC 34304 genomic DNA as a template, the DNA was amplified with a PrimeSTAR HS DNA polymerase with GC Buffer (Takara Bio) using the PCR primers set in the downstream sequence (SEQ ID NO: 97) found in Example 4-2. The amplification yielded a 1,000-bp DNA fragment (SEQ ID NO: 114). This was used as the 3' homologous region of the targeting vector. The PCR primers used are as follows. A linker sequence NcoI site was added to the both primers [RHO29: 28 mer: 5'-CCC CCA TGG TGT TGC TGT GGG ATT GGT C-3' (SEQ ID NO: 115), RHO30: 30 mer: 5'-CCC CCA TGG CTC GGT TAC ATC TCT GAG GAA-3' (SEQ ID NO: 116)] [PCR cycles: 98° C. 2 min/98° C. 30 sec, 57° C. 30 sec, 72° C. 1 min, 30 cycles/72° C. 3 min].

The amplified upstream sequence was joined to the EcoRI site and the HindIII site in the pRH5 of FIG. 24. The amplified downstream sequence was joined to the NcoI site. This vector was named pRH21.

The produced targeting vector (pRH21) using the artificial neomycin-resistant gene is shown in FIG. 25.

Example 4-4

Production of PUFA PKS Pathway-Associated Gene OrfA Targeting Vector (Hygromycin-Resistant Gene)

By using the pRH32 (FIG. 15) of Example 3-3 as a template, a ubiqitin promoter-hygromycin-resistant gene fragment (1,632 bp, SEQ ID NO: 117) was amplified with a PrimeSTAR HS DNA polymerase with GC Buffer (Takara Bio). The PCR primers used are as follows. RHO59 was set on the ubiquitin promoter, and a linker sequence HindIII site was added. RHO60 contains a hygromycin-resistant gene sequence stop codon, and has linker sequences SphI and SalI [RHO59: 36 mer: 5'-CCC AAG CTT GCC GCA GCG CCT GGT GCA CCC GCC GGG-3' (SEQ ID NO: 118), RHO60: 43 mer: 5'-CCC GCA TGC GTC GAC TAT TCC TTT GCC CTC GGA CGA GTG CTG G-3' (SEQ ID NO: 119)] [PCR cycles: 98° C. 2 min/98° C. 30 sec, 68° C. 2 min, 30 cycles/68° C. 2 min].

The amplified fragment was joined to the HindIII and SphI sites of the pRH21 (FIG. 25) of Example 4-3 (FIG. 26, pRH30).

By using the *Thraustochytrium aureum* ATCC 34304 genomic DNA as a template, the gene was amplified with a PrimeSTAR HS DNA polymerase with GC Buffer (Takara Bio) using the PCR primers produced in the downstream sequence (SEQ ID NO: 97) found in Example 4-2. The amplification yielded a 1,000-bp DNA fragment (SEQ ID NO: 120). This was used as the 3' homologous region of the targeting vector. The PCR primers used are as follows. A linker sequence SalI site was added to the both primers [RHO61: 29 mer: 5'-CCC GTC GAC GTG TTG CTG TGG GAT TGG TC-3' (SEQ ID NO: 121), RHO62: 29 mer: 5'-CCC GTC GAC TCG GTT ACA TCT CTG AGG AA-3' (SEQ ID NO: 122)] [PCR cycles: 98° C. 2 min/98° C. 30 sec, 57° C. 30 sec, 72° C. 1 min, 30 cycles/72° C. 3 min].

The amplified downstream sequence was joined to the SalI site of pRH30 (FIG. 26). This was named pRH33. The produced targeting vector (pRH33) using the hygromycin-resistant gene is shown in FIG. 27.

Example 4-5

Introduction of PUFA PKS Pathway-Associated Gene OrfA Targeting Vector

By using the targeting vectors produced in Examples 4-3 and 4-4 as templates, the gene was amplified with a PrimeSTAR Max DNA polymerase (Takara Bio) using the RHO30

(Example 4-3; SEQ ID NO: 116) and RHO33 (Example 4-3; SEQ ID NO: 112) as primers [PCR cycles: 98° C. 2 min/98° C. 30 sec, 60° C. 30 sec, 72° C. 1 min, 30 cycles/72° C. 3 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH21 (FIG. 25) of Example 4-3 as a template was 3,705 bp, and had the following sequence order: *Thraustochytrium aureum* OrfA gene upstream-EF1α promoter sequence-artificial neomycin-resistant gene sequence-*Thraustochytrium aureum* OrfA gene downstream (SEQ ID NO: 123). The introduced fragment obtained from using the pRH33 (FIG. 27) of Example 4-4 as a template was 3,826 bp, and had the following sequence order: Upstream of *Thraustochytrium aureum* OrfA gene-ubiquitin promoter sequence-hygromycin-resistant gene sequence-downstream of *Thraustochytrium aureum* OrfA gene (SEQ ID NO: 124).

The *Thraustochytrium aureum* ATCC 34304 strain was cultured in a GY medium for 4 days, and cells in the logarithmic growth phase were used for gene introduction. The DNA fragment (0.625 μg) was then introduced into cells corresponding to OD600=1 to 1.5 using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene were applied onto a PDA agar plate medium (containing 2 mg/ml G418 or 2 mg/ml hygromycin). As a result, 100 to 200 drug resistant strains were obtained per penetration.

Example 4-6

Identification of PUFA PKS Pathway-Associated Gene OrfA Gene Targeting Homologous Recombinant Genomic DNA was extracted from the *Thraustochytrium aureum* ATCC 34304, the hetero homologous recombinant, and the homo homologous recombinant (PKS pathway-associated gene disrupted strain) by using the method described in Example 3-2. The DNA concentration was calculated by measuring A260/280.

The genomic DNA was cut with restriction enzymes, and electrophoresed in about 2 to 3 μg per well with a 0.7% SeaKem GTG agarose gel (Takara Bio). This was transferred to a nylon membrane, and hybridized at 54° C. for 16 hours with the probes produced by using a DIG system (Roche Applied Science). The following primers were used for the probe production.

```
5' end
                                        (SEQ ID NO: 125)
[RHO37: 22 mer:
5'-GAA GCG TCC CGT AGA TGT GGT C-3', (SEQ ID NO: 126)
RHO38: 21 mer:
5'-GCC CGA GAG GTC AAA GTA CGC-3']

3' end
                                        (SEQ ID NO: 127)
[RHO39: 20 mer:
5'-GCG AGC CCA GGT CCA CTT GC-3', (SEQ ID NO: 128)
RHO40: 22 mer:
5'-CAG CCC GAT GAA AAA CTT GGT C-3']
```

PCR cycles: 98° C. 2 min/98° C. 30 sec, 60° C. 30 sec, 72° C. 2 min, 30 cycles/72° C. 3 min The restriction enzymes used and the probe positions are as shown in FIG. 28. Detection of the hybridized probes was made by using the chromogenic method (NBT/BCIP solution).

Bands of the sizes expected from the homologous recombination of the drug resistant genes were observed in the analyses of both the 5' end and the 3' end (FIG. 29).

Example 4-7

Changes in Fatty Acid Composition by Disruption of PUFA PKS Pathway-Associated Gene OrfA The *Thraustochytrium aureum* ATCC 34304 and the gene disrupted strain were cultured and freeze dried according to the methods of Example 3-9, and the fatty acids were methylesterificated, and GC analyzed.

FIG. 30 represents changes in fatty acid composition. FIG. 31 represents the proportions relative to the wild-type strain taken as 100%. FIG. 31 represents the proportion of each component based on the total amount of the fatty acids, which includes AA: 3.1%, DGLA: 0.2%, ETA: 0.04%, EPA: 6.8%, n-6DPA: 10.7%, and DHA: 22.6%, which can also be described as the values of GC area such as n-6DPA/DTA: 5.3, DHA/n-3DPA: 20.0, CO2OPUFA/C22PUFA: 0.3, and n-6PUFA/n-3PUFA: 0.5. As can be seen from these results, disrupting the PUFA PKS pathway-associated gene OrfA in the *Thraustochytrium aureum* tended to increase the DPA (C22: 5n-6) and decrease the DHA (C22: 6n-3).

EXAMPLE 5

[Disruption of C20 Elongase Gene in *Thraustochytrium aureum* OrfA Disrupted Strain]

Example 5-1

Cloning of Upstream Sequence of *Thraustochytrium aureum* C20 Elongase Gene

The genome cassette library produced in Example 4-1 was used as a template. A PCR lower primer [RHO71: 22 mer: 5'-GGG AGC GCA GGG AAAACG GTC T-3' (SEQ ID NO: 129)] was produced on the C20 elongase gene upstream sequence (SEQ ID NO: 24) of Example 2-5, and the gene was amplified by using this primer with the cassette primer attached to the kit used in Example 4-1 [1st PCR cycles: 98° C. 2 min/98° C. 30 sec, 56° C. 30 sec, 72° C. 4 min, 30 cycles/72° C. 5 min]. The 1st PCR amplification product was diluted 100 times, and the gene was amplified by using the PCR lower primer [RHO72: 20 mer: 5'-CCA GCC CAC GTC GTC GGA GC-3' (SEQ ID NO: 130)] with the nested primer attached to the kit used in Example 4-1 [2nd PCR cycles: 98° C. 2 min/98° C. 30 sec, 56° C. 30 sec, 72° C. 4 min, 30 cycles/72° C. 5 min]. The resulting DNA fragment was cloned into a pGEM-T easy vector, amplified with *Escherichia coli*, and the sequence was confirmed by using a Dye Terminator Cycle Sequencing Kit (BECKMAN COULTER).

The 2,297-bp DNA fragment (SEQ ID NO: 131) containing the upstream-3,277 bp to-981 bp region of the C20 elongase gene was cloned.

Example 5-2

Cloning of C20 Elongase Gene Downstream Sequence

The genome cassette library produced in Example 4-1 was used as a template. A PCR upper primer [RHO87: 23 mer: 5'-GCC GCT CAT GCC CAC GCT CAA AC-3' (SEQ ID NO: 132)] was produced on the C20 elongase gene downstream sequence (SEQ ID NO: 25) of Example 2-5, and the gene was amplified by using this primer with the cassette primer attached to the kit used in Example 4-1 [1st PCR cycles: 98° C. 2 min/98° C. 30 sec, 56° C. 30 sec, 72° C. 4 min, 30 cycles/72° C. 5 min]. The 1st PCR amplification product was diluted 100 times, and the gene was amplified by using the PCR lower primer [RHO73: 23 mer: 5'-CTT TCG GCT GCC AGG AAT CTA CG-3' (SEQ ID NO: 133)] with the nested primer attached to the kit used in Example 4-1 [2nd PCR cycles: 98° C. 2 min/98° C. 30 sec, 56° C. 30 sec, 72° C. 4 min, 30 cycles/72° C. 5 min]. The resulting DNA fragment was cloned into a pGEM-T easy vector, amplified with *Escherichia coli*, and the sequence was confirmed by using a Dye Terminator Cycle Sequencing Kit (BECKMAN COULTER).

The 2,189-bp DNA fragment (SEQ ID NO: 134) containing the downstream 1,106 bp to 3,294 bp region of the C20 elongase gene was cloned.

Example 5-3

Production of Blasticidin-Resistant Gene Cassette

A ubiquitin promoter sequence (618 bp, SEQ ID NO:135) was amplified with a PrimeSTAR HS DNA polymerase with GC Buffer (Takara Bio), using the *Thraustochytrium aureum* ATCC 34304 genomic DNA as a template. The PCR primers used are as follows. RHO53 was set on the ubiquitin promoter sequence, and contains a BglII linker sequence (Example 3-2, SEQ ID NO: 55). RHO48 contains the ubiquitin promoter sequence and a blasticidin-resistant gene sequence [RHO48: 58 mer: 5'-CTT CTT GAG ACA AAG GCT TGG CCA TGT TGG CTA GTG TTG CTT AGG TCG CTT GCT GCT G-3' (SEQ ID NO: 136)] [PCR cycles: 98° C. 2 min/98° C. 10 sec, 68° C. 1 min, 30 cycles/68° C. 1 min].

By using pTracer-CMV/Bsd/lacZ as a template, the blasticidin-resistant gene (432 bp, SEQ ID NO: 137) was amplified with a PrimeSTAR HS DNA polymerase with GC Buffer. The PCR primers used are as follows. RHO47 contains the ubiquitin promoter sequence and the blasticidin-resistant gene sequence. RHO49 contains the blasticidin-resistant gene sequence, and has a BglII linker sequence [RHO47: 54 mer:5'-AGC GAC CTA AGC AAC ACT AGC CAA CAT GGC CAA GCC TTT GTC TCA AGA AGA ATC-3' (SEQ ID NO: 138), RHO49: 38 mer: 5'-CCC AGA TCT TAG CCC TCC CAC ACA TAA CCA GAG GGC AG-3' (SEQ ID NO: 139)] [PCR cycles: 98° C. 2 min/98° C. 10 sec, 68° C. 1 min, 30 cycles/68° C. 1 min].

By using SEQ ID NOS: 135 and 137 as templates, a fusion PCR was performed with RHO53 (Example 3-2, SEQ ID NO: 55) and RHO49 (SEQ ID NO: 139) according to the method described in Non-Patent Document 19. An LA taq Hot start version (Takara Bio) was used as the enzyme. After the amplification performed under the following conditions, the product was digested with BglII [PCR cycles: 94° C. 2 min/94° C. 20 sec, 55° C. 30 sec, 68° C. 1 min, 30 cycles/68° C. 1 min (1° C./10 sec from 55° C. to 68° C.)] (FIG. 32).

The fused *Thraustochytrium aureum* ATCC 34304-derived ubiquitin promoter-pTracer-CMV/Bsd/lacZ-derived blasticidin-resistant gene (1,000 bp, SEQ ID NO: 140) was digested with BglII, and ligated to the BamHI site of the pRH27 (FIG. 11) of Example 3-1. The resulting plasmid was amplified with *Escherichia coli*, and the sequence was confirmed by using a Dye Terminator Cycle Sequencing Kit (BECKMAN COULTER). This was named pRH38.

The product blasticidin-resistant gene cassette (pRH38) is shown in FIG. 33.

Example 5-4

Production of GFP-Fused Zeocin-Resistant Gene Cassette

By using the *Thraustochytrium aureum* ATCC 34304 genomic DNA as a template, a ubiquitin promoter sequence (812 bp, SEQ ID NO: 141) was amplified with a PrimeSTAR HS DNA polymerase with GC Buffer (Takara Bio). The PCR primers used are as follows. TMO38 was set on the ubiquitin promoter sequence. TMO39 contains the ubiquitin promoter sequence and an enhanced GFP gene sequence [TMO38: 29 mer: 5'-TCG GTA CCC GTT AGA ACG CGT AAT ACG AC-3' (SEQ ID NO: 142), TMO39: 41 mer: 5'-TCC TCG CCC TTG CTC ACC ATG TTG GCT AGT GTT GCT TAG GT-3' (SEQ ID NO: 143)] [PCR cycles: 98° C. 10 sec/98° C. 10 sec, 58° C. 30 sec, 72° C. 1 min, 30 cycles/72° C. 1 min].

By using the enhanced GFP gene sequence (clontech) as a template, an enhanced GFP gene sequence (748 bp, SEQ ID NO: 144) was amplified with a PrimeSTAR HS DNA polymerase (Takara Bio). The PCR primers used are as follows. TMO40 contains the ubiquitin promoter sequence and the enhanced GFP gene sequence. RHO91 contains the enhanced GFP sequence and a zeocin-resistant gene sequence [TMO40: 41 mer: 5'-ACC TAA GCA ACA CTA GCC AAC ATG GTG AGC AAG GGC GAG GA-3' (SEQ ID NO: 145), RHO91: 58 mer: 5'-GAA CGG CAC TGG TCA ACT TGG CGT CCA TGC CGA GAG TGA TCC CGG CGG CGG TCA CGA A-3' (SEQ ID NO: 146)] [PCR cycles: 98° C. 10 sec/98° C. 10 sec, 58° C. 30 sec, 72° C. 2 min, 30 cycles/72° C. 2 min].

By using SEQ ID NOS: 141 and 144 as templates, a fusion PCR was performed with an LA taq Hot start version (Takara Bio) according to the method described in Non-Patent Document 19. TMO38 (SEQ ID NO: 142) and RHO91 (SEQ ID NO: 146) were used as primers, and the reaction was performed under the following conditions [PCR cycles: 94° C. 2 min/94° C. 20 sec, 55° C. 30 sec, 68° C. 2 min, 30 cycles/68° C. 2 min (1° C./10 sec from 55° C. to 68° C.)] (FIG. 34, 1,519 bp, SEQ ID NO: 147).

By using SEQ ID NO: 147 as a template, the ubiquitin promoter sequence-enhanced GFP gene sequence (1,319 bp, SEQ ID NO: 148) was amplified with a PrimeSTAR HS DNA polymerase (Takara Bio). The primers used are as follows. RHO53 (Example 3-2, SEQ ID NO: 55) contains the ubiquitin promoter sequence, and has a BglII site. RHO91 (SEQ ID NO: 146) contains the enhanced GFP sequence and the zeocin-resistant gene sequence [PCR cycles: 98° C. 2 min/98° C. 10 sec, 68° C. 2 min, 30 cycles/68° C. 2 min].

By using pcDNA3.1 Zeo(+) as a template, the zeocin-resistant gene sequence (408 bp, SEQ ID NO: 149) was amplified with a PrimeSTAR HS DNA polymerase (Takara Bio). RHO92 contains the enhanced GFP sequence and the zeocin-resistant gene sequence. RHO64 contains the zeocin-resistant gene sequence, and has a BglII site [RHO92: 54 mer: 5'-CGC CGC CGG GAT CAC TCT CGG CAT GGA CGC CAA GTT GAC CAG TGC CGT TCC GGT-3' (SEQ ID NO: 150), RHO64: 38 mer: 5'-CCC AGA TCT CAG TCC TGC TCC TCG GCC ACG AAG TGC AC-3' (SEQ ID NO: 151)] [PCR cycles: 98° C. 2 min/98° C. 10 sec, 68° C. 1 min, 30 cycles/68° C. 1 min].

By using SEQ ID NOS: 148 and 149 as templates, a fusion PCR was performed with an LA taq Hot start version (Takara Bio) according to the method described in Non-Patent Document 19. RHO53 (Example 3-2, SEQ ID NO: 55) and RHO64 (SEQ ID NO: 151) were used as primers, and the reaction was performed under the following conditions [PCR cycles: 94° C. 2 min/94° C. 20 sec, 68° C. 2 min, 30 cycles/68° C. 2 min (1° C./10 sec from 55° C. to 68° C.)] (FIG. 35).

The fused *Thraustochytrium aureum* ATCC 34304-derived ubiquitin promoter-enhanced GFP gene-pcDNA3.1 Zeo(+) -derived zeocin-resistant gene (FIG. 35, 1,677 bp, SEQ ID NO: 152) was digested with BglII, and ligated to the BamHI site of the pRH27 (FIG. 11) of Example 3-1. The resulting plasmid was amplified with *Escherichia coli*, and the sequence was confirmed by using a Dye Terminator Cycle Sequencing Kit (BECKMAN COULTER). This was named pRH51.

The product GFP-fused zeocin-resistant gene cassette (pRH51) is shown in FIG. 36.

Example 5-5

Production of Base Plasmid for C20 Elongase Gene Targeting Vector Production

By using the *Thraustochytrium aureum* ATCC 34304 genomic DNA as a template, the C20 elongase gene and the nearby sequences (2,884 bp, SEQ ID NO: 153) were PCR amplified with a PrimeSTAR HS DNA polymerase (Takara Bio). The PCR primers used are as follows. The both primers contain EcoRI linker sequences. KSO9 was set upstream of the C20 elongase gene (SEQ ID NO: 24), and KSO10 downstream of the C20 elongase gene (SEQ ID NO: 25) [K509: 50 mer: 5'-CCC GAA TTC ACT AGT GAT TCT CCC GGG TGG ACC TAG CGC GTG TGT CAC CT-3' (SEQ ID NO: 154), KS010: 40 mer: 5'-CCC GAA TTC GAT TAT CCC GGG GCC GAG AAC GGG GTC GCC C-3' (SEQ ID NO: 155)] [PCR cycles: 98° C. 2 min/98° C. 10 sec, 68° C. 3.5 min, 30 cycles/68° C. 10 min]. A PrimeSTAR HS DNA Polymerase (Takara Bio) was used as the enzyme. After the amplification, the product was digested with EcoRI, and cloned into the EcoRI site of the pBluescript (SK) (stratagene) vector. After amplification with *Escherichia coli*, the sequence was confirmed by using a Dye Terminator Cycle Sequencing Kit (BECKMAN COULTER) (FIG. 37).

By using the plasmid of FIG. 37 as a template, amplification was performed with a PrimeSTAR Max DNA Polymerase (TakaraBio), using a primer set of the reverse orientation prepared for the deletion of the C20 elongase gene sequence portion and the insertion of a BglII site (1,939 bp, SEQ ID NO: 156). The PCR primers used are as follows. The both primers have BglII linker sequences [RHO69: 38 mer: 5'-CCC AGA TCT ACC TGT TTC CGG CTG GCT CCC GAG CCA TG-3' (SEQ ID NO: 157), RHO70: 38 mer: 5'-CCC AGA TCT GGT CGC GTT TAC AAA GCA GCG CAG CAA CA-3' (SEQ ID NO: 158)] [PCR cycles: 98° C. 2 min/98° C. sec, 68° C. 1.5 min, 30 cycles/68° C. 1.5 min]. After the amplification performed under these conditions, the product was digested with BglII, and allowed to self ligate. The ligated sample was amplified with *Escherichia coli*, and the sequence was confirmed with a Dye Terminator Cycle Sequencing Kit (BECKMAN COULTER). This was named pRH40.

The produced base plasmid (pRH40) for the production of the C20 elongase gene targeting vector is shown in FIG. 38.

Example 5-6

Production of Targeting Vectors (Blasticidin-Resistant Gene and GFP-Fused Zeocin-Resistant Gene)

The pRH38 (FIG. 33) of Example 5-3 was digested with BglII, and the DNA fragment containing the blasticidin-resistant gene cassette was ligated to the BglII site of the pRH40 (FIG. 38) of Example 5-5. This was named pRH43.

The pRH51 (FIG. 36) of Example 5-4 was digested with BglII, and the DNA fragment containing the GFP-fused zeocin-resistant gene cassette was ligated to the BglII site of the pRH40 (FIG. 38) of Example 5-5. This was named pRH54.

The two targeting vectors (pRH43 and 54) produced are shown in FIG. 39.

Example 5-7

Introduction of C20 Elongase Gene Targeting Vector into *Thraustochytrium aureum* OrfA Disrupted Strain By using the two targeting vectors produced in Example 5-6 as templates, the gene was amplified with a PrimeSTAR Max DNA polymerase (Takara Bio), using KSO11 and KSO12 as primers. KSO11 was set upstream of the *Thraustochytrium aureum* C20 elongase gene, and KSO12 downstream of the *Thraustochytrium aureum* C20 elongase gene [KSO11: 31 mer: 5'-CTC CCG GGT GGA CCT AGC GCG TGT GTC ACC T-3' (SEQ ID NO: 159), KSO12: 27 mer: 5'-ATC CCG GGG CCG AGA ACG CCC TCG CCC-3' (SEQ ID NO: 160)] [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH43 (FIG. 39) of Example 5-6 as a template was 3,215 bp, and had the following sequence order: Upstream of *Thraustochytrium aureum* C20 elongase gene-ubiquitin promoter-blasticidin-resistant gene sequence-SV40 terminator sequence-downstream of *Thraustochytrium aureum* C20 elongase gene (SEQ ID NO: 161). The introduced fragment obtained from using the pRH54 (FIG. 39) of Example 5-6 as a template was 3,887 bp, and had the following sequence order: Upstream of *Thraustochytrium aureum* C20 elongase gene-ubiquitin promoter-enhanced GFP gene sequence-zeocin-resistant gene sequence-SV40 terminator sequence-downstream of *Thraustochytrium aureum* C20 elongase gene (SEQ ID NO: 162).

The disrupted strain of the PUFA PKS pathway-associated gene OrfA gene described in Example 4 was cultured in a GY medium for 4 days, and cells in the logarithmic growth phase were used for gene introduction. The DNA fragment (0.625 µg) was then introduced into cells corresponding to OD600=1 to 1.5 using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene were applied onto a PDA agar plate medium (containing 2 mg/ml G418 or 2 mg/ml hygromycin). As a result, 100 to 200 drug resistant strains were obtained per penetration.

Example 5-8

Identification of C20 Elongase Gene Gene Targeting Homologous Recombinant

Genomic DNA was extracted from the *Thraustochytrium aureum* and the C20 elongase gene disrupted strain of the *Thraustochytrium aureum* OrfA disrupted strain by using the method described in Example 3-2. The DNA concentration was calculated by measuring A260/280.

The genomic DNA was cut with restriction enzymes, and electrophoresed in about 2 to 3 µg per well in a 0.7% SeaKem GTG agarose gel (Takara Bio). This was transferred to a nylon membrane, and hybridized at 51° C. for 16 hours with the probes produced by using a DIG system (Roche Applied Science). The following primers were used for the probe production.

```
5' end
                                      (SEQ ID NO: 163)
[RHO94: 21 mer:
5'-ACG TCC GCT TCA AAC ACC TCG-3', (SEQ ID NO: 164)
RHO95: 24 mer:
5'-TCG GAA CAA CTG GAA CAA CTA AAG-3']

3' end
                                      (SEQ ID NO: 165)
[RHO96: 22 mer:
5'-ATG TCG CTC TCC TTC TTC TCA G-3', (SEQ ID NO: 166)
RHO97: 21 mer:
5'-TCG GCT CCT GGA AAG TGC TCT-3']
```

PCR cycles: 98° C. 2 min/98° C. 30 sec, 58° C. 30 sec, 72° C. 1 min, 30 cycles/72° C. 3 min The restriction enzymes used and the probe positions are as shown in FIG. 40. Detection of the hybridized probes was made by using a chromogenic method (NBT/BCIP solution).

Bands of the sizes expected from the homologous recombination of the drug resistant genes were observed in the analyses of both the 5' end and the 3' end (FIG. 41). It was found by the experiment that the *Thraustochytrium aureum* ATCC 34304 strain did not become auxotrophic even with the deletion of the PKS pathway-associated gene OrfA and the C20 elongase gene.

Example 5-9

Changes in Fatty Acid Composition by Disruption of C20 Elongase Gene in *Thraustochytrium aureum* OrfA Disrupted Strain The *Thraustochytrium aureum* ATCC 34304 and the gene disrupted strain were cultured and freeze dried according to the method of Example 3-9, and the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

Changes in fatty acid composition are represented in FIG. 42. FIG. 43 represents the proportions relative to the wild-type strain taken as 100%. FIG. 43 represents the proportion of each component based on the total amount of the fatty acids, which includes AA: 19.5%, DGLA: 1.8%, ETA: 0.3%, EPA: 24.9%, n-6D PA: 5.9%, and DHA: 6.8%, which can also be described as the values of GC area such as n-6DPA/DTA: 12.6, DHA/n-3DPA: 11.7, CO2PUFA/C22PUFA: 3.4, and n-6PUFA/n-3PUFA: 0.8.

As can be seen from these results, disrupting the C20 elongase gene in the *Thraustochytrium aureum* OrfA disrupted strain increased the C20:4n-6 (AA) about eight-fold, and the C20:5n3 (EPA) about four-fold, and decreased the C22:6n-3 (DHA) to about ⅕.

EXAMPLE 6

[Expression of ω3 Desaturase Gene in *Thraustochytrium aureum* OrfA Disrupted Strain]

Example 6-1

Cloning of *Saprolegnia Diclina*-Derived ω3 Desaturase Gene and Production of Gene Expression Plasmid Genomic DNA was extracted from the *Thraustochytrium aureum* ATCC 34304 by using the method of Example 3-2, and the DNA concentration was calculated by measuring A260/280. By using this as a template, the ubiquitin promoter sequence (longer) (812 bp, SEQ ID NO: 167) was amplified with an LA Taq with GC Buffer (Takara Bio, Buffer II was used). The PCR primers used are as follows. TMO42 was set on the ubiquitin promoter sequence, upstream of RHO53 (Example 3-2, SEQ ID NO: 55), and contains a KpnI linker sequence. TMO43 contains the ubiquitin promoter sequence and a *Saprolegnia diclina*-derived ω3 desaturase gene sequence [TMO42: 29 mer: 5'-TCG GTA CCC GTT AGA ACG CGT AAT ACG AC-3' (SEQ ID NO: 168), TMO43: 45 mer: 5'-TTC GTC TTA TCC TCA GTC ATG TTG GCT AGT GTT GCT TAG GTC GCT-3' (SEQ ID NO: 169)] [PCR cycles: 96° C. 2 min/98° C. 20 sec, 60° C. 30 sec, 72° C. 1 min, 30 cycles/72° C. 1 min].

Then, *Saprolegnia diclina* was cultured in a medium (adjusted with deionized water) containing D-Glucose (31.8 g) and yeast extract (10.6 g) per liter. Cells in the late stage of the logarithmic growth phase were centrifuged at 4° C., 3,500×g for 5 min to form a pellet, and disrupted by being frozen with liquid nitrogen. After being extracted with phenol, the cell disruption liquid was precipitated with ethanol, and the precipitate was dissolved in a TE solution. The nucleic acids dissolved in the TE solution were treated with RNase at 37° C. for 30 min to degrade RNA. After being reextracted with phenol, the product was precipitated with ethanol, and the precipitate was dissolved in a TE solution.

The DNA purity and concentration were calculated by measuring A260/280. By using the resulting *Saprolegnia diclina* genomic DNA as a template, the *Saprolegnia diclina*-derived ω3 desaturase gene sequence (1,116 bp, SEQ ID NO: 170) was amplified with an LA Taq with GC Buffer (Takara Bio, Buffer II was used). The PCR primers used are as follows. TMO44 contains the ubiquitin promoter sequence and the *Saprolegnia diclina*-derived ω3 desaturase gene sequence. TMO45 contains the *Saprolegnia diclina*-derived ω3 desaturase gene sequence and the ubiquitin terminator [TMO44: 43 mer: 5'-CCT AAG CAA CAC TAG CCA ACA TGA CTG AGG ATA AGA CGA AGG T-3' (SEQ ID NO: 171), TMO45: 40 mer: 5'-ATA CTA CAG ATA GCT TAG TTT TAG TCC GAC TTG GCC TTG G-3' (SEQ ID NO: 172)] [PCR cycles: 96° C. 2 min/98° C. 20 sec, 60° C. 30 sec, 72° C. 1 min 30 sec, 30 cycles/72° C. 1 min 30 sec].

By using the *Thraustochytrium aureum* ATCC 34304 genomic DNA as a template, the ubiquitin terminator sequence (614 bp, SEQ ID NO: 173) was amplified with an LA Taq with GC Buffer (Takara Bio, Buffer II was used). The primers used are as follows. TMO46 contains the *Saprolegnia diclina*-derived ω3 desaturase gene sequence and the ubiquitin terminator. TMO47 was designed on the ubiquitin terminator sequence, and contains a KpnI linker sequence [TMO46: 44 mer: 5'-CCA AGG CCA AGT CGG ACT AAA ACT AAG CTA TCT GTA GTA TGT GC-3' (SEQ ID NO: 174), TMO47: 45 mer: 5'-TCG GTA CCA CCG CGT AAT ACG ACT CAC TAT AGG GAG ACT GCA GTT-3' (SEQ ID NO: 175)] [PCR cycles: 96° C. 2 min/98° C. 20 sec, 60° C. 30 sec, 72° C. 1 min, 30 cycles/72° C. 1 min].

By using SEQ ID NOS: 167, 170, and 173 as templates, a fusion PCR was performed with TMO42 (SEQ ID NO: 168) and TMO47 (SEQ ID NO: 175) according to the method described in Non-Patent Document 19. An LA Taq with GC Buffer (Takara Bio, Buffer II was used) was used as the enzyme, and the amplification was performed under the following conditions [PCR cycles: 96° C. 2 min/98° C. 20 sec, 55° C. 30 sec, 68° C. 3 min, 30 cycles/68° C. 3 min (1° C./10 sec from 55° C. to 68° C.] (FIG. 44, 2,463 bp, SEQ ID NO: 176).

By using the pRH38 (FIG. 33) of Example 5-3 as a template, a PCR was performed with RHO84 (SEQ ID NO: 177, the sequence is presented below) and RHO52 (Example 3-1, SEQ ID NO: 52). RHO84 was set on the ubiquitin promoter, and has a KpnI linker sequence. RHO52 was set on the SV40 terminator sequence, and has a BglII linker. An LA taq Hot start version was used as the enzyme, and, after the amplification performed under the following conditions, the product was cloned into a pGEM-T easy vector [RHO84: 36 mer: 5'-CCC GGT ACC GCC GCA GCG CCT GGT GCA CCC GCC GGG-3' (SEQ ID NO: 177)] [PCR cycles: 98° C. 2 min/98° C. 10 sec, 68° C. 1 min 30 sec, 30 cycles/68° C. 3 min]. After amplification with *Escherichia coli*, the sequence was confirmed by using a Dye Terminator Cycle Sequencing Kit (BECKMAN COULTER). This was named pRH45 (FIG. 45).

The fused *Thraustochytrium aureum* ATCC 34304-derived ubiquitin promoter-*Saprolegnia diclina*-derived ω3 desaturase gene-*Thraustochytrium aureum* ATCC 34304-derived ubiquitin terminator (SEQ ID NO: 176; FIG. 44) was digested with KpnI, and ligated to the KpnI site of pRH45 (FIG. 45). The resulting plasmid was amplified with *Escherichia coli*, and the sequence was confirmed by using a Dye Terminator Cycle Sequencing Kit (BECKMAN COULTER). This was named pRH48.

The product *Saprolegnia diclina*-derived ω3 desaturase gene expression plasmid (pRH48) is shown in FIG. 46.

Example 6-2

Introduction of *Saprolegnia Diclina*-Derived ω3 Desaturase Expression Plasmid into *Thraustochytrium aureum* OrfA Disrupted Strain By using the targeting vector produced in Example 6-1 as a template, DNA was amplified with a PrimeSTAR Max DNA polymerase (Takara Bio), using TMO42 (SEQ ID NO: 168) and RHO52 (Example 3-1, SEQ ID NO: 52) as primers [PCR cycles: 94° C. 30 sec, 72° C. 1 min, 5 cycles/94° C. 30 sec, 70° C. 30 sec, 72° C. 1 min, 5 cycles/94° C. 30 sec, 68° C. 30 sec, 72° C. 1 min, 25 cycles/72° C. 2 min]. The amplification product was collected from the 1.0% agarose gel, and precipitated with ethanol. The precipitate was then dissolved in 0.1×TE. The DNA concentration was calculated by measuring A260/280. The introduced fragment obtained by PCR was 3,777 bp, and had the following sequence order: ubiquitin promoter-ω3 desaturase gene-ubiquitin terminator-ubiquitin promoter-blasticidin-resistant gene sequence-SV40 terminator sequence (SEQ ID NO: 178).

The *Thraustochytrium aureum* OrfA disrupted strain produced in Example 4 was cultured in a GY medium for 4 days, and cells in the logarithmic growth phase were used for gene introduction. The DNA fragment (0.625 µg) was then introduced into cells corresponding to OD600=1 to 1.5 using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene were applied to a PDA agar plate medium (containing 0.2 mg/ml blasticidin). As a result, 20 to 30 drug resistant strains were obtained per penetration.

Example 6-3

Acquisition of *Saprolegnia Diclina*-Derived ω3 Desaturase Gene Expression Strain Genomic DNA was extracted from the *Thraustochytrium aureum* OrfA disrupted strain produced in Example 3 and the ω3 desaturase gene expressing strain by using the method described in Example 3-2. The DNA concentration was calculated by measuring A260/280. By using this as a template, a PCR was performed with an LA taq Hot start version to confirm the genome structure. The positions of the primers, combinations used for the amplification, and the expected size of the amplification product are shown in FIG. 47. TMO42 (Example 6-1, SEQ ID NO: 168) was set on the ubiquitin promoter. RHO49 (Example 5-3, SEQ ID NO: 139) was set on the blasticidin-resistant gene [PCR cycles: 98° C. 2 min/98° C. 10 sec, 68° C. 4 min, 30 cycles/68° C. 7 min].

The result of the amplification confirmed a band of the expected size (FIG. 48). That is, a strain was isolated that contained the introduced expression fragment stably introduced into its genome.

Example 6-4

Changes in Fatty Acid Composition by ω3 Desaturase Expression in PUFA PKS Pathway Disrupted Strain The *Thraustochytrium aureum* OrfA disrupted strain produced in Example 4, and the ω3 desaturase expressing strain produced in Example 6-3 were cultured by using the method described in Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

The ω3 desaturase expressing strain had reduced levels of the n-6 series fatty acids, and there was a tendency for the n-3 series fatty acids to increase (FIG. 49). FIG. 50 represents the proportions relative to the wild-type strain taken as 100%. FIG. 50 represents the proportion of each component based on the total amount of the fatty acids, which includes AA: 1.5%, DGLA: 1.8%, ETA: 0.5%, EPA: 11.4%, n-6DPA: 1.2%, and DHA: 22.0%, which can also be described as the values of GC area such as n-6DPA/DTA: 0.6, DHA/n-3DPA: 5.7, C20PUFA/C22PUFA: 0.5, and n-6PUFA/n-3PUFA: 0.2.

As a result, the arachidonic acid was reduced to about ⅕, and the DPA to about ⅒. EPA and DHA increased by a factor of about 3.

EXAMPLE 7

[Disruption of *Thraustochytrium roseum* C20 Elongase Gene]

Example 7-1

Cloning of *T. Roseum*-Derived C20 Elongase Gene

A forward denatured oligonucleotide (EL020F;5'-ATH GAR TWY TKB RTI TTY GTI CA-3') (SEQ ID NO: 179) and a reverse denatured oligonucleotide (EL020R;5'-TAR TRI SWR TAC ATI ADI AMR TG-3') (SEQ ID NO: 180) were synthesized by targeting a conserved region in the C20 elongase gene of the *Thraustochytrium roseum* ATCC 28210 strain. Then, a PCR was performed with an Advantage 2 Polymerase Mix (Clontech), using the *T. roseum* genomic DNA extracted by using the same technique described in the method of Example 2-5 as a template [PCR cycles: 94° C. 1 min/94° C. 30 sec, 55° C. 30 sec, 72° C. 1 min, 30 cycles/72° C. 7 min/4° C. ∞]. The resulting specific product was isolated by 2% agarose gel electrophoresis, and purified. The DNA fragment was then TA cloned with a pGEM-T easy Vector (Promega), and the base sequence was analyzed. The sequence showed significant sequence identity with the sequence of a known *T. aureum*-derived C20 elongase gene, suggesting that the sequence was a partial sequence of the T. roseum-derived C20 elongase gene.

This was followed by cloning of the *T. roseum*-derived C20 elongase gene by 3'- and 5'-RACE, as in Example 2-2. First, the following oligonucleotide primers were designed.

```
Forward oligonucleotide primer
                                     (SEQ ID NO: 181)
(8 F1; 5'-CTG ACA AAG TTT CTC GAC TGG AGC GAC

A-3')

Reverse oligonucleotide primers
                                     (SEQ ID NO: 182)
(8 R1; 5'-TAC GCG GCG GTG CCC GAG CCC CAG-3')
and
```

-continued
```
                                     (SEQ ID NO: 183)
(8 R2; 5'-TGC CGA TCG TTG CGT GGT GGA ACA CCT

G-3')
```

This was followed by 3'- and 5'-RACE using a synthetic adapter-specific oligonucleotide, and the oligonucleotide 8 F1 or 8 R1, using the cDNA library created with a SMART™ RACE cDNA Amplification Kit (clontech) as a template [PCR cycles: 94° C. 30 sec 5 cycles/94° C. 30 sec, 70° C. 30 sec, 72° C. 3 min, 5 cycles/94° C. 30 sec, 68° C. 30 sec, 72° C. 3 min, 25 cycles/4° C. ∞]. In the 5'RACE, a nested PCR was performed by using a synthetic adapter-specific oligonucleotide and the oligonucleotide 8 R2, using the RACE product as a template [PCR cycles: 94° C. 1 min/94° C. 30 sec, 68° C. 30 sec, 72° C. 3 min, 25 cycles/72° C. 10 min/4° C. ∞]. The both specific products were gel purified, and the base sequence was analyzed after being TA cloned with a pGEM-T easy Vector (Promega). There was a complete match with the *T. aureum*. ATCC 34304-derived C20 elongase (TaELO2) (SEQ ID NO: 16) of Example 2-2.

Then, a forward oligonucleotide (8 ORF F; 5'-ATG GCG ACG CGC ACC TCG AA-3') (SEQ ID NO: 184) and a reverse oligonucleotide (8 ORF R; 5'-TTA CTC GGA CTT GGT GGG GGC G-3') (SEQ ID NO: 185) for amplifying a putative translated sequence were synthesized, and a PCR was performed with an Advantage GC 2 polymerase Mix (Clontech), using the *T. roseum* genomic DNA as a template [PCR cycles: 94° C. 1 min/94° C. 30 sec, 65° C. 30 sec, 72° C. 1 min, 30 cycles/72° C. 7 min/4° C. ∞]. The resulting specific product was gel purified, and the base sequence was analyzed by direct sequencing. The *T. roseum*-derived C20 elongase gene was found to be identical to the TaELO2. As demonstrated above, the sequence had a complete match with the sequence of the *Thraustochytrium aureum* C20 elongase. The base sequence is represented by SEQ ID NO: 186, and the amino acid sequence by SEQ ID NO: 187.

Example 7-2

Production of Base Plasmid for C20 Elongase Gene Targeting Vector Production

The *Thraustochytrium aureum* ATCC 34304 strain was cultured in a GY medium. Cells at the late stage of the logarithmic growth phase were centrifuged at 4° C., 3,500×g for 5 min to form a pellet, and disrupted after being frozen with liquid nitrogen. After being extracted with phenol, the cell disruption liquid was precipitated with ethanol, and the precipitate was dissolved in a TE solution. The nucleic acids dissolved in the TE solution were treated with RNase at 37° C. for 30 min to degrade the RNA. After being reextracted with phenol, the product was precipitated with ethanol, and the precipitate was dissolved in a TE solution. The DNA concentration was calculated by measuring A260/280. By using this as a template, the sequence (3,193 bp, SEQ ID NO: 188) containing the C20 elongase gene sequence was amplified with an LA taq Hot start version (Takara Bio) [PCR cycles: 98° C. 2 min/98° C. 10 sec, 68° C. 1 min, 30 cycles/68° C. 2 min]. The E2 KO ProF EcoRV (SEQ ID NO: 33) and E2KO TermR EcoRV (SEQ ID NO: 34) of Example 2-8 were used as PCR primers. The resulting DNA fragment was cloned into a pGEM-T easy vector (Promega), amplified with *Escherichia coli*, and the sequence was confirmed by using a Dye Terminator Cycle Sequencing Kit (BECKMAN COULTER). This was named pRH59 (FIG. 51).

By using the pRH59 (FIG. 51) as a template, amplification was performed with a PrimeSTAR Max DNA Polymerase (Takara Bio) using a primer set of the reverse orientation prepared for the insertion of the BglII site in a portion halfway along the C20 elongase gene sequence. The primers used are as follows. The both primers have BglII linker sequences [RHO120: 27 mer: 5'-GAC AAA GAT CTC GAC TGG AGC GAC CAC-3' (SEQ ID NO: 189), RHO121: 27 mer: 5'-GTC GAG ATC TTT TGT CAG GAG GTG CAC-3' (SEQ ID NO: 190)] [PCR cycles: 98° C. 2 min/98° C. 10 sec, 56° C. 15 sec, 72° C. 1 min, 30 cycles/72° C. 1 min]. After the amplification performed under these conditions, the product was digested with BglII, and allowed to self ligate. The ligated sample was amplified with *Escherichia coli*, and the sequence was confirmed by using a Dye Terminator Cycle Sequencing Kit (BECKMAN COULTER). This was named pRH64. The C20 elongase gene sequence 951 bp with the inserted BglII site is represented by SEQ ID NO: 191.

The produced base plasmid (pRH64) for the production of the *Thraustochytrium roseum* C20 elongase gene targeting vector is shown in FIG. 52.

Example 7-3

Production of Targeting Vectors (Artificial Neomycin-Resistant Gene and Hygromycin-Resistant Gene)

The pRH31 (FIG. 13) of Example 3-2 was digested with BglII, and the DNA fragment containing an artificial neomycin-resistant gene cassette was ligated to the BglII site of the pRH64 (FIG. 52) of Example 7-2. This was named pRH65.

The pRH32 (FIG. 15) of Example 3-3 was digested with BglII, and the DNA fragment containing a hygromycin-resistant gene cassette was ligated to the BglII site of the pRH64 (FIG. 52) of Example 7-2. This was named pRH66.

The two targeting vectors (pRH65 and 66) produced are shown in FIG. 53.

Example 7-4

Introduction of C20 Elongase Gene Targeting Vector

By using the two targeting vectors produced in Example 7-3 as templates, the gene was amplified with a PrimeSTAR GXL polymerase (Takara Bio), using a forward primer containing a translation initiation site (RHO130: 5'-ATG GCG ACG CGC ACC TCG AAG AG-3') (SEQ ID NO: 192) and a reverse primer containing a translation termination site (RHO131: 5'-TTA CTC GGA CTT GCT GGG GGC GC) (SEQ ID NO: 193) as primers [PCR cycles: 98° C. 2 min/98° C. 30 sec, 60 30 sec, 72° C. 3 min, 30 cycles]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH65 (FIG. 53) of Example 7-3 as a template was 2,655 bp, and had the following sequence order: First half of *Thraustochytrium aureum* C20 elongase gene-SV40 terminator sequence-artificial neomycin-resistant gene sequence-ubiquitin promoter sequence-second half of *Thraustochytrium aureum* C20 elongase gene (SEQ ID NO: 194). The introduced fragment obtained from using the pRH66 (FIG. 53) of Example 7-3 as a template was 2,887 bp, and had the following sequence order: First half of *Thraustochytrium aureum* C20 elongase gene-ubiquitin promoter sequence-hygromycin-resistant gene sequence-SV40 terminator sequence-second half of *Thraustochytrium aureum* C20 elongase gene (SEQ ID NO: 195).

The *Thraustochytrium roseum* strain was cultured in a GY medium for 7 days, and cells in the logarithmic growth phase were used for gene introduction. The DNA fragment (0.625 μg) was then introduced into cells corresponding to OD600=1 to 1.5 using the gene-gun technique under the following conditions (microcarrier: 0.6-micron gold particles, target distance: 6 cm, chamber vacuum: 26 mmHg, rupture disk: 900 PSI). After a 24-hour recovery time, the cells with the introduced gene were applied to a PDA plate medium (containing 2 mg/ml G418 or 2 mg/ml hygromycin).

As a result, about 20 drug resistant strains were obtained per penetration.

Example 7-5

Identification of C20 Elongase Gene Gene Targeting Homologous Recombinant

The *Thraustochytrium roseum* ATCC 28210 strain, the C20 elongase gene hetero homologous recombinant, and the C20 elongase gene homo homologous recombinant (gene disrupted strain) were cultured in GY media. The resulting cells were centrifuged at 4° C., 3,000 rpm for 10 min to form a pellet, and lysed at 55° C., 6 h/99.9° C., 5 min after being suspended in a 20-μl SNET solution [20 mM Tris-HCl; pH 8.0, 5 mM NaCl, 0.3% SDS, 200 μg/ml Proteinase K (nacalaitesque)]. The resulting cell lysate was diluted 10 times and used as a template in a PCR performed with a Mighty Amp DNA polymerase (Takara Bio) to confirm the genome structure. The positions of the primers, combinations used for the amplification, and the expected sizes of the amplification products are shown in FIG. 54. RoseumF and RoseumR were set upstream and downstream of the C20 elongase, respectively. NeoF and NeoR were set on the artificial neomycin-resistant gene. HygF and HygR were set on the hygromycin-resistant gene [RoseumF: 26 mer: 5'-GCT CGG CTG GAA GTT GAG TAG TTT GC-3' (SEQ ID NO: 196), RoseumR: 24 mer: 5'-TCT TTC TTC GTC GAC GTC CCA CTG-3' (SEQ ID NO: 197), NeoF: 24 mer: 5'-ATG ATT GAA CAG GAC GGC CTT CAC-3' (SEQ ID NO: 198), NeoR: 24 mer: 5'-TCA AAA GAA CTC GTC CAG GAG GCG-3' (SEQ ID NO: 199), HygF: 24 mer: 5'-ATG AAA AAG CCT GAA CTC ACC GCG-3' (SEQ ID NO: 200), HygR: 25 mer: 5'-CTA TTC CTT TGC CCT CGG ACG AGT G-3' (SEQ ID NO: 201)] [PCR cycles: 98° C. 2 min/98° C. 10 sec, 60° C. 15 sec, 68° C. 4 min, 30 cycles].

C20 elongase knockout strains were obtained that showed no amplification of the wild-type allele (Wt allele) but showed amplification of the artificial neomycin-resistant gene allele (NeoR allele) and hygromycin-resistant gene allele (HygR allele) (FIG. 55).

Example 7-6

Changes in Fatty Acid Composition by C20 Elongase Disruption

The *Thraustochytrium roseum* ATCC 28210 strain and the gene disrupted strain were cultured in GY media. Cells at the late stage of the logarithmic growth phase were centrifuged at 4° C., 3,000 rpm for 10 min to form a pellet, suspended in 0.9% NaCl, and washed. The cells were further centrifuged at 4° C., 3,000 rpm for 10 min, and the pellet was suspended in sterile water, and washed. This was centrifuged at 3,000 rpm for 10 min, and freeze dried after removing the supernatant. Then, 2 ml-methanolic KOH (7.5% KOH in 95% methanol) was added to the freeze dried cells, and, after being vortexed, the cells were ultrasonically disrupted (80° C., 30 min). The cells were vortexed after adding sterile water (500 µl), and vortexed again after adding n-hexane (2 ml). This was followed by centrifugation at 3,000 rpm for 10 min, and the upper layer was discarded. The cells were vortexed again after adding n-hexane (2 ml), and centrifuged at 3,000 rpm for 10 min. After discarding the upper layer, 6 N HCl (1 ml) was added to the remaining lower layer, and the mixture was vortexed. The mixture was vortexed again after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. The collected upper layer was then concentrated and dried with nitrogen gas. The concentrated dry sample was incubated overnight at 80° C. after adding 3 N methanolic HCl (2 ml).

The sample was allowed to cool to room temperature, and 0.9% NaCl (1 ml) was added. The mixture was vortexed after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. After adding a small amount of anhydrous sodium sulfate to the collected upper layer, the mixture was vortexed, and centrifuged at 3,000 rpm for 10 min. After collecting the upper layer, the upper layer was concentrated and dried with nitrogen gas. The concentrated dry sample was dissolved in n-hexane (0.2 ml), and 2 µl of the sample was GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

As a result, knocking out the C20 elongase in the *Thraustochytrium roseum* increased fatty acids of 20 carbon chain length (FIG. 56). FIG. 57 represents the proportions relative to the wild-type strain taken as 100%. FIG. 57 represents each proportion of the components based on the total amount of the fatty acids, which include AA: 5.5%, EPA: 8.5%, n-6DPA: 13.2%, and DHA: 43.9%.

As can be seen from these results, the arachidonic acid increased about 1.2-fold, EPA about 1.6-fold, DPA about 1.2-fold, and DHA about 1.5-fold.

EXAMPLE 8

Disruption of Δ4 Desaturase Gene in *Thraustochytrium aureum* ATCC 34304 OrfA Disrupted Strain Example 8-1

Cloning of Sequence from 1,071 bp Upstream of 44 Desaturase Gene to 1,500 bp within 44 Desaturase Gene in *Thraustochytrium aureum* ATCC 34304 Strain The genomic DNA of the *Thraustochytrium aureum* ATCC 34304 strain extracted by using the method described in Example 3-2 was decoded. Then, a search was made for a gene sequence highly homologous to a known 44 desaturase, and two PCR primers were designed by using the search result. TMO3 is a sequence located 1,071 to 1,049 bp upstream of the Δ4 desaturase gene of the *Thraustochytrium aureum* ATCC 34304 strain. TMO4 is a sequence within the protein coding region, located 1,477 to 1,500 bp from the start codon [TMO3: 23 mer: 5'-GGC GGA GCG AAG TGT GAA AGT TA-3' (SEQ ID NO: 202), TMO4: 24 mer: 5'-GCG ACA GCA TCT TGA AAT AGG CAG-3' (SEQ ID NO: 203)]. By using the genomic DNA of the *Thraustochytrium aureum* ATCC 34304 strain as a template, the sequence from 1,071 bp upstream of the Δ4 desaturase gene to 1,500 bp within the Δ4 desaturase gene of the *Thraustochytrium aureum* ATCC 34304 strain was amplified with the two primers, using an LA taq Hot start version (Takara Bio). The amplification was performed under the following conditions [PCR cycles: 98° C. 2 min/98° C. 20 sec, 60° C. 30 sec, 72° C. 3 min, 30 cycles/72° C. 8 min]. The resulting DNA fragment was cloned into a pGEM-T easy vector, amplified with *Escherichia coli*, and the sequence was confirmed by using a Dye Terminator Cycle Sequencing Kit (BECKMAN COULTER). This was named pTM1 (FIG. 58).

Example 8-2

Production of Base Plasmid for Δ4 Desaturase Gene Targeting Vector Production

By using the pTM1 (FIG. 58) of Example 8-1 as a template, a primer set of the reverse orientation was prepared in a manner that allows the 60 bp upstream of the Δ4 desaturase gene and a 556-bp sequence containing the start codon within the Δ4 desaturase gene (616 bp, SEQ ID NO: 205) to be deleted, and a BglII site to occur in the deleted portion. TMO7 and TMO8 both contain BglII sequences. A PrimeSTAR Max DNA Polymerase (Takara Bio) was used for the amplification [TMO7: 25 mer: 5'-CAG GAG ATC TCC AAG TCG CGA TTC A-3' (SEQ ID NO: 206), TMO8: 26 mer: 5'-CTT GGA GAT CTC CTG CCC GTC CCG AA-3' (SEQ ID NO: 207)] [PCR cycles: 98° C. 3 min/98° C. 10 sec, 55° C. 15 sec, 72° C. 30 sec, 30 cycles/72° C. 30 sec]. After the amplification performed under these conditions, the product was electrophoresed on an agarose gel, and purified. The resulting DNA fragment was introduced into *Escherichia coli* and amplified, and the sequence was confirmed by using a Dye Terminator Cycle Sequencing Kit (BECKMAN COULTER). This was named pTM2.

The product base plasmid (pTM2) for the Δ4 desaturase gene targeting vector production is shown in FIG. 59.

Example 8-3

Production of Targeting Vectors (Blasticidin-Resistant Gene and GFP-Fused Zeocin-Resistant Gene)

The pRH38 (FIG. 33) of Example 5-3 was digested with BglII, and the DNA fragment containing a blasticidin-resistant gene cassette was ligated to the BglII site of the pTM2 (FIG. 59) of Example 8-2. This was named pTM6.

The pRH51 (FIG. 36) of Example 5-4 was digested with BglII, and the DNA fragment containing a GFP-fused zeocin-resistant gene cassette was ligated to the BglII site of the pTM2 (FIG. 59) of Example 8-2. This was named pTM8.

The two targeting vectors (pTM6 and 8) produced are shown in FIG. 60.

Example 8-4

Introduction of Δ4 Desaturase Gene Targeting Vector into *Thraustochytrium aureum* OrfA Disrupted Strain By using the two targeting vectors produced in Example 8-3 as templates, the gene was amplified with a PrimeSTAR HS DNA polymerase (Takara Bio), using TMO3 (Example 8-1; SEQ ID NO: 202) and TMO4 (Example 8-1; SEQ ID NO: 203) as primers [PCR cycles: 98° C. 3 min/98° C. 10 sec, 55° C. 5 sec, 72° C. 4 min, 30 cycles/72° C. 3 min].

After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pTM6 (FIG. 60) of Example 8-3 as a template was 3,264 bp, and had the following sequence order: Upstream of *Thraustochytrium aureum* Δ4 desaturase gene-SV40 terminator sequence-blasticidin-resistant gene sequence-ubiquitin promoter-sequence within *Thraustochytrium aureum* Δ4 desaturase gene (SEQ ID NO: 208). The introduced fragment obtained from using the pTM8 (FIG. 60) of Example 8-3 as a template was 3,935 bp, and had the following sequence order: Upstream of *Thraustochytrium aureum* Δ4 desaturase gene-SV40 terminator sequence-zeocin-resistant gene sequence-enhanced GFP gene sequence-ubiquitin promoter-sequence within *Thraustochytrium aureum* Δ4 desaturase gene (SEQ ID NO: 209).

The gene disrupted strain of the PUFA PKS pathway-associated gene OrfA of Example 4 was cultured in a GY medium for 4 days, and cells in the logarithmic growth phase were used for gene introduction. The DNA fragment (0.625 μg) was then introduced into cells corresponding to OD600=1 to 1.5 by using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene was applied to a PDA agar plate medium (containing 20 mg/ml Zeocin or 0.2 mg/ml blasticidin). As a result, 100 to 200 drug resistant strains were obtained per penetration.

Example 8-5

Identification of Δ4 Desaturase Gene Gene Targeting Homologous Recombinant

Genomic DNA was extracted from *Thraustochytrium aureum*, and the Δ4 desaturase gene disrupted strain of the *Thraustochytrium aureum* OrfA disrupted strain by using the method of Example 3-2.

The DNA concentration was calculated by measuring A260/280. By using this as a template, a PCR was performed with a Mighty Amp DNA polymerase (Takara Bio) to confirm the genome structure. The positions of the primers, combinations used for the amplification, and the expected sizes of the amplification products are shown in FIG. 61. TMO1 was set upstream of the Δ4 desaturase gene. TMO2 was set downstream of the Δ4 desaturase gene. RHO198 and RHO49 (Example 5-3; SEQ ID NO: 139) were set on the blasticidin-resistant gene. RHO128 was set on the enhanced GFP gene. RHO64 (Example 5-4; SEQ ID NO: 151) was set on the zeocin-resistant gene [TMO1: 23 mer: 5'-AAA AGA ACA AGC CCT CTC CTG GA-3' (SEQ ID NO: 210), TMO2: 23 mer: 5'-GAG GTT TGT ATG TTC GGC GGT TT-3' (SEQ ID NO: 211), RHO198: 26 mer: 5'-TGG GGG ACC TTG TGC AGA ACT CGT GG-3' (SEQ ID NO: 212), RHO128: 22 mer: 5'-GAC CTA CGG CGT GCA GTG CTT C-3' (SEQ ID NO: 213)] [PCR cycles: 98° C. 2 min/98° C. 10 sec, 68° C. 4 min 30 sec, 30 cycles/68° C. 4 min].

Δ4 desaturase gene knockout strains were obtained that showed no amplification of the wild-type allele (Wt allele) but showed amplification of the blasticidin-resistant gene allele (BlaR allele) and zeocin-resistant gene allele (ZeoR allele) (FIG. 62). It was found by the experiment that the *Thraustochytrium aureum* ATCC 34304 strain did not become auxotrophic even with the deletion of the PKS pathway-associated gene OrfA and the Δ4 desaturase gene.

Example 8-6

Changes in Fatty Acid Composition by Disruption of Δ4 Desaturase Gene in *Thraustochytrium aureum* OrfA Disrupted Strain The *Thraustochytrium aureum* ATCC 34304 and the gene disrupted strain were cultured by using the method of Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

Changes in fatty acid composition are represented in FIG. 63. FIG. 64 represents the proportions relative to the wild-type strain taken as 100%. FIG. 64 represents the proportion of each component based on the total amount of the fatty acids, which includes AA: 8.4%, DGLA: 0.8%, ETA: 0.3%, EPA: 6.2%, n-6DPA: 0.2%, and DHA: 0.5%, which can also be described as the values of GC area such as n-6DPA/DTA: 0.02, DHA/n-3DPA: 0.03, C20PUFA/C22PUFA: 0.6, and n-6PUFA/n-3PUFA: 0.9.

As can be seen from the results, disrupting the Δ4 desaturase gene in the *Thraustochytrium aureum* OrfA disrupted strain resulted in hardly peforming C22:5n-6 (DPA) and C22:6n-3(DHA) biosyntheses, and C22:4n-6 (DTA) and C22:5n-3 (DPA) accumulated.

EXAMPLE 9

Disruption of C20 Elongase Gene in *Parietichytrium* sp. SEK358 Strain

Example 9-1

Introduction of C20 Elongase Gene Targeting Vector into *Parietichytrium* sp. SEK358 Strain By using the targeting vector produced with the pRH85 (FIG. 18) of Example 3-6 as a template, the gene was amplified with a PrimeSTAR Max DNA polymerase (Takara Bio), using RHO153 (Example 3-4; SEQ ID NO: 74) and RHO154 (Example 3-4; SEQ ID NO: 75) as primers [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH85 (FIG. 18) of Example 3-6 as a template was 2,661 bp, and had the following sequence order: First half of *Parietichytrium* C20 elongase gene-SV40 terminator sequence-artificial neomycin-resistant gene sequence-ubiquitin promoter sequence-second half of *Parietichytrium* C20 elongase gene (Example 3-7; SEQ ID NO: 81). The *Parietichytrium* sp. SEK358 strain was cultured in a GY medium for 3 days, and cells in the logarithmic growth phase were used for gene introduction. The DNA fragment (0.625 µg) was then introduced into cells corresponding to OD600=1 to 1.5 using the gene-gun technique (microcarrier: 0.6-micron gold particles, target distance: 6 cm, chamber vacuum: 26 mmHg, rupture disk: 900 PSI). After a 24-hour recovery time, the cells with the introduced gene were applied to a PDA agar plate medium containing 0.5 mg/ml G418. As a result, 10 to 30 drug resistant strains were obtained per penetration.

Example 9-2

Identification of C20 Elongase Gene Gene Targeting Homologous Recombinant

Genomic DNA was extracted from the *Parietichytrium* sp. SEK358 strain and the C20 elongase gene disrupted strain by using the method of Example 3-2. The DNA concentration was calculated by measuring A260/280. By using this as a template, a PCR was performed with a Mighty Amp DNA polymerase (Takara Bio) to confirm the genome structure. The positions of the primers, combinations used for the amplification, and the expected sizes of the amplification products are as described in Example 3-8 (FIG. 19).

RHO184 (Example 3-8; SEQ ID NO: 87) was set upstream of the C20 elongase. RHO185 (Example 3-8; SEQ ID NO: 88) was set downstream of the C20 elongase. RHO142 (Example 3-8; SEQ ID NO: 85) and RHO143 (Example 3-8; SEQ ID NO: 86) were set on the artificial neomycin-resistant gene [PCR cycles: 98° C. 2 min/98° C. 10 sec, 68° C. 2 min, 30 cycles/68° C. 7 min].

C20 elongase knockout strains were obtained that showed no amplification of the wild-type allele (Wt allele), but showed amplification of the artificial neomycin-resistant gene allele (NeoR allele) (FIG. 65).

Example 9-3

Changes in Fatty Acid Composition by Disruption of C20 Elongase

The *Parietichytrium* sp. SEK358 strain and the gene disrupted strain were cultured by using the method of Example 3-9. After freeze drying, the fatty acids were methylesterificated, and GC analyzed. The GC analysis was performed with a gas chromatograph GC-2014 (Shimadzu Corporation) under the following conditions:
Column: HR-SS-10 (30 m×0.25 mm; Shinwa Chemical Industries Ltd.)
Column temperature: 150° C.⌐(5° C./min)→220° C. (10 min)
Carrier gas: He (1.3 mL/min).
Changes in fatty acid composition are represented in FIG. 66. FIG. 67 represents the proportions relative to the wild-type strain taken as 100%. FIG. 67 represents the proportion of each component based on the total amount of the fatty acids, which includes AA: 21.4%, DGLA: 8.6%, ETA: 2.1%, EPA: 23.8%, n-6DPA: 0.5%, DHA: 0.9%, which can also be described as the values of GC area such as n-6DPA/DTA: 1.8, DHA/n-3DPA: 4.1, CO2PUFA/C22PUFA: 29.6, and n-6PUFA/n-3PUFA: 1.1. As can be seen from the results, knocking out the C20 elongase in the *Parietichytrium* sp. SEK358 strain caused reduction of fatty acids of 22 or greater carbon chain length, and increased fatty acids of 20 carbon chain length. Specifically, the arachidonic acid increased about seven-fold, and the EPA about eleven-fold. The DPA and DHA reduced to about ¹⁄₁₅ and about ⅛, respectively.

EXAMPLE 10

Disruption of C20 Elongase Gene in *Parietichytrium* sp. SEK571 Strain

Example 10-1

Introduction of C20 Elongase Gene Targeting Vector into *Parietichytrium* sp. SEK571 Strain By using the targeting vector produced with the pRH85 (FIG. 18) of Example 3-6 as a template, the gene was amplified with a PrimeSTAR Max DNA polymerase (Takara Bio), using RHO153 (Example 3-4; SEQ ID NO: 74) and RHO154 (Example 3-4; SEQ ID NO: 75) as primers [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH85 (FIG. 18) of Example 3-6 as a template was 2,661 bp, and had the following sequence order: First half of *Parietichytrium* C20 elongase gene-SV40 terminator sequence-artificial neomycin-resistant gene sequence-ubiquitin promoter sequence-second half of *Parietichytrium* C20 elongase gene (Example 3-7; SEQ ID NO: 81). The *Parietichytrium* sp. SEK571 strain was cultured in a GY medium for 3 days, and cells in the logarithmic growth phase were used for gene introduction. The DNA fragment (0.625 1.1 g) was then introduced into cells corresponding to OD600=1 to 1.5 using the gene-gun technique (microcarrier: 0.6-micron gold particles, target distance: 6 cm, chamber vacuum: 26 mmHg, rupture disk: 1550 PSI). After a 24-hour recovery time, the cells with the introduced gene were applied to a PDA agar plate medium containing 0.5 mg/ml G418. As a result, 5 to 15 drug resistant strains were obtained per penetration.

Example 10-2

Identification of C20 Elongase Gene Gene Targeting Homologous Recombinant

Genomic DNA was extracted from the *Parietichytrium* sp. SEK571 strain and the C20 elongase gene disrupted strain by using the method of Example 3-2, and the DNA concentration was calculated by measuring A260/280. By using this as a template, a PCR was performed with a Mighty Amp DNA polymerase (Takara Bio) to confirm the genome structure. The positions of the primers, combinations used for the amplification, and the expected sizes of the amplification products are as described in Example 3-8 (FIG. 19).

RHO184 (Example 3-8; SEQ ID NO: 87) was set upstream of the C20 elongase. RHO185 (Example 3-8; SEQ ID NO: 88) was set downstream of the C20 elongase. RHO142 (Example 3-8; SEQ ID NO: 85) and RHO143 (Example 3-8; SEQ ID NO: 86) were set on the artificial neomycin-resistant gene [PCR cycles: 98° C. 2 min/98° C. 10 sec, 68° C. 2 min, 30 cycles/68° C. 7 min].

C20 elongase knockout strains were obtained that showed no amplification of the wild-type allele (Wt allele), but showed amplification of the artificial neomycin-resistant gene allele (NeoR allele) (FIG. 68).

Example 10-3

Changes in Fatty Acid Composition by C20 Elongase Disruption

The *Parietichytrium* sp. SEK571 strain and the gene disrupted strain were cultured by using the method of Example 3-9. After freeze drying, the fatty acids were methylesterificated, and GC analyzed. The GC analysis was performed with a gas chromatograph GC-2014 (Shimadzu Corporation) under the following conditions:
Column: HR-SS-10 (30 m×0.25 mm; Shinwa Chemical Industries Ltd.)
Column temperature: 150° C.→(5° C./min)→220° C. (10 min)
Carrier gas: He (1.3 mL/min).
Changes in fatty acid composition are represented in FIG. 69. FIG. 70 represents the proportions relative to the wild-type strain taken as 100%. FIG. 70 represents the proportion of each component based on the total amount of the fatty acids, which includes AA: 13.2%, DGLA: 1.9%, ETA: 1.1%, EPA: 20.6%, n6DPA: 1.0%, and DHA: 1.2%, which can also be described as the values of GC area such as n-6DPA/DTA: 6.4, DHA/n-3DPA: 4.7, CO2PUFA/C22PUFA: 14.6, and n-6PUFA/n-3PUFA: 0.7. As can be seen from the results, knocking out the C20 elongase in the *Parietichytrium* sp. SEK571 strain caused reduction of fatty acids of 22 or greater carbon chain length, and increased fatty acids of 20 carbon chain length. Specifically, the arachidonic acid increased about four-fold, and the EPA about eight-fold. The DPA and DHA both reduced to about ⅟₁₂.

EXAMPLE 11

Disruption of *Thraustochytrium aureum* ATCC 34304-Derived Δ12 Desaturase Gene

Example 11-1

Isolation of *Thraustochytrium aureum* ATCC 34304-Derived Δ12 Desaturase Gene

Figure 71:
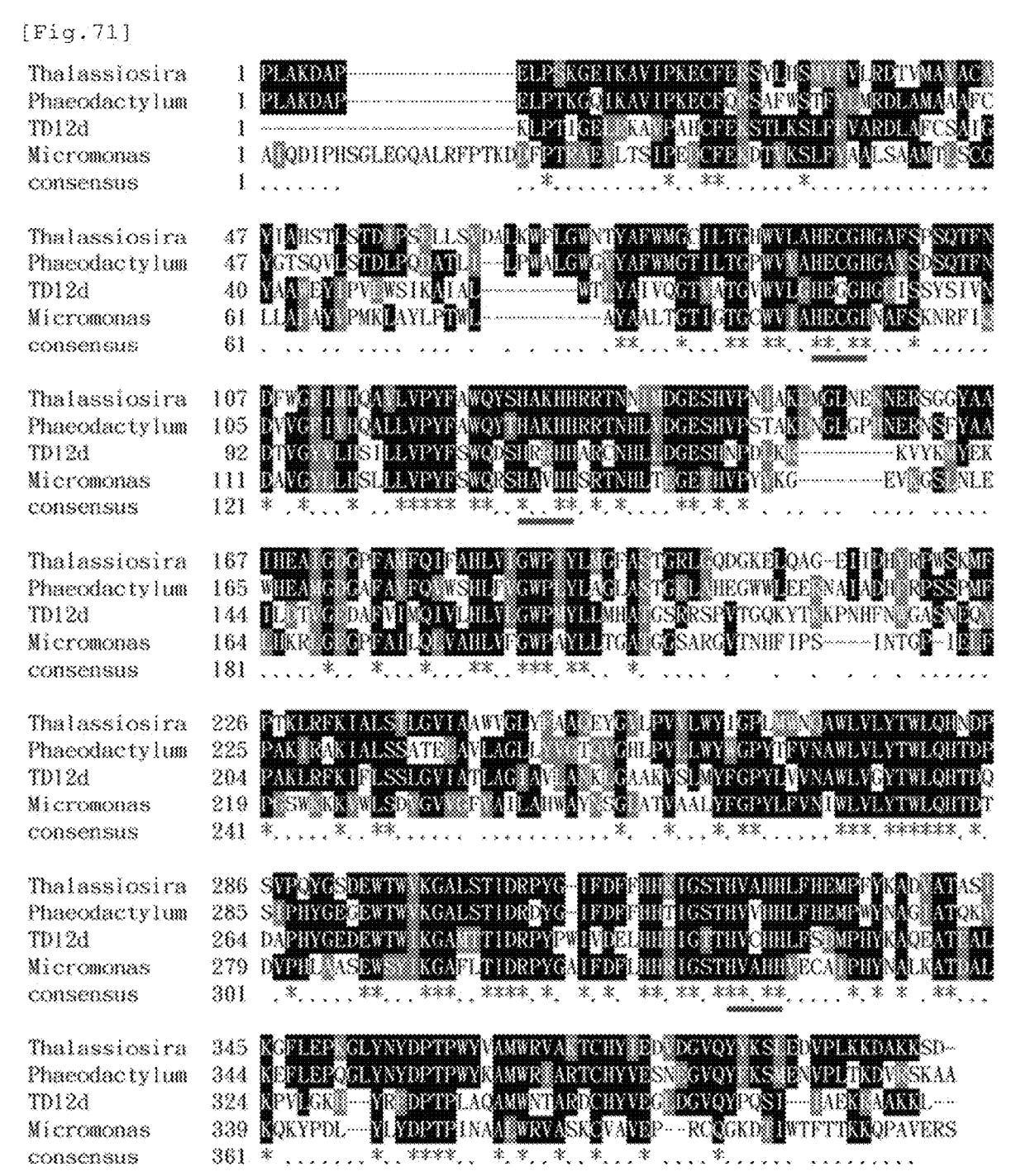

By using the genomic DNA of the *Thraustochytrium aureum* ATCC 34304 as a template, a *Thraustochytrium aureum* ATCC 34304-derived Δ12 desaturase gene was amplified by a PCR performed with a forward oligonucleotide primer Tw3-F1 (22 mer: 5'-ATG TGC AAG GTC GAT GGG ACA A-3') (SEQ ID NO: 214) and a reverse oligonucleotide primer Tω3-R1 (22 mer: 5'-TCA CAA ACA TCG CAG CCT TCG G-3') (SEQ ID NO: 215) (enzyme used: LA taq Hot Start Version, TaKaRa; PCR cycles: 98° C. 2 min/98° C. 30 sec, 53° C. 30 sec, 72° C. 1 min, 30 cycles/72° C. 7 min/4° C. ∞). As a result, a novel gene sequence having a 1,185-bp (SEQ ID NO: 217) ORF, encoding 395 amino acids (SEQ ID NO: 216) was obtained. In the amino acid sequence of the gene, three histidine boxes commonly conserved in desaturases, believed to construct the active site were conserved (FIG. 71). Further, because the gene showed high identity (41%, Δ4%, 41%) at the amino acid level with the *Thalassiosira pseudonana*-, *Micromonas* sp.-, and *Phaeodactylum tricornutum*-derived Δ12 desaturases in a Blast search (FIG. 71), it was strongly suggested that the gene was a *Thraustochytrium aureum* ATCC 34304-derived Δ12 desaturase gene. In the following, the gene will be referred to as TΔ12d.

Example 11-2

Expression of TΔ12d Using Budding Yeast *Saccharomyces cerevisiae* as Host, and Analysis of Fatty Acid Composition of Gene Introduced Strain By using the genomic DNA of the *Thraustochytrium aureum* ATCC 34304 as a template, a DNA fragment containing HindIII and Xba I sites added to the both ends of TΔ12d was prepared in a PCR performed with a forward oligonucleotide primer Tw3-Hind3-F (30 mer: 5'-GGA AGC TTA TGT GCA AGG TCG ATG GGA CAA-3') (SEQ ID NO: 218) and a reverse oligonucleotide primer Tw3-XbaI-R (29 mer: 5'-TTC TAG ACT AGA GCT TTT TGG CCG CAC GC-3') (SEQ ID NO: 219) (enzyme used: LA taq Hot Start Version, TaKaRa; PCR cycles: 98° C. 2 min/98° C. 30 sec, 53° C. 30 sec, 72° C. 1 min, 30 cycles/72° C. 7 min/4° C. Go). The DNA fragment was then incorporated in the HindII/Xba I site of a pYES2/CT vector to construct a TΔ12d expression vector pYESTD12. The pYESTD12 and pYES2/CT were then introduced into yeasts by using the lithium acetate method. In the GC analysis of the fatty acid composition of the TΔ12d overexpressing strain (pYESTD12 introduced strain), novel peaks were confirmed at positions corresponding to the retention times of LA (C18:2Δ9, 12) and C16:2Δ9, 12, but not in the mock introduced strain (pYES2/CT introduced strain). FIG. 72 represents a GC analysis chart, and fatty acid levels per dry cell. On the other hand, no conversion activity for other fatty acids [LA, GLA (C18:3Δ6, 9, 12), C20:2Δ11, 14, DGLA (C20:3Δ8, 11, 14), ARA (C20:4Δ5, 8, 11, 14), DTA (C22:4Δ7, 10, 13, 16)] was confirmed in the TΔ12d overexpressing strain. It became clear from these results that the TΔ12d was a *Thraustochytrium aureum* ATCC 34304-derived Δ12 desaturase gene.

Example 11-3

Construction of TΔ12d Targeting Vector

By using the genomic DNA of the *Thraustochytrium aureum* ATCC 34304 as a template, the upstream and downstream sequences (1,001 bp each) of the TΔ12d ORF were amplified in a PCR performed under the following conditions (enzyme used: PrimeSTAR GXL, TaKaRa); PCR cycles: 98° C. 2 min/98° C. 30 sec, 53° C. 30 sec, 72° C. 1 min, 30 cycles/72° C. 7 min/4° C. ∞). The following forward and reverse oligonucleotide primers were used.

TD12d-up-F
(SEQ ID NO: 220)
(23 mer: 5'-AGT CAG CCC AGG CAC CGA TGA CG-3')
and

```
TD12d-up-R
                                          (SEQ ID NO: 221)
(39 mer: 5'-AGC CAG AGC TAG ATC TCT TGT GCT CCT

TTT CAA TCC TTT-3')

TD12d-down-F
                                          (SEQ ID NO: 222)
(39 mer: 5'-GGA GCA CAA GAG ATC TAG CTC TGG CTC AAG GGA CAC CGT-3')
and TD12d-down-R
                                          (SEQ ID NO: 223)
(24 mer: 5'-CAC AGA AAC TGC CTT CAC GGG TCT-3')
```

The resulting both DNA fragments were joined by fusion PCR with a Bgl II site inserted therebetween, and incorporated in a pGEM-T easy Vector (Promega). Then, the hygromycin-resistant gene cassette of Example 3-3, and the blasticidin-resistant gene cassette of Example 5-3 were incorporated at the Bgl II site of the resulting vector to construct TΔ12d KO targeting vectors. These were named pTD12dKOHyg and pTD12dKOBla. The construction scheme of the TΔ12d KO targeting vectors are shown in FIG. 73.

Example 11-4

Introduction of TΔ12d Targeting Vector to *Thraustochytrium aureum* ATCC 34304, and Acquisition of TΔ12d Disrupted Strain In order to obtain an efficient homologous recombinant by using a split marker method, two homologous recombination fragments were amplified by a PCR performed by using pTD12dKOHyg as a template [enzyme used: LA taq Hot Start Version, TaKaRa; PCR cycles: 98° C. 2 min/98° C. 30 sec, 60° C. 30 sec, 72° C. X min (X=1 min/kbp), 30 cycles/72° C. 7 min/4° C. 00] (FIG. 74). The fragments were then introduced to the *Thraustochytrium aureum* ATCC 34304 by using the gene-gun technique. The following forward and reverse oligonucleotide primers were used for the amplification of the homologous recombination fragments.

TD12d-up-F (SEQ ID NO: 220) and Hyg-Knock-R (24 mer: 5'-TGT TAT GCG GCC ATT GTC CGT CAG-3') (SEQ ID NO: 224), and Hyg-Knock-F (24 mer: 5'-TGC GAT CGC TGC GGC CGA TCT TAG-3') (SEQ ID NO: 225) and TD12d-down-R (SEQ ID NO: 223)

As a result, a homologous recombinant with the disrupted TΔ12d first allele was obtained. Thereafter, by using pTD12dKOBla as a template, a homologous recombination fragment for disrupting the second allele was amplified by a PCR performed with the forward and reverse oligonucleotide primers TD12d-up-F (SEQ ID NO: 220) and TD12d-down-R (SEQ ID NO: 223) (enzyme used: LA taq Hot Start Version, TaKaRa) [PCR cycles: 98° C. 2 min/98° C. 30 sec, 60° C. 30 sec, 72° C. 3 min, 30 cycles/72° C. 7 min/4° C. ∞]. The fragment was then introduced to the homologous recombinant containing the disrupted first allele. Complete disruption of TΔ12d was verified by a PCR (using the genomic DNA below as a template) and a RT-PCR performed for the detection of hygromycin-resistant gene, blasticidin-resistant gene, and TΔ12d, or by southern blotting.

FIG. 75 represents the amplification results for the hygromycin-resistant gene, blasticidin-resistant gene, and TΔ12d amplified by a PCR performed by using the genomic DNAs of the wild-type strain, the TΔ12d first allele disrupted strain, and the TΔ12d disrupted strain (two alleles are disrupted) as templates.

As a result, amplification of the hygromycin-resistant gene and the blasticidin-resistant gene contained in the introduced homologous recombination fragment was confirmed in the TΔ12d disrupted strain. However, no amplification of the disrupted TΔ12d was confirmed. The following forward and reverse oligonucleotide primers were used for the amplification of the hygromycin-resistant gene, blasticidin-resistant gene, and TΔ12d.

```
Hyg-F
                                          (SEQ ID NO: 226)
(26 mer: 5'-ATG AAA AAG CCT GAA CTC ACC GCG AC-3')
and Hyg-R
                                          (SEQ ID NO: 227)
(25 mer: 5'-CTA TTC CTT TGC CCT CGG ACG AGT G-3'), Bla-F
                                          (SEQ ID NO: 228)
(27 mer: 5'-ATG GCC AAG CCT TTG TCT CAA GAA GAA-3'),
and Bla-R
                                          (SEQ ID NO: 229)
(30 mer: 5'-TTA GCC CTC CCA CAC ATA ACC AGA GGG

CAG-3'), (SEQ ID NO: 214)
Tw3-F1,
and (SEQ ID NO: 215)
Tw3-R1
```

FIG. 76 represents the results of the mRNA detection performed by RT-PCR for the hygromycin-resistant gene, blasticidin-resistant gene, and TΔ12d in the wild-type strain, the TΔ12d first allele disrupted strain, and the TΔ12d disrupted strain. As a result, mRNA was detected for the hygromycin-resistant gene and the blasticidin-resistant gene contained in the introduced homologous recombination fragment in the TΔ12d disrupted strain. However, mRNA was not detected for the disrupted TΔ12d. Note that the primers used are the same primers as used for the PCR in which the genomic DNA was used as a template.

By using the genomic DNA of the *Thraustochytrium aureum* ATCC 34304 as a template, two DIG-labeled probes were prepared, and southern blotting was performed with these probes. The following forward and reverse oligonucleotide primers were used for the preparation of the DIG-labeled probes.

```
KNO up-probe-F1
                                          (SEQ ID NO: 230)
(23 mer: 5'-GGG GTC GGC CGG TGC AGC CTT AG-3')
and KO up-probe-R1
                                          (SEQ ID NO: 231)
(24 mer: 5'-GGC GGT CAG CGA TCG GTC GGA CTC-3'),
and
```

-continued

KO down-probe-F3
(SEQ ID NO: 232)
(23 mer: 5'-GCT TGC GGC TCC TGT TGG GTG AC-3')
and KO down-probe-R3
(SEQ ID NO: 233)
(23 mer: 5'-ACG CCT GGC TGC CCA CCA TAA AC-3')

As a result, the bands of the wild-type allele (upstream side 2,028 bp, downstream side 2,334 bp) disappeared in the TΔ12d disrupted strain, and bands of the homologous recombination fragments (upstream side 5,880 bp and 5,253 bp; downstream side 1,496 bp and 2,334 bp) containing the hygromycin-resistant gene and the blasticidin-resistant gene were detected instead (FIG. 77).

The PCR using the genomic DNA as a template, the RT-PCR, and southern blotting made it clear that the TΔ12d was disrupted.

Example 11-5

Phenotypic Analysis of TΔ12d Disrupted Strain

Cells cultured in a 250-ml GY liquid medium for 5 days were collected in 10 ml portions, and absorbance at OD 600 nm was measured (n=3). After the measurement, the cells were collected, and washed once with sterilized ultrapure water. After freeze drying, the dry cell weight was measured after 1-hour drying with a desiccator (n=3). As a result, no significant difference was observed in the proliferation among the wild-type strain, the first allele disrupted strain, and the TΔ12d disrupted strain (FIG. 78). The wild-type strain, the first allele disrupted strain, and the TΔ12d disrupted strain were GC analyzed for their fatty acid compositions.

As a result, large fatty acid composition changes were observed. Accumulation of C18:1n9 (OA) in the TΔ12d disrupted strain was particularly prominent. FIG. 79 represents the proportion of each component in the fatty acid composition. FIG. 80 represents fatty acid levels per milligram of dry cells.

EXAMPLE 12

Disruption of C20 Elongase Gene and Expression of ω3 Desaturase Gene in *Thraustochytrium aureum* ATCC 34304 OrfA Gene Disrupted Strain Example 12-1

Production of C20 Elongase Gene Targeting and *Saprolegnia Diclina*-Derived ω3 Desaturase Expression Vector (Blasticidin-Resistant Gene)

By using the pRH43 (FIG. 39) of Example 5-6 as a template, a primer set of the reverse orientation was prepared in a manner that allows the two restriction enzyme KpnI sites to be deleted, and a BamHI site to occur in the deleted portion. RHO189 and RHO190 both contain BamHI sequences. A PrimeSTAR Max DNA Polymerase (Takara Bio) was used for the amplification [RHO189: 28 mer: 5'-TTA GCG GGA TCC CAA TTC GCC CTA TAG T-3' (SEQ ID NO: 234), RHO190: 27 mer: 5'-AAT TGG GAT CCC GCT AAG TAT CTC CCG-3' (SEQ ID NO: 235)] [PCR cycles: 98° C. 2 min/98° C. 10 sec, 55° C. 15 sec, 72° C. 40 sec, 31 cycles/72° C. 1 min]. After the amplification performed under these conditions, the product was electrophoresed on an agarose gel, and purified. The resulting DNA fragment was introduced into *Escherichia coli* and amplified, and the sequence was confirmed by using a Dye Terminator Cycle Sequencing Kit (BECKMAN COULTER). This was named pRH101 (FIG. 81).

By using the pRH101 as a template, a primer set of the reverse orientation was prepared in a manner that allows for insertion of a restriction enzyme KpnI site. RHO191 and RHO192 both contain KpnI sequences. A PrimeSTAR Max DNA Polymerase (Takara Bio) was used for the amplification [RHO191: 28 mer: 5'-AGA TCT GGT ACC GCA GCG CCT GGT GCA C-3' (SEQ ID NO: 236), RHO192: 27 mer: 5'-GCT GCG GTA CCA GAT CTG GTC GCG TTT-3' (SEQ ID NO: 237)] [PCR cycles: 98° C. 2 min/98° C. 10 sec, 55° C. 15 sec, 72° C. 40 sec, 31 cycles/72° C. 1 min]. After the amplification performed under these conditions, the product was electrophoresed on an agarose gel, and purified. The resulting DNA fragment was introduced into *Escherichia coli* and amplified, and the sequence was confirmed by using a Dye Terminator Cycle Sequencing Kit (BECKMAN COULTER). This was named pRH102 (FIG. 82).

The pRH48 (FIG. 46) of Example 6-1 was digested with KpnI, and a DNA fragment containing a *Saprolegnia diclina*-derived ω3 desaturase expression cassette was ligated to the KpnI site of the pRH102 (FIG. 82). This was named pRH103.

The product C20 elongase gene targeting and *Saprolegnia diclina*-derived ω3 desaturase expression vector pRH103 is shown in FIG. 83.

Example 12-2

Introduction of C20 Elongase Gene Targeting and *Saprolegnia Diclina*-Derived ω3 Desaturase Expression Vector into *Thraustochytrium aureum* OrfA Disrupted Strain By using the C20 elongase gene targeting vector pRH54 (FIG. 39) of Example 5-6 as a template, the gene was amplified with a PrimeSTAR Max DNA polymerase (Takara Bio) using KSO11 (Example 5-7; SEQ ID NO: 159) and KSO12 (Example 5-7; SEQ ID NO: 160) as primers [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was calculated by measuring A260/280. The introduced fragment was 3,887 bp, and had the following sequence order: Upstream of *Thraustochytrium aureum* C20 elongase gene-ubiquitin promoter-Enhanced GFP gene sequence-zeocin-resistant gene sequence-SV40 terminator sequence-downstream of *Thraustochytrium aureum* C20 elongase gene (Example 5-7; SEQ ID NO: 162). The C20 elongase gene targeting and *Saprolegnia diclina*-derived ω3 desaturase expression vector pRH103 (FIG. 83) of Example 12-1 was digested with a restriction enzyme BamHI. After being extracted with phenol-chloroform and then with chloroform, the DNA was precipitated with ethanol, and the precipitate was dissolved in 0.1×TE. The DNA concentration was calculated by measuring A260/280. The introduced fragment was 5,611 bp, and had the following sequence order: Upstream of *Thraustochytrium aureum* C20 elongase gene-ubiquitin promoter-*Saprolegnia diclina*-derived ω3 desaturase gene sequence-ubiquitin terminator-ubiquitin promoter-blasticidin-resistant gene sequence-SV40 terminator-downstream of *Thraustochytrium aureum* C20 elongase gene (SEQ ID NO: 238).

The PUFA PKS pathway-associated gene OrfA gene disrupted strain of Example 4 was cultured in a GY medium for 4 days, and cells in the logarithmic growth phase were used for gene introduction. The DNA fragment (0.625 µg) was introduced into cells corresponding to OD600=1 to 1.5 by using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene were applied to a PDA agar plate medium (containing 20 mg/ml Zeocin or 0.2 mg/ml blasticidin). As a result, 20 to 60 drug resistant strains were obtained.

Example 12-3

Introduction of Homologous Recombinant Containing C20 Elongase Gene Targeting and *Saprolegnia Diclina*-Derived ω3 Desaturase Expression Vector Inserted in Genome Genomic DNA was extracted from the *Thraustochytrium aureum* PUFA PKS pathway-associated gene OrfA disrupted strain, the C20 elongase gene first allele homologous recombinant of the *Thraustochytrium aureum* OrfA disrupted strain, and the disrupted strain by using the method described in Example 3-2. The DNA concentration was then calculated by measuring A260/280.

The genomic DNA was cut with restriction enzymes, and electrophoresed on a 0.7% SeaKem GTG agarose gel (Takara Bio) in about 2 to 3 µg per well. This was transferred to a nylon membrane, and hybridized at 51° C. for 16 hours with probes produced with a DIG system (Roche Applied Science). RHO94 (Example 5-8; SEQ ID NO: 163) and RHO95 (Example 5-8; SEQ ID NO: 164) were used for the production of the 5'-end probe. RHO96 (Example 5-8; SEQ ID NO:165) and RHO97 (Example 5-8; SEQ ID NO: 166) were used for the production of the 3'-end probe. The amplification was performed under the following conditions, and an LA taq Hot start version (Takara Bio) was used for the amplification [PCR cycles: 98° C. 2 min/98° C. 30 sec, 58° C. 30 sec, 72° C. 1 min, 30 cycles/72° C. 3 min]. The restriction enzymes used, and the probe positions are as shown in FIG. 84. Detection of the hybridized probes was made by using a chromogenic method (NBT/BCIP solution). Bands of the sizes expected from the homologous recombination of the drug resistant genes were observed in the analyses of both the 5' end and the 3' end (FIG. 85).

Example 12-4

Disruption of C20 Elongase Gene in *Thraustochytrium aureum* OrfA. Disrupted Strain and Changes in Fatty Acid Composition by *Saprolegnia Diclina*-Derived ω3 Desaturase Expression The *Thraustochytrium aureum* ATCC 34304 wild-type strain, and the *Saprolegnia diclina*-derived ω3 desaturase expressing strain with the double disruption of the PKS pathway (orfA gene) and the C20 elongase gene were cultured by using the method of Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C.(10 min)

Carrier gas: He (1.3 mL/min).

Changes in fatty acid composition are represented in FIG. 86. FIG. 87 represents the proportions relative to the wild-type strain taken as 100%. FIG. 87 represents the proportion of each component based on the total amount of the fatty acids, which includes AA: 16.0%, DGLA: 2.2%, ETA: 0.3%, EPA: 21.6%, n-6DPA: 2.1%, and DHA: 2.2%, which can also be described as the values of GC area such as n-6DPA/DTA: 9.5, DHA/n-3DPA: 10.3, CO2PUFA/C22PUFA: 8.5, and n-6PUFA/n-3PUFA: 0.8.

It was found as a result that disrupting the C20 elongase gene and expressing the *Saprolegnia diclina*-derived ω3 desaturase in the *Thraustochytrium aureum* OrfA disrupted strain increases the C20:4n-6 (AA) about six-fold and the C20:5n3 (EPA) about ten-fold, and decreases the C22:6n-3 (DHA) to about $\frac{1}{16}$.

EXAMPLE 13

Expression of ω3 Desaturase Gene in *Parietichytrium* sp. SEK571 C20 Elongase Gene Disrupted Strain Example 13-1

Production of *Saprolegnia Diclina*-Derived ω3 Desaturase Expression Plasmid Using Hygromycin as Drug-Resistance Marker For the production of a *Saprolegnia diclina*-derived ω3 desaturase expression plasmid using hygromycin as a drug-resistance marker, a plasmid pRH107 (FIG. 88) was used as the base plasmid after partially modifying the restriction enzyme site by subcloning the Parietichytrium C20 elongase upstream sequence (904 bp, SEQ ID NO: 239) and *Parietichytrium* C20 elongase downstream sequence (721 bp, SEQ ID NO: 240) into a pGEM-T easy vector. For reference, the total pRH107 sequence is presented (4,592 bp, SEQ ID NO: 241). The sequence as the base of the expression plasmid production is not actively used for the introduction of cells in this experiment, and as such it is not necessarily required to use pRH107 as the base vector in similar experiments. In conducting a similar experiment, a cloning vector having a KpnI site and a BamHI site in proximity can be used instead. Here, the sequence between the KpnI site and the BamHI site should be as short as possible, because it is introduced into cells as a linker between the ω3 desaturase gene expression cassette and the drug resistant gene expression cassette. In this experiment example, the sequence corresponds to the *Parietichytrium* C20 elongase downstream sequence 37 bp (SEQ ID NO: 242).

The pRH48 (FIG. 46) of Example 6-1 was digested with KpnI, and the DNA fragment containing the *Saprolegnia diclina*-derived ω3 desaturase gene cassette was ligated to the KpnI site of pRH107 (FIG. 88). This was named pRH108 (FIG. 89).

The pRH32 (FIG. 15) of Example 3-3 was digested with BglII, and the DNA fragment containing the hygromycin-resistant gene cassette was ligated to the BamHI site of pRH108 (FIG. 89). This was named pRH109 (FIG. 90).

Example 13-2

Introduction of *Saprolegnia Diclina*-Derived ω3 Desaturase Expression Plasmid into *Parietichytrium* sp. SEK571 C20 Elongase Gene Disrupted Strain By using the pRH109 (FIG. 90) produced in Example 13-1 as a template, the DNA was amplified with a Prime-STAR Max DNA polymerase (Takara Bio), using TMO42 (Example 6-1, SEQ ID NO: 168) and RHO52 (Example 3-1, SEQ ID NO: 52) as primers [PCR cycles: 94° C. 30 sec, 72° C. 1 min, 5 cycles/94° C. 30 sec, 70° C. 30 sec, 72° C. 1 min, 5 cycles/94° C. 30 sec, 68° C. 30 sec, 72° C. 1 min, 25 cycles/72° C. 2 min]. The amplification product was collected form a 1.0% agarose gel, and precipitated with ethanol. The precipitate was then dissolved in 0.1×TE. The DNA concentration was calculated by measuring A260/280. The introduced fragment obtained by the PCR was 4,448 bp, and had the following sequence order: Ubiquitin promoter-ω3 desaturase gene-ubiquitin terminator-ubiquitin promoter-hygromycin-resistant gene sequence-SV40 terminator sequence (SEQ ID NO: 243).

The *Parietichytrium* sp. SEK571 C20 elongase gene disrupted strain produced in Example 10 was cultured in a GY medium for 3 days, and cells in the logarithmic growth phase were used for gene introduction. The DNA fragment (0.625 μg) was introduced into cells corresponding to OD600=1 to 1.5 by using the gene-gun technique (microcarrier: 0.6-micron gold particles, target distance: 6 cm, chamber vacuum: 26 mmHg, rupture disk: 1550 PSI). After a 24-hour recovery time, the cells with the introduced gene were applied to a PDA agar plate medium (containing 1.0 mg/ml hygromycin). As a result, 5 to 20 drug resistant strains were obtained per penetration.

Example 13-3

Acquisition of *Saprolegnia Diclina*-Derived ω3 Desaturase Gene Expressing Strain Genomic DNA was extracted from the *Parietichytrium* sp. SEK571 C20 elongase gene disrupted strain produced in Example 10 and the ω3 desaturase gene expressing strain by using the method described in Example 3-2, and the DNA concentration was calculated by measuring A260/280. By using this as a template, a PCR was performed with an LA taq Hot start version to confirm the genome structure. The positions of the primers, combinations used for the amplification, and the expected size of the amplification product are shown in FIG. 91. RHO90 (27 mer: 5'-CGT TAG AAC GCG TAA TAC GAC TCA CTA-3' SEQ ID NO: 244) was set on the ubiquitin promoter, and RHO141 (Example 3-8, SEQ ID NO: 84) was set on the hygromycin-resistant gene [PCR cycles: 98° C. 2 min/98° C. 10 sec, 68° C. 4 min, 30 cycles/68° C. 7 min].

The result of amplification confirmed a band of the expected size (FIG. 92). That is, a strain was isolated that contained the introduced expression fragment stably introduced into its genome.

Example 13-4

Changes in Fatty Acid Composition by ω3 Desaturase Expression in *Parietichytrium* sp. SEK571 C20 Elongase Gene Disrupted Strain The *Parietichytrium* sp. SEK571 strain, and the ω3 desaturase gene expressing strain were cultured by using the method of Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

The ω3 desaturase expressing strain reduced levels of the n-6 series fatty acids, and there was a tendency for the n-3 series fatty acids to increase (FIG. 93). FIG. 94 represents the proportions relative to the wild-type strain taken as 100%. FIG. 94 represents the proportion of each component based on the total amount of the fatty acids, which includes AA: 1.5%, DGLA: 0.2%, ETA: 0.5%, EPA: 5.4%, n-6DPA: 0.3%, and DHA: 0.4%, which can also be described as the values of GC area such as DHA/n-3DPA: 1.9, CO2PUFA/C22PUFA: 8.2, and n-6PUFA/n-3PUFA: 0.3. As a result, the arachidonic acid was reduced to about ½, and EPA increased by a factor of about 1.4.

EXAMPLE 14

Disruption of *Schizochytrium* C20 Elongase Gene

Example 14-1

Cloning of *Schizochytrium*-Derived C20 Elongase Gene

By using the genomic DNA extracted from *Schizochytrium* as a template, a *Schizochytrium*-derived C20 elongase gene was amplified by a PCR performed with a forward oligonucleotide primer RHO134 (32 mer: 5'-CCC GGA TCC ATG GTG GCC AGC GAG GTG CTC AG-3') (SEQ ID NO: 245) containing a BamHI site, and a reverse oligonucleotide primer RHO135 (34 mer: 5'-CCC GGA TCC TTA GTC GCG CTT GAG CTC AGC ATC C-3') (SEQ ID NO: 246) containing a BamHI site (enzyme used: LA taq Hot Start Version, TaKaRa; PCR cycles: 98° C. 2 min/98° C. 30 sec, 53° C. 30 sec, 72° C. 1 min, 30 cycles/72° C. 7 min/4° C. ∞). The both specific products were gel purified, cloned into a pGEM-T easy vector (Promega), and amplified with *Escherichia coli*. The sequence was then confirmed by using a Dye Terminator Cycle Sequencing Kit (BECKMAN COULTER). This was named pRH70 (FIG. 95). As a result of abase sequence analysis, a novel gene sequence having a 945-bp (SEQ ID NO: 248) ORF, encoding 315 amino acids (SEQ ID NO: 247) was obtained.

Example 14-2

Production of Base Plasmid for ?C20 Elongase Gene Targeting Vector Production

By using the pRH70 (FIG. 95) produced in Example 14-1 as a template, the gene was amplified with a Prime STAR Max DNA Polymerase (Takara Bio), using a primer set of the reverse orientation prepared for insertion of a BglII site in a portion halfway along the C20 elongase gene sequence. The primers used are as follows. The both had BglII linker sequences [RHO136: 25 mer: 5'-CAT CGA GAT CTT CGT GTT TGT CCA C-3' (SEQ ID NO: 249), RHO137: 25 mer: 5'-ACG AAG ATC TCG ATG CGG GCG TCC C-3' (SEQ ID NO: 250)] [PCR cycles: 98° C. 2 min/98° C. 10 sec, 56° C. 15 sec, 72° C. 1 min, 30 cycles/72° C. 1 min]. After the amplification performed under these conditions, the product was digested with BglII, and allowed to self ligate. The ligated sample was amplified with *Escherichia coli*, and the sequence was confirmed by using a Dye Terminator Cycle Sequencing Kit (BECKMAN COULTER). This was named pRH71. The C20 elongase gene sequence 945 bp with the inserted BglII site is represented by SEQ ID NO: 251.

The product base plasmid (pRH71) for the production of the *Schizochytrium* C20 elongase gene targeting vector is shown in FIG. 96.

Example 14-3

Production of Targeting Vectors (Artificial Neomycin-Resistant Gene and Hygromycin-Resistant Gene)

The pRH31 (FIG. 13) of Example 2-2 was digested with BglII, and the DNA fragment containing an artificial neomycin-resistant gene cassette was ligated to the BglII site of the pRH71 (FIG. 96) of Example 14-2. This was named pRH73.

The pRH32 (FIG. 15) of Example 2-3 was digested with BglII, and the DNA fragment containing a hygromycin-resistant gene cassette was ligated to the BglII site of the pRH71 (FIG. 96) of Example 14-2. This was named pKS-SKO.

The two targeting vectors (pRH73 and pKS-SKO) produced are shown in FIG. 97.

Example 14-4

Introduction of C20 Elongase Gene Targeting Vector

By using the two targeting vectors produced in Example 14-3 as templates, the gene was amplified with a Prime STAR GXL polymerase, using a forward primer (SorfF: 20 mer: 5'-AGA TGG TGG CCA GCG AGG TG-3') (SEQ ID NO: 252) containing a translation initiation site, and a reverse primer (SorfR: 25 mer: 5'-TTA GTC GCG CTT GAG CTC AGC ATC C-3') (SEQ ID NO: 253) containing a translation termination site [PCR cycles: 98° C. 2 min/98° C. 30 sec, 60 30 sec, 72° C. 3 min, 30 cycles]. After being extracted with phenol-chloroform and then with chloroform, the DNA was precipitated with ethanol, and the precipitate was dissolved in 0.1×TE. The DNA concentration was then calculated by measuring A260/280. The introduced fragment obtained from using the pRH73 (FIG. 97) of Example 14-3 as a template was 2,644 bp, and had the following sequence order: First half of *Schizochytrium* C20 elongase gene-SV40 terminator sequence-artificial neomycin-resistant gene sequence-ubiquitin promoter sequence-second half of *Schizochytrium* C20 elongase gene (SEQ ID NO: 254). The introduced fragment obtained from using the pKS-SKO (FIG. 97) of Example 14-3 as a template was 2,881 bp, and had the following sequence order: First half of *Schizochytrium* C20 elongase gene-ubiquitin promoter sequence-hygromycin-resistant gene sequence-SV40 terminator sequence-second half of *Schizochytrium* C20 elongase gene (SEQ ID NO: 255).

The *Schizochytrium* sp. TY12Ab strain was cultured in a GY medium for 7 days, and cells in the logarithmic growth phase were used for gene introduction. The DNA fragment (0.625 μg) was introduced into cells corresponding to OD600=1 to 1.5 using the gene-gun technique (microcarrier: 0.6-micron gold particles, target distance: 6 cm, chamber vacuum: 26 mmHg, rupture disk: 1,100 PSI). After a 24-hour recovery time, the cells with the introduced gene were applied to a PDA plate medium (containing 2 mg/ml G418 or 2 mg/ml hygromycin).

As a result, about 20 drug resistant strains were obtained per penetration.

Example 14-5

Identification of C20 Elongase Gene Gene Targeting Homologous Recombinant

The *Schizochytrium* sp. TY12Ab strain (FERM BP-11421), the C20 elongase gene hetero homologous recombinant, and the C20 elongase gene homo homologous recombinant (gene disrupted strain) were cultured in GY media, and the resulting cells were centrifuged at 4° C., 3,000 rpm for 10 min to form a pellet. The cells were then lysed at 55° C., 6 h/99.9° C., 5 min after being suspended in a 20-μl SNET solution [20 mM Tris-HCl; pH 8.0, 5 mM NaCl, 0.3% SDS, 200 μg/ml Proteinase K (nacalai tesque)]. The resulting cell lysate was diluted 10 times and used as a template in a PCR performed with a Mighty Amp DNA polymerase (Takara Bio) to confirm the genome structure. The positions of the primers, and the expected size of the amplification product are shown in FIG. 98. The primers were used in the SorfF and SorfR combination used in Example 14-4 [PCR cycles: 98° C. 2 min/98° C. 10 sec, 60° C. 15 sec, 68° C. 4 min, 30 cycles].

C20 elongase knockout strains were obtained that showed no amplification of the wild-type allele (Wt allele), but showed amplification of the artificial neomycin-resistant gene allele (NeoR allele) and hygromycin-resistant gene allele (HygR allele) (FIG. 99).

Example 14-6

Changes in Fatty Acid Composition by C20 Elongase Disruption

The *Schizochytrium* sp. TY12Ab strain and the gene disrupted strain were cultured in GY media. Cells at the late stage of the logarithmic growth phase were centrifuged at 4° C., 3,000 rpm for 10 min to form a pellet, suspended in 0.9% NaCl, and washed. The cells were further centrifuged at 4° C., 3,000 rpm for 10 min, and the pellet was suspended in sterile water, and washed. This was centrifuged at 3,000 rpm for 10 min, and freeze dried after removing the supernatant. Then, 2 ml-methanolic KOH (7.5% KOH in 95% methanol) was added to the freeze dried cells, and, after being vortexed, the cells were ultrasonically disrupted (80° C., 30 min).

The cells were vortexed after adding sterile water (500 μl), and vortexed again after adding n-hexane (2 ml). This was followed by centrifugation at 3,000 rpm for 10 min, and the upper layer was discarded. The cells were vortexed again after adding n-hexane (2 ml), and centrifuged at 3,000 rpm for 10 min. After discarding the upper layer, 6 N HCl (1 ml) was added to the remaining lower layer, and the mixture was vortexed. The mixture was vortexed again after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. The collected upper layer was then concentrated and dried with nitrogen gas. The concentrated dry sample was incubated overnight at 80° C. after adding 3 N methanolic HCl (2 ml).

The sample was allowed to cool to room temperature, and 0.9% NaCl (1 ml) was added. The mixture was vortexed after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. After adding a small amount of anhydrous sodium sulfate to the collected upper layer, the mixture was vortexed, and centrifuged at 3,000 rpm for 10 min. After collecting the upper layer, the upper layer was concentrated and dried with nitrogen gas. The concentrated dry sample was dissolved in n-hexane (0.2 ml), and 2 µl of the sample was GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

As a result, knocking out the C20 elongase in the *Schizochytrium* sp. TY12Ab strain increased fatty acids of 20 carbon chain length (FIG. 100). FIG. 101 represents the proportions relative to the wild-type strain taken as 100%. FIG. 101 represents the proportion of each component based on the total amount of the fatty acids, which includes AA: 17.2%, EPA: 3.8%, n-6DPA: 13.7%, and DHA: 15.5%, which can also be described as the value of GC area such as DHA/n-3DPA: 38.8.

As can be seen from these results, the arachidonic acid increased about 1.7-fold, EPA about 1.3-fold, DPA (n-6) about 1.1-fold, and DHA about 0.9-fold.

INDUSTRIAL APPLICABILITY

The present invention provides a method for transforming stramenopile through disruption of stramenopile genes and/or inhibition of expression thereof, modification of the fatty acid composition produced by a stramenopile, and a method for highly accumulating fatty acids in a stramenopile. The present invention thus enables more efficient production of polyunsaturated fatty acids.

---

What is claimed is:

1. A microbial oil comprising a fatty acid obtained from a microorganism in which the fatty acid is highly accumulated, the microbial oil comprising:
   (a) 1.5% or more of arachidonic acid (AA) based on a total amount of fatty acid;
   (b) 0.2% or more of dihomo-γ-linolenic acid (DGLA) based on the total amount of fatty acid;
   (c) 0.04% or more of eicosatetraenoic acid (ETA) based on the total amount of fatty acid;
   (d) 3.8% or more of eicosapentaenoic acid (EPA) based on the total amount of fatty acid;
   (e) 13.7% or less of n-6 docosapentaenoic acid (n-6DPA) based on the total amount of fatty acid; and
   (f) 43.9% or less of docosahexaenoic acid (DHA) based on the total amount of fatty acid,
   wherein the microorganism belongs to a class of Labyrinthulomycetes in which a gene associated with fatty acid biosynthesis has been disrupted or an expression of the gene has been inhibited.

2. The microbial oil according to claim 1, wherein the gene associated with fatty acid biosynthesis is a gene of polyketide synthase (PKS), fatty acid chain elongase, and/or fatty acid desaturase.

3. The microbial oil according to claim 1, wherein n-6DPA/DTA measured as a gas chromatograph (GC) area is 12.6 or less.

4. The microbial oil according to claim 1, wherein DHA/n-3DTA measured as a gas chromatograph (GC) area is 38.8 or less.

5. The microbial oil according to claim 1, wherein C20 polyunsaturated fatty acid (PUFA)/C22 PUFA measured as a gas chromatograph (GC) area is 0.3-29.6.

6. The microbial oil according to claim 1, wherein n-6PUFA/n-3 PUFA measured as a gas chromatograph (GC) area is 0.2 or more.

7. The microbial oil according to claim 1, wherein the microorganism satisfies either of the following (1) or (2):
   (1) the class of Labyrinthulomycetes in which a gene of polyketide synthase (PKS), fatty acid chain elongase, and/or fatty acid desaturase which is the gene associated with fatty acid biosynthesis is disrupted or an expression of the gene is inhibited such that fatty acid composition in the microorganism is modified; or
   (2) the class of Labyrinthulomycetes in which the gene of fatty acid chain elongase and/or fatty acid desaturase is disrupted or an expression of the gene is inhibited, and another fatty acid chain elongase and/or another fatty acid desaturase is introduced into the microorganism such that fatty acid composition in the microorganism is modified.

8. The microbial oil according to claim 1, wherein the microorganism is able to grow in media which do not contain PUFA.

9. The microbial oil according to claim 1, wherein the gene is OrfA.

10. The microbial oil according to claim 2, wherein the fatty acid chain elongase is a C20 elongase.

11. The microbial oil according to claim 1, wherein the gene of fatty acid desaturase is the gene of Δ4 desaturase, Δ12 desaturase, and/or ω3 desaturase.

12. The microbial oil according to claim 1, wherein the gene has been disrupted by electroporation or a gene-gun technique.

13. The microbial oil according to claim 1, wherein the expression of the gene has been inhibited by an antisense technique or RNA interference.

14. The microbial oil according to claim 1, wherein the microorganism belongs to a genus of *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium*, or *Sicyoidochytrium*.

15. The microbial oil according to claim 14, wherein the microorganism is *Thraustochytrium aureum, Parietichytrium sarkarianum, Thraustochytrium roseum, Parietichytrium* sp., or *Schizochytrium* sp.

16. The microbial oil according to claim 15, wherein the microorganism is *Thraustochytrium aureum* (ATCC 34304), *Parietichytrium sarkarianum* SEK364 (FERM BP-11298), *Thraustochytrium roseum* (ATCC 28210), *Parietichytrium* sp. SEK358 (FERM BP-11405), *Parietichytrium* sp. SEK571 (FERM BP-11406), or *Schizochytrium* sp. TY12Ab (FERM BP-11421).

17. A food, feed, drug or industrial product, which contains the microbial oil according to claim 1.

* * * * *